US007122580B2

(12) United States Patent
Mjalli et al.

(10) Patent No.: US 7,122,580 B2
(45) Date of Patent: Oct. 17, 2006

(54) ARYL AND HETEROARYL COMPOUNDS AND METHODS TO MODULATE COAGULATION

(75) Inventors: Adnan M. M. Mjalli, Jamestown, NC (US); Robert C. Andrews, Jamestown, NC (US); Xiao-Chuan Guo, High Point, NC (US); Daniel Peter Christen, High Point, NC (US); Devi Reddy Gohimmukkula, Jamestown, NC (US); Guoxiang Huang, Greensboro, NC (US); Robert Rothlein, Summerfield, NC (US); Sameer Tyagi, High Point, NC (US); Tripura Yaramasu, Greensboro, NC (US); Christopher Behme, Jamestown, NC (US)

(73) Assignee: TransTech Pharma, Inc., High Point, NC (US)

( * ) Notice: Subject to any disclaimer, the term of this patent is extended or adjusted under 35 U.S.C. 154(b) by 427 days.

(21) Appl. No.: 10/637,900

(22) Filed: Aug. 8, 2003

(65) Prior Publication Data

US 2004/0110832 A1    Jun. 10, 2004

Related U.S. Application Data

(60) Provisional application No. 60/402,272, filed on Aug. 9, 2002.

(51) Int. Cl.
*A61K 31/245* (2006.01)
*C07C 233/87* (2006.01)
(52) U.S. Cl. ...................... 514/576; 562/445
(58) Field of Classification Search ............... 560/41; 514/576; 562/445
See application file for complete search history.

(56) References Cited

U.S. PATENT DOCUMENTS

| | | | |
|---|---|---|---|
| 4,675,439 A | 6/1987 | Mita et al. | |
| 4,717,736 A | 1/1988 | Rokach et al. | |
| 5,273,990 A | 12/1993 | De Lombaert et al. | |
| 5,354,905 A | 10/1994 | Sato et al. | |
| 5,397,798 A | 3/1995 | Fitch et al. | |
| 5,514,719 A | 5/1996 | LaTorse et al. | |
| 5,518,735 A | 5/1996 | Sturzebecher et al. | |
| 5,679,671 A | 10/1997 | Oinuma et al. | |
| 5,703,106 A | 12/1997 | Fruh et al. | |
| 5,750,520 A | 5/1998 | Danilewicz et al. | |
| 5,780,498 A | 7/1998 | Saika et al. | |
| 5,908,843 A | 6/1999 | Gante et al. | |
| 5,977,075 A | 11/1999 | Ksander et al. | |
| 5,977,178 A | 11/1999 | Wise et al. | |
| 6,001,820 A | 12/1999 | Hirsh et al. | |
| 6,087,380 A | 7/2000 | Hauel et al. | |
| 6,127,341 A | 10/2000 | Hansen et al. | |
| 6,191,171 B1 | 2/2001 | DeLaszlo et al. | |
| 6,194,448 B1 | 2/2001 | Bredrget et al. | |
| 6,194,458 B1 | 2/2001 | Baker et al. | |
| 6,262,084 B1 | 7/2001 | Biediger et al. | |
| 6,284,871 B1 | 9/2001 | Mertens et al. | |
| 6,291,511 B1 | 9/2001 | Durette et al. | |
| 6,300,330 B1 | 10/2001 | Stocker et al. | |
| 6,306,840 B1 | 10/2001 | Adams et al. | |
| 6,331,564 B1 | 12/2001 | Brugnara et al. | |
| 6,342,504 B1 | 1/2002 | Brunk et al. | |
| 6,358,978 B1 | 3/2002 | Ritzeler et al. | |
| 6,362,204 B1 | 3/2002 | Head et al. | |
| 6,388,138 B1 | 5/2002 | Lee et al. | |
| 6,388,148 B1 | 5/2002 | Heilmann et al. | |
| 6,403,584 B1 | 6/2002 | De Laszlo et al. | |
| 6,420,396 B1 | 7/2002 | Albers et al. | |
| 6,423,727 B1 | 7/2002 | De Lombaert et al. | |
| 6,469,047 B1 | 10/2002 | Jackson et al. | |
| 6,521,666 B1 * | 2/2003 | Sircar et al. ................. | 514/576 |
| 6,528,275 B1 | 3/2003 | Quibell et al. | |
| 6,528,655 B1 | 3/2003 | N'Zemba et al. | |
| 6,559,174 B1 | 5/2003 | Lin et al. | |
| 6,743,790 B1 | 6/2004 | Klingler et al. | |
| 2002/0016461 A1 | 2/2002 | Albers et al. | |
| 2002/0095041 A1 | 7/2002 | Chan et al. | |
| 2002/0103192 A1 | 8/2002 | Curtin et al. | |
| 2002/0151595 A1 | 10/2002 | Ries et al. | |
| 2002/0173656 A1 | 11/2002 | Peyman et al. | |

(Continued)

FOREIGN PATENT DOCUMENTS

DE    199 28 424    12/2000

(Continued)

OTHER PUBLICATIONS

Burdick et al, "N-Benzoyl Amino Acids as LFA-1/ICAM Inhibitors 1: Amino Acid Structure-Activity Relationship" Bioorganic Medicinal Chemistry Letters, vol. 13, pp. 1015-1018. (2003).

(Continued)

*Primary Examiner*—Kamal A. Saeed
*Assistant Examiner*—Joseph R. Kosack
(74) *Attorney, Agent, or Firm*—Samuel B. Rollins

(57) ABSTRACT

This invention provides certain compounds, methods of their preparation, pharmaceutical compositions comprising the compounds, and their use in treating human or animal disorders. The compounds of the invention are useful as antagonists, or more preferably, partial antagonist of factor IX and thus, may be used to inhibit the intrinsic pathway of blood coagulation. The compounds are useful in a variety of applications including the management, treatment and/or control of diseases caused in part by the intrinsic clotting pathway utilizing factor IX. Such diseases or disease states include stroke, myocardial infarction, aneurysm surgery, and deep vein thrombosis associated with surgical procedures, long periods of confinement, and acquired or inherited pro-coagulant states.

36 Claims, 2 Drawing Sheets

U.S. PATENT DOCUMENTS

| | | |
|---|---|---|
| 2002/0198195 A1 | 12/2002 | Nazare et al. |
| 2003/0045480 A1 | 3/2003 | Safar et al. |
| 2003/0149083 A1 | 8/2003 | Tanaka et al. |
| 2004/0106626 A1 | 6/2004 | South et al. |
| 2004/0126856 A1 | 7/2004 | Bajaj et al. |
| 2004/0152888 A1 | 8/2004 | Bourguignon et al. |
| 2004/0198780 A1 | 10/2004 | Liu et al. |
| 2004/0220180 A1 | 11/2004 | Glick et al. |
| 2004/0241781 A1 | 12/2004 | Glick et al. |
| 2005/0049310 A1* | 3/2005 | Mjalli et al. ............ 514/567 |
| 2005/0053600 A1 | 3/2005 | Lane |
| 2005/0059705 A1 | 3/2005 | Mjalli et al. |
| 2005/0059713 A1 | 3/2005 | Mjalli et al. |
| 2005/0065346 A1 | 3/2005 | Ries et al. |
| 2005/0165107 A1 | 7/2005 | Inoue et al. |
| 2005/0187390 A1 | 8/2005 | Schmitz et al. |
| 2005/0187409 A1 | 8/2005 | Powers et al. |
| 2005/0203135 A1 | 9/2005 | Burdick et al. |
| 2005/0256116 A1 | 11/2005 | Clary et al. |

FOREIGN PATENT DOCUMENTS

| | | |
|---|---|---|
| EP | 0150118 | 9/1987 |
| EP | 1213288 | 12/2002 |
| FR | 2 847 251 | 5/2004 |
| GB | 1 501 541 | 2/1978 |
| GB | 2354440 | 3/2001 |
| GB | 2354440 A1 * | 3/2001 |
| JP | 61227555 | 10/1986 |
| JP | 09124569 | 5/1997 |
| JP | 2001-089368 | 4/2001 |
| JP | 2003-321358 | 11/2003 |
| JP | 2004-323487 | 11/2004 |
| WO | WO 95/12611 | 5/1995 |
| WO | WO 1996-33170 | 10/1996 |
| WO | WO 1997-23508 | 7/1997 |
| WO | WO 1997-23508 | 9/1997 |
| WO | WO 1997-40065 | 10/1997 |
| WO | WO 1997-42216 | 11/1997 |
| WO | WO 98/37075 | 8/1998 |
| WO | WO 98/53817 | 12/1998 |
| WO | WO 1998-58950 | 12/1998 |
| WO | WO 99/26923 | 6/1999 |
| WO | WO 99/36393 | 7/1999 |
| WO | WO 9936393 A1 * | 7/1999 |
| WO | WO 00/37429 | 6/2000 |
| WO | WO 2000-35864 | 6/2000 |
| WO | WO 00/67746 | 11/2000 |
| WO | WO 00/68188 | 11/2000 |
| WO | WO 00/76971 | 12/2000 |
| WO | WO 01/10823 | 2/2001 |
| WO | WO 01/21584 | 3/2001 |
| WO | WO 01/38309 | 5/2001 |
| WO | WO 2001-056994 | 8/2001 |
| WO | WO 01/68586 | 9/2001 |
| WO | WO 02/18320 | 3/2002 |
| WO | WO 02/26717 | 4/2002 |
| WO | WO 02/062748 | 8/2002 |
| WO | WO 02/085841 | 10/2002 |
| WO | WO 2002-083842 | 10/2002 |
| WO | WO 03/007945 | 1/2003 |
| WO | WO 2003-002545 | 1/2003 |
| WO | WO 2003-006444 | 1/2003 |
| WO | WO 03/033496 | 4/2003 |
| WO | WO 2003-072536 | 9/2003 |
| WO | WO 04/046091 | 6/2004 |
| WO | WO 04/080970 | 9/2004 |
| WO | WO 04/084842 | 10/2004 |
| WO | WO 2004-110983 | 12/2004 |
| WO | WO 2005-012288 | 2/2005 |
| WO | WO 2005-039494 | 5/2005 |

OTHER PUBLICATIONS

Castanedo et al, "Solid-Phase synthesis of dual alpha4beta1/alpha4beta7 Integrin antagonists: Two Scaffolds with Overlapping Pharmacophores", Bioorganic & Medicinal Chemistry Letters, Oxford, GB vol. 12, pp. 2913-2917. (2002).

Greenspan P.D. et al., "N-aryl Cinnamides: A Novel Class of Rigid and Highly Potent Leukotriene B4 Receptor Antagonists", Bioorganic and Medicinal Chemistry Letters, vol. 7, No. 7, 1997, pp. 949-954.

International Search Report for PCT application PCT/US2004/025463 mailed Jan. 26, 2005.

International Search Report for PCT application PCT/US2004/025478 mailed Jan. 26, 2005.

International Search Report for PCT application PCT/US2004/025429 mailed Jan. 26, 2005.

International Search Report for related PCT application PCT/US03/25045 mailed Mar. 14, 2005.

Knowles, H.S. et al., A photochemical approach to phenylalanines and related compounds by alkylation of glycine, Tetrahedron, vol. 57, pp. 98115-98124. (2001).

O'Donnell M.J. et al., "Enantioselective Solid-Phase Synthesis of α-Amino Acid Derivatives", Tetrahedron, vol. 55, pp. 6347-6362. (1999).

Sircar et al, "Synthesis and SAR of N-benzoyl-L-Biphenylalanine derivatives: Discovery of TR-14035, A Dual Alpha4Beta7/Alpha4Beta1 Intergrin Antagonist", Bioorganic & Medicinal Chemistry, vol. 10, pp. 2051-2066. (2002).

Bebernitz et al., "Anilides of R-Trifluoro-2-hydroxy-2-methylpropionic Acid as Inhibitors of Pyruvate Dehydrogenase Kinase", Journal of Medicinal Chemistry, vol. 43, pp. 7121-7124, (2000).

Shrader et al., "Neutral Inhibitors of the Serine Protease Factor Xa", Bioorganic & Medicinal Chemistry Letters, vol. 11, pp. 1801-1804, (2001).

Knowles et al., "Photochemical alkylation of glycine leading to phenylalanines", Tetrahedron Letters, vol. 41, pp. 7121-7124, (2000).

Alves et al., "A novel 3-step enantioselective synthesis of pyrenylalanine with subsequent incorporation into opioid, CCK and melanotropin ligands" Biochemical and Biophysical Research Communications, vol. 318, pp. 335-340, (2004).

Amino et al., "Phenylalanine derivatives enhancing intestinal absorption of insulin in mice" Chemical and Pharmaceutical Bulletin, vol. 36, pp. 4426-4434, (1988).

Ankersen et al., "Demonstration of the strength of focused combinatorial libraries in SAR optimisation of growth hormone secretagogues" European Journal of Medicinal Chemistry, vol. 34, pp. 783-790, (1999).

Balwierczak et al., "Characterization of a potent and selective endothelin-B receptor antagonist, IRL 2500" Journal of Cardiovascular Pharmacology, vol. 26, pp. S393-S396, (1995).

Boitano et al., "Structure activity studies of a novel cytotoxic benzodiazepine" Bioorganic & Medicinal Chemistry Letters, vol. 13, pp. 3327-3330, (2003).

Burk et al., "A versatile tandem catalysis procedure for the preparation of novel amino acids and peptides" Journal of the American Chemical Society, vol. 116, pp. 10847-10848, (1994).

Burk et al., "Asymmetric catalytic routes to chiral building blocks of medicinal interest" Pure and Applied Chemistry, vol. 68, pp. 37-44, (1996).

Au-Yeung et al., "Unnatural a-amino acids via asymmetric hydrogenation of enamides" Transition Metals for Organic Synthesis and Fine Chemicals, vol. 2, pp. 14-25, (1998).

Chapman et al., "Synthesis of functionalised phenylalanines using rhodium catalysis in water" Advanced Synthesis & Catalysis, vol. 345, pp. 353-355, (2003).

Chisholm et al., "Identification of the enantioselective step in the asymmetric catalytic hydrogenation of a prochiral olefin" Journal of the American Chemical Society, vol. 102, pp. 5952-5954, (1980).

DeLaszio et al., "Identification of Unique VLA-4 Antagonists from a Combinatorial Library" Bioorganic & Medicinal Chemistry Letters, vol. 12, pp. 685-688, (2002).

Dobler et al., "Unusual amino acids IV. Asymmetric synthesis of thienylalanines" Tetrahedron:Asymmetry, vol. 4, pp. 1833-1842, (1993).

Doherty et al., "N-Aryl 2, 6-Dimethoxybiphenylalanine Analogues as VLA-4 Antagonists" Bioorganic & Medicinal Chemistry Letters, vol. 12, pp. 729-731, (2002).

Egger et al., "A small molecule $\alpha_4\beta_1/\alpha_4\beta_7$ antagonist differentiates between the low-affinity states of $\alpha 4\beta_1$ and $\alpha_4\beta_7$: Characterization of divalent cation dependence" Journal of Pharmacology and Experimental Therapeutics, vol. 306, pp. 903-913, (2003).

Egusa et al., "One-dimensional aromatic crystals in solution. 4. Ground-and excited-state interactions of poly(L-1 pyrenylalanine) studied by chiroptical spectroscopy including circularly polarized fluorescence and fluorescence-detected circular dichroism" Macromolecules, vol. 18, pp. 882-889, (1985).

Firooznia et al., "Synthesis of 4-substituted phenylalanines by cross-coupling reactions: extension of the methodology to aryl chlorides" Tetrahedron Letters, vol. 39, pp. 3985-3988, (1998).

Früh et al., "IRL 2500: a potent $ET_B$ selective endothelin antagonist" Bioorganic & Medicinal Chemistry Letters, vol. 6, pp. 2323-2328, (1996).

Gadek et al., "Generation of an LFA-1 antagonist by the transfer of the ICAM-1 immunoregulatory epitope to a small molecule" Science, vol. 295, pp. 1086-1089, (2002).

Hoshina et al. "2, 3-Diphenylpropionic acids as potent VLA-4 antagonists" Bioorganic & Medicinal Chemistry Letters, vol. 15, pp. 217-220, (2005).

Hsieh et al., "Topographic probes of angiotensin and receptor: potent angiotensin II agonist containing diphenylalanine and long-acting antagonists containing biphenylalanine and 2-indan amino acid in position 8" Journal of Medicinal Chemistry, vol. 32, pp. 898-903, (1989).

Ikeda, et al., "Diastereoselective hydrogenation of dehydrodipeptides with a polycondensed aromatic ring at β-position of dehydroamino acid residue" Chemistry Express, vol. 5, pp. 29-32, (1990).

Kagan et al., "Asymmetric catalytic reduction with transition metal complexes. I. A catalytic system of rhodium (I) with (-)-2,3-0-isopropylidene-2,3-dihydroxy-1,4-bis(diphenylphosphino)butane, a new chiral diphosphine" Journal of the American Chemical Society, vol. 94, pp. 6429-6433, (1972).

Kannan et al., "Stereochemistrhy of the cyclic tripeptide antibiotic WS-43708A" Journal of Organic Chemistry, vol. 52, pp. 5435-5437, (1987).

Kato et al., "Novel benzamides as selective and potent gastrokinetic agents. III. Synthesis and structure-activity relationships of 4-amino-5-chloro-2-methoxy-and 2-ethoxy-N-[(4-substituted 2-morpholinyl)methyl]-benzamides" Chemical and Pharmaceutical Bulletin, vol. 40, pp. 652-660, (1992).

Krause et al., "Unusual amino acids VI. substituted arylamino acids by asymmetric hydrogenation of N-Cbz and N-Boc protected dehydroamino acid derivatives" Chirality, vol. 8, pp. 173-188, (1996).

Kreuzfeld et al., "Unusual amino acids v. asymmetric hydrogenation of (z)-N-acylaminocinnamic acid dervatives bearing different protective groups" Tetrahedron:Asymmetry, vol. 4, pp. 2047-2051, (1993).

Ksander et al., "Dipeptide sulfonamides as endothelin $ET_A/ET_B$ receptor antagonists" Canadian Journal of Physiology and Pharmacology, vol. 80, pp. 464-469, (2002).

Kudlacz et al., "Pulmonary eosinophilia in a murine model of allergic inflammation is attenuated by small molecule α4β1 antagonists" Journal of Pharmacology and Experimental Therapeutics, vol. 301, pp. 747-752, (2002).

Lettre et al., "Chemically labelled antigens. III. Introduction of 4-ring systems into proteins" Hoppe-Seyler's Zeitschrift fur physiologische Chemie, vol. 267, pp. 108-114, (1940).

Leung et al., "Use of A-192621 and IRL-2500 to unmask the mesenteric and renal vasodilator role of endothelin ETb receptors", Journal of Cardiovascular Pharmacology, vol. 39, pp. 533-543 (2002).

Lopez-Arbeloa et al., "Chiral discrimination of the intermolecular excimer of N-acetyl-1-pyrenylalanine methyl ester" Journal of the American Chemical Society, vol. 109, pp. 3068-3076, (1987).

Ma et al., "Synthesis of the biaryl moiety of the proteasome inhibitors TMC-95 via a ligandless $Pd(Oac)_2$-catalyzed suzuki-coupling reaction" Tetrahedron Letters, vol. 42, pp. 5279-5281, (2001).

Macchia et al., "Toward the rational development of peptidomimetic analogs of the C-terminal endothelin hexapeptide: development of a theoretical model" Farmaco, vol. 53, pp. 545-556, (1998).

Macchiarulo et al., "Insights into phenylalanine derivatives recognition of VLA-4 integrin: from a pharmacophoric study to 3D-QSAR and molecular docking analyses" Journal of Chemical Information and Computer Sciences, vol. 44, pp. 1829-1839, (2004).

Mazaleyrat et al. "Practical resolution of an atropoisomeric α,α-disubstituted glycine with L-phenylalanine cyclohexylamide as chiral auxiliary" Tetrahedron:Asymmetry, vol. 9, pp. 2701-2713, (1998).

Melillo et al., "Practical enantioselective Synthesis of a Homotyrosine derivative and (R,R)-4-propyl-9-hydroxynaphthoxazine, a potent dopamine agonist" Journal of Organic Chemistry, vol. 52, pp. 5143-5150, (1987).

Mimatsu et al., "Circularly polarized luminescence generated by intramolecular excimer of a chiral pyrenyl compound" New Technologies & Medicine, vol. 2, pp. 45-47, (2001).

Mustafa et al., "Reactivity of unsaturated centres in heterocycles and chalkones toward diazoalkanes" Tetrahedron, vol. 21, pp. 2215-2229, (1965).

O'Donnell et al., "An efficient homogeneous catalytic enantioselective synthesis of α-amino acid derivatives" Tetrahedron Letters, vol. 39, pp. 8775-8778, (1998).

Ojima et al., "Asymmetric hydrogenation of prochiral olefins catalyzed by rhodium complexes with chiral pyrrolidinodiphosphines. Crucial factors for the effective asymmetric induction" Journal of Organic Chemistry, vol. 45, pp. 4728-4739, (1980).

Okamoto et al., "Optical resolution of amino acid derivatives by high-performance liquid chromatography on tris(phenylcarbamate)s of cellulose and amylose" Journal of Chromatography, vol. 477, pp. 367-376, (1989).

Omote et al., "Synthesis and melanogenesis of the DOPA dimer" Bulletin of the Chemical Society of Japan, vol. 42, pp. 1752-1754, (1969).

Ooi et al., "Design of N-spiro $C_2$-symmetric chiral quaternary ammonium bromides as novel chiral phase-transfer catalysts: synthesis and application to practical asymmetric synthesis of α-amino acids" Journal of the American Chemical Society, vol. 125, pp. 5139-5151, (2003).

Pawlowska et al, "Synthesis of dextro-and laevorotatory N-acetyl-β-(2-dibenzofuryl)alanines" Polish Journal of Chemsitry, vol. 58, pp. 619-620, (1984).

Pierson et al., "Catalytic asymmetric oxonium ylide—[2,3] sigmatropic rearrangement with diazocarbonyl compounds: First use of $C_2$-symmetry in Rh(II) carboxylates" Tetrahedron Letters, vol. 38, pp. 4705-4708, (1997).

Russell et al., "Characterization of the binding of endothelin $ET_a$ selective ligands in human and rat heart" British Journal fo Pharmacology, vol. 119, pp. 631-636, (1996).

Sakaguchi et al., "Synthesis, gastrointestinal prokinetic activity and structure-activity relationships of novel N-[(2-(dialkylamino)ethoxy]benzyl]benzamide derivatives" Chemical and Pharmaceutical Bulletin, vol. 40, pp. 202-211, (1992).

Sakaki et al., "Discovery of IRL 3461: a novel and potent endothelin antagonist with balanced $ET_A/ET_B$ affinity" Bioorganic & Medicinal Chemistry Letters, vol. 8, pp. 2241-2246, (1998).

Satoh et al., "Synthesis of 4-substituted phenylalanine derivatives by cross-coupling reaction of p-boronophenylalanines" Tetrahedron Letters, vol. 38, pp. 7645-7648 (1997).

Shieh et al., "A simple asymmetric synthesis of 4-arylphenylalanines via palladium-catalyzed cross-coupling reaction of arylboronic acids with tyrosine triflate" Journal of Organic Chemistry, vol. 57, pp. 379-381, (1992).

Strauss et al., "Optically active cyclic hexapeptides with covalently attached pyrene probes: selective alkaline earth metal ion recognition using excimer emission" Organic Letters, vol. 4, pp. 683-686, (2002).

Taudien et al., "Unusual amino acids III. Asymmetric synthesis of 3-arylalanines" Tetrahedron:Asymmetry, vol. 4, pp. 73-84, (1993).

Urbahns et al., "Biphenyls as potent vitronectin receptor antagonists. Part 2: biphenylalanine ureas" Bioorganic & Medicinal Chemistry Letters, vol. 13, pp. 1071-1074, (2003).

Webb et al., "Effects of the $ET_a$-selective antagonist IRL 2500 in conscious spontaneously hypertensive and Wistar-Kyoto Rats" Journal of Cardiovascular Pharmacology, vol. 26, pp. S389-S392, (1995).

Yabe et al., "Analogues of luteinizing hormone-releasing hormone with modification in position $3^1$" Chemical & Pharmaceutical Bulletin, vol. 24, pp. 3149-3157, (1976).

Ohmomo et al., "Synthesis and evaluation of iodinated benzamide derivatives as selective and reversible monoamine oxidase B inhibitors" Chemical and Pharmacuetical Bulletin, vol. 40, pp. 1789-1792, (1992).

Zhang et al., "Acylation of 2,5-dimethoxycarbonyl[60]fulleropyrrolidine and synthesis of its multifullerene derivatives" Journal of Organic Chemistry, vol. 67, pp. 883-891, (2002).

Database Caplus Chemical Abstracts Service, Columbus, Ohio, US, XP002319820, rerieed from STN Database accession No. 1973: 504834 abstract; RN 42787-97-3 abstract & I. Hahnemann et al, Journal Fuer Praktische Chemie, vol. 315, No. 4, 1973, pp. 796-800.

Ma et al., "Synthesis of the biaryl moiety of the proteasome inhibitors TMC-95 via a ligandless $Pd(Oac)_2$-catalyzed suzuki-coupling reaction" Tetrahedron Letters, vol. 42, pp. 5279-5281, (2001).

Macchia et al., "Toward the rational development of peptidomimetic analogs of the C-terminal endothelin hexapeptide: development of a theoretical model" Farmaco, vol. 53, pp. 545-556, (1998).

Macchiarulo et al., "Insights into phenylalanine derivatives recognition of VLA-4 integrin: from a pharmacophoric study to 3D-QSAR and molecular docking analyses" Journal of Chemical Information and Computer Sciences, vol. 44, pp. 1829-1839, (2004).

Mazaleyrat et al. "Practical resolution of an atropoisomeric α,α-disubstituted glycine with L-phenylalanine cyclohexylamide as chiral auxiliary" Tetrahedron:Asymmetry, vol. 9, pp. 2701-2713, (1998).

Melillo et al., "Practical enantioselective Synthesis of a Homotyrosine derivative and (R,R)-4-propyl-9-hydroxynaphthoxazine, a potent dopamine agonist" Journal of Organic Chemistry, vol. 52, pp. 5143-5150, (1987).

Mimatsu et al., "Circularly polarized luminescence generated by intramolecular excimer of a chiral pyrenyl compound" New Technologies & Medicine, vol. 2, pp. 45-47, (2001).

Mustafa et al., "Reactivity of unsaturated centres in heterocycles and chalkones toward diazoalkanes" Tetrahedron, vol. 21, pp. 2215-2229, (1965).

O'Donnell et al., "An efficient homogeneous catalytic enantioselective synthesis of α-amino acid derivatives" Tetrahedron Letters, vol. 39, pp. 8775-8778, (1998).

Ojima et al., "Asymmetric hydrogenation of prochiral olefins catalyzed by rhodium complexes with chiral pyrrolidinodiphosphines. Crucial factors for the effective asymmetric induction" Journal of Organic Chemistry, vol. 45, pp. 4728-4739, (1980).

Okamoto et al., "Optical resolution of amino acid derivatives by high-performance liquid chromatography on tris(phenylcarbamate)s of cellulose and amylose" Journal of Chromatography, vol. 477, pp. 367-376, (1989).

Omote et al., "Dopa dimer" Chemical Communications, vol. 4, p. 190, (1968).

Omote et al., "Synthesis and melanogenesis of the DOPA dimer" Bulletin of the Chemical Society of Japan, vol. 42, pp. 1752-1754, (1969).

Ooi et al., "Design of N-spiro $C_2$symmetric chiral quaternary ammonium bromides as novel chiral phase-transfer catalysts: synthesis and application to practical asymmetric synthesis of α-amino acids" Journal of the American Chemical Society, vol. 125, pp. 5139-5151, (2003).

Pawlowska et al, "Synthesis of dextro-and laevorotatory N-acetyl-β-(dibenzofuryl)alanines" Polish Journal of Chemsitry, vol. 58, pp. 619-620, (1984).

Pierson et al., "Catalytic asymmetric oxonium ylide—[2,3] sigmatropic rearrangement with diazocarbonyl compounds: First use of $C_2$-symmetry in Rh(II) carboxylates" Tetrahedron Letters, vol. 38, pp. 4705-4708, (1997).

Batt et al., "5-Amidinoindoles as dual inhibitors of coagulation factors IXa and Xa" Bioorganic & Medicinal Chemistry Letters, vol. 14, pp. 5269-5273, (2004).

Bedsted et al., "Heparin and calcium ions dramatically enhance antithrombin reactivity with factor IXa by generating new interaction exosites" Biochemistry, vol. 42, pp. 8143-8152, (2003).

Benincosa et al., "Pharmacokinetics and pharmacodynamics of a humanized monoclonal antibody to factor IX in cynomolgus monkeys" The Journal of Pharmacology and Experimental Therapeutics, vol. 292, pp. 810-816, (2000).

Blostein et al., "The Gla domain of factor IXa binds to factor VIIIa in the Tenase Complex" The Journal of Biological Chemistry, vol. 278, pp. 31297-31302, (2003).

Burger et al., "Ein Neuer allgemeiner zugang zu α-trifluormethyl-substituierten aromatischen und heteroaromatischen α-aminosäuren" Synthesis, vol. 11, pp. 850-855, (1989).

Cui et al., "An oxyanion-hole selective serine protease inhibitor in complex with tryspin" Bioorganic & Medicinal Chemistry Letters, vol. 10, pp. 41-46, (2002).

Das et al., "Molecular design and structure—activity relationships leading to the potent, selective, and orally active thrombin active site inhibitor BMS—189664" Bioorganic & Medicinal Chemistry Letters, vol. 12, pp. 45-49, (2002).

Database Caplus Chemical Abstracts Service, Columbus, Ohio, US, XP002319820, retrieved from STN Database accession No. 1973: 504834 abstract; RN 42787-97-3 abstract & I. Hahnemann et al, Journal Fuer Praktische Chemie, vol. 315, No. 4, 1973, pp. 796-800.

Feuerstein et al., "Antithrombotic efficacy of a novel murine anti-human factor IX antibody in rats" Arteriosclerosis, Thrombosis, and Vascular Biology, vol. 19, pp. 2554-2562, (1999).

Hirayama et al., "The discovery of YM-60828: a potent, selective and orally-bioavailable factor Xa inhibitor" Bioorganic & Medicinal Chemistry Letters, vol. 10, pp. 1509-1523, (2002).

Hsu et al., "The distinct roles that gIn-192 and Glu-217 of factor IX play in selectivity for macromolecular substrates and inhibitors" Biochemistry, vol. 40, pp. 11261-11269, (2001).

Kolkman et al., "Surface-loop residue $Lys^{316}$ in blood coagulation factor IX is a major determinant for factor X but not antithrombin recognition" Biochemistry, vol. 350, pp. 701-707, (2000).

Omote et al., "DOPA Dimer" Chemical Communications, vol. 4, p. 190, (1968).

Rose et al., "Substrate recognition drives the evolution of serine proteases" The Journal of Biological Chemistry, vol. 277, pp. 19243-19246, (2002).

Schmidt et al., "Structure-function relationships in factor IX and factor IXa" Trends in Cardiovascular Medicine, vol. 13, pp. 39-45, (2003).

Shikamoto et al., "Crystal Structure of $Mg^{2+}$-and $Ca^{2+}$-bound Gla Domain of Factor IX Complexed with Binding Protein" The Journal of Biological Chemistry, vol. 278, pp. 24090-24094, (2003).

Smallheer et al., "SAR and factor IXa crystal structure of a dual inhibitor of factors IXa and Xa" Bioorganic & Medicinal Chemistry Letters, vol. 14, pp. 5263-5267, (2004).

Stoilova-McPhie et al., "3-Dimensional structure of membrane-bound coagulation factor VIII: modeling of the factor VIII heterodimer within a 3-dimensional density map derived by electron crystallography" Blood, vol. 99, pp. 1215-1223, (2002).

Toomey et al., "Inhibition of factor IX(a) is protective in a rat model of thromboembolic stroke" Stroke, vol. 33, pp. 578-585, (2002).

Weltz et al., "New anticoagulant drugs" Chest, vol. 119, pp. 95s-107s, (2001).

Yang et al., "Localization of the heparin binding exosites of factor IXa" The Journal of Biological Chemistry, vol. 277, pp. 50756-50760, (2002).

* cited by examiner

ARYL AND HETEROARYL COMPOUNDS AND METHODS TO MODULATE COAGULATION

STATEMENT OF RELATED APPLICATION

The present application claims priority under 35 USC 119 from the following U.S. Provisional Application: Ser. No. 60/402,272, filed Aug. 9, 2002, entitled "Aryl and Heteroaryl Compounds and Methods to Modulate Coagulation," the entirety of which is herein incorporated by reference.

FIELD OF THE INVENTION

This invention relates to compounds which are antagonists of the intrinsic clotting pathway by binding to and inhibiting the function of factor IX.

BACKGROUND OF THE INVENTION

Hemostasis, the arrest of bleeding from an injured blood vessel, requires the concerted activity of vascular, platelet, and plasma factors to eventually form a hemostatic seal or a blood clot. In normal hemostasis, the combined activity of these factors is counterbalanced by regulatory mechanisms to limit the accumulation of platelets and fibrin in the area of injury.

Upon injury to a blood vessel, vascular factors reduce blood flow from the blood vessel by local vasoconstriction and compression of injured vessels. At the same time, platelets adhere to the site of vessel wall injury and form aggregates called hemostatic plugs, which form the first key element of the hemostatic seal. Platelets also release factors that provide surface membrane sites and components for the formation of enzyme/cofactor complexes in blood coagulation reactions. Through a series of interacting and propagating zymogen activations, the activated form of one plasma factor catalyzes the activation of the next plasma factor. This cascade of blood coagulation reactions eventually forms a fibrin clot. The fibrin clot, an insoluble fibrin matrix that radiates from and anchors the hemostatic plug, is the second key element of the hemostatic seal Specifically, the cascade of blood coagulation reactions discussed involvse two interdependent pathways, an intrinsic pathway and an extrinsic pathway. Each pathway ultimately catalyzes the proteolytic activation of factor X to factor Xa.

Damage to the blood vessel or a negatively charged surface initiates blood clotting by the intrinsic pathway. As seen in FIG. 1, the major components of the intrinsic pathway include factor VIII, a non-enzymatic co-factor, and factors IX and XI, zymogen serine proteases. The initiation of the intrinsic pathway results in the activation of factor XI to XIa. Factor XIa, as well as the presence of the factor VIIa/tissue factor complex involved in the extrinsic pathway, catalyzes the activation of factor IX to factor IXa. The presence of factor IXa, in combination with the activated form of factor VIII on an appropriate phospholipid surface, results in the formation of a tenase complex (10). The tenase complex catalyzes the formation of factor Xa from its zymogen, factor X.

Exposure of blood to injured tissue initiates blood clotting by the extrinsic pathway. As is shown in FIG. 1, the major components of the extrinsic pathway are factor VII, a zymogen serine protease, and tissue factor, a membrane bound protein. Tissue factor serves as the requisite non-enzymatic co-factor for factor VII. The initiation of the extrinsic pathway is thought to be an autocatalytic event resulting from the activation of factor VII by trace levels of activated factor VII (factor VIIa), both of which are bound to newly exposed tissue factor on membrane surfaces at sites of vascular damage (20). The factor VIIa/tissue factor complex directly catalyzes the formation of factor Xa from factor X.

Once the initial intrinsic or extrinsic cascade results in the activation of factor X, factor Xa catalyzes the penultimate step in the blood coagulation cascade, the formation of serine protease thrombin. As seen in FIG. 2, thrombin formation occurs when a prothrombinase complex, comprising of factor Xa, the non-enzymatic co-factor Va and the substrate prothrombin, is assembled on an appropriate phospholipid surface (30). Once formed, thrombin functions as part of a feedback loop, controlling the activation of factors V and VIII. It additionally catalyzes both the activation of factor VIII and the conversion of fibrinogen to fibrin. Finally, the factor VIIIa interacts with fibrin to catalyze the formation of a thrombus, or crosslinked fibrin clot.

In normal hemostasis, the process of clot formation (blood coagulation) and clot dissolution (fibrinolysis) is delicately balanced. A slight imbalance between the processes of clot formation and dissolution can lead to excessive bleeding or thrombosis. Many significant disease states are related to abnormal hemostasis. With respect to the coronary arterial vasculature, abnormal thrombus formation due to the rupture of an established atherosclerotic plaque is the major cause of acute myocardial infarction and unstable angina. Moreover, treatment of an occlusive coronary thrombus by either thrombolytic therapy or percutaneous transluminal coronary angioplasty (PTCA) is often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a predisposition to pulmonary embolism. Disseminated intravascular coagulopathy commonly occurs within both vascular systems during septic shock, certain viral infections and cancer and is characterized by the rapid consumption of coagulation factors and systemic coagulation which results in the formation of life-threatening thrombi occurring throughout the vasculature leading to widespread organ failure.

Pathogenic thrombosis in the arterial vasculature is a major clinical concern in today's medicine. It is the leading cause of acute myocardial infarction which is one of the leading causes of death in the western world. Recurrent arterial thrombosis also remains one of the leading causes of failure following enzymatic or mechanical recanalization of occluded coronary vessels using thrombolytic agents or percutaneous transluminal coronary angioplasty (PTCA), respectively [Ross, A. M., Thrombosis in Cardiovascular Disorder, p. 327, W.B. Saunders Co. (Fuster, V. and Verstraete, M. edit. 1991); Califf, R. M. and Willerson, J. T., Id. at p 389]. In contrast to thrombotic events in the venous vasculature, arterial thrombosis is the result of a complex interaction between fibrin formation resulting from the blood coagulation cascade and cellular components, particularly platelets, which make up a large percentage of arterial thrombi. Heparin, the most widely used clinical anticoagulant administered intravenously, has not been shown to be universally effective in the treatment or prevention of acute arterial thrombosis or rethrombosis [Prins, M. H. and Hirsh, J., J. Am. Coll. Cardiol., 67: 3A (1991)].

Besides the unpredictable, recurrent thrombotic reocclusion which commonly occurs following PTCA, a profound restenosis of the recanalized vessel occurs in 30 to 40% of patients 1 to 6 months following this procedure [Califf, R. M. et al., J. Am. Coll. Cardiol., 17: 2B (1991)]. These patients require further treatment with either a repeat PTCA or coronary artery bypass surgery to relieve the newly formed stenosis. Restenosis of a mechanically damaged vessel is not a thrombotic process but instead is the result of a hyperproliferative response in the surrounding smooth muscle cells which over time results in a decreased luminal diameter of the affected vessel due to increased muscle mass. Id. As for arterial thrombosis, there is currently no effective pharmacologic treatment for the prevention of vascular restenosis following mechanical recanalization.

Numerous strategies have been developed for the treatment of thrombotic disorders. Many antithrombotic therapies are based on interference in the hemostatic system. This approach carries the inherent risk of bleeding, since the hemostatic system is no longer fully responsive to potential injury. Therefore, antithrombotic benefits are normally associated with antihemostatic risks. In attempts to improve the benefit-to-risk ratio, antithrombotic agents are continuously being developed. Various antithrombotic strategies include administering general inhibitors of thrombin formation such as heparin or vitamin K antagonists; administering specific thrombin inhibitors; administering specific factor Xa inhibitors; and administering inhibitors of platelet activation and adhesion.

Evaluation of current antithrombotic strategies in terms of antithrombotic benefits versus antihemostatic risks reveals that the benefit-to-risk ratio tends to be more favorable for strategies that interfere with one specific step rather than in a more general phase of the hemostatic system [L. A. Harker, Biomedical Progress vol 8, 1995, 17–26]. For example, the development of inhibitors specific for factor Xa is an improvement from general and specific thrombin inhibitors. But, this approach still blocks the common (intrinsic and extrinsic) pathway of thrombin generation (see FIG. 1), and thereby thrombin-dependent platelet activation. Thus, a need exists for more specific antithrombotic agents that selectively inhibit one single hemostatic pathway, while leaving other pathways unaffected.

SUMMARY OF THE INVENTION

The present invention provides compositions and methods for the treatment of cardiovascular diseases. More particularly, the present invention relates to modifying thrombus formation and growth by administering an agent or agents that inhibit the clotting activity of factor IX in the intrinsic clotting pathway. Embodiments of the present invention provide compounds of Formula (I) as depicted below. Embodiments of the present invention also provide methods for the preparation of compounds of Formula (I); pharmaceutical compositions comprising compounds of Formula (I); and methods for the use of compounds of Formula (I) and pharmaceutical compositions comprising compounds of Formula (I) in treating human or animal disorders. Compounds of Formula (I) are useful as modulators of the intrinsic clotting pathway by inhibiting the biological activity of factor IX. Compounds of Formula (I) are useful in a variety of applications including management, treatment, control, and/or as an adjunct of diseases in humans caused in part by the intrinsic clotting pathway utilizing factor IX. Such diseases or disease states include cardiopulmonary bypass, stroke, myocardial infarction, deep vein thrombosis associated with surgical procedures or long periods of confinement, acute and chronic inflammation and clotting associated with hemodialysis.

BRIEF DESCRIPTION OF THE FIGURES

The present invention will be described with reference to the accompanying drawings, wherein.

DETAILED DESCRIPTION

Figure 1:
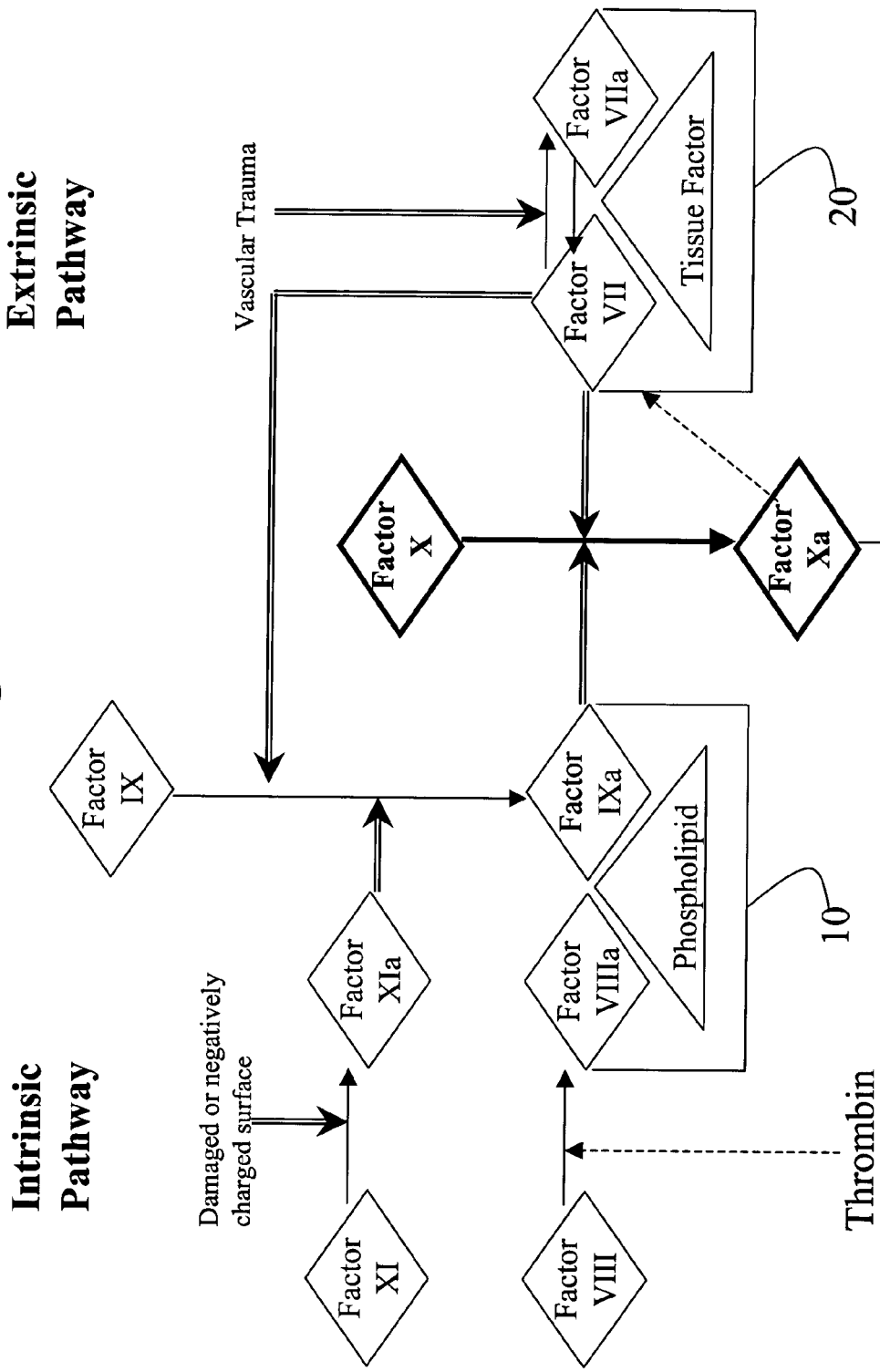
FIG. 1 is a diagram depicting the steps involved in the intrinsic and extrinsic blood clotting cascades, from time of trauma to the activation of factor X.
Figure 2:
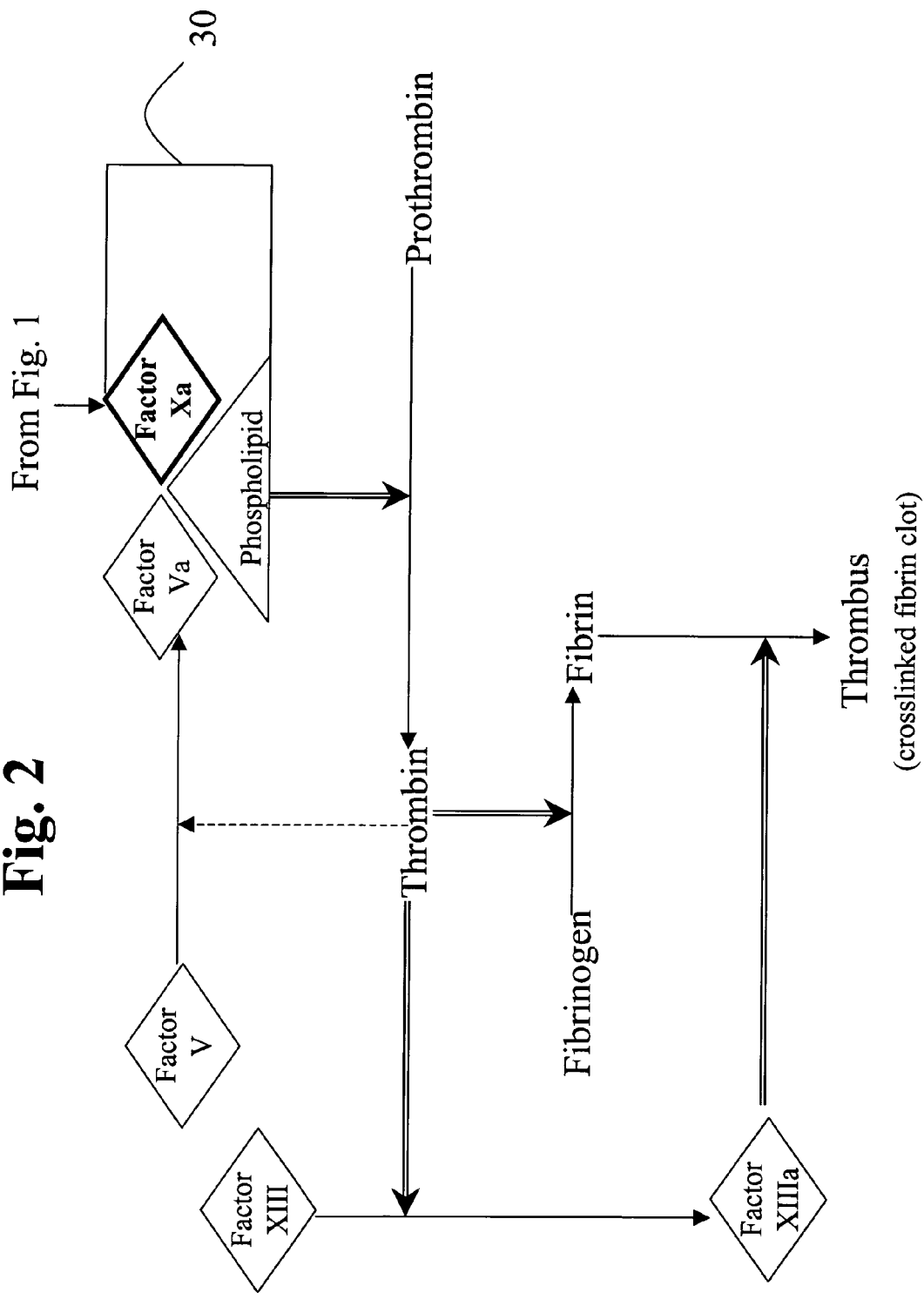
FIG. 2 is a diagram depicting the steps following initial intrinsic and extrinsic blood clotting cascades, beginning with the formation of Xa and culminating in the formation of a thrombus.

Two blood coagulation pathways are associated with normal hemostasis: intrinsic and extrinsic. These two coagulation pathways converge in the formation of factor Xa. But, these two coagulation pathways are interdependent because complete elimination of the intrinsic pathway leads to uncontrolled bleeding. For example, Type B hemophiliacs completely lack factor IX or factor IX function and have a phenotype characterized by a severe bleeding disorder. Thus, the direct factor VIIa/tissue factor activation of factor X, which bypasses the need for factor VIII and factor IX, is insufficient for normal hemostasis. Conversely, formation of the factor VIIIa/IXa phospholipid factor X activator (tenase complex) (20) is essential for normal hemostasis.

Selective inhibition of the intrinsic pathway of coagulation with a factor IX antagonist can provide a method to inhibit the clotting cascade associated with some surgery, stroke, myocardial infarction and hemodialysis while leaving the clotting pathway associated with external lesions such as trauma or abscess intact. Factor IX is primarily associated with the intrinsic clotting pathway. A specific antagonist of factor IX should have a therapeutic benefit in diseases associated with intrinsic pathway clotting by inhibiting intravascular thrombosis. Also, a specific antagonist of factor IX should not have the side effect of unwanted or uncontrollable bleeding by impairing extravascular hemostasis associated with wound healing.

Some point mutations in factor IX partially inhibit its function and result in a mild or moderate phenotype manifested as a non-life threatening bleeding disorder [Bowen, D. J., J. Clin. Pathol: Mol. Pathol. 55:1–18 (2002)]. These point mutations cause factor IX to behave as if it were subject to a partial antagonist. In the presence of a partial antagonist, factor IX should maintain some activity, even at saturation levels of the partial antagonist. As a result of the point mutations in factor IX, its activity is reduced along with clotting associated with the intrinsic pathway, but some residual activity remains that leaves the extrinsic pathway intact.

The present invention provides compositions and methods that inhibit the clotting activity of factor IX. Inhibition of hemostasis with agents that selectively inhibit the intrinsic pathway of factor X activation should leave the extrinsic pathway intact and allow the formation of small, but hemostatically important amounts of factor Xa and thrombin.

Embodiments of the present invention provide compounds of Formula (I) as depicted below. Embodiments of the present invention also provide methods of the preparation of compounds of Formula (I); pharmaceutical compositions comprising compounds of Formula (I); and methods for the use of compounds of Formula (I) and pharmaceutical compositions comprising compounds of Formula (I) in treating human or animal disorders. Compounds of the Formula (I) are useful as modulators of the intrinsic clotting pathway by inhibiting the biological activity of factor IX. Compounds of Formula (I) are useful in a variety of applications including management, treatment, control, and/or as an adjunct of diseases in humans caused in part by the intrinsic clotting pathway utilizing factor IX. Such diseases or disease states include cardiopulmonary bypass, stroke, myocardial infarction, deep vein thrombosis associated with surgical procedures or long periods of confinement, acute and chronic inflammation and clotting associated with hemodialysis.

In a first aspect, the present invention provides a compound comprising at least one moiety of the formula I. Such compounds are useful in a variety of applications including for the management, treatment, control, and/or as an adjunct of diseases in humans caused in part by the intrinsic clotting pathway utilizing factor IX, will be discussed in more detail below.

In one aspect, the present invention provides compounds which are represented by Formula I:

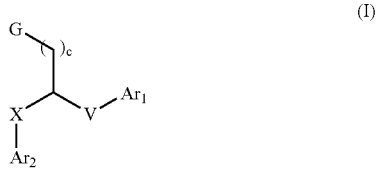

(I)

wherein c is equal to 0, 1, or 2; wherein the values of 0, 1, and 2 comprise a direct bond, —$CH_2$—, and —$CH_2$—$CH_2$—, optionally substituted 1 to 4 times with a substituent group, wherein said substituent group(s) or the term substituted refers to groups comprising: -alkyl, -aryl, -alkylene-aryl, -arylene-alkyl, -alkylene-arylene-alkyl, —O-alkyl, —O-aryl, or -hydroxyl. In preferred embodiments, c is equal to 0 or 1. In especially preferred embodiments, c is equal to 0.

G comprises: -hydrogen, —$CO_2R_1$, —$CH_2OR_1$, —C(O)—$R_1$, —C($R_1$)=N—O—$R_2$, or an acid isostere; wherein $R_1$ and $R_2$ independently comprise: -hydrogen, -alkyl, -aryl, -arylene-alkyl, -alkylene-aryl, or -alkylene-arylene-alkyl. In preferred embodiments, G comprises: -hydrogen or —$CO_2R_1$; wherein $R_1$ comprises: -hydrogen, -alkyl, or -aryl. In especially preferred embodiments, G comprises: -hydrogen or —$CO_2H$.

V comprises: —$(CH_2)_b$—O—$(CH_2)_a$—, —$(CH_2)_b$—N($R_7$)—$(CH_2)_a$—, —$(CH_2)_b$—O—, —$(CH_2)_b$—N($R_7$), —$(CH_2)_a$—, or a direct bond; in which a is equal to 0, 1, or 2, b is equal to 1 or 2, and $R_7$ comprises: -hydrogen, -alkyl, -aryl, -arylene-alkyl, -alkylene-aryl, or -alkylene-arylene-alkyl; wherein the values of 0, 1, and 2 comprise a direct bond, —$CH_2$—, and —$CH_2$—$CH_2$—, optionally substituted 1 to 4 times with a substituent group, wherein said substituent group(s) or the term substituted refers to groups comprising: -alkyl, -aryl, -alkylene-aryl, -arylene-alkyl, -alkylene-arylene-alkyl, —O-alkyl, —O-aryl, or -hydroxyl. In preferred embodiments, V comprises: —$(CH_2)_a$—, —$(CH_2)_b$—O—$(CH_2)_a$—, or a direct bond, wherein a is equal to 1 or 2, and b is equal to 1. In especially preferred embodiments, V comprises: —$(CH_2)_a$— or a direct bond, wherein a is equal to 1.

X comprises: —N($R_8$)—, —CON($R_8$)—, —N($R_8$)CO—, —N($R_8$)CON($R_9$)—, —OC(O)N($R_8$)—, —$SO_2$N($R_8$)—, or —N($R_8$)$SO_2$N($R_9$)—; wherein $R_8$ and $R_9$ independently comprise: -hydrogen, -alkyl, -aryl, -arylene-alkyl, -alkylene-aryl, -alkylene-arylene-alkyl, -alkylene-cycloalkylene-C(O)-alkylene-aryl, -alkylene-heterocyclylene-C(O)-alkylene-aryl, -alkylene-C(H)($R_{10}$)($R_{11}$), or -alkylene-N—($R_{10}$)($R_{11}$), wherein $R_{10}$ comprises H, alkyl, alkylene-aryl, alkylene-heteroaryl, aryl, or heteroaryl, and $R_{11}$ comprises H, -alkyl, -alkylene-aryl, -alkylene-heteroaryl, -aryl, -heteroaryl, —C(O)—O-alkyl, —C(O)—O-alkylene-aryl, —C(O)—O-alkylene-heteroaryl, —C(O)-alkyl, —C(O)-alkylene-aryl, —C(O)-alkylene-heteroaryl, —S(O)$_2$-alkyl, —S(O)$_2$-aryl, —S(O)$_2$-heteroaryl, —S(O)$_2$-alkylene-aryl, —S(O)$_2$-alkylene-heteroaryl, —S(O)$_2$—NH-alkyl, —S(O)$_2$—NH-alkylene-aryl, —S(O)$_2$—NH-alkylene-heteroaryl, —S(O)$_2$—NH-aryl, or —S(O)$_2$—NH-heteroaryl;

$R_{10}$ and $R_{11}$ may be taken together to form a ring having the formula —$(CH_2)_m$-Z-$(CH_2)_n$— bonded to the nitrogen or carbon atom to which $R_{10}$ and $R_{11}$ are attached, wherein m and n are, independently, 1, 2, 3, or 4; Z independently comprises —$CH_2$—, —C(O)—, —O—, —N(H)—, —S—, —S(O)—, —S(O$_2$)—, —CON(H)—, —NHC(O)—, —NHC(O)N(H)—, —NH(SO$_2$)—, —S(O$_2$)N(H)—, —(O)CO—, —NHS(O$_2$)NH—, —OC(O)—, —N($R_{12}$)—, —N(C(O)$R_{12}$)—, —N(C(O)NHR$_{12}$)—, —N(S(O$_2$)NHR$_{12}$)—, —N(SO$_2$R$_{12}$)—, or —N(C(O)OR$_{12}$)—; or $R_{10}$ and $R_{11}$ may be taken together, with the nitrogen or carbon atom to which they are attached, to form a heterocyclyl or heteroaryl ring.

$R_{12}$ comprises hydrogen, aryl, alkyl, or alkylene-aryl;

In preferred embodiments, X comprises: —N($R_8$)—, —CON($R_8$)—, —N($R_8$)CO—, or —N($R_8$)CON($R_9$)—, wherein $R_8$ and $R_9$ independently comprise: -hydrogen, -alkyl, -aryl, -arylene-alkyl, -alkylene-aryl, or -alkylene-arylene-alkyl. In especially preferred embodiments, X comprises: —N($R_8$)—, —CON($R_8$)—, or —N($R_8$)CO—, wherein $R_8$ comprises: -hydrogen, -alkyl, -aryl, -arylene-alkyl, -alkylene-aryl, or -alkylene-arylene-alkyl.

$Ar_1$ comprises an aryl, heteroaryl, fused cycloalkylaryl, fused cycloalkylheteroaryl, fused heterocyclylaryl, or fused heterocyclylheteroaryl group optionally substituted 1 to 7 times. In preferred embodiments, $Ar_1$ comprises a mono- or bicyclic aryl or heteroaryl group optionally substituted 1 to 7 times. In especially preferred embodiments, $Ar_1$ comprises a phenyl group having 1 to 5 substituents, wherein the substituents independently comprise:

a) -fluoro;
b) -chloro;
c) -bromo;
d) -iodo;
e) -cyano;
f) -nitro;
g) -perfluoroalkyl;
h) -$D_1$-$R_{13}$;
i) -alkyl;
j) -aryl;
k) -heteroaryl;
l) -heterocyclyl;
m) -cycloalkyl;
n) -alkylene-aryl;
o) -alkylene-heteroaryl;
p) -alkylene-arylene-$D_1$-$R_{13}$;
q) -alkylene-heteroarylene-$D_1$-$R_{13}$;

r) -alkylene-arylene-aryl;
s) -alkylene-heteroarylene-aryl;
t) -alkylene-arylene-heteroaryl
u) -alkylene-arylene-arylene-$D_1$-$R_{13}$;
v) -alkylene-arylene-alkyl;
w) -alkylene-heteroarylene-alkyl;
x) -arylene-alkyl;
y) -arylene-cycloalkyl;
z) -heteroarylene-alkyl;
aa) -arylene-arylene-alkyl;
bb) -$D_1$-alkyl;
cc) -$D_1$-aryl;
dd) -$D_1$-heteroaryl;
ee) -$D_1$-arylene-$D_2$-$R_{14}$;
ff) -$D_1$-heteroarylene-$D_2$-$R_{14}$;
gg) -$D_1$-alkylene-heteroaryl;
hh) -$D_1$-alkylene-aryl;
ii) -$D_1$-alkylene-arylene-$D_2$-$R_{14}$
jj) -$D_1$-alkylene-heteroarylene-$D_2$-$R_{14}$
kk) -$D_1$-arylene-alkyl;
ll) -$D_1$-heteroarylene-alkyl;
mm) -$D_1$-alkylene-arylene-aryl;
nn) -$D_1$-alkylene-heteroarylene-aryl;
oo) -$D_1$-arylene-arylene-aryl;
pp) -$D_1$-arylene-arylene-alkyl;
qq) -$D_1$-alkylene-heteroarylene-alky
ss) -alkylene-$D_1$-alkylene-aryl;
tt) -alkylene-$D_1$-alkylene-arylene-$D_2$-$R_{14}$
uu) -arylene-$D_1$-alkyl;
vv) -arylene-$D_1$-cycloalkyl;
ww) -arylene-$D_1$-heterocyclyl;
xx) -alkylene-$D_1$-aryl;
yy) -alkylene-$D_1$-heteroaryl;
zz) -alkylene-$D_1$-arylene-$D_2$-$R_{14}$
aaa) -alkylene-$D_1$-heteroarylene-$D_2$-$R_{14}$
bbb) -alkylene-$D_1$-heteroaryl;
ccc) -alkylene-$D_1$-cycloalkyl;
ddd) -alkylene-$D_1$-heterocyclyl;
eee) -alkylene-$D_1$-arylene-alkyl;
fff) -alkylene-$D_1$-heteroarylene-alkyl;
ggg) -alkylene-$D_1$-alkylene-arylene-alkyl;
hh) -alkylene-$D_1$-alkylene-heteroarylene-alkyl;
iii) -alkylene-$D_1$-alkyl;
jjj) -alkylene-$D_1$-$R_{13}$;
kkk) -arylene-$D_1$-$R_{13}$;
lll) -heteroarylene-$D_1$-$R_{13}$; or
mmm) -hydrogen;
wherein $D_1$ comprises —$CH_2$—, -alkylene-, -alkenylene-, -alkylene-S—, —S-alkylene-, -alkylene-O—, —O-alkylene-, -alkylene-$S(O)_2$—, —$S(O)_2$-alkylene, —O—, —$N(R_{15})$—, —C(O)—, —$CON(R_{15})$—, —$N(R_{15})C(O)$—, —$N(R_{15})CON(R_{16})$—, —$N(R_{15})C(O)O$—, —$OC(O)N(R_{15})$—, —$N(R_{15})SO_2$—, —$SO_2N(R_{15})$—, —C(O)—O—, —O—C(O)—, —S—, —S(O)—, —$S(O_2)$—, —$N(R_{15})SO_2N(R_{16})$—,

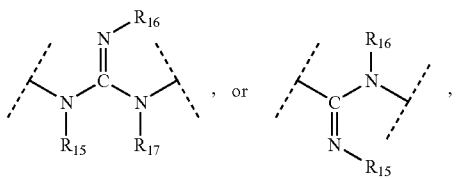

and wherein $R_{13}$, $R_{15}$, $R_{16}$, and $R_{17}$ independently comprise: -hydrogen, -alkyl, -aryl, -heteroaryl, -arylene-alkyl, -heteroarylene-alkyl, -alkylene-aryl, -alkylene-heteroaryl, -alkylene-arylene-alkyl, or -alkylene-heteroarylene-alkyl.

$D_2$ comprises —$CH_2$—, -alkylene-, -alkenylene-, -alkylene-S—, —S-alkylene-, -alkylene-O—, —O-alkylene-, -alkylene-$S(O)_2$—, —$S(O)_2$-alkylene, —O—, —$N(R_{25})$—, —C(O)—, —$CON(R_{25})$—, —$N(R_{18})C(O)$—, —$N(R_{18})CON(R_{19})$—, —$N(R_{18})C(O)O$—, —$OC(O)N(R_{18})$—, —$N(R_{18})SO_2$—, —$SO_2N(R_{18})$—, —C(O)—O—, —O—C(O)—, —S—, —S(O)—, —$S(O_2)$—, —$N(R_{18})SO_2N(R_{19})$—, and wherein $R_{18}$ and $R_{19}$ independently comprise: -hydrogen, -alkyl, -aryl, -arylene-alkyl, -alkylene-aryl, or -alkylene-arylene-alkyl.

$R_{14}$ comprises -hydrogen, -alkyl, -aryl, -heteroaryl, -arylene-alkyl, -heteroarylene-alkyl, -alkylene-aryl, -alkylene-heteroaryl, -alkylene-arylene-alkyl, or -alkylene-heteroarylene-alkyl.

The most preferred embodiments of $Ar_1$ are those in which $Ar_1$ comprises a mono-substituted phenyl group wherein the substituent comprises: -aryl, -arylene-alkyl, -$D_1$-aryl, -$D_1$-alkylene-arylene-alkyl, or -arylene-$D_1$-alkyl; wherein $D_1$ comprises —O—, —$N(R_{15})$—, —$CON(R_{15})$—, or —$N(R_{15})C(O)$—, and wherein $R_{15}$ comprises: -hydrogen; -alkyl; or -aryl.

$Ar_2$ comprises an aryl or heteroaryl group optionally substituted 1 to 7 times. In preferred embodiments, $Ar_2$ comprises a phenyl, naphthyl, pyridyl, isoquinolyl, pyrimidyl or quinazolyl group optionally substituted 1 to 7 times. In especially preferred embodiments, $Ar_2$ comprises a substituted phenyl, 2-naphthyl, 2-pyridyl, 3-isoquinolyl, 2-pyrimidyl or 2-quinazolyl group having 1 to 5 substituents wherein the substituents independently comprise:
a) -fluoro;
b) -chloro;
c) -bromo;
d) -iodo;
e) -cyano;
f) -nitro;
g) -perfluoroalkyl;
h) -$T_1$-$R_{20}$;
i) -alkyl;
j) -aryl;
k) -heteroaryl;
l) -heterocyclyl;
m) -cycloalkyl;
n) -alkylene-aryl;
o) -alkylene-arylene-aryl;
p) -alkylene-arylene-alkyl;
q) -arylene-alkyl;
r) -arylene-aryl;
s) -arylene-heteroaryl;
t) -heteroarylene-aryl;
u) -heteroarylene-heteroaryl;
v) -heteroarylene-heterocyclyl;
w) -arylene-heterocyclyl;
x) -arylene-arylene-alkyl;
y) -$T_1$-alkyl;
z) -$T_1$-aryl;
aa) -$T_1$-alkylene-aryl;
bb) -$T_1$-alkenylene-aryl;
cc) -$T_1$-alkylene-heteroaryl;
dd) -$T_1$-alkenylene-heteroaryl;
ee) -$T_1$-cycloalkylene-aryl;
ff) -$T_1$-cycloalkylene-heteroaryl;
gg) -$T_1$-heterocyclylene-aryl;

hh) -T₁-heterocyclylene-heteroaryl;
ii) -T₁-arylene-alkyl;
jj) -T₁-arylene-alkenyl;
kk) -T₁-alkylene-arylene-aryl;
ll) -T₁-arylene-T₂-aryl;
mm) -T₁-arylene-arylene-aryl;
nn) -T₁-alkylene-arylene-alkyl;
oo) -alkylene-T₁-alkylene-aryl;
pp) -arylene-T₁-alkyl;
qq) -arylene-T₁-alkylene-aryl;
rr) -T₁-alkylene-T₂-aryl;
ss) -T₁-alkylene-aryl;
tt) -alkylene-T₁-heteroaryl;
uu) -alkylene-T₁-cycloalkyl;
vv) -alkylene-T₁-heterocyclyl;
ww) -alkylene-T-arylene-alkyl;
xx) -alkylene-T₁-alkylene-arylene-alkyl;
yy) -alkylene-T₁-alkyl;
zz) -alkylene-T₁-R₂₀;
aaa) -arylene-T₁-R₂₀; or
bbb) -hydrogen;

wherein T₁ comprises —CH₂—, —O—, —N(R₂₁)—, —C(O)—, —CON(R₂₁)—, —N(R₂₁)C(O)—, —N(R₂₁)CON(R₂₂)—, —N(R₂₁)C(O)O—, —OC(O)N(R₂₁)—, —N(R₂₁)SO₂—, —SO₂N(R₂₁)—, —C(O)—O—, —O—C(O)—, —S—, —S(O)—, —S(O₂)—, —N(R₂₁)SO₂N(R₂₂)—,

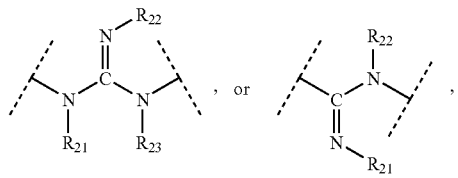

and wherein R₂₀, R₂₁, R₂₂ and R₂₃, independently comprise: -hydrogen, -alkyl, -alkenyl, -alkylene-cycloalkyl, -alkynene-heterocyclyl, -aryl, -heteroaryl, -arylene-alkyl, -alkylene-aryl, -alkylene-arylene-alkyl, -alkylene-arylene-aryl, -alkylene-arylene-alkylene-aryl, -alkylene-arylene-O-arylene, or alkylene-arylene-O-alkylene-aryl; and wherein T₂ comprises a direct bond, —CH₂—, —O—, —N(R₂₄)—, —C(O)—, —CON(R₂₄)—, —N(R₂₄)C(O)—, —N(R₂₄)CON(R₂₅)—, —N(R₂₄)C(O)O—, —OC(O)N(R₂₄)—, —N(R₂₄)SO₂—, —SO₂N(R₂₄)—, —C(O)—O—, —O—C(O)—, —S—, —S(O)—, —S(O₂)—, —N(R₂₄)SO₂N(R₂₅)—, wherein R₂₄ and R₂₅ independently comprise; -hydrogen, -alkyl, -alkenyl, -alkylene-cycloalkyl, alkynene-heterocyclyl, -aryl, -heteroaryl, -arylene-alkyl, -alkylene-aryl, and -alkylene-arylene-alkyl.

The most preferred embodiments of Ar₂ are those in which Ar₂ comprises a substituted phenyl, 2-naphthyl, 2-pyridyl, 3-isoquinolyl, 2-pyrimidyl or 2-quinazolyl group having 1 to 5 substituents independently comprising:
a) -fluoro;
b) -chloro;
c) -bromo;
d) -iodo;
e) -cyano;
f) -nitro;
g) -perfluoroalkyl;
h) -T₁-R₂₀;
i) -alkyl;
j) -aryl;
k) -arylene-alkyl;
l) -T₁-alkyl;
m) -T₁-alkylene-aryl;
n) -T₁-alkylene-arylene-aryl;
o) -T₁-alkylene-arylene-alkyl;
p) -arylene-T₁-alkyl; or
q) -hydrogen;

wherein T₁ comprises —CH₂—, —O—, —N(R₂₁)—, —CON(R₂₁)—, or —N(R₂₁)C(O)—; wherein R₂₀ and R₂₁ independently comprise: -hydrogen, -alkyl, or -aryl.

The alkyl, aryl, heteroaryl, alkylene, and arylene groups in Ar₁, Ar₂, R₁, R₂, R₃, R₄, R₅, R₆, R₇, R₈, R₉, R₁₀, R₁₁, R₁₂, R₁₃, R₁₄, R₁₅, R₁₆, R₁₇, R₁₈, R₁₉, R₂₀, R₂₁, R₂₂, and R₂₃ may be optionally substituted 1 to 4 times with a substituent group, wherein said substituent group(s) or the term substituted refers to groups comprising:
a) -hydrogen;
b) -fluoro;
c) -chloro;
d) -bromo;
e) -iodo;
f) -cyano;
g) -nitro;
h) -perfluoroalkyl;
i) -Q-perfluoroalkyl
j) -Q-R₂₄;
k) -Q-alkyl;
l) -Q-aryl;
m) -Q-alkylene-aryl;
n) -Q-alkylene-NR₂₅R₂₆; or
o) -Q-alkyl-W—R₂₇;

wherein Q and W independently comprise: —CH₂—, —O—, —N(R₂₈)—, —C(O)—, —CON(R₂₈)—, —N(R₂₈)C(O)—, —N(R₂₈)CON(R₂₉)—, —N(R₂₈)C(O)O—, —OC(O)N(R₂₈)—, —N(R₂₈)SO₂—, —SO₂N(R₂₈)—, —C(O)—O—, —O—C(O)—, or —N(R₂₈)SO₂N(R₂₉)—, wherein R₂₄, R₂₅, R₂₆, R₂₇, R₂₈, and R₂₉ independently comprise: -hydrogen, -alkyl, -aryl, -arylene-alkyl, -alkylene-aryl, or -alkylene-arylene-alkyl.

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

In one group of particularly preferred embodiments, the compounds are represented by Formula (I), in which c is equal to 0; G comprises: -hydrogen or —CO₂H; V comprises: —CH₂— or a direct bond; X comprises: —CON(R₈)—, or —N(R₈)CO— wherein R₈ comprises: -hydrogen; Ar₁ comprises a mono-substituted phenyl group wherein the substituent comprises: -aryl, -arylene-alkyl, -D₁-aryl -D₁-alkylene-arylene-alkyl, or -arylene-D₁-alkyl, wherein D₁ comprises —O—, or —N(R₁₅)—, wherein R₁₅ comprises: -hydrogen, -alkyl, or -aryl; and Ar₂ comprises a substituted phenyl, 2-naphthyl, 2-pyridyl, 3-isoquinolyl, 2-pyrimidyl or 2-quinazolyl group having 1 to 5 substituents independently comprising: -hydrogen, -fluoro, -chloro, -bromo, iodo, -cyano, -nitro, -perfluoroalkyl, -T₁-R₁₄, -alkyl, -aryl, -arylene-alkyl, -T₁-alkyl, -T₁-alkylene-aryl, -T₁-alkylene-arylene-aryl, -T₁-alkylene-arylene-alkyl, or -arylene-T₁-alkyl; wherein T₁ comprises —CH₂—, —O—, —N(R₂₁)—, —CON($R_{21}$)—, or —N($R_{21}$)C(O)—; wherein $R_{21}$ comprises: -hydrogen, -alkyl, or -aryl. The alkyl, aryl, alkylene, and arylene groups in $Ar_1$, and $Ar_2$ may be optionally substituted 1 to 4 times with a substituent group, wherein said substituent group(s) or the term substituted refers to groups comprising: -hydrogen, -fluoro, -chloro, -bromo, iodo, cyano, -nitro, or -perfluoroalkyl.

Compounds of the present invention having biological activity are listed below in Table 1.

Unless indicated otherwise, the structures of Examples of compounds of Formula (I) in Table 1 and elsewhere having vacant connectivity for heteroatoms, such as oxygen and nitrogen, are assumed to have a hydrogen atom attached thereto.

TABLE 1

| Example | Structure | Name |
|---|---|---|
| 1 | 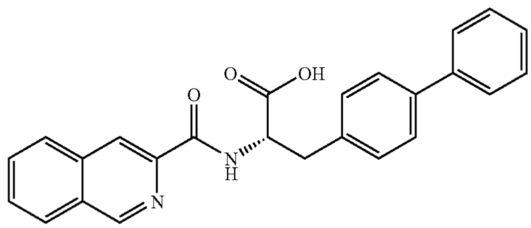 | 3-Biphenyl-4-yl-(2S)-[(isoquinoline-3-carbonyl)-amino]-propionic acid |
| 2 | 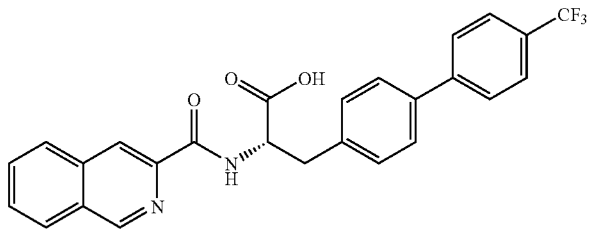 | (2S)-[(Isoquinoline-3-carbonyl)-amino]-3-(4'-trifluoromethyl-biphenyl-4-yl)-propionic acid |
| 3 | 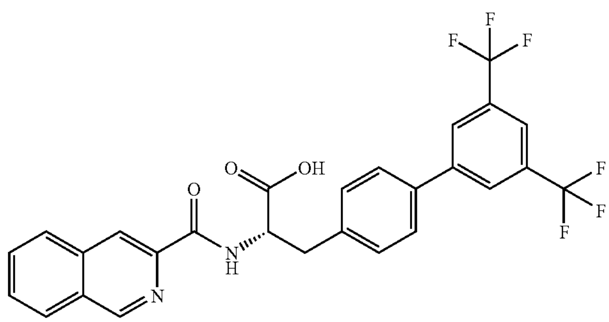 | (2S)-[(Isoquinoline-3-carbonyl)-amino]-3-(3;5'-bistrifluoromethyl-biphenyl-4-yl)-propionic acid |
| 4 | 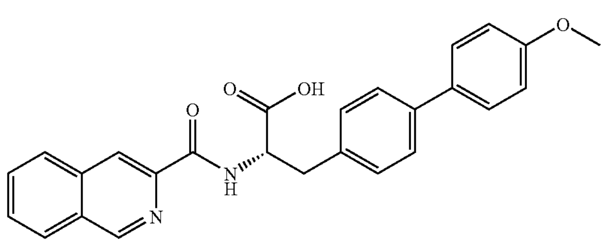 | (2S)-[(Isoquinoline-3-carbonyl)-amino]-3-(4'-methoxy-biphenyl-4-yl)-propionic acid |
| 5 | 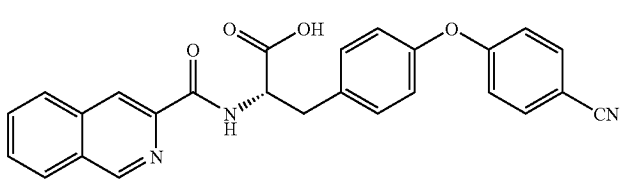 | 3-[4-(4'-Cyano-phenoxy)-phenyl]-(2S)-[(isoquinoline-3-carbonyl)-amino]-propionic acid |
| 6 | 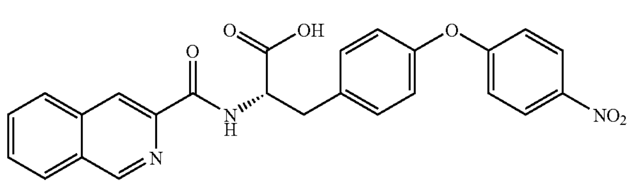 | 3-[4-(4'-Nitro-phenoxy)-phenyl]-(2S)-[(isoquinoline-carbonyl)-amino]-propionic acid |

TABLE 1-continued

| Example | Structure | Name |
|---|---|---|
| 7 | 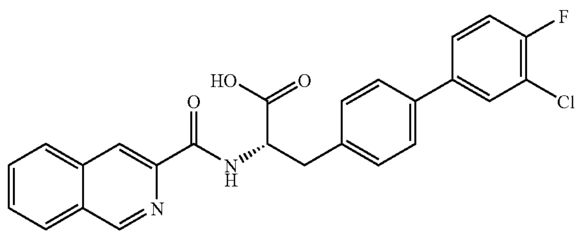 | 3-(3'-Chloro-4'-fluoro-biphenyl-4-yl)-(2S)-[(isoquinoline-3-carbonyl)-amino]-propionic acid |
| 8 | 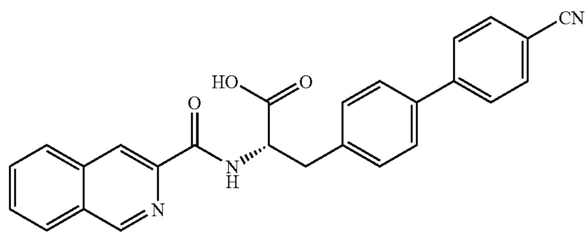 | 3-(4'-Cyano-biphenyl-4-yl)-(2S)-[(isoquinoline-3-carbonyl)-amino]-propionic acid |
| 9 | 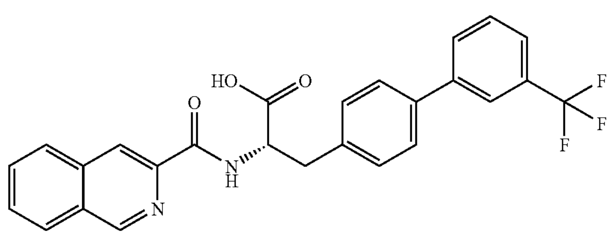 | (2S)-[(Isoquinoline-3-carbonyl)-amino]-3-(3'-trifluoromethyl-biphenyl-4-yl)-propionic acid |
| 10 | 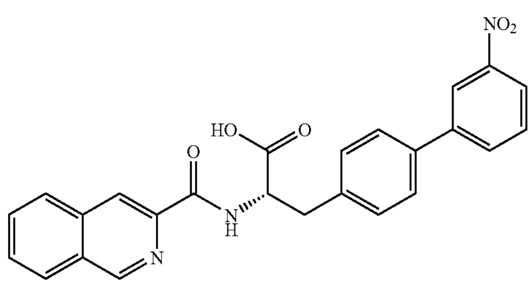 | (2S)-[(Isoquinoline-3-carbonyl)-amino]-3-(3'-nitro-biphenyl-4-yl)-propionic acid |
| 11 | 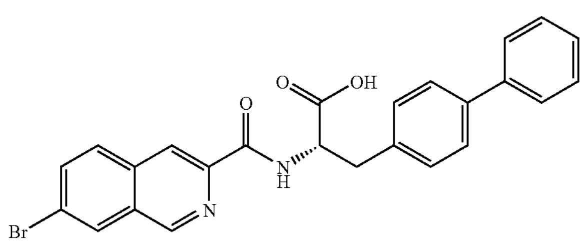 | 3-Biphenyl-4-yl-(2S)-[(7-bromo-isoquinoline-3-carbonyl)-amino]-propionic acid |

TABLE 1-continued

| Example | Structure | Name |
| --- | --- | --- |
| 12 | 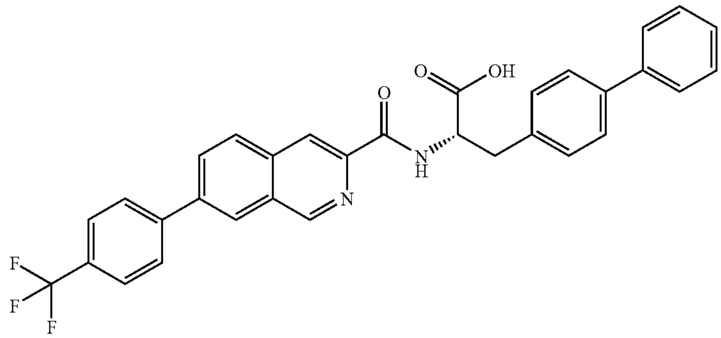 | 3-Biphenyl-4-yl-(2S)-{[7-(4-trifluoromethyl-phenyl)-isoquinoline-3-carbonyl]-amino}-propionic acid |
| 13 | 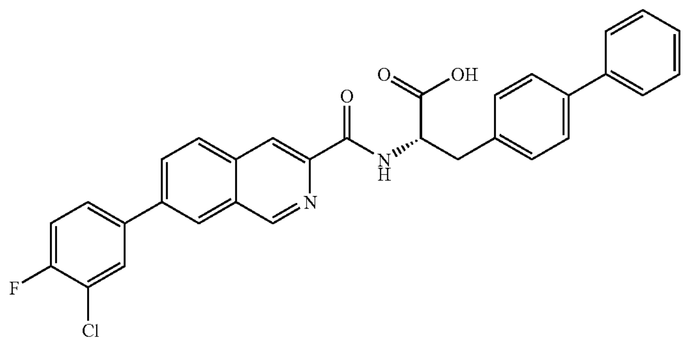 | 3-Biphenyl-4-yl-(2S)-{[7-(3-chloro-4-fluoro-phenyl)-isoquinoline-3-carbonyl]-amino}-propionic acid |
| 14 | 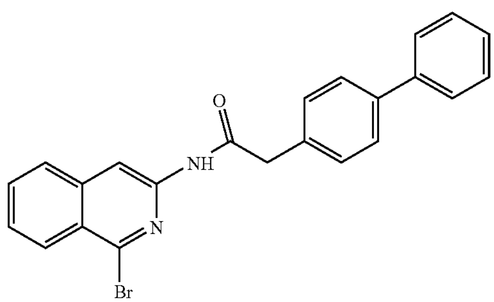 | 2-Biphenyl-4-yl-N-(1-bromo-isoquinolin-3-yl)-acetamide |
| 15 | 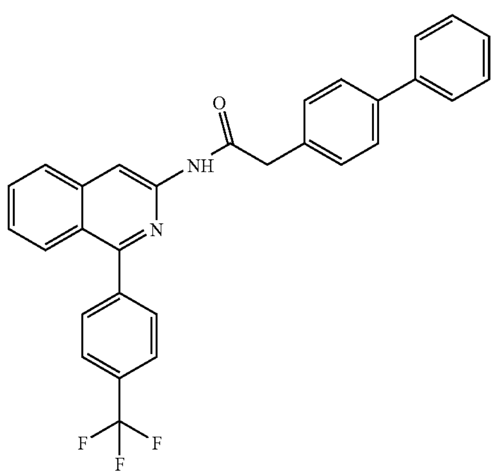 | 2-Biphenyl-4-yl-N-[1(4-trifluoromethyl-phenyl)-isoquinolin-3-yl]-acetamide |

TABLE 1-continued

| Example | Structure | Name |
|---|---|---|
| 16 | 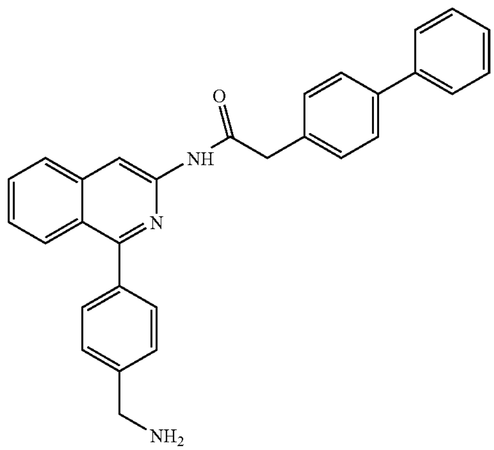 | N-[1(4-aminomethyl-phenyl)-isoquinolin-3-yl]-2-biphenyl-4-yl-acetamide |
| 17 | 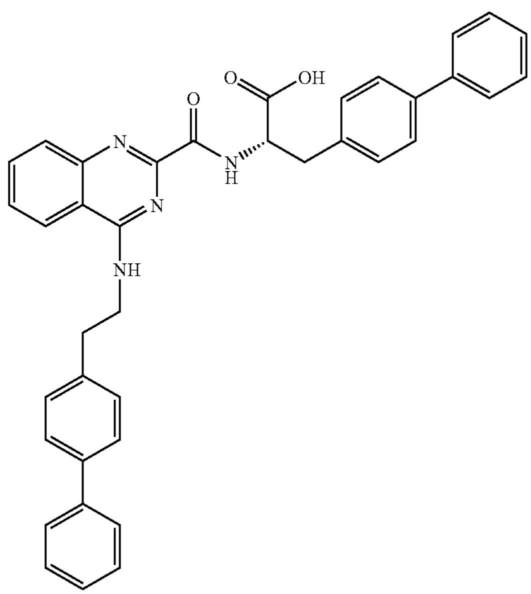 | 3-Biphenyl-4-yl-(2S)-{[4-(2-biphenyl-4-yl-ethylamino)-quinazoline-2-carbonyl]-amino}-propionic acid |
| 18 | 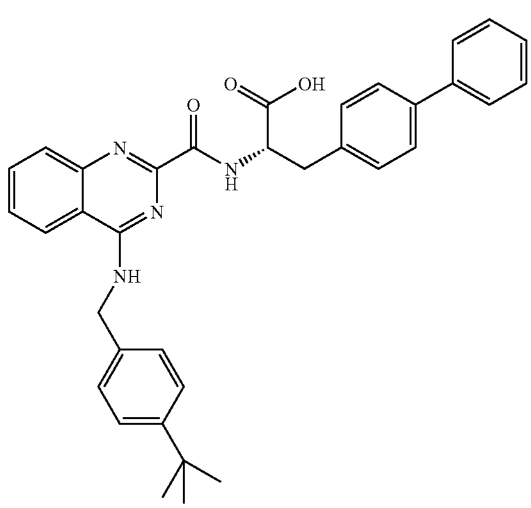 | 3-Biphenyl-4-yl-(2S)-{[4-tert-butyl-benzylamino)-quinazoline-2-carbonyl]-amino}-propionic acid |

TABLE 1-continued

| Example | Structure | Name |
|---|---|---|
| 19 | 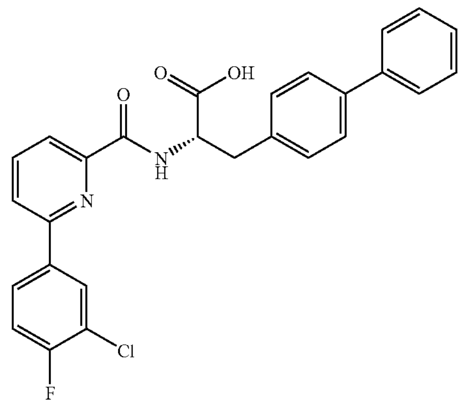 | 3-Biphenyl-4-yl-(2S)-{[6-(3-chloro-4-fluoro-phenyl)-pyridine-2-carbonyl]-amino}-propionic acid |
| 20 | 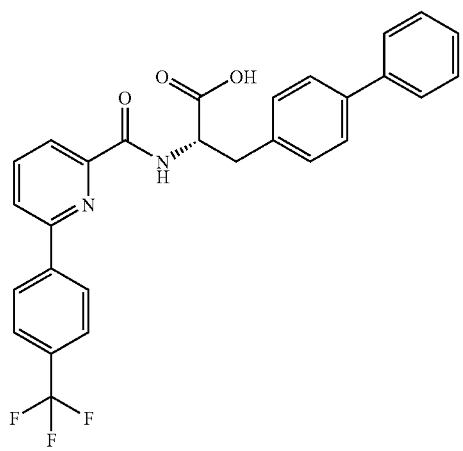 | 3-Biphenyl-4-yl-(2S)-{[6-(3-chloro-4-fluoro-phenyl)-pyridine-2-carbonyl]-amino}-propionic acid |
| 21 | 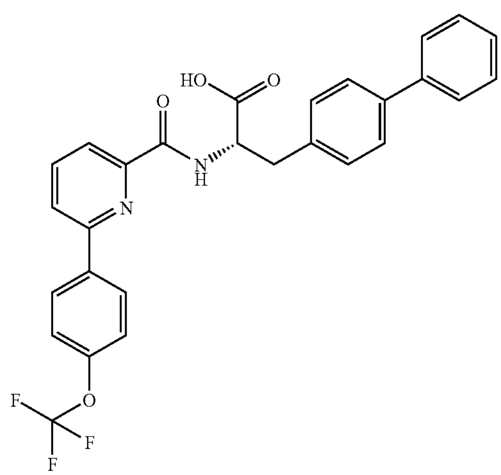 | 3-Biphenyl-4-yl-(2S)-{[6-(4-trifluoromethoxy-phenyl)-pyridine-2-carbonyl]-amino}-propionic acid |

TABLE 1-continued

| Example | Structure | Name |
|---|---|---|
| 22 | 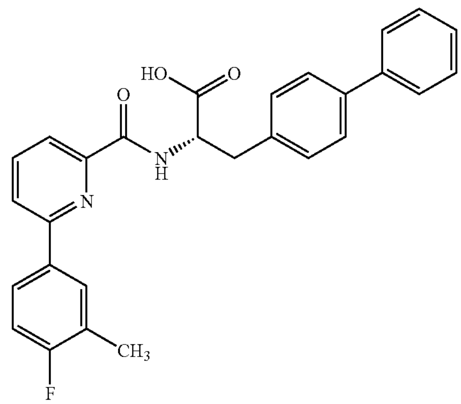 | 3-Biphenyl-4-yl-(2S)-{[6-(4-fluoro-3-methyl-phenyl)-pyridine-2-carbonyl]-amino}-propionic acid |
| 23 | 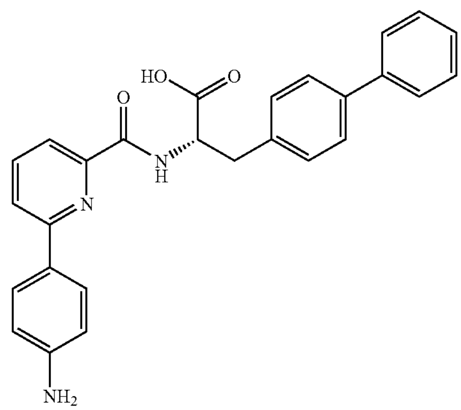 | (2S){[6-(4-Amino-phenyl)-pyridine-2-carbonyl]-amino}-3-biphenyl-4-yl-propionic acid |
| 24 | 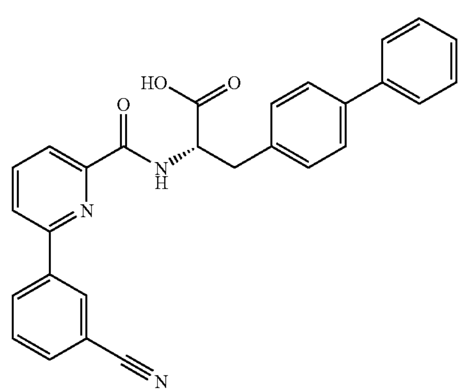 | 3-Biphenyl-4-yl-(2S)-{[6-(3-cyano-phenyl)-pyridine-2-carbonyl]-amino}-propionic acid |

TABLE 1-continued

| Example | Structure | Name |
|---|---|---|
| 25 | 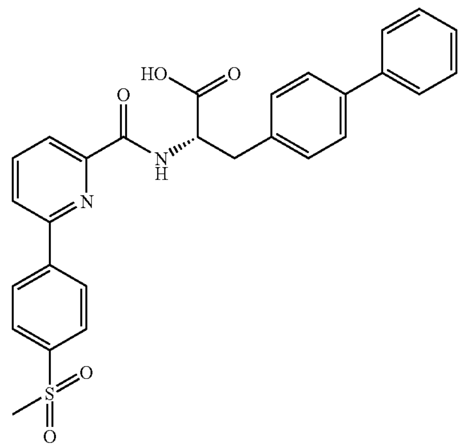 | 3-Biphenyl-4-yl-(2S)-{[6-(4-methanesulfonyl-phenyl)-pyridine-2-carbonyl]-amino}-propionic acid |
| 26 | 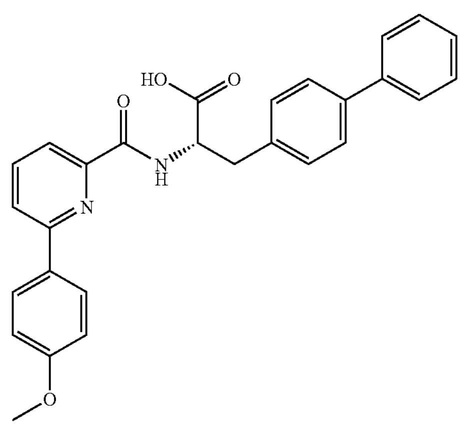 | 3-Biphenyl-4-yl-(2S)-{[6-(4-methoxy-phenyl)-pyridine-2-carbonyl]-amino}-propionic acid |
| 27 | 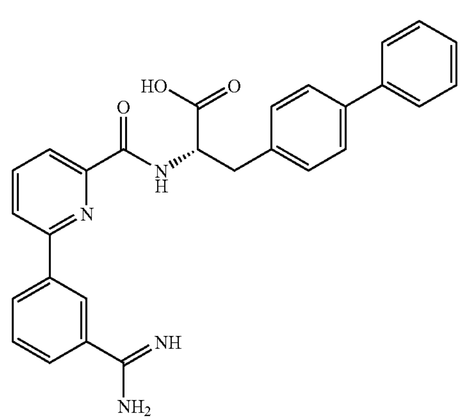 | 3-Biphenyl-4-yl-(2S)-{[6-(3-carboxamidinoyl-phenyl)-pyridine-2-carbonyl]-amino}-propionic acid |

TABLE 1-continued

| Example | Structure | Name |
|---|---|---|
| 28 | 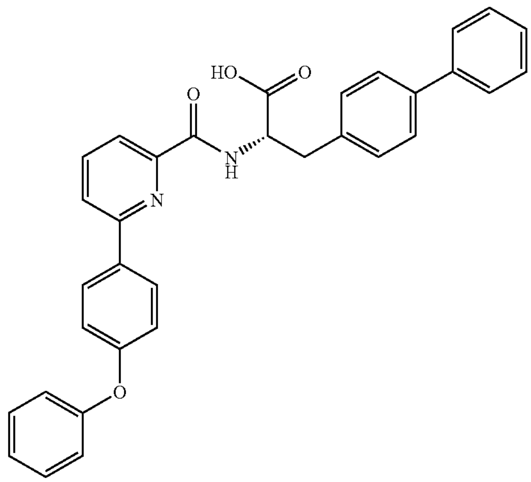 | 3-Biphenyl-4-yl-(2S)-{[6-(4-phenoxy-phenyl)-pyridine-2-carbonyl]-amino}-propionic acid |
| 29 | 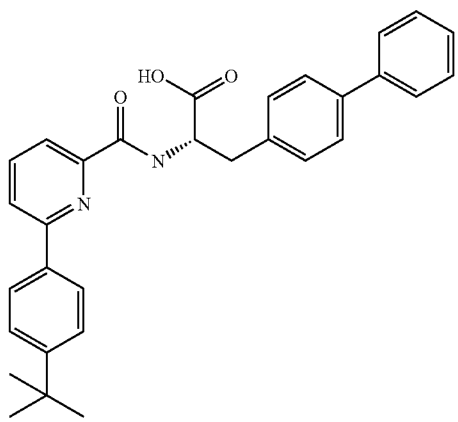 | 3-Biphenyl-4-yl-(2S)-{[6-(4-tert-butyl-phenyl)-pyridine-2-carbonyl]-amino}-propionic acid |
| 30 | 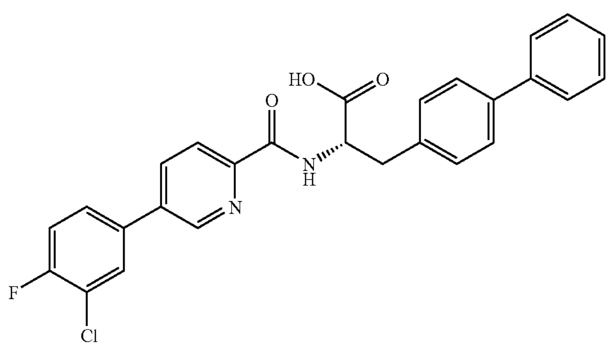 | 3-Biphenyl-4-yl-(2S)-{[5-(3-chloro-4-fluoro-phenyl)-pyridine-2-carbonyl]-amino}-propionic acid |
| 31 | 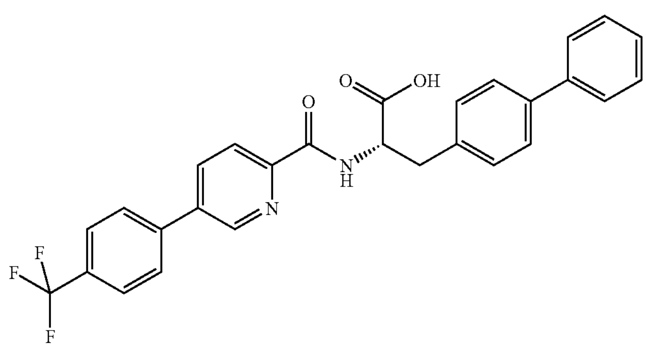 | 3-Biphenyl-4-yl-(2S)-{[5-(4-rifluoromethyl-phenyl)-pyridine-2-carbonyl]-amino}-propionic acid |

TABLE 1-continued

| Example | Structure | Name |
|---|---|---|
| 32 | 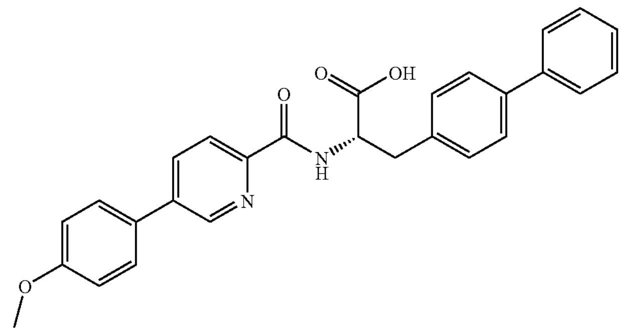 | 3-Biphenyl-4-yl-(2S)-{[5-(4-methoxy-phenyl)-pyridine-2-carbonyl]-amino}-propionic acid |
| 33 | 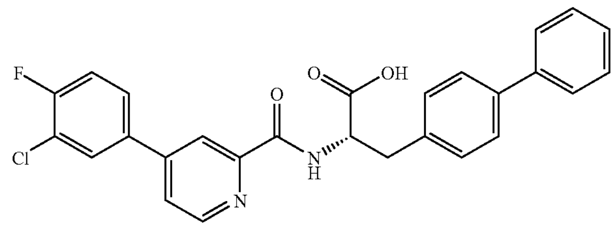 | 3-Biphenyl-4-yl-(2S)-{[4-(3-chloro-4-fluoro-phenyl)-pyridine-2-carbonyl]-amino}-propionic acid |
| 34 | 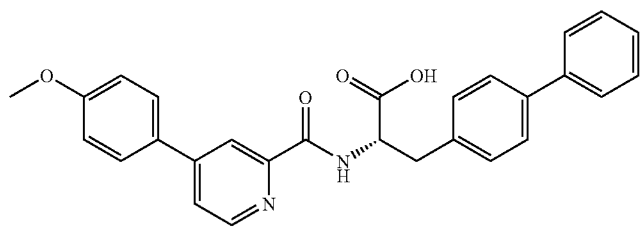 | 3-Biphenyl-4-yl-(2S)-{[4-(4-methoxy-phenyl)-pyridine-2-carbonyl]-amino}-propionic acid |
| 35 | 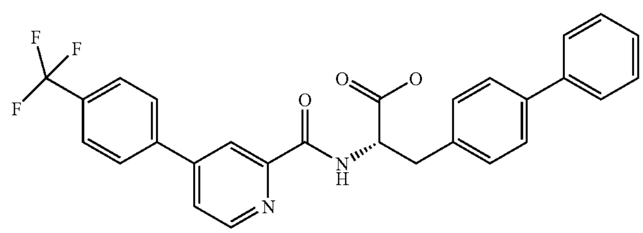 | 3-Biphenyl-4-yl-(2S)-{[4-(4-trifluoromethyl-phenyl)-pyridine-2-carbonyl]-amino}-propionic acid |
| 36 | 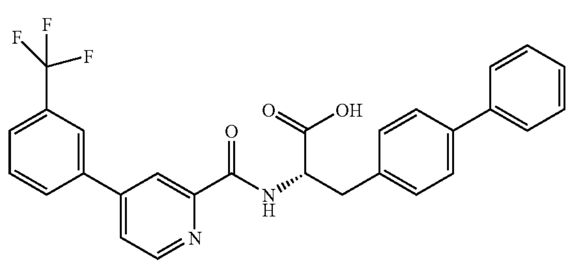 | 3-Biphenyl-4-yl-(2S)-{[4-(3-trifluoromethyl-phenyl)-pyridine-2-carbonyl]-amino}-propionic acid |
| 37 | 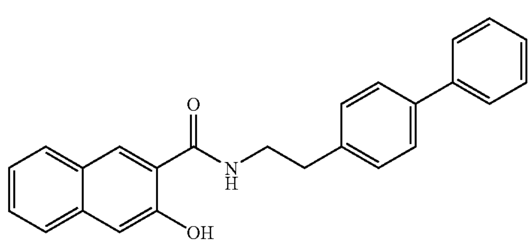 | 3-Hydroxy-napthalene-2-carboxylic acid (2-biphenyl-4-yl-ethyl)-amide |

TABLE 1-continued

| Example | Structure | Name |
| --- | --- | --- |
| 38 | 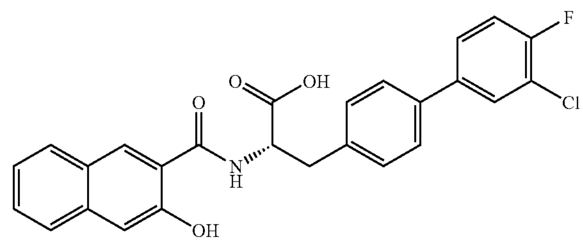 | 3-[(3'-Chloro-4'-fluoro)-biphenyl-4-yl]-(2S)-[(3-hydroxy-naphthalene-2-carbonyl)-amino]-propionic acid |
| 39 | 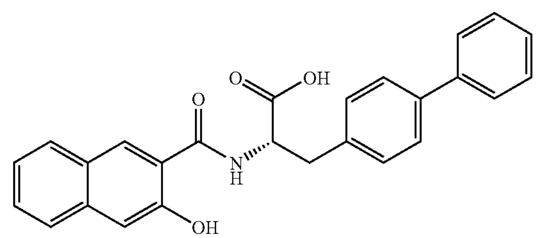 | 3-(Biphenyl-4-yl)-(2S)-[(3-hydroxy-napthalene-2-carbonyl)-amino]-propionic acid |
| 40 | 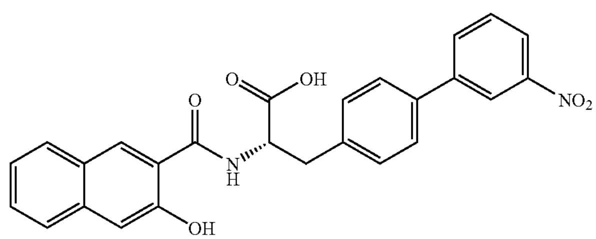 | (2S)-[(3-Hydroxy-napthalene-2-carbonyl)-amino]-3-[(3'-nitro)-biphenyl-4-yl]-propionic acid |
| 41 | 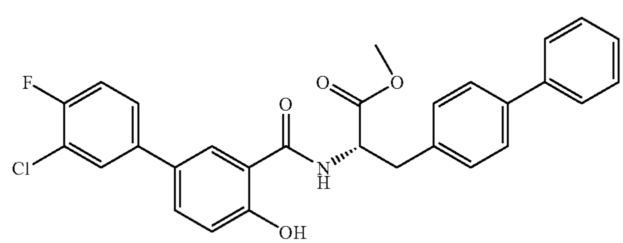 | 3-(Biphenyl-4-yl)-(2S)-[(3'-chloro-4'-fluoro-4-hydroxy-biphenyl-3-carbonyl)-amino]-propionic acid methyl ester |
| 42 | 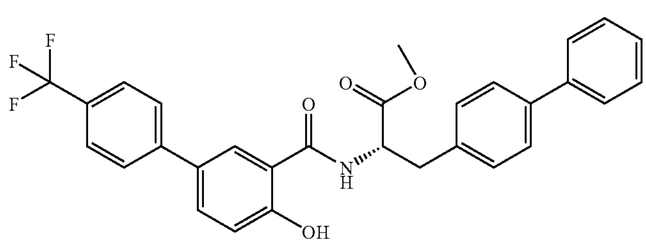 | 3-(Biphenyl-4-yl)-(2S)-[(4'-trifluoromethyl-4-hydroxy-biphenyl-3-carbonyl)-amino]-propionic acid methyl ester |
| 43 | 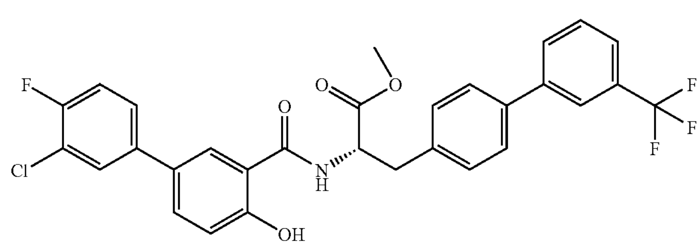 | (2S)-[(3'-Chloro-4'-fluoro-4-hydroxy-biphenyl-3-carbonyl)-amino]-3-(3'-trifluoromethyl-biphenyl-4-yl)-propionic acid methyl ester |

TABLE 1-continued

| Example | Structure | Name |
|---|---|---|
| 44 | 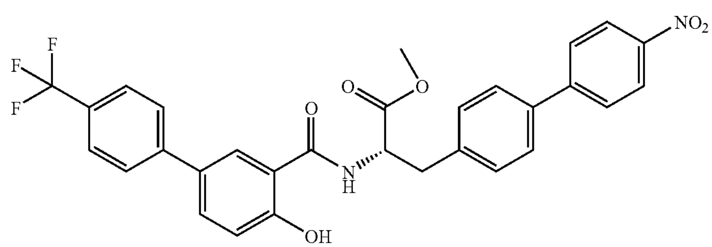 | 3-(4'-Nitro-biphenyl-4-yl)-(2S)-[(4'-trifluoromethyl-4-hydroxy-biphenyl-3-carbonyl)-amino]-propionic acid methyl ester |
| 45 | 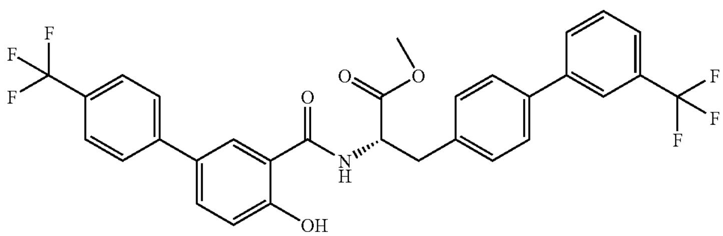 | 3-(3'-Trifluoromethyl-biphenyl-4-yl)-(2S)-[(4'-trifluoromethyl-4-hydroxy-propionic acid methyl ester |
| 46 | 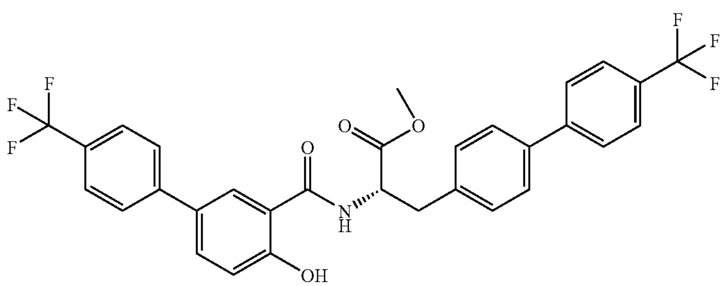 | 3-(4'-Trifluoromethyl-biphenyl-4-yl)-(2S)-[(4'-trifluoromethyl-4-hydroxy-biphenyl-3-carbonyl)-amino]-propionic acid methyl ester |
| 47 | 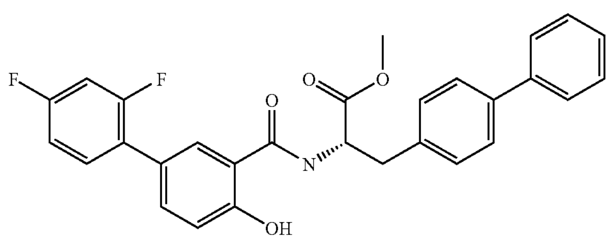 | 3-Biphenyl-4-yl-(2S)-[(2',4'-difluoro-4-hydroxy-biphenyl-3-carbonyl)-amino]-propionic acid |
| 48 | 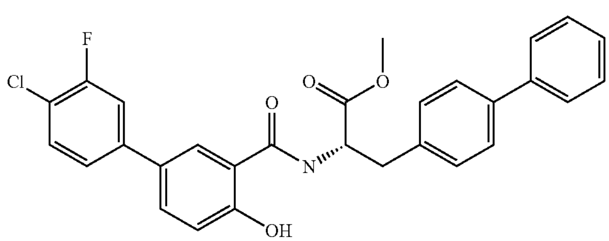 | 3-Biphenyl-4-yl-(2S)-[(4'-chloro-3'-fluoro-4-hydroxy-biphenyl-3-carbonyl)-amino]-propionic acid methyl ester |
| 49 | 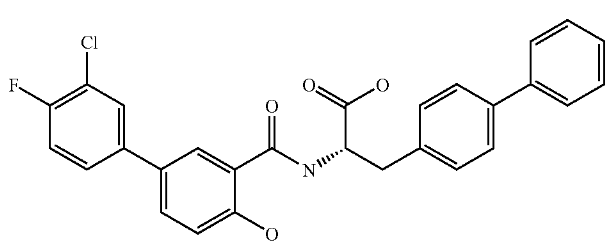 | 3-Biphenyl-4-yl-(2S)-[(3'-chloro-4'-fluoro-4-hydroxy-biphenyl-3-carbonyl)-amino]-propionic acid |

TABLE 1-continued

| Example | Structure | Name |
|---|---|---|
| 50 | 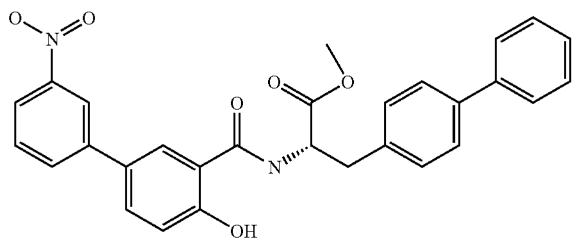 | 3-Biphenyl-4-yl-(2S)-[(4-hydroxy-3'-nitro-biphenyl-3-carbonyl)-amino]-propionic acid methyl ester |
| 51 | 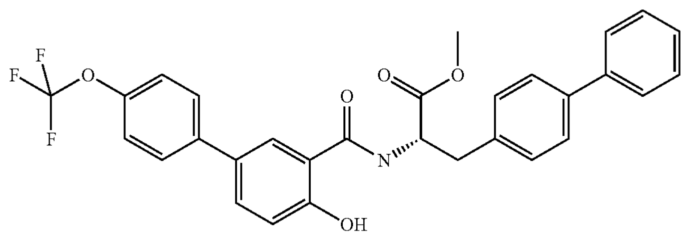 | 3-Biphenyl-4-yl-(2S)-[(4-hydroxy-4'-trifluoromethoxy-biphenyl-3-carbonyl)-amino]-propionic acid methyl ester |
| 52 | 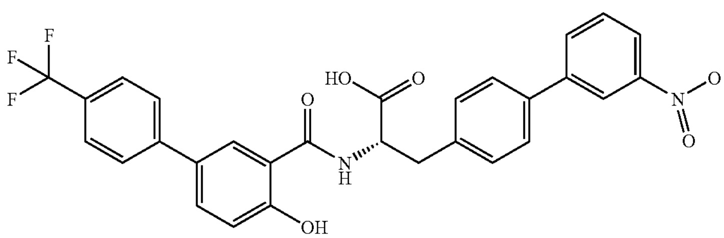 | (2S)-[(4-Hydroxy-4'-trifluoromethyl-biphenyl-3-carbonyl)-amino]-3-(3'-nitro-biphenyl-4-yl)-propionic acid |
| 53 | 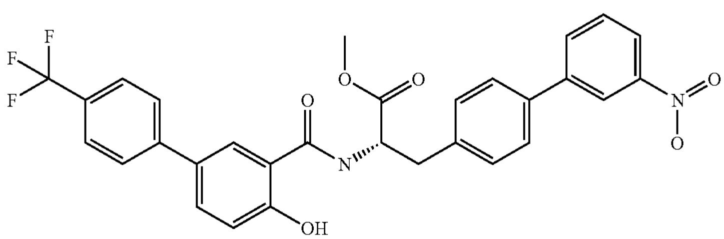 | (2S)-[(4-Hydroxy-4'-trifluoromethyl-biphenyl-3-carbonyl)-amino]-3-(3'-nitro-biphenyl-4-yl)-propionic acid methyl ester |
| 54 | 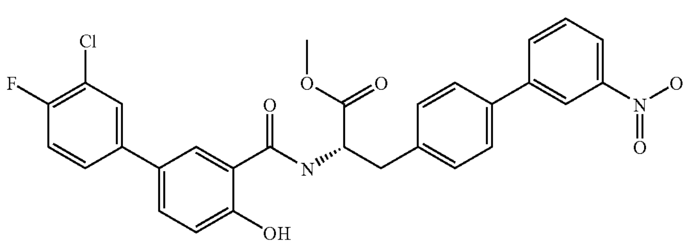 | (2S)-[(3'-Chloro-4'-fluoro-4-hydroxy-biphenyl-3-carbonyl)-amino]-3-(3'-nitro-biphenyl-4-yl)-propionic acid methyl ester |
| 55 | 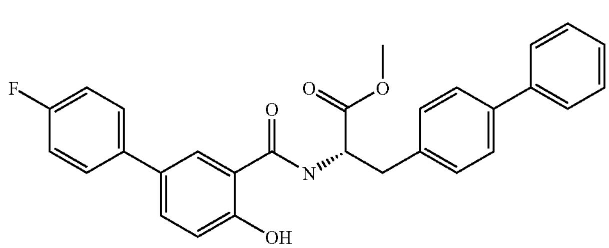 | 3-Biphenyl-4-yl-(2S)-[(4'-fluoro-4-hydroxy-biphenyl-3-carbonyl)-amino]-propionic acid methyl ester |

TABLE 1-continued

| Example | Structure | Name |
| --- | --- | --- |
| 56 | 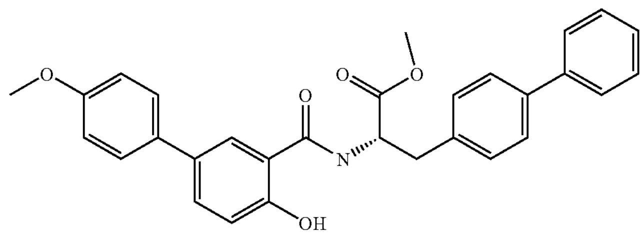 | 3-Biphenyl-4-yl-(2S)-[(4-hydroxy-4'-methoxy-biphenyl-3-carbonyl)-amino]-propionic acid methyl ester |
| 57 | 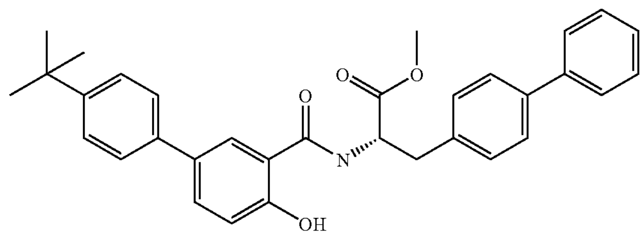 | 3-Biphenyl-4-yl-(2S)-[(4'-tert-butyl-4-hydroxy-biphenyl-3-carbonyl)-amino]-propionic acid methyl ester |
| 58 | 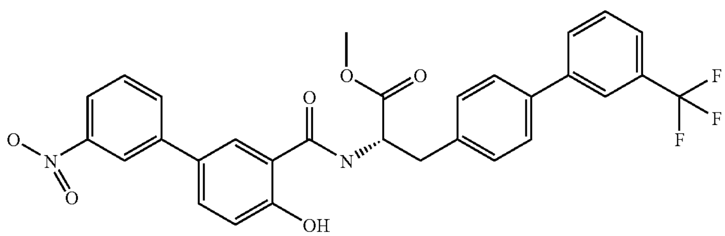 | (2S)-[(4-Hydroxy-3'-nitro-biphenyl-3-carbonyl)-amino]-3-(3'-trifluoromethyl-biphenyl-4-yl)-propionic acid methyl ester |
| 59 | 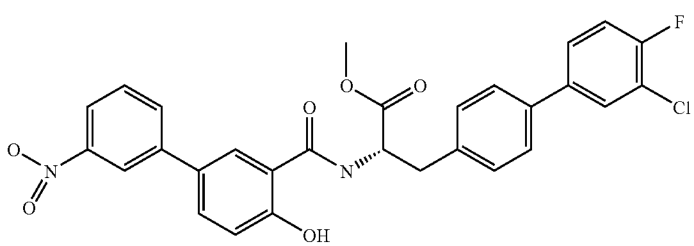 | 3-(3'-Chloro-4'-fluoro-biphenyl-4-yl-(2S)-[(4-hydroxy-3'-nitro-biphenyl-3-carbonyl)-amino]-propionic acid methyl ester |
| 60 | 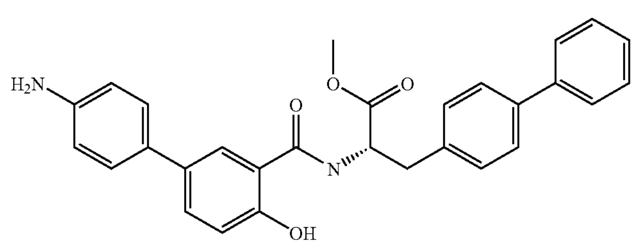 | (2S)-[(4'-Amino-4-hydroxy-biphenyl-3-carbonyl)-amino]-3-biphenyl-4-yl-propionic acid methyl ester |
| 61 | 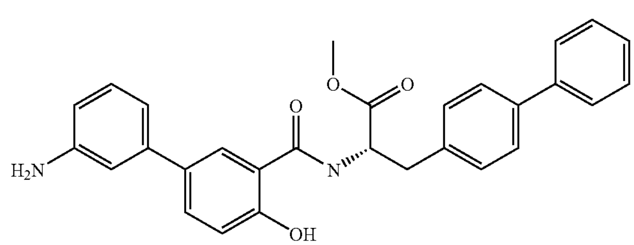 | (2S)-[(3'-Amino-4-hydroxy-biphenyl-3-carbonyl)-amino]-3-biphenyl-4-yl-propionic acid methyl ester |

TABLE 1-continued

| Example | Structure | Name |
|---|---|---|
| 62 | 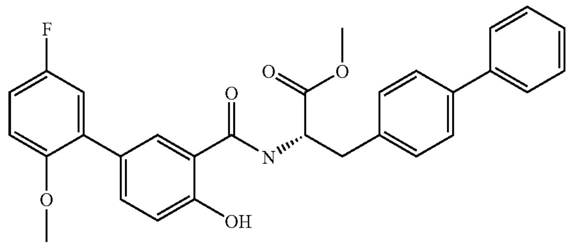 | 3-Biphenyl-4-yl-(2S)-[(5'-fluoro-4-hydroxy-2'-methoxy-biphenyl-3-carbonyl)-amino]-propionic acid methyl ester |
| 63 | 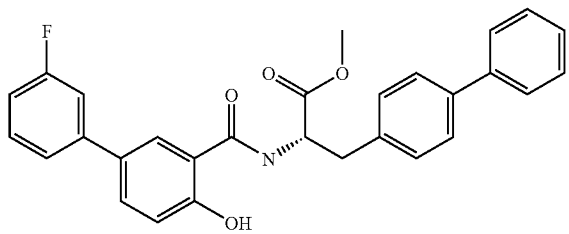 | 3-Biphenyl-4-yl-(2S)-[(3'-fluoro-4-hydroxy-biphenyl-3-carbonyl)-amino]-propionic acid methyl ester |
| 64 | 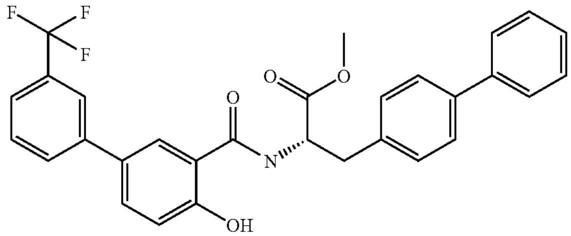 | 3-Biphenyl-4-yl-(2S)-[(4-hydroxy-3'-trifluoromethyl-biphenyl-3-carbonyl)-amino]-propionic acid methyl ester |
| 65 | 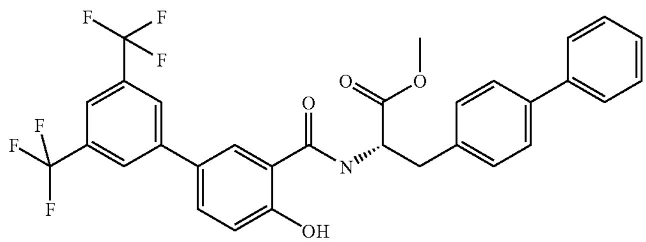 | 3-Biphenyl-4-yl-(2S)-[(4-hydroxy-3',5'-bis-trifluoromethyl-biphenyl-3-carbonyl)-amino]-propionic acid methyl ester |
| 66 | 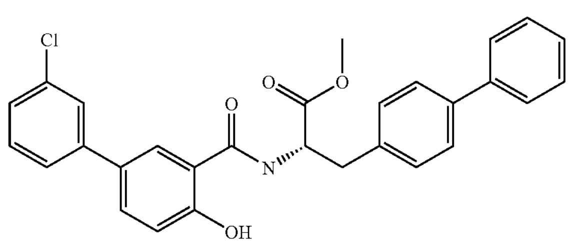 | 3-Biphenyl-4-yl-(2S)-[(3'-chloro-4-hydroxy-biphenyl-3-carbonyl)-amino]-propionic acid methyl ester |
| 67 | 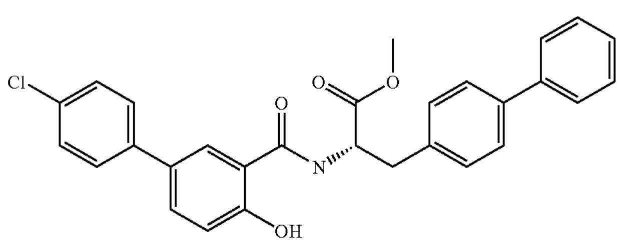 | 3-Biphenyl-4-yl-(2S)-[(4'-chloro-4-hydroxy-biphenyl-3-carbonyl)-amino]-propionic acid methyl ester |

TABLE 1-continued

| Example | Structure | Name |
|---|---|---|
| 68 | 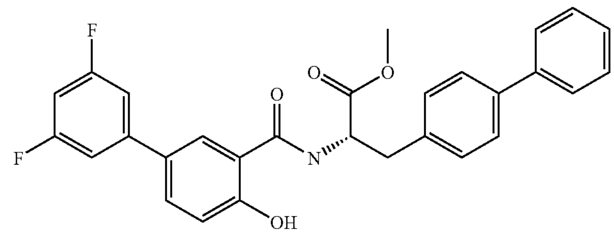 | 3-Biphenyl-4-yl-(2S)-[(3',5'-difluoro-4-hydroxy-biphenyl-3-carbonyl)-amino]-propionic acid methyl ester |
| 69 | 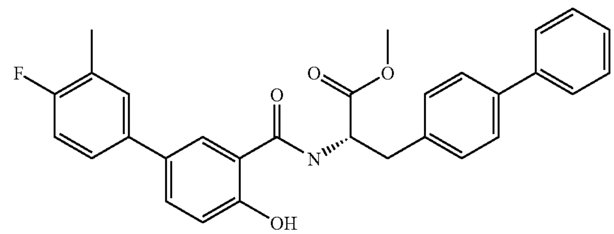 | 3-Biphenyl-4-yl-(2S)-[(4'-fluoro-4-hydroxy-3'-methyl-biphenyl-3-carbonyl)-amino]-propionic acid methyl ester |
| 70 | 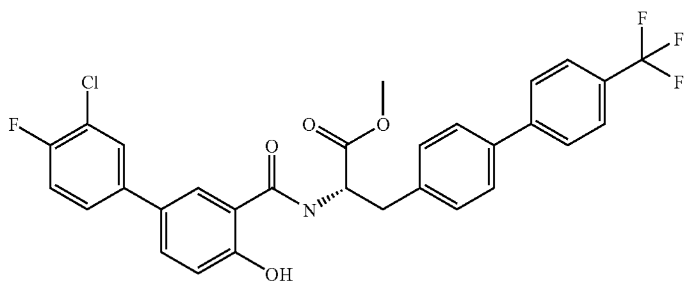 | (2S)-[(3'-Chloro-4'-fluoro-4-hydroxy-biphenyl-3-carbonyl)-amino]-3-(4'-trifluoromethyl-biphenyl-4-yl)-propionic acid methyl ester |
| 71 | 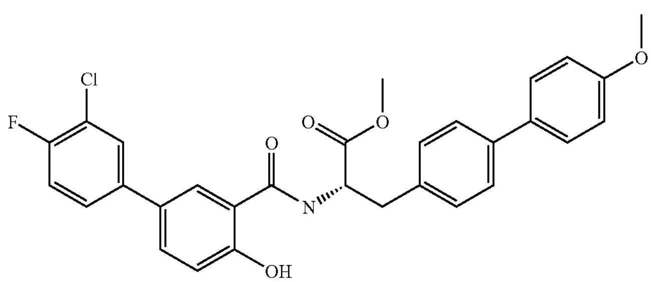 | (2S)-[(3'-Chloro-4'-fluoro-4-hydroxy-biphenyl-3-carbonyl)-amino]-3-(4'-methoxy-biphenyl-4-yl)-propionic acid methyl ester |
| 72 | 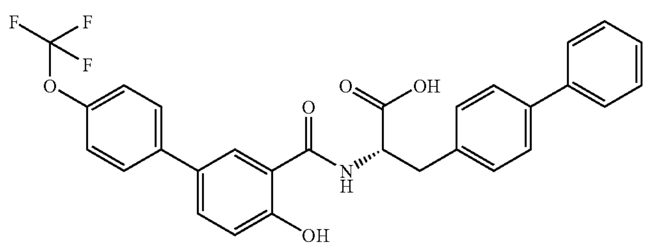 | 3-Biphenyl-4-yl-(2S)-[(4-hydroxy-4'-trifluoromethoxy-biphenyl-3-carbonyl)-amino]-propionic acid |
| 73 | 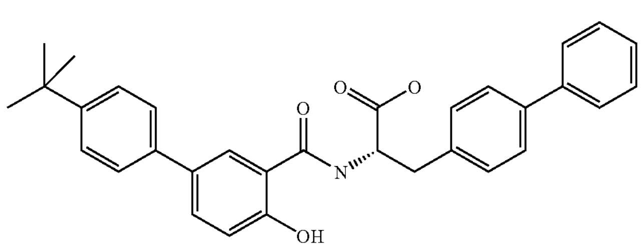 | 3-Biphenyl-4-yl-(2S)-[(4'-tert-butyl-4-hydroxy-biphenyl-3-carbonyl)-amino]-propionic acid |

TABLE 1-continued

| Example | Structure | Name |
|---|---|---|
| 74 | 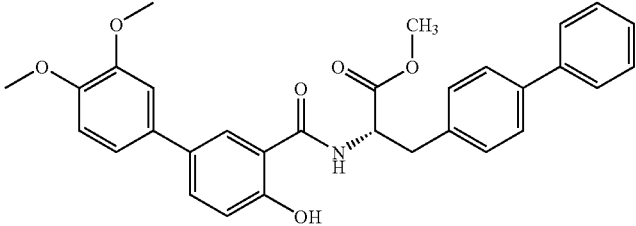 | 3-Biphenyl-4-yl-(2S)-[(4-hydroxy-3',4'-dimethoxy-biphenyl-3-carbonyl)-amino]-propionic acid methyl ester |
| 75 | 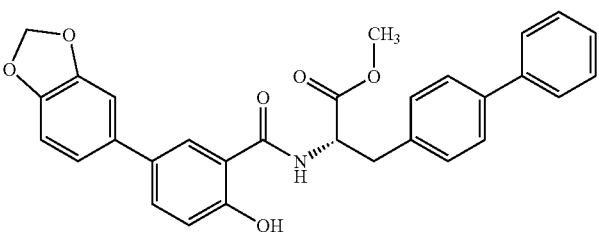 | (2S)-(5-Benzo[1,3]dioxol-5-yl-2-hydroxy-benzoylamino)-3-biphenyl-4-yl-propionic acid methyl ester |
| 76 | 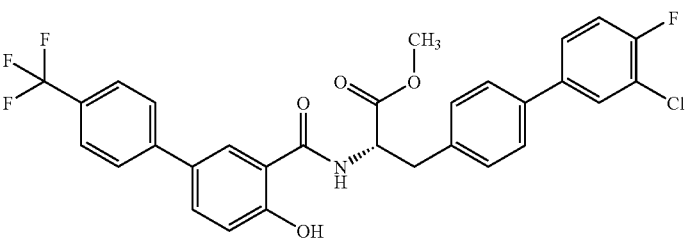 | 3-(3'-Chloro-4'-fluoro-biphenyl-4-yl-(2S)-[(4-hydroxy-4'-trifluoromethyl-biphenyl-3-carbonyl)-amino]-propionic acid methyl ester |
| 77 | 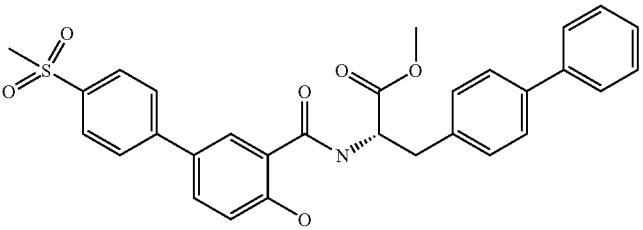 | 3-Biphenyl-4-yl-(2S)-[(4-hydroxy-4'-methanesulfonyl-biphenyl-3-carbonyl)-amino]-propionic acid methyl ester |
| 78 | 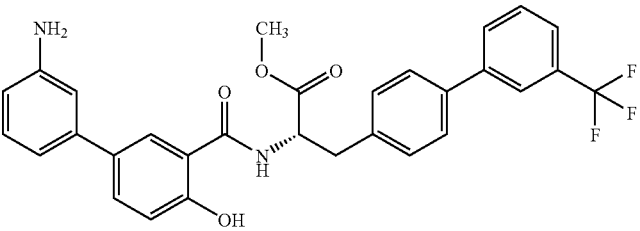 | (2S)-[(3'-Amino-4-hydroxy-biphenyl-3-carbonyl)-amino]-3-(3'-trifluoromethyl-biphenyl-4-yl-propionic acid methyl ester |
| 79 | 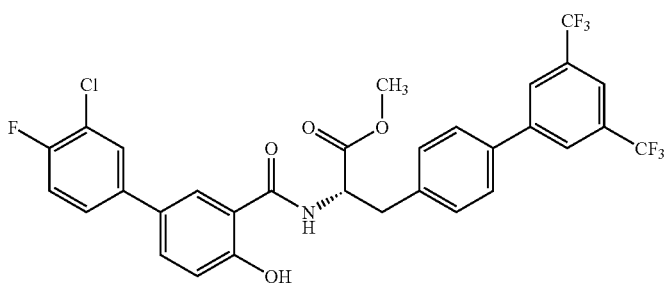 | 3-(3',5'-Bis-trifluoromethyl-biphenyl-4-yl)-(2S)-[(3'-chloro-4'-fluoro-4-hydroxy-biphenyl-3-carbonyl)-amino]-propionic acid methyl ester |

TABLE 1-continued

| Example | Structure | Name |
|---|---|---|
| 80 | 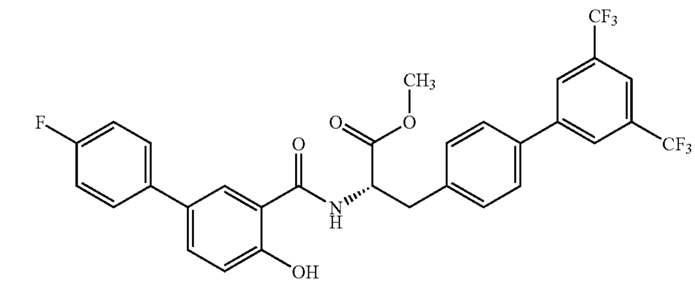 | 3-(3',5'-Bis-trifluoromethyl-biphenyl-4-yl)-(2S)-[(4'-fluoro-4-hydroxy-biphenyl-3-carbonyl)-amino]-propionic acid methyl ester |
| 81 | 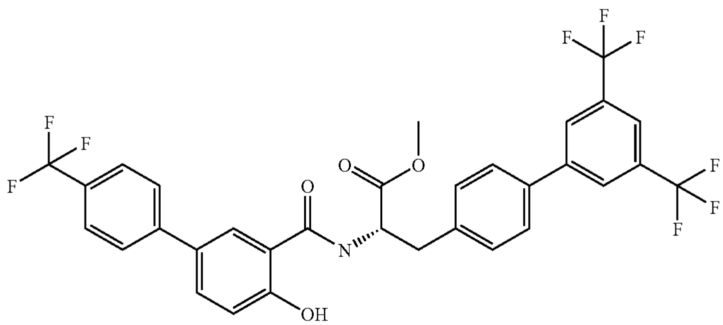 | 3-(3',5'-Bis-trifluoromethyl-biphenyl-4-yl)-(2S)-[(4-hydroxy-4'-trifluoromethyl-biphenyl-3-carbonyl)-amino]-propionic acid methyl ester |
| 82 | 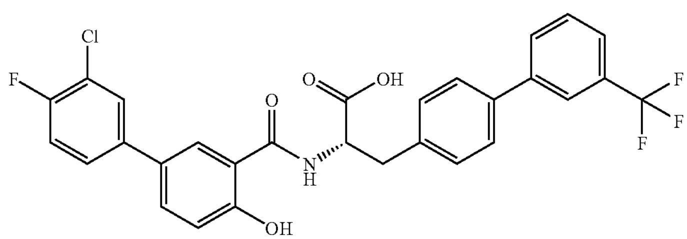 | (2S)-[(3'-Chloro-4'-fluoro-4-hydroxy-biphenyl-3 carbonyl)-amino]-3-(3'-trifluoromethyl-biphenyl-4-yl)-propionic acid |
| 83 | 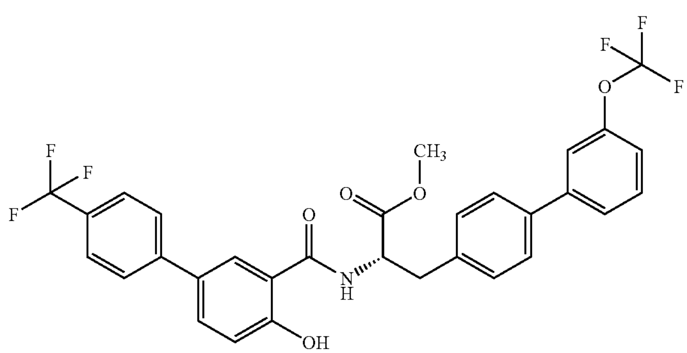 | (2S)-[(4-Hydroxy-4'-trifluoromethyl-biphenyl-3-carbonyl)-amino]-3-(3'-trifluoromethoxy-biphenyl-4-yl)-propionic acid methyl ester |
| 84 | 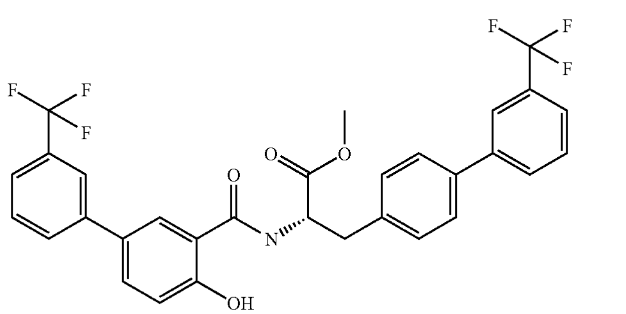 | (2S)-[(4-Hydroxy-3'-trifluoromethyl-biphenyl-3-carbonyl)-amino]-3-(3'-trifluoromethyl-biphenyl-4-yl)-propionic acid methyl ester |

TABLE 1-continued

| Example | Structure | Name |
|---|---|---|
| 85 | 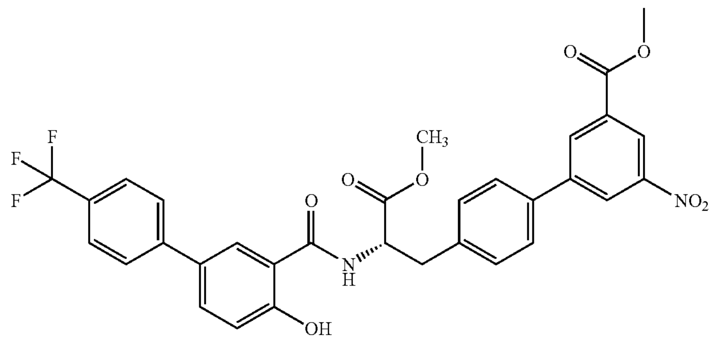 | 4'-{(2S)-[(4-Hydroxy-4'-trifluoromethyl-biphenyl-3-carbonyl)-amino]-2-methoxycarbonyl-ethyl}-5-nitro biphenyl-3-carboxylic acid methyl ester |
| 86 | 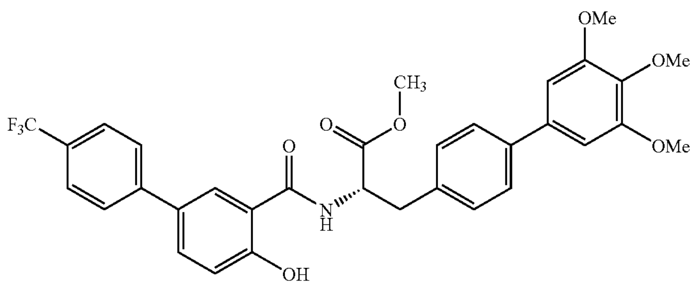 | (2S)-[(4-Hydroxy-4'-trifluoromethyl-biphenyl-3-carbonyl)-amino]-3-(3',4',5'-trimethoxy-biphenyl-4-yl)-propionic acid methyl ester |
| 87 | 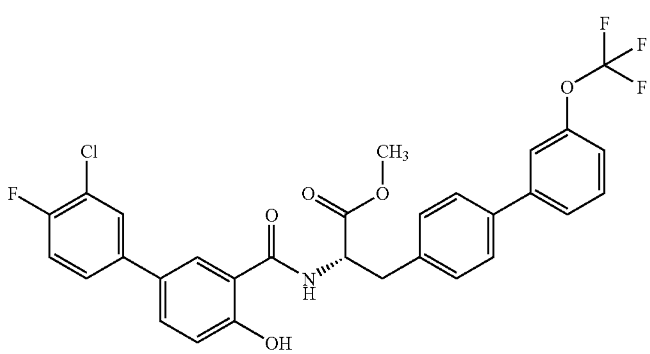 | (2S)-[(3'-Chloro-4'-fluoro-4-hydroxy-biphenyl-3-carbonyl)-amino]-3-(3'-trifluoromethoxy-biphenyl-4-yl)-propionic acid methyl ester |
| 88 | 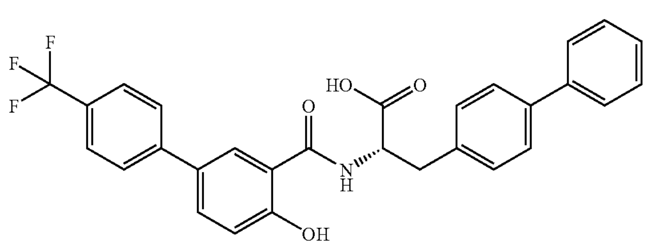 | 3-Biphenyl-4-yl-(2S)-[(4-hydroxy-4'-trifluoromethyl-biphenyl-3-carbonyl)-amino]-propionic acid |
| 89 | 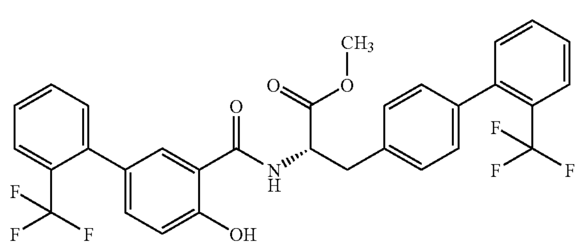 | (2S)-[(4-Hydroxy-2'-trifluoromethyl-biphenyl-3-carbonyl)-amino]-3-(2'-trifluoromethyl-biphenyl-4-yl)-propionic acid methyl ester |

TABLE 1-continued

| Example | Structure | Name |
|---|---|---|
| 90 | 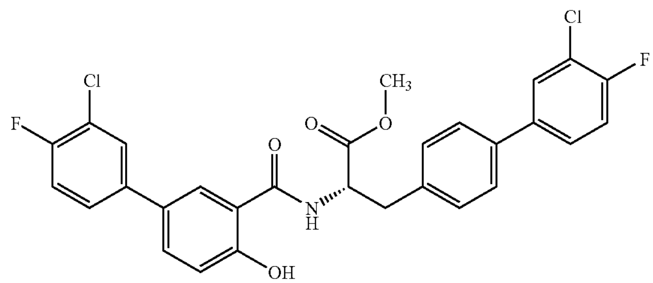 | 3-(3'-Chloro-4'-fluoro-biphenyl-4-yl)-(2S)-[(3'-chloro-4'-fluoro-4-hydroxy-biphenyl-3-carbonyl)-amino]-propionic acid methyl ester |
| 91 | 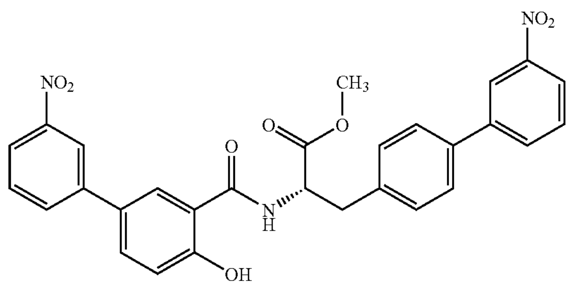 | (2S)-[(4-Hydroxy-3'-nitro-biphenyl-3-carbonyl)-amino]-3-(3'-nitro-biphenyl-4-yl)-propionic acid methyl ester |
| 92 | 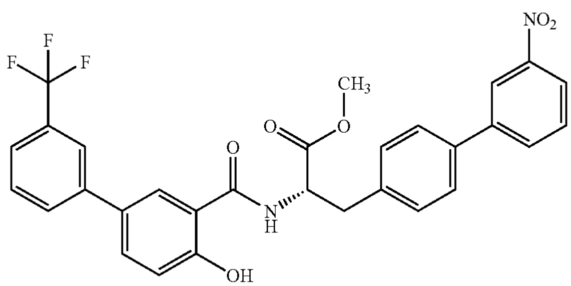 | (2S)-[(4-Hydroxy-3'-trifluoromethyl-biphenyl-3-carbonyl)-amino]-3-(3'-nitro-biphenyl-4-yl)-propionic acid methyl ester |
| 93 | 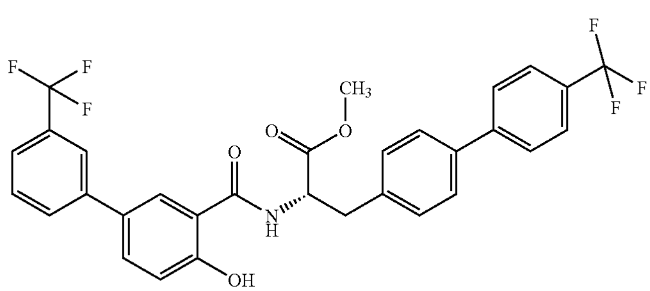 | (2S)-[(4-Hydroxy-3'-trifluoromethyl-biphenyl-3-carbonyl)-amino]-3-(4'-trifluoromethyl-biphenyl-4-yl)-propionic acid methyl ester |
| 94 | 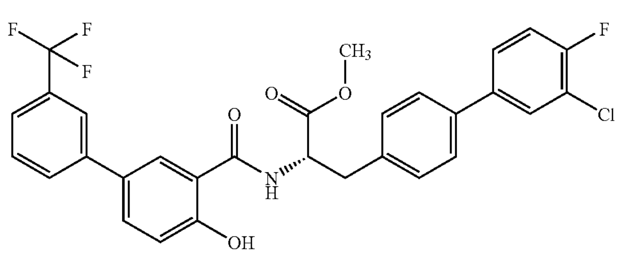 | 3-(3'-Chloro-4'-fluoro-biphenyl-4-yl)-(2S)-[(4-hydroxy-3'-trifluoromethyl-biphenyl-3-carbonyl)-amino]-propionic acid methyl ester |

TABLE 1-continued

| Example | Structure | Name |
| --- | --- | --- |
| 95 | 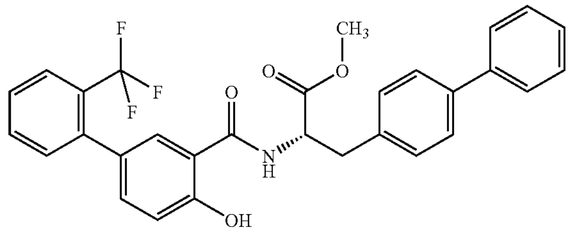 | 3-Biphenyl-4-yl-(2S)-[(4-hydroxy-2'-trifluoromethyl-biphenyl-3-carbonyl)-amino]-propionic acid methyl ester |
| 96 | 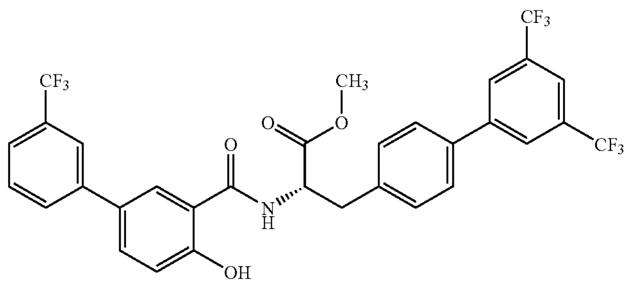 | 3-(3',5'-Bis-trifluoromethyl-biphenyl-4-yl)-(2S)-[(4-hydroxy-3'-trifluoromethyl-biphenyl-3-carbonyl)-amino]-propionic acid methyl ester |
| 97 | 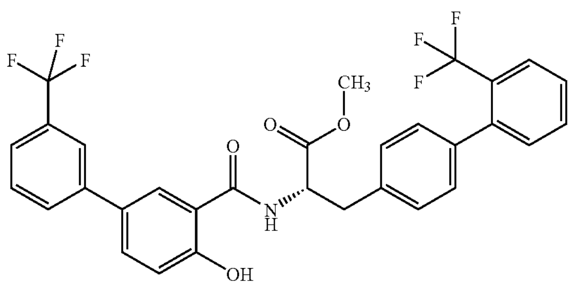 | (2S)-[(4-Hydroxy-3'-trifuloromethyl-biphenyl-3-carbonyl)-amino]-3-(2'-trifluoromethyl-biphenyl-4-yl)-propionic acid methyl ester |
| 98 | 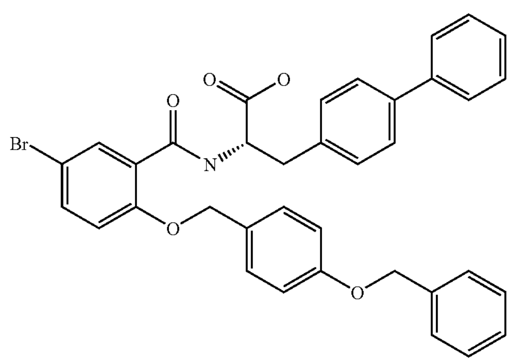 | (2S)-[2-(4-Benzyloxy-benzyloxy)-5-bromo-benzoylamino]-3-biphenyl-4-yl-propionic acid |
| 99 | 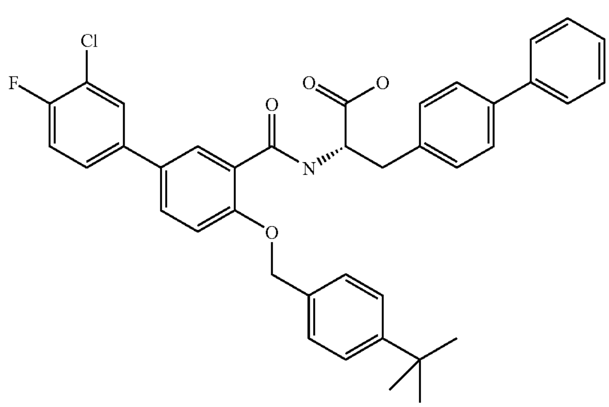 | 3-Biphenyl-4-yl-2S-{[4-(4-tert-butyl-benzyloxy)-3'-chloro-4'-fluoro-biphenyl-3-carbonyl]-amino}-propionic acid |

TABLE 1-continued

| Example | Structure | Name |
| --- | --- | --- |
| 100 | 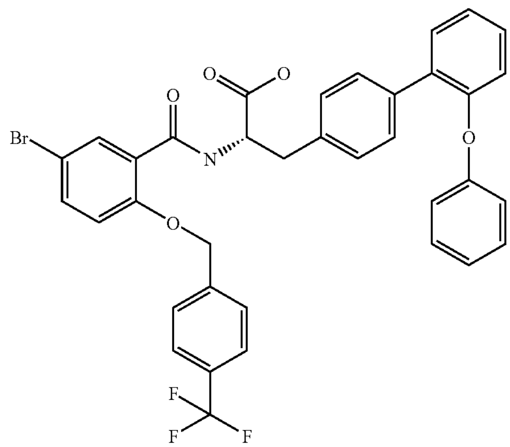 | (2S)-[5-Bromo-2-(4-trifluoromethyl-benzyloxy)-benzoylamino]-3-(2'-phenoxy-biphenyl-4-yl)-propionic acid |
| 101 | 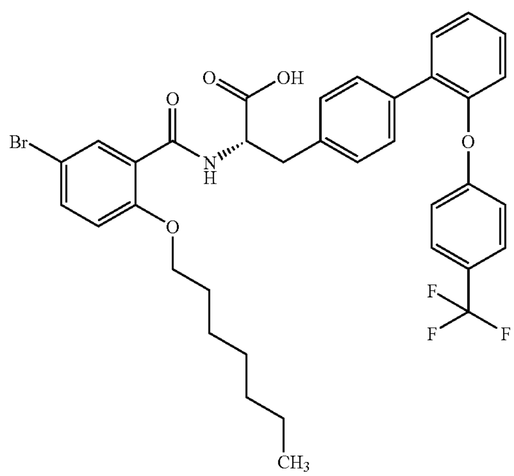 | (2S)-(5-Bromo-2-heptyloxy-benzoylamino)-3-[2'-(4-trifluoromethyl-phenoxy)-biphenyl-4-yl]-propionic acid |
| 102 | 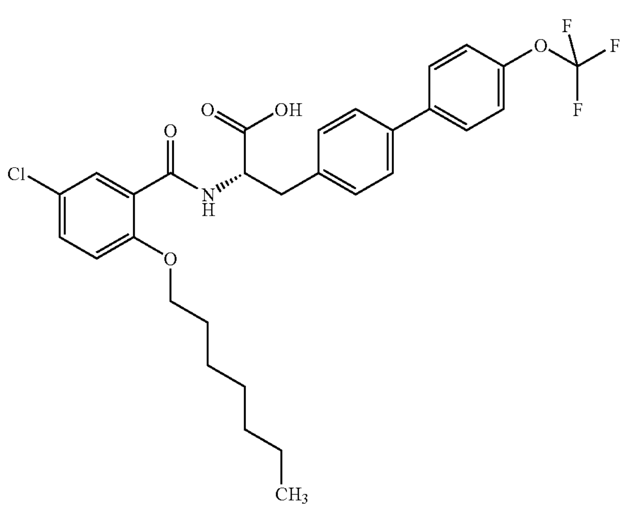 | (2S)-(5-Chloro-2-heptyloxy-benzoylamino)-3-(4'-trifluoromethoxy-biphenyl-4-yl)-propionic acid |

TABLE 1-continued

| Example | Structure | Name |
| --- | --- | --- |
| 103 | 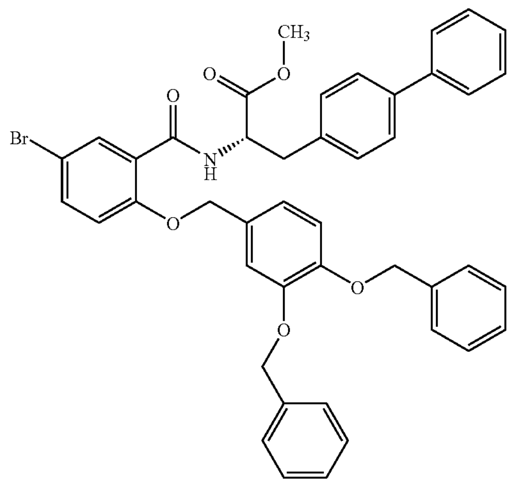 | 3-Biphenyl-4-yl-(2S)-[2-(3,4-bis-benzyloxy-benzyloxy)-5-bromo-benzoylamino]-propionic acid methyl ester |
| 104 | 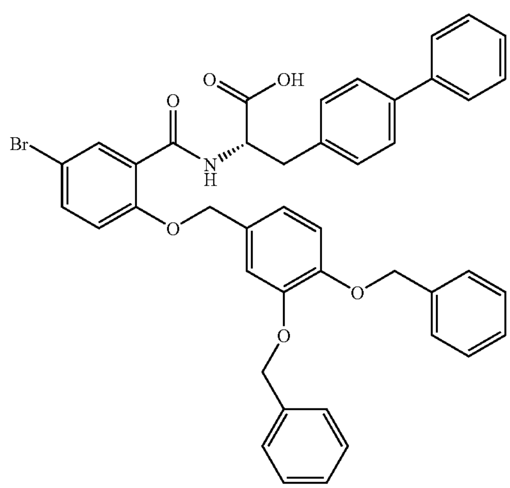 | 3-Biphenyl-4-yl-(2S)-[2-(3,4-bis-benzyloxy-benzyloxy)-5-bromo-benzoylamino]-propionic acid |
| 105 | 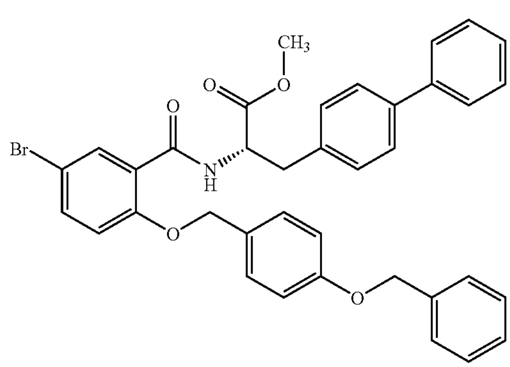 | (2S)-[2-(4-Benzyloxybenzyloxy)-5-bromo-benzoylamino]-3-biphenyl-4-yl-propionic acid methyl ester |

TABLE 1-continued
| Example | Structure | Name |
|---|---|---|
| 106 | 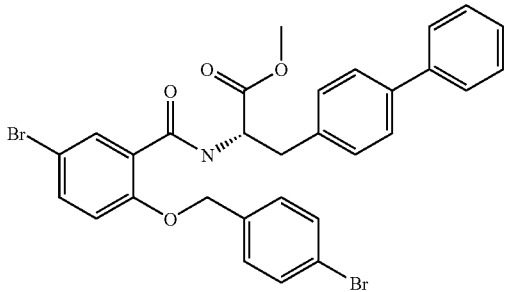 | 3-Biphenyl-4-yl-(2S)-[5-bromo-2-(4-bromo-benzyloxy)-benzoylamino]-propionic acid methyl ester |
| 107 | 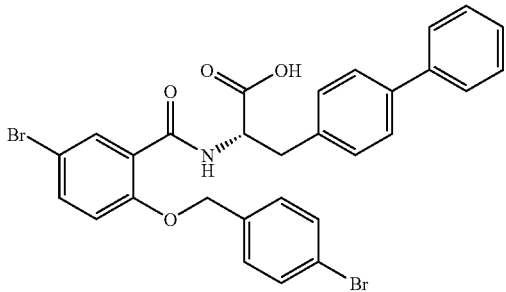 | 3-Biphenyl-4-yl-(2S)-[5-bromo-2-(4-bromo-benzyloxy)-benzoylamino]-propionic acid |
| 108 | 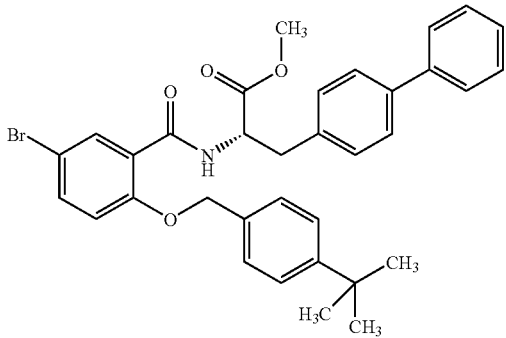 | 3-Biphenyl-4-yl-(2S)-[5-bromo-2-(4-tert-butyl-benzyloxy)-benzoylamino]-propionic acid methyl ester |
| 109 | 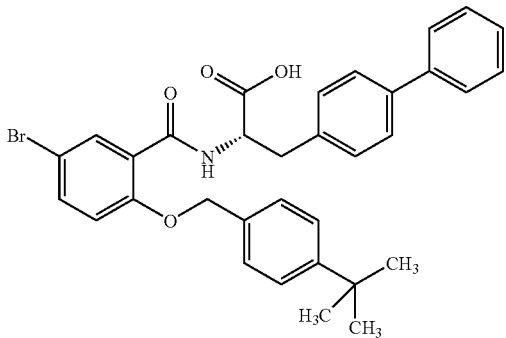 | 3-Biphenyl-4-yl-(2S)-[4-bromo-2-(4-tert-butyl-benzyloxy)-benzoylamino]-propionic acid |

TABLE 1-continued

| Example | Structure | Name |
| --- | --- | --- |
| 110 | 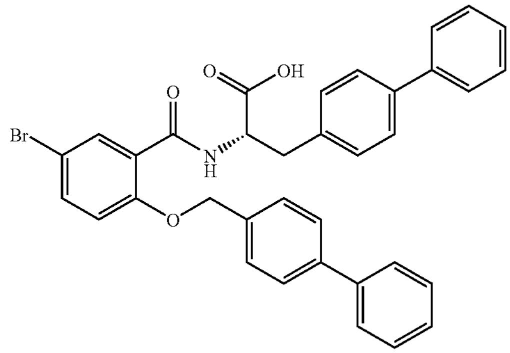 | 3-Biphenyl-4-yl-(2S)-[2-(biphenyl-4-ylmethoxy)-5-bromo-benzoylamino]-propionic acid |
| 111 | 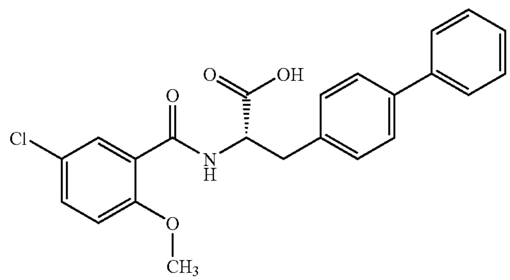 | 3-Biphenyl-4-yl-(2S)-(5-chloro-2-methoxy-benzoylamino)-propionic acid |
| 112 | 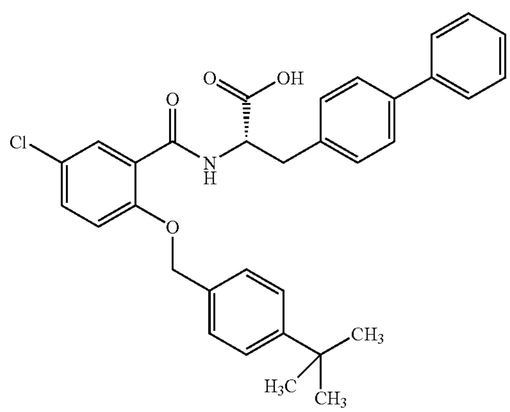 | 3-Biphenyl-4-yl-(2S)-[2-(4-tert-butyl-benzyloxy)-5-chloro-benzoylamino]-propionic acid |
| 113 | 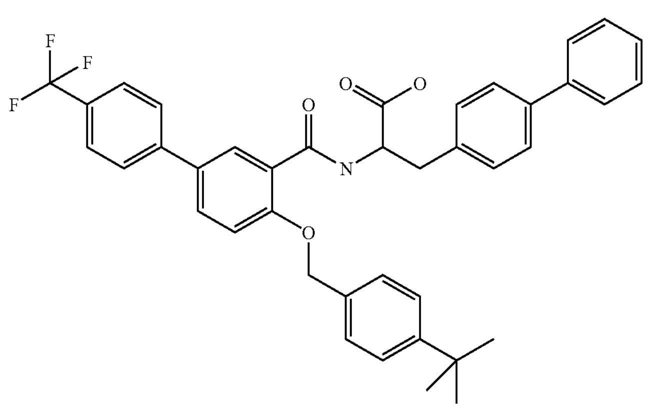 | 3-Biphenyl-4-yl-(2S)-[2-(4-tert-butyl-benzyloxy)-5-(4-trifluoromethylphenyl)-benzoylamino]-propionic acid |

TABLE 1-continued

| Example | Structure | Name |
|---|---|---|
| 114 | 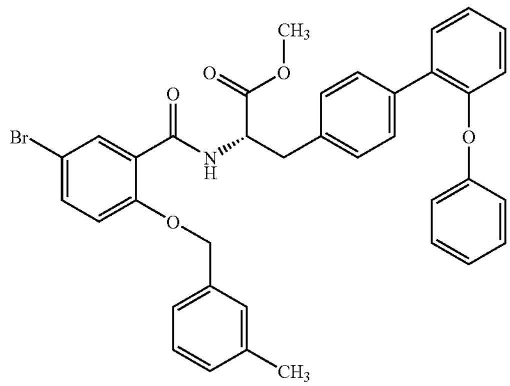 | (2S)-[5-Bromo-2-(3-methyl-benzyloxy)-benzoylamino]-3-(2'-phenoxy-biphenyl-4-yl)-propionic acid methyl ester |
| 115 | 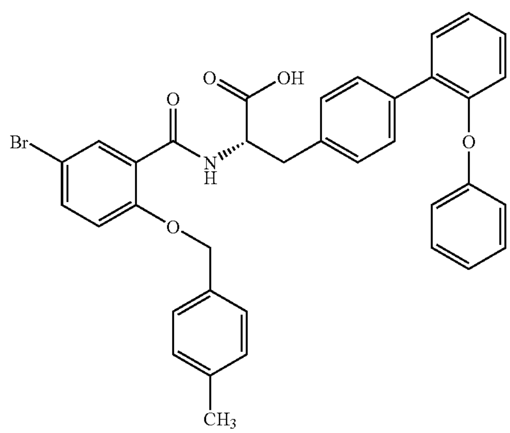 | (2S)-[5-Bromo-2-(4-methyl-benzyloxy)-benzoylamino]-3-(2'-phenoxy-biphenyl-4-yl)-propionic acid |
| 116 | 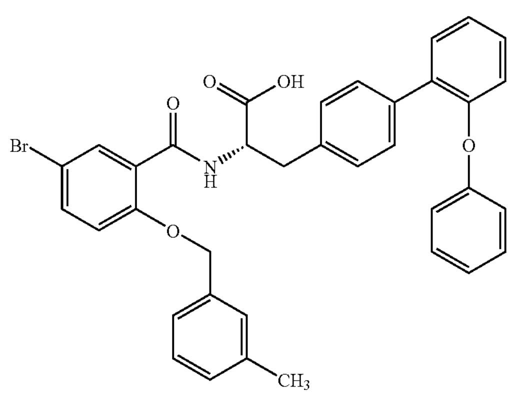 | (2S)-[5-Bromo-2-(3-methyl-benzyloxy)-benzoylamino]-3-(2'-phenoxy-biphenyl-4-yl)-propionic acid |

TABLE 1-continued

| Example | Structure | Name |
|---|---|---|
| 117 | 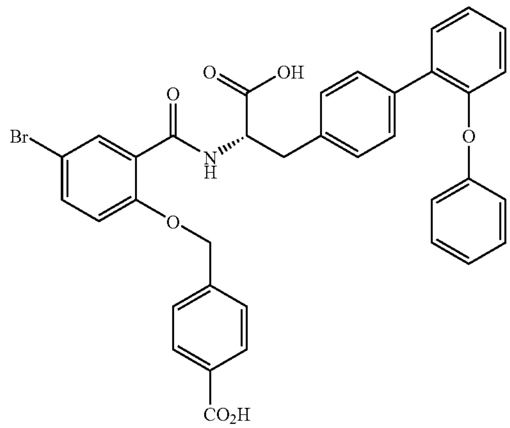 | (2S)-[5-Bromo-2-(4-carboxy-benzyloxy)-benzoylamino]-3-(2'-phenoxy-biphenyl-4-yl)-propionic acid |
| 118 | 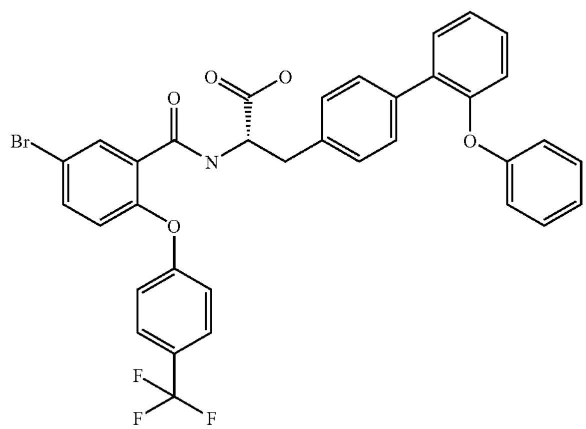 | (2S)-[5-Bromo-2-(4-trifluoromethyl-phenoxy)-benzoylamino[-3-(2'-phenoxy-biphenyl-4-yl)-propionic acid |
| 119 | 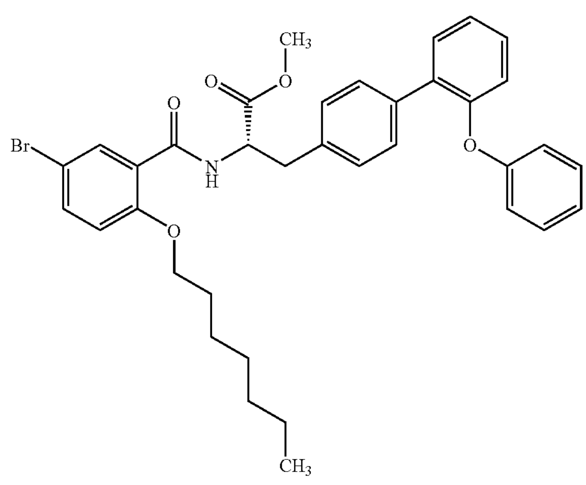 | (2S)-[5-Bromo-2-heptyloxy-benzoylamino-3-(2'-phenoxy-biphenyl-4-yl)-propionic acid methyl ester |

TABLE 1-continued
| Example | Structure | Name |
|---|---|---|
| 120 | 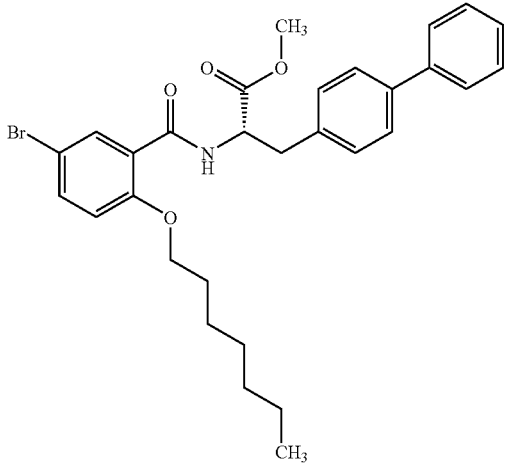 | 3-Biphenyl-4-yl-(2S)-(5-bromo-2-heptyloxy-benzoylamino)-propionic acid methyl ester |
| 121 | 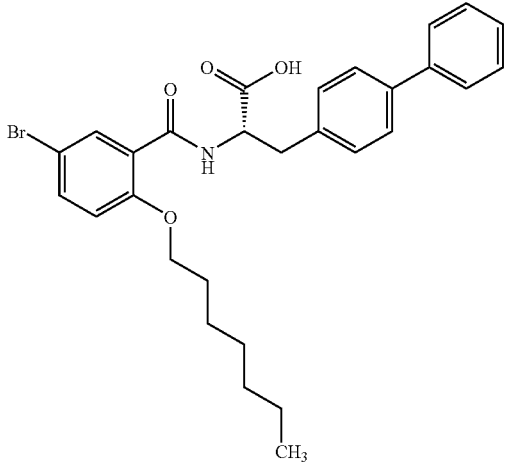 | 3-Biphenyl-4-yl-(2S)-(5-bromo-2-heptyloxy-benzoylamino)-propionic acid |
| 122 | 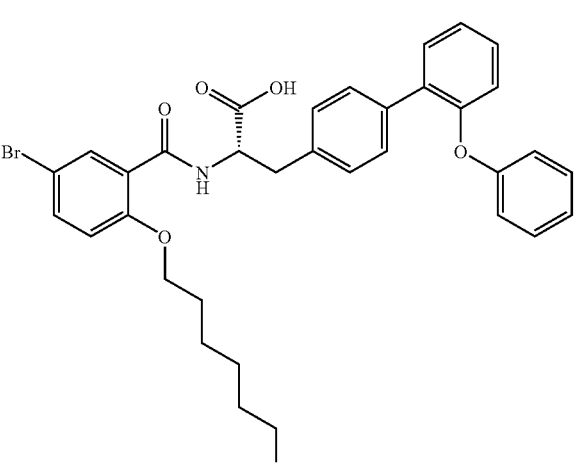 | (2S)-(5-Bromo-2-heptyloxy-benzoylamino)-3-(2'-phenoxy-biphenyl-4-yl)-propionic acid |

TABLE 1-continued

| Example | Structure | Name |
|---|---|---|
| 123 | 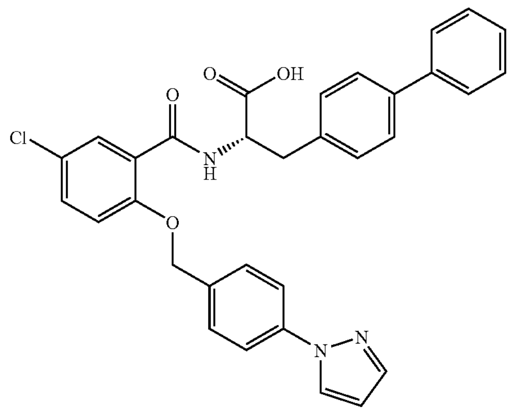 | 3-Biphenyl-4-yl-(2S)-[5-chloro-2-(4-pyrazol-1-yl-benzyloxy)-benzoylamino]-propionic acid |
| 124 | 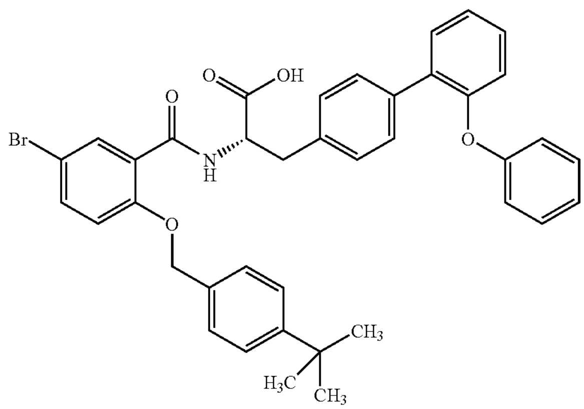 | (2S)-[5-Bromo-2-(4-tert-butyl-benzyloxy)-benzoylamino]-3-(2'-phenoxy-biphenyl-4-yl)-propionic acid |
| 125 | 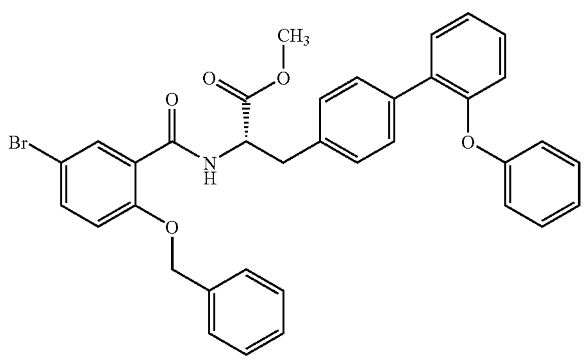 | (2S)-(2-Benzyloxy-5-bromo-benzoylamino)-3-(2'-phenoxy-biphenyl-4-yl)-propionic acid methyl ester |
| 126 | 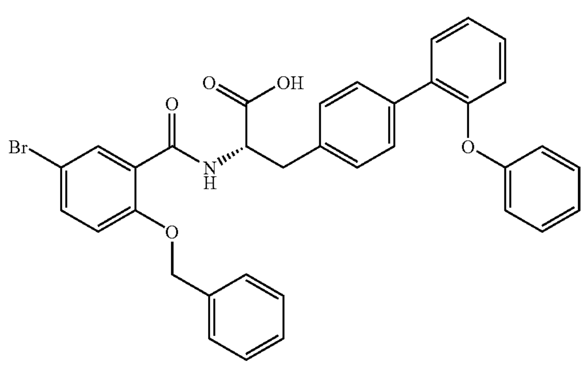 | (2S)-(2-Benzyloxy-5-bromo-benzoylamino)-3-(2'-phenoxy-biphenyl-4-yl)-propionic acid |

TABLE 1-continued

| Example | Structure | Name |
| --- | --- | --- |
| 127 | 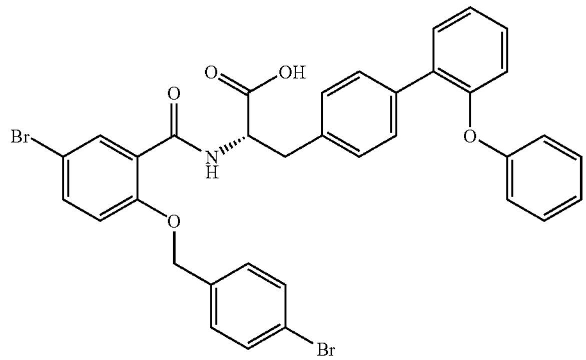 | (2S)-[5-Bromo-2-(4-bromo-benzyloxy)-benzoylamino]-3-(2'-phenoxy-biphenyl-4-yl-propionic acid |
| 128 | 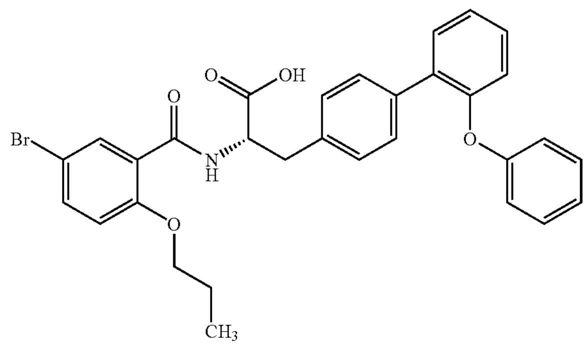 | (2S)-(5-Bromo-2-propoxy-benzoylamino)-3-2'-phenoxy-biphenyl-4-yl)-propionic acid |
| 129 | 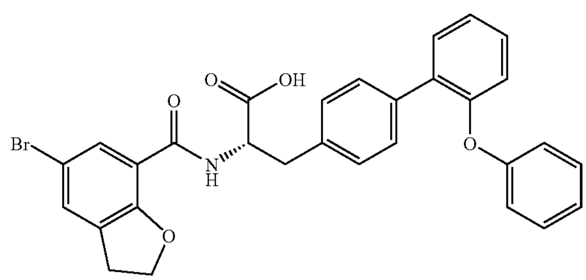 | (2S)-[(5-Bromo-2,3-dihydro-benzofuran-7-carbonyl)-amino]-3-(2'-phenoxy-biphenyl-4-yl)-propionic acid |
| 130 | 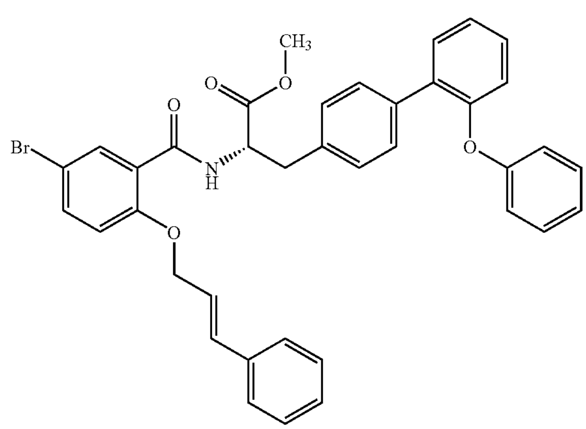 | (2S)-[5-Bromo-2-(3-phenyl-allyloxy)-benzoylamino]-3-(2'-phenoxy-biphenyl-4-yl)-propionic acid methyl ester |

TABLE 1-continued

| Example | Structure | Name |
|---|---|---|
| 131 | 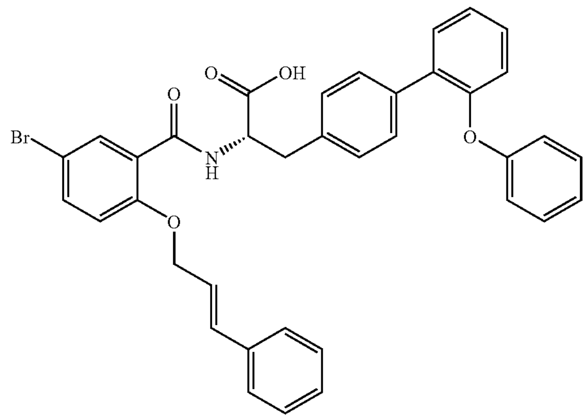 | (2S)-[5-Bromo-2-(3-phenyl-allyloxy)-benzoylamino]-3-(2'-phenoxy-biphenyl-4-yl)-propionic acid |
| 132 | 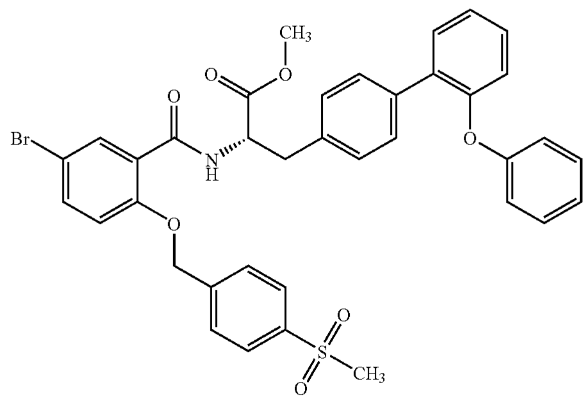 | (2S)-[5-Bromo-2-(4-methanesulfonyl-benzyloxy)-benzoylamino]-3-(2'-phenoxy-biphenyl-4-yl)-propionic acid methyl ester |
| 133 | 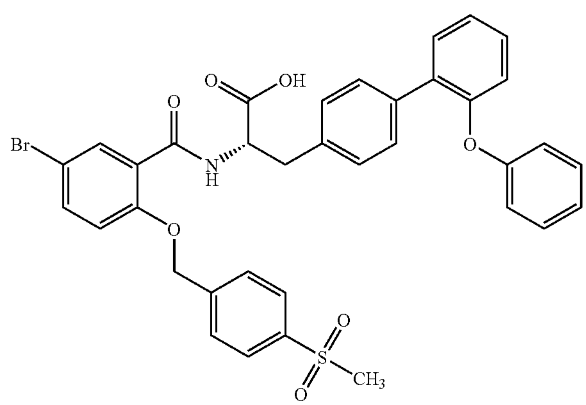 | (2S)-[5-Bromo-2-(4-methanesulfonyl-benzyloxy)-benzoylamino]-3-(2'-phenoxy-biphenyl-4-yl)-propionic acid |
| 134 | 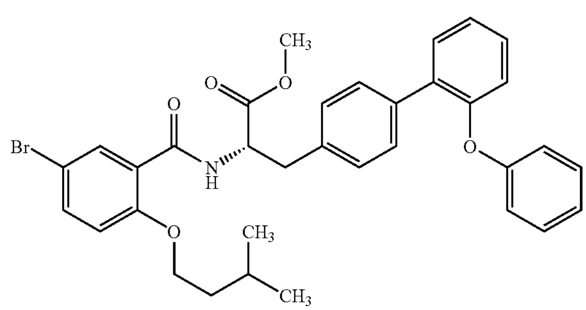 | (2S)-]5-Bromo-2-(3-methyl-butoxy)-benzoylamino]-3-(2'-phenoxy-biphenyl-4-yl)-propionic acid methyl ester |

TABLE 1-continued

| Example | Structure | Name |
| --- | --- | --- |
| 135 | 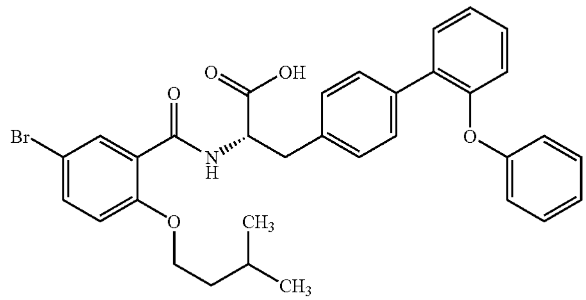 | (2S)-[5-Bromo-2-(3-methyl-butoxy)-benzoylamino]-3-(2'-phenoxy-biphenyl-4-yl)-propionic acid |
| 136 | 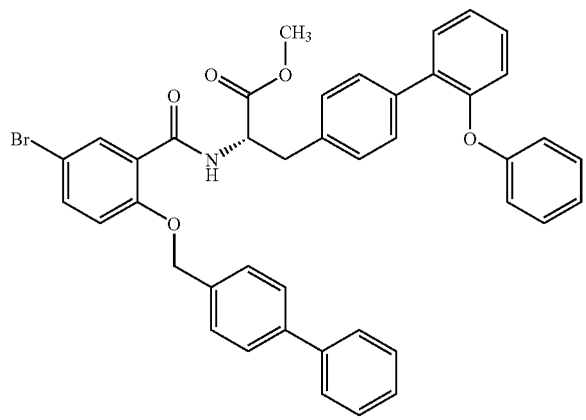 | (2S)-[2-(Biphenyl-4-ylmethoxy)-5-bromo-benzoylamino]-3-(2'-phenoxy-biphenyl-4-yl)-propionic acid methyl ester |
| 137 | 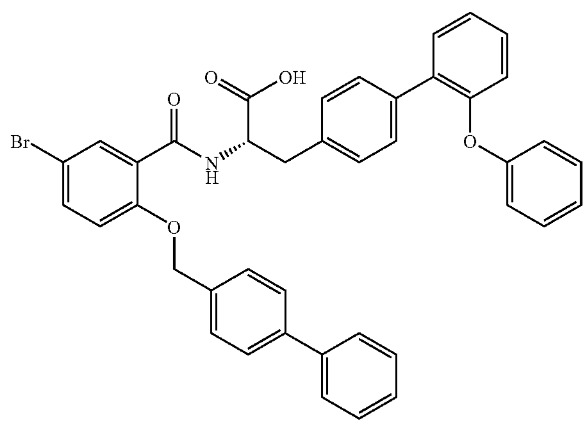 | (2S)-[2-(Biphenyl-4-ylmethoxy)-5-bromo-benzoylamino]-3-(2'-phenoxy-biphenyl-4-yl)-propionic acid |
| 138 | 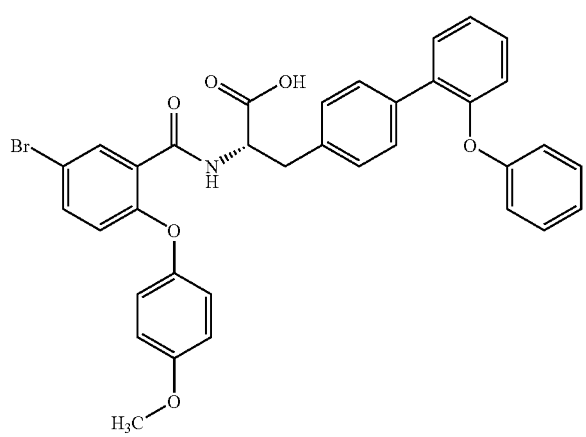 | (2S)-[5-Bromo-2-(4-methoxy-phenoxy)-benzoylamino]-3-(2'-phenoxy-biphenyl-4-yl)-propionic acid |

TABLE 1-continued

| Example | Structure | Name |
|---|---|---|
| 139 | 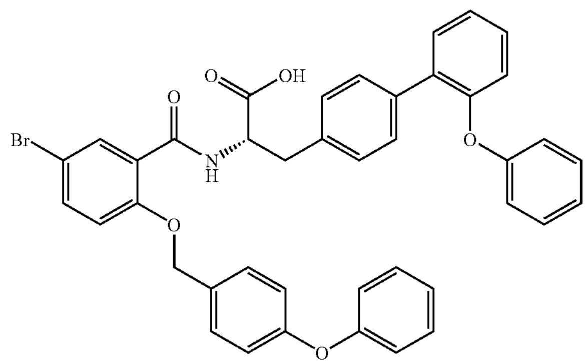 | (2S)-[5-Bromo-2-(4-phenoxy-benzoylamino]-3-(2'-phenoxy-biphenyl-4-yl)-propionic acid |
| 140 | 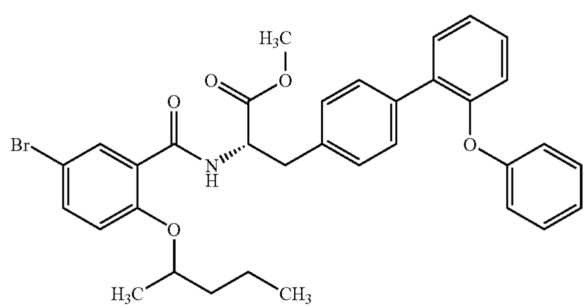 | (2S)-[5-Bromo-2-(1-methyl-butoxy)-benzoylamino]-3-(2'-phenoxy-biphenyl-4-yl)-propionic acid methyl ester |
| 141 | 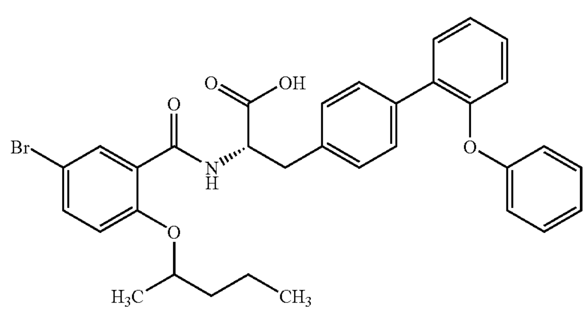 | (2S)-[5-Bromo-2-(1-methyl-butoxy)-benzoylamino]-3-(2'-phenoxy-biphenyl-4-yl)-propionic acid |
| 142 | 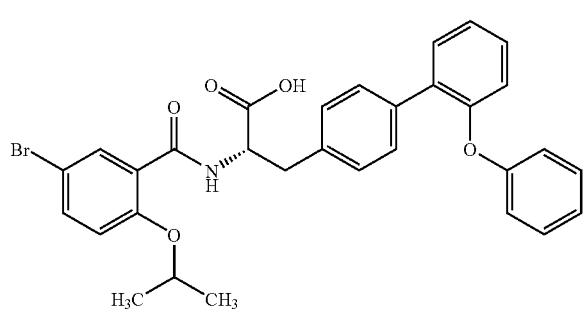 | (2S)-(5-Bromo-2-isopropoxy-benzoylamino)-3-(2'-phenoxy-biphenyl-4-yl)-propionic acid |

TABLE 1-continued

| Example | Structure | Name |
|---|---|---|
| 143 | 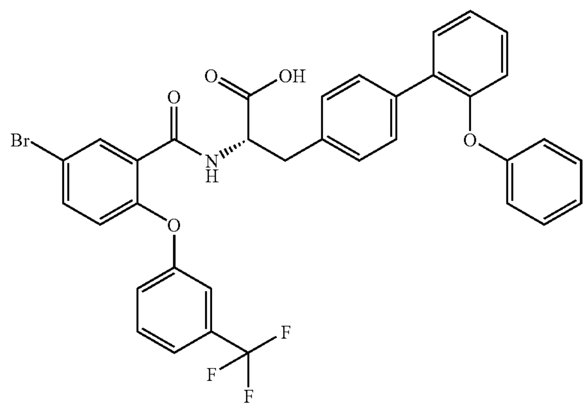 | (2S)-[5-Bromo-2-(3-trifluoromethyl-phenoxy)-benzoylamino]-3-(2'-phenoxy-biphenyl-4-yl)-propionic acid |
| 144 | 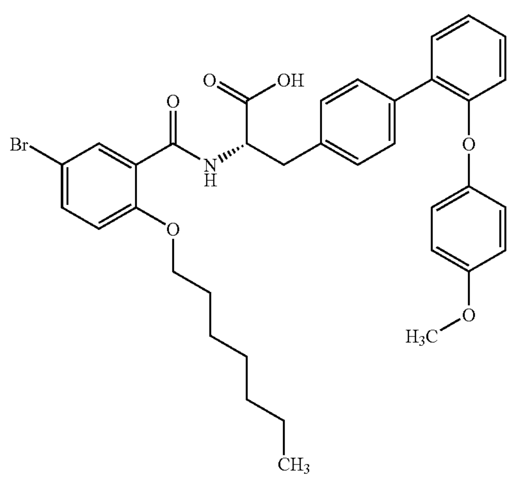 | (2S)-(5-Bromo-2-heptyloxy-benzoylamino)-3-[2'-(4-methoxy-phenoxy)-biphenyl-4-yl]-propionic acid |
| 145 | 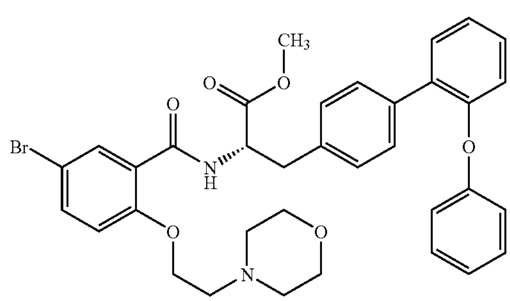 | (2S)-[5-Bromo-2-(2-morpholin-4-yl-ethoxy)-benzoylamino]-3-(2'-phenoxy-biphenyl-4-yl)-propionic acid methyl ester |
| 146 | 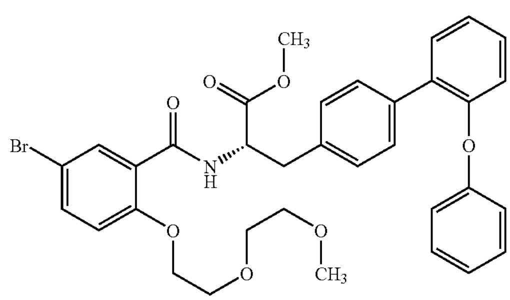 | (2S)-{5-Bromo-2-[2-(2-methoxy-ethoxy)-ethoxy]-benzoylamino}-3-(2'-phenoxy-biphenyl-4-yl)-propionic acid methyl ester |

TABLE 1-continued

| Example | Structure | Name |
| --- | --- | --- |
| 147 | 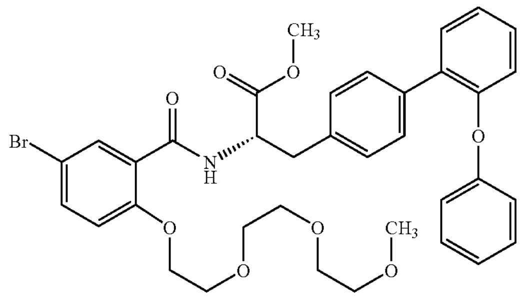 | (2S)-(5-Bromo-2-{2-[2-(2-methoxy-ethoxy)-ethoxy]-ethoxy}-benzoylamino)-3-(2'-phenoxy-biphenyl-4-yl)-propionic acid methyl ester |
| 148 | 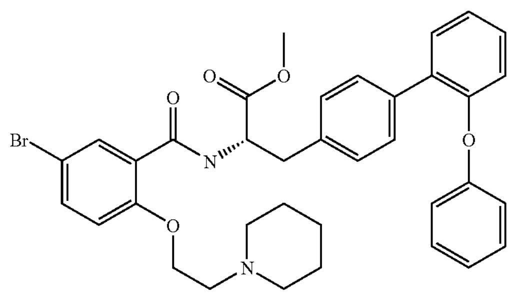 | (2S)-(5-Bromo-2-{2-[2-(2-methoxy-ethoxy)-ethoxy]-ethoxy}-benzoylamino)-3-(2'-phenoxy-biphenyl-4-yl)-propionic acid methyl ester |
| 149 | 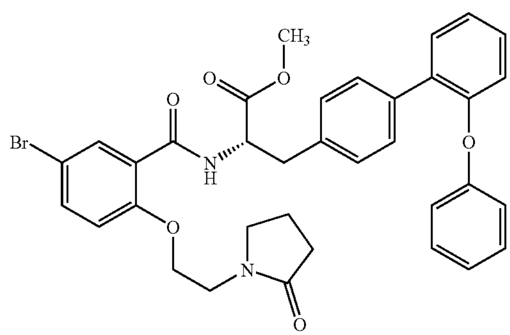 | (2S)-{5-Bromo-2-[2-(2-oxo-pyrrolidin-1-yl)-ethoxy]-benzoylamino}-3-(2'-phenoxy-biphenyl-4-yl)-propionic acid methyl ester |
| 150 | 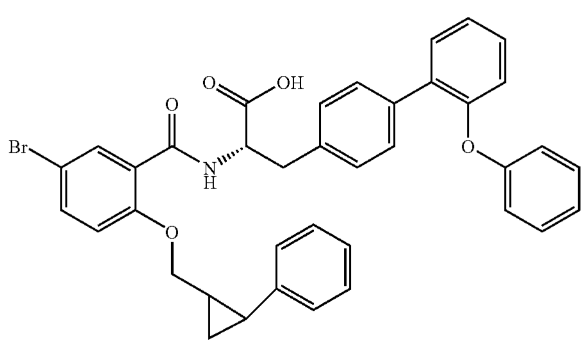 | (2S)-[5-Bromo-2-(2-phenyl-cyclopropylmethoxy)-benzoylamino]-3-(2'-phenoxy-biphenyl-4-yl)-propionic acid |

TABLE 1-continued

| Example | Structure | Name |
|---|---|---|
| 151 | 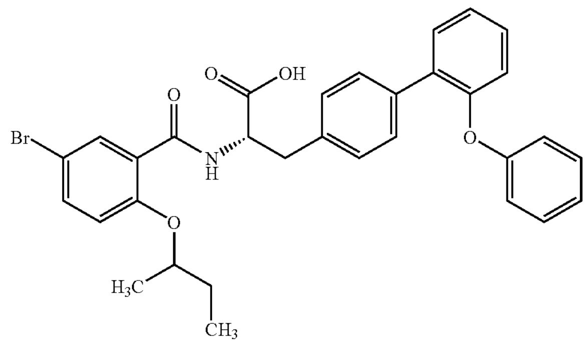 | (2S)-(5-Bromo-2-sec-butoxy-benzoylamino)-3-(2'-phenoxy-biphenyl-4-yl-propionic acid |
| 152 | 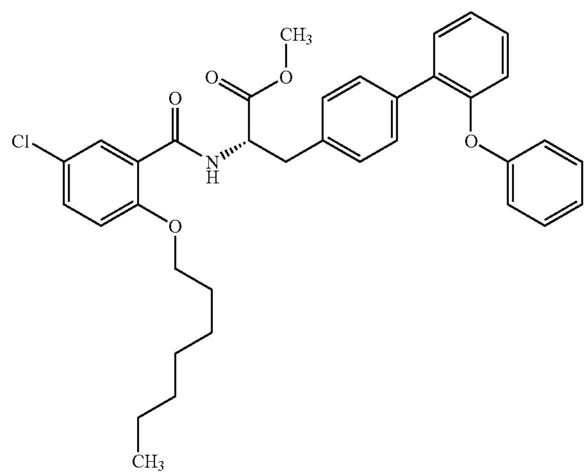 | (2S)-(5-Chloro-2-heptyloxy-benzoylamino)-3-(2'-phenoxy-biphenyl-4-yl)-propionic acid methyl ester |
| 153 | 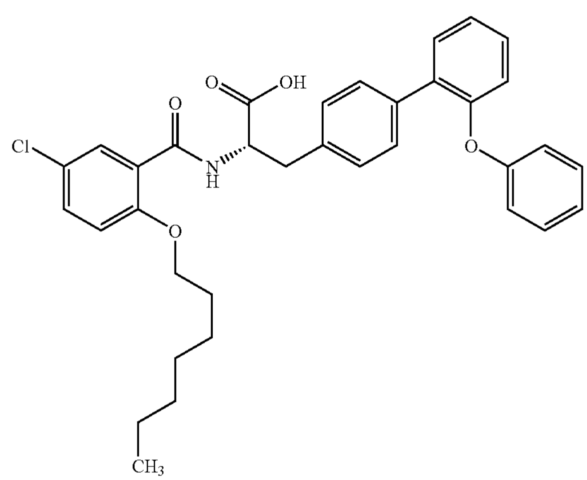 | (2S)-(5-Chloro-2-heptyloxy-benzoylamino)-3-(2'-phenoxy-biphenyl-4-yl)-propionic acid |

TABLE 1-continued

| Example | Structure | Name |
|---|---|---|
| 154 | 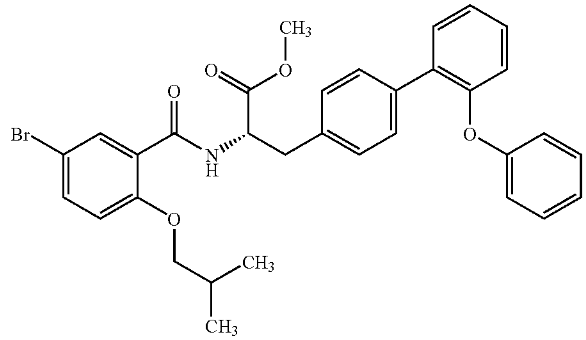 | (2S)-(5-Bromo-2-isobutoxy-benzoylamino)-3-(2'-phenoxy-biphenyl-4-yl)-propionic acid methyl ester |
| 155 | 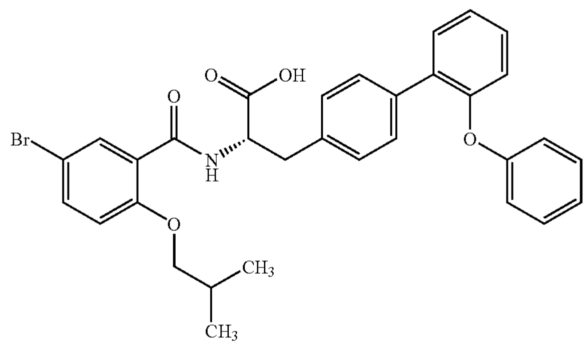 | (2S)-(5-Bromo-2-isobutoxy-benzoylamino)-3-(2'-phenoxy-biphenyl-4-yl)-propionic acid |
| 156 | 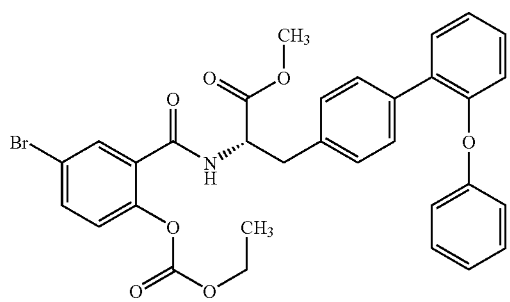 | (2S)-(5-Bromo-2-ethoxycarbonyloxy-benzoylamino)-3-(2'-phenoxy-biphenyl-4-yl)-propionic acid methyl ester |
| 157 | 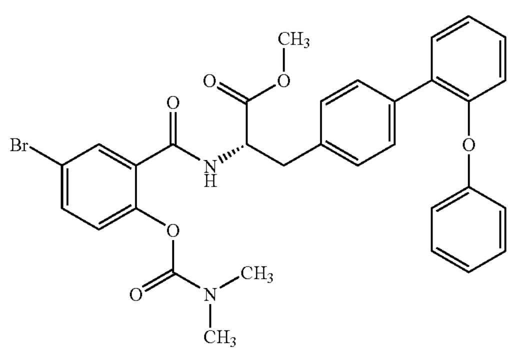 | (2S)-(5-Bromo-2-dimethylcarbamoyloxy-benzoylamino)-3-(2'-phenoxy-biphenyl-4-yl)-propionic acid methyl ester |

TABLE 1-continued

| Example | Structure | Name |
|---|---|---|
| 158 | 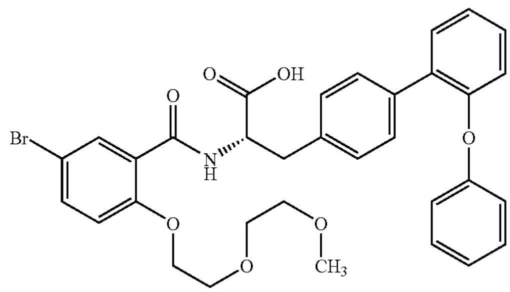 | (2S)-{5-Bromo-2-[2-(2-methoxy-ethoxy)-ethoxy]-benzoylamino}-3-(2'-phenoxy-biphenyl-4-yl)-propionic acid |
| 159 | 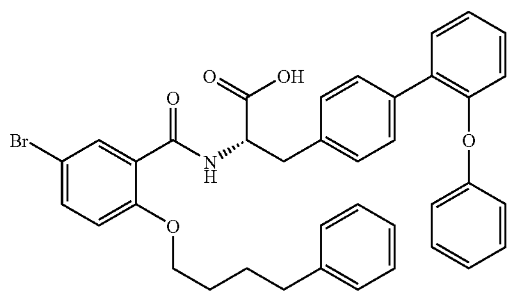 | (2S)[5-Bromo-2-(4-phenyl-butoxy)-benzoylamino]-3-(2'-phenoxy-biphenyl-4-yl)-propionic acid |
| 160 | 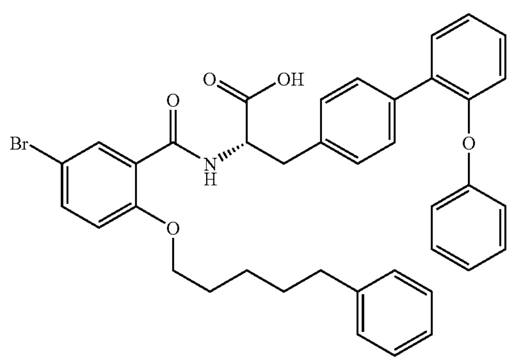 | (2S)-[5-Bromo-2-(5-phenyl-pentyloxy)-benzoylamino]-3-(2'-phenoxy-biphenyl-4-yl)-propionic acid |
| 161 | 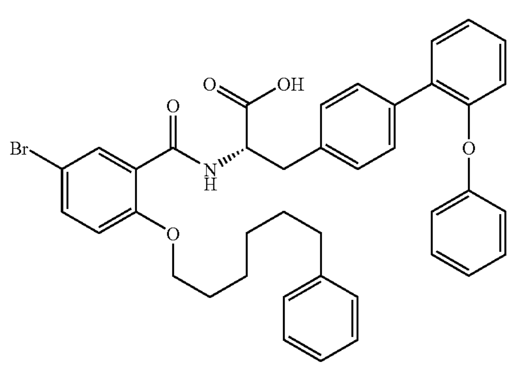 | (2S)-[5-Bromo-2-(6-phenyl-hexyloxy)-benzoylamino]-3-(2'-phenoxy-biphenyl-4-yl)-propionic acid |

TABLE 1-continued

| Example | Structure | Name |
|---|---|---|
| 162 | 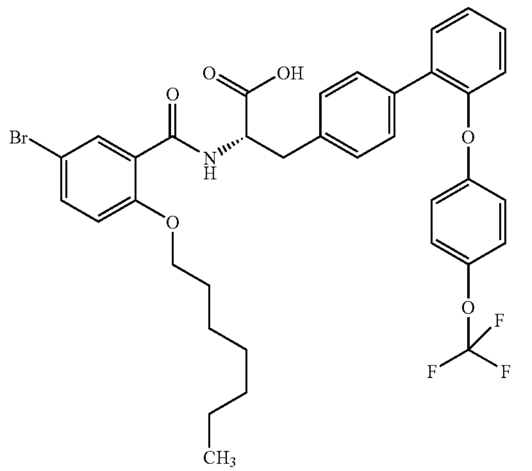 | (2S)-(5-Bromo-2-heptyloxy-benzoylamino)-3-[2'-(4-trifluoromethoxy-phenoxy)-biphenyl-4-yl]-propionic acid |
| 163 | 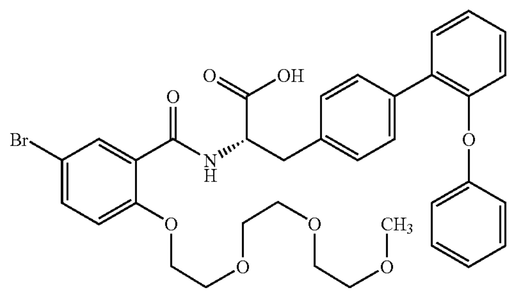 | (2S)-(5-Bromo-2-{2-[2-(2-methoxy-ethoxy)-ethoxy]-ethoxy}-benzoylamino)-3-(2'-phenoxy-bipheny-4-yl)-propionic acid |
| 164 | 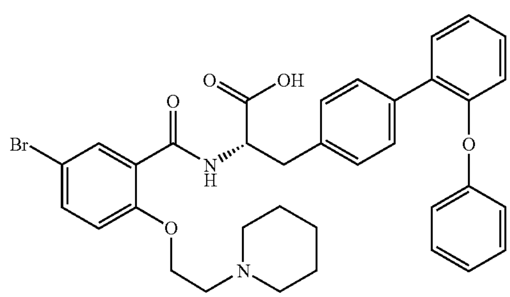 | (2S)-[5-Bromo-2-(2-piperidin-1-yl-ethoxy)-benzoylamino]-3-(2'-phenoxy-biphenyl-4-yl)-propionic acid |
| 165 | 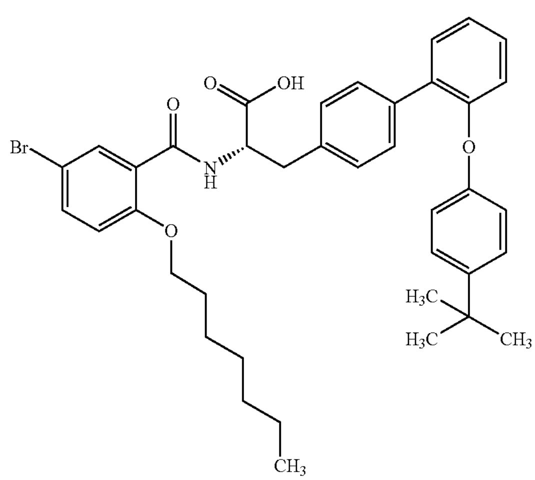 | (2S)-(5-Bromo-2-heptyloxy-benzoylamino)-3-[2'-(4-tert-butyl-phenoxy)-biphenyl-4-yl]-propionic acid |

TABLE 1-continued
| Example | Structure | Name |
|---|---|---|
| 166 | 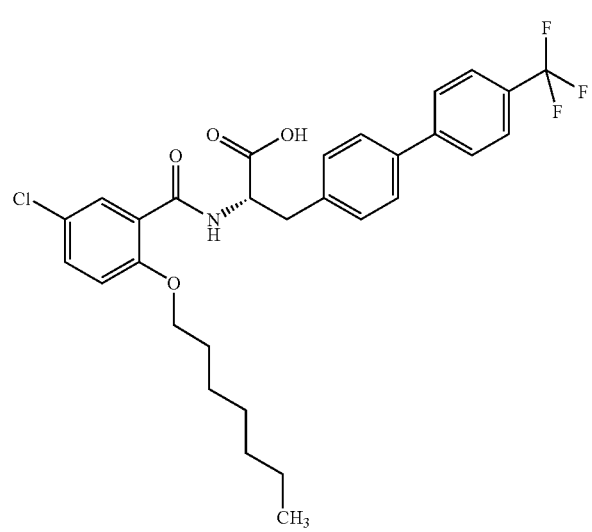 | (2S)-(5-Chloro-2-heptyloxy-benzoylamino)-3-(4'-trifluoromethyl-biphenyl-4-yl)-propionic acid |
| 167 | 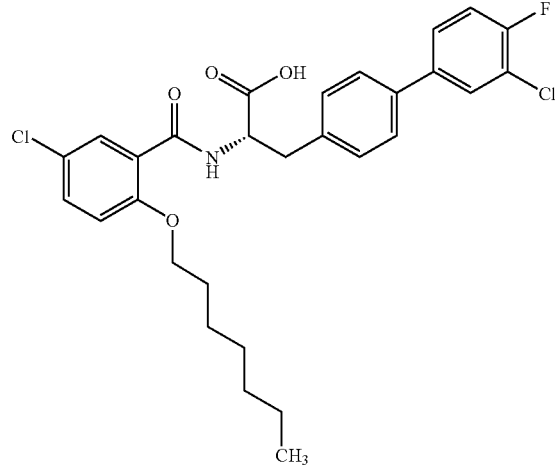 | 3-(3'-Chloro-4'-fluoro-biphenyl-4-yl)-(2S)-(5-chloro-2-heptyloxy-benzoylamino)-propionic acid |
| 168 | 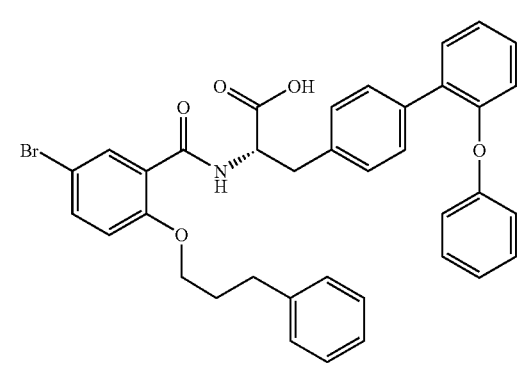 | (2S)-[5-Bromo-2-(3-phenyl-propoxy)-benzoylamino]-3-(2'-phenoxy-biphenyl-4-yl)-propionic acid |

TABLE 1-continued

| Example | Structure | Name |
|---------|-----------|------|
| 169 | 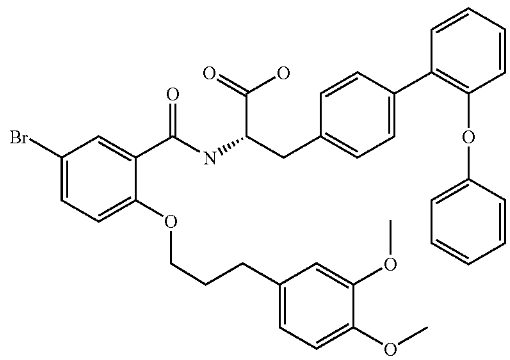 | (2S)-{5-Bromo-2-[3-(3,4-dimethoxy-phenyl)-propoxy]-benzoylamino}-3-(2'-phenoxy-biphenyl-4-yl)-propionic acid |
| 170 | 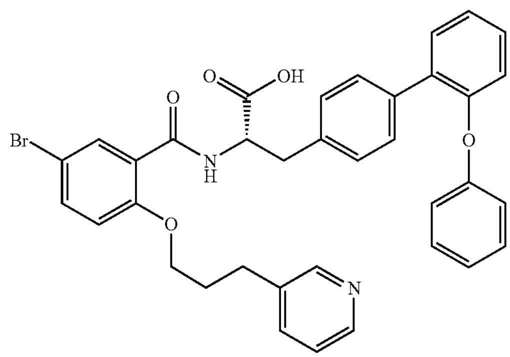 | (2S)-[5-Bromo-2-(3-pyridin-3-yl-propoxy)-benzoylamino]-3-(2'-phenoxy-biphenyl-4-yl)-propionic acid |
| 171 | 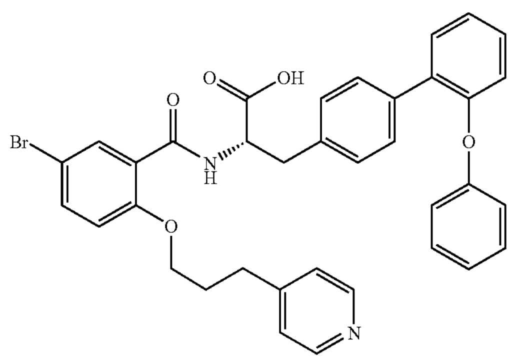 | (2S)-[5-Bromo-2-(3-pyridin-4-yl-propoxy)-benzoylamino]-3-(2'-phenoxy-biphenyl-4-yl)-propionic acid |
| 172 | 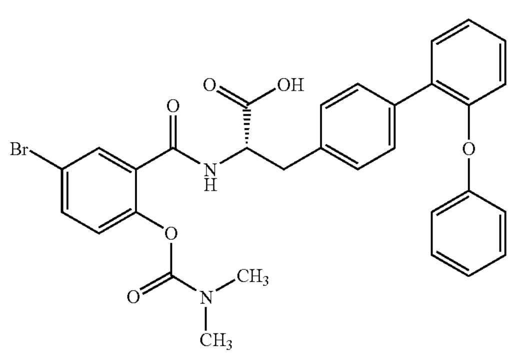 | (2S)-(5-Bromo-2-dimethylcarbamoyloxy-benzoylamino)-3-(2'-phenoxy-biphenyl-4-yl)-propionic acid |

TABLE 1-continued

| Example | Structure | Name |
|---|---|---|
| 173 | 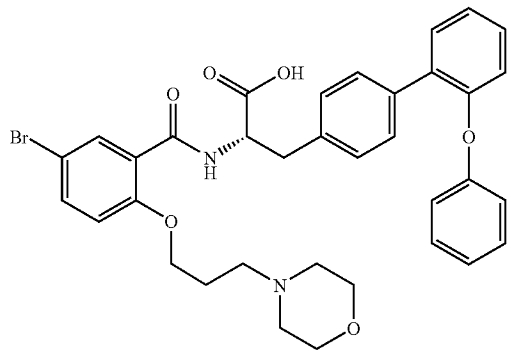 | (2S)-[5-Bromo-2-(3-morpholin-4-yl-propoxy)-benzoylamino]-3-(2'-phenoxy-biphenyl-4-yl)-propionic acid |
| 174 | 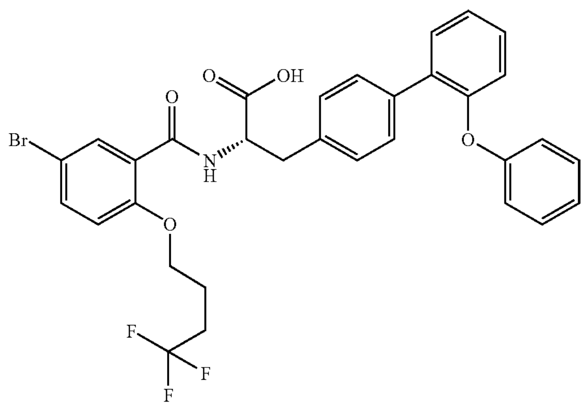 | (2S)-[5Bromo-2-(4,4,4-trifluoro-butoxy)-benzoylamino]-3-(2'-phenoxy-biphenyl-4-yl)-propionic acid |
| 175 | 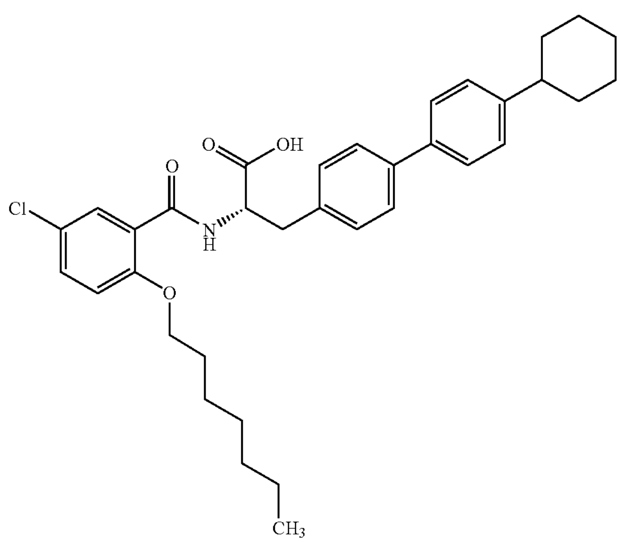 | (2S)-(5-Chloro-2-heptyloxy-benzoylamino)-3-(4'-cyclohexyl-biphenyl-4-yl)-propionic acid |

TABLE 1-continued

| Example | Structure | Name |
| --- | --- | --- |
| 176 | 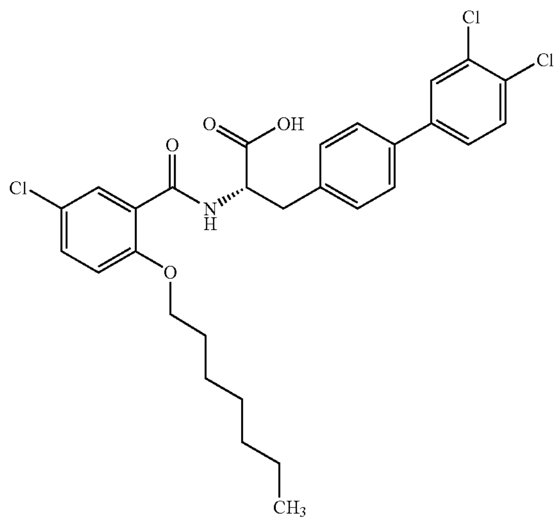 | (2S)-(5-Chloro-2-heptyloxy-benzoylamino)-3-(3',4'-dichloro-biphenyl-4-yl)-propionic acid |
| 177 | 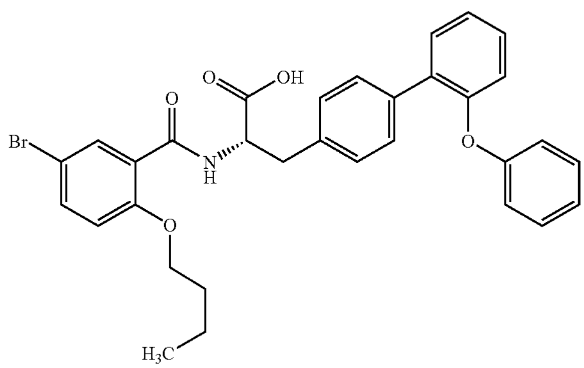 | (2S)-(5-Bromo-2-butoxy-benzoylamino)-3-(2'-phenoxy-biphenyl-4-yl)-propionic acid |
| 178 | 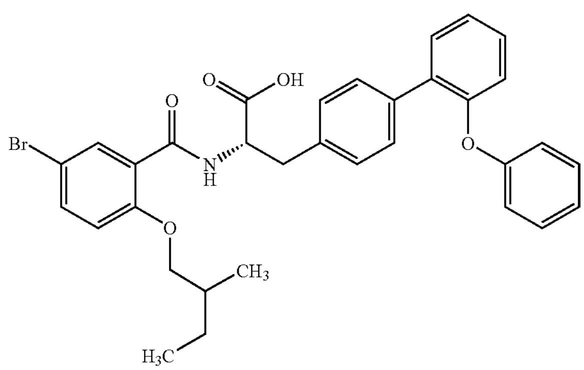 | (2S)-[5-Bromo-2-(2-methyl-butoxy)-benzoylamino]-3-(2'-phenoxy-biphenyl-4-yl)-propionic acid |
| 179 | 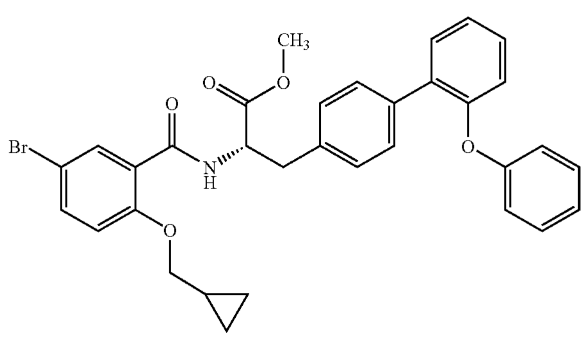 | (2S)-(5-Bromo-2-cyclopropylmethoxy-benzoylamino)-3-(2'-phenoxy-biphenyl-4-yl)-propionic acid methyl ester |

TABLE 1-continued

| Example | Structure | Name |
| --- | --- | --- |
| 180 | 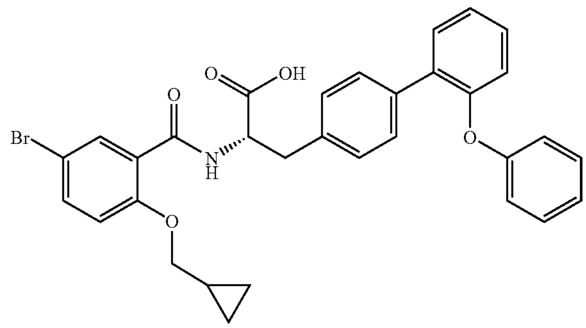 | (2S)-(5-Bromo-2-cyclopropylmethoxy-benzoylamino)-3-(2'-phenoxy-biphenyl-4-yl)-propionic acid |
| 181 | 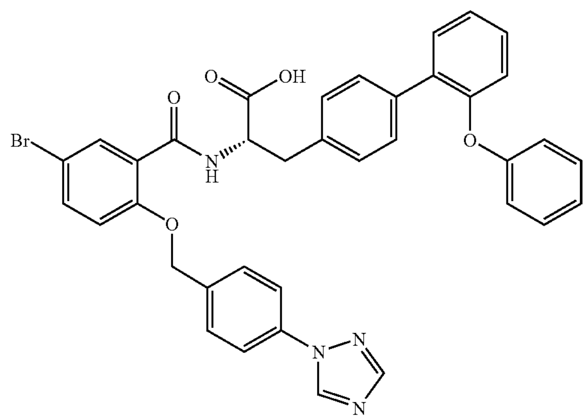 | (2S)-[5-Bromo-2-(4-[1,2,4]triazol-1-yl-benzyloxy)-benzoylamino]-3-(2'-phenoxy-biphenyl-4-yl)-propionic acid |
| 182 | 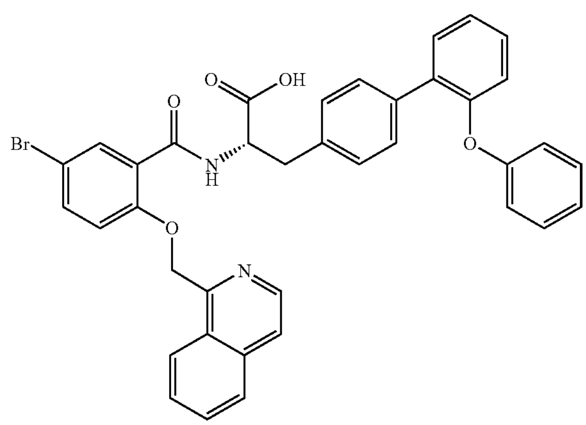 | (2S)-[5-Bromo-2-(isoquinolin-1-ylmethoxy)-benzoylamino]-3-(2'-phenoxy-biphenyl-4-yl)-propionic acid |
| 183 | 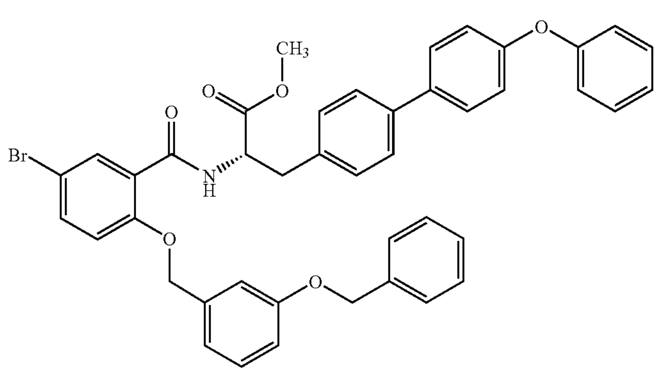 | (2S)-[2-(3-Benzyloxy-benzyloxy)-5-bromo-benzoylamino]-3-(4'-phenoxy-biphenyl-4-yl)-propionic acid methyl ester |

TABLE 1-continued

| Example | Structure | Name |
|---|---|---|
| 184 | 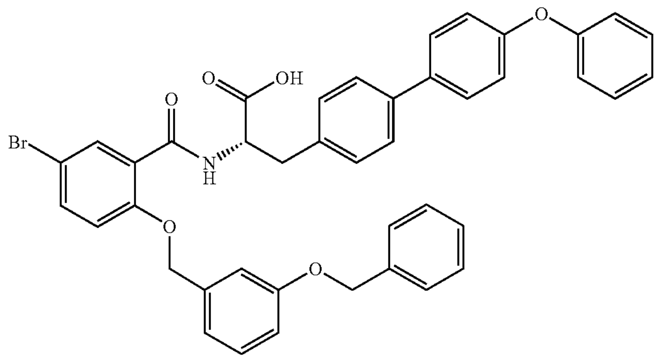 | (2S)-[2-(3-Benzyloxy-benzyloxy)-5-bromo-benzoylamino]-3-(4'-phenoxy-biphenyl-4-yl)-propionic acid |
| 185 | 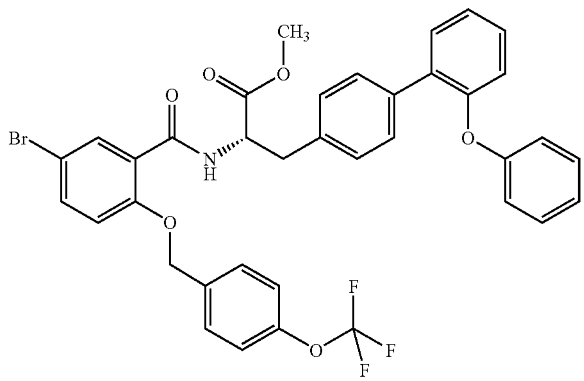 | (2S)-[5-Bromo-2-(4-trifluoromethoxy-benzyloxy)-benzoylamino]-3-(2'-phenoxy-biphenyl-4-yl)-propionic acid methyl ester |
| 186 | 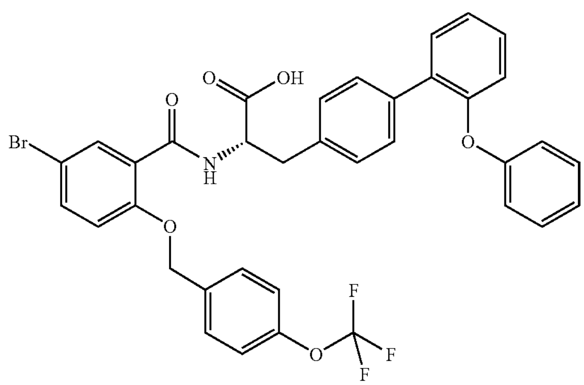 | (2S)-[5-Bromo-2-(4-trifluoromethoxy-benzyloxy)-benzoylamino]-3-(2'-phenoxy-biphenyl-4-yl)-propionic acid |
| 187 | 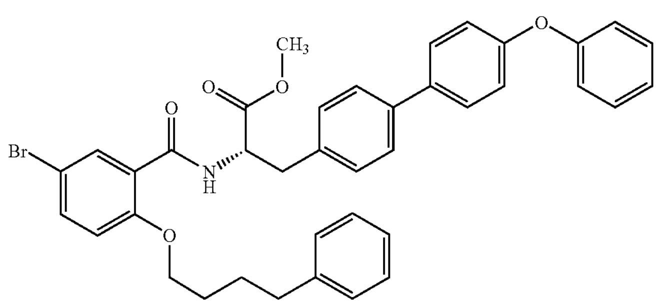 | (2S)-[5-Bromo-2-(4-phenyl-butoxy)-benzoylamino]-3-(4'-phenoxy-biphenyl-4-yl)-propionic acid methyl ester |

TABLE 1-continued

| Example | Structure | Name |
| --- | --- | --- |
| 188 | 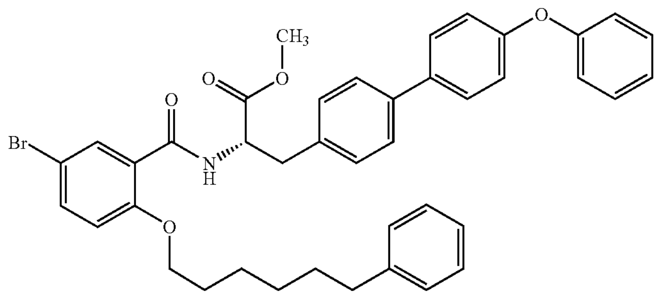 | (2S)-[5-Bromo-2-(6-phenyl-hexloxy)-benzoylamino]-3-(4'-phenoxy-biphenyl-4-yl)-propionic acid methyl ester |
| 189 | 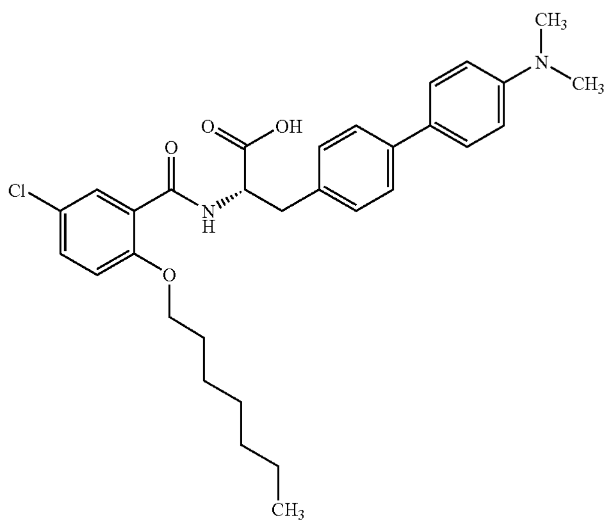 | (2S)-(5-Chloro-2-heptyloxy-benzoylamino)-3-(4'-dimethylamino-biphenyl-4-yl)-propionic acid |
| 190 | 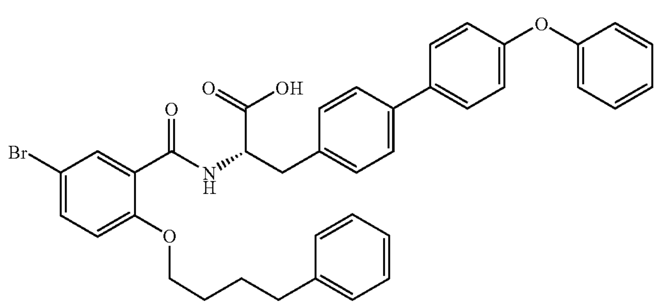 | (2S)-[5-Bromo-2-(4-phenyl-butoxy)-benzoylamino]-3-(4'-phenoxy-biphenyl-4-yl)-propionic acid |
| 191 | 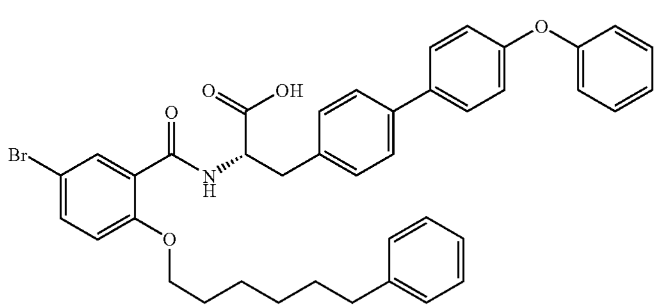 | (2S)-[5-Bromo-2-(6-phenyl-hexyloxy)-benzoylamino]-3-(4'-phenoxy-biphenyl-4-yl)-propionic acid |

TABLE 1-continued

| Example | Structure | Name |
|---|---|---|
| 192 | 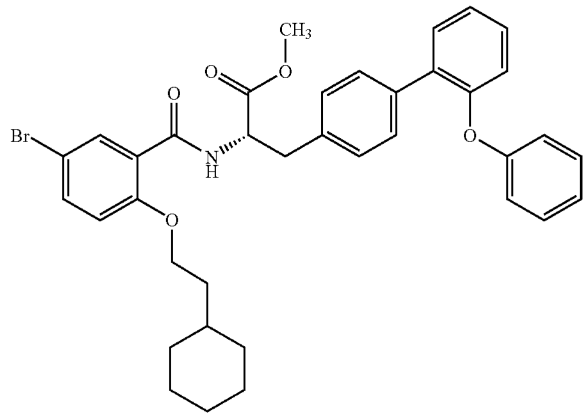 | (2S)-[5-Bromo-2-(2-cyclohexyl-ethoxy)-benzoylamino]-3-(2'-phenoxy-biphenyl-4-yl)-propionic acid methyl ester |
| 193 | 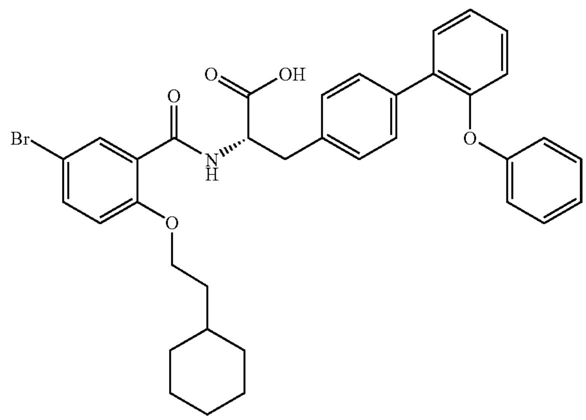 | (2S)-[5-Bromo-2-(2-cyclohexyl-ethoxy)-benzoylamino]-3-(2'-phenoxy-biphenyl-4-yl)-propionic acid |
| 194 | 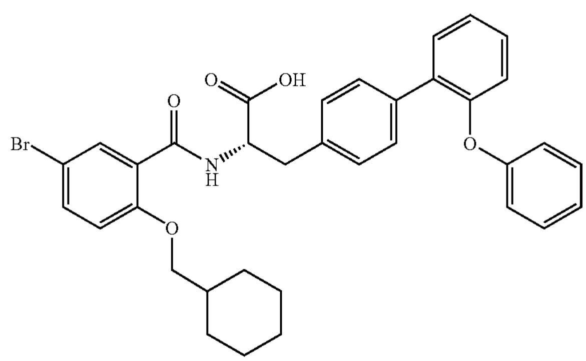 | (2S)-(5-Bromo-2-cyclohexylmethoxy-benzoylamino)-3-(2'-phenoxy-biphenyl-4-yl)-propionic acid |
| 195 | 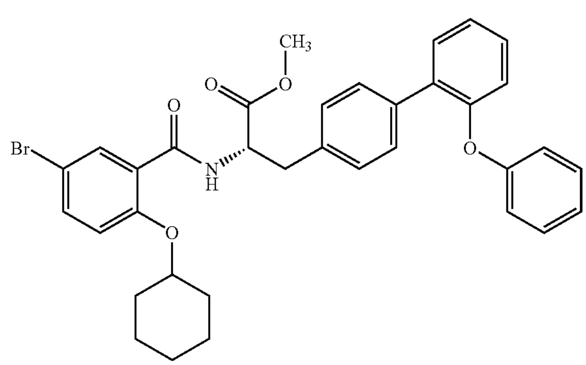 | (2S)-(5-Bromo-2-cyclohexyloxy-benzoylamino)-3-(2'-phenoxy-biphenyl-4-yl)-propionic acid methyl ester |

TABLE 1-continued

| Example | Structure | Name |
|---------|-----------|------|
| 196 | 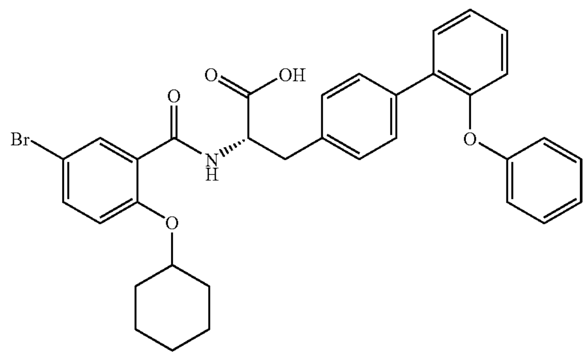 | (2S)-(5-Bromo-2-cyclohexyloxy-benzoylamino)-3-(2'-phenoxy-biphenyl-4-yl)-propionic acid |
| 197 | 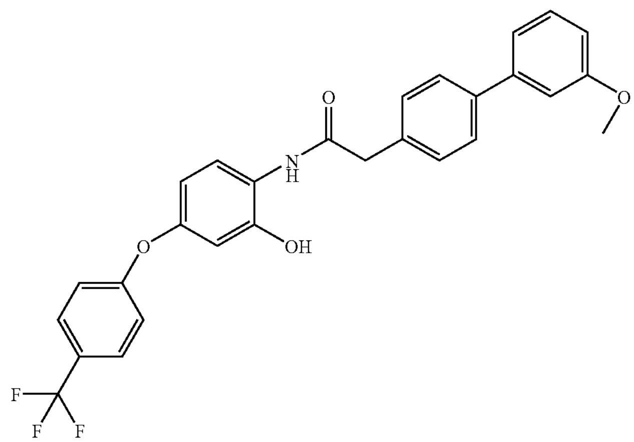 | N-[2-Hydroxy-4-(4-trifluoromethyl-phenoxy)-phenyl]-2-(3'-methoxy-biphenyl-4-yl)-acetamide |
| 198 | 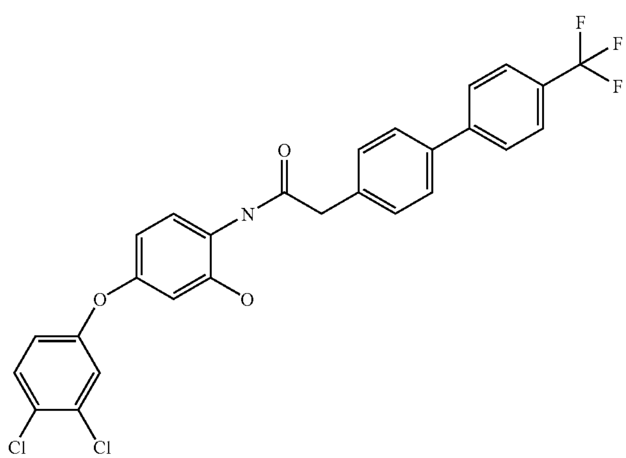 | N-[2-Hydroxy-4-(3,4-dichloro-phenoxy)-phenyl]-2-(4'-trifluoromethyl-biphenyl-4-yl)-acetamide |

TABLE 1-continued

| Example | Structure | Name |
|---|---|---|
| 199 | 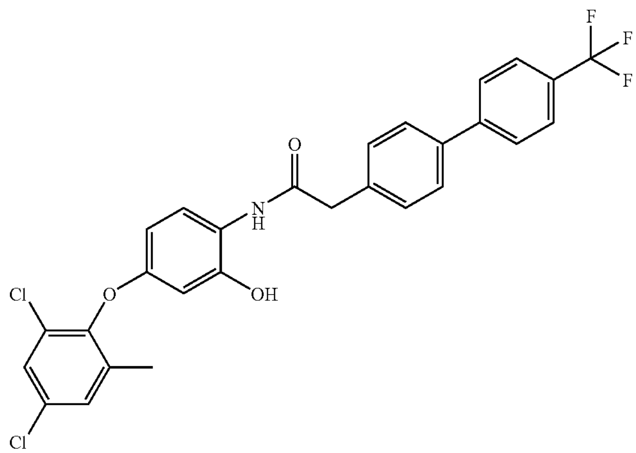 | N-[2-Hydroxy-4-(2,4-dichloro-6-methyl-phenoxy)-phenyl]-2-(4'-trifluoromethyl-biphenyl-4-yl)-acetamide |
| 200 | 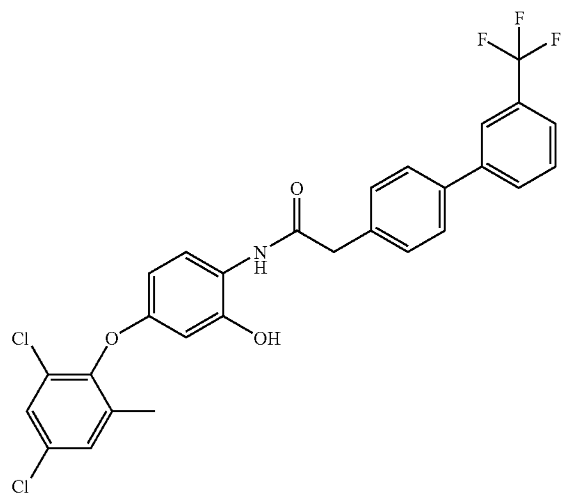 | N-[2-Hydroxy-4-(2,4-dichloro-6-methyl-phenoxy)-phenyl]-2-(3'-trifluoromethyl-biphenyl-4-yl)-acetamide |
| 201 | 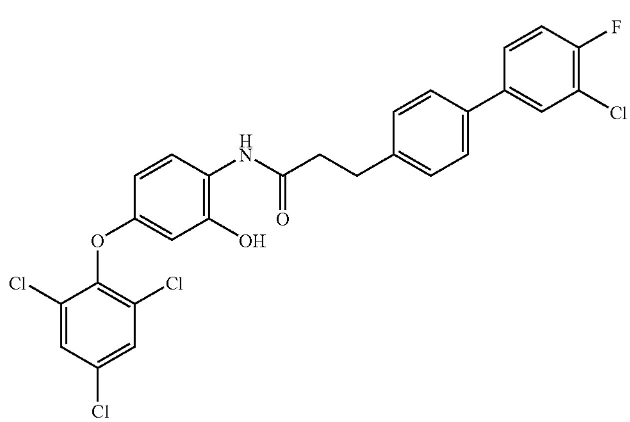 | 3-(3'-Chloro-4'-fluoro-biphenyl-4-yl)-N-[4-(2,4-dichloro-6-methyl-phenoxy)-2-hydroxy-phenyl]-propionamide |

TABLE 1-continued

| Example | Structure | Name |
|---|---|---|
| 202 | 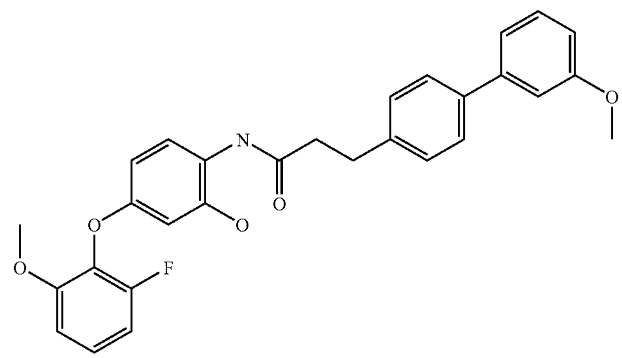 | N-[4-(2-Fluoro-6-methoxy-phenoxy)-2-hydroxy-phenyl]-3-(3'-methoxy-biphenyl-4-yl)-propionamide |
| 203 | 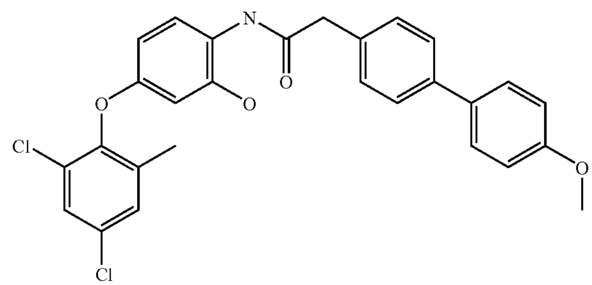 | N-[4-(2,4-Dichloro-6-methyl-phenoxy)-2-hydroxy-phenyl]-2-(4'-methoxy-biphenyl-4-yl-acetamide |
| 204 | 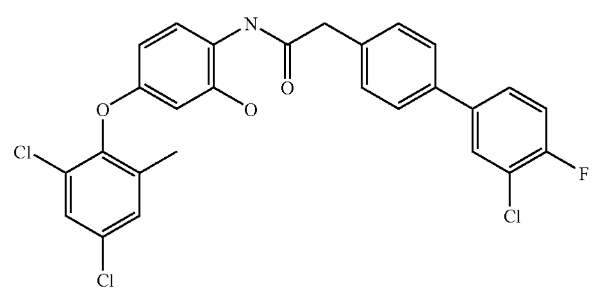 | 2-(3'-Chloro-4'-fluoro-biphenyl-4-yl)-N-[4-(2,4-dichloro-6-methyl-phenoxy)-2-hydroxy-phenyl]-acetamide |
| 205 | 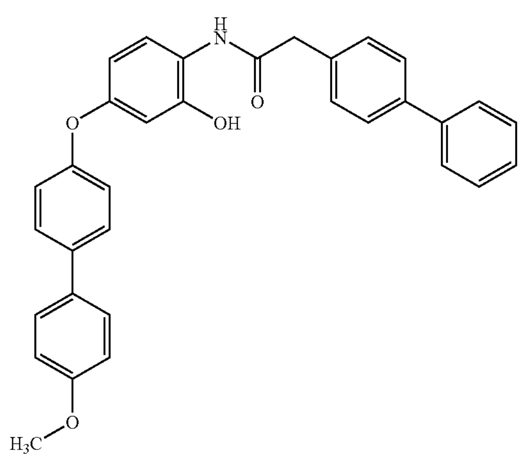 | 2-Biphenyl-4-yl-N-[2-hydroxy-4-)4'-methoxy-biphenyl-4-yloxy)-phenyl]-acetamide |

TABLE 1-continued

| Example | Structure | Name |
|---|---|---|
| 206 | 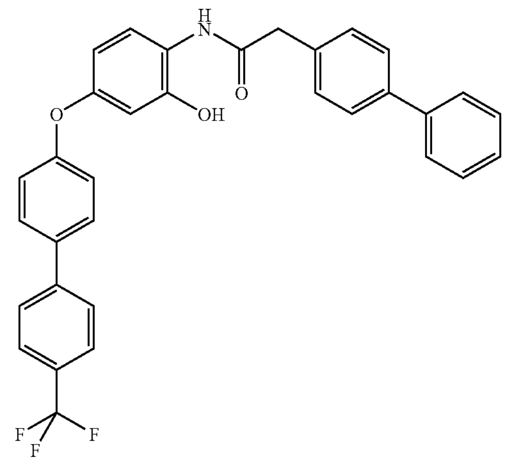 | 2-Biphenyl-4-yl-N-[2-hydroxy-4-(4'-trifluoromethyl-biphenyl-4-yloxy)-phenyl]-acetamide |
| 207 | 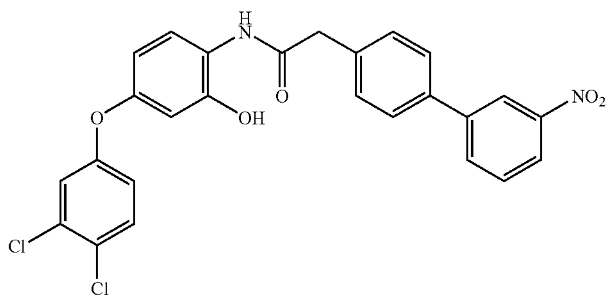 | N-[4-(3,4-Dichloro-phenoxy)-2-hydroxy-phenyl]-2-(3'-nitro-biphenyl-4-yl)-acetamide |
| 208 | 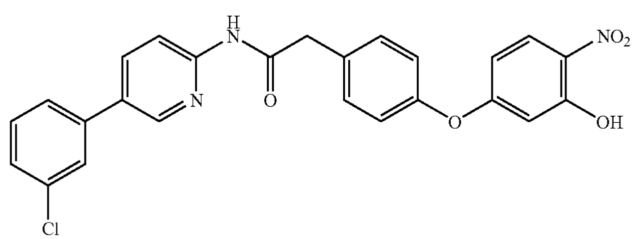 | N-[5-(3-Chloro-phenyl)-pyridin-2-yl]-2-[4-(3-hydroxy-4-nitro-phenoxy)-phenyl]-acetamide |
| 209 | 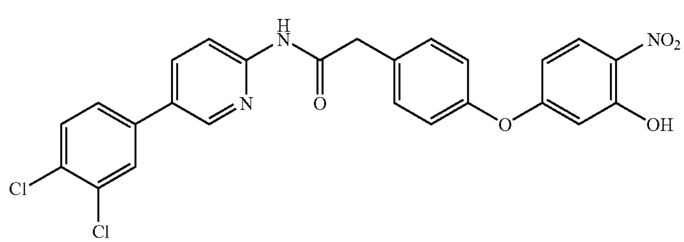 | N-[5-(3,4-Dichloro-phenyl)-pyridin-2-yl]-2-[4-(3-hydroxy-4-nitro-phenoxy)-phenyl]-acetamide |
| 210 | 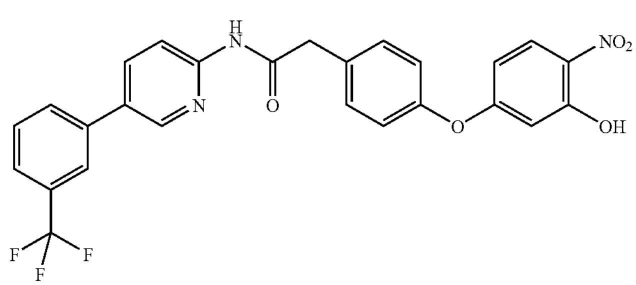 | N-[5-(3-Trifluromethyl-phenyl)-pyridin-2-yl]-2-[4-(3-hydroxy-4-nitro-phenoxy)-phenyl]-acetamide |

TABLE 1-continued

| Example | Structure | Name |
|---|---|---|
| 211 | 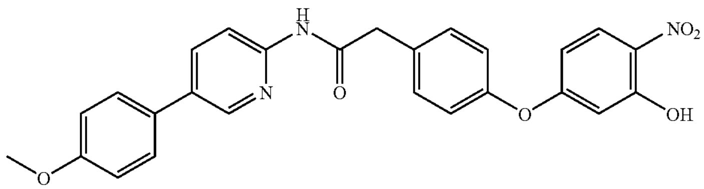 | N-[5-(4-Methoxy-phenyl)-pyridin-2-yl]-2-[4-(3-hydroxy-4-nitro-phenoxy)-phenyl]-acetamide |
| 212 | 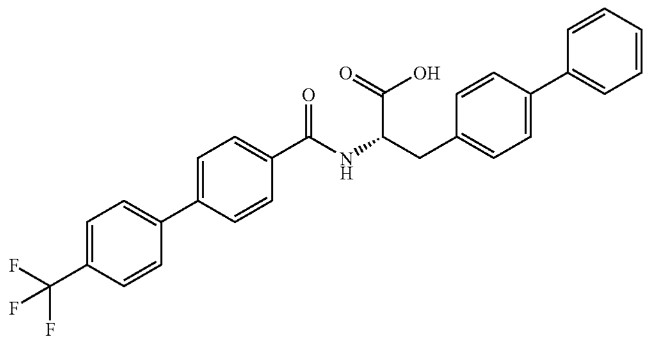 | 3-Biphenyl-4-yl-(2S)-[(4'-trifluoromethyl-bipheynl-4-carbonyl)-amino]-propionic acid |
| 213 | 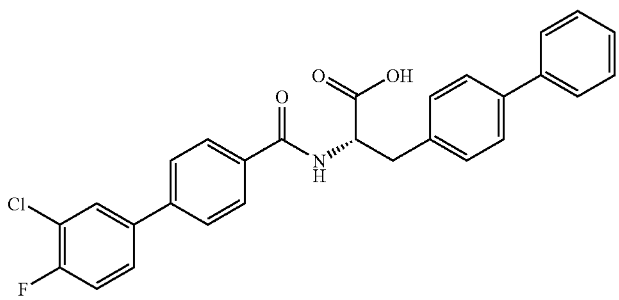 | 3-Biphenyl-4-yl-(2S)-[(3'-chloro-4'-fluoro-biphenyl-4-carbonyl)-amino]-propionic acid |
| 214 | 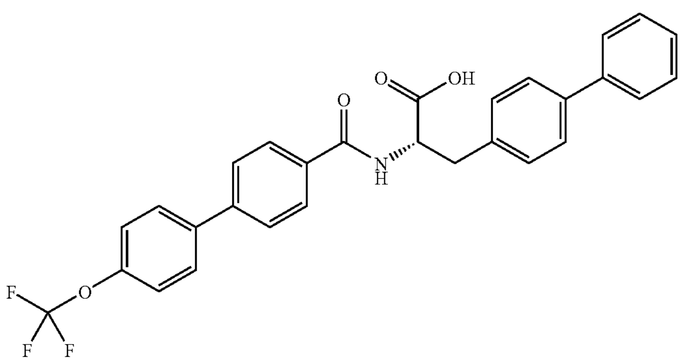 | 3-Biphenyl-4-yl-(2S)-[(4'-trifluoromethoxy-biphenyl-4-carbonyl)-amino]-propionic acid |
| 215 | 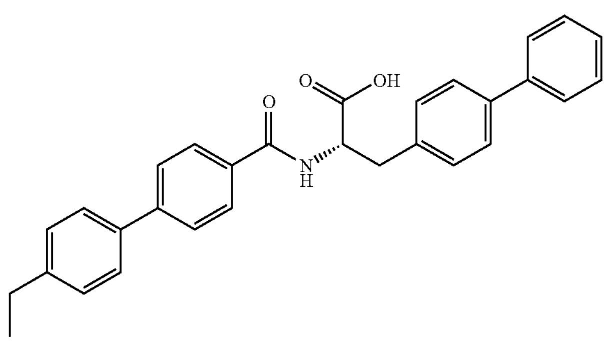 | 3-Biphenyl-4-yl-(2S)-[(4'-ethyl-biphenyl-4-carbonyl)-amino]-propionic acid |

TABLE 1-continued

| Example | Structure | Name |
|---|---|---|
| 216 | 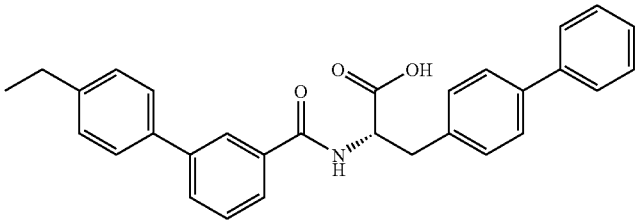 | 3-Biphenyl-4-yl-(2S)-[(3'-ethyl-biphenyl-3-carbonyl)-amino]-propionic acid |
| 217 | 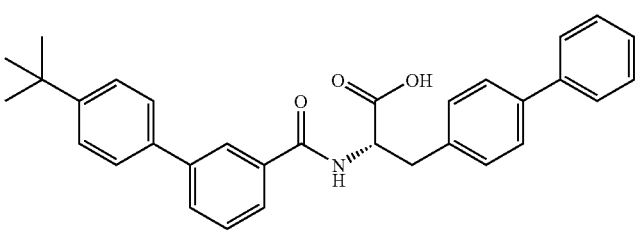 | 3-Biphenyl-4-yl-(2S)-[(4'-tert-butylbiphenyl-3-carbonyl)-amino]-propionic acid |
| 218 | 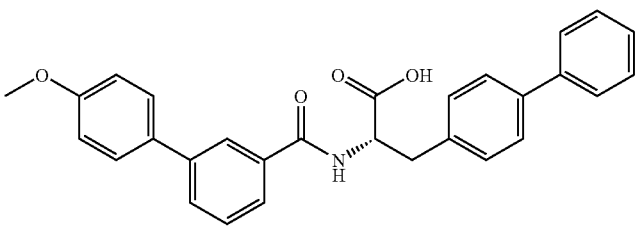 | 3-Biphenyl-4-yl-(2S)-[(4'-methoxy-biphenyl-3-carbonyl)-amino]-propionic acid |
| 219 | 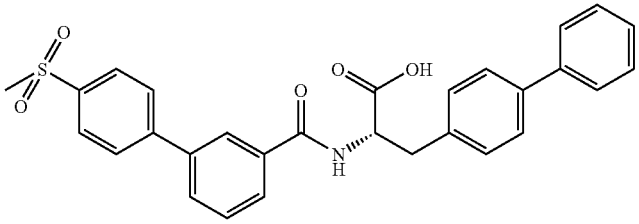 | 3-Biphenyl-4-yl-(2S)-[(4'-methane-sulfonyl-biphenyl-3-carbonyl)-amino]-propionic acid |
| 220 | 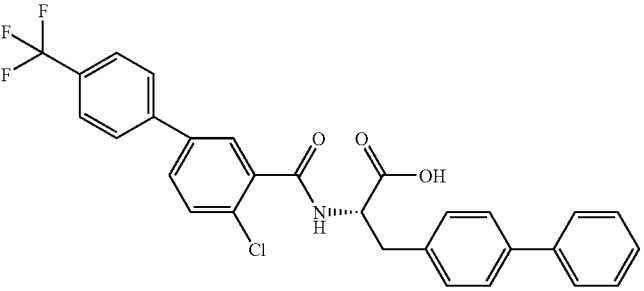 | 3-Biphenyl-4-yl-(2S)-[(4'-tert-butyl-4-chloro-biphenyl-3-carbonyl)-amino]-propionic acid |
| 221 | 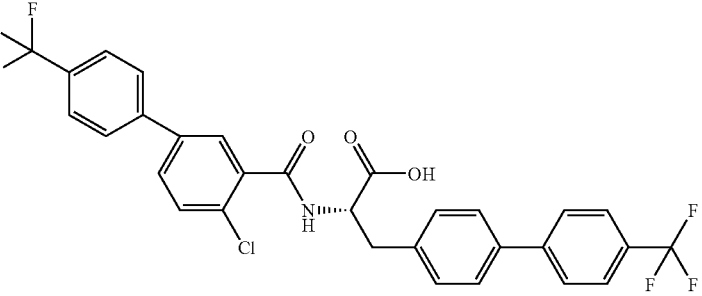 | (2S)-[(4-Chloro-4'-trifluoromethyl-biphenyl-3-carbonyl)-amino]-3-(4'-trifluoromethyl-biphenyl-4-yl)-propionic acid |

TABLE 1-continued

| Example | Structure | Name |
|---|---|---|
| 222 | 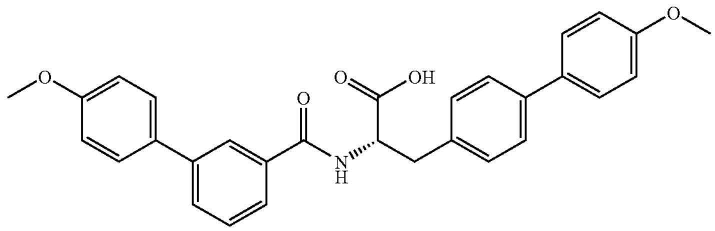 | (2S)-[(-4'-Methoxy-biphenyl-3-carbonyl)-amino]-3-(4'-methoxyl-biphenyl-4-yl)-propionic acid |
| 223 | 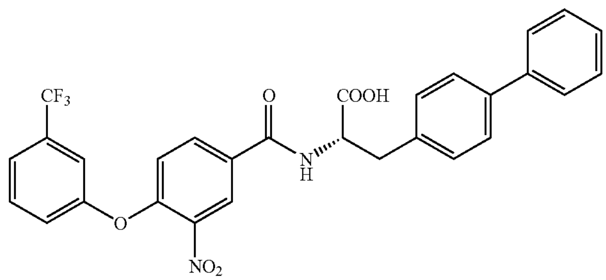 | 3-Biphenyl-4-yl-(2S)-[3-nitro-4-(3-trifluoromethyl-phenoxy)-benzoylamino]-propionic acid |
| 224 | 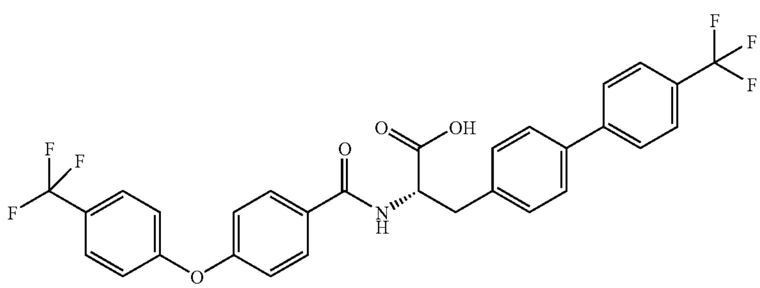 | 3-(4'-Trifluoromethyl-biphenyl-4-yl)-(2S)-[4-(4-trifluoromethyl-phenoxy)-benzoylamino]-propionic acid |
| 225 | 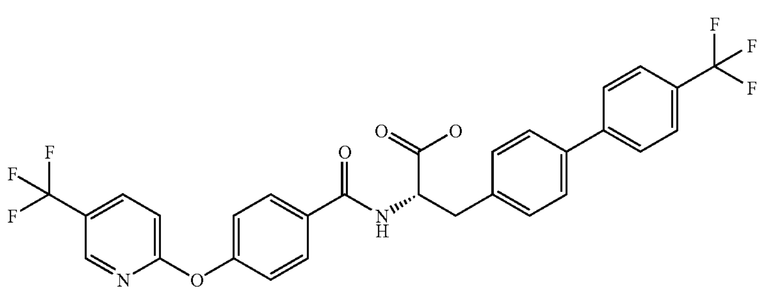 | 3-(4'-Trifluoromethyl-biphenyl-4-yl)-(2S)-[4-(5-trifluoromethyl-pyridin-2-yloxy)-benzoylamino]-propionic acid |
| 226 | 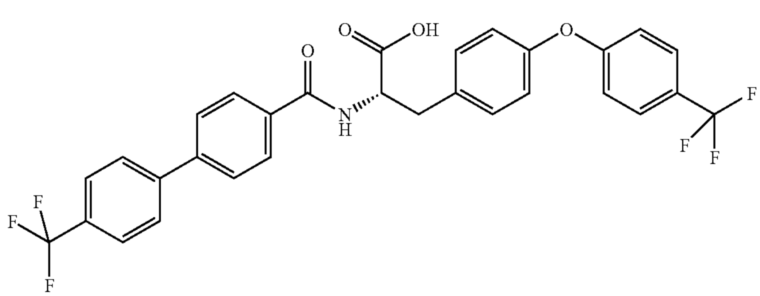 | 3-[4-(4-Trifluoromethyl-phenoxy)-phenyl]-(2S)-[(4'-trifluoromethyl-biphenyl-4-carbonyl)-amino]-propionic acid |

TABLE 1-continued

| Example | Structure | Name |
|---|---|---|
| 227 | 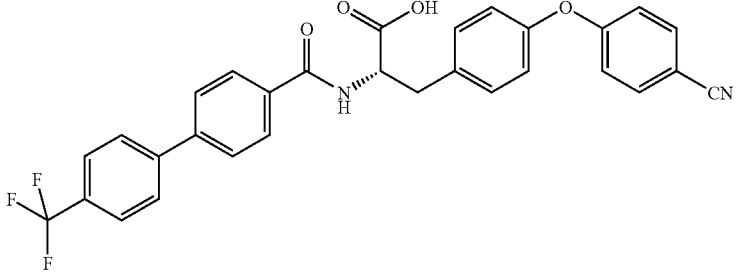 | 3-[4-(4-Cyano-phenoxy)-phenyl]-(2S)-[(4'-trifluoromethyl-biphenyl-4-carbonyl)-amino]-propionic acid |
| 228 | 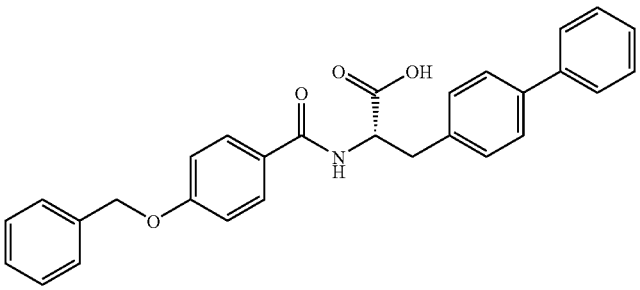 | 2S-(4-Benzyloxy-benzoylamino)-3-biphenyl-4-yl-propionic acid |
| 229 | 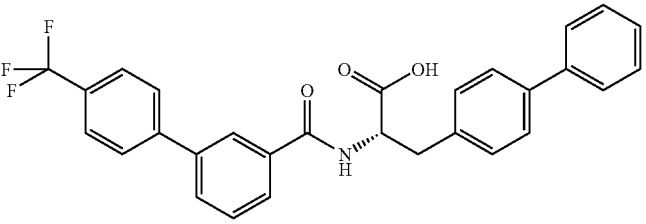 | 3-Biphenyl-4-yl-(2S)-[(4'-trifluoromethyl-biphenyl-3-carbonyl)-amino]-propionic acid |
| 230 | 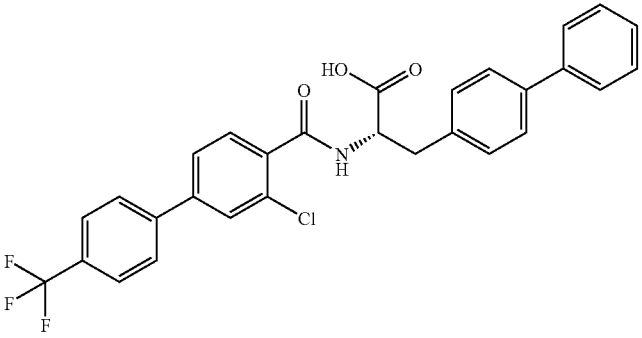 | 3-Biphenyl-4-yl-(2S)-[(3-chloro-4'-trifluoromethyl-biphenyl-4-carbonyl)-amino]-propionic acid |
| 231 | 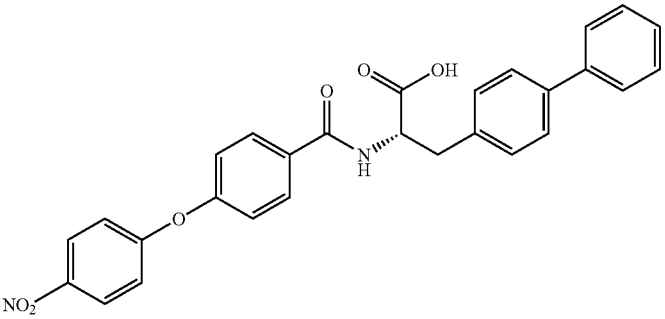 | 3-Biphenyl-4-yl-(2S)-[4-(4-nitro phenoxy)-benzoylamino]- propionic acid |

TABLE 1-continued

| Example | Structure | Name |
|---|---|---|
| 232 | 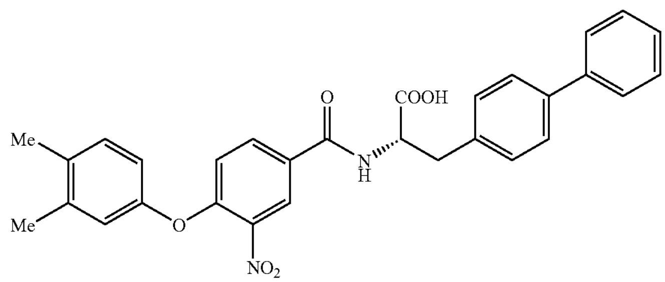 | 3-Biphenyl-4-yl-(2S)-[4-(3,4-dimethyl-phenoxy)-3-nitro-benzoylamino]-propionic acid |
| 233 | 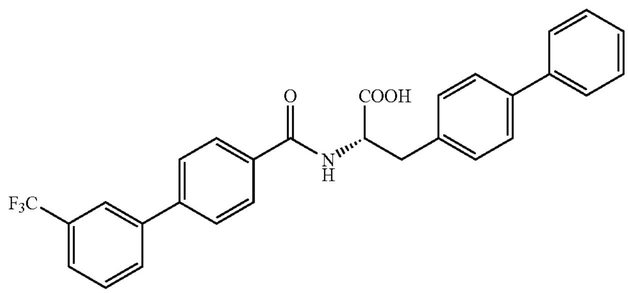 | 3-Biphenyl-4-yl-(2S)-[(3'-trifluoromethyl-biphenyl-4-carbonyl)-amino]-propionic acid |
| 234 | 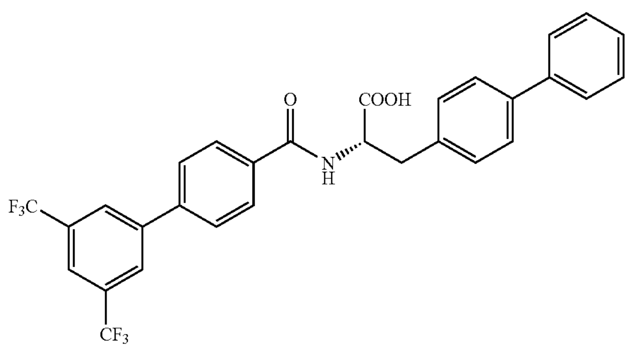 | 3-Biphenyl-4-yl-(2S)-[(3',5'-bis-trifluoromethyl-biphenyl-4-carbonyl)-amino]-propionic acid |
| 235 | 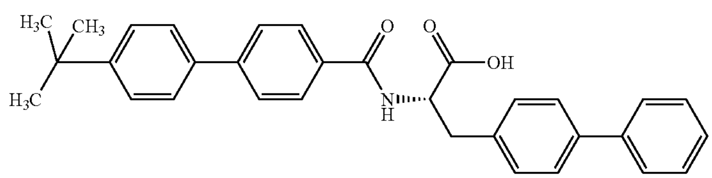 | 3-Biphenyl-4-yl-(2S)-[4'-tert-butyl-biphenyl-4-carbonyl)-amino]-propionic acid |
| 236 | 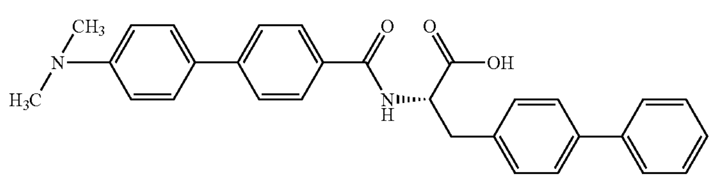 | 3-Biphenyl-4-yl-(2S)-[(4'-dimethylamino-biphenyl-4-carbonyl)-amino]-propionic acid |
| 237 | 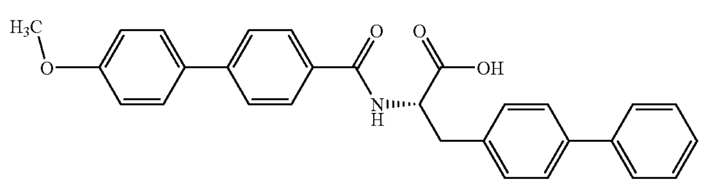 | 3-Biphenyl-4-yl-(2S)-[(4'-methoxy-biphenyl-4-carbonyl)-amino]-propionic acid |

TABLE 1-continued

| Example | Structure | Name |
|---|---|---|
| 238 | 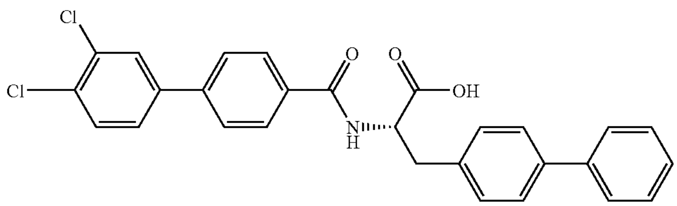 | 3-Biphenyl-4-yl-2-[(3',4'-dichloro-biphenyl-4-carbonyl)-amino]-propionic acid |
| 239 | 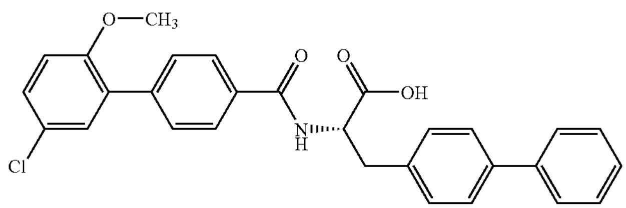 | 3-Biphenyl-4-yl-(2S)-[(5'-chloro-2'-methoxy-biphenyl-4-carbonyl)-amino]-propionic acid |
| 240 | 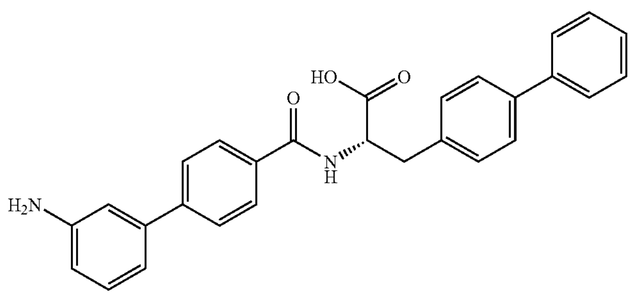 | (2S)-[(3'-Amino-biphenyl-4-carbonyl)-amino]-3-biphenyl-4-yl-propionic acid |
| 241 | 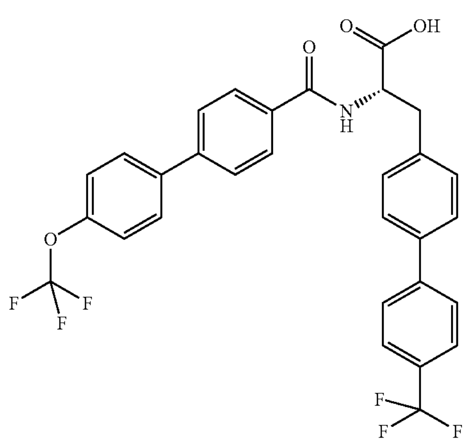 | (2S)-[(4'-Trifluoromethoxy-biphenyl-4-carbonyl)-amino]-3-(4'-trifluoromethyl-biphenyl-4-yl)-propionic acid |

TABLE 1-continued

| Example | Structure | Name |
|---|---|---|
| 242 | 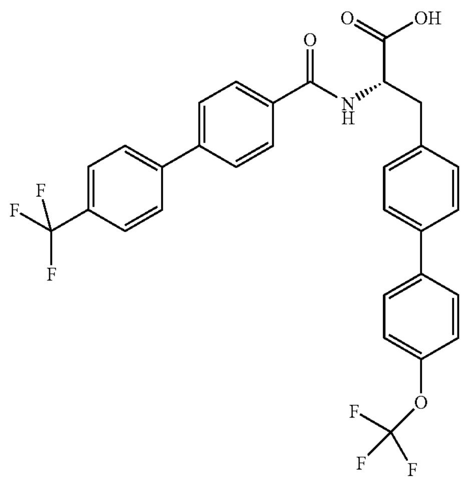 | 3-(4'-Trifluoromethoxy-biphenyl-4-yl)-(2S)-[(4'-trifluoromethyl-biphenyl-4-carbonyl)-amino]-propionic acid |
| 243 | 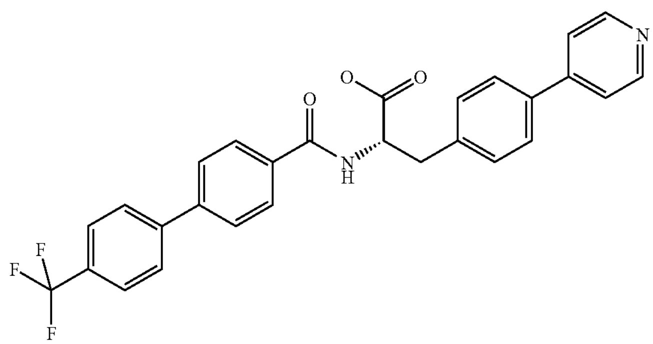 | 3-(4-Pyridin-4-yl-phenyl)-(2S)-[(4'-trifluormethyl-biphenyl-4-carbonyl)-amino]-propionic acid |
| 244 | 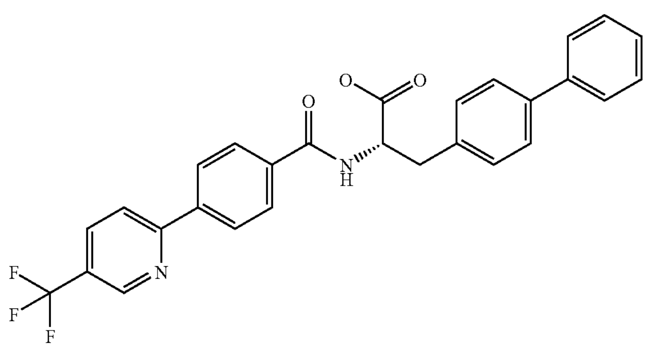 | 3-Biphenyl-4-yl-(2S)-[4-(5-trifluoromethyl-pyridin-2-yl)-benzoylamino]-propionic acid |
| 245 | 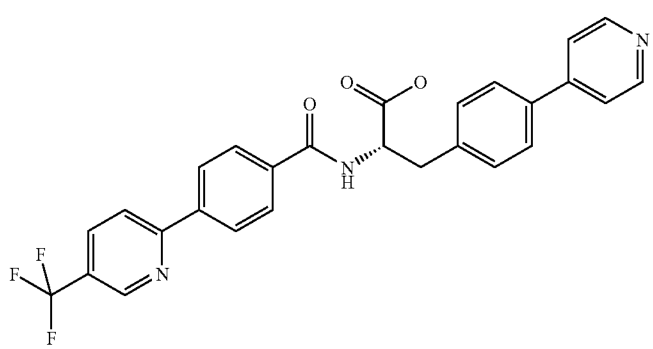 | 3-(4-Pyridin-4-yl-phenyl)-(2S)-[4-(5-trifluoromethyl-pyridin-2-yl-)benzoylamino]-propionic acid |

TABLE 1-continued

| Example | Structure | Name |
| --- | --- | --- |
| 246 | 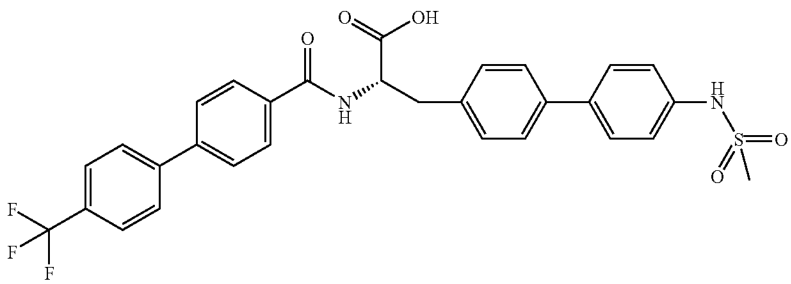 | 3-(4'-Methanesulfonylamino-biphenyl-4-yl)-(2S)-[(4'-trifluoromethyl-biphenyl-4-carbonyl)-amino]-propionic acid |
| 247 | 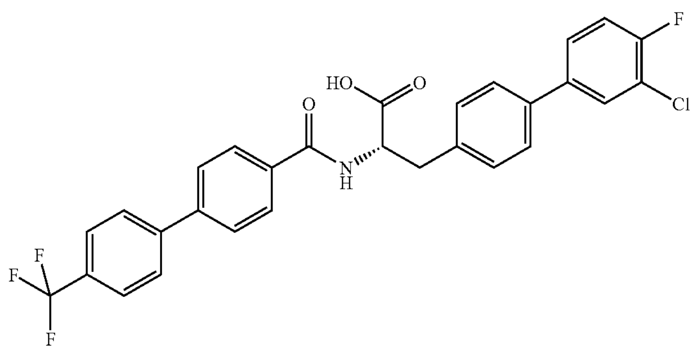 | 3-(3'-Chloro-4'-fluoro-biphenyl-4-yl)-(2S)-[('-trifluoromethyl-biphenyl-4-carbonyl)-amino]-propionic-acid |
| 248 | 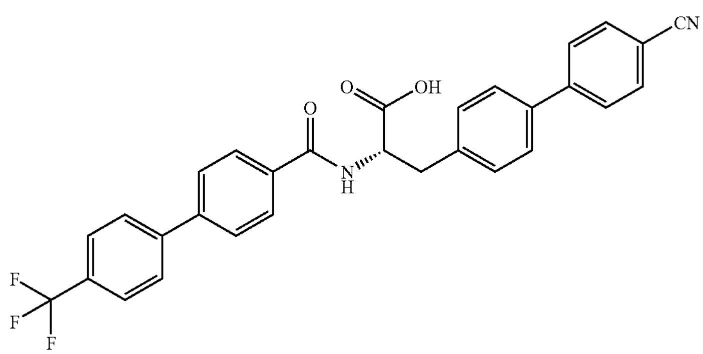 | 3-(4'-Cyano-biphenyl-4-yl)-(2S)-[(4'-trifluoromethyl-biphenyl-4-carbonyl)-amino]-propionic acid |
| 249 | 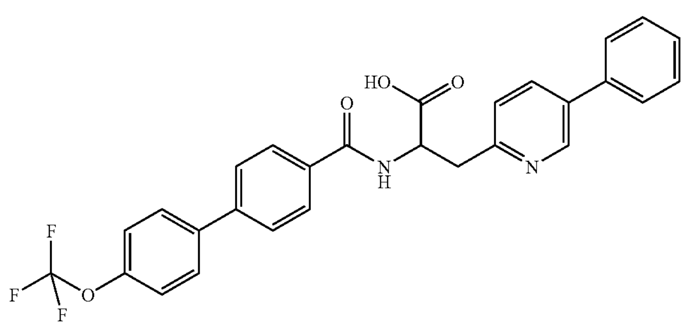 | 3-(5-Phenyl-pyridin-2-yl)-2-[(4'-trifluoromethoxy-biphenyl-4-carbonyl)-amino]-propionic acid |

TABLE 1-continued

| Example | Structure | Name |
|---|---|---|
| 250 | 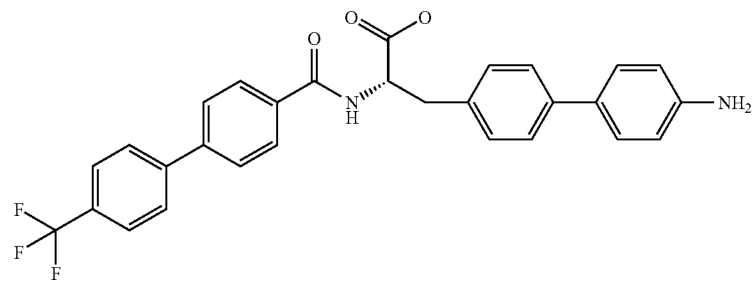 | 3-(4'-Amino-biphenyl-4-yl)-(2S)-[(4'-trifluoromethyl-biphenyl-4-carbonyl)-amino]-propionic acid |
| 251 | 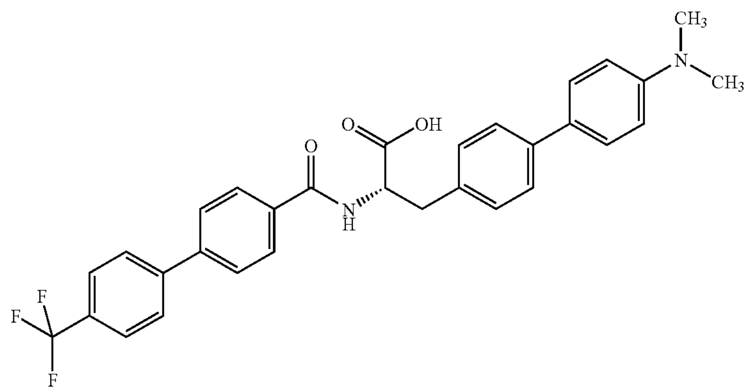 | 3-(4'-Dimethylamino-biphenyl-4-yl)-(2S)-[(4'-trifluoromethyl-biphenyl-4-carbonyl-amino]-propionic acid |
| 252 | 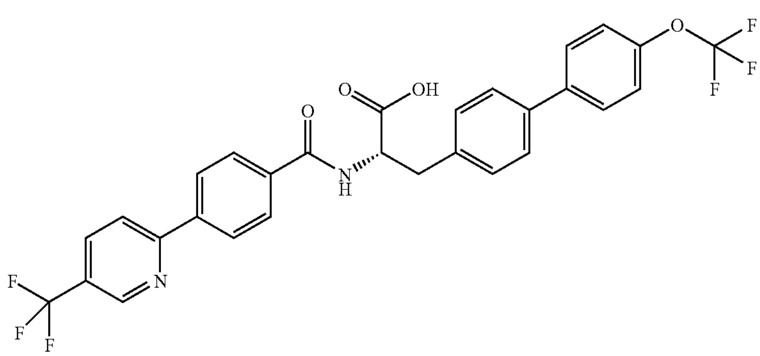 | 3-(4'-Trifluoromethoxy-biphenyl-4-yl)-(2S)-[4-(5-trifluoromethyl-pyridin-2-yl)-benzoylamino]-propionic acid |
| 253 | 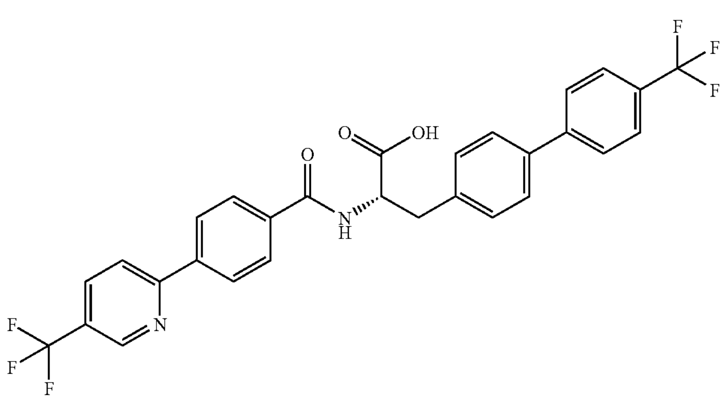 | 3-(4'-Trifluoromethyl-biphenyl-4-yl)-(2S)-[4-(5-trifluoromethyl-pyridin-2-yl)-benzoylamino]-propionic acid |

TABLE 1-continued

| Example | Structure | Name |
| --- | --- | --- |
| 254 | 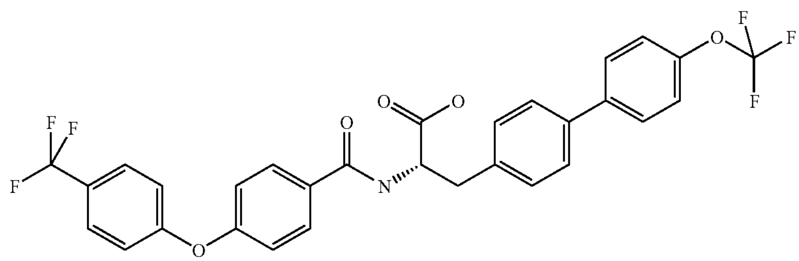 | 3-(4'-Trifluoromethoxy-biphenyl-4-yl)-(2S)-[4-(4-trifluoromethyl-phenoxy)-benzoylamino]-propionic acid |
| 255 | 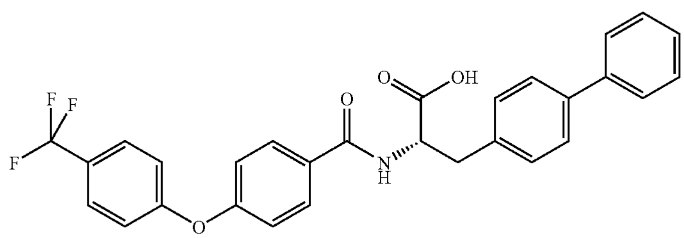 | 3-Biphenyl-4-yl-(2S)-[4-(4-trifluoromethyl-phenoxy)-benzoylamino]-propionic acid |
| 256 | 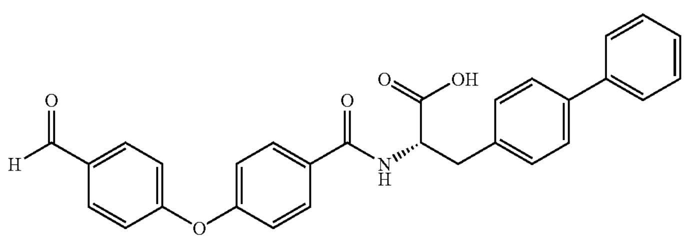 | 3-Biphenyl-4-yl-(2S)-[4-(4-formyl-phenoxy)-benzoylamino]-propionic acid |
| 257 | 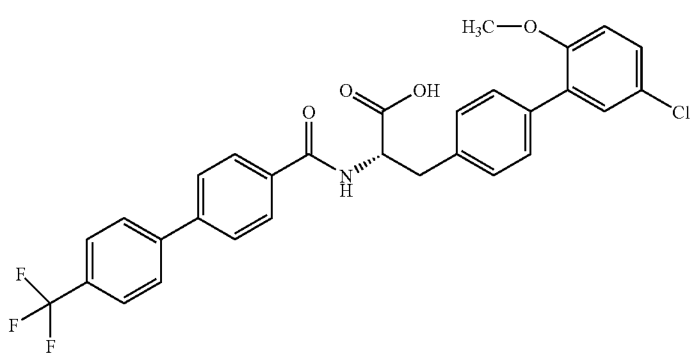 | 3-(5'-Chloro-2'-methoxy-biphenyl-4-yl)-(2S)-[(4'-trifluoromethyl-biphenyl-4-carbonyl)-amino]-propionic acid |
| 258 | 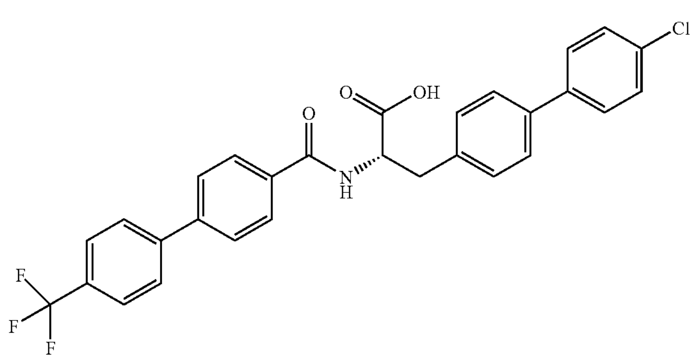 | 3-(4'-Chloro-biphenyl-4-yl)-(2S)-[(4'-trifluoromethyl-biphenyl-4-carbonyl)-amino]-propionic acid |

TABLE 1-continued

| Example | Structure | Name |
|---|---|---|
| 259 | 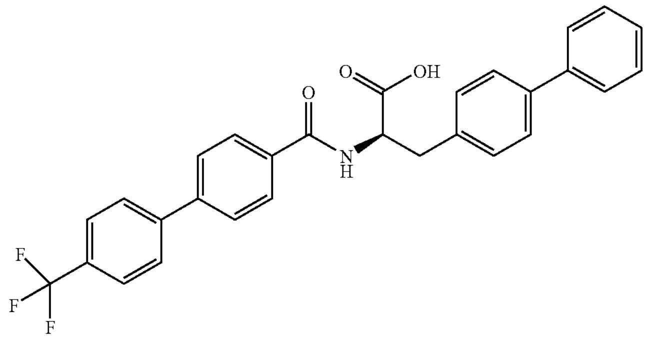 | 3-Biphenyl-4-yl-(2R)-[(4'-trifluoromethyl-biphenyl-4-carbonyl)-amino]-propionic acid |
| 260 | 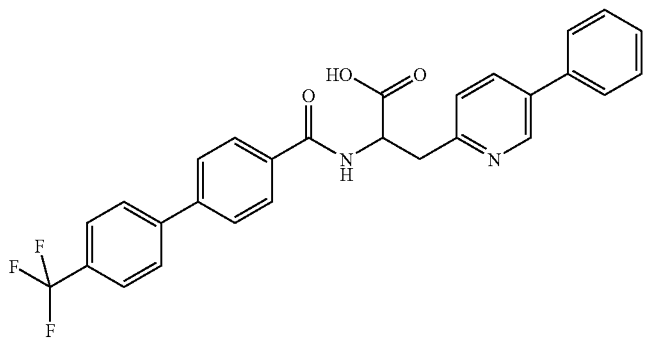 | 3-(5-Phenyl-pyridin-2-yl)-2-[(4'-trifluoromethyl-biphenyl-4-carbonyl)-amino]-propionic acid |
| 261 | 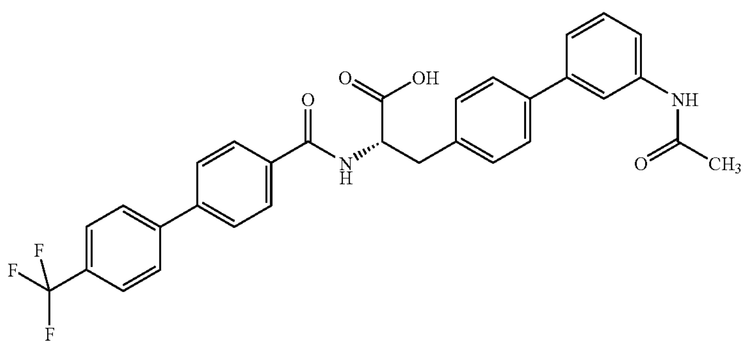 | 3-(3'-Acetylamino-biphenyl-4-yl)-(2S)-[(4'-trifluoromethyl-biphenyl-4-carbonyl)-amino]-propionic acid |
| 262 | 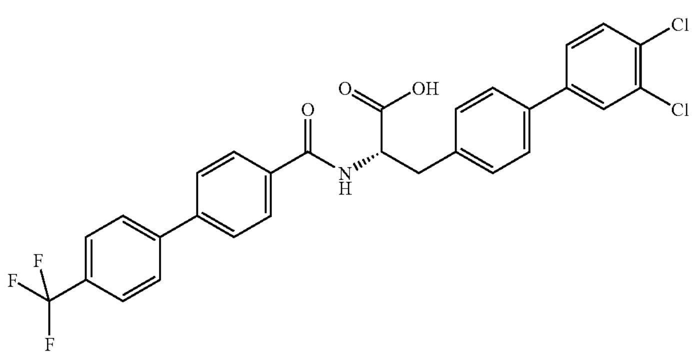 | 3-(3',4'-Dichloro-biphenyl-4-yl)-(2S)-[(4'-trifluoromethyl-biphenyl-4-carbonyl)-amino]-propionic acid |

TABLE 1-continued

| Example | Structure | Name |
| --- | --- | --- |
| 263 | 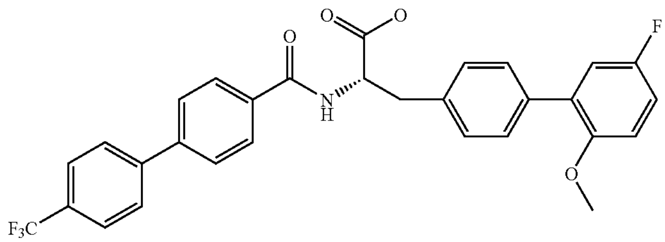 | 3-(5'-Fluoro-2'-methoxy-biphenyl-4-yl)-(2S)-[(4'-trifluoromethyl-biphenyl-4-carbonyl)-amino]-propionic acid |
| 264 | 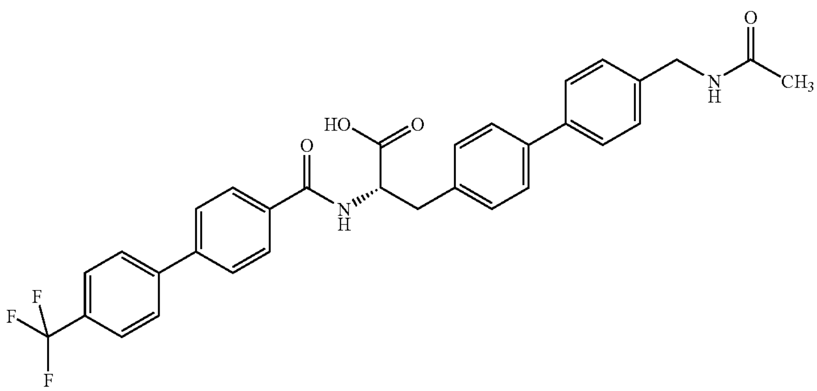 | 3-[4'-(Acetylamino-methyl)-biphenyl-4-yl]-(2S)-[(4'-trifluoromethyl-biphenyl-4-carbonyl)-amino]-propionic acid |
| 265 | 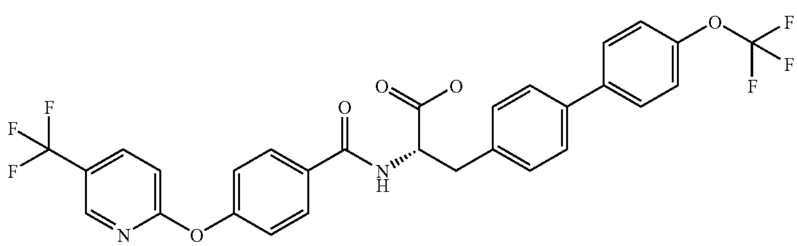 | 3-(4'-Trifluoromethoxy-biphenyl-4-yl)-(2S)-[4-(5-trifluoromethyl-pyridin-2-yloxy)-benzoylamino]-propionic acid |
| 266 | 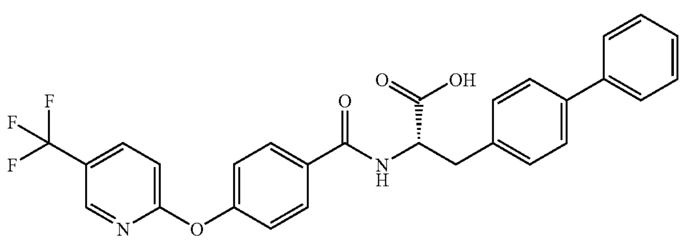 | 3-Biphenyl-4-yl-(2S)-[4-(5-trifluoromethyl-pyridin-2-yloxy)-benzoylamino]-propionic acid |
| 267 | 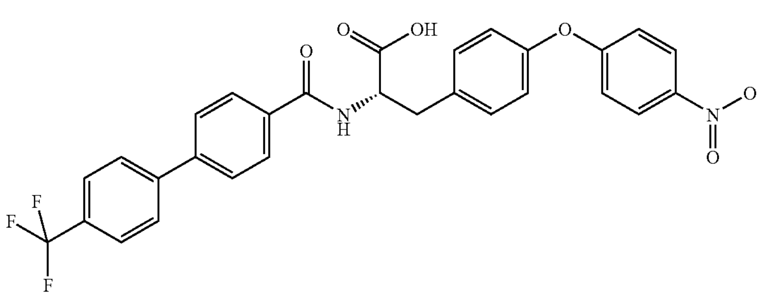 | 3-[4-(4-Nitro-phenoxy)-phenyl]-(2S)-[(4'-trifluoromethyl-biphenyl-4-carbonyl)-amino]-propionic acid |

TABLE 1-continued

| Example | Structure | Name |
|---|---|---|
| 268 | 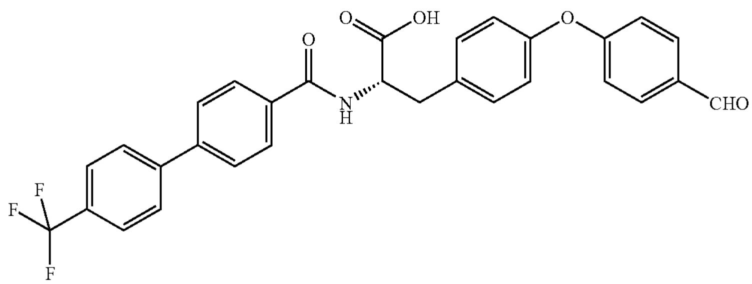 | 3-[4-(4-Formyl-phenoxy)-phenyl]-(2S)-[(4'-trifluoromethyl-biphenyl-4-carbonyl)-amino]-propionic acid |
| 269 | 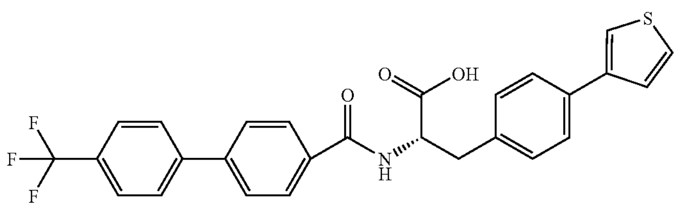 | 3-(4-Thiophen-3-yl-phenyl)-(2S)-[(4'-trifluoromethyl-biphenyl-4-carbonyl)-amino]-propionic acid |
| 270 | 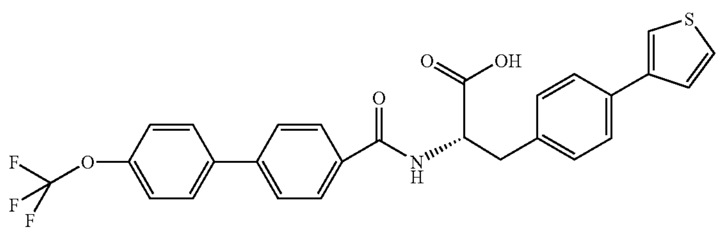 | 3-(4-Thiophen-3-yl-phenyl)-(2S)-[(4'-trifluoromethoxy-biphenyl-4-carbonyl)-amino]-propionic acid |
| 271 | 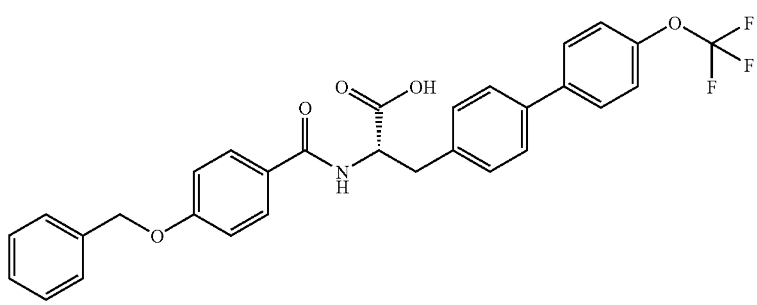 | (2S0-(4-Benzyloxy-benzoylamino)-3-(4'-trifluoromethoxy-biphenyl-4-yl)-propionic acid |
| 272 | 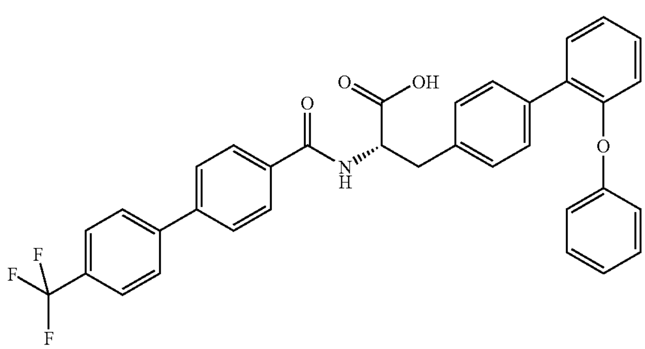 | 3-(2'-Phenoxy-biphenyl-4-yl)-(2S)-[(4'-trifluoromethyl-biphenyl-4-carbonyl)-amino]-propionic acid |

TABLE 1-continued

| Example | Structure | Name |
|---|---|---|
| 273 | 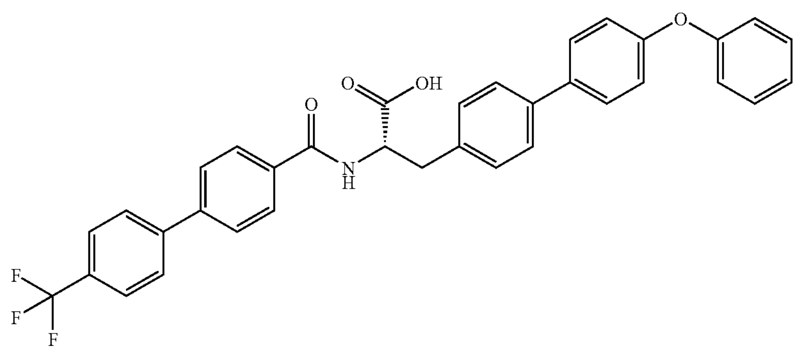 | 3-(4'-Phenoxy-biphenyl-4-yl)-(2S)-[(4'-trifluoromethyl-biphenyl-4-carbonyl)-amino]-propionic acid |
| 274 | 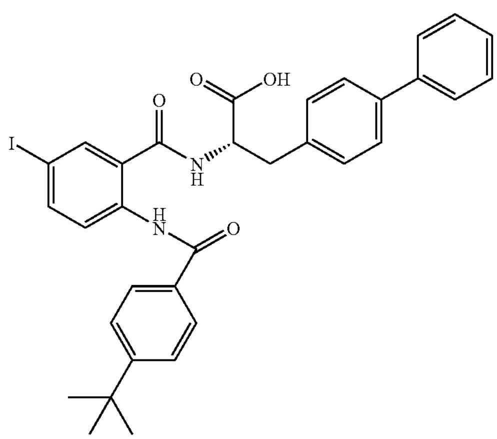 | 3-Biphenyl-4-yl-(2S)-[2-(4-tert-butyl-benzoylamino)-5-iodo-benzoyl-amino]-propionic acid |
| 275 | 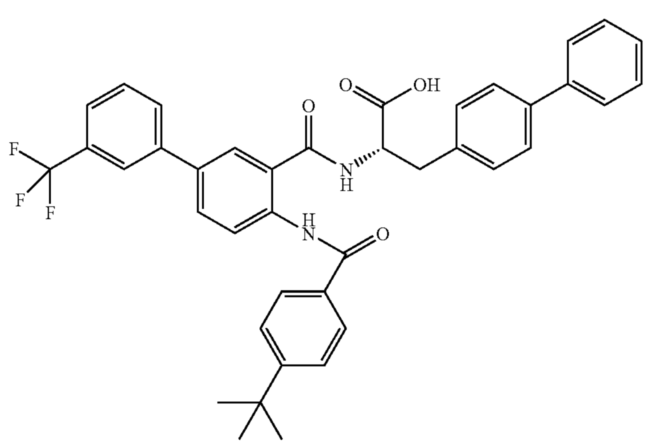 | 3-Biphenyl-4-yl-(2S)-{[4-(4-tert-butyl-benzoylamino)-3'-trifluoromethyl-biphenyl-3-carbonyl]-amino}-propionic acid |

TABLE 1-continued

| Example | Structure | Name |
|---|---|---|
| 276 | 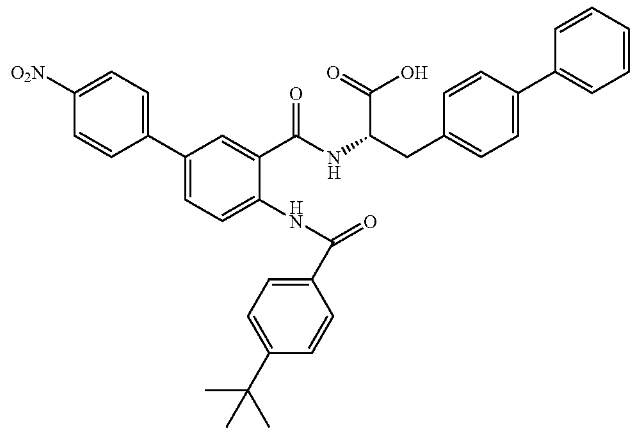 | 3-Biphenyl-4-yl-(2S0-{[4-(4-tert-butyl-benzoylamino)-4'-nitro-iphenyl-3-carbonyl]-mino}-propionic acid |
| 277 | 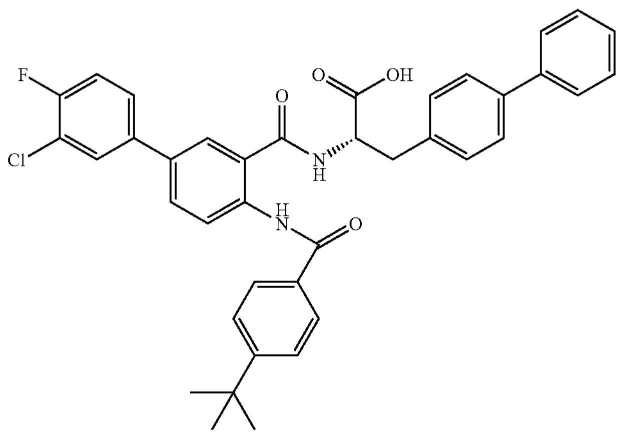 | 3-Biphenyl-4-yl-(2S)-{[4-(4-tert-butyl-benzoylamino)-3'-chloro-4'-fluoro-biphenyl-3-carbonyl]-amino}-propionic acid |
| 278 | 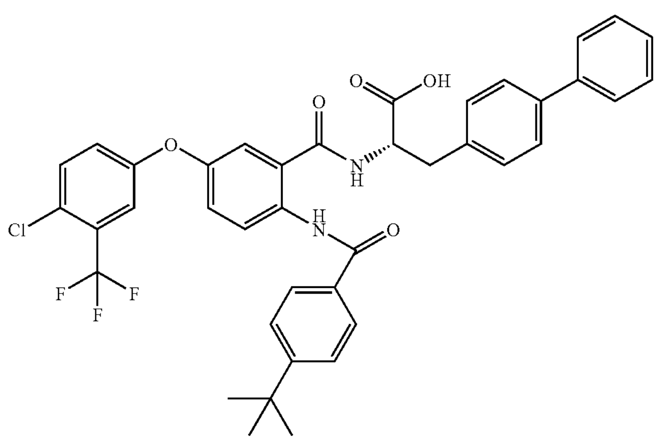 | 3-Biphenyl-4-yl-(2S)-[4-(4-tert-butyl-benzoylamino)-5-(4-chloro-3-trifluromethyl-phenoxy)-benzoylamino]-propionic acid |

TABLE 1-continued
| Example | Structure | Name |
|---|---|---|
| 279 | 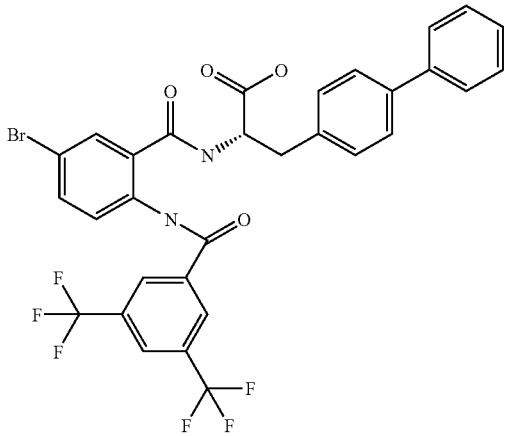 | 3-Biphenyl-4-yl-(2S)-[2-(3,5-bis-trifluoromethyl-benzoylamino)-5-bromo-benzoylamino]-propionic acid |
| 280 | 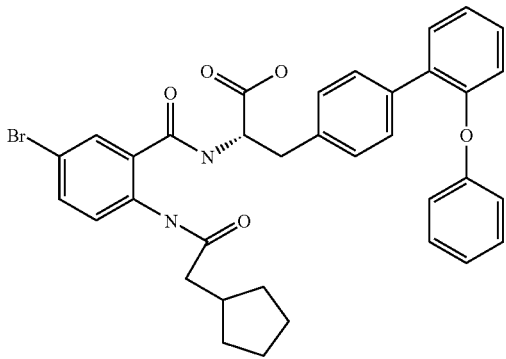 | (2S)-[5-bromo-2-(2-cyclopentyl-acetylamino)-benzoylamino]-3-(2'-phenoxy-biphenyl-4-yl)-propionic acid |
| 281 | 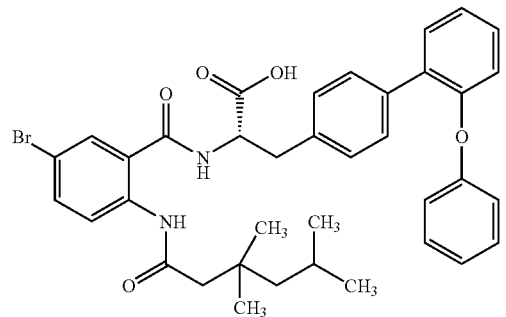 | (2S)-[5-Bromo-2(3,3,5-trimethyl-hexanoylamino)-benzoylamino]-3-(2'-phenoxy-biphenyl-4-yl)-propionic acid |

TABLE 1-continued

| Example | Structure | Name |
|---|---|---|
| 282 | 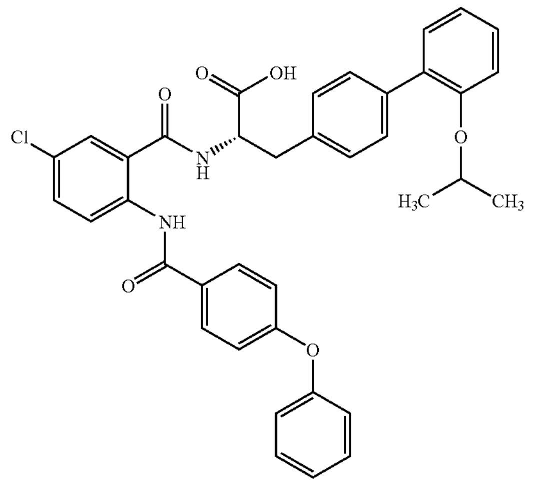 | (2S)-[5-Chloro-2-(4-phenoxy-benzoylamino)-benzoylamino]-3-(2'-isopropoxy-biphenyl-4-yl)-propionic acid |
| 283 | 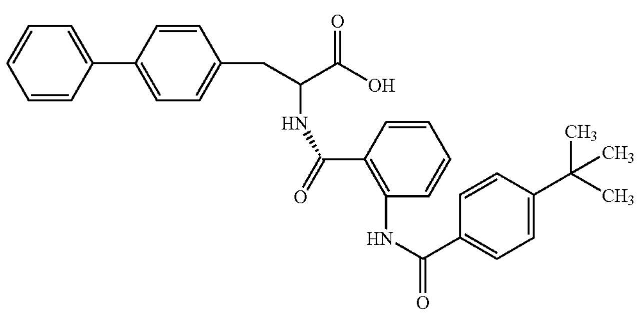 | 3-Biphenyl-4-yl-(2S)-[2-(4-tert-butyl-benzoylamino)-benzoylamino]-propionic acid |
| 284 | 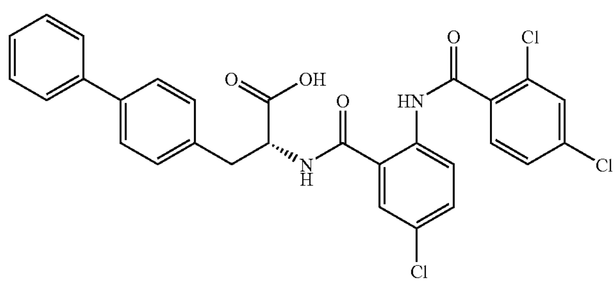 | 3-Biphenyl-4-yl-(2S)-[5-chloro-2-(2,4-dichloro-benzoylamino)-benzoylamino]-propionic acid |
| 285 | 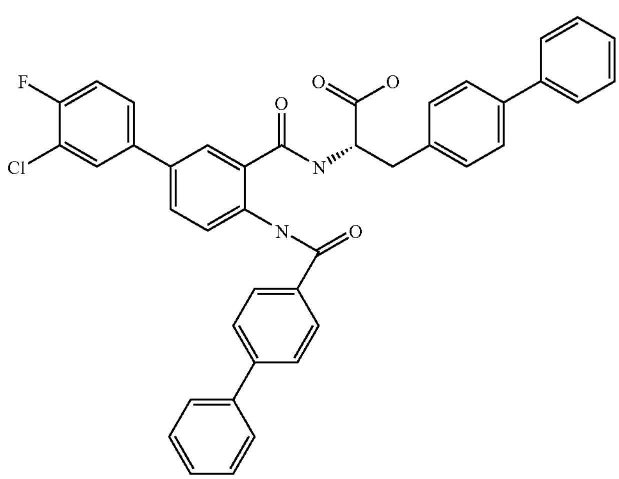 | (2S)-({4-[(Biphenyl-4-carbonyl)-amino]-3'-chloro-4'-fluoro-biphenyl-3-carbonyl}-amino)-3-biphenyl-4-yl-propionic acid |

TABLE 1-continued

| Example | Structure | Name |
|---|---|---|
| 286 | 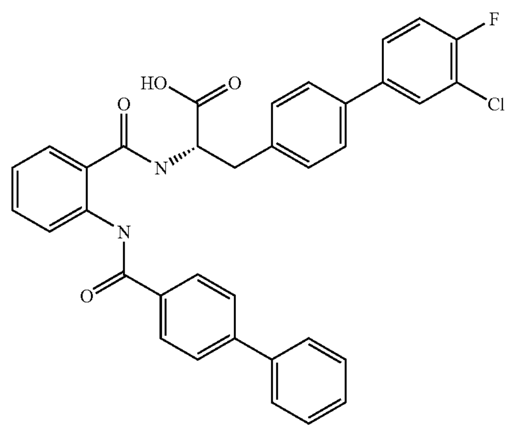 | (2S)-{2-[Biphenyl-4-carbonyl)-amino]-benzoylamino}-3-(3'-chloro-4'-fluoro-biphenyl-4-yl)-propionic acid |
| 287 | 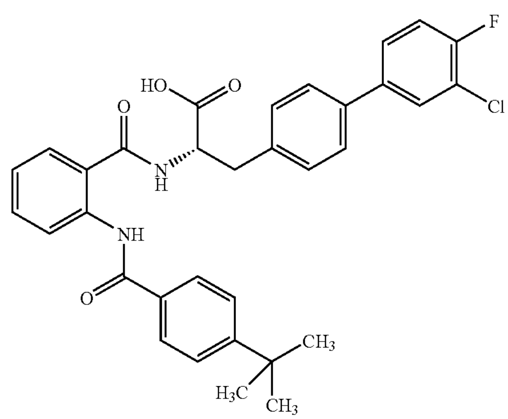 | (2S)-[2-(4-tert-Butyl-benzoylamino)-benzoylamino]-3-(3'-chloro-4'-fluoro-biphenyl-4-yl)-propionic acid |
| 288 | 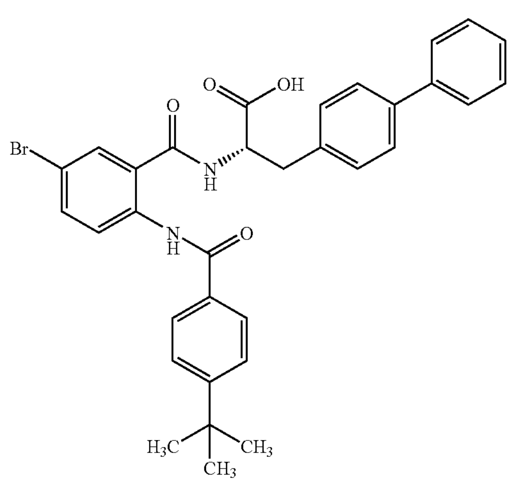 | 3-Biphenyl-4-yl-(2S)-[5-bromo-2-(4-tert-butyl-benzoylamino)-benzoylamino]- propionic acid |

TABLE 1-continued

| Example | Structure | Name |
|---|---|---|
| 289 | 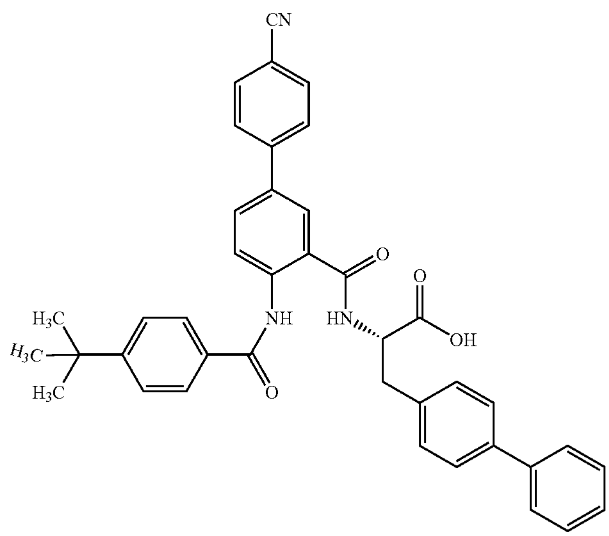 | 3-Biphenyl-4-yl-(2S)-{[4-(4-tert-butyl-benzoylamino)-4'-cyano-biphenyl-3-carbonyl]-amino}-propionic acid |
| 290 | 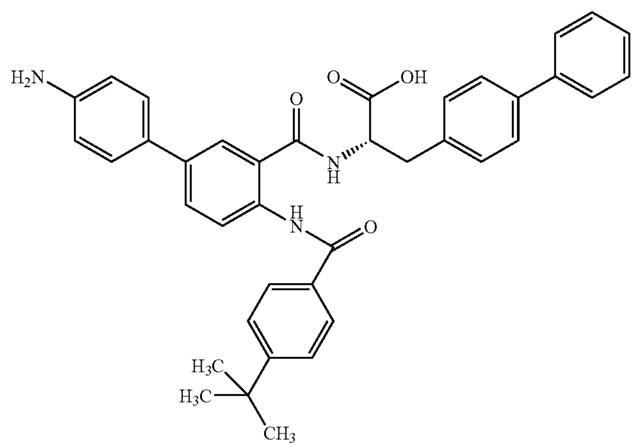 | (2S)-{[4'-Amino-4-(4-tert-butyl-benzoylamino)-biphenyl-3-carbonyl]-amino}-3-biphenyl-4-yl-propionic acid |
| 291 | 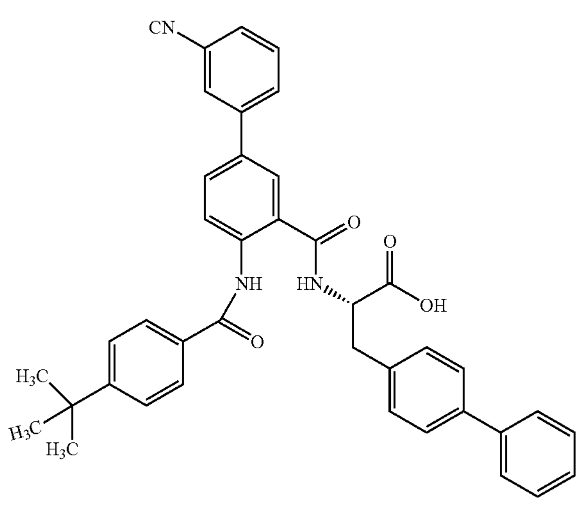 | 3-Biphenyl-4-yl-(2S)-{[4-(4-tert-butyl-benzoylamino)-3'-cyano-biphenyl-3-carbonyl]-amino}-propionic acid |

TABLE 1-continued

| Example | Structure | Name |
|---|---|---|
| 292 | 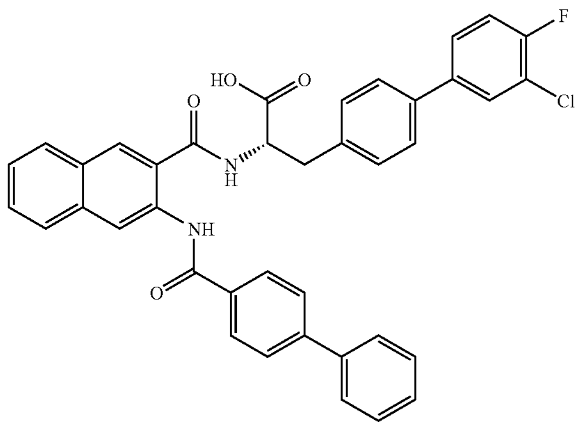 | (2S)-({3-[(Biphenyl-4-carbonyl)-amino]-naphthalene-2-carbonyl}-amino)-3-(3'-chloro-4'-fluoro-biphenyl-4-yl)-propionic acid |
| 293 | 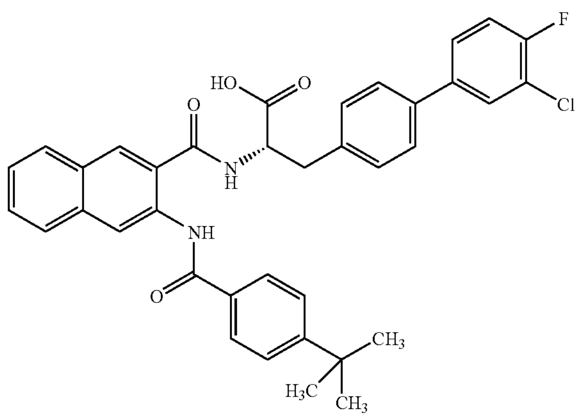 | (2S)-{[3-(4-tert-Butyl-benzoylamino)-naphthalene-2-carbonyl]-amino}-3-(3'-chloro-4'-fluoro-biphenyl-4-yl)-propionic acid |
| 294 | 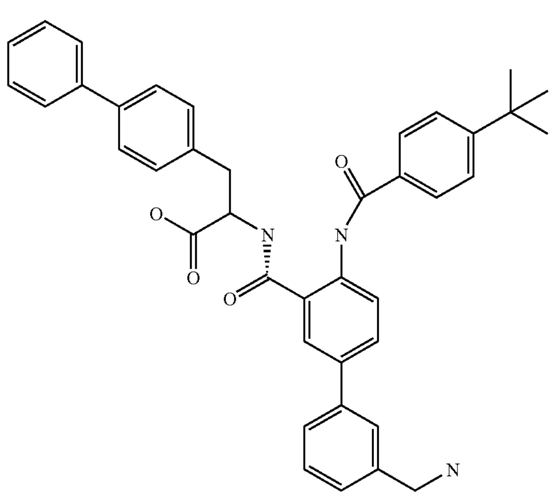 | (2S)-{[3'-Aminomethyl-4-(4-tert-butyl-benzoylamino)-biphenyl-3-carbonyl]-amino}-3-biphenyl-4-yl-propionic acid |

TABLE 1-continued

| Example | Structure | Name |
|---|---|---|
| 295 | 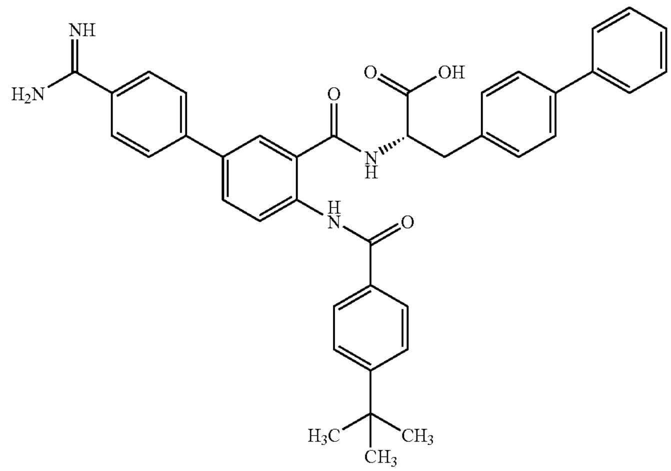 | 3-Biphenyl-4-yl-(2S)-{[4-(4-tert-butyl-benzoylamino)-4'-carbamimidoyl-biphenyl-3-carbonyl]-amino}-propionic acid |
| 296 | 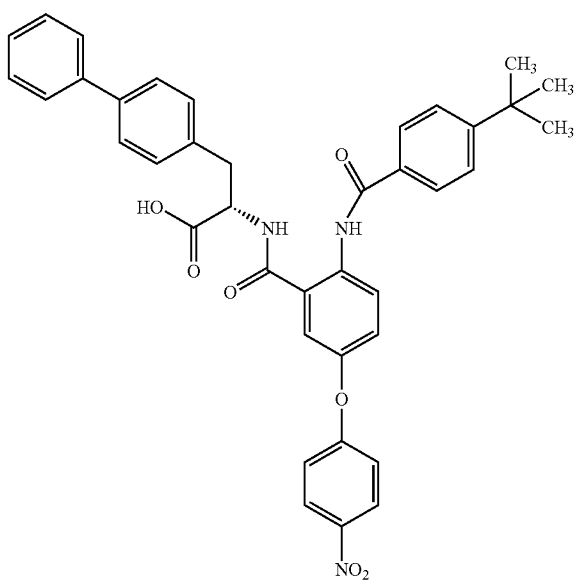 | 3-Biphenyl-4-yl-(2S)-[2-(4-tert-butyl-benzoylamino)-5-(4-nitro-phenoxy)-benzoylamino]-propionic acid |
| 297 | 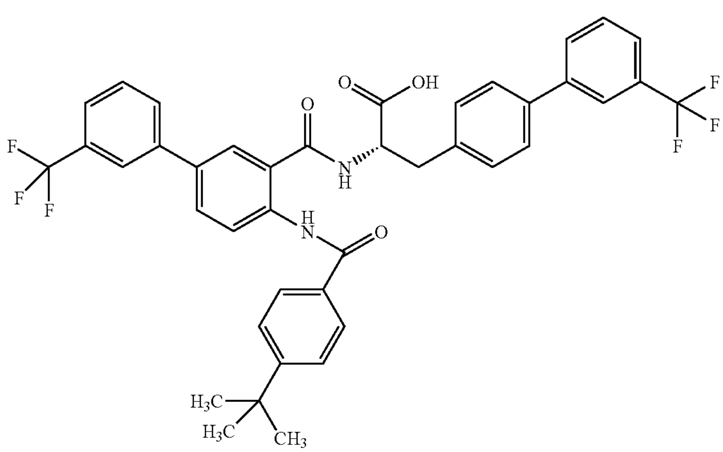 | (2S)-{[4-(4-tert-Butyl-benzoylamino)-3'-trifluoromethyl-biphenyl-3-carbonyl]-amino}-3-(3'-trifluoromethyl-biphenyl-4-yl)-propionic acid |

TABLE 1-continued

| Example | Structure | Name |
|---|---|---|
| 298 | 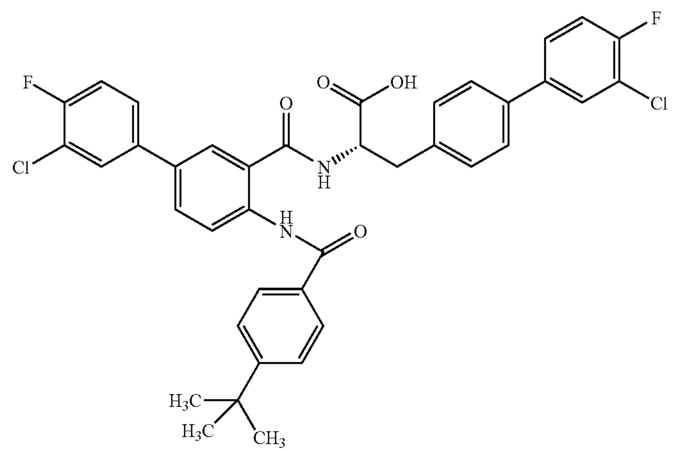 | (2S)-{[4-(4-tert-Butyl-benzoylamino)-3'-chloro-4'-fluoro-biphenyl-3-carbonyl]-amino}-3-(3'-chloro-4'-fluoro-biphenyl-4-yl)-propionic acid |
| 299 | 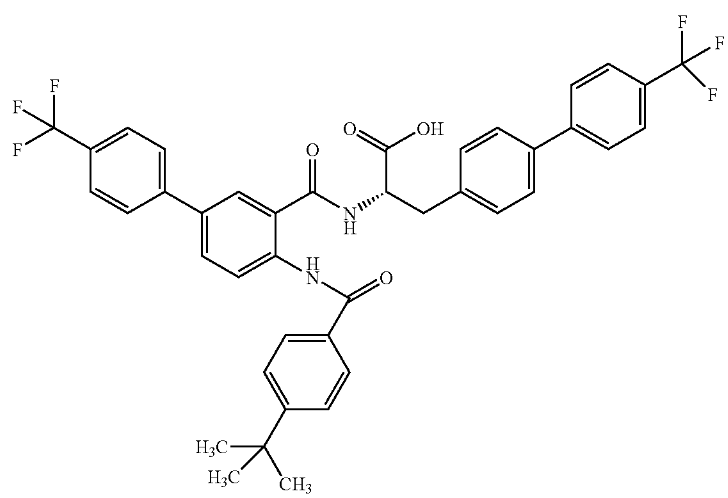 | (2S)-{[4-(4-tert-Butyl-benzoylamino)-4'-trifluoromethyl-biphenyl-3-carbonyl]-amino}-3-(4'-trifluoromethyl-biphenyl-4-yl)-propionic acid |
| 300 | 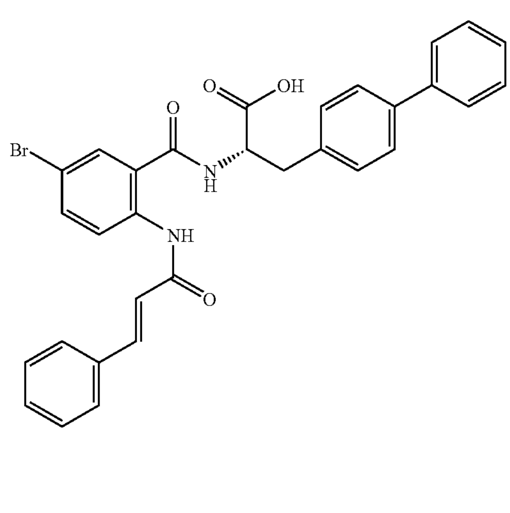 | 3-Biphenyl-4-yl-(2S)-[5-bromo-2-(3-phenyl-acryloylamino)-benzoylamino]-propionic acid |

TABLE 1-continued

| Example | Structure | Name |
| --- | --- | --- |
| 301 | 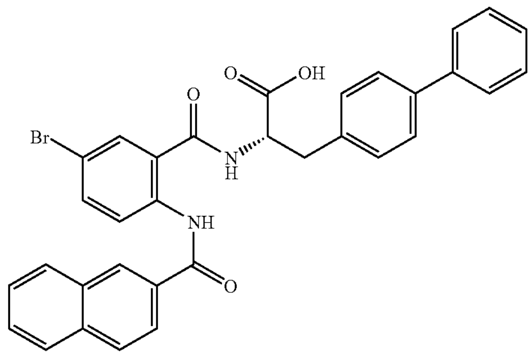 | 3-Biphenyl-4-yl-(2S)-{5-bromo-2-[(naphthalene-2-carbonyl)-amino]-benzoylamino}-propionic acid |
| 302 | 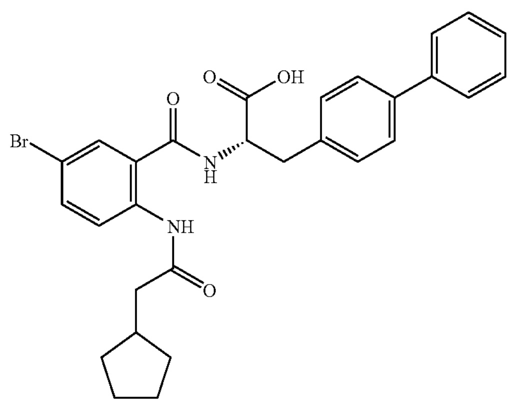 | 3-Biphenyl-4-yl-(2S)-[5-bromo-2-(2-cyclopentyl-acetylamino)-benzoylamino]-propionic acid |
| 303 | 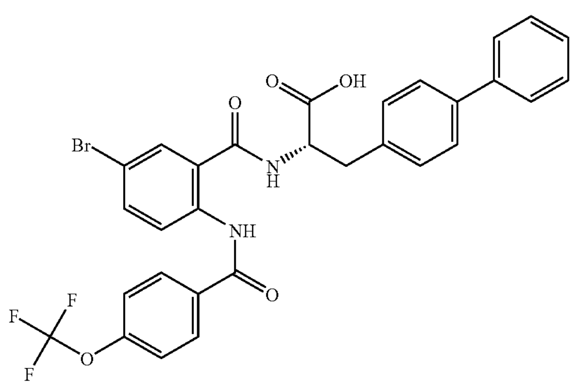 | 3-Biphenyl-4-yl-(2S)-[5-bromo-2-(4-trifluoromethoxy-benzoylamino)-benzoylamino]-propionic acid |

TABLE 1-continued
| Example | Structure | Name |
|---|---|---|
| 304 | 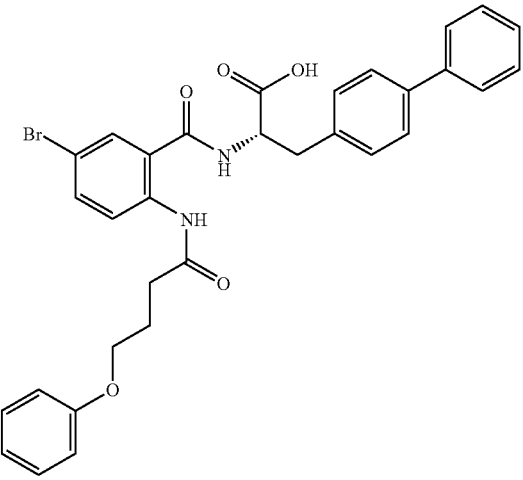 | 3-Biphenyl-4-yl-(2S)-[5-bromo-2-(4-phenoxy-butyrylamino)-benzoylamino]-propionic acid |
| 305 | 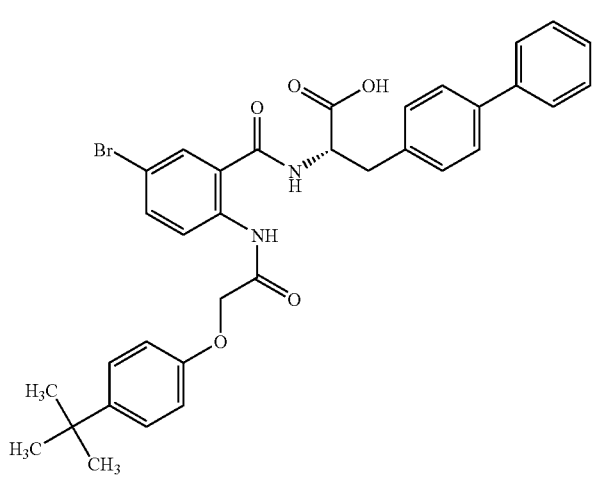 | 3-Biphenyl-4-yl-(2S)-(5-bromo-2-[2-(4-tert-butyl-phenoxy)-acetylamino]-benzoylamino)-propionic acid |
| 306 | 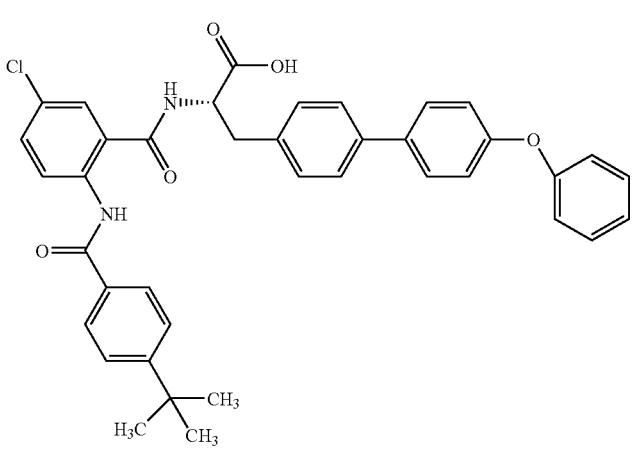 | (2S)-[2-(4-tert-Butyl-benzoylamino)-5-chloro-benzoylamino]-3-(4'-phenoxy-biphenyl-4-yl)-propionic acid |

TABLE 1-continued

| Example | Structure | Name |
|---|---|---|
| 307 | 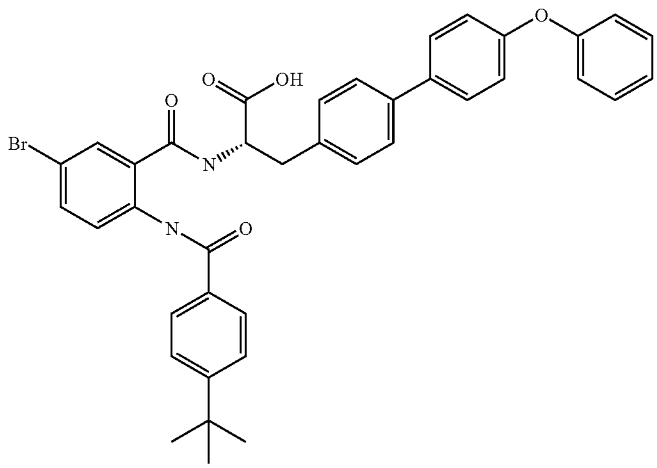 | 2-[5-Bromo-(2S)-(4-tert-butyl-benzoylamino)-benzoylamino]-3-(4'-phenoxy-biphenyl-4-yl)-propionic acid |
| 308 | 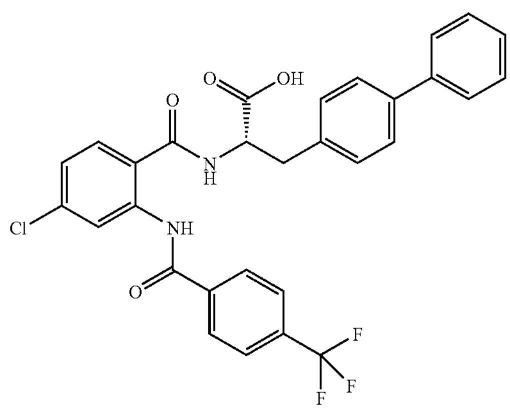 | 3-Biphenyl-4-yl-(2S)-[4-chloro-2-(4-trifluoromethyl-benzoylamino)-benzoylamino]-propionic acid |
| 309 | 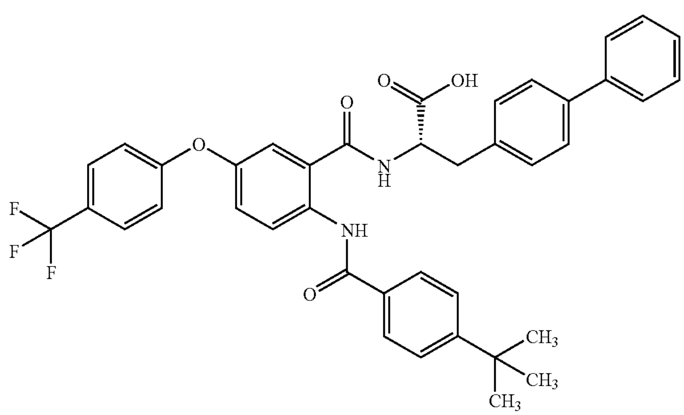 | 3-Biphenyl-4-yl-(2S)-[2-(4-tert-butyl-benzoylamino)-5-(4-trifluoromethyl-phenoxy)-benzoylamino]-propionic acid |

TABLE 1-continued

| Example | Structure | Name |
| --- | --- | --- |
| 310 | 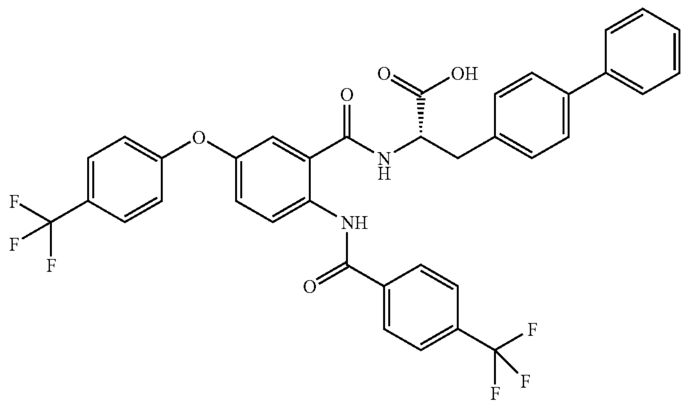 | 3-Biphenyl-4-yl-(2S)-[2-(4-trifluoromethyl-benzoylamino)-5-(4-trifluoromethyl-phenoxy)-benzoylamino]-propionic acid |
| 311 | 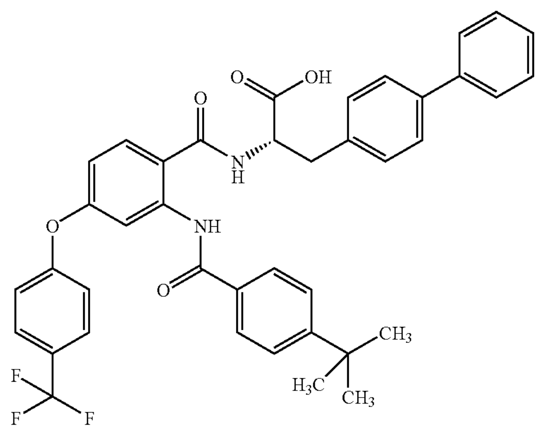 | 3-Biphenyl-4-yl-(2S)-[2-(4-tert-butyl-benzoylamino)-4-(4-trifluoromethyl-phenoxy)-benzoylamino]-propionic acid |
| 312 | 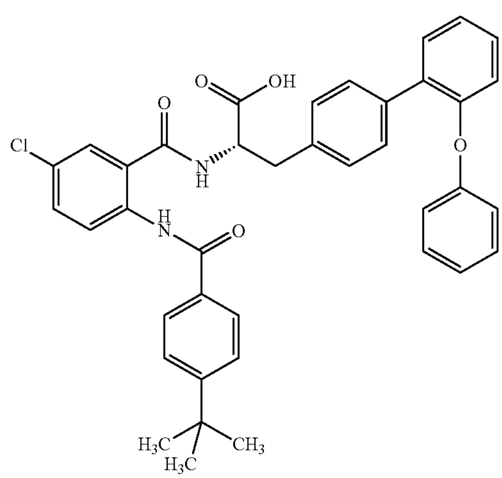 | (2S)-[2-(4-tert-Butyl-benzoylamino)-5-chloro-benzoylamino]-3-(2'-phenoxy-biphenyl-4-yl)-propionic acid |

TABLE 1-continued

| Example | Structure | Name |
|---|---|---|
| 313 | 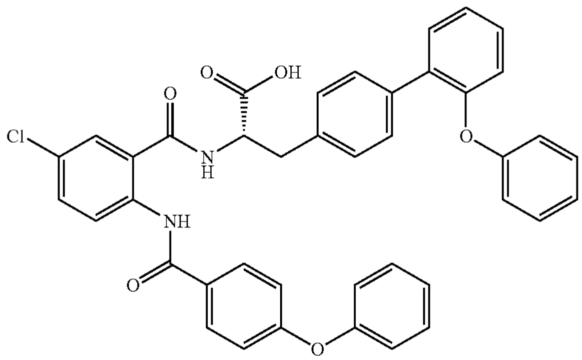 | (2S)-[5-Chloro-2-(4-phenoxy-benzoylamino)-benzoylamino]-3-(2'-phenoxy-biphenyl-4-yl)-propionic acid |
| 314 | 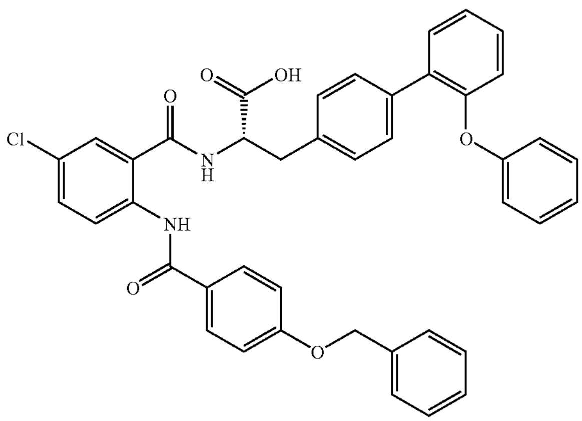 | (2S)-[2-(4-Benzyloxy-benzoylamino)-5-chloro-benzoylamino]-3-(2'-phenoxy-biphenyl-4-yl)-propionic acid |
| 315 | 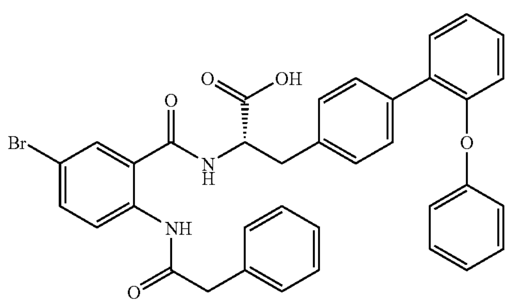 | (2S)-(5-Bromo-2-phenylacetylamino-benzoylamino)-3-(2'-phenoxy-biphenyl-4-yl)-propionic acid |
| 316 | 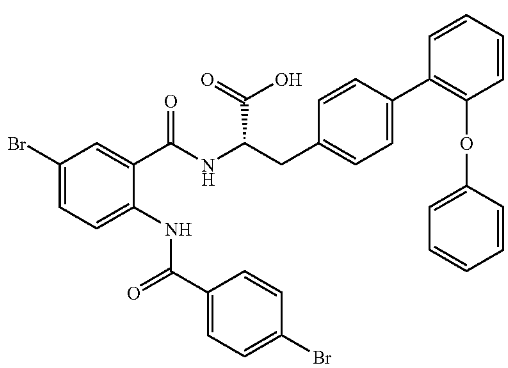 | (2S)-[5-Bromo-2-(4-bromo-benzoylamino)-benzoylamino]-3-(2'-phenoxy-biphenyl-4-yl)-propionic acid |

TABLE 1-continued

| Example | Structure | Name |
| --- | --- | --- |
| 317 | 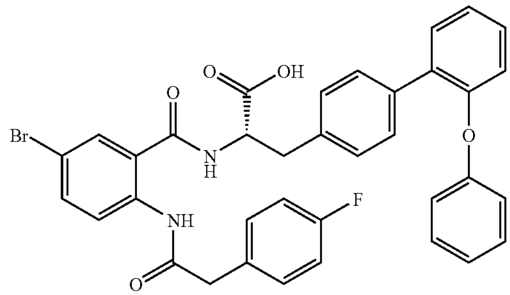 | (2S)-{5-Bromo-2-[2-(4-fluoro-phenyl)-acetylamino]-benzoylamino}-3-(2'-phenoxy-biphenyl-4-yl)-propionic acid |
| 318 | 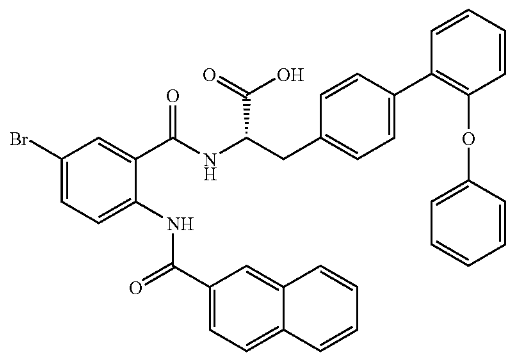 | 2-{5-Bromo-(2S)-[(naphthalene-2-carbonyl)-amino]-benzoylamino}-3-(2'-phenoxy-biphenyl-4-yl)-propionic acid |
| 319 | 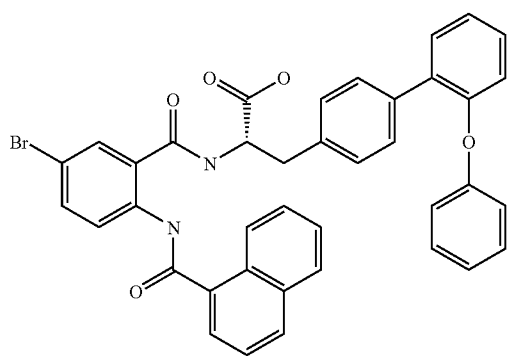 | (2S)-{5-Bromo-2-[(naphthalene-1-carbonyl)-amino]-benzoylamino}-3-(2'-phenoxy-biphenyl-4-yl)-propionic acid |
| 320 | 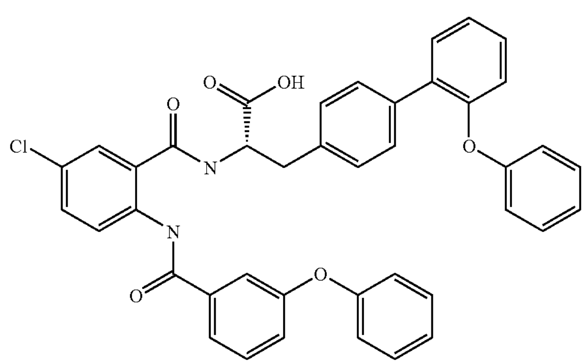 | (2S)-[5-Chloro-2-(3-phenoxy-benzoylamino)-benzoylamino]-3-(2'-phenoxy-biphenyl-4-yl)-propionic acid |

TABLE 1-continued

| Example | Structure | Name |
|---|---|---|
| 321 | 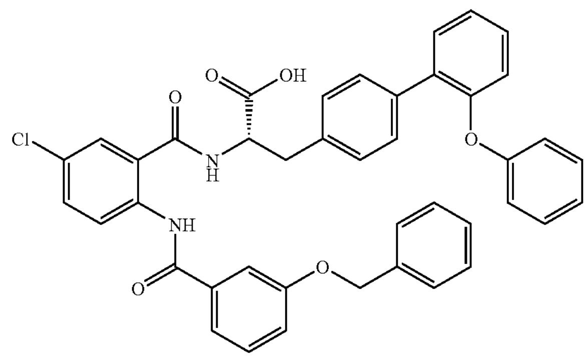 | -S-[2-(3-Benzyloxy-benzoylamino)-5-chloro-benzoylamino]-3-(2'-phenoxy-biphenyl-4-yl)-propionic acid |
| 322 | 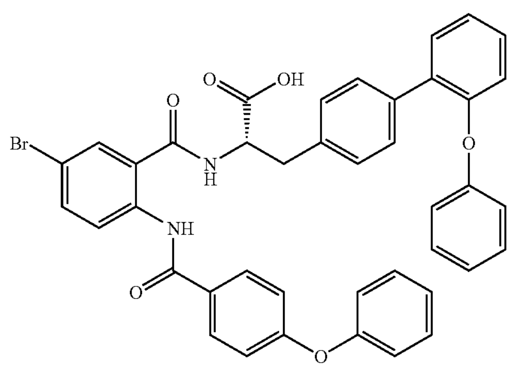 | (2S)-[5-Bromo-2-(4-phenoxy-benzoylamino)-benzoylamino]-3-(2'-phenoxy-biphenyl-4-yl)-propionic acid |
| 323 | 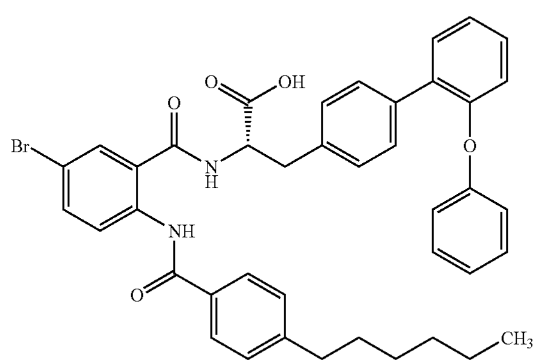 | (2S)-[5-Bromo-2-(4-hexyl-benzoylamino)-benzoylamino]-3-(2'-phenoxy-biphenyl-4-yl)-propionic acid |
| 324 | 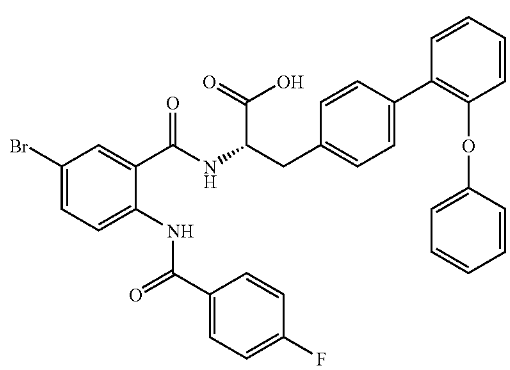 | (2S)-[5-Bromo-2-(4-fluoro-benzoylamino)-benzoylamino]-3-(2'-phenoxy-biphenyl-4-yl)-propionic acid |

TABLE 1-continued

| Example | Structure | Name |
| --- | --- | --- |
| 325 | 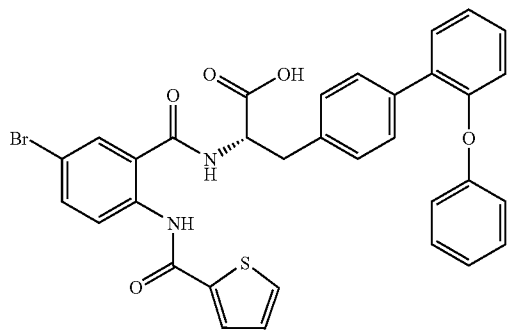 | (2S)-{5-Bromo-2-[(thiophene-2-carbonyl)-amino]-benzoylamino}-3-(2'-phenoxy-biphenyl-4-yl)-propionic acid |
| 326 | 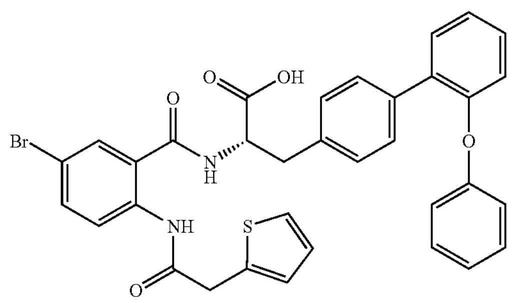 | (2S)-[5-Bromo-2-(2-thiophen-2-yl-acetylamino)-benzoylamino]-3-(2'-phenoxy-biphenyl-4-yl)-propionic acid |
| 327 | 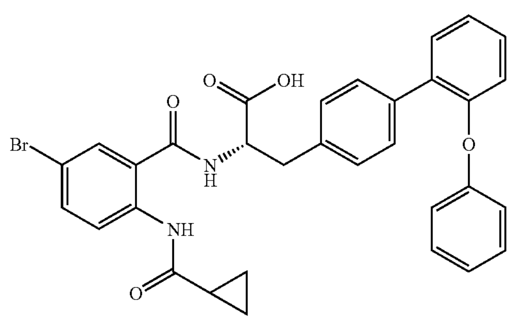 | (2S)-[5-Bromo-2-(cyclopropanecarbonyl-amino)-benzoylamino]-3-(2'-phenoxy-biphenyl-4-yl)-propionic acid |
| 328 | 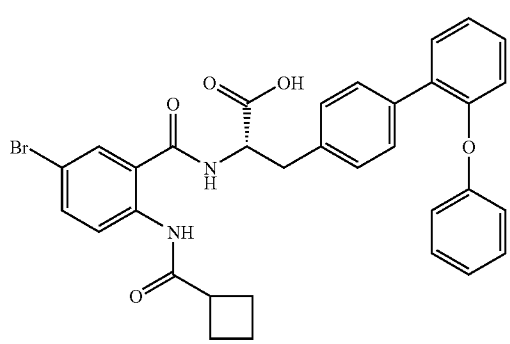 | (2S)-[5-Bromo-2-(cyclobutanecarbonyl-amino)-benzoylamino]-3-(2'-phenoxy-biphenyl-4-yl)-propionic acid |

TABLE 1-continued

| Example | Structure | Name |
|---|---|---|
| 329 | 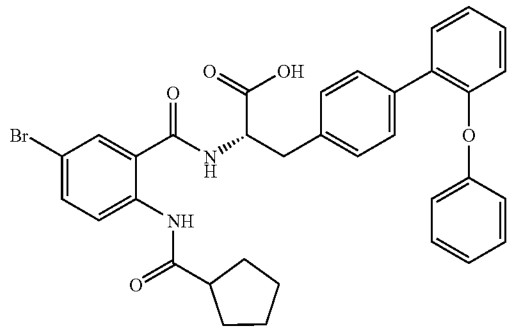 | (2S)-{5-Bromo-2-(cyclopentanecarbonyl-amino)-benzoylamino]-3-(2'-phenoxy-biphenyl-4-yl)-propionic acid |
| 330 | 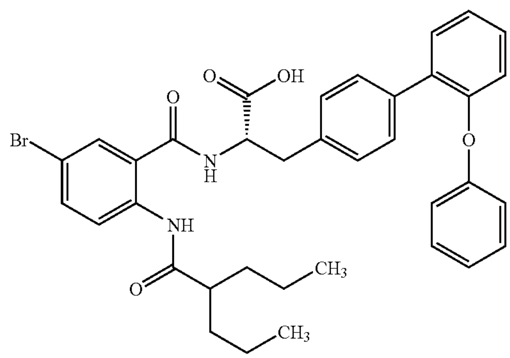 | (2S)-[5-Bromo-2-(2-propyl-pentanoylamino)-benzoylamino]-3-(2'-phenoxy-biphenyl-4-yl)-propionic acid |
| 331 | 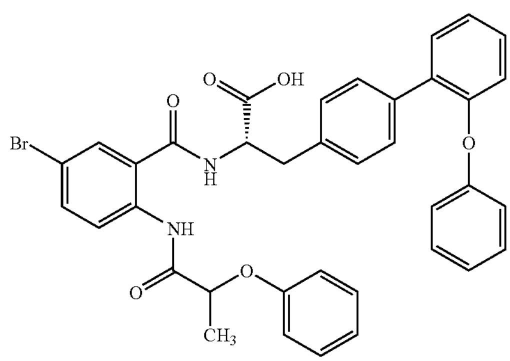 | (2S)-[5-Bromo-2-(2-phenoxy-propionylamino)-benzoylamino]-3-(2'-phenoxy-biphenyl-4-yl)-propionic acid |
| 332 | 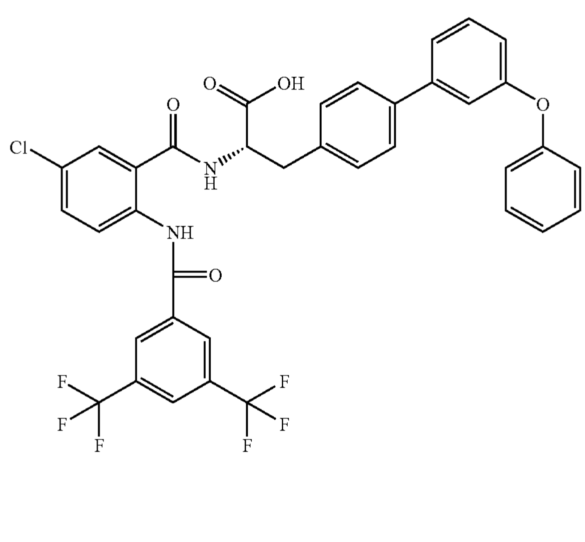 | (2S)-[2-(3,5-Bis-rifluoromethyl-benzoylamino)-5-chloro-benzoylamino]-3-(3'-phenoxy-biphenyl-4-yl)-propionic acid |

TABLE 1-continued

| Example | Structure | Name |
|---|---|---|
| 333 | 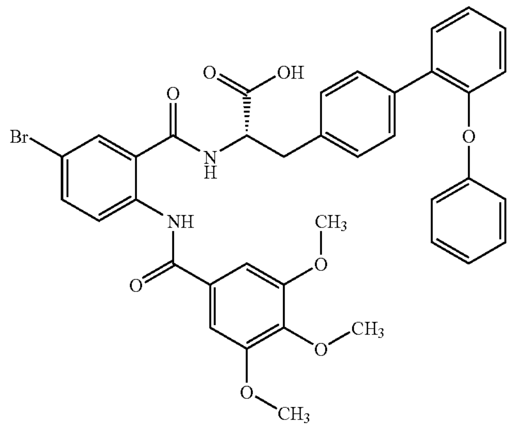 | (2S)-[5-Bromo-2-(3,4,5-trimethoxy-benzoylamino)-benzoylamino]-3-(2'-phenoxy-biphenyl-4-yl)-propionic acid |
| 334 | 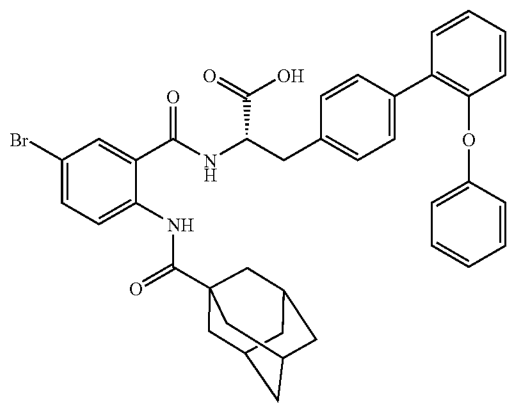 | (2S)-{2-[(Adamantane-1-carbonyl)-amino]-5-bromo-benzoylamino}-3-(2'-phenoxy-biphenyl-4-yl)-propionic acid |
| 335 | 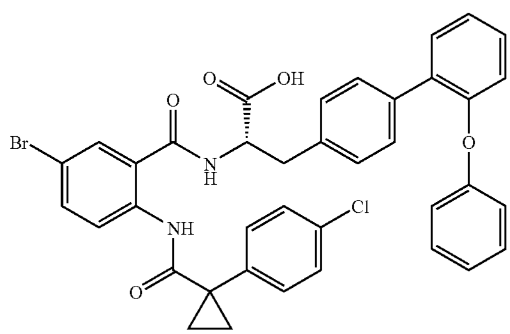 | (2S)-(5-Bromo-2-{[1-(4-chloro-phenyl)-cyclopropanecarbonyl]-amino}-benzoylamino)-3-(2'-phenoxy-biphenyl-4-yl)-propionic acid |
| 336 | 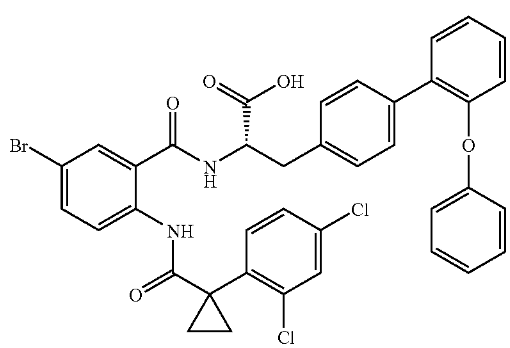 | (2S)-(5-Bromo-2-{[1-(2,4-dichloro-phenyl)-cyclopropanecarbonyl]-amino}-benzoylamino)-3-(2'-phenoxy-biphenyl-4-yl)-propionic acid |

TABLE 1-continued

| Example | Structure | Name |
|---|---|---|
| 337 | 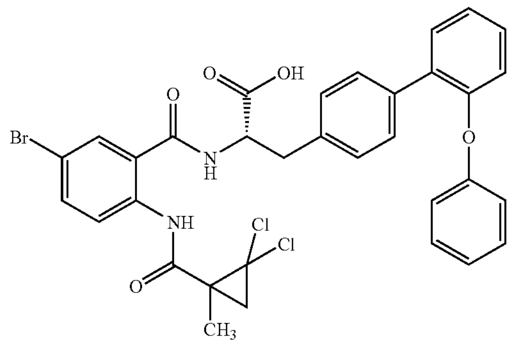 | (2S)-{5-Bromo-2-[(2,2-dichloro-1-methyl-cyclopropanecarbonyl)-amino]-benzoylamino}-3-(2'-phenoxy-biphenyl-4-yl)-propionic acid |
| 338 | 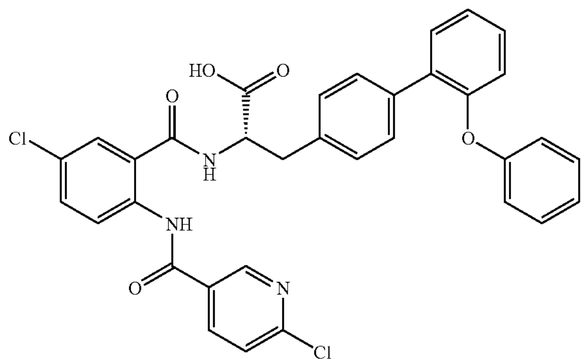 | (2S)-{5-Chloro-2-[(6-chloro-pyridine-3-carbonyl)-amino]-benzoylamino}-3-(2'-phenoxy-biphenyl-4-yl)-propionic acid |
| 339 | 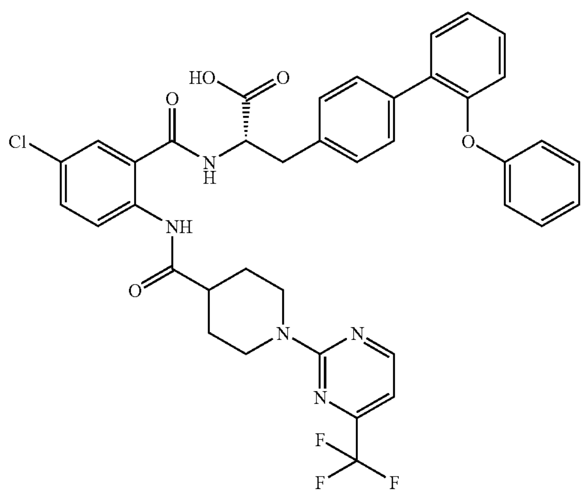 | (2S)-(5-Chloro-2-{1-(4-trifluoromethyl-pyrimidin-2-yl)-piperidine-4-carbonyl]-amino}-benzoylamino)-3-(2'-phenoxy-biphenyl-4-yl)-propionic acid |
| 340 | 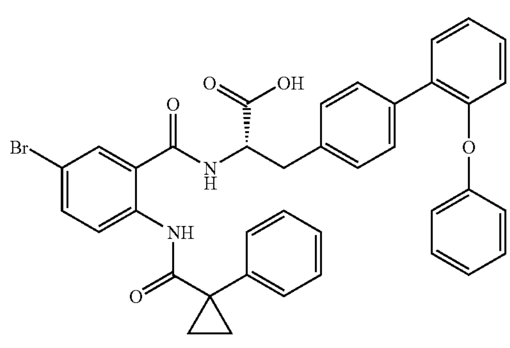 | (2S)-{5-Bromo-2-[(1-phenyl-cyclopropanecarbonyl)-amino]-benzoylamino}-3-(2'-phenoxy-biphenyl-4-yl)-propionic acid |

TABLE 1-continued

| Example | Structure | Name |
|---|---|---|
| 341 | 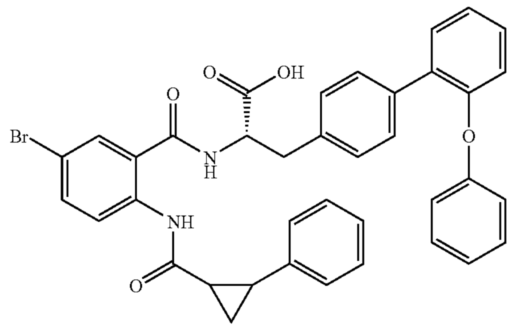 | (2S)-{5-Bromo-2-[(2-phenyl-cyclopropanecarbonyl)-amino]-benzoylamino}-3-(2'-phenoxy-biphenyl-4-yl)-propionic acid |
| 342 | 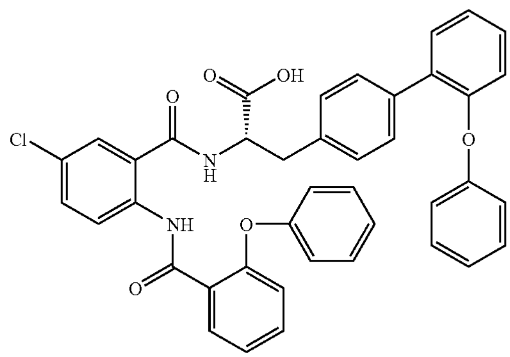 | (2S)-[5-Chloro-2-(2-phenoxy-benzoylamino)-benzoylamino]-3-(2'-phenoxy-biphenyl-4-yl)-propionic acid |
| 343 | 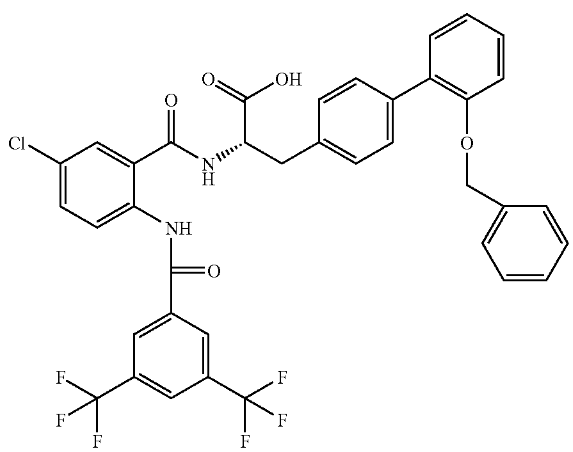 | 3-(2'-Benzyloxy-biphenyl-4-yl)-(2S)-[2-(3,5-bis-trifluoromethyl-benzoylamino)-5-chloro-benzoylamino]-propionic acid |

TABLE 1-continued

| Example | Structure | Name |
|---|---|---|
| 344 | 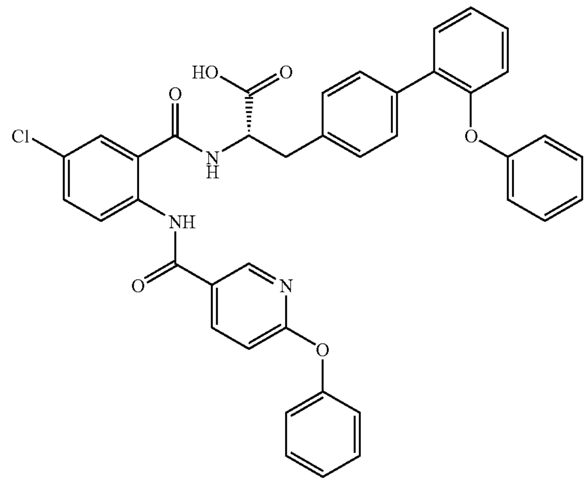 | (2S)-{5-Chloro-2-[(6-phenoxy-pyridine-3-carbonyl)-amino]-benzoylamino{-3-(2'-phenoxy-biphenyl-4-yl)-propionic acid |
| 345 | 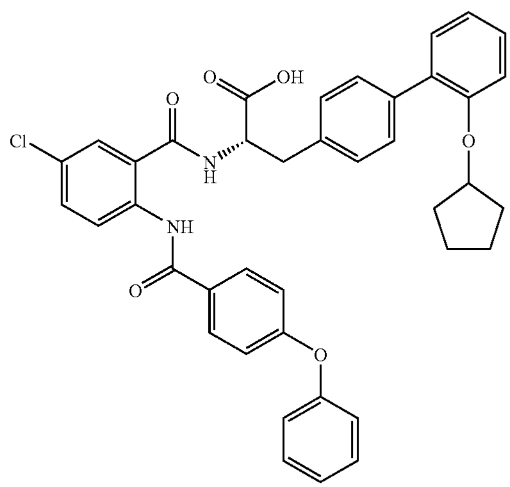 | (2S)-[5-Chloro-2-(4-phenoxy-benzoylamino)-benzoylamino]-3-(2'-cyclopentyloxy-biphenyl-4-yl)-propionic acid |
| 346 | 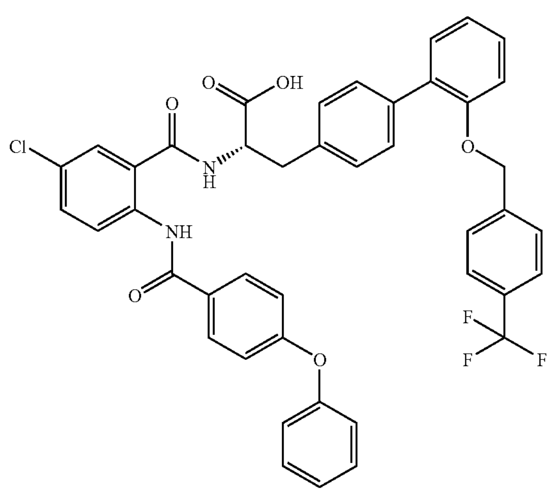 | (2S)-[5-Chloro-2-(4-phenoxy-benzoylamino)-benzoylamino]-3-[2'-(4-trifluoromethyl-benzyloxy)-biphenyl-4-yl]-propionic acid |

TABLE 1-continued

| Example | Structure | Name |
|---|---|---|
| 347 | 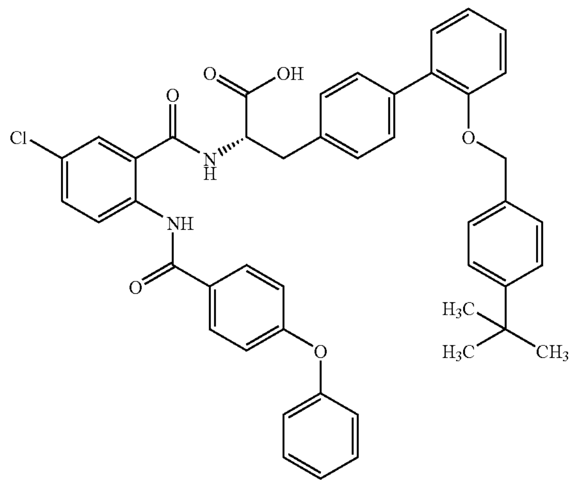 | 3-[2'-(4-tert-Butyl-benzyloxy)-biphenyl-4-yl]-(2S)-[5-chloro-2-(4-phenoxy-benzoylamino)-benzoylamino]-propionic acid |
| 348 | 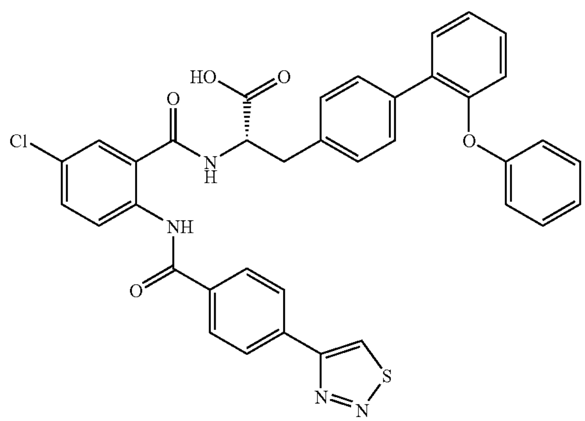 | (2S)-[5-Chloro-2-(4-[1,2,3]thiadiazol-4-yl-benzoylamino)benzoylamin]-3-(2'-phenoxy-biphenyl-4-yl)-propionic acid |
| 349 | 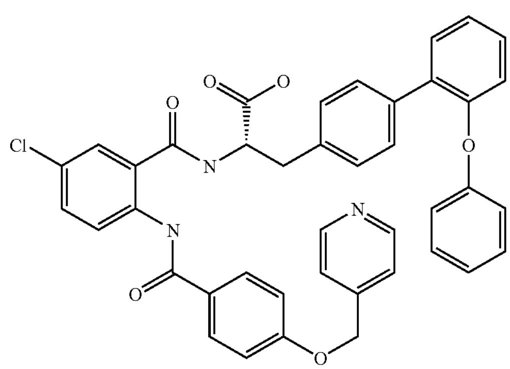 | (2S)-{5-Chloro-2-[4-(pyridin-4-ylmethoxy)-benzoylamino]-benzoylamino}-3-(2'-phenoxy-biphenyl-4-yl)-propionic acid |

TABLE 1-continued

| Example | Structure | Name |
|---|---|---|
| 350 | 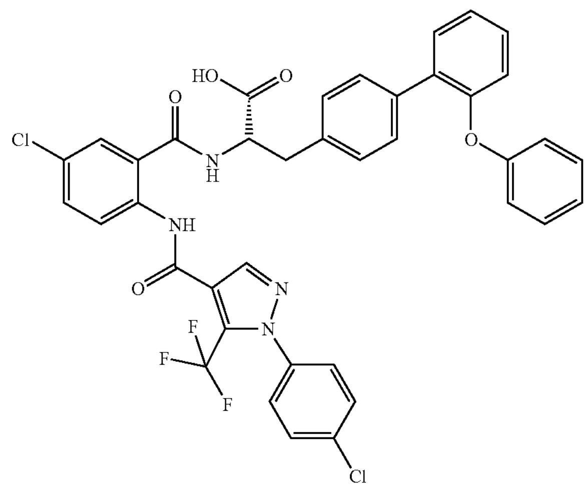 | (2S)-(5-Chloro-2-{[1-(4-chloro-phenyl)-5-trifluoromethyl-1H-pyrazole-4-carbonyl]-amino}-benzoylamino)-3-(2'-phenoxy-biphenyl-4-yl)-propionic acid |
| 351 | 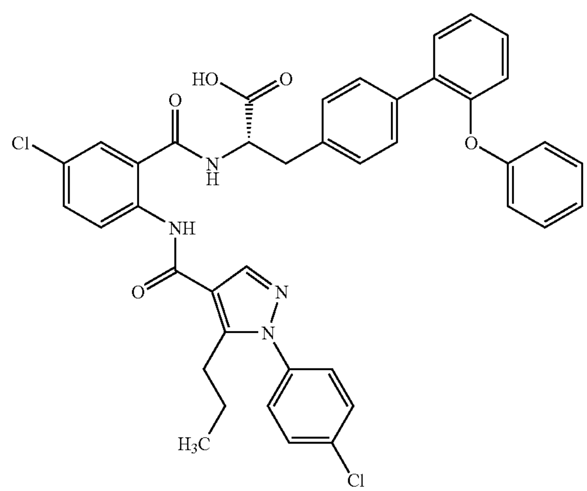 | (2S)-(5-Chloro-2-{[1-(4-chloro-phenyl)-5-propyl-1H-pyrazole-4-carbonyl]-amino}-benzoylamino)-3-(2'-phenoxy-biphenyl-4-yl)-propionic acid |
| 352 | 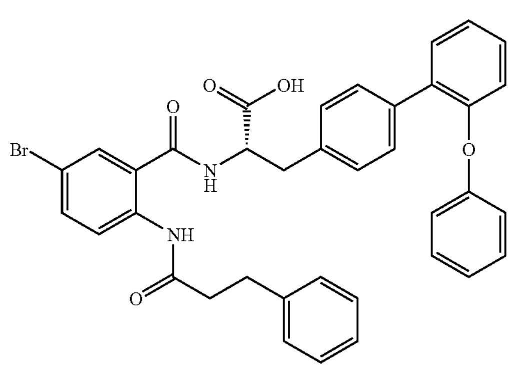 | (2S)-[5-Bromo-2-(3-phenyl-propionylamino)-benzoylamino]-3-(2'-phenoxy-biphenyl-4-yl)-propionic acid |

TABLE 1-continued

| Example | Structure | Name |
|---|---|---|
| 353 | 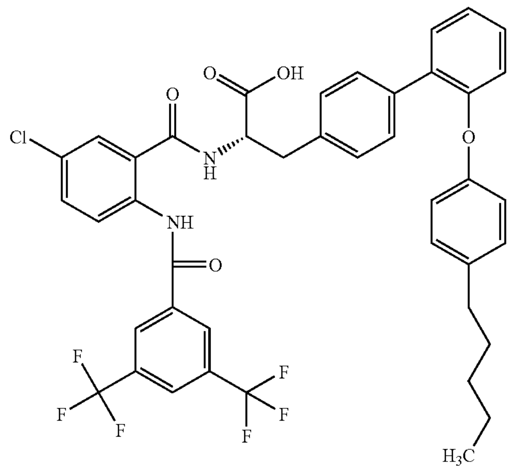 | (2S)-[2-(3,5-Bis-trifluoromethyl-benzoylamino)-5-chloro-benzoylamino]-3-[2'-(4-pentyl-phenoxy)-biphenyl-4-yl]-propionic acid |
| 354 | 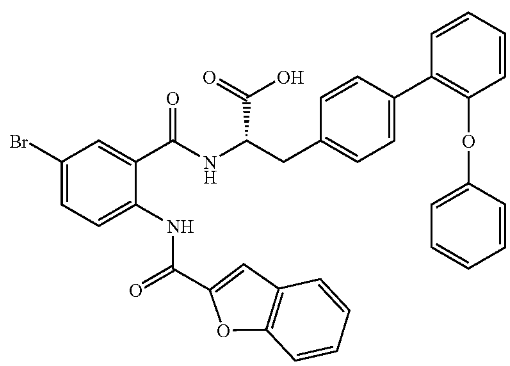 | (2S)-{2-[(Benzofuran-2-carbonyl)-amino]-5-bromo-benzoylamino}-3-(2'-phenoxy-biphenyl-4-yl)-propionic acid |
| 355 | 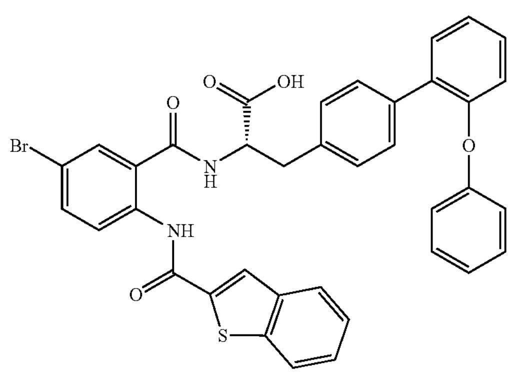 | (2S)-{2-[(Benzo[b]thiophene-2-carbonyl)-amino]-5-bromo-benzoylamino}-3-(2'-phenoxy-biphenyl-4-yl)-propionic acid |
| 356 | 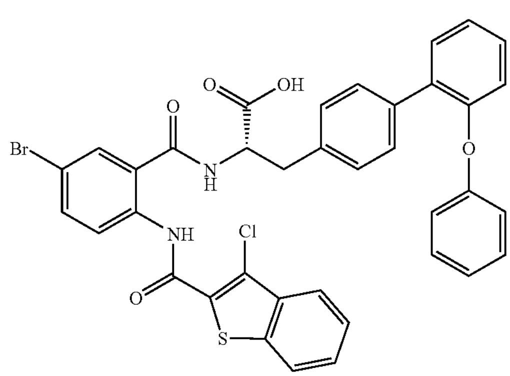 | (2S)-{5-Bromo-2-[(3-chloro-benzo[b]thiophene-2-carbonyl)-amino]-benzoylamino}-3-(2'-phenoxy-biphenyl-4-yl)-propionic acid |

TABLE 1-continued

| Example | Structure | Name |
|---------|-----------|------|
| 357 | 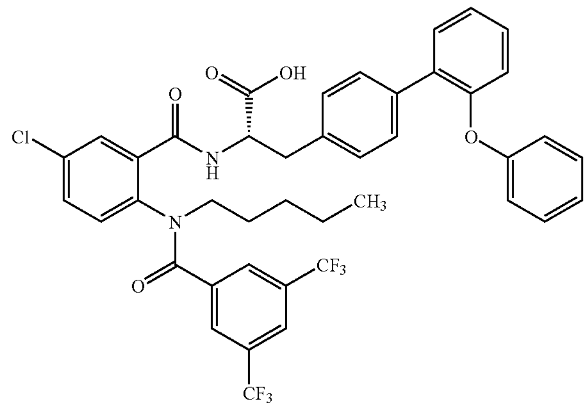 | (2S)-{2-[(3,5-Bis-trifluoromethyl-benzoyl)-pentyl-amino]-5-chloro-benzoylamino}-3-(2'-phenoxy-biphenyl-4-yl)-propionic acid |
| 358 | 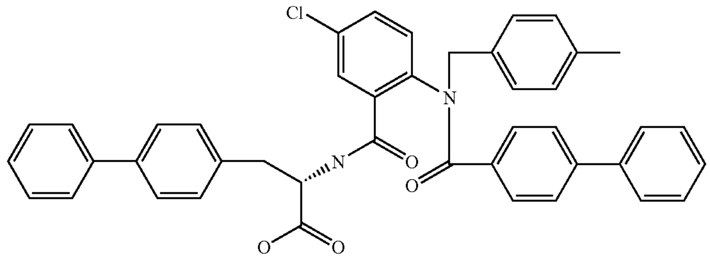 | (2S)-{2-[(Biphenyl-4-carbonyl)-(4-methyl-benzyl)-amino]-5-chloro-benzoylamino}-3-biphenyl-4-yl)-propionic acid |
| 359 | 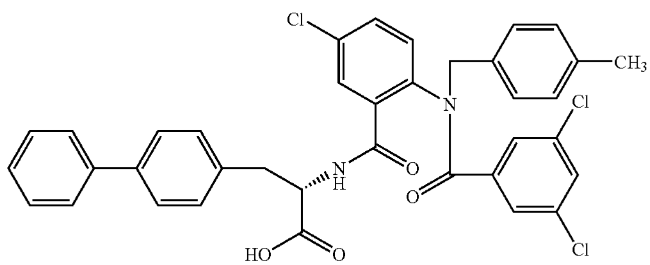 | 3-Biphenyl-4-yl-(2S){5-chloro-2-[(3,5-dichloro-benzoyl)-(4-methyl-benzyl)-amino]-benzoylamino}-propionic acid |
| 360 | 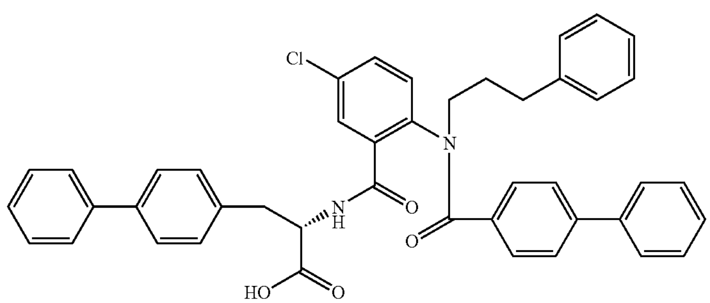 | (2S)-{2-[(Biphenyl-4-carbonyl)-(3-phenyl-propyl)-amino]-5-chloro-benzoylamino}-3-biphenyl-4-yl-propionic acid |
| 361 | 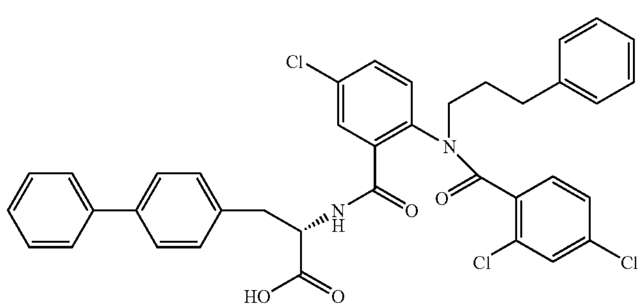 | 3-Biphenyl-4-yl-(2S)-{5-chloro-2-[(2,4-dichloro-benzoyl)-(3-phenyl-propyl)-amino]-benzoylamino}-propionic acid |

TABLE 1-continued

| Example | Structure | Name |
|---|---|---|
| 362 | 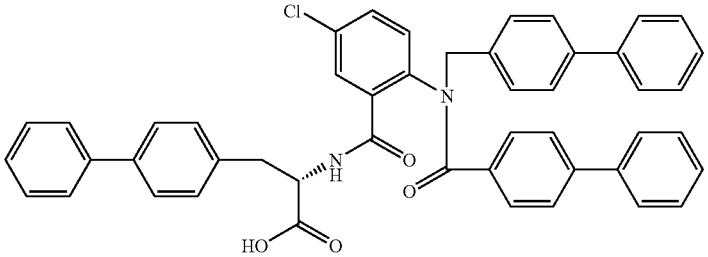 | (2S)-{2-[(Biphenyl-4-carbonyl)-biphenyl-4-ylmethyl-amino]-5-chloro-benzoylamino}-3-biphenyl-4-yl-propionic acid |
| 363 | 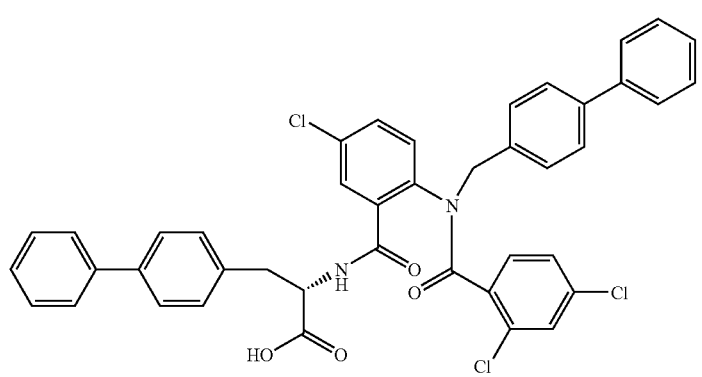 | 3-Biphenyl-4-yl-(2S)-{2-[biphenyl-4-ylmethyl-(2,4-dichloro-benzoyl)-amino]-5-chloro-benzoylamino}-propionic acid |
| 364 | 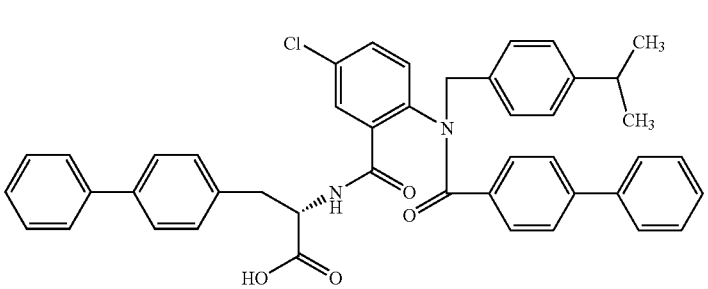 | (2S)-{2[(Biphenyl-4-carbonyl)-(4-isopropyl-benzyl)-amino]-5-chloro-benzoylamino}-3-biphenyl-4-yl-propionic acid |
| 365 | 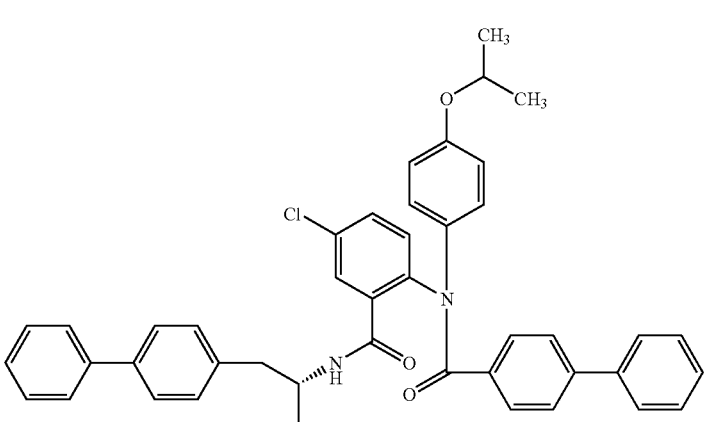 | (2S)-{2-[(Biphenyl-4-carbonyl)-(4-isopropoxy-benzyl)-amino]-5-chloro-benzoylamino}-3-biphenyl-4-yl-propionic acid |

TABLE 1-continued

| Example | Structure | Name |
|---|---|---|
| 366 | 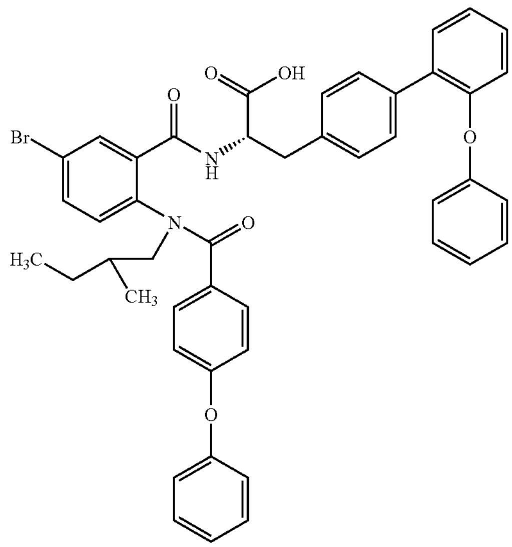 | (2S)-{5-Bromo-2-[(2-methyl-butyl)-(4-phenoxy-benzoyl)-amino]-benzoylamino}-3-(2'-phenoxy-biphenyl-4-yl)-propionic acid |
| 367 | 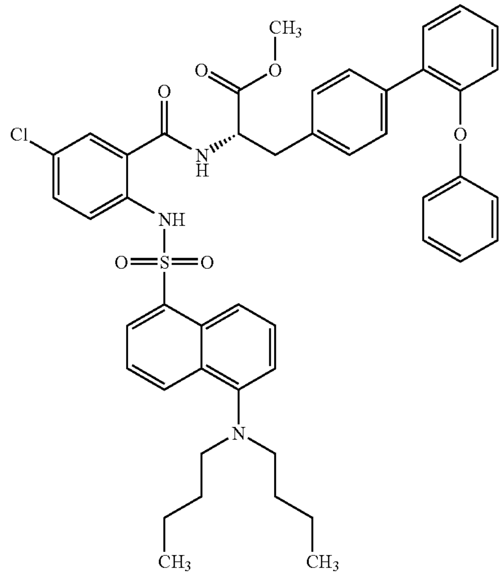 | (2S)-[5-Chloro-2-(5-dibutylamino-naphthalene-1-sulfonylamino)-benzoylamino]-3-(2'-phenoxy-biphenyl-4-yl)-propionic acid methyl ester |
| 368 | 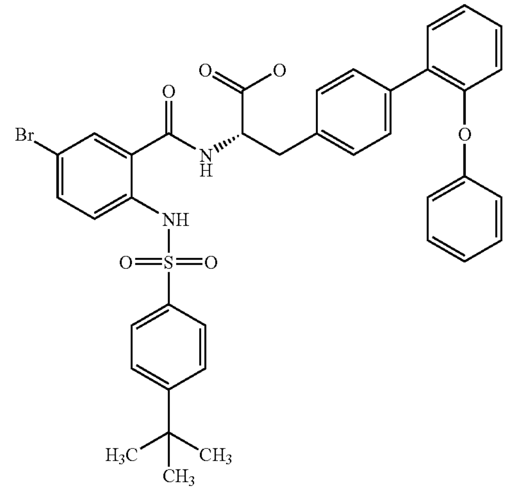 | (2S)-[5-Bromo-2-(4-tert-butyl-benzenesulfonylamino)-benzoylamino]-3-(2'-phenoxy-biphenyl-4-yl)-propionic acid |

TABLE 1-continued

| Example | Structure | Name |
|---|---|---|
| 369 | 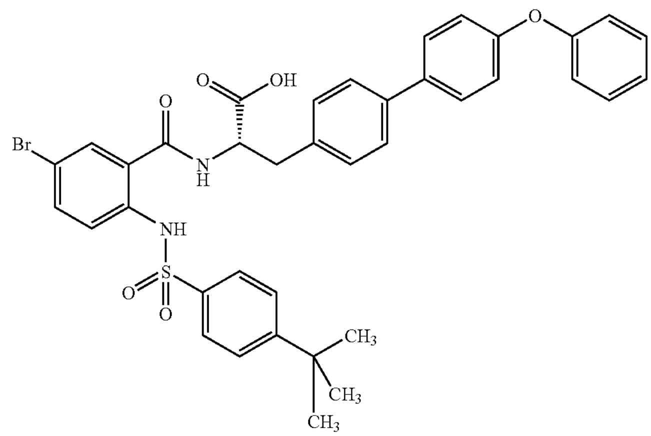 | (2S)-[5-Bromo-2-(4-tert-butyl-benzenesulfonylamino)-benzoylamino]-3-(4'-phenoxy-biphenyl-4-yl)-propionic acid |
| 370 | 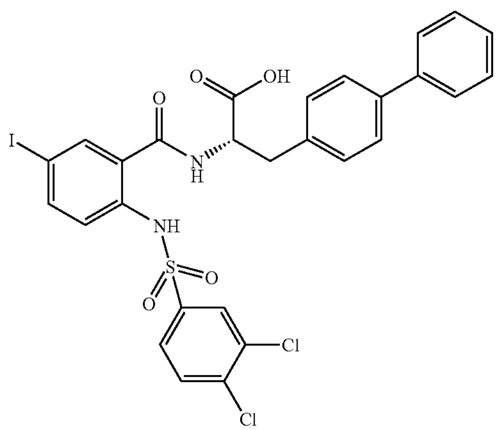 | 3-Biphenyl-4-yl-(2S)-[2-(3,4-dichloro-benzenesulfonylamino)-5-iodo-benzoylamino]-propionic acid |
| 371 | 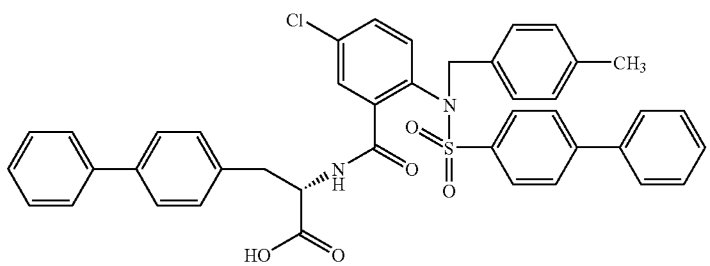 | (2S)-{2-[(Biphenyl-4-sulfonyl)-(4-methyl-benzyl)-amino]-5-chloro-benzoylamino}-3-biphenyl-4-yl-propionic acid |
| 372 | 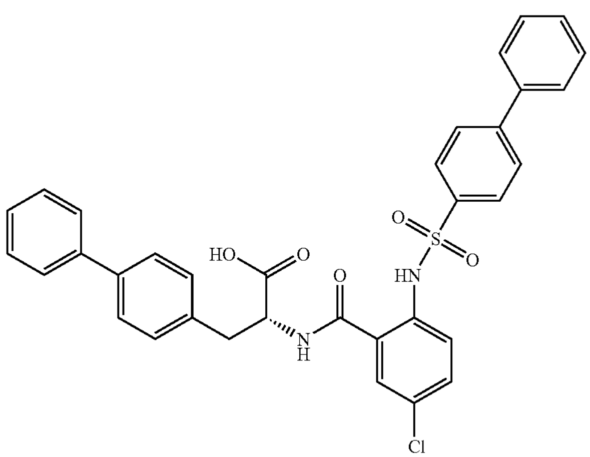 | (2S)-[2-(Biphenyl-4-sulfonylamino)-5-chloro-benzoylamino]-3-biphenyl-4-yl-propionic acid |

TABLE 1-continued

| Example | Structure | Name |
|---|---|---|
| 373 | 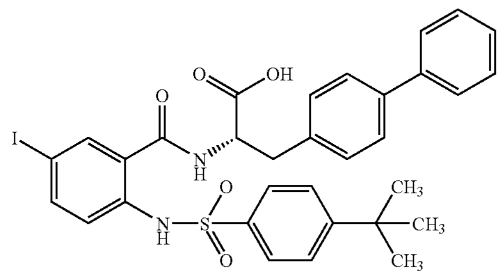 | 3-Biphenyl-4-yl-(2S)[2-(4-tert-butyl-benzenesulfonylamino)-5-propionic acid |
| 374 | 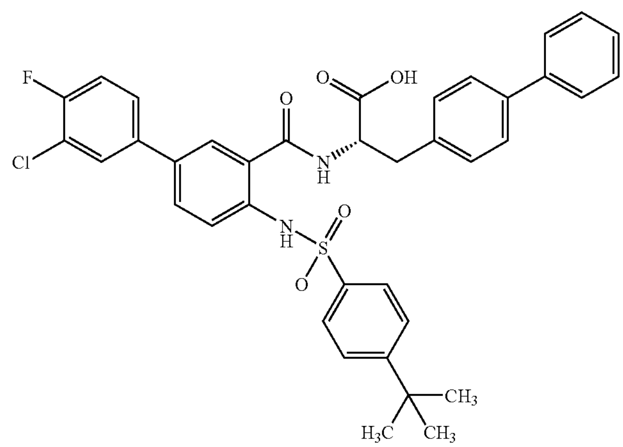 | 3-Biphenyl-4-yl-(2S){[4-(4-tert-butyl-benzenesulfonylamino)-3'-chloro-4'-fluoro-biphenyl-3-carbonyl]-amino}-propionic acid |
| 375 | 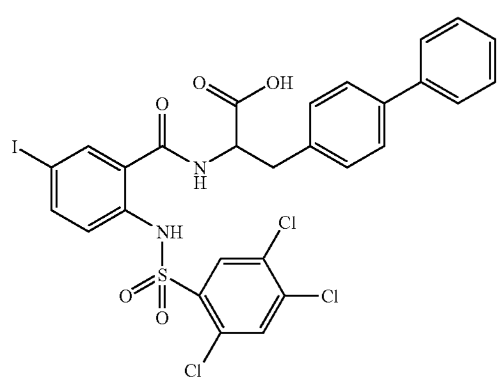 | 3-Biphenyl-4-yl-(2S)[5-iodo-2-(2,4,5-trichloro-benzenesulfonylamino)-benzoylamino]-propionic acid |
| 376 | 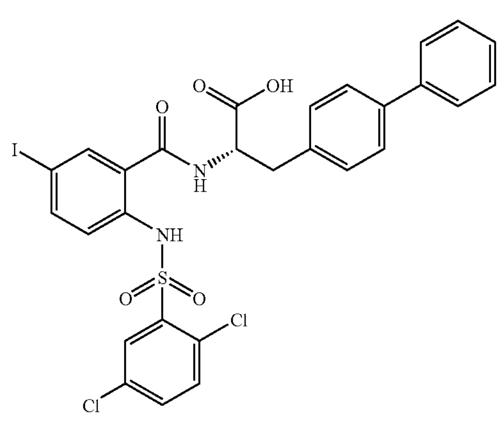 | 3-Biphenyl-4-yl-(2S)-[2-(2,5-dichloro-benzenesulfonylamino)-5-iodo-benzoylamino]-propionic acid |

TABLE 1-continued
| Example | Structure | Name |
|---|---|---|
| 377 | 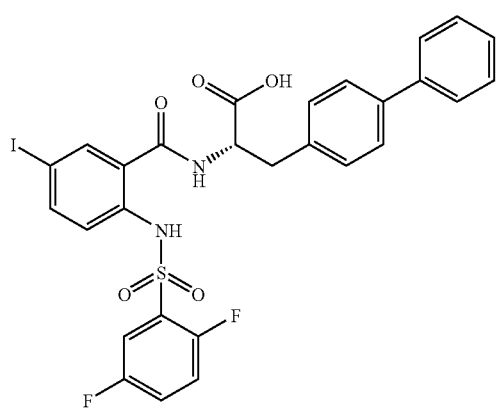 | 3-Biphenyl-4-yl-(2S)-[2-(2,4-difluoro-benzenesulfonylamino)-5-iodo-benzoylamino]-propionic acid |
| 378 | 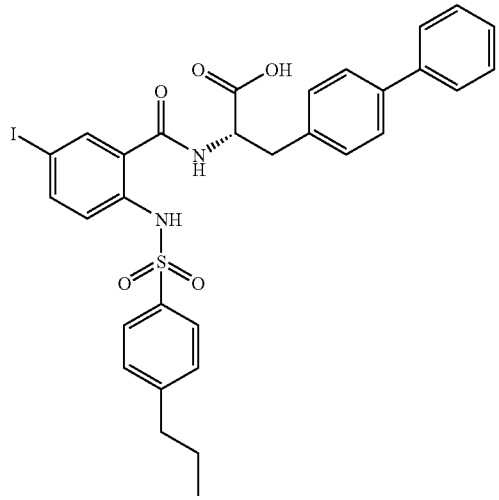 | 3-Biphenyl-4-yl-(3S)-[5-iodo-2-(4-propyl-benzenesulfonylamino)-benzoylamino]-propionic acid |
| 379 | 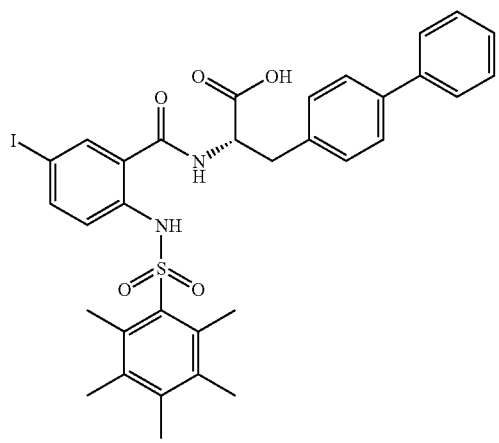 | 3-Biphenyl-4-yl-(2S)-(5-iodo-2-pentamethylbenzenesulfonyl-amino-benzoylamino)-propionic acid |

TABLE 1-continued

| Example | Structure | Name |
| --- | --- | --- |
| 380 | 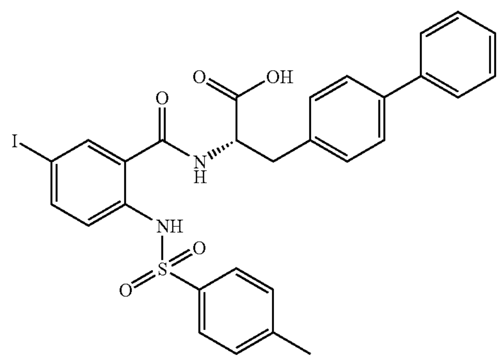 | 3-Biphenyl-4-yl-(2S)-[5-iodo-2-(toluene-4-sulfonylamino)-benzoylamino]-propionic acid |
| 381 | 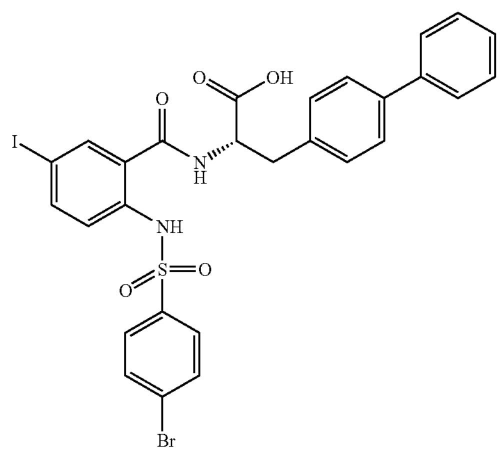 | 3-Biphenyl-4-yl-(2S)-[2-(4-bromo-benzenesulfonylamino)-5-iodo-benzoylamino]-propionic acid |
| 382 | 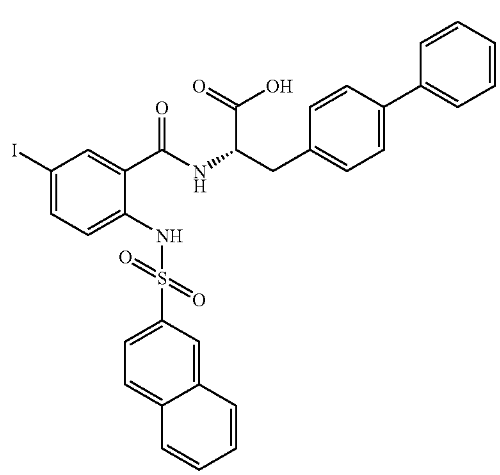 | 3-Biphenyl-4-yl-(2S)-[5-iodo-2-(naphthalene-2-sulfonylamino)-benzoylamino]-propionic acid |

TABLE 1-continued

| Example | Structure | Name |
|---|---|---|
| 383 | 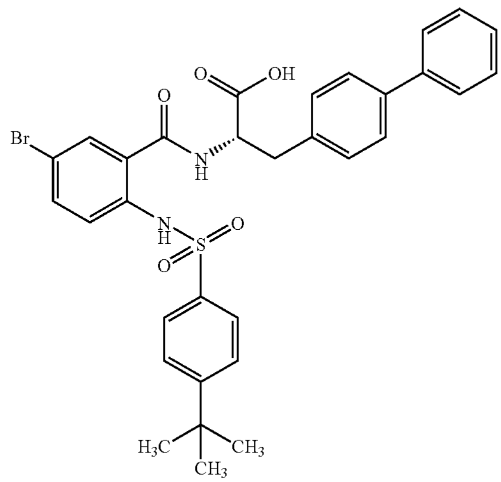 | 3-Biphenyl-4-yl-(2S)-[5-bromo-2-(4-tert-butyl-benzenesulfonylamino)-benzoylamino]-propionic acid |
| 384 | 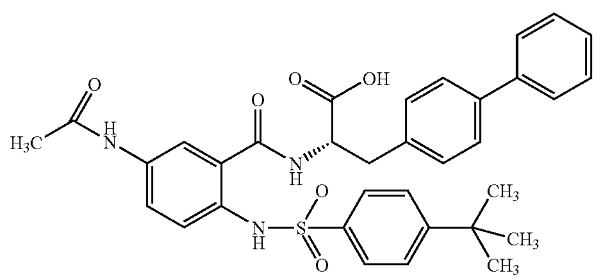 | 2-[5-Acetylamino-(2S)-(4-tert-butyl-benzenesulfonylamino)-benzoylamino]-3-biphenyl-4-yl-propionic acid |
| 385 | 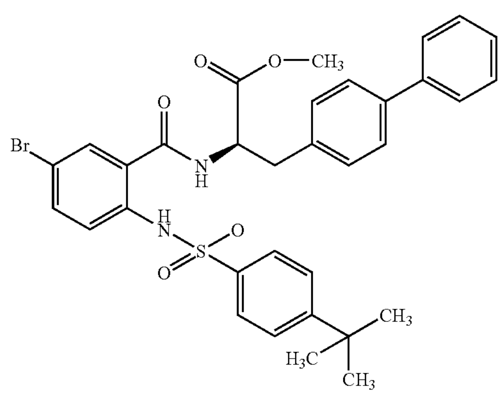 | 3-Biphenyl-4-yl-(2R)-[5-bromo-2-(4-tert-butyl-benzenesulfonylamino)-benzoylamino]-propionic acid methyl ester |

TABLE 1-continued

| Example | Structure | Name |
|---|---|---|
| 386 | 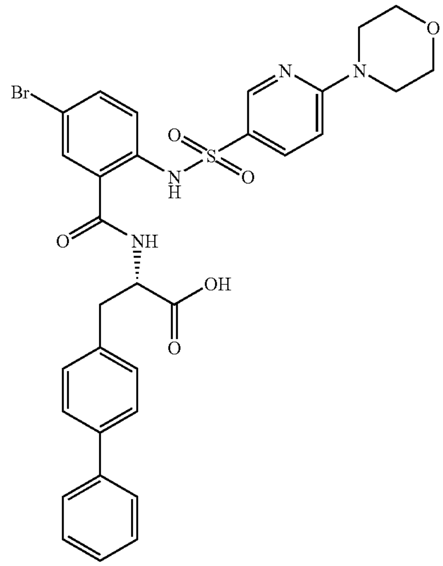 | 3-Biphenyl-4-yl-(2S)-[5-bromo-2-(6-morpholin-4-yl-pyridine-3-sulfonylamino)-benzoylamino]propionic acid |
| 387 | 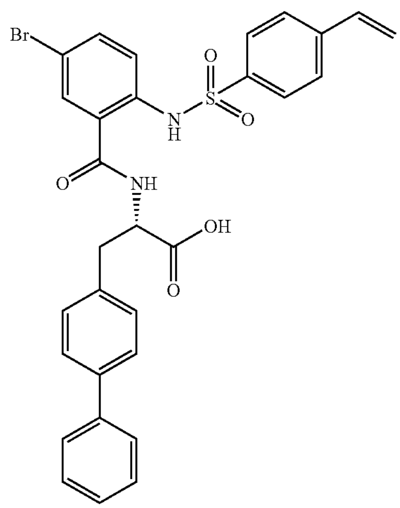 | 3-Biphenyl-4-yl-(2S)-[5-bromo-2-(4-vinyl-benzenesulfonylamino)-benzoylamino]-propionic acid |
| 388 | 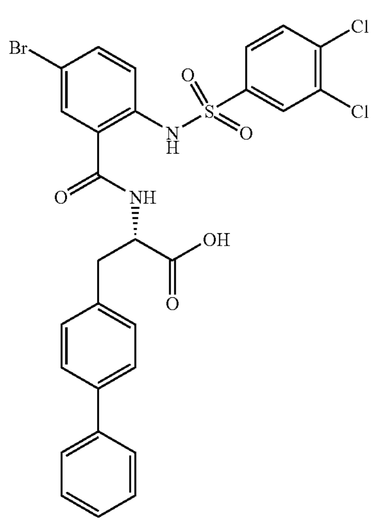 | 3-Biphenyl-4-yl-(2S)-[5-bromo-2-(3,4-dichloro-benzenesulfonylamino)-benzoylamino]-propionic acid |

TABLE 1-continued

| Example | Structure | Name |
|---|---|---|
| 389 | 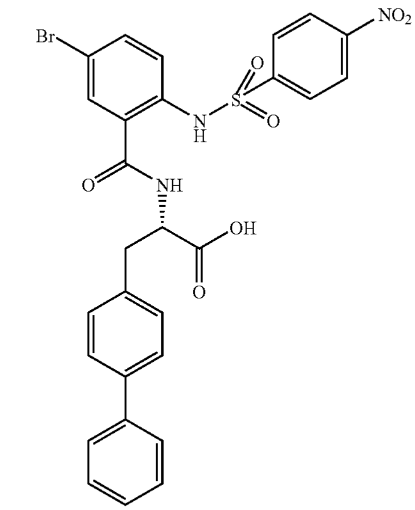 | 3-Biphenyl-4-yl-(2S)-[5-bromo-2-(4-nitro-bensenesulfonylamino)-benzoylamino]-propionic acid |
| 390 | 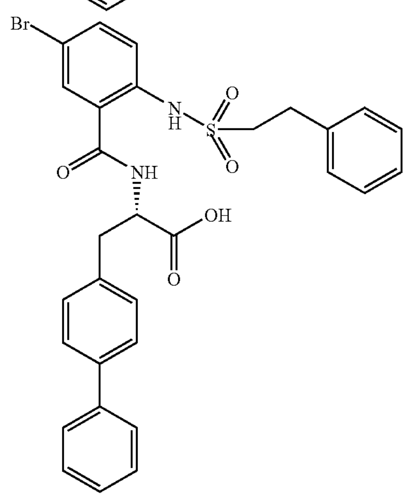 | 3-Biphenyl-4-yl-(2S)-[5-bromo-2-(2-phenyl-ethenesulfonylamino)-benzoylamino]-propionic acid |
| 391 | 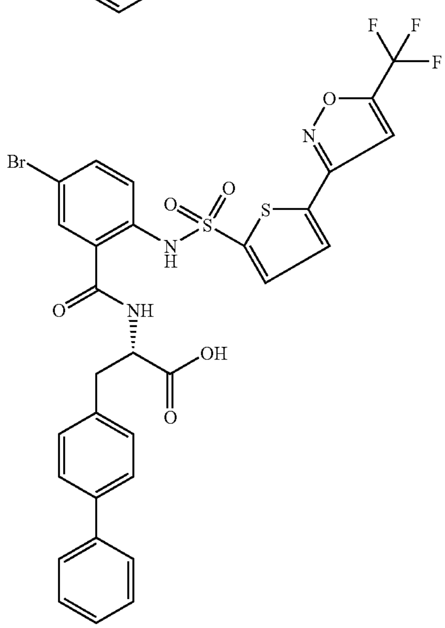 | 3-Biphenyl-4-yl-(2S)-{5-bromo-2-[5-(5-trifluoromethyl-isoxazol-3-yl)-thiophene-2-sulfonylamino]-benzoylamino}-propionic acid |

TABLE 1-continued
| Example | Structure | Name |
|---|---|---|
| 392 | 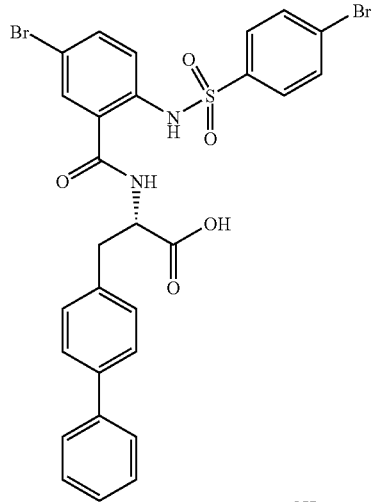 | 3-Biphenyl-4-yl-(2S)-[5-bromo-2-(4-bromo-benzenesulfonylamino)-benzoylamino]-propionic acid |
| 393 | 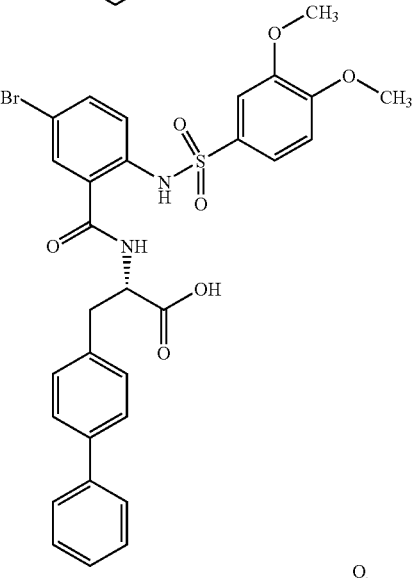 | 3-Biphenyl-4-yl-(2S)-[5-bromo-2-(3,4-dimethoxy-benzenesulfonylamino)-benzoylamino]-propionic acid |
| 394 | 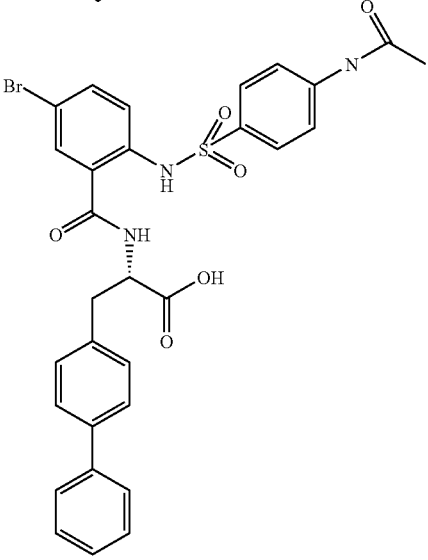 | (2S)-[2-(4-Acetylamino-benzenesulfonylamino)-5-bromo-benzoylamino]-3-biphenyl-4-yl-propionic acid |

TABLE 1-continued
| Example | Structure | Name |
|---|---|---|
| 395 | 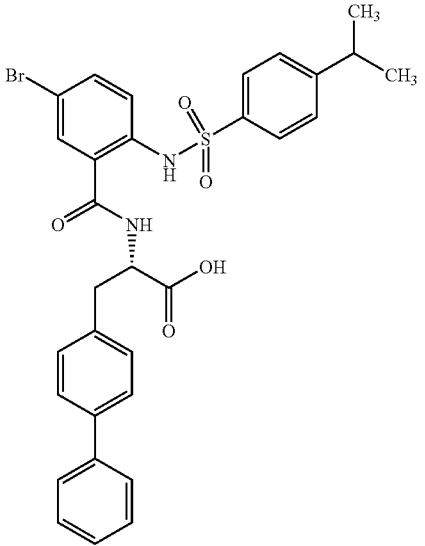 | 3-Biphenyl-4-yl-(2S)-[5-bromo-2-(4-isopropyl-benzenesulfonylamino)-benzoylamino]-propionic acid |
| 396 | 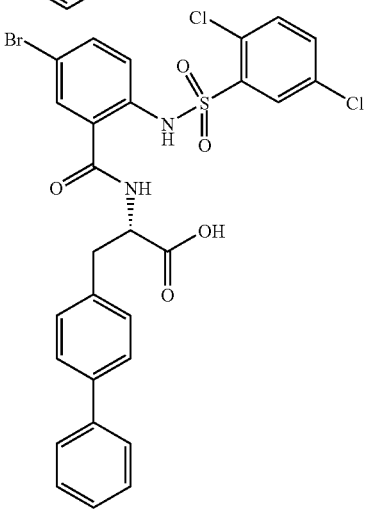 | 3-Biphenyl-4-yl-(2S)-[5-bromo-2-(2,5-dichloro-benzenesulfonylamino)-benzoylamino]-propionic acid |
| 397 | 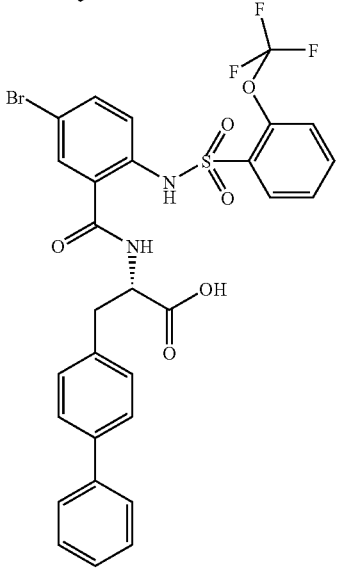 | 3-Biphenyl-4-yl-(2S)-[5-bromo-2-(2-rifluoromethoxy-benzenesulfonylamino)-benzoylamino]-propionic acid |

TABLE 1-continued

| Example | Structure | Name |
|---|---|---|
| 398 | 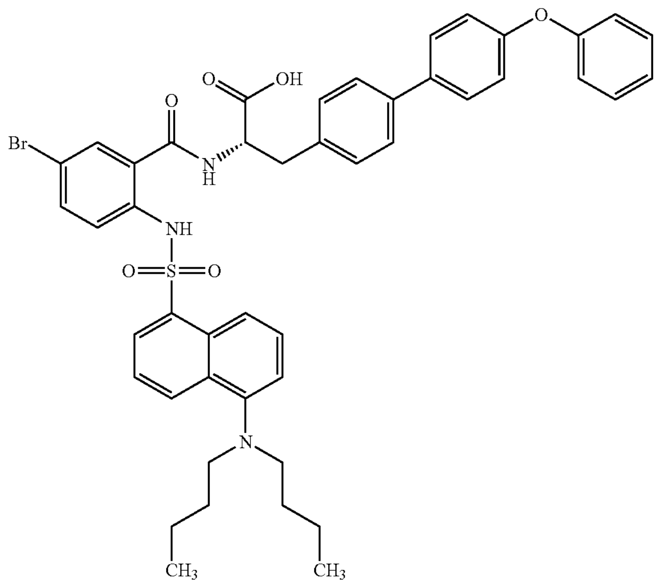 | (2S)-[5-Bromo-2-(5-dibutylamino-naphthalene-1-sulfonylamino)-benzoylamino]-3-(4'-phenoxy-biphenyl-4-yl)-propionic acid |
| 399 | 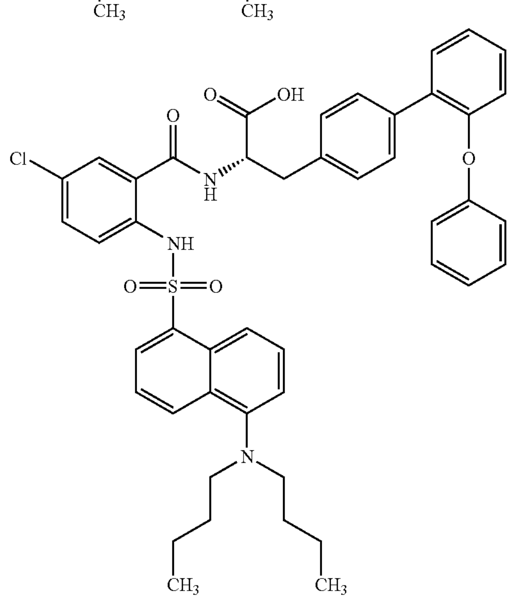 | (2S)-[5-Chloro-2-(5-dibutylamino-naphthalene-1-sulfonylamino)-benzoylamino]-3-(2'-phenoxy-biphenyl-4-yl)-propionic acid |
| 400 | 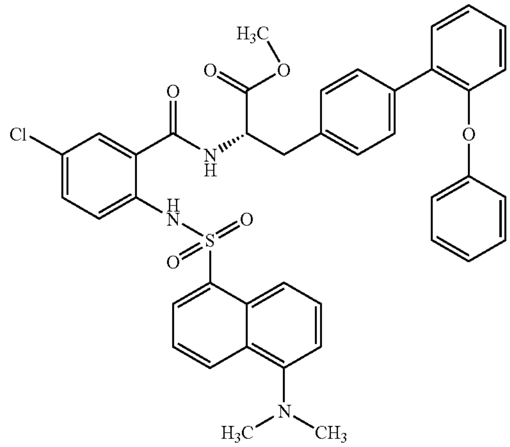 | (2S)-[5-Chloro-2-(5-dimethylamino-naphthalene-1-sulfonylamino)-benzoylamino]-3-(2'-phenoxy-biphenyl-4-yl)-propionic acid methyl ester |

TABLE 1-continued

| Example | Structure | Name |
|---|---|---|
| 401 | 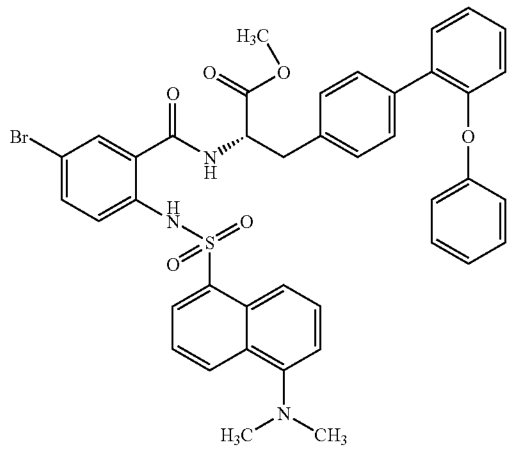 | (2S)-[5-Bromo-2-(5-dimethylamino-naphthalene-1-sulfonylamino)-benzoylamino]-3-(2'-phenoxy-biphenyl-4-yl)-propionic acid methyl ester |
| 402 | 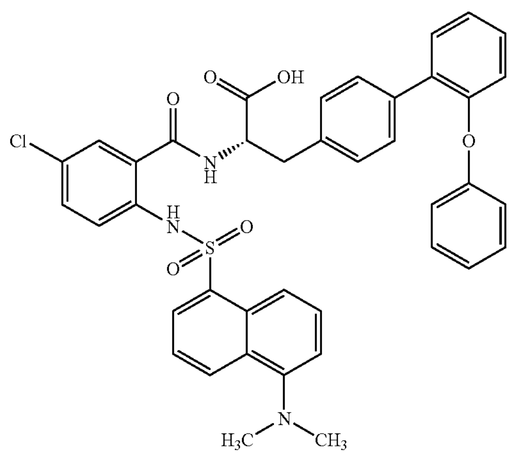 | (2S)-[5-Chloro-2-(5-dimethylamino-naphthalene-1-sulfonylamino)-benzoylamino]-3-(2'-phenoxy-biphenyl-4-yl)-propionic acid |
| 403 | 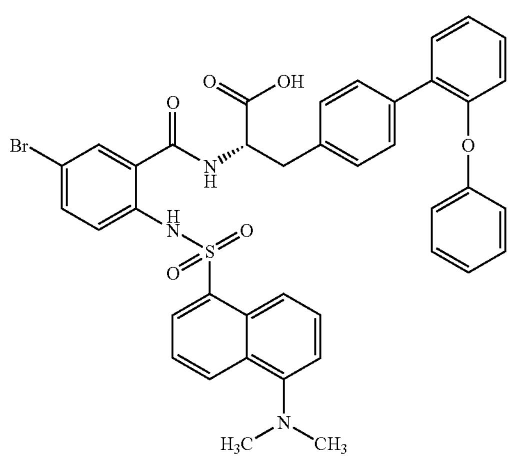 | (2S)-[5-Bromo-2-(5-dimethylamino-naphthalene-1-sulfonylamino)-benzoylamino]-3-(2'-phenoxy-biphenyl-4-yl)-propionic acid |

TABLE 1-continued

| Example | Structure | Name |
| --- | --- | --- |
| 404 | 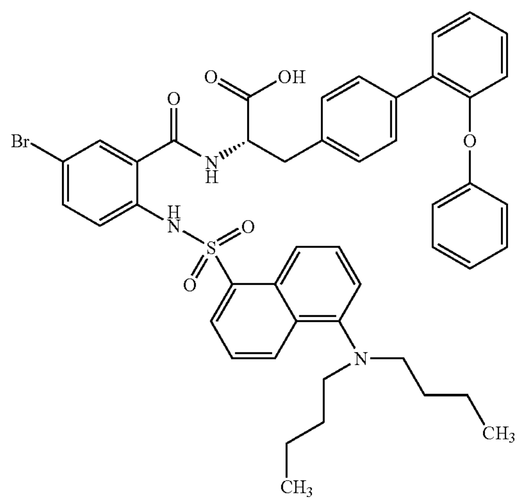 | (2S)-[5-Bromo-2-(5-dibutylamino-naphthalene-1-sulfonylamino)-benzoylamino]-3-(2'-phenoxy-biphenyl-4-yl)-propionic acid |
| 405 | 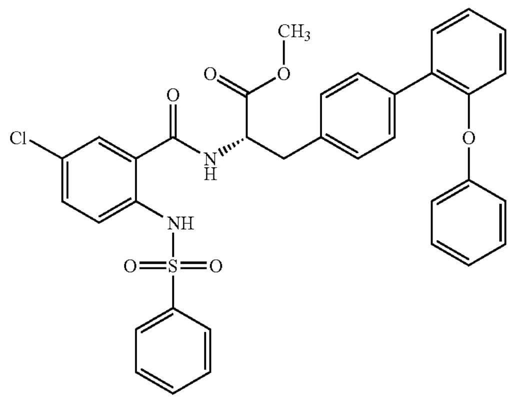 | (2S)-(2-Benzenesulfonylamino-5-chloro-benzoylamino)-3-(2'-phenoxy-biphenyl-4-yl)-propionic acid methyl ester |
| 406 | 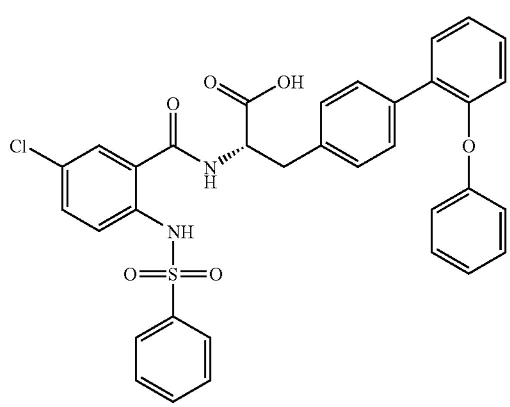 | (2S)-(2-Benzenesulfonylamino-5-chloro-benzoylamino)-3-(2'-phenoxy-biphenyl-4-yl)-propionic acid |

TABLE 1-continued

| Example | Structure | Name |
|---|---|---|
| 407 | 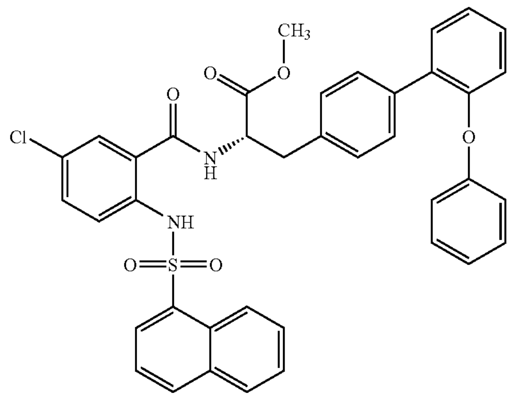 | (2S)-[5-Chloro-2-(naphthalene-1-sulfonylamino)-benzoylamino]-3-(2'-phenoxy-biphenyl-4-yl)-propionic acid methyl ester |
| 408 | 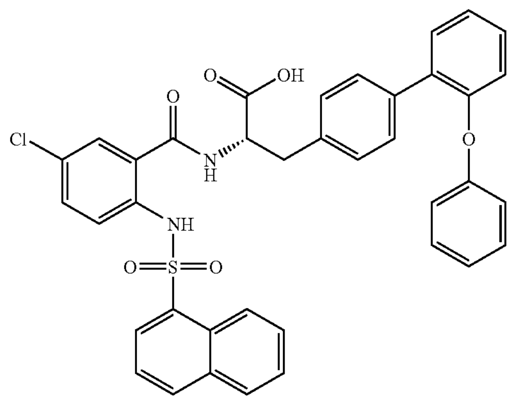 | (2S)-[5-Chloro-2-(naphthalene-1-sulfonylamino)-benzoylamino]-3-(2'-phenoxy-biphenyl-4-yl)-propionic acid |
| 409 | 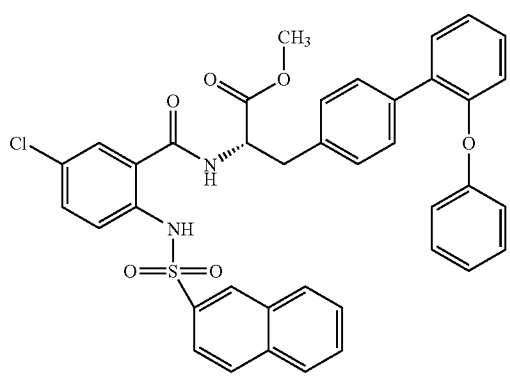 | (2S)-[5-Chloro-2-(naphthalene-2-sulfonylamino)-benzoylamino]-3-(2'-phenoxy-biphenyl-4-yl)-propionic acid methyl ester |
| 410 | 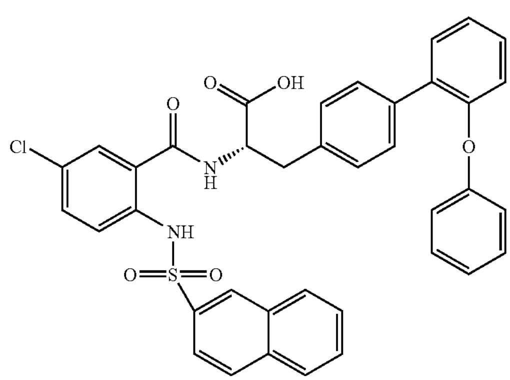 | (2S)-[5-Chloro-2-(naphthalene-2-sulfonylamino)-benzoylamino]-3-(2'-phenoxy-biphenyl-4-yl)-propionic acid |

TABLE 1-continued

| Example | Structure | Name |
|---|---|---|
| 411 | 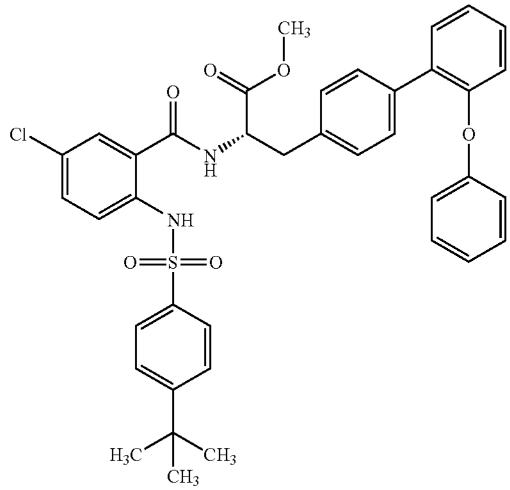 | (2S)-[2-(4-tert-Butyl-benzenesulfonylamino)-5-chloro-benzoylamino]-3-(2'-phenoxy-biphenyl-4-yl)-propionic acid methyl ester |
| 412 | 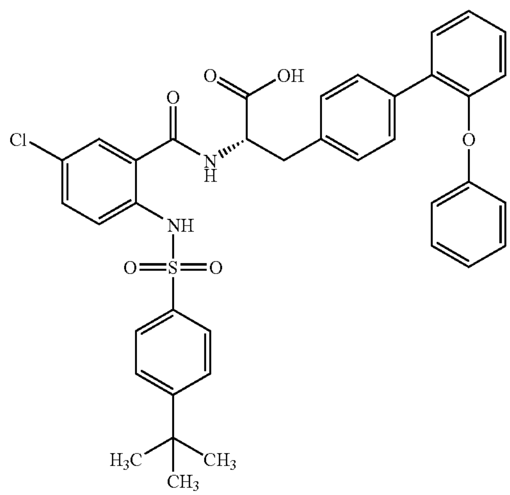 | (2S)-[2-(4-tert-Butyl-benzenesulfonylamino)-5-chloro-benzoylamino]-3-(2'-phenoxy-biphenyl-4-yl)-propionic acid |
| 413 | 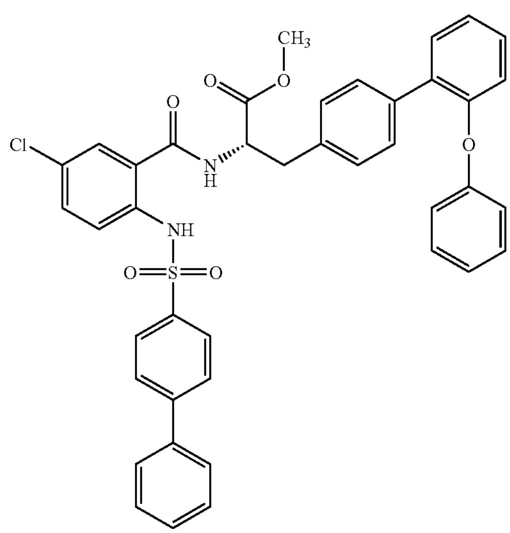 | (2S)-[2-(Biphenyl-4-sulfonylamino)-5-chloro-benzoylamino]-3-(2'-phenoxy-biphenyl-4-yl)-propionic acid methyl ester |

TABLE 1-continued
| Example | Structure | Name |
|---|---|---|
| 414 | 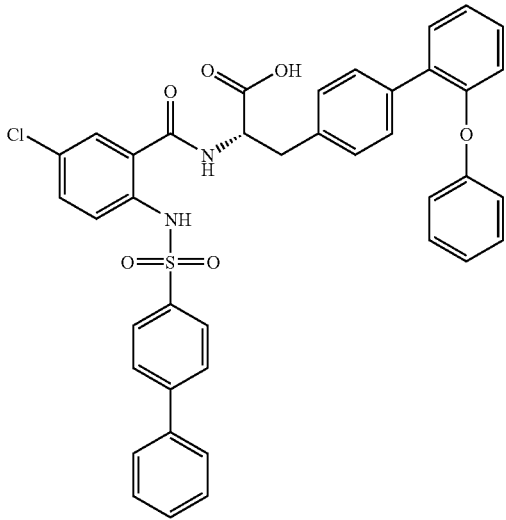 | (2S)-[2-(Biphenyl-4-sulfonylamino)-5-chloro-benzoylamino]-3-(2'-phenoxy-biphenyl-4-yl)-propionic acid |
| 415 | 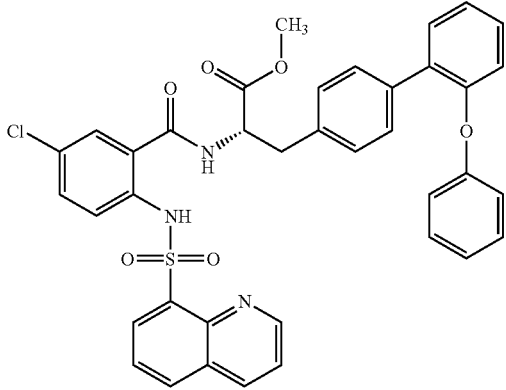 | (2S)-[5-Chloro-2-(quinoline-8-sulfonylamino)-benzoylamino]-3-(2'-phenoxy-biphenyl-4-yl)-propionic acid methyl ester |
| 416 | 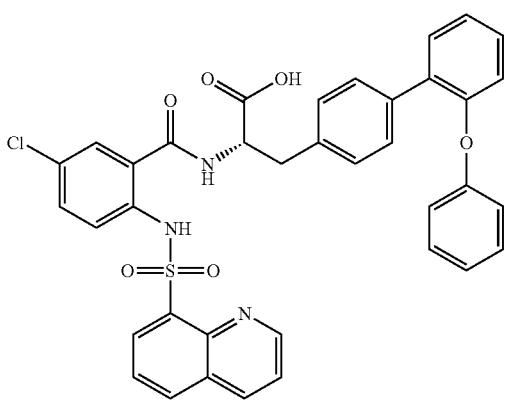 | (2S)-[5-Chloro-2-(quinoline-8-sulfonylamino)-benzoylamino]-3-(2'-phenoxy-biphenyl-4-yl)-propionic acid |

TABLE 1-continued

| Example | Structure | Name |
|---|---|---|
| 417 | 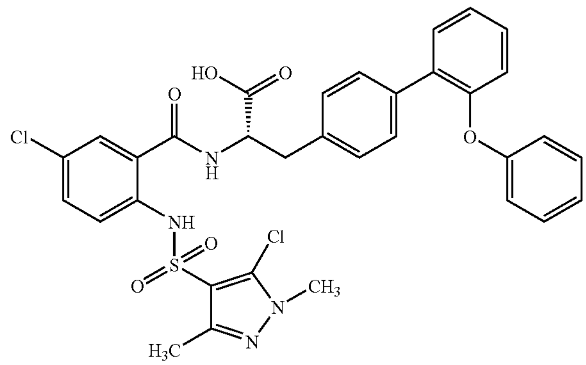 | (2S)-[5-Chloro-2-(5-chloro-1,3-dimethyl-1H-pyrazole-4-sulfonylamino)-benzoylamino]-3-(2'-phenoxy-biphenyl-4-yl)-propionic acid |
| 418 | 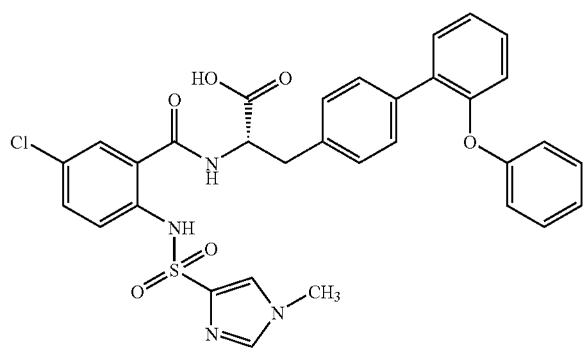 | (2S)-[5-Chloro-2-(1-methyl-1H-imidazole-4-sulfonylamino)-benzoylamino]-3-(2'-phenoxy-biphenyl-4-yl)-propionic acid |
| 419 | 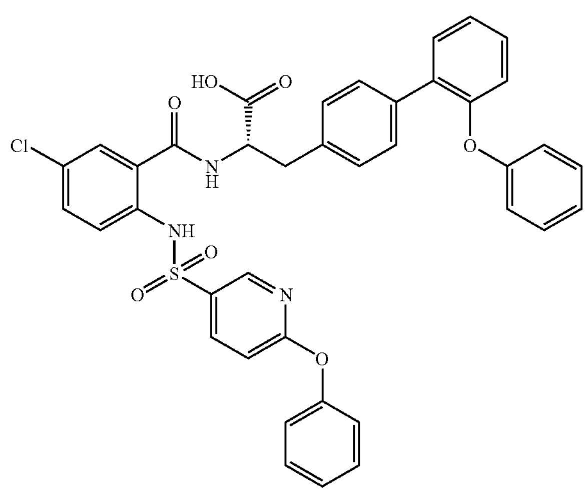 | (2S)-[5-Chloro-2-(6-phenoxy-pyridine-3-sulfonylamino)-benzoylamino]-3-(2'-phenoxy-biphenyl-4-yl)-propionic acid |

TABLE 1-continued

| Example | Structure | Name |
| --- | --- | --- |
| 420 | 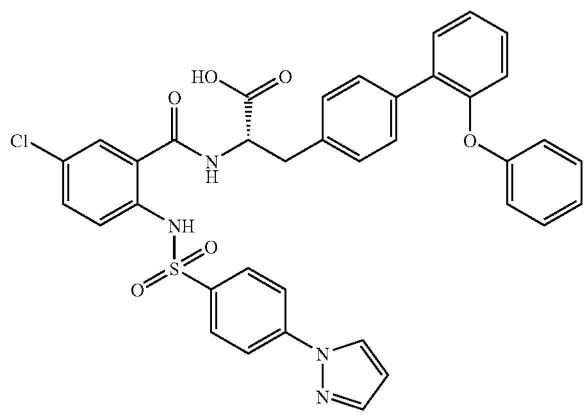 | (2S)-[5-Chloro-2-(4-pyrazol-1-yl-benzenesulfonylamino)-benzoylamino]-3-(2'-phenoxy-biphenyl-4-yl)-propionic acid |
| 421 | 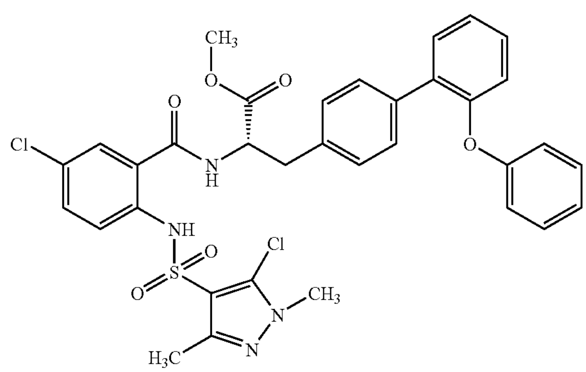 | (2S)-[5-Chloro-2-(5-chloro-1,3-dimethyl-1H-pyrazole-4-sulfonylamino)-benzoylamino]-3-(2'-phenoxy-biphenyl-4-yl)-propionic acid methyl ester |
| 422 | 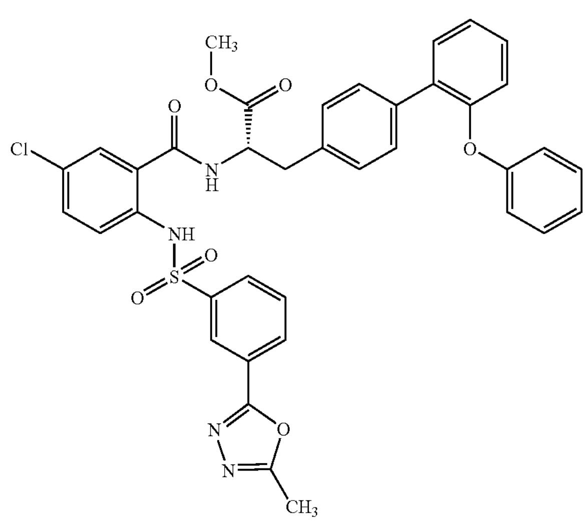 | (2S)-{5-Chloro-2-[3-(5-methyl-[1,3,4]oxadiazol-2-yl)-benzenesulfonylamino]-benzoylamino}-3-(2'-phenoxy-biphenyl-4-yl)-propionic acid methyl ester |

TABLE 1-continued

| Example | Structure | Name |
|---|---|---|
| 423 | 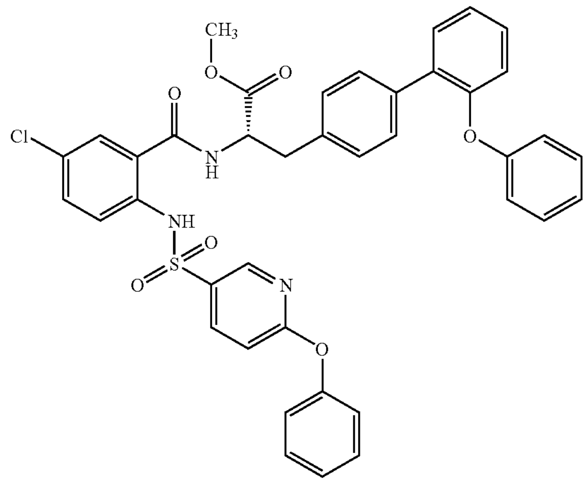 | (2S)-[5-Chloro-2-(6-phenoxy-pyridine-3-sulfonylamino)-benzoylamino]-3-(2'-phenoxy-biphenyl-4-yl)-propionic acid methyl ester |
| 424 | 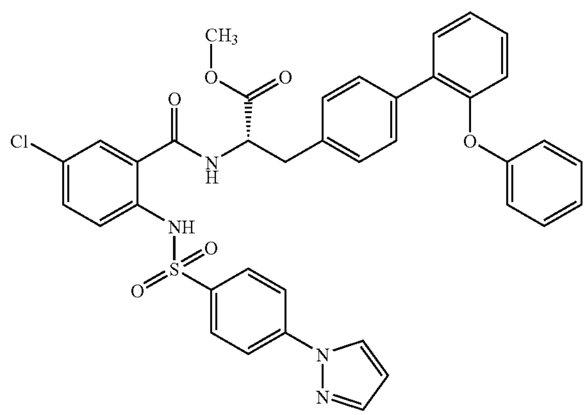 | (2S)-[5-Chloro-2-(4-pyrazol-1-yl-benzenesulfonylamino)-benzoylamino]-3-(2'-phenoxy-biphenyl-4-yl)-propionic acid methyl ester |
| 425 | 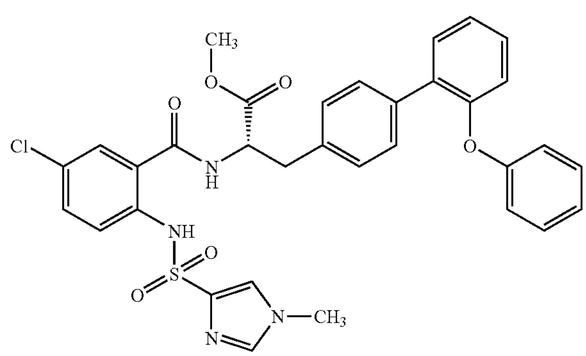 | (2S)-[5-Chloro-2-(1-methyl-1H-imidazole-4-sulfonylamino)-benzoylamino]-3-(2'-phenoxy-biphenyl-4-yl)-propionic acid methyl ester |

TABLE 1-continued

| Example | Structure | Name |
|---|---|---|
| 426 | 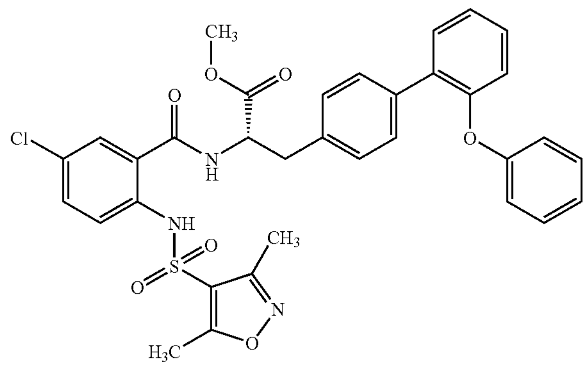 | (2S)-[5-Chloro-2-(3,5-dimethyl-isoxazole-4-sulfonylamino)-benzoylamino]-3-(2'-phenoxy-biphenyl-4-yl)-propionic acid methyl ester |
| 427 | 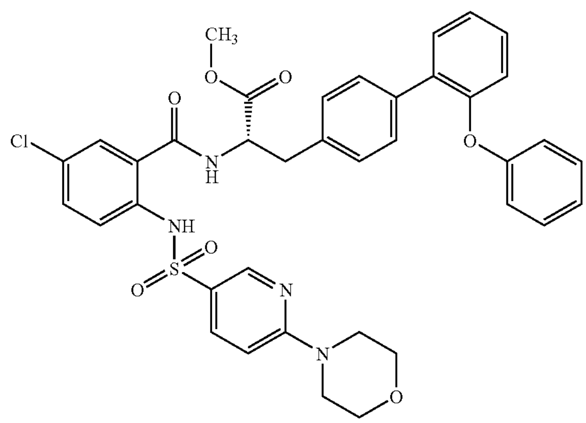 | (2S)-[5-Chloro-2-(6-morpholin-4-yl-pyridine-3-sulfonylamino)-benzoylamino]-3-(2'-phenoxy-biphenyl-4-yl)-propionic acid methyl ester |
| 428 | 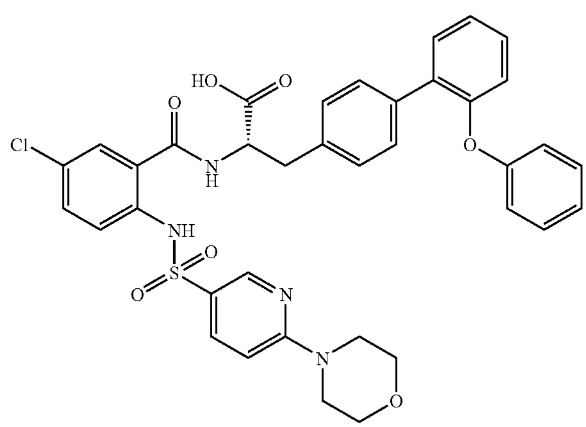 | (2S)-[5-Chloro-2-(6-morpholin-4-yl-pyridine-3-sulfonylamino)-benzoylamino]-3-(2'-phenoxy-biphenyl-4-yl)-propionic acid |

TABLE 1-continued

| Example | Structure | Name |
|---------|-----------|------|
| 429 | 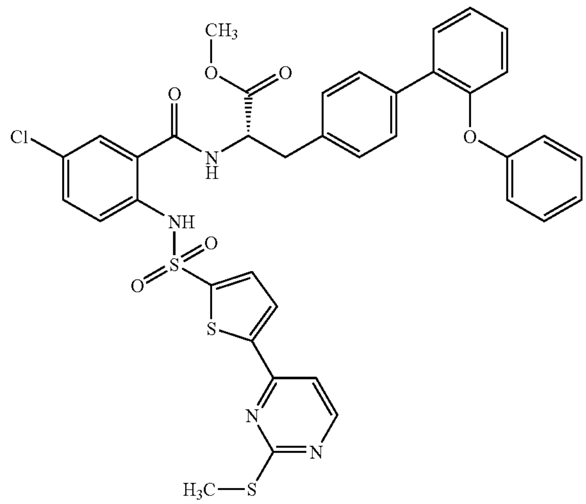 | (2S)-{5-Chloro-2-[5-(2-methylsulfanyl-pyrimidin-4-yl)-thiophene-2-sulfonylamino]-benzoylamino}-3-(2'-phenoxy-biphenyl-4-yl)-propionic acid methyl ester |
| 430 | 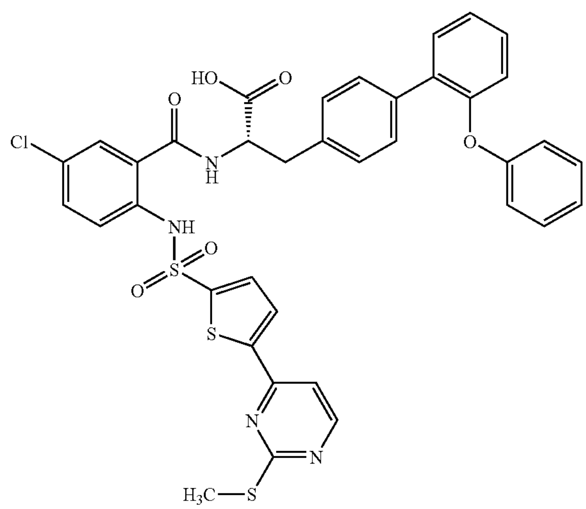 | (2S)-{5-Chloro-2-[5-(2-methylsulfanyl-pyrimidin-4-yl)-thiophene-2-sulfonylamino]-benzoylamino}-3-(2'-phenoxy-biphenyl-4-yl)-propionic acid |
| 431 | 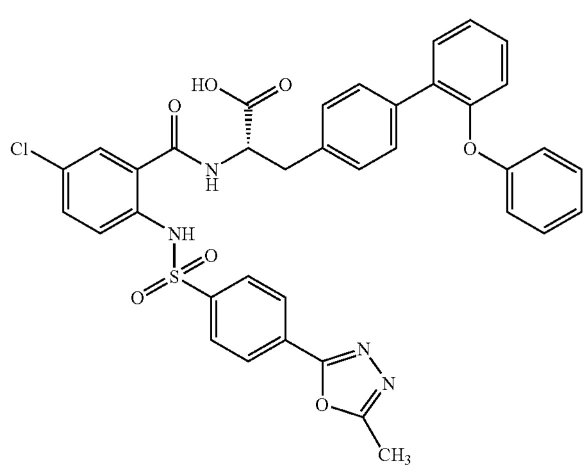 | (2S)-{5-Chloro-2-[4-(5-methyl-[1,3,4]oxadiazol-2-yl)-benzenesulfonylamino]-benzoylamino}-3-(2'-phenoxy-biphenyl-4-yl)-propionic acid |

TABLE 1-continued

| Example | Structure | Name |
|---|---|---|
| 432 | 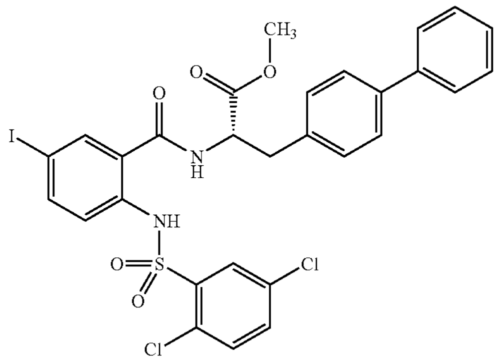 | 3-Biphenyl-4-yl-(2S)-[2-(2,5-dichloro-benzenesulfonylamino)-5-iodo-benzoylamino]-propionic acid methyl ester |
| 433 | 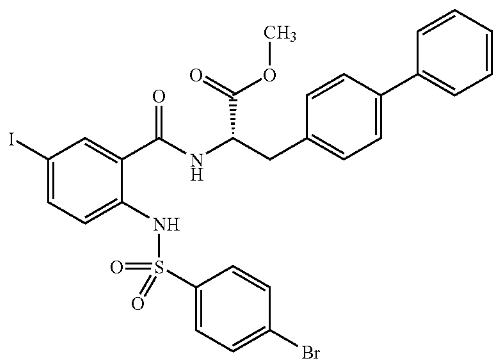 | 3-Biphenyl-4-yl-(2S)-[2-(4-bromo-benzenesulfonylamino)-5-iodo-benzoylamino]-propionic acid methyl ester |
| 434 | 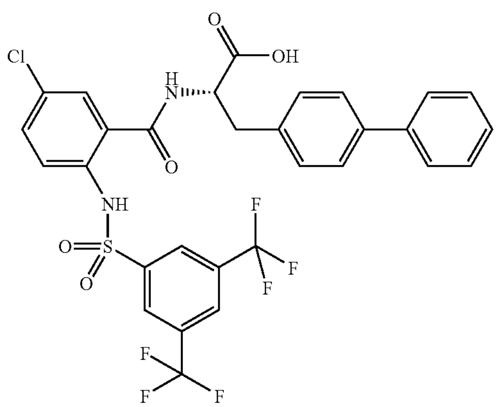 | 3-Biphenyl-4-yl-(2S)-[2-(3,5-bis-trifluoromethyl-benzenesulfonylamino)-5-chloro-benzoylamino]-propionic acid |
| 435 | 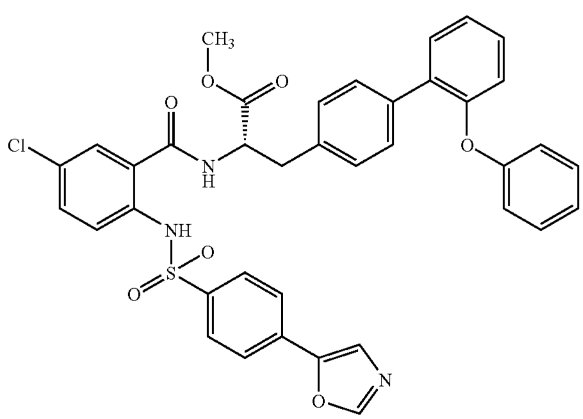 | (2S)-[5-Chloro-2-(4-oxazol-5-yl-benzenesulfonylamino)-benzoylamino]-3-(2'-phenoxy-biphenyl-4-yl)-propionic acid methyl ester |

TABLE 1-continued

| Example | Structure | Name |
|---|---|---|
| 436 | 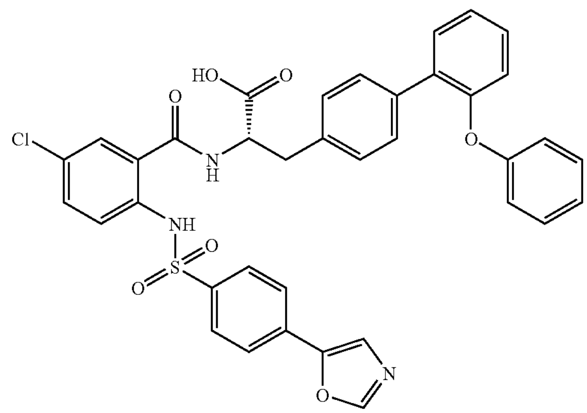 | (2S)-[5-Chloro-2-(4-oxazol-5-yl-benzenesulfonylamino)-benzoylamino]-3-(2'-phenoxy-biphenyl-4-yl)-propionic acid |
| 437 | 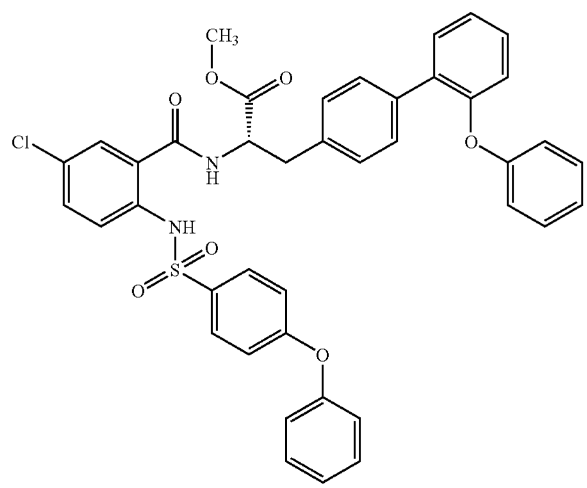 | (2S)-[5-Chloro-2-(4-phenoxy-benzenesulfonylamino)-benzoylamino]-3-(2'-phenoxy-biphenyl-4-yl)-propionic acid methyl ester |
| 438 | 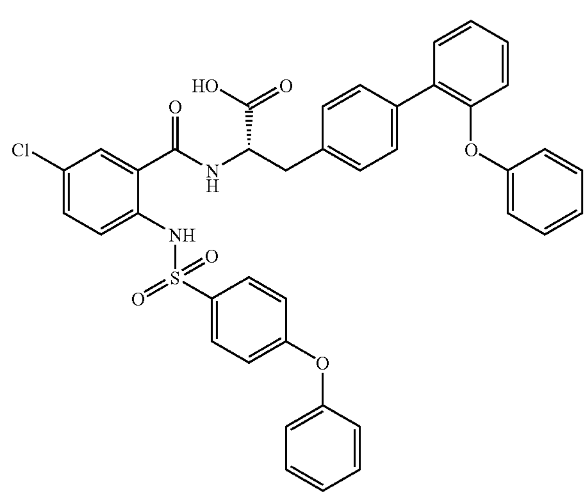 | (2S)-[5-Chloro-2-(4-phenoxy-benzenesulfonylamino)-benzoylamino]-3-(2'-phenoxy-biphenyl-4-yl)-propionic acid |

TABLE 1-continued

| Example | Structure | Name |
|---|---|---|
| 439 | 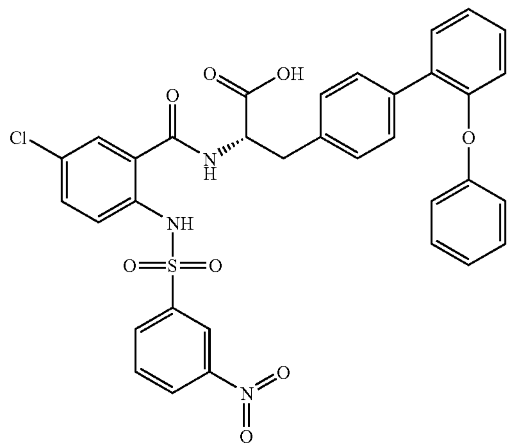 | (2S)-[5-Chloro-2-(3-nitro-benzenesulfonylamino)-benzoylamino]-3-(2'-phenoxy-biphenyl-4-yl)-propionic acid |
| 440 | 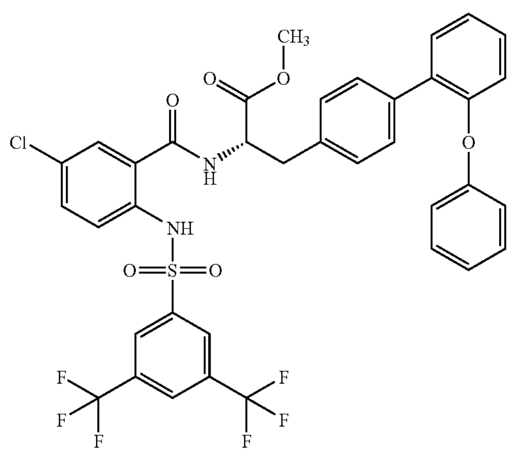 | (2S)-[2-(3,5-Bis-trifluoromethyl-benzenesulfonylamino)-5-chloro-benzoylamino]-3-(2'-phenoxy-biphenyl-4-yl)-propionic acid methyl ester |
| 441 | 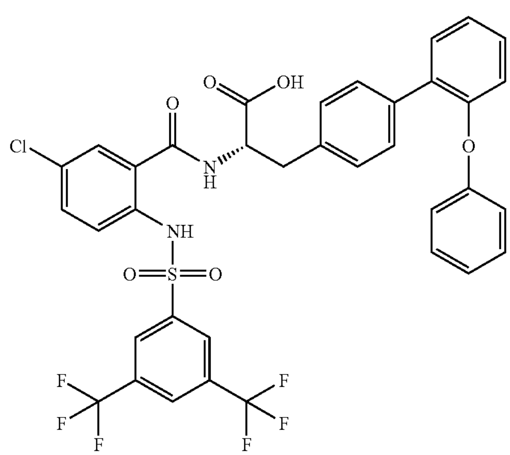 | (2S)-[2-(3,5-Bis-trifluoromethyl-benzenesulfonylamino)-5-chloro-benzoylamino]-3-(2'-phenoxy-biphenyl-4-yl)-propionic acid |

TABLE 1-continued

| Example | Structure | Name |
|---|---|---|
| 442 | 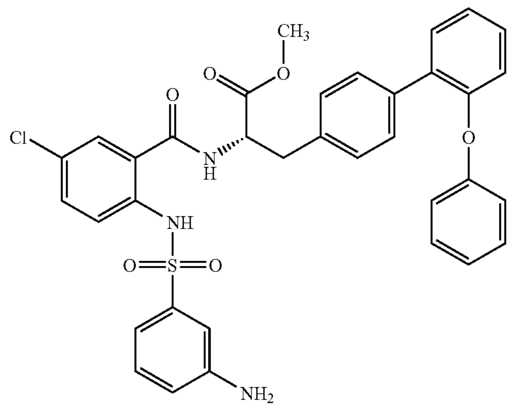 | (2S)-[2-(3-Amino-benzenesulfonylamino)-5-chloro-benzoylamino]-3-(2'-phenoxy-biphenyl-4-yl)-propionic acid methyl ester |
| 443 | 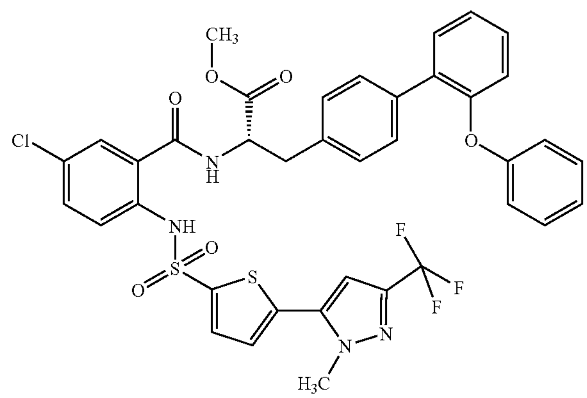 | (2S)-{5-Chloro-2-[5-(2-methyl-5-trifluoromethyl-2H-pyrazol-3-yl)-thiophene-2-sulfonylamino]-benzoylamino}-3-(2'-phenoxy-biphenyl-4-yl)-propionic acid methyl ester |
| 444 | 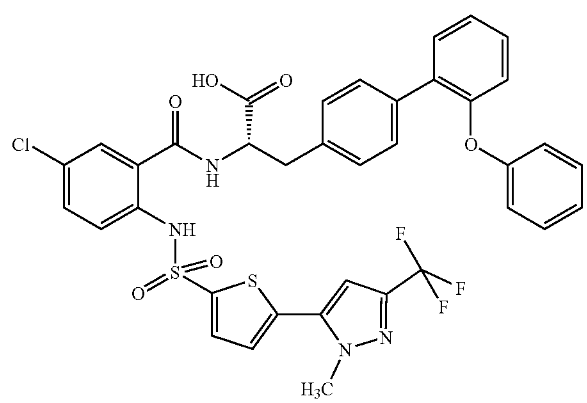 | (2S)-{5-Chloro-2-[5-(2-methyl-5-trifluoromethyl-2H-pyrazol-3-yl)-thiophene-2-sulfonylamino]-benzoylamino}-3-(2'-phenoxy-biphenyl-4-yl)-propionic acid |

TABLE 1-continued

| Example | Structure | Name |
|---|---|---|
| 445 | 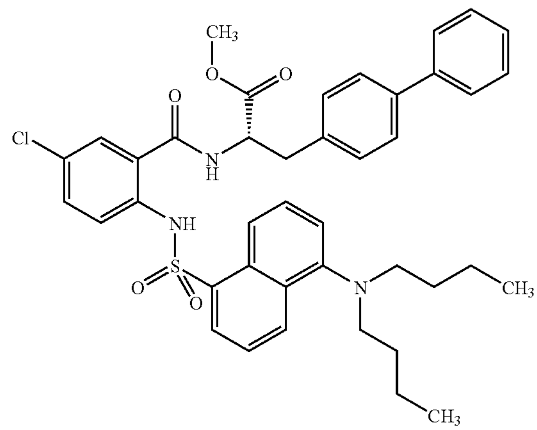 | 3-Biphenyl-4-yl-(2S)-[5-chloro-2-(5-dibutylamino-naphthalene-1-sulfonylamino)-enzoylamino]-propionic acid methyl ester |
| 446 | 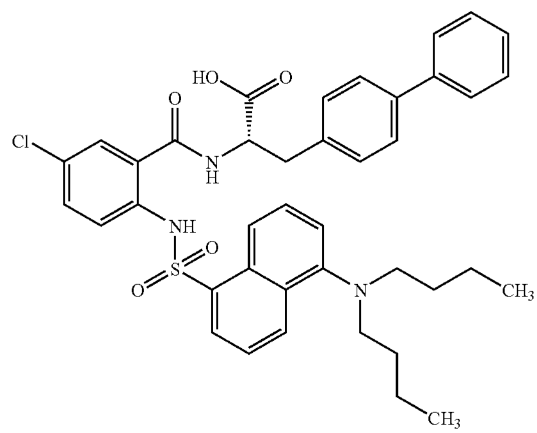 | 3-Biphenyl-4-yl-(2S)-[5-chloro-2-(5-dibutylamino-naphthalene-1-sulfonylamino)-benzoylamino]-propionic acid |
| 447 | 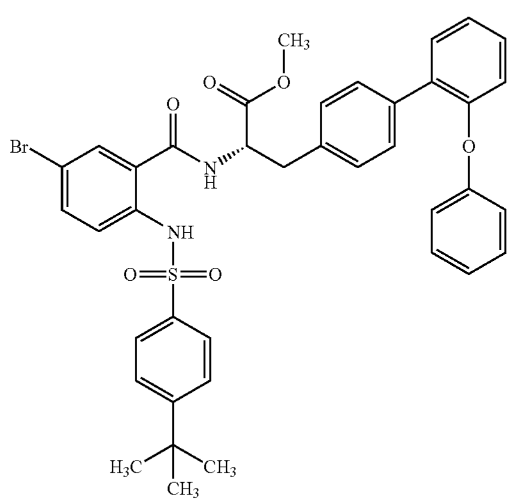 | (2S)-[5-Bromo-2-(4-tert-butyl-benzenesulfonylamino)-benzoylamino]-3-(2'-phenoxy-biphenyl-4-yl)-propionic acid methyl ester |

TABLE 1-continued

| Example | Structure | Name |
|---|---|---|
| 448 | 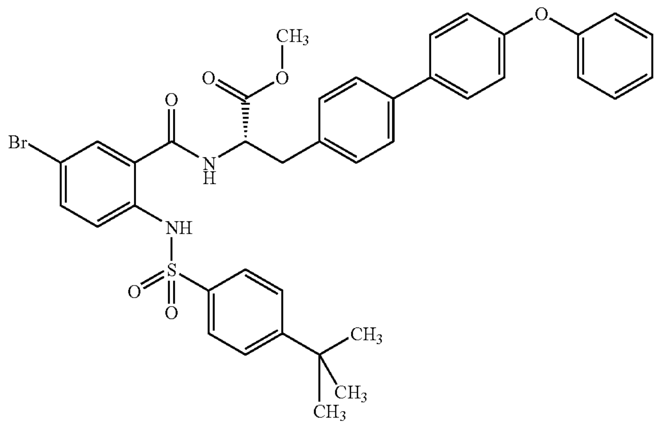 | (2S)-[5-Bromo-2-(4-tert-butyl-benzenesulfonylamino)-benzoylamino]-3-(4'-phenoxy-biphenyl-4-yl)-propionic acid methyl ester |
| 449 | 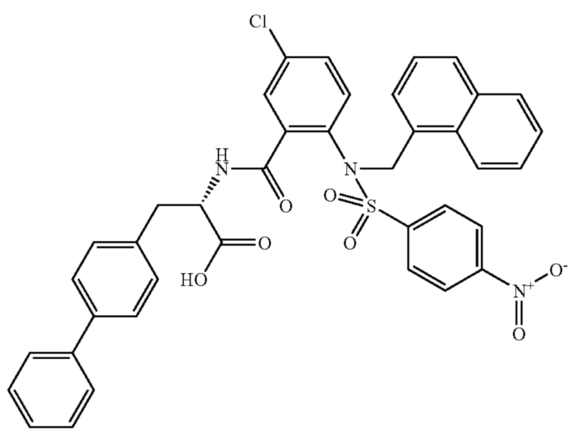 | 3-Biphenyl-4-yl-(2S)-{5-chloro-2-[naphthalene-1-ylmethyl-(4-nitro-benzenesulfonyl)-amino]-benzoylamino}-propionic acid |
| 450 | 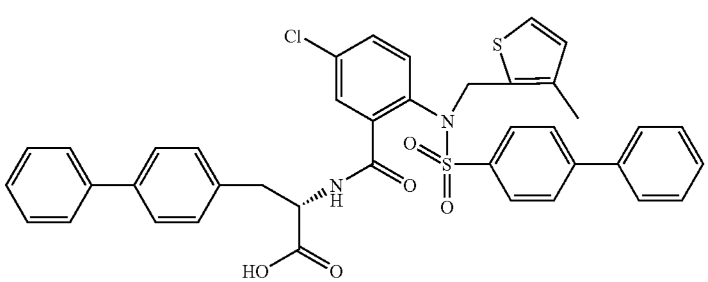 | (2S)-{2-[(Biphenyl-4-sulfonyl)-(3-methyl-thiophen-2-ylmethyl)-amino]-5-chloro-benzoylamino}-3-biphenyl-4-yl-propionic acid |
| 451 | 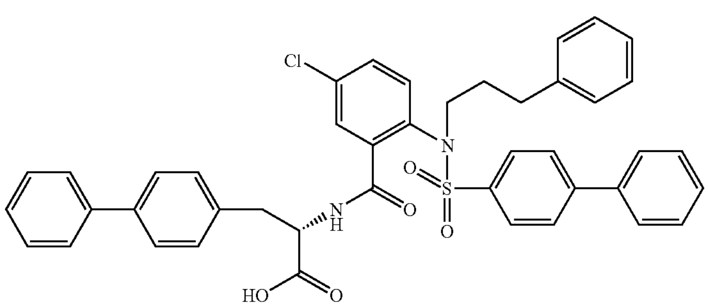 | (2S)-{2-[(Biphenyl-4-sulfonyl)-(3phenyl-propyl)-amino]-5-chloro-benzoylamino}-3-biphenyl-4-yl-propionic acid |

TABLE 1-continued

| Example | Structure | Name |
|---|---|---|
| 452 | 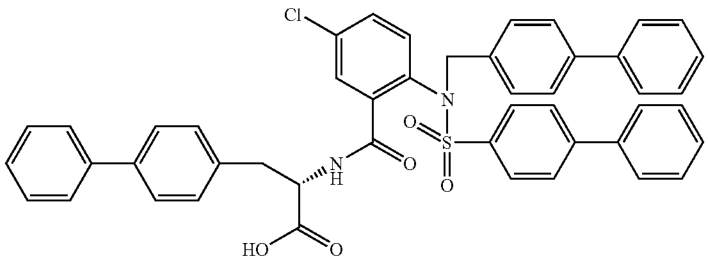 | (2S)-{2-[(Biphenyl-4-sulfonyl)-biphenyl-4-ylmethyl-amino]-5-chloro-benzoylamino}-3-biphenyl-4-yl-propionic acid |
| 453 | 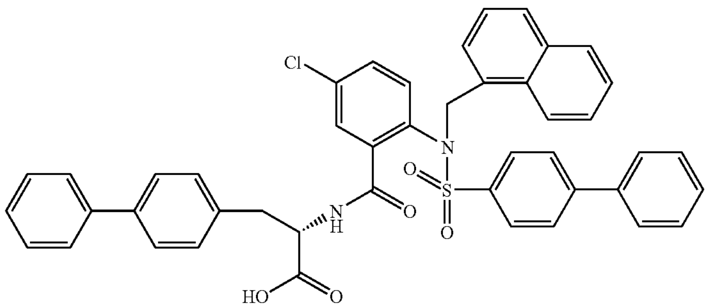 | (2S)-{2-[(Biphenyl-4-sulfonyl)-naphthalen-1-ylmethyl-amino]-5-chloro-benzoylamino}-3-biphenyl-4-yl-propionic acid |
| 454 | 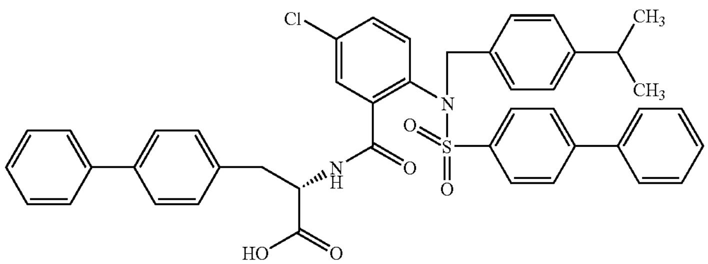 | (2S)-{2-[(Biphenyl-4-sulfonyl)-(4-isopropyl-benzyl)-amino]-5-chloro-benzoylamino}-3-biphenyl-4-yl-propionic acid |
| 455 | 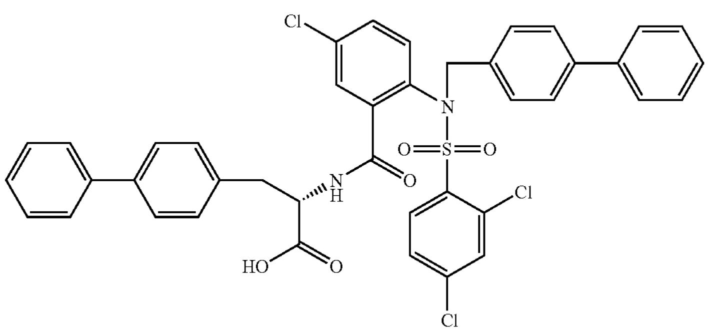 | 3-Biphenyl-4-yl-(2S)-{2-[biphenyl-4-ylmethyl-(2,4-dichloro-benzenesulfonyl)-amino]-5-chloro-benzoylamino}-propionic acid |
| 456 | 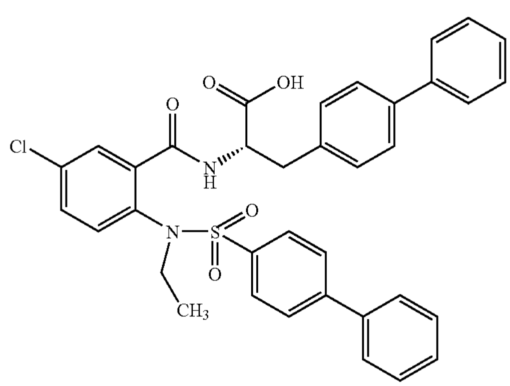 | (2S)-{2-[(Biphenyl-4-sulfonyl)-ethyl-amino]-5-chloro-benzoylamino}-3-biphenyl-4-yl-propionic acid |

TABLE 1-continued

| Example | Structure | Name |
|---|---|---|
| 457 | 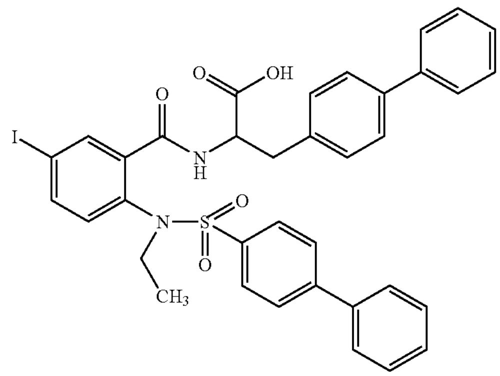 | (2S)-{2-[(Biphenyl-4-sulfonyl)-ethyl-amino]-5-iodo-benzoylamino}-3-biphenyl-4-yl-propionic acid |
| 458 | 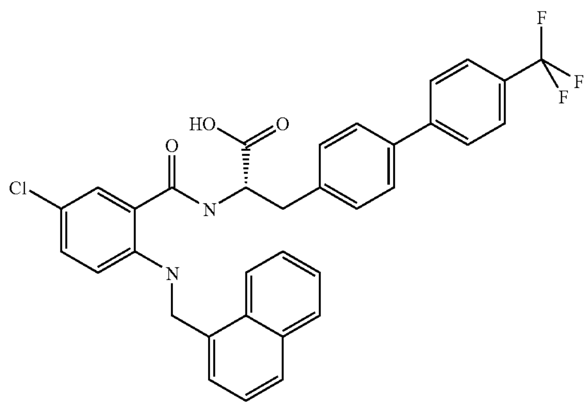 | 2-{5-Chloro-2-[(naphthalen-1-ylmethyl)-amino]-benzoylamino}-3-(4'-trifluoromethyl-biphenyl-4-yl)-propionic acid |
| 459 | 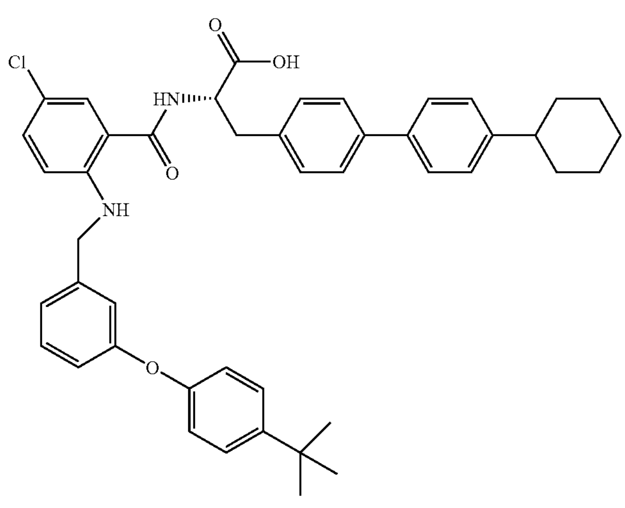 | (S)-2-{2-[3-(4-tert-Butyl-phenoxy)-benzylamino]-5-chloro-benzoylamino}-3-(4'-cyclohexyl-biphenyl-4-yl)-propionic acid |

TABLE 1-continued

| Example | Structure | Name |
|---|---|---|
| 460 | 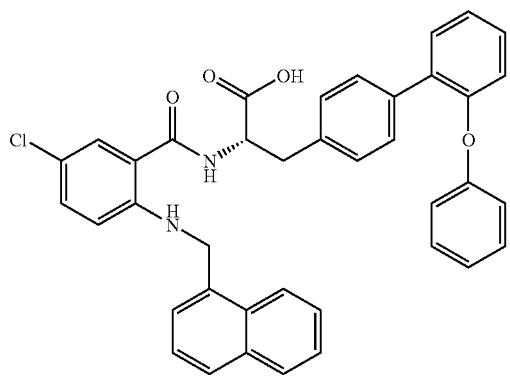 | (2S)-{5-Chloro-2-[(naphthalen-1-ylmethyl)-amino]-benzoylamino}-3-(2'-phenoxy-biphenyl-4-yl)-propionic acid |
| 461 | 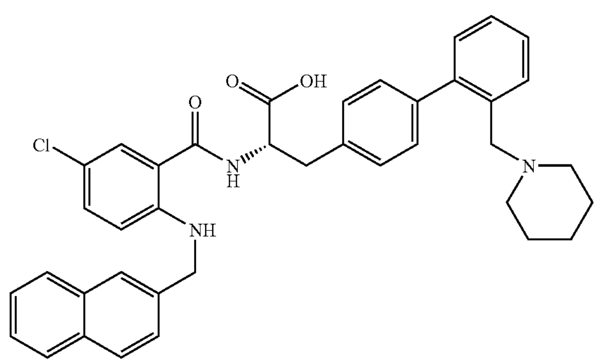 | (2S)-{5-Chloro-2-[(naphthalen-2-ylmethyl)-amino]-benzoylamino}-3-(2'-piperidin-1-ylmethyl-biphenyl-4-yl)-propionic acid |
| 462 | 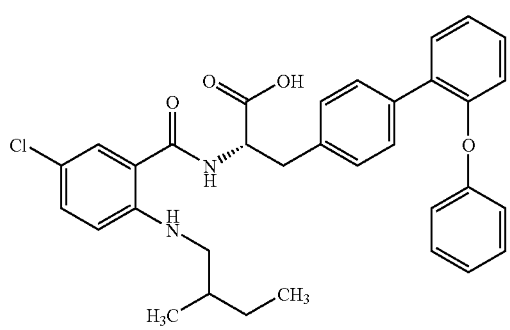 | 2S-[5-Chloro-2-(2-methyl-butylamino)-benzoylamino]-3-(2'-phenoxy-biphenyl-4-yl)-propionic acid |
| 463 | 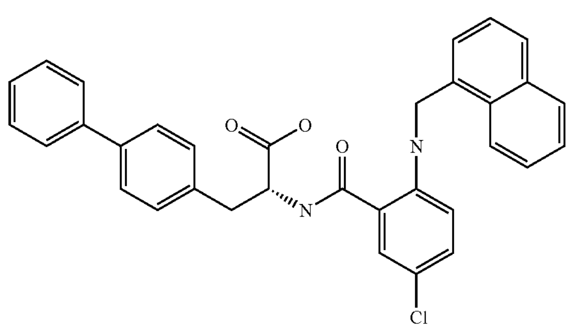 | 3-Biphenyl-4-yl-2S-{5-chloro-2-[(naphthalen-1-ylmethyl)-amino]-benzoylamino}-propionic acid |

TABLE 1-continued

| Example | Structure | Name |
|---|---|---|
| 464 | 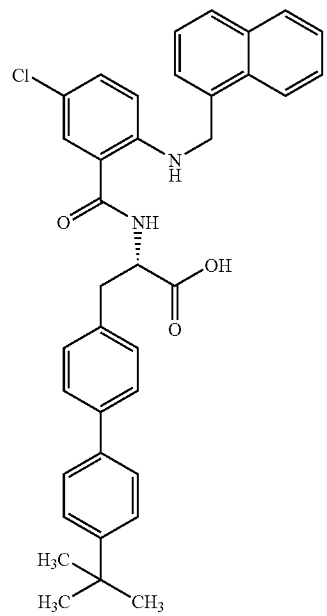 | 3-(4'-tert-Butyl-biphenyl-4-yl)-(2S)-{5-chloro-2-[(naphthalen-1-ylmethyl)-amino]-benzoylamino}-propionic acid |
| 465 | 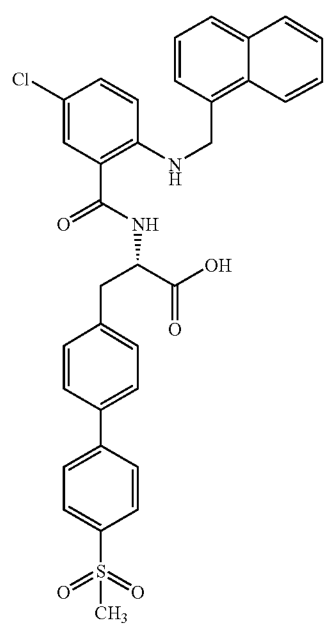 | (2S)-{5-Chloro-2-[(naphthalen-1-ylmethyl)-amino]-benzoylamino}-3-(4'-methanesulfonyl-biphenyl-4-yl)-propionic acid |

TABLE 1-continued
| Example | Structure | Name |
|---|---|---|
| 466 | 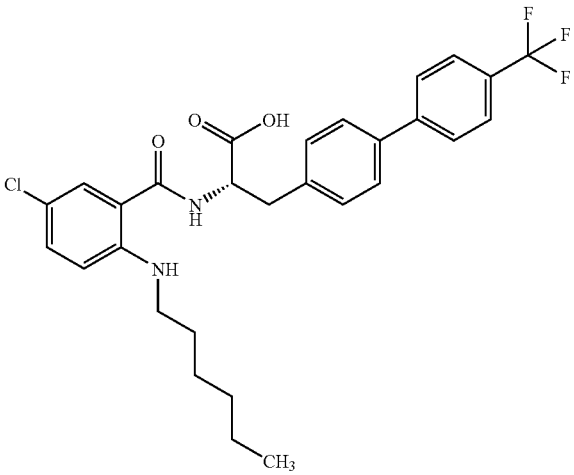 | (2S)-(5-Chloro-2-hexylamino-benzoylamino)-3-(4'-trifluoromethyl-biphenyl-4-yl)-propionic acid |
| 467 | 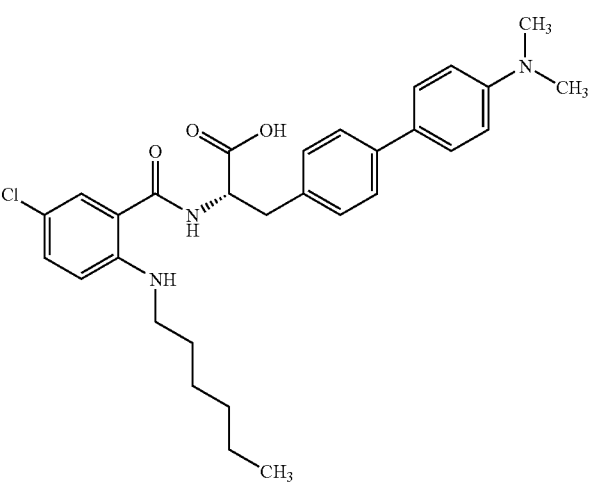 | (2S)-(5-Chloro-2-hexylamino-benzoylamino)-3-(4'-dimethylamino-biphenyl-4-yl)-propionic acid |
| 468 | 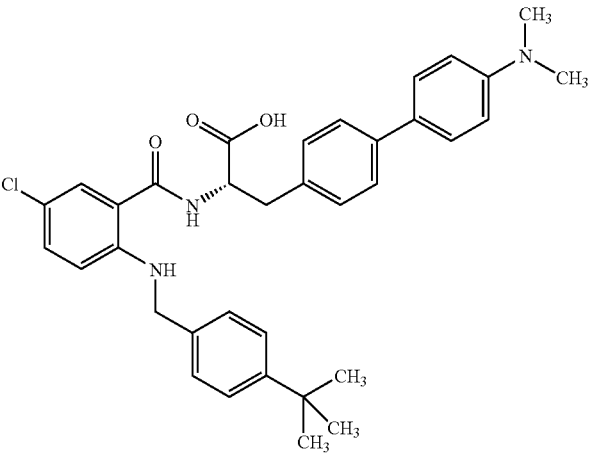 | (2S)-[2-(4-tert-Butyl-benzylamino)-5-chloro-benzoylamino]-3-(4'-dimethylamino-biphenyl-4-yl)-propionic acid |

TABLE 1-continued

| Example | Structure | Name |
|---|---|---|
| 469 | 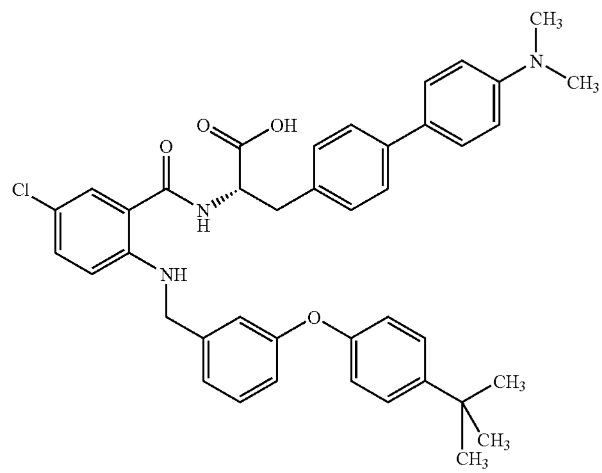 | (2S)-{2-[3-(4-tert-Butyl-phenoxy)-benzylamino]-5-chloro-benzoylamino}-3-(4'-dimethylamino-biphenyl-4-yl)-propionic acid |
| 470 | 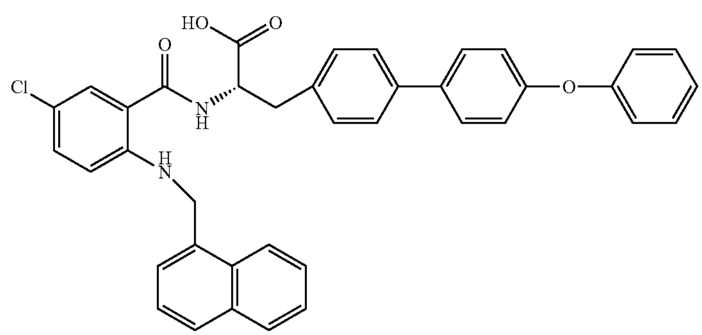 | (2S)-{5-Chloro-2-[(naphthalen-1-ylmethyl)-amino]-benzoylamino}-3-(4'-phenoxy-biphenyl-4-yl)-propionic acid |
| 471 | 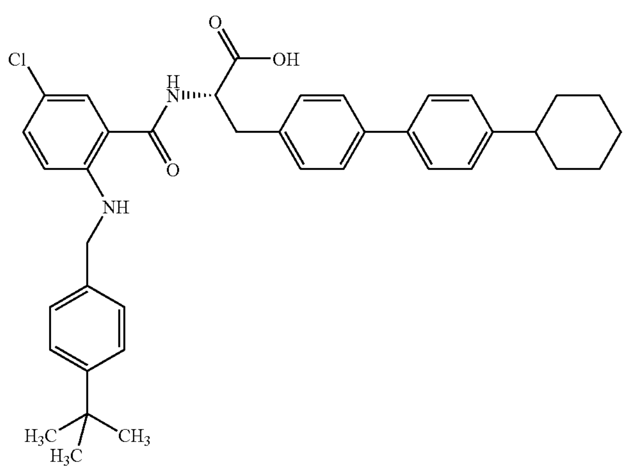 | (2S)-[2-(4-tert-Butyl-benzylamino)-5-chloro-benzoylamino]-3-)4'-cyclohexyl-biphenyl-4-yl)-propionic acid |
| 472 | 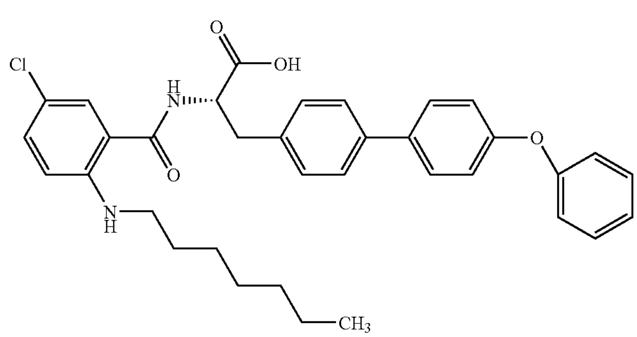 | (2S)-(5-Chloro-2-heptylamino-benzoylamino)-3-(4'-phenoxy-biphenyl-4-yl)-propionic acid |

TABLE 1-continued

| Example | Structure | Name |
|---|---|---|
| 473 | 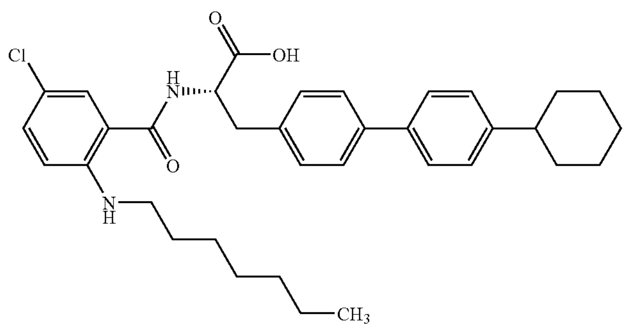 | (2S)-(5-Chloro-2-heptylamino-benzoylamino)-3-(4'-cyclohexyl-biphenyl-4-yl)-propionic acid |
| 474 | 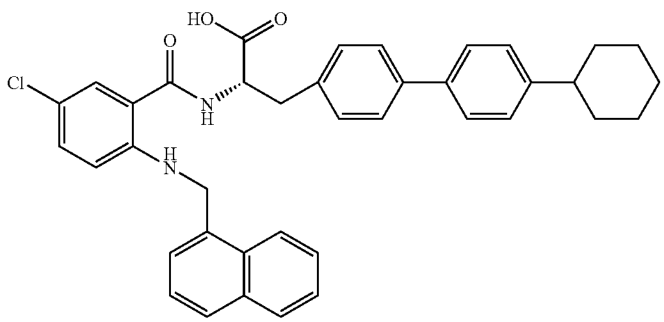 | (2S)-{5-Chloro-2-[(naphthalen-1-ylmethyl)-amino]-benzoylamino}-3-(4'-cyclohexyl-biphenyl-4-yl)-propionic acid |
| 475 | 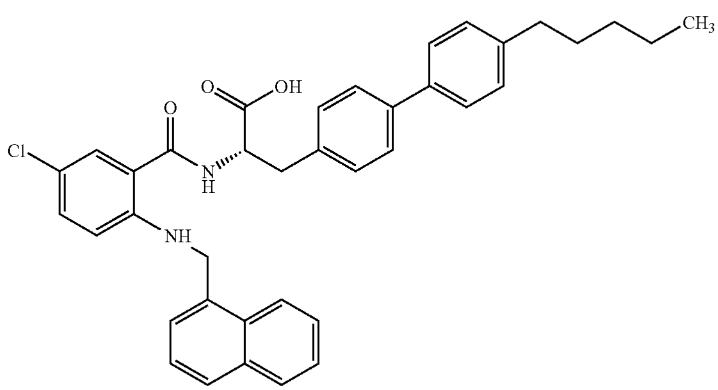 | (2S)-{5-Chloro-2-[(naphthalen-1-ylmethyl)-amino]-benzoylamino}-3-(4'-pentyl-biphenyl-4-yl)-propionic acid |
| 476 | 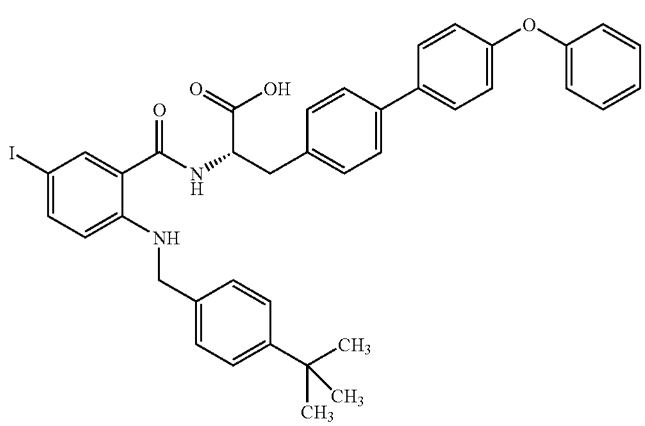 | (2S)-[2-(4-tert-Butyl-benzylamino)-5-iodo-benzoylamino]-3-(4'-phenoxy-biphenyl-4-yl)-propionic acid |

TABLE 1-continued

| Example | Structure | Name |
|---|---|---|
| 477 | 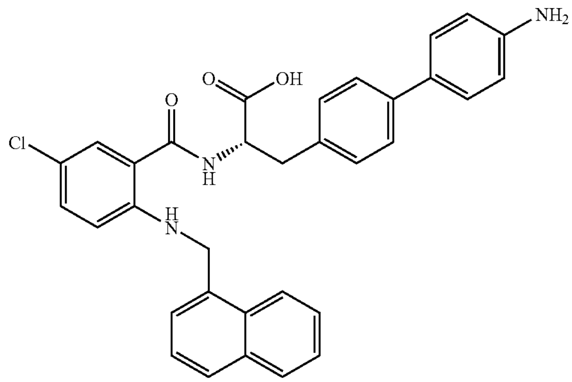 | 3-(4'-Amino-biphenyl-4-yl)-2S)-{5-chloro-2-[(naphthalen-1-ylmethyl)-amino]-benzoylamino}-propionic acid |
| 478 | 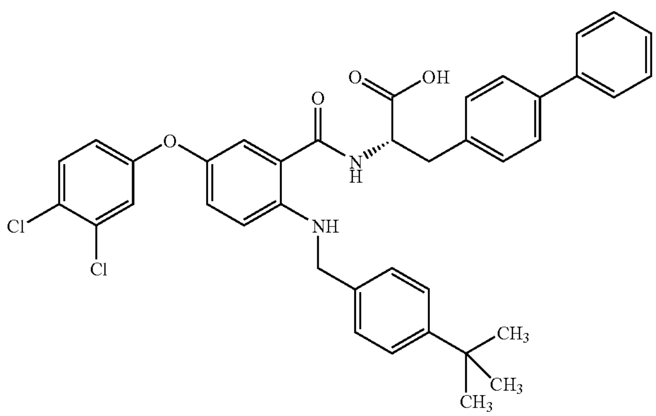 | 3-Biphenyl-4-yl-2S-[2-(4-tert-butyl-benzylamino)-5-(3,4-dichloro-phenoxy)-benzoylamino]-propionic acid |
| 479 | 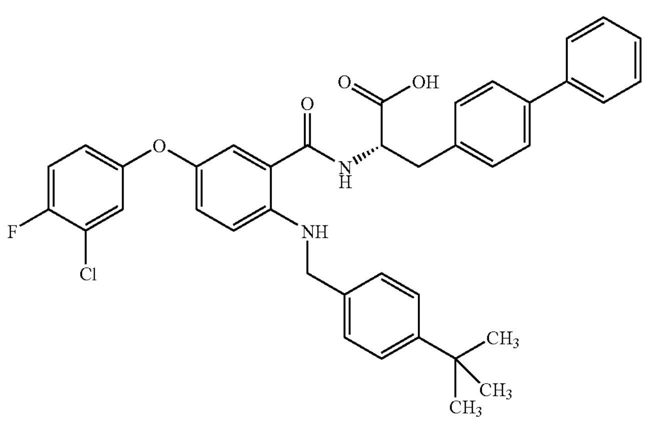 | 3-Biphenyl-4-yl-2S-[2-(4-tert-butyl-benzylamino)-5-(3-chloro-4-fluoro-phenoxy)-benzoylamino]-propionic acid |

TABLE 1-continued

| Example | Structure | Name |
| --- | --- | --- |
| 480 | 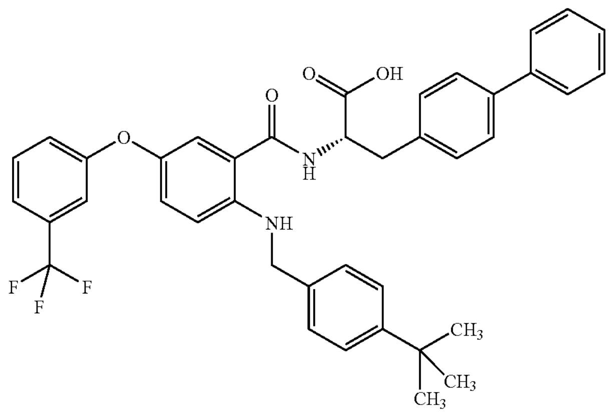 | 3-Biphenyl-4-yl-(2S)-[2-(4-tert-butyl-benzylamino)-5-(3-trifluoromethyl-phenoxy)-benzoylamino]-propionic acid |
| 481 | 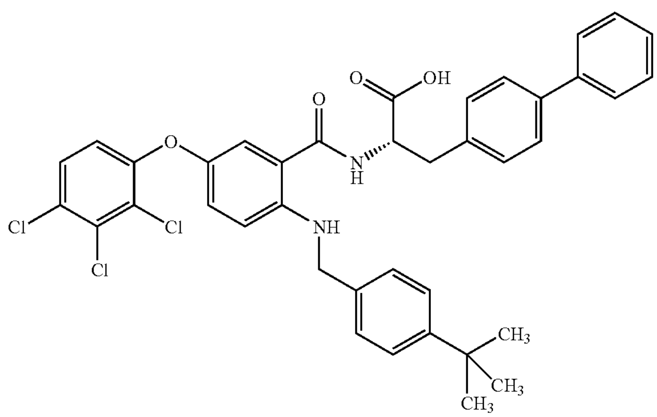 | 3-Biphenyl-4-yl-(2S)-[2-(4-tert-butyl-benzylamino)-5-(2,3,4-trichloro-phenoxy)-benzoylamino]- propionic acid |
| 482 | 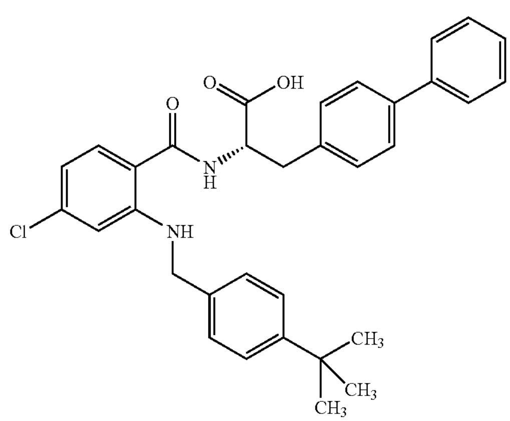 | 3-Biphenyl-4-yl-(2S)-[2-(4-tert-butyl-benzylamino)-4-chloro-benzoylamino]-propionic acid |

TABLE 1-continued

| Example | Structure | Name |
|---|---|---|
| 483 | 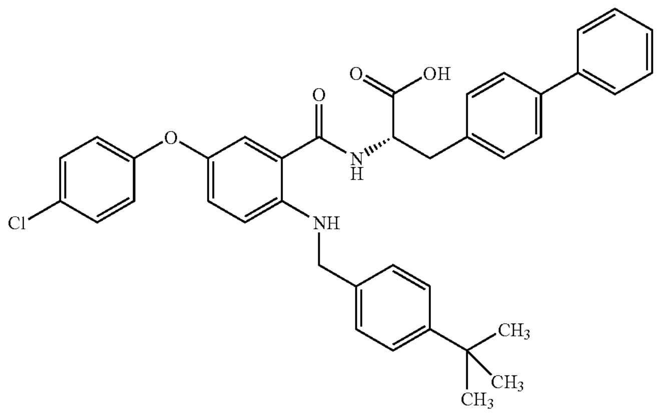 | 3-Biphenyl-4-yl-(2S)-[2-(4-tert-butyl-benzylamino)-5-(4-chloro-phenoxy)-benzoylamino]- propionic acid |
| 484 | 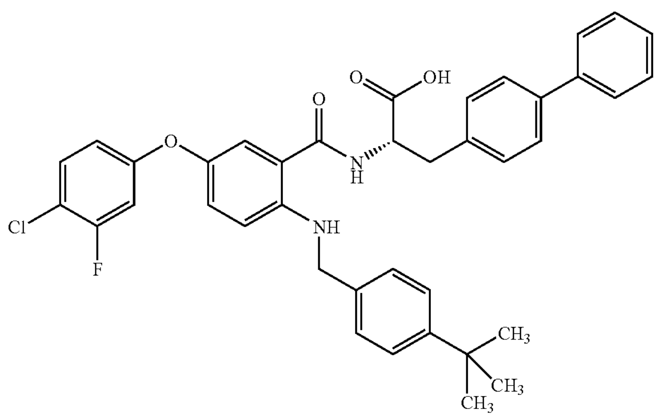 | 3-Biphenyl-4-yl-2S-[2-(4-tert-butyl-benzylamino)-5-(4-chloro-3-fluoro-phenoxy)-benzoylamino]- propionic acid |
| 485 | 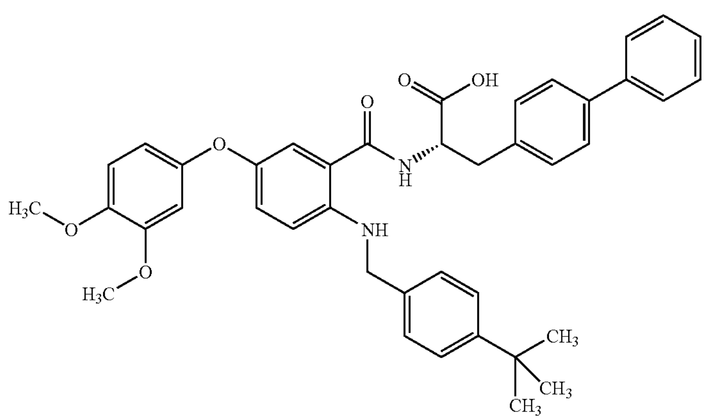 | 3-Biphenyl-4-yl-(2S)-[2-(4-tert-butyl-benzylamino)-5-(3,4-dimethoxy-phenoxy)-benzoylamino]-propionic acid |

TABLE 1-continued

| Example | Structure | Name |
|---|---|---|
| 486 | 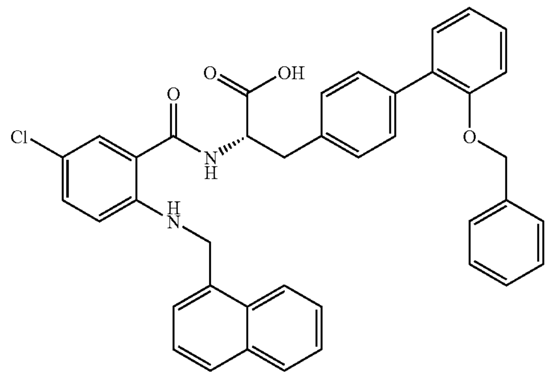 | 3-(2'-Benzyloxy-biphenyl-4-yl)-(2S)-{5-chloro-2-[(naphthalen-1-ylmethyl)-amino]-benzoylamino}-propionic acid |
| 487 | 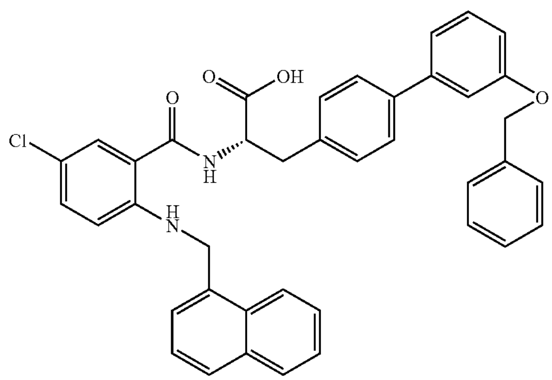 | 3-(3'-Benzyloxy-biphenyl-4-yl)-(2S)-{5-chloro-2-[(naphthalen-1-ylmethyl)-amino]-benzoylamino}-propionic acid |
| 488 | 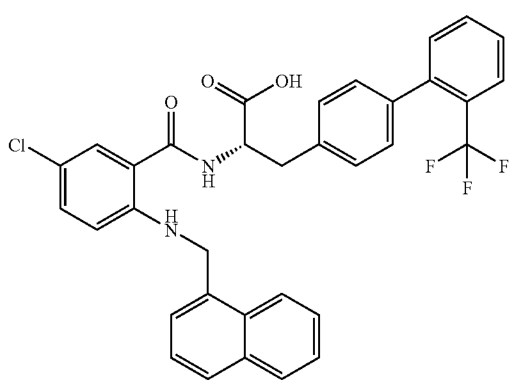 | (2S)-{5-Chloro-2-[(naphthalen-1-ylmethyl)-amino]-benzoylamino}-3-(2'-trifluoromethyl-biphenyl-4-yl)-propionic acid |

TABLE 1-continued

| Example | Structure | Name |
|---|---|---|
| 489 | 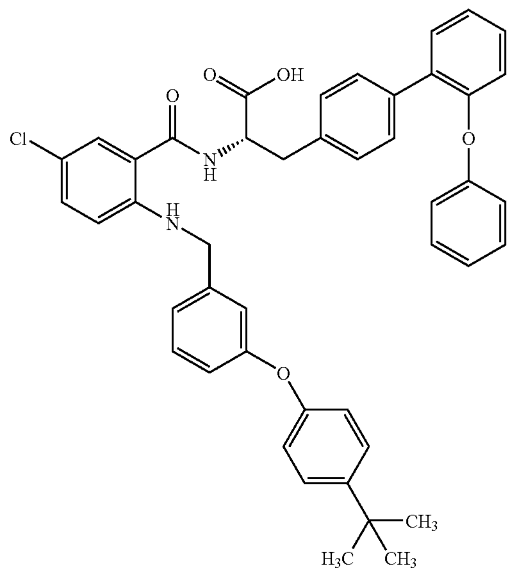 | (2S)-{2-[3-(4-tert-Butyl-phenoxy)-benzylamino]-5-chloro-benzoylamino}-3-(2'-phenoxy-biphenyl-4-yl)-propionic acid |
| 490 | 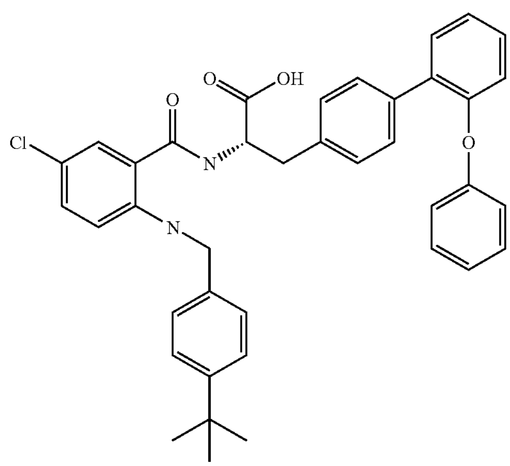 | (2S)-[2-(4-tert-Butyl-benzylamino)-5-chloro-benzoylamino]-3-(2'-phenoxy-biphenyl-4-yl)-propionic acid |
| 491 | 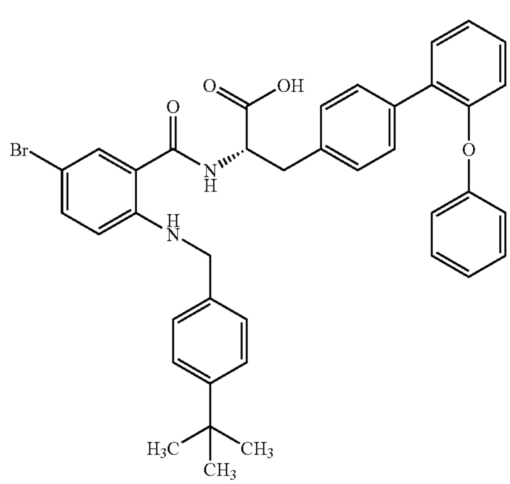 | (2S)-[5-Bromo-2-(4-tert-butyl-benzylamino)-benzoylamino]-3-(2'-phenoxy-biphenyl-4-yl)-propionic acid |

TABLE 1-continued

| Example | Structure | Name |
|---|---|---|
| 492 | 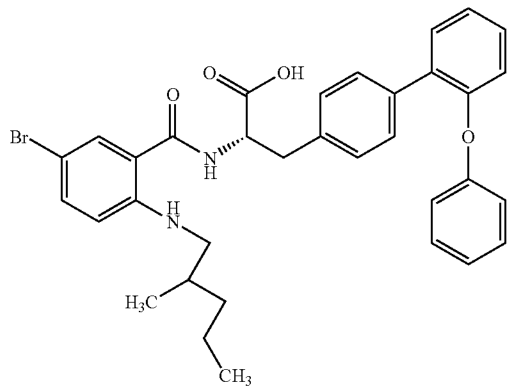 | (2S)-[5-Bromo-2-(2-methyl-pentylamino)-benzoylamino]-3-(2'-phenoxy-biphenyl-4-yl)-propionic acid |
| 493 | 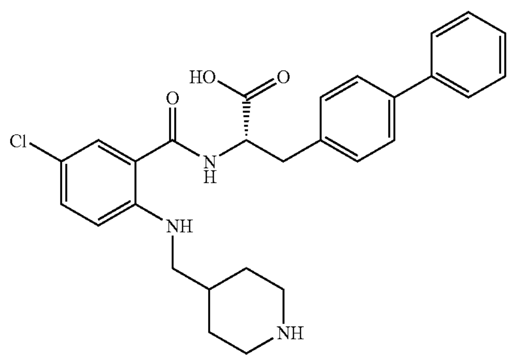 | 3-Biphenyl-4-yl-(2S)-{5-chloro-2-[(piperidin-4-ylmethyl)-amino]-benzoylamino}-propionic acid |
| 494 | 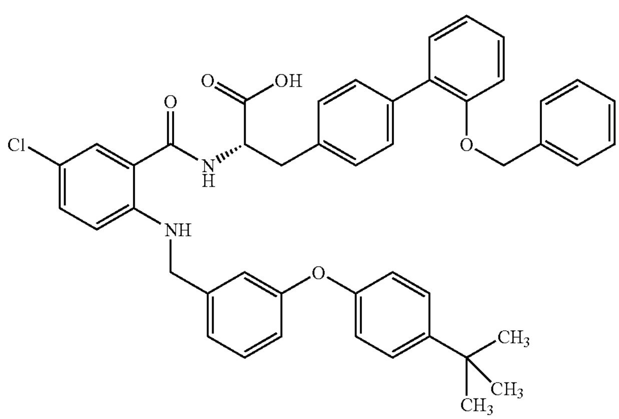 | 3-(2'-Benzyloxy-biphenyl-4-yl)-(2S)-{2-]3-(4-tert-butyl-phenoxy)-benzylamino]-5-chloro-benzoylamino}-propionic acid |
| 495 | 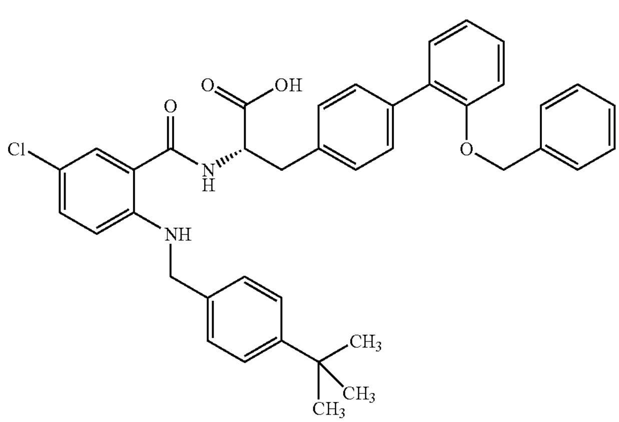 | 3-(2'-Benzyloxy-biphenyl-4-yl)-(2S)-[2-(4-tert-butyl-benzylamino)-5-chloro-benzoy-lamino]-propionic acid |

TABLE 1-continued

| Example | Structure | Name |
| --- | --- | --- |
| 496 | 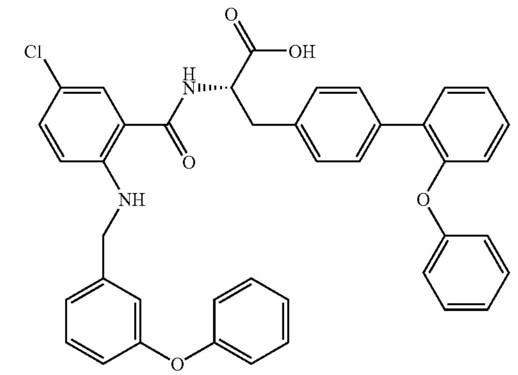 | (2S)-[5-Chloro-2-(3-phenoxy-benzylamino)-benzoylamino]-3-(2'-phenoxy-biphenyl-4-yl)-propionic acid |
| 497 | 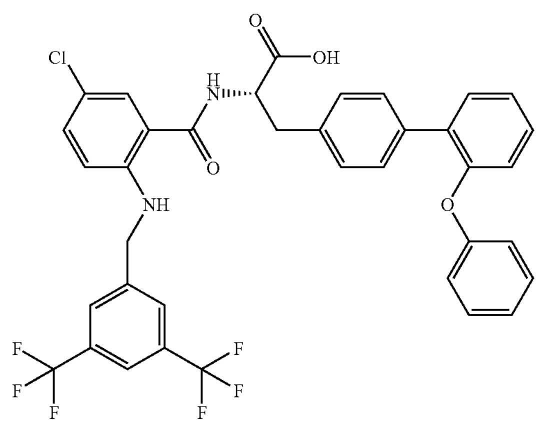 | (2S)-[2-(3,5-Bis-trifluoromethyl-benzylamino)-5-chloro-benzoylamino]-3-(2'-phenoxy-biphenyl-4-yl)-propionic acid |
| 498 | 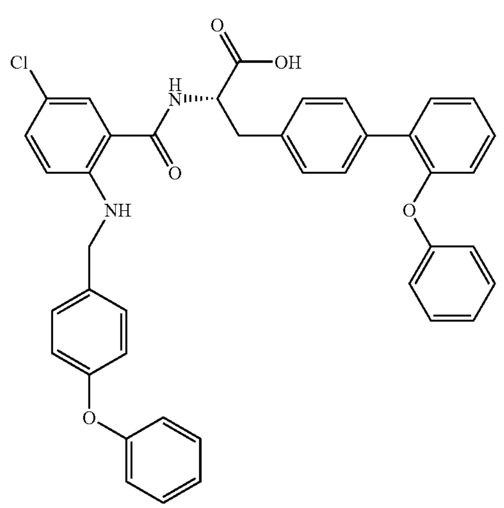 | (2S)-[5-Chloro-2-(4-phenoxy-benzylamino)-benzoylamino]-3-(2'-phenoxy-biphenyl-4-yl)-propionic acid |

TABLE 1-continued

| Example | Structure | Name |
|---|---|---|
| 499 | 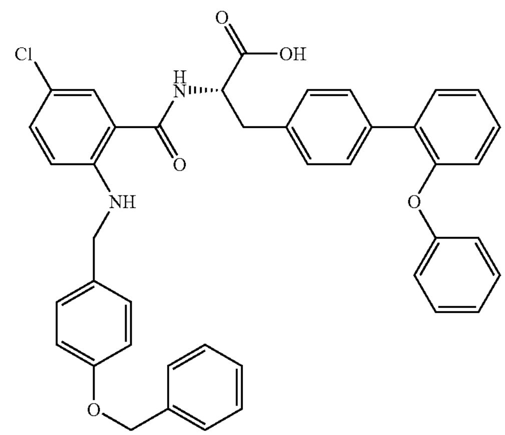 | (2S)-[2-(4-Benzyloxy-benzylamino)-5-chloro-benzoylamino]-3-(2'-phenoxy-biphenyl-4-yl)-propionic acid |
| 500 | 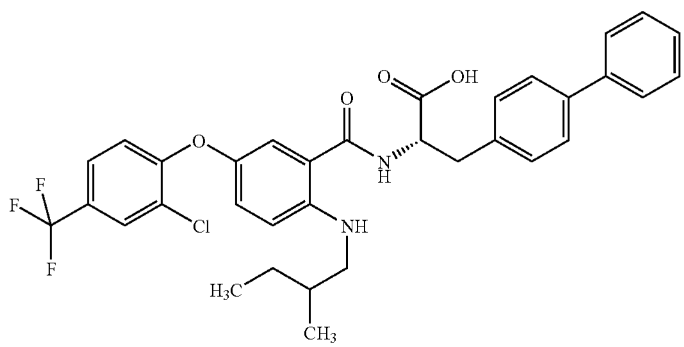 | 3-Biphenyl-4-yl-(2S)-[5-(2-chloro-4-trifluoromethyl-phenoxy)-2-(2-methyl-butylamino)-benzoylamino]-propionicacid |
| 501 | 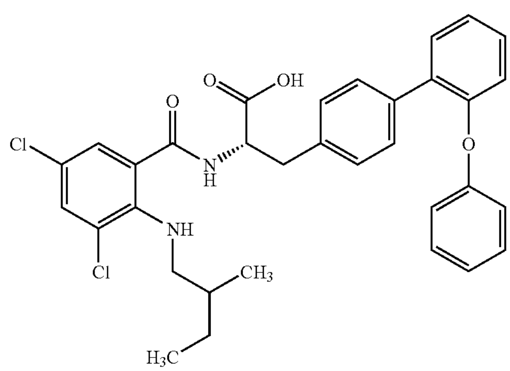 | (2S)-[3,5-Dichloro-2-(2-methyl-butylamino)-benzoylamino]-3-(2'-phenoxy-biphenyl-4-yl)-propionic acid |
| 502 | 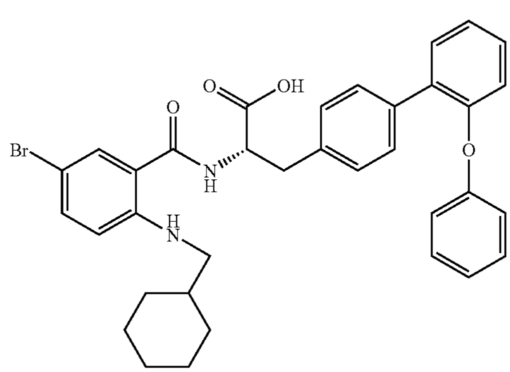 | (2S)-[5-Bromo-2-(cyclohexylmethyl-amino)-benzoylamino]-3-(2'-phenoxy-biphenyl-4-yl)-propionic acid |

TABLE 1-continued

| Example | Structure | Name |
|---|---|---|
| 503 | 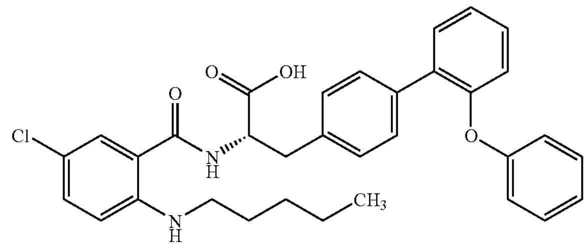 | (2S)-(5-Chloro-2-pentylamino-benzoylamino)-3-(2'-phenoxy-biphenyl-4-yl)-propionic acid |
| 504 | 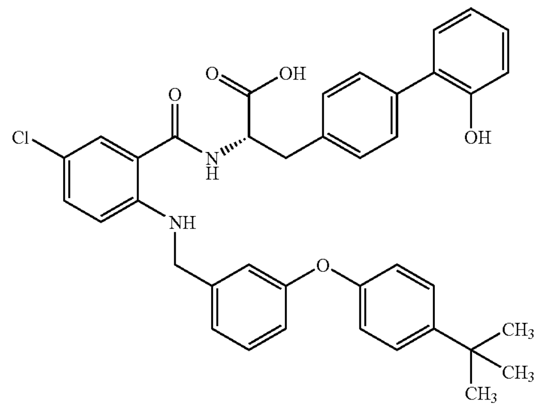 | (2S)-{2-[3-(4-tert-Butyl-phenoxy)-benzylamino]-5-chloro-benzoylamino}-3-(2'-hydroxy-biphenyl-4-yl)-propionic acid |
| 505 | 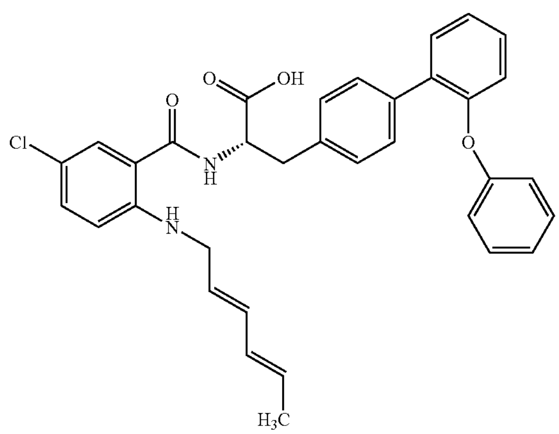 | (2S)-(5-Chloro-2-hexa-2,4-dienylamino-benzoylamino)-3-(2'-phenoxy-biphenyl-4-yl)-propionic acid |
| 506 | 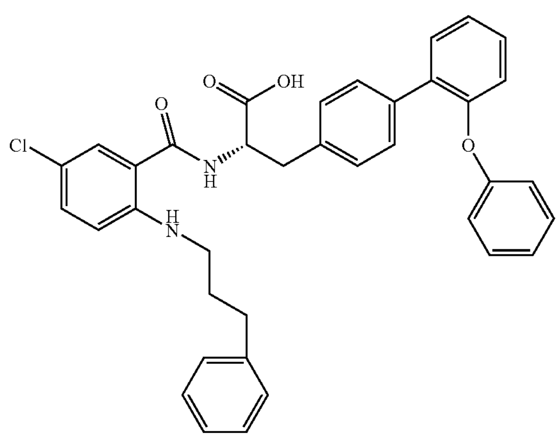 | (2S)-[5-Chloro-2-(3-phenyl-propylamino)-benzoylamino]-3-(2'-phenoxy-biphenyl-4-yl)-propionic acid |

TABLE 1-continued

| Example | Structure | Name |
|---|---|---|
| 507 | 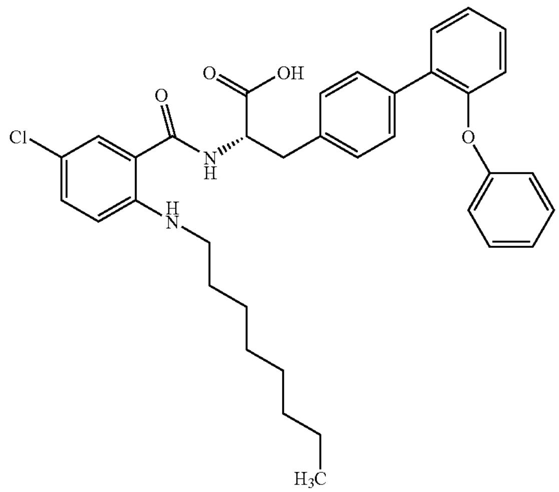 | (2S)-(5-Chloro-2-octylamino-benzoylamino)-3-(2'-phenoxy-biphenyl-4-yl)-propionic acid |
| 508 | 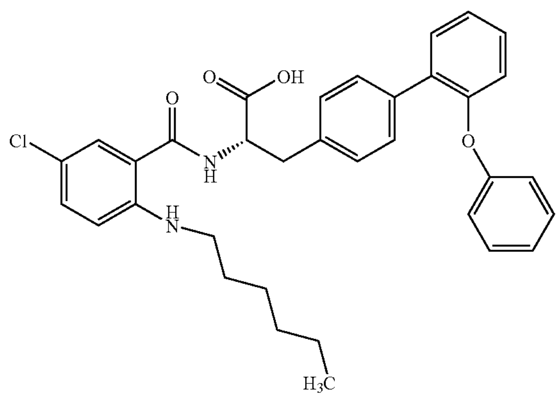 | (2S)-(5-Chloro-2-hexylamino-benzoylamino)-3-(2'-phenoxy-biphenyl-4-yl)-propionic acid |
| 509 | 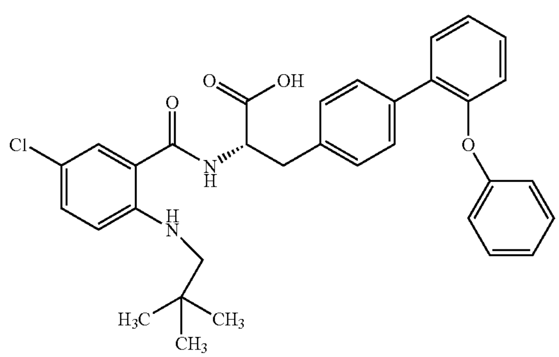 | (2S)-[5-Chloro-2-(2,2-dimethyl-propylamino)-benzoylamino]-3-(2'-phenoxy-biphenyl-4-yl)-propionic acid |

TABLE 1-continued

| Example | Structure | Name |
|---|---|---|
| 510 | 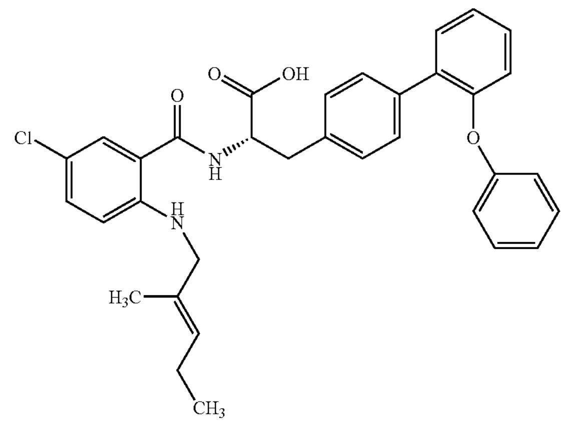 | (2S)-[5-Chloro-2-(2-methyl-pent-2-enylamino)-benzoylamino]-3-(2'-phenoxy-biphenyl-4-yl)-propionic acid |
| 511 | 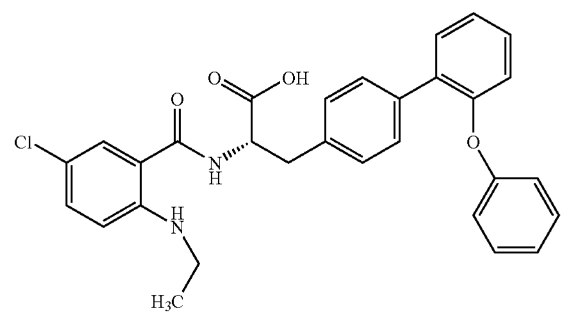 | (2S)-(5-Chloro-2-ethylamino-benzoylamino)-3-(2'-phenoxy-biphenyl-4-yl)-propionic acid |
| 512 | 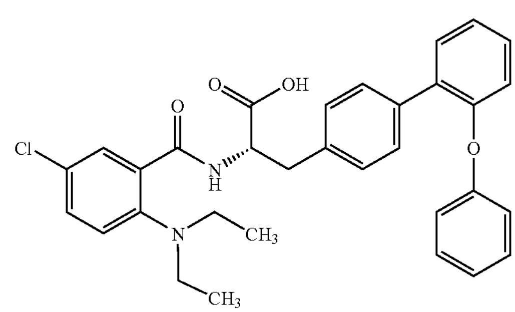 | :(2S)-(5-Chloro-2-diethylamino-benzoylamino)-3-(2'-phenoxy-biphenyl-4-yl)-propionic acid |
| 513 | 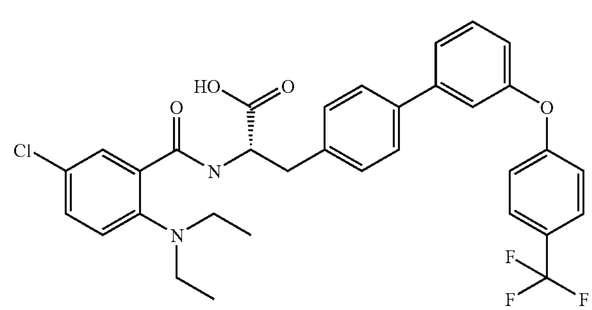 | 2-(5-Chloro-2-diethylamino-benzoylamino)-3-[3'-(4-trifluoromethyl-phenoxy)-biphenyl-4-yl]-propionic acid |

TABLE 1-continued

| Example | Structure | Name |
|---|---|---|
| 514 | 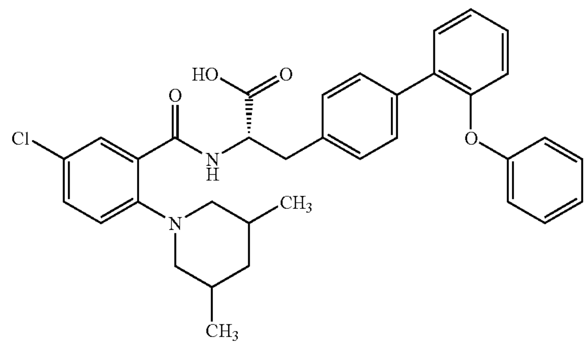 | (2S)-[5-Chloro-2-(3,5-dimethyl-piperidin-1-yl)-benzoylamino]-3-(2'-phenoxy-biphenyl-4-yl)-propionic acid |
| 515 | 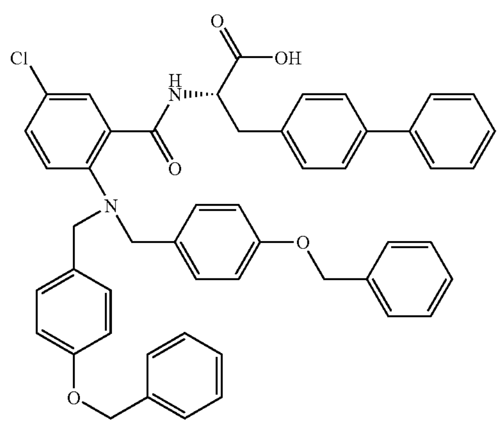 | 3-Biphenyl-4-yl-(2S)-{2-[bis-(4-benzyloxy-benzyl)-amino]-5-chloro-benzoylamino}-propionic acid |
| 516 | 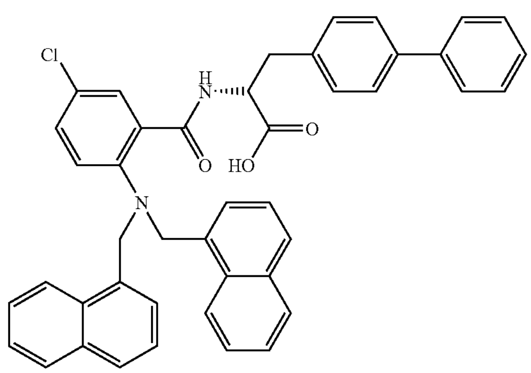 | 3-Biphenyl-4-yl-(2S)-[2-(bis-naphthalen-1-ylmethyl-amino)-5-chloro-benzoylamino]-propionic acid |

TABLE 1-continued

| Example | Structure | Name |
| --- | --- | --- |
| 517 | 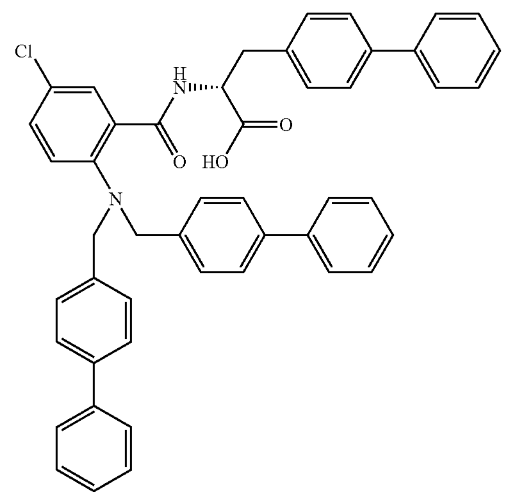 | 3-Biphenyl-4-yl-(2S)-[2-(bis-biphenyl-4-methyl-amino)-5-chloro-benzoylamino]-propionic acid |
| 518 | 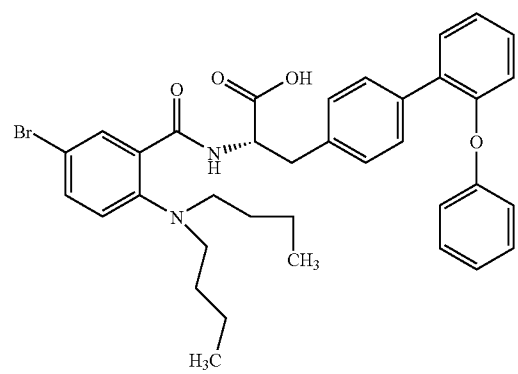 | (2S)-(5-Bromo-2-dibutylamino-benzoylamino)-3-(2'-phenoxy-biphenyl-4-yl)-propionic acid |
| 519 | 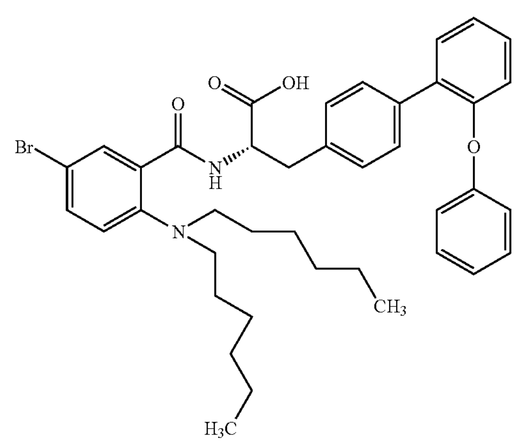 | (2S)-(5-Bromo-2-dihexylamino-benzoylamino)-3-(2'-phenoxy-biphenyl-4-yl)-propionic acid |

TABLE 1-continued

| Example | Structure | Name |
|---|---|---|
| 520 | 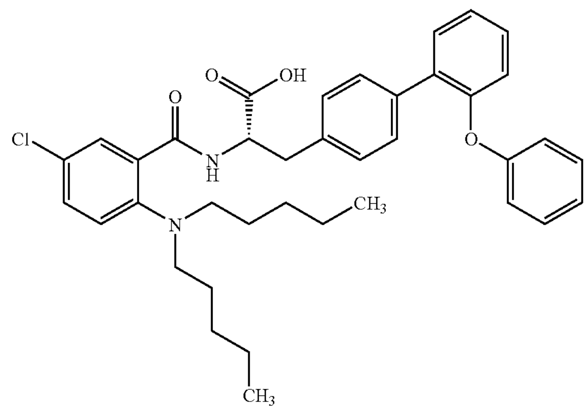 | (2S)-(5-Chloro-2-dipentylamino-benzoylamino)-3-(2'-phenoxy-biphenyl-4-yl)-propionic acid |
| 521 | 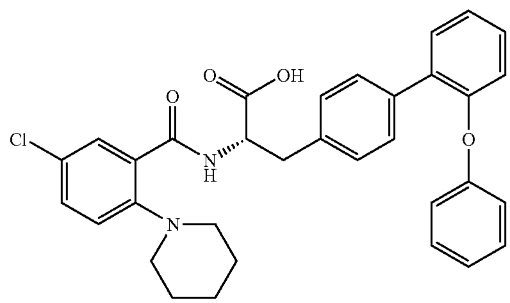 | (2S)-(5-Chloro-2-piperidin-1-yl-benzoylamino)-3-(2'-phenoxy-biphenyl-4-yl)-propionic acid |
| 522 | 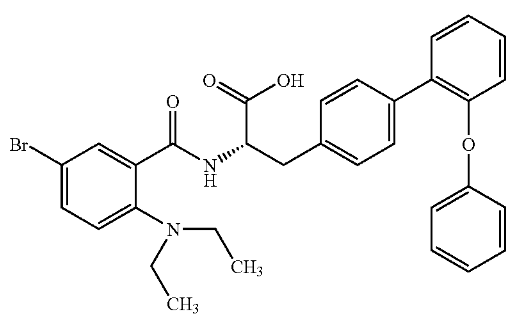 | (2S)-(5-Bromo-2-diethylamino-benzoylamino)-3-(2'-phenoxy-biphenyl-4-yl)-propionic acid |
| 523 | 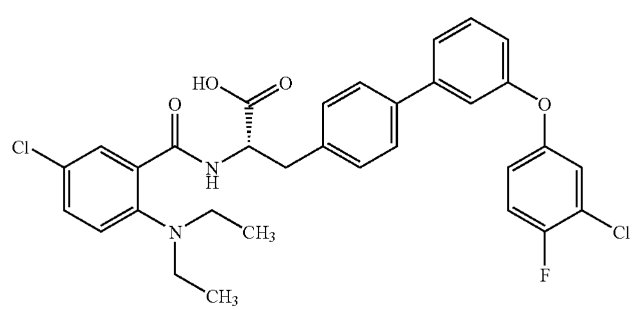 | (2S)-(5-Chloro-2-diethylamino-benzoylamino)-3-[3'-(3-chloro-4-fluorophenoxy)-biphenyl-4-yl]-propionic acid |

TABLE 1-continued

| Example | Structure | Name |
|---|---|---|
| 524 | 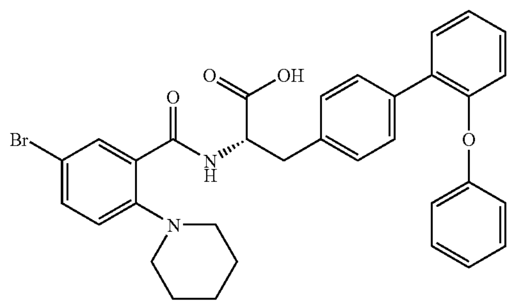 | (2S)-(5-Bromo-2-piperidin-1-yl-benzoylamino)-3-(2'-phenoxy-biphenyl-4-yl)-propionic acid |
| 525 | 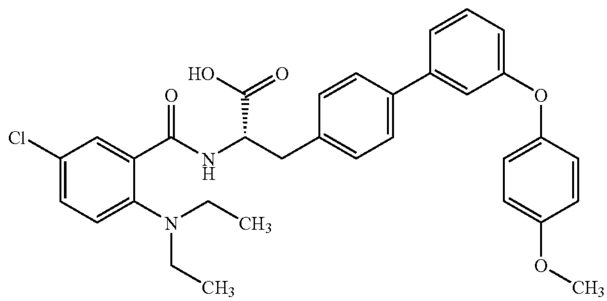 | (2S)-(5-Chloro-2-diethylamino-benzoylamino)-3-[3'-(4-methoxy-phenoxy)-biphenyl-4-yl]-propionic |
| 526 | 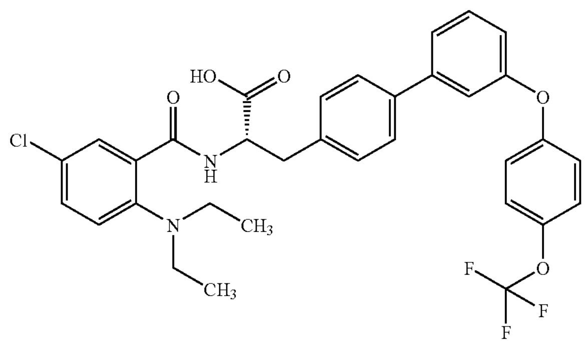 | (2S)-(5-Chloro-2-diethylamino-benzoylamino)-3-[3'-(4-trifluoromethoxy-phenoxy)-biphenyl-4-yl]-propionic acid |
| 527 | 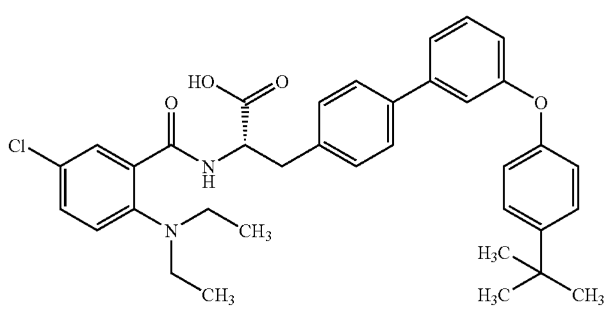 | 3-[3'-(4-tert-Butyl-phenoxy)-biphenyl-4-yl]-(2S)-(5-chloro-2-diethylamino-benzoylamino)-propionic acid |
| 528 | 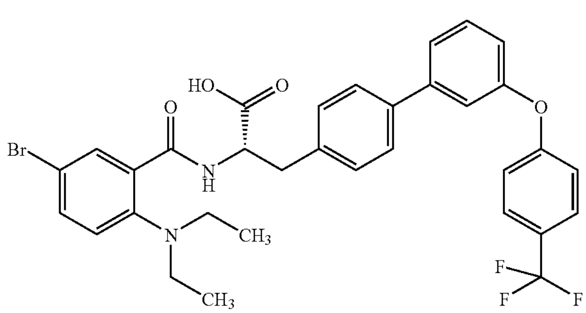 | (2S)-(5-Bromo-2-diethylamino-benzoylamino)-3-[3'-(4-trifluoromethyl-phenoxy)-biphenyl-4-yl]-propionic acid |

TABLE 1-continued

| Example | Structure | Name |
|---|---|---|
| 529 | 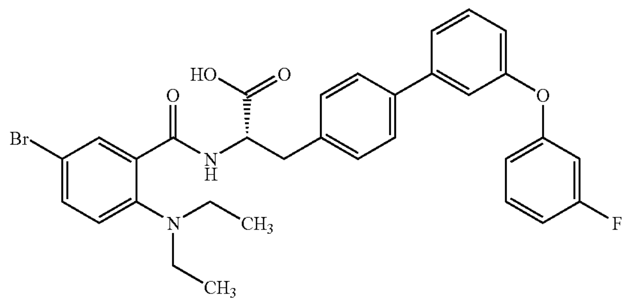 | (2S)-(5-Bromo-2-diethylamino-benzoylamino)-3-[3'-(3-fluoro-phenoxy)-biphenyl-4-yl]-propionic acid |
| 530 | 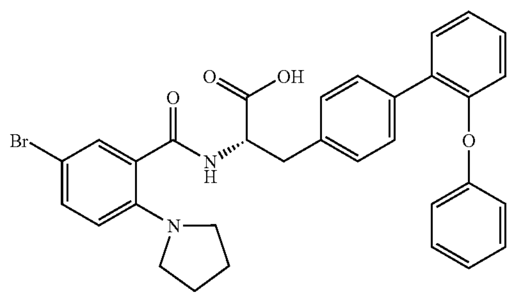 | (2S)-(5-Bromo-2-pyrrolidin-1-yl-benzoylamino)-3-(2'-phenoxy-biphenyl-4-yl)-propionic acid |
| 531 | 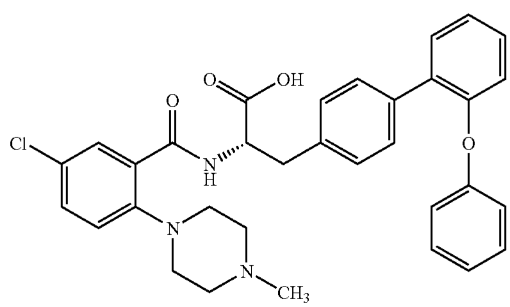 | (2S)-[5-Chloro-2-(4-methyl-piperazin-1-yl)-benzoylamino]-3-(2'-phenoxy-biphenyl-4-yl)-propionic acid |
| 532 | 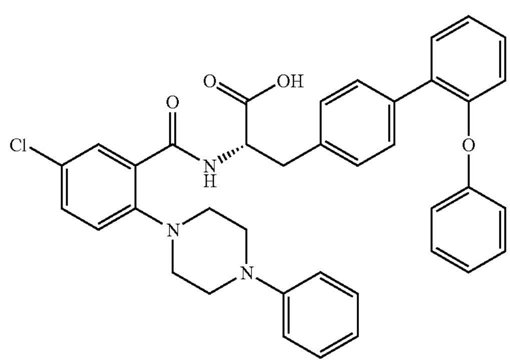 | (2S)-[5-Chloro-2-(4-phenyl-piperazin-1-yl)-benzoylamino]-3-(2'-phenoxy-biphenyl-4-yl)-propionic acid |

TABLE 1-continued

| Example | Structure | Name |
|---|---|---|
| 533 | 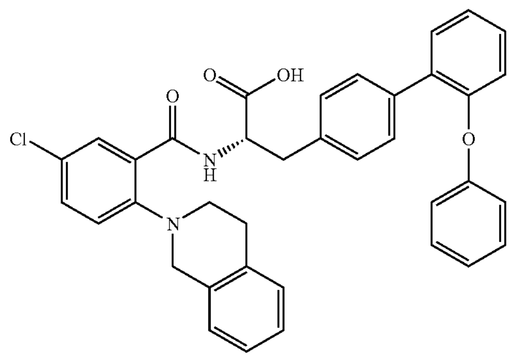 | (2S)-[5-Chloro-2-(3,4-dihydro-1H-isoquinolin-2-yl)-benzoylamino]-3-(2'-phenoxy-biphenyl-4-yl)-propionic acid |
| 534 | 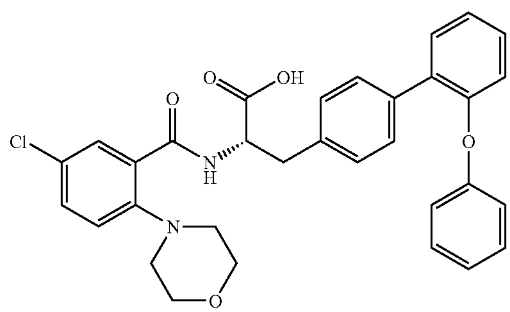 | (2S)-(5-Chloro-2-morpholin-4-yl-benzoylamino)-3-(2'-phenoxy-biphenyl-4-yl)-propionic acid |
| 535 | 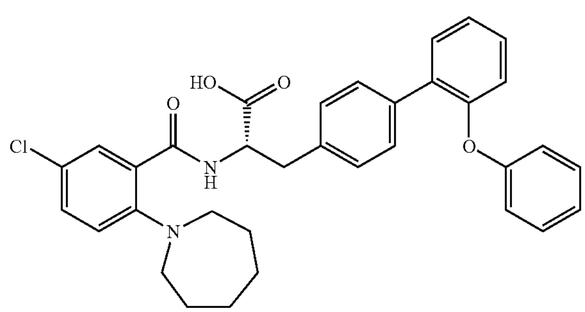 | (2S)-(2-Azepin-1-yl-5-chloro-benzoylamino)-3-(2'-phenoxy-biphenyl-4-yl)-propionic acid |
| 536 | 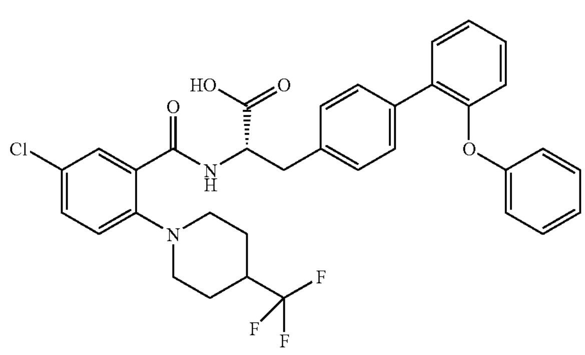 | (2S)-[5-Chloro-2-(4-trifluoromethyl-piperidin-1-yl)-benzoylamino]-3-(2'-phenoxy-biphenyl-4-yl)-propionic acid |

TABLE 1-continued

| Example | Structure | Name |
| --- | --- | --- |
| 537 | 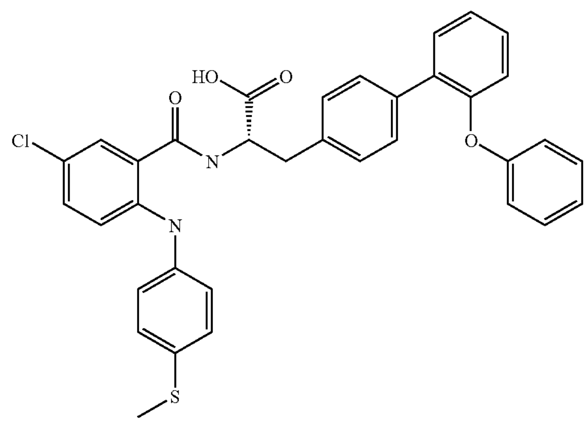 | (2S)-[5-Chloro-2-(4-methylsulfanyl-phenylamino)-benzoylamino]-3-(2'-phenoxy-biphenyl-4-yl)-propionic acid |
| 538 | 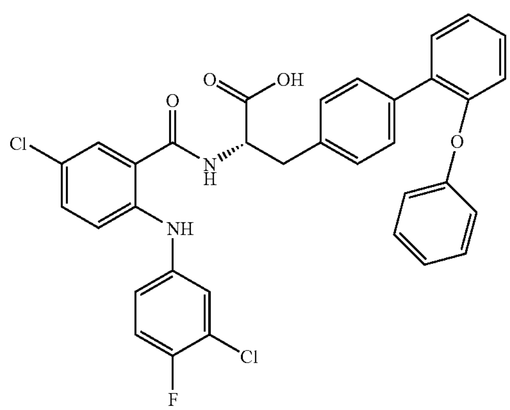 | (2S)-[5-Chloro-2-(3-chloro-4-fluoro-phenylamino)-benzoylamino]-3-(2'-phenoxy-biphenyl-4-yl)-propionic acid |
| 539 | 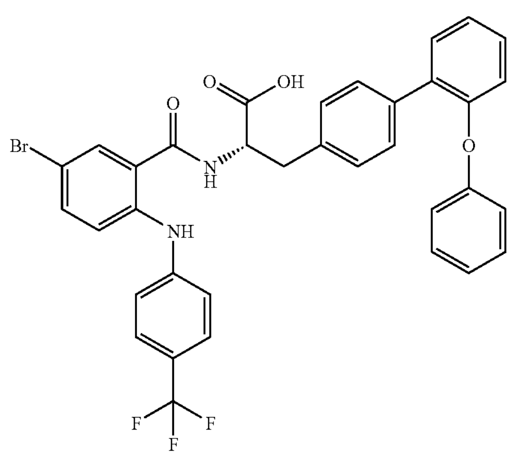 | (2S)-[5-Bromo-2-(4-trifluoromethyl-phenylamino)-benzoylamino]-3-(2'-phenoxy-biphenyl-4-yl)-propionic acid |

TABLE 1-continued

| Example | Structure | Name |
|---|---|---|
| 540 | 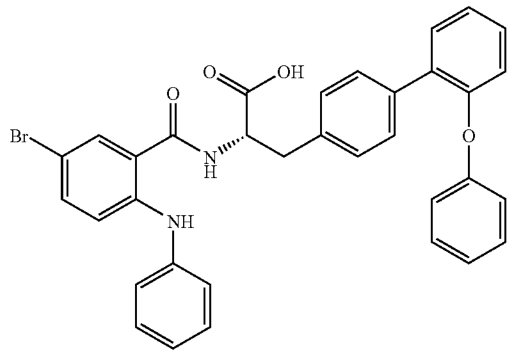 | (2S)-(5-Bromo-2-phenylamino-benzoylamino)-3-(2'-phenoxy-biphenyl-4-yl)-propionic acid |
| 541 | 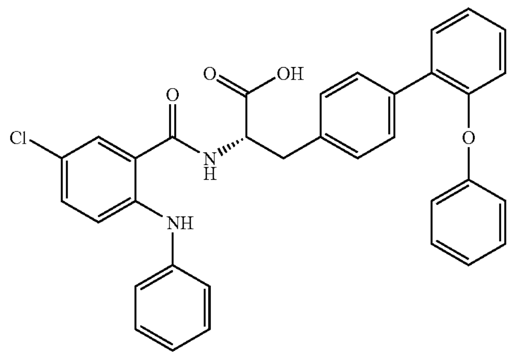 | (2S)-(5-Chloro-2-phenylamino-benzoylamino)-3-(2'-phenoxy-biphenyl-4-yl)-propionic acid |
| 542 | 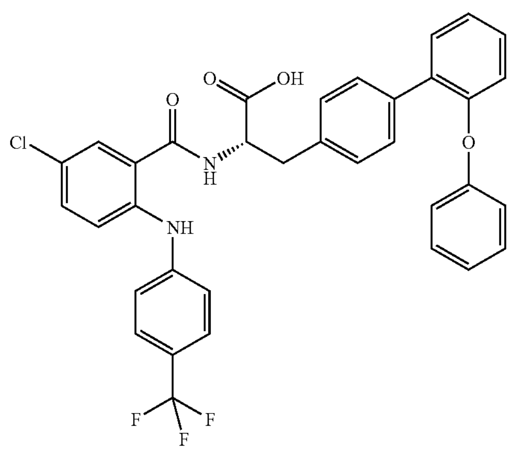 | (2S)-[5-Chloro-2-(4-trifluoromethyl-phenylamino)-benzoylamino]-3-(2'-phenoxy-biphenyl-4-yl)-propionic acid |
| 543 | 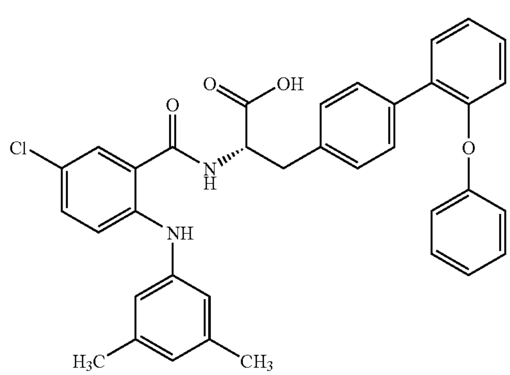 | (2S)-[5-Chloro-2-(3,5-dimethyl-phenylamino)-benzoylamino]3-(2'-phenoxy-biphenyl-4-yl)-propionic acid |

TABLE 1-continued

| Example | Structure | Name |
|---|---|---|
| 544 | 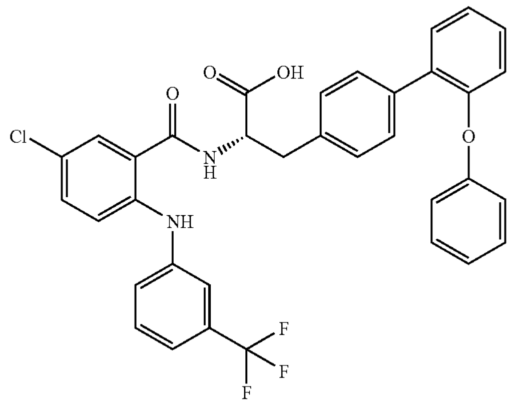 | (2S)-[5-Chloro-2-(3-trifluoromethyl-phenylamino)-benzoylamino]-3-(2'-phenoxy-biphenyl-4-yl)-propionic acid |
| 545 | 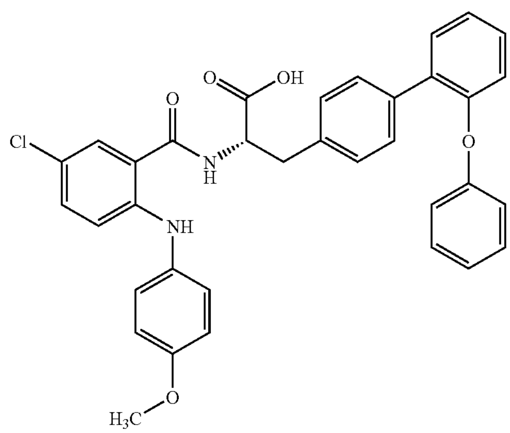 | (2S)-[5-Chloro-2-(4-methoxy-phenylamino)-benzoylamino]-3-(2'-phenoxy-biphenyl-4-yl)-propionic acid |
| 546 | 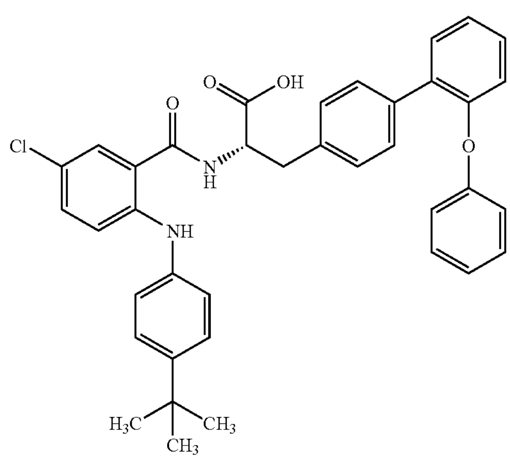 | (2S)-[2-(4-tert-Butyl-phenylamino)-5-chloro-benzoylamino]-3-(2'-phenoxy-biphenyl-4-yl)-propionic acid |

TABLE 1-continued

| Example | Structure | Name |
| --- | --- | --- |
| 547 | 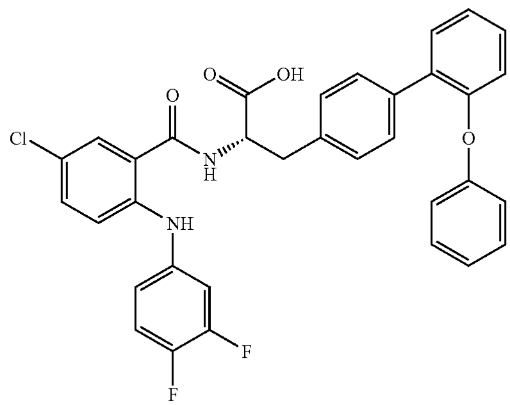 | (2S)-[5-Chloro-2-(3,4-difluoro-phenylamino)-benzoylamino]-3-(2'-phenoxy-biphenyl-4-yl)-propionic acid |
| 548 | 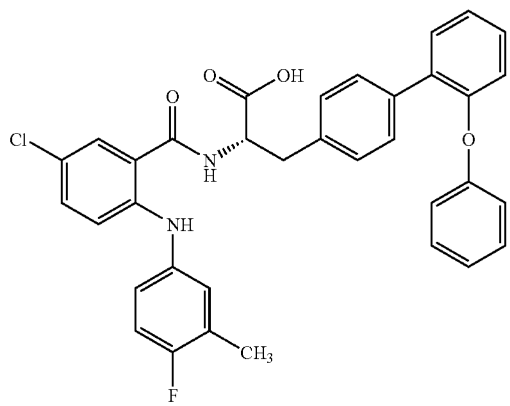 | (2S)-[5-Chloro-2-(4-fluoro-3-methyl-phenylamino)-benzoylamino]-3-(2'-phenoxy-biphenyl-4-yl)-propionic acid |
| 549 | 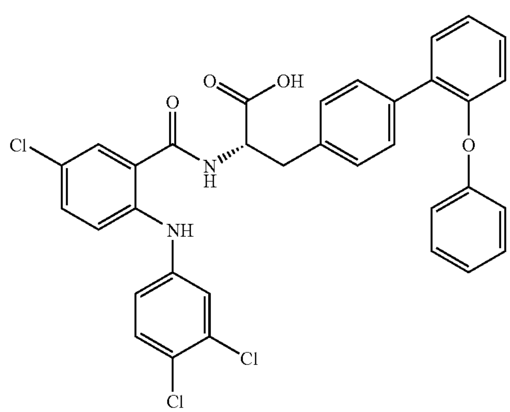 | (2S)-[5-Chloro-2-(3,4-dichloro-phenylamino)-benzoylamino]-3-(2'-phenoxy-biphenyl-4-yl)-propionic acid |

TABLE 1-continued

| Example | Structure | Name |
|---|---|---|
| 550 | 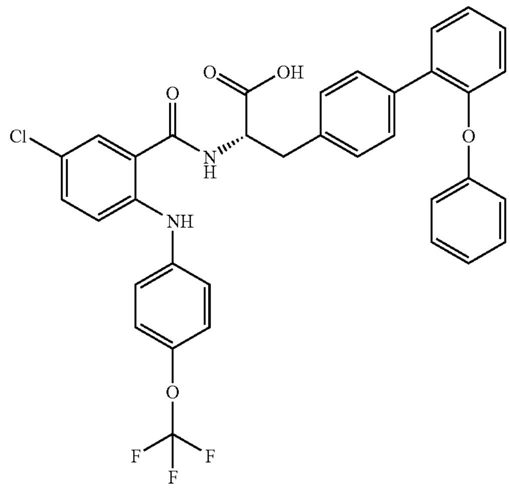 | (2S)-[5-Chloro-2-(4-trifluoromethoxy-phenylamino)-benzoylamino]-3-(2'-phenoxy-biphenyl-4-yl)-propionic acid |
| 551 | 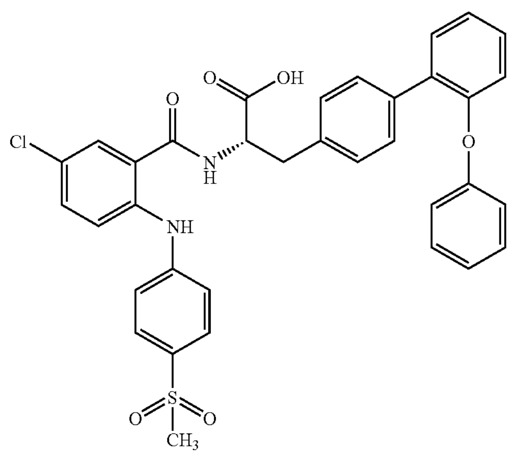 | (2S)-[5-Chloro-2-(4-methanesulfonyl-phenylamino)-benzoylamino]-3-(2'-phenoxy-biphenyl-4-yl)-propionic acid |
| 552 | 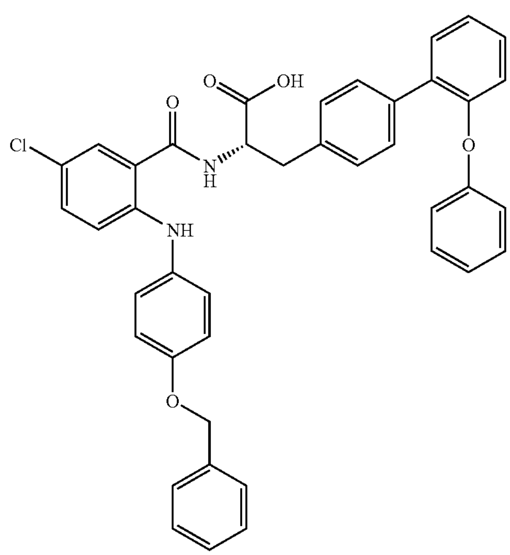 | (2S)-[2-(4-Benzyloxy-phenylamino)-5-chloro-benzoylamino[-3-(2'-phenoxy-biphenyl-4-yl)-propionic acid |

TABLE 1-continued

| Example | Structure | Name |
|---|---|---|
| 553 | 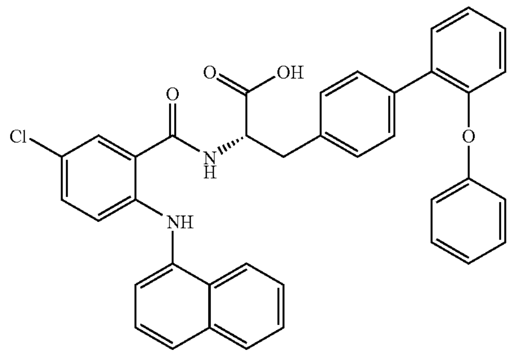 | (2S)-[5-Chloro-2-(naphthalen-1-ylamino)-benzoylamino]-3-(2'-phenoxy-biphenyl-4-yl)-propionic acid |
| 554 | 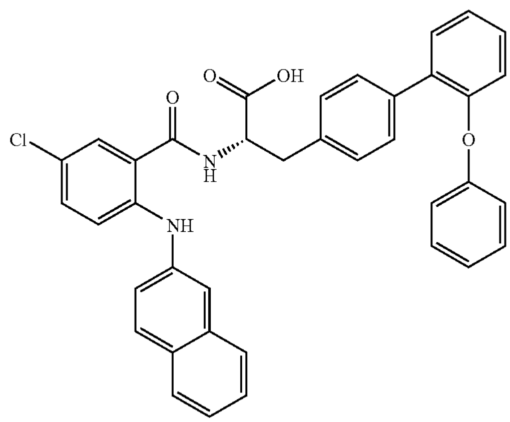 | (2S)-[5-Chloro-2-(naphthalen-2-ylamino)-benzoylamino]-3-(2'-phenoxy-biphenyl-4-yl)-propionic acid |
| 555 | 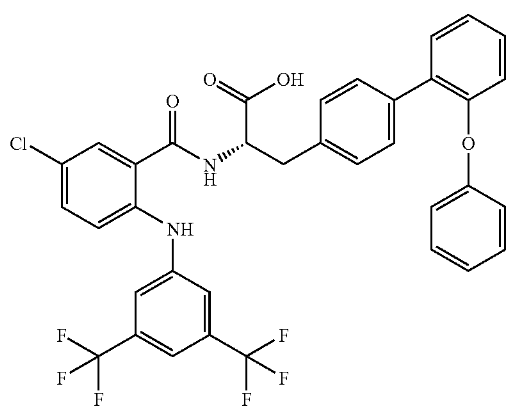 | (2S)-[2-(3,5-Bis-trifluoromethyl-phenylamino)-5-chloro-benzoylamino]-3-(2'-phenoxy-biphenyl-4-yl)-propionic acid |

TABLE 1-continued

| Example | Structure | Name |
|---|---|---|
| 556 | 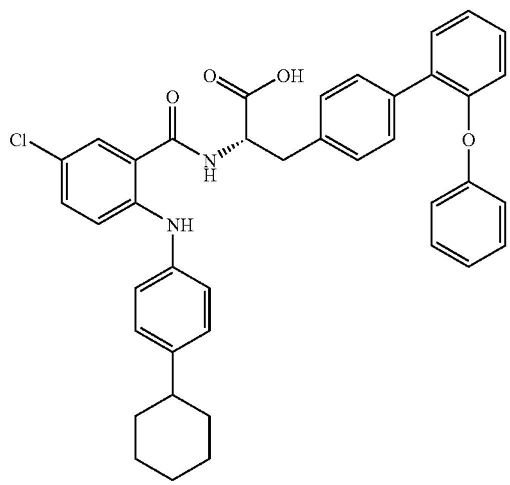 | (2S)-[5-Chloro-2-(4-cyclohexyl-phenylamino)-benzoylamino]-3-(2'-phenoxy-biphenyl-4-yl)-propionic acid |
| 557 | 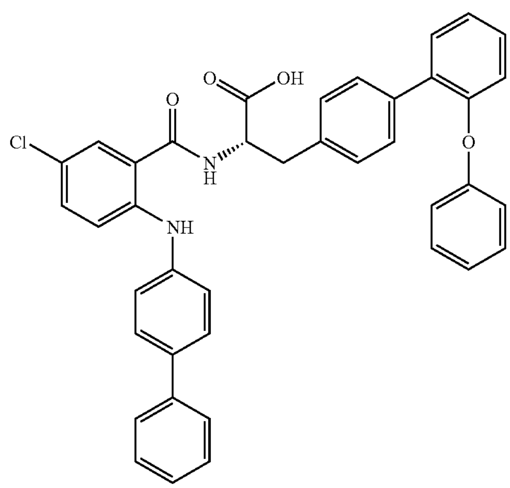 | (2S)-[2-(Biphenyl-4-ylamino)-5-chloro-benzoylamino]-3-(2'-phenoxy-biphenyl-4-yl)-propionic acid |
| 558 | 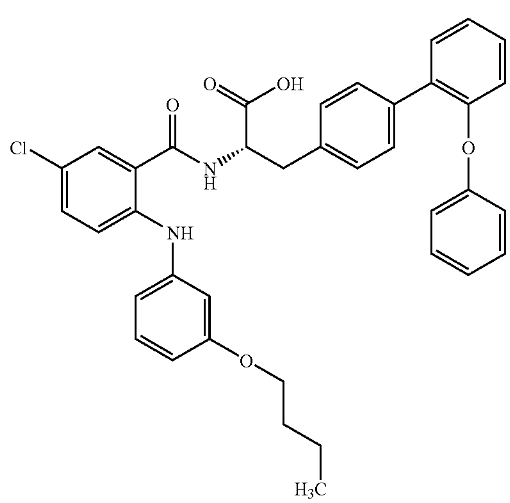 | (2S)-[2-(3-Butoxy-phenylamino)-5-chloro-benzoylamino]-3-(2'-phenoxy-biphenyl-4-yl)-propionic acid |

TABLE 1-continued

| Example | Structure | Name |
|---|---|---|
| 559 | 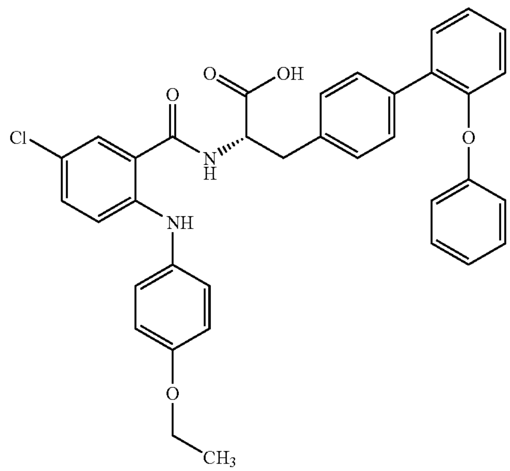 | (2S)-[5-Chloro-2-(4-ethoxy-phenylamino)-benzoylamino]-3-(2'-phenoxy-biphenyl-4-yl)-propionic acid |
| 560 | 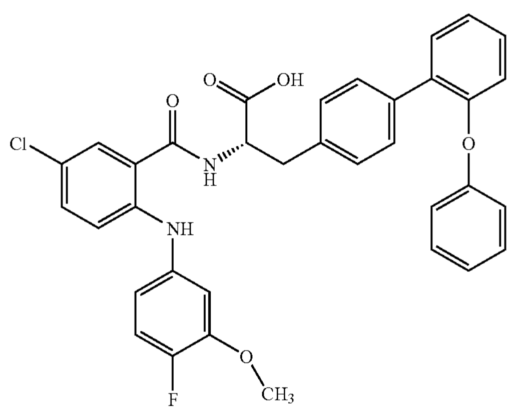 | (2S)-[5-Chloro-2-(4-fluoro-3-methoxy-phenylamino)-benzoylamino]-3-(2'-phenoxy-biphenyl-4-yl)-propionic acid |
| 561 | 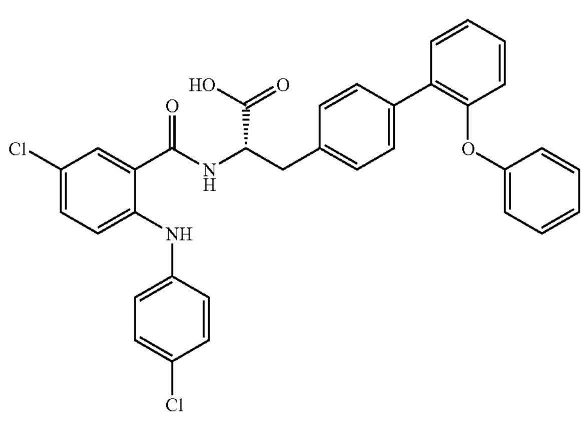 | (2S)-[5-Chloro-2-(4-chloro-phenylamino)-benzoylamino]-3-(2'-phenoxy-biphenyl-4-yl)-propionic acid |

TABLE 1-continued

| Example | Structure | Name |
|---|---|---|
| 562 | 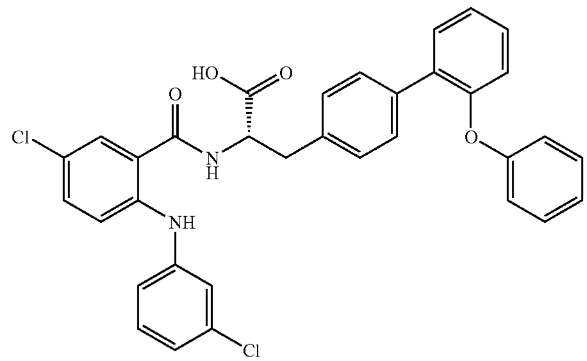 | (2S)-[5-Chloro-2-(3-chloro-phenylamino)-benzoylamino]-3-(2'-phenoxy-biphenyl-4-yl)-propionic acid |
| 563 | 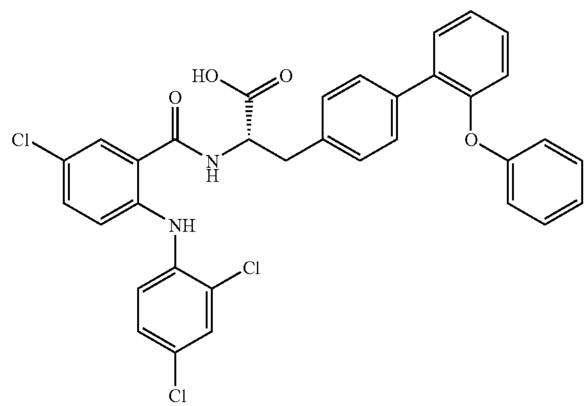 | (2S)-[5-Chloro-2-(2,4-dichloro-phenylamino)-benzoylamino]-3-(2'-phenoxy-biphenyl-4-yl)-propionic acid |
| 564 | 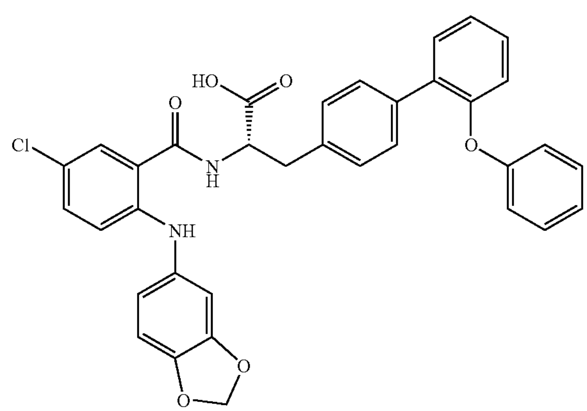 | (2S)-[2-(benzo[1,3]dioxol-5-ylamino)-5-chloro-benzoylamino]-3-(2'-phenoxy-biphenyl-4-yl)-propionic acid |

TABLE 1-continued

| Example | Structure | Name |
|---------|-----------|------|
| 565 | 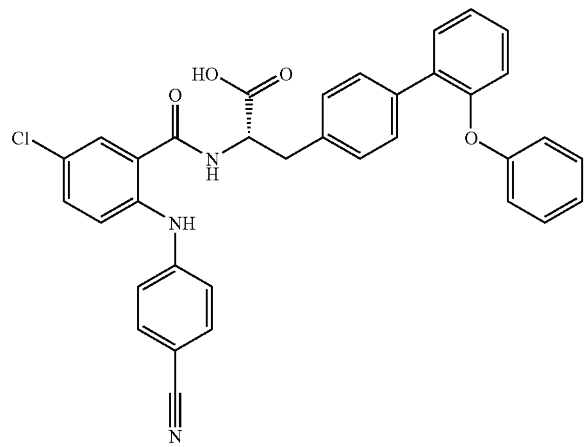 | (2S)-[5-Chloro-2-(4-cyano-phenylamino)-benzoylamino]-3-(2'-phenoxy-biphenyl-4-yl)-propionic acid |
| 566 | 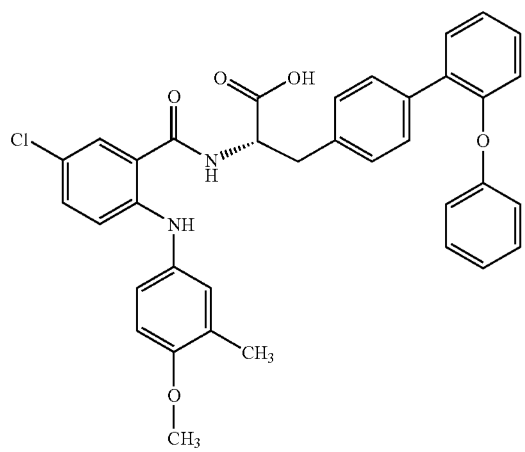 | (2S)-[5-Chloro-2-(4-methoxy-3-methyl-phenylamino)-benzoylamino]-3-(2'-phenoxy-biphenyl-4-yl)-propionic acid |
| 567 | 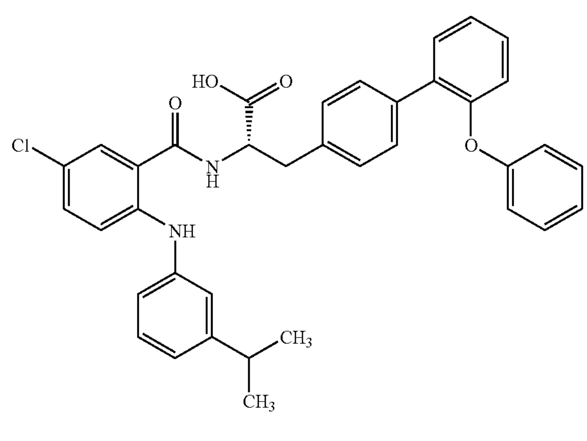 | (2S)-[5-Chloro-2-(3-isopropyl-phenylamino)-benzoylamino]-3-(2'-phenoxy-biphenyl-4-yl)-propionic acid |

TABLE 1-continued

| Example | Structure | Name |
|---|---|---|
| 568 | 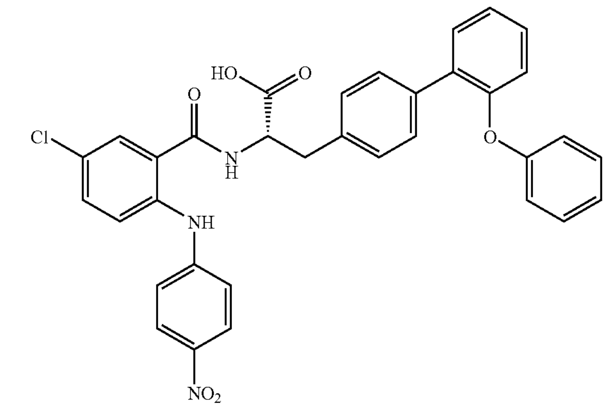 | (2S)-[5-Chloro-2-(4-nitro-phenylamino)-benzoylamino]-3-(2'-phenoxy-biphenyl-4-yl)-propionic acid |
| 569 | 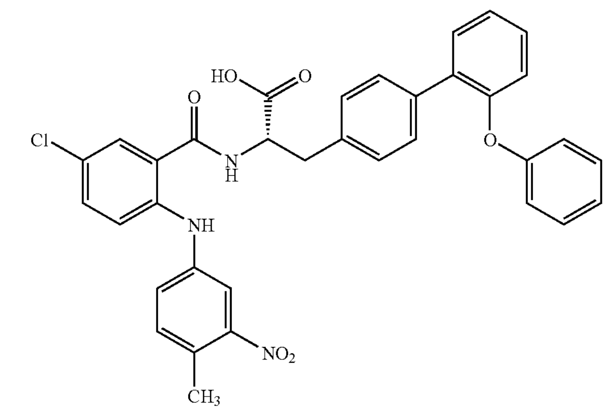 | (2S)-[5-Chloro-2-(4-methyl-3-nitro-phenylamino)-benzoylamino]-3-(2'-phenoxy-biphenyl-4-yl)-propionic acid |
| 570 | 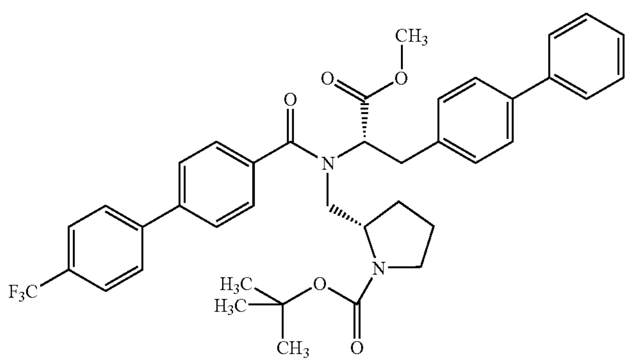 | (2S)-{[(2-Biphenyl-4-yl-methoxycarbonyl-ethyl)-(4'-trifluoromethyl-biphenyl-carbonyl)-amino]-methyl}-(2S)-pyrrolidine-1-carboxylic acid tert-butyl ester |
| 571 | 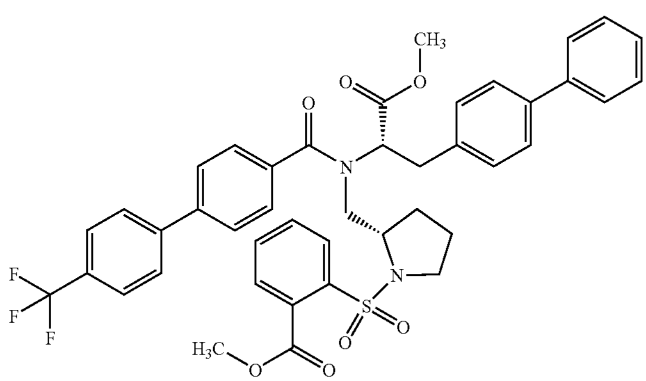 | (2S)-(2-{[(2-Biphenyl-4-yl-1-methoxycarbonyl-ethyl)-(4'-trifluoromethyl-biphenyl-4-carbonyl)-amino]-methyl}-(2S)-pyrrolidine-1-sulfonyl)-benzoic acid methyl ester |

TABLE 1-continued

| Example | Structure | Name |
|---|---|---|
| 572 | 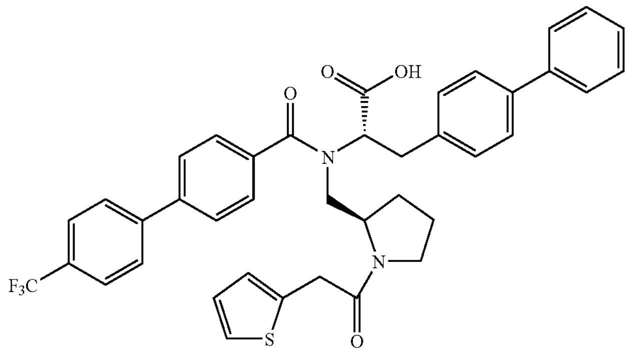 | 3-Biphenyl-4-yl-(2S)-[[(2R)-1-(2-thiophen-2-yl-acetyl)-pyrrolidine-2-methyl]-(4'-trifluoromethyl-biphenyl-4-carbonyl)-amino]-propionic acid |
| 573 | 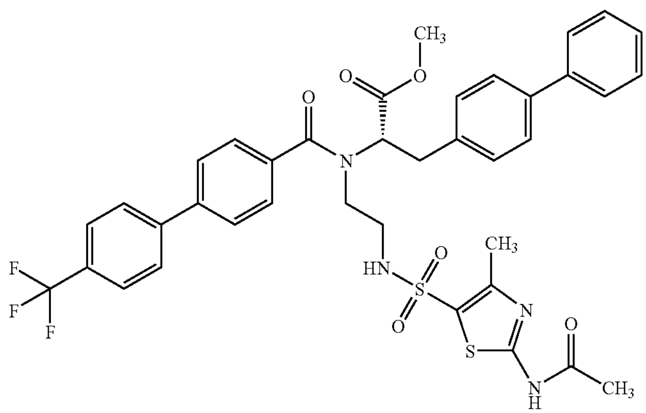 | (2S)-[[2-(2-Acetylamino-4-methyl-thiazole-5-sulfonylamino)-ethyl]-(4'-trifluoromethyl-biphenyl-4-carbonyl)-amino]-3-biphenyl-4-yl-propionic acid methyl ester |
| 574 | 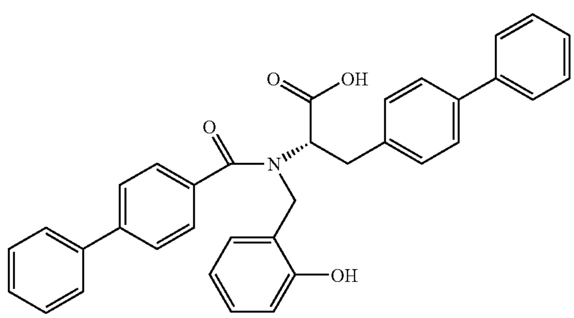 | (2S)-[(Biphenyl-4-carbonyl)-(2-hydroxy-benzyl)-amino]-3-biphenyl-4-yl-propionic acid |
| 575 | 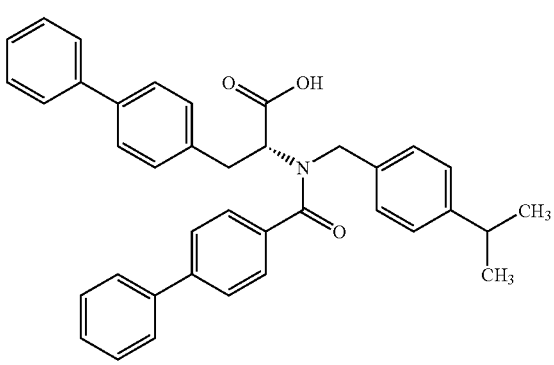 | (2S)-[(Biphenyl-4-carbonyl)-(4-isopropyl-benzyl)-amino]-3-biphenyl-4-yl-propionic acid |

TABLE 1-continued

| Example | Structure | Name |
| --- | --- | --- |
| 576 | 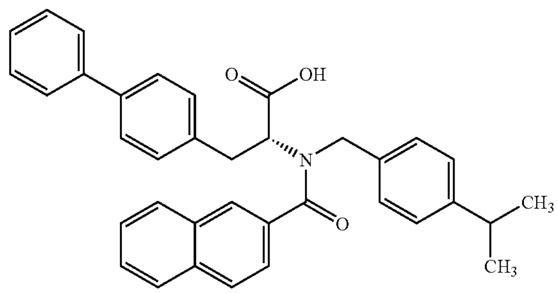 | 3-Biphenyl-4-yl-(2S)-[(4-isopropyl-benzyl)-(naphthalene-2-carbonyl)-amino]-propionic acid |
| 577 | 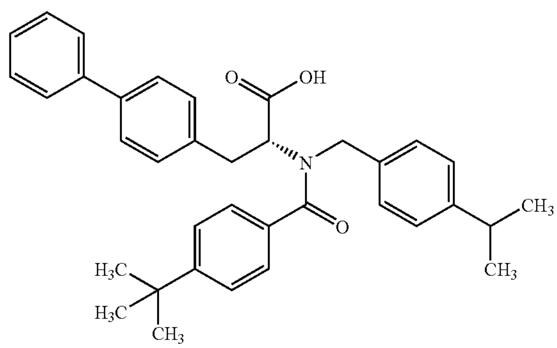 | 3-Biphenyl-4-yl-(2S)-[(4-tert-butyl-benzoyl)-(4-isopropyl-benzyl)amino]-propionic acid |
| 578 | 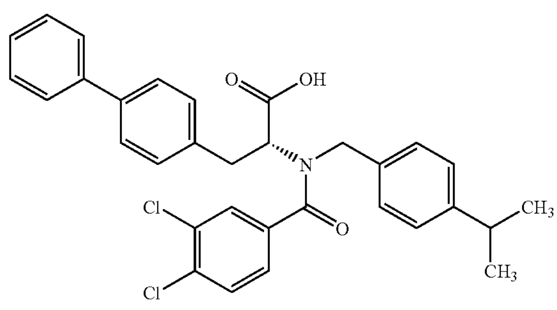 | 3-Biphenyl-4-yl-(2S)-[(3,4-dichloro-benzoyl)-(4-isopropyl-benzyl)-amino]-propionic acid |
| 579 | 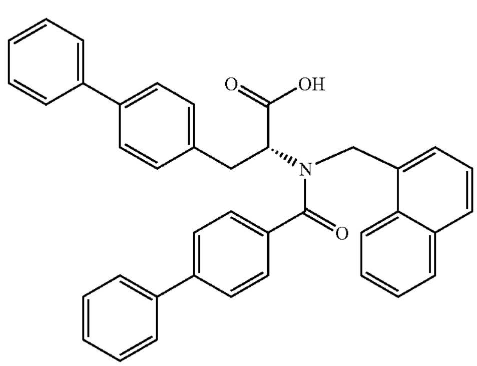 | (2S)-[(Biphenyl-4-carbonyl)-naphthalen-1-ylmethyl-amino]-3-biphenyl-4-yl-propionic acid |

TABLE 1-continued

| Example | Structure | Name |
| --- | --- | --- |
| 580 | 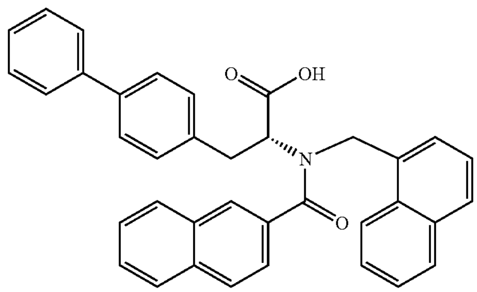 | 3-Biphenyl-4-yl-(2S)-[(naphthalene-2-carbonyl)-naphthalen-1-ylmethyl-amino]-propionic acid |
| 581 | 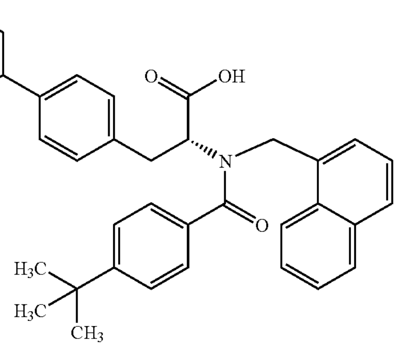 | 3-Biphenyl-4-yl-(2S)-[(4-tert-butyl-benzoyl)-naphthalen-1-ylmethyl-amino]-propionic acid |
| 582 | 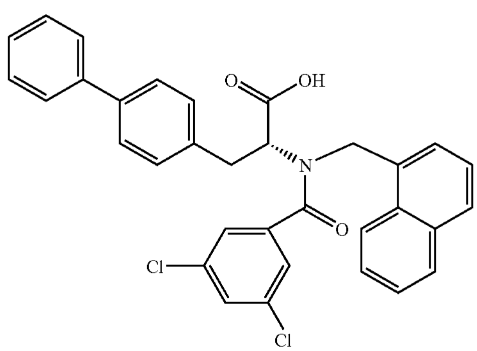 | 3-Biphenyl-4-yl-(2S)-[(3,5-dichloro-benzoyl)-naphthalen-1-ylmethyl-amino]-propionic acid |
| 583 | 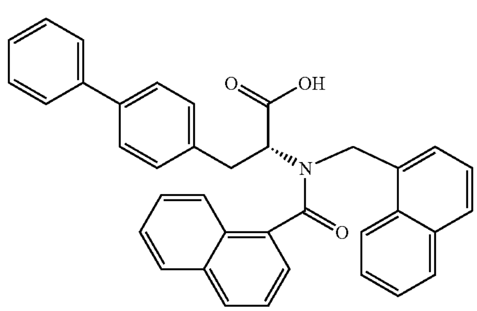 | 3-Biphenyl-4-yl-(2S)-[(naphthalene-1-carbonyl)-naphthalen-1-ylmethyl-amino]-propionic acid |

TABLE 1-continued

| Example | Structure | Name |
|---|---|---|
| 584 | 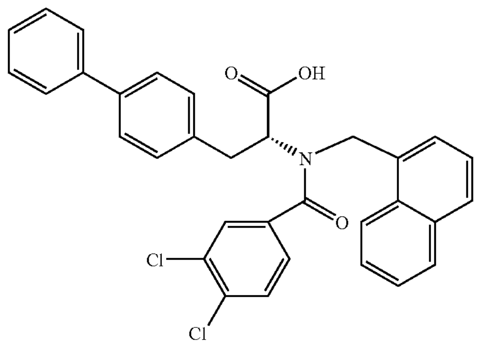 | 3-Biphenyl-4-yl-(2S)-[(3,4-dichloro-benzoyl)-naphthalen-1-ylmethyl-amino]-propionic acid |
| 585 | 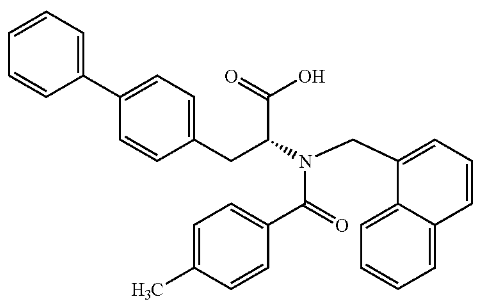 | 3-Biphenyl-4-yl-(2S)-[(4-methyl-benzoyl)-naphthalen-1-ylmethyl-amino]-propionic acid |
| 586 | 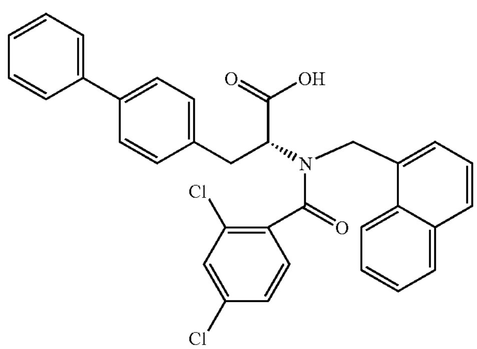 | 3-Biphenyl-4-yl-(2S)-[(2,4-dichloro-benzoyl)-naphthalen-1-ylmethyl-amino]-propionic acid |
| 587 | 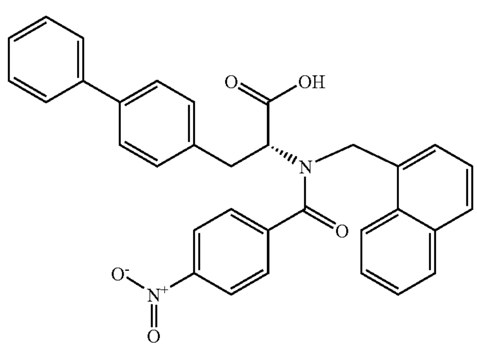 | 3-Biphenyl-4-yl-(2S)-[naphthalen-1-yl-methyl-(4-nitro-benzoyl)-amino]-propionic acid |

TABLE 1-continued

| Example | Structure | Name |
|---|---|---|
| 588 | 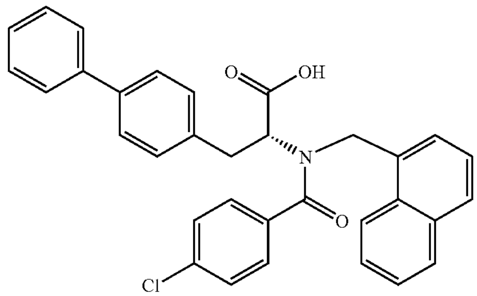 | 3-Biphenyl-4-yl-(2S)-[(4-chloro-benzoyl)-naphthalen-1-ylmethyl-amino]-propionic acid |
| 589 | 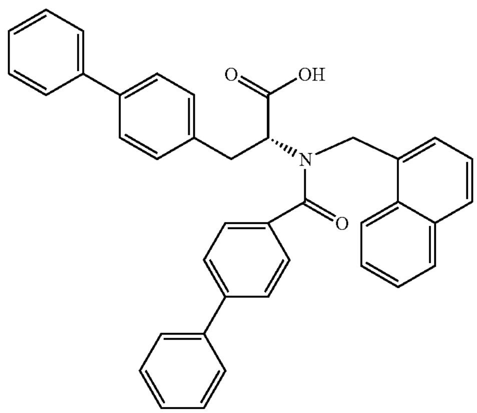 | (2S)-[(Biphenyl-4-carbonyl)-(4-chloro-benzyl)-amino]-3-biphenyl-4-yl-propionic acid |
| 590 | 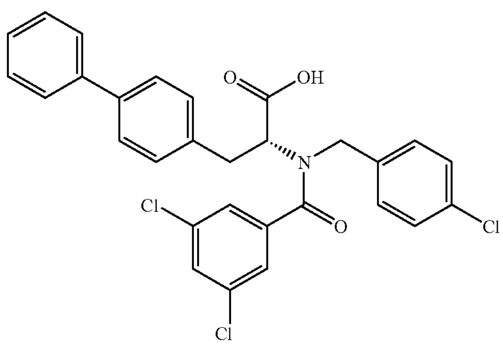 | 3-Biphenyl-4-yl-(2S)-[(4-chloro-benzyl)-(3,5-dichloro-benzoyl)-amino]-propionic acid |
| 591 | 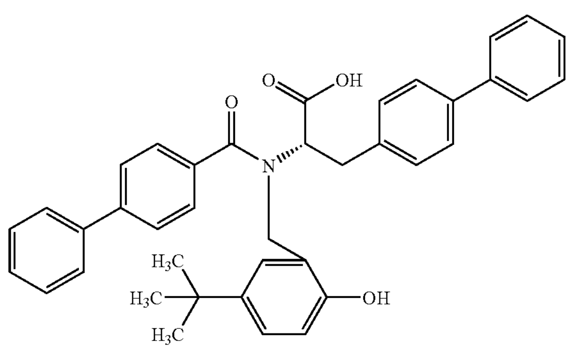 | (2S)-[(Biphenyl-4-carbonyl)-(5-tert-butyl-2-hydroxy-benzyl)-amino]-3-biphenyl-4-yl-propionic acid |

TABLE 1-continued

| Example | Structure | Name |
|---|---|---|
| 592 | 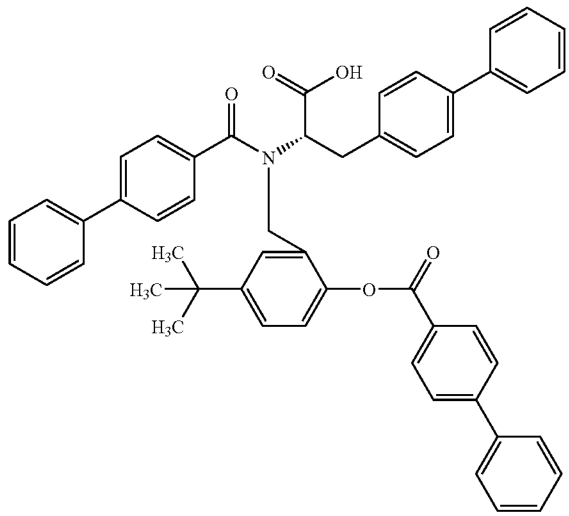 | Biphenyl-4-carboxylic acid (2S)-{[(biphenyl-4-carbonyl)-(2-biphenyl-4-yl-1-carboxy-ethyl)-amino]-methyl}-4-tert-butyl-phenyl ester |
| 593 | 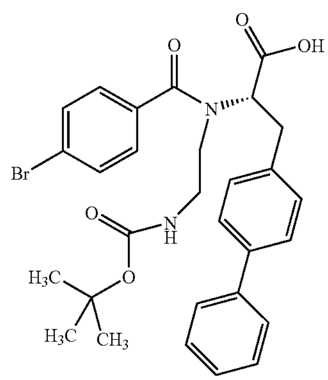 | 3-Biphenyl-4-yl-(2S)-[(4-bromo-benzoyl)-(2-tert-butoxycarbonylamino-ethyl)-amino]-propionic acid |
| 594 | 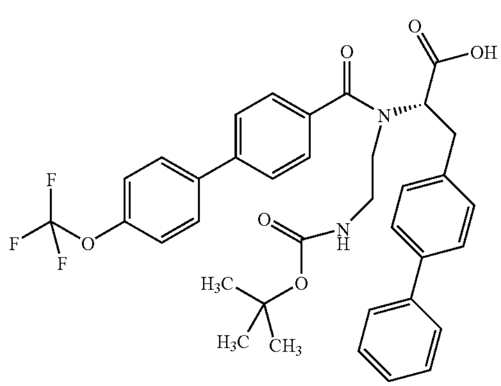 | 3-Biphenyl-4-yl-(2S)-[(2-tert-butoxycarbonylamino-ethyl)-(4'-trifluoromethoxy-biphenyl-4-carbonyl)-amino]-propionic acid |

TABLE 1-continued

| Example | Structure | Name |
|---|---|---|
| 595 | 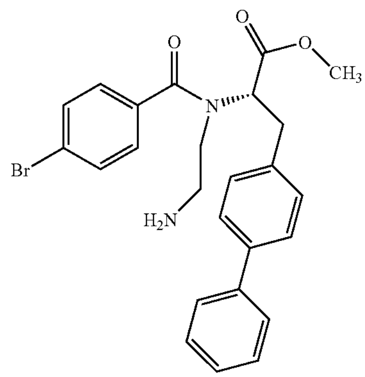 | (2S)-[(2-Amino-ethyl)-(4-bromo-benzoyl)-amino]-3-biphenyl-4-yl-propionic acid methyl ester |
| 596 | 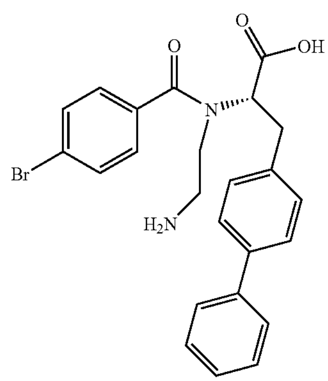 | (2S)-[(2-Amino-ethyl)-(4-bromo-benzoyl)-amino]-3-biphenyl-4-yl-propionic acid |
| 597 | 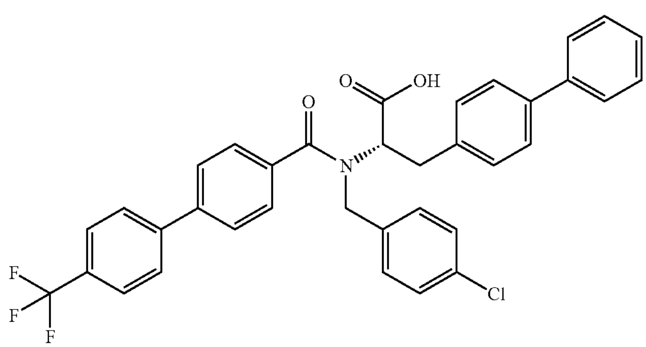 | 3-Biphenyl-4-yl-(2S)-[(4-chloro-benzyl)-(4'-trifluoromethyl-biphenyl-4-carbonyl)-amino]-propionic acid |
| 598 | 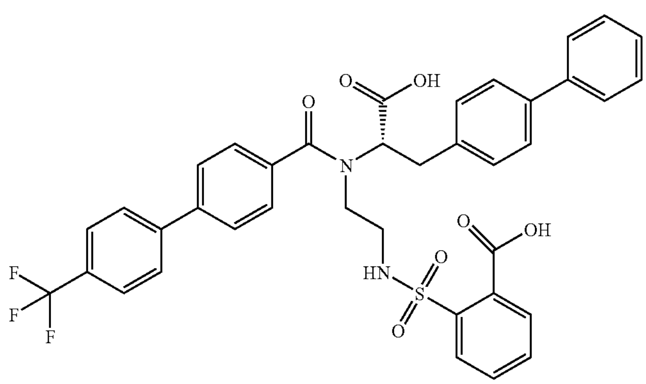 | (2S)-{2-[(2-Biphenyl-4-yl-1-carboxy-ethyl)-(4'-trifluoromethyl-biphenyl-4-carbonyl)-amino]-ethylsulfamoyl}-benzoic acid |

TABLE 1-continued

| Example | Structure | Name |
|---|---|---|
| 599 | 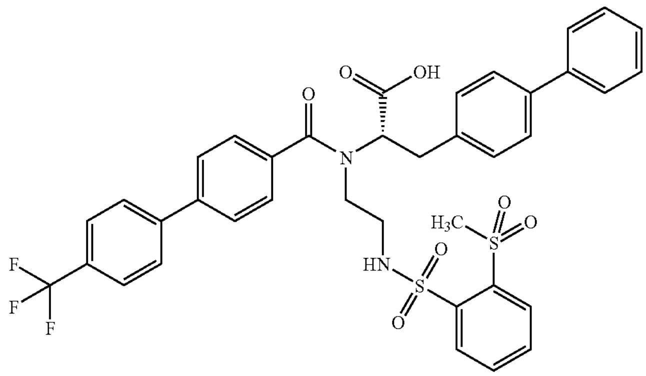 | 3-Biphenyl-4-yl-(2S)-[[2-(2-methanesulfonyl-benzenesulfonylamino)-ethyl]-(4'-trifluoromethyl-biphenyl-4-carbonyl)-amino]-propionic acid |
| 600 | 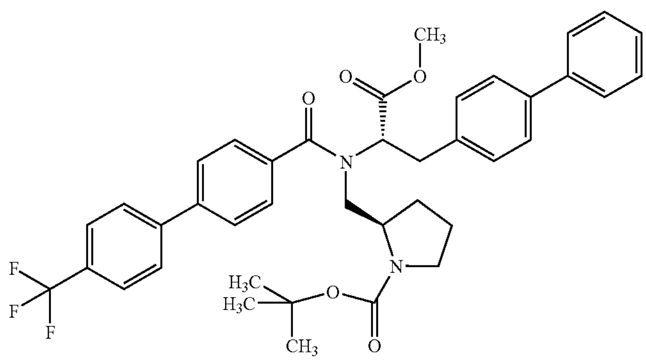 | (2S)-{[(2-Biphenyl-4-yl-1-methoxycarbonyl-ethyl)-(4'-trifluoromethyl-biphenyl-4-carbonyl)-amino]-methyl}-(2R)-pyrrolidine-1-carboxylic acid tert-butyl ester |
| 601 | 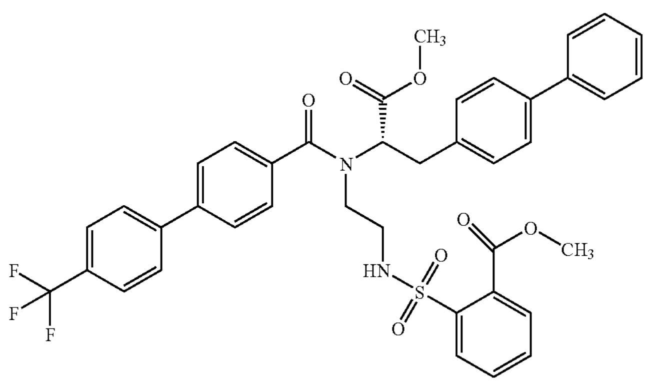 | (2S)-{2-[(2-Biphenyl-4-yl-1-methoxycarbonyl-ethyl)-(4'-trifluoromethyl-biphenyl-4-carbonyl)-amino]-ethylsulfamoyl}-benzoic acid methyl ester |
| 602 | 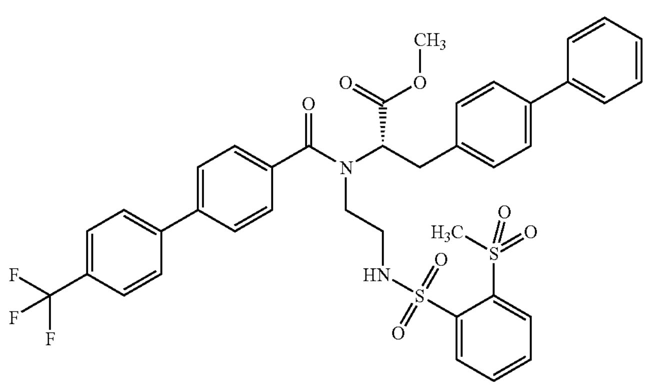 | 3-Biphenyl-4-yl-(2S)-[[2-(2-methanesulfonyl-benzenesulfonylamino)-ethyl]-(4'-trifluoromethyl-biphenyl-4-carbonyl)-amino]-propionic acid methyl ester |

TABLE 1-continued

| Example | Structure | Name |
| --- | --- | --- |
| 603 | 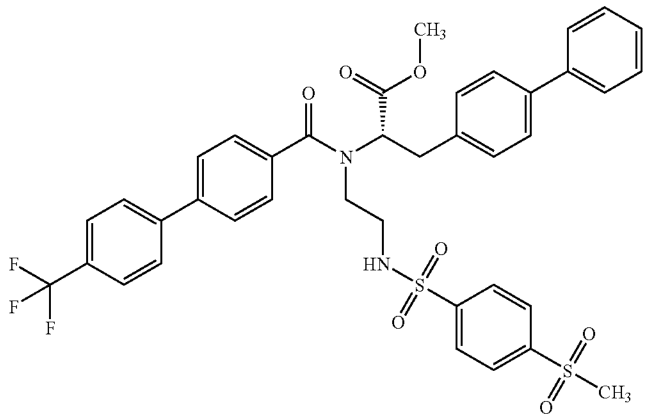 | 3-Biphenyl-4-yl-(2S)-[[2-(4-methanesulfonyl-benzenesulfonylamino)-ethyl]-(4'-trifluoromethyl-biphenyl-4-carbonyl)-amino]-propionic acid methyl ester |
| 604 | 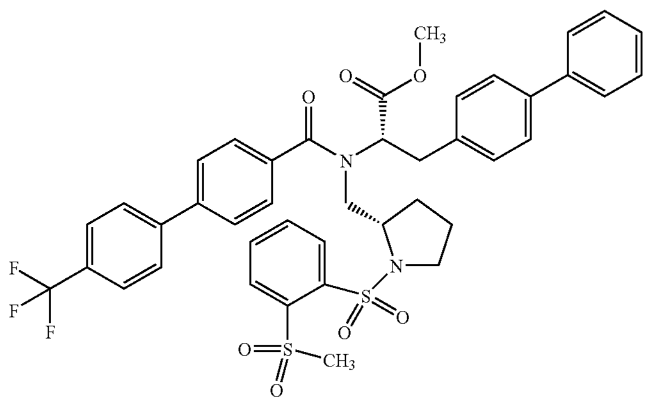 | 3-Biphenyl-4-yl-(2S)-[[1-(2-methanesulfonyl-benzenesulfonyl)-(2S)-pyrrolidin-2-ylmethyl]-(4'-trifluoromethyl-biphenyl-4-carbonyl)-amino]-propionic acid methyl ester |
| 605 | 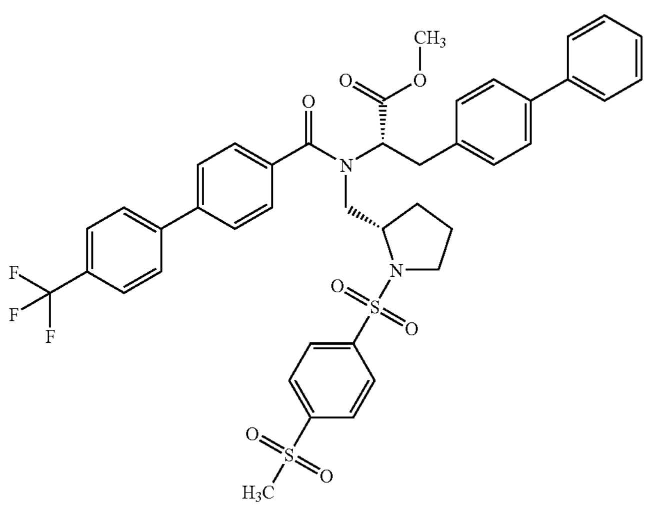 | 3-Biphenyl-4-yl-(2S)-[[1-(4-methanesulfonyl-benzenesulfonyl)-(2S)-pyrrolidin-2-ylmethyl]-(4'-trifluoromethyl-biphenyl-4-carbonyl)-amino]-propionic acid methyl ester |

TABLE 1-continued

| Example | Structure | Name |
|---|---|---|
| 606 | 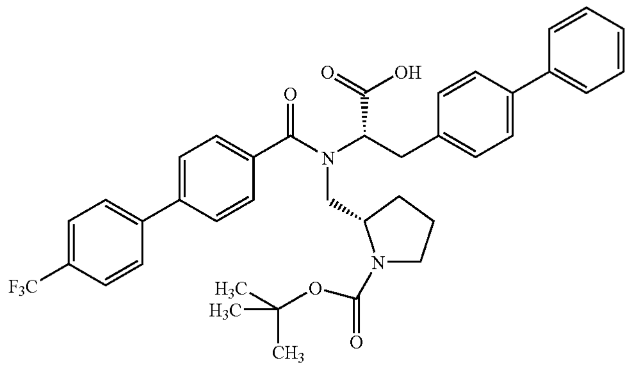 | (2S)-{[(2-Biphenyl-4-yl-1-carboxy-ethyl)-(4'-trifluoromethyl-biphenyl-4-carbonyl)-amino]-methyl}-(2S)-pyrrolidine-1-carboxylic acid tert-butyl ester |
| 607 | 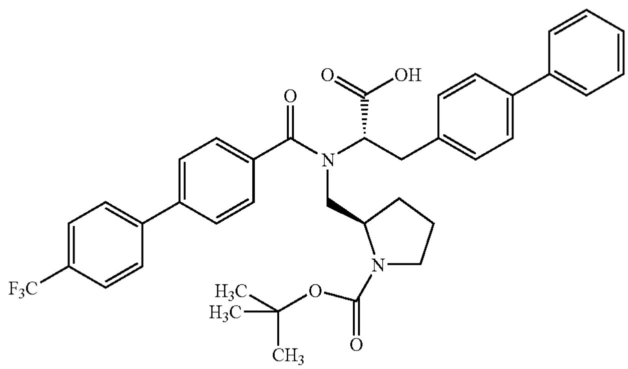 | (2S)-{[(2-Biphenyl-4-yl-1-carboxy-ethyl)-(4'-trifluoromethyl-biphenyl-4-carbonyl)-amino]-methyl}-(2R)-pyrrolidine-1-carboxylic acid tert-butyl ester |
| 608 | 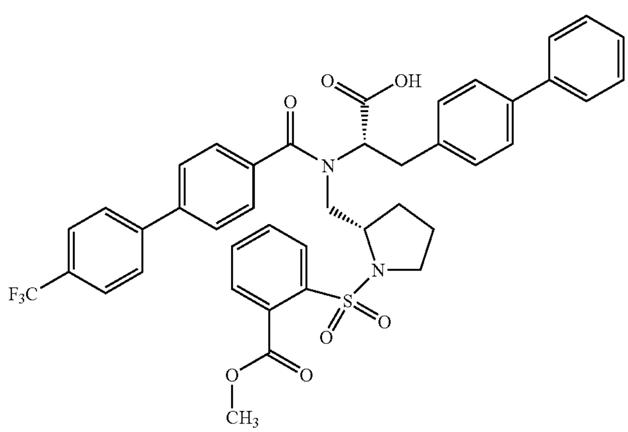 | (2S)-(2-{[(2-Biphenyl-4-yl-1-carboxy-ethyl)-(4'-trifluoromethyl-biphenyl-4-carbonyl)-amino]-methyl}-(2S)-pyrrolidine-1-sulfonyl)-benzoic acid methylester |
| 609 | 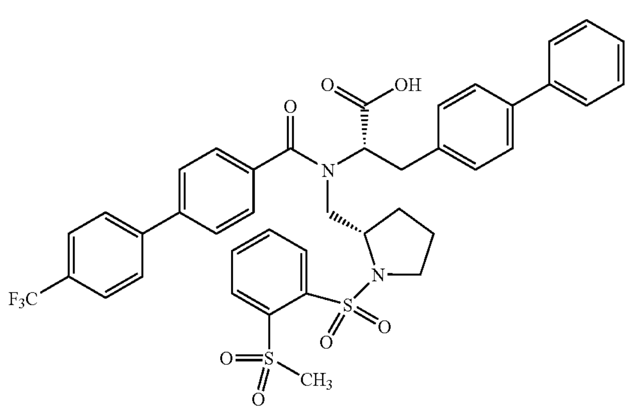 | 3-Biphenyl-4-yl-(2S)-[[1-(2-methanesulfonyl-benzenesulfonyl)-(2S)-pyrrolidin-2-ylmethyl]-(4'-trifluoromethyl-biphenyl-4-carbonyl)-amino]-propionic acid |

TABLE 1-continued

| Example | Structure | Name |
|---|---|---|
| 610 | 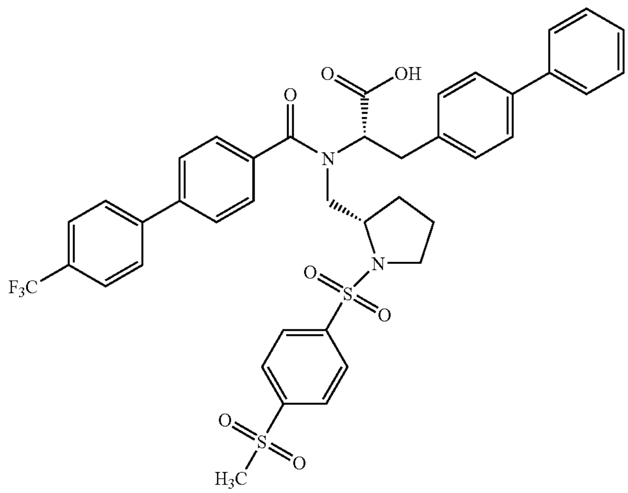 | 3-Biphenyl-4-yl-(2S)-[[1-(4-methanesulfonyl-benzenesulfonyl)-(2S)-pyrrolidin-2-ylmethyl]-(4'-trifluoromethyl-biphenyl-4-carbonyl)-amino]-propionic acid |
| 611 | 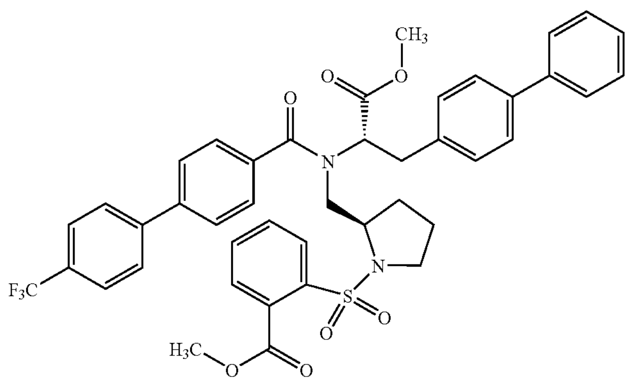 | (2S)-(2-{[(2-Biphenyl-4-yl-1-methoxycarbonyl-ethyl)-(4'-trifluoromethyl-biphenyl-4-carbonyl)-amino]-methyl}-(2R)-pyrrolidine-1-sulfonyl)-benzoic acid methyl ester |
| 612 | 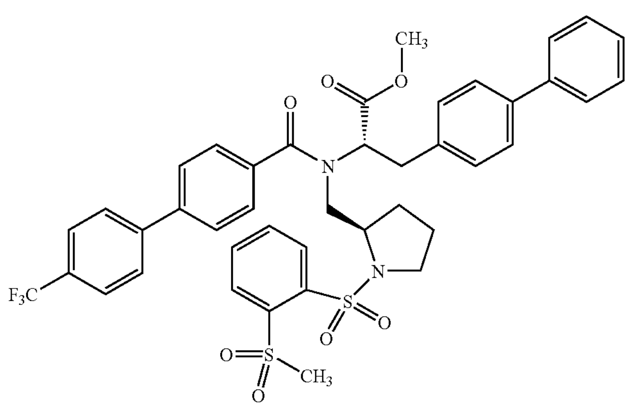 | 3-Biphenyl-4-yl-(2S)-[[1-(2-methanesulfonyl-benzenesulfonyl)-(2R)-pyrrolidin-2-ylmethyl]-(4'-trifluoromethyl-biphenyl-4-carbonyl)-amino]-propionic acid methyl ester |

TABLE 1-continued

| Example | Structure | Name |
|---|---|---|
| 613 | 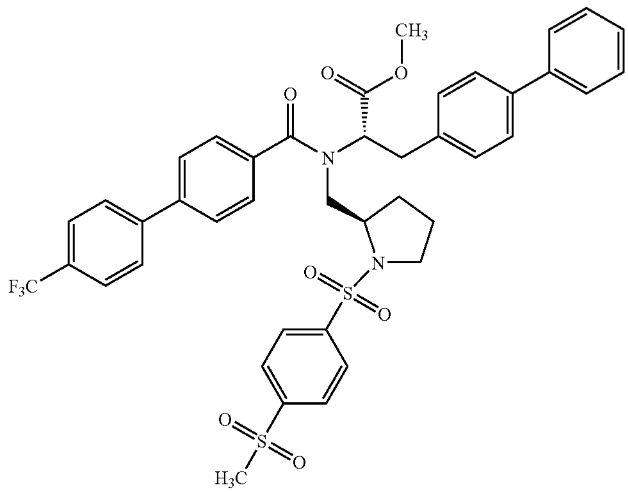 | 3-Biphenyl-4-yl-(2S)-[[1-(4-methanesulfonyl-benzenesulfonyl)-(2R)-pyrrolidin-2-ylmethyl]-(4'-trifluoromethyl-biphenyl-4-carbonyl)-amino]-propionic acid methyl ester |
| 614 | 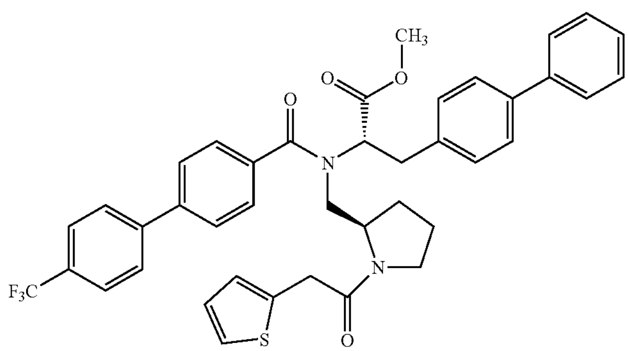 | 3-Biphenyl-4-yl-(2S)-[[1-(2-thiophen-2-yl-acetyl)-(2R)-pyrrolidin-2-ylmethyl]-(4'-trifluoromethyl-biphenyl-4-carbonyl)-amino]-propionic acid methyl ester |
| 615 | 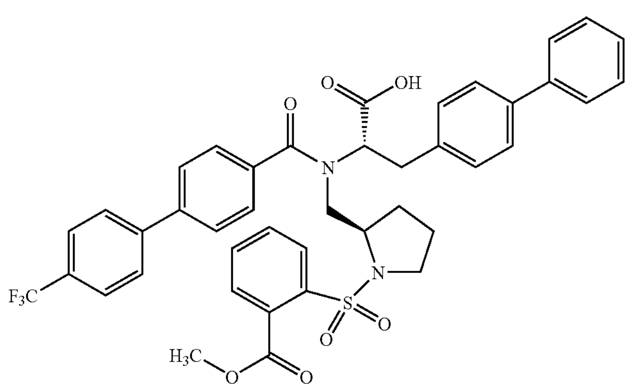 | (2S)-(2-{[(2-Biphenyl-4-yl-1-carboxy-ethyl)-(4'-trifluoromethyl-biphenyl-4-carbonyl)-amino]-methyl}-(2R)-pyrrolidine-1-sulfonyl)-benzoic acid methyl ester |

TABLE 1-continued

| Example | Structure | Name |
|---|---|---|
| 616 | 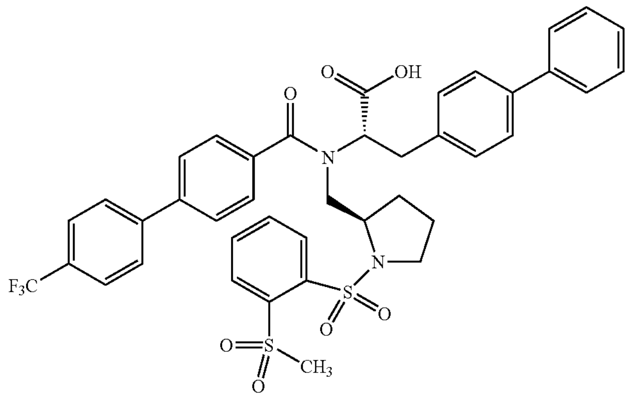 | 3-Biphenyl-4-yl-(2S)-[[1-(2-methanesulfonyl-benzenesulfonyl)-(2R)-pyrrolidin-2-ylmethyl]-(4'-trifluoromethyl-biphenyl-4-carbonyl)-amino]-propionic acid |
| 617 | 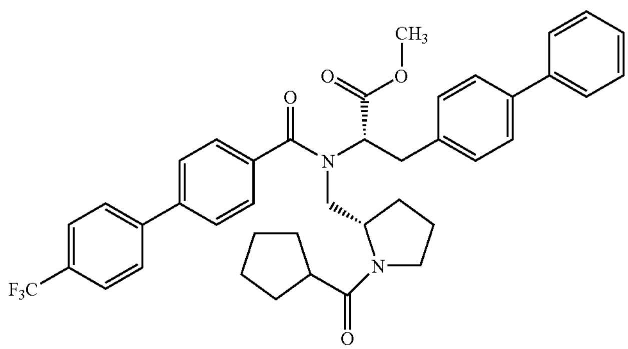 | 3-Biphenyl-4-yl-(2S)-[(1-cyclopentanecarbonyl-(2S)-pyrrolidin-2-ylmethyl)-(4'-trifluoromethyl-biphenyl-4-carbonyl)-amino]-propionic acid methyl ester |
| 618 | 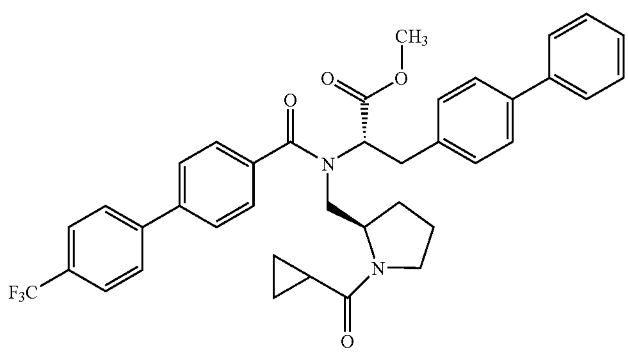 | 3-Biphenyl-4-yl-(2S)-[(1-cyclopropanecarbonyl-(2R)-pyrrolidin-2-ylmethyl)-(4'-trifluoromethyl-biphenyl-4-carbonyl)-amino]-propionic acid methyl ester |
| 619 | 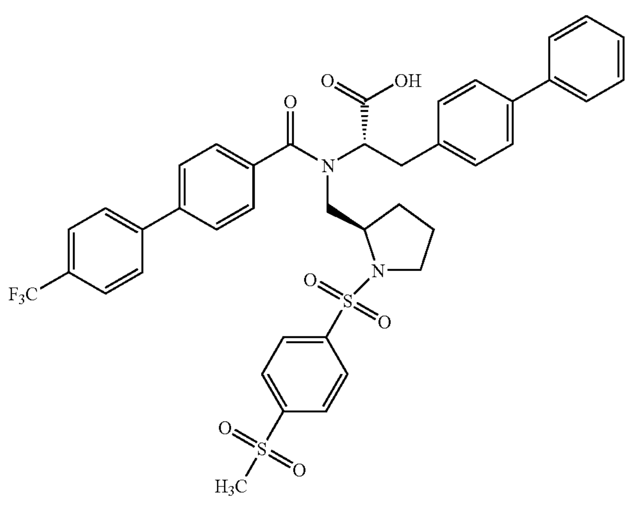 | 3-Biphenyl-4-yl-(2S)-[[1-(4-methanesulfonyl-benzenesulfonyl)-(2R)-pyrrolidin-2-ylmethyl]-(4'-trifluoromethyl-biphenyl-4-carbonyl)-amino]-propionic acid |

TABLE 1-continued

| Example | Structure | Name |
|---|---|---|
| 620 | 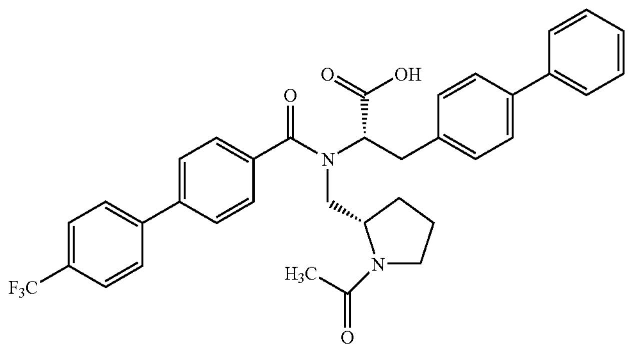 | (2S)-[(1-Acetyl-(2S)-pyrrolidin-2-ylmethyl)-(4'-trifluoromethyl-biphenyl-4-carbonyl)-amino]-3-biphenyl-4-yl-propionic acid |
| 621 | 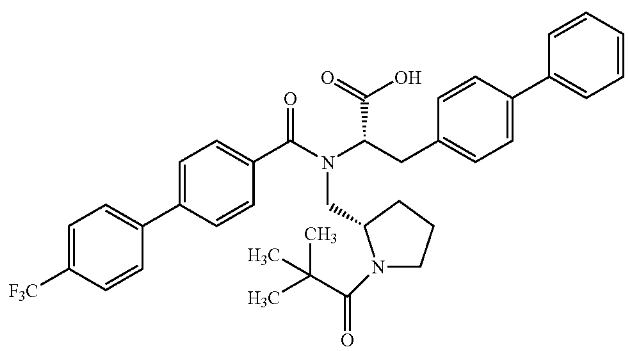 | 3-Biphenyl-4-yl-(2S)-[[1-(2,2-dimethyl-propionyl)-(2S)-pyrrolidin-2-ylmethyl]-(4'-trifluoromethyl-biphenyl-4-carbonyl)-amino]-propionic acid |
| 622 | 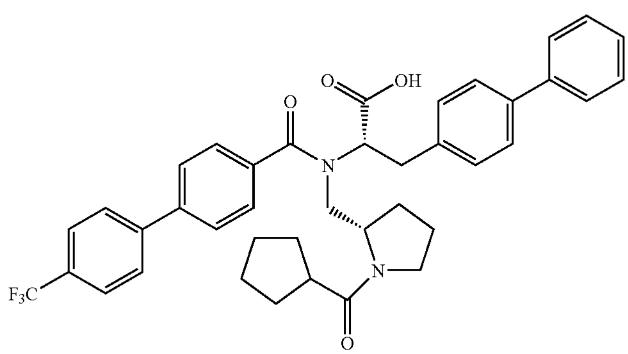 | 3-Biphenyl-4-yl-(2S)-[(1-cyclopentanecarbonyl-(2S)-pyrrolidin-2-ylmethyl)-(4'-trifluoromethyl-biphenyl-4-carbonyl)-amino]-propionic acid |
| 623 | 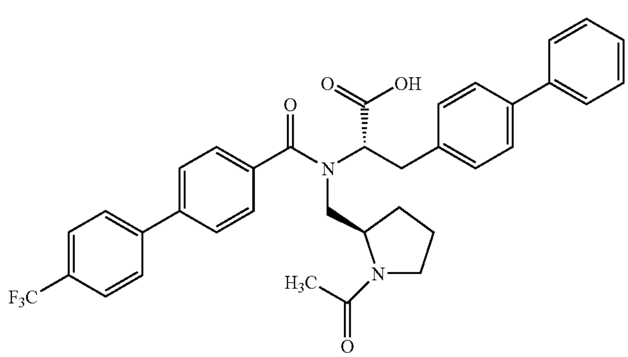 | (2S)-[(1-Acetyl-(2R)-pyrrolidin-2-ylmethyl)-(4'-trifluoromethyl-biphenyl-4-carbonyl)-amino]-3-biphenyl-4-yl-propionic acid |

TABLE 1-continued

| Example | Structure | Name |
|---|---|---|
| 624 | 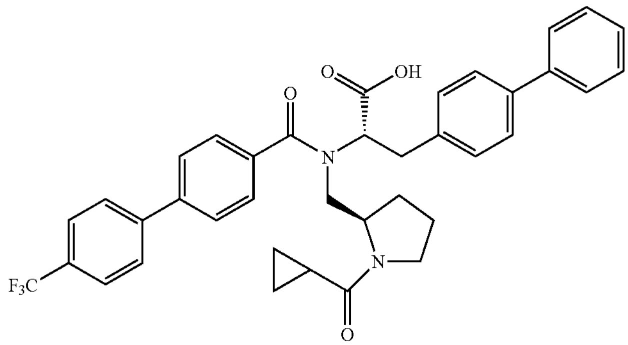 | 3-Biphenyl-4-yl-(2S)-[(1-cyclopropanecarbonyl-(2R)-pyrrolidin-2-ylmethyl)-(4'-trifluoromethyl-biphenyl-4-carbonyl)-amino]-propionic acid |
| 625 | 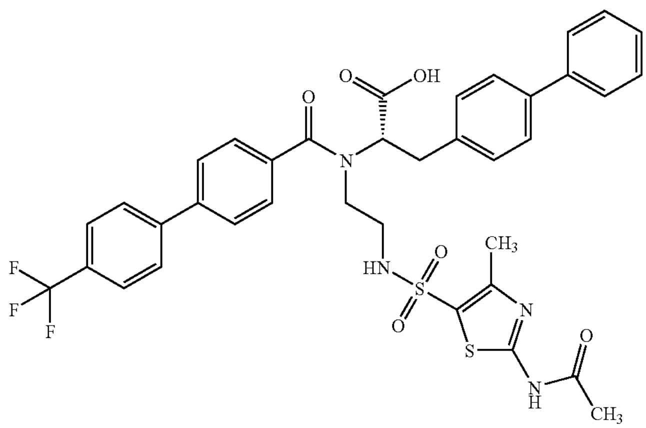 | (2S)-[[2-(2-Acetylamino-4-methyl-thiazole-5-sulfonylamino)-ethyl]-(4'-trifluoromethyl-biphenyl-4-carbonyl)-amino]-3-biphenyl-4-yl-propionic acid |
| 626 | 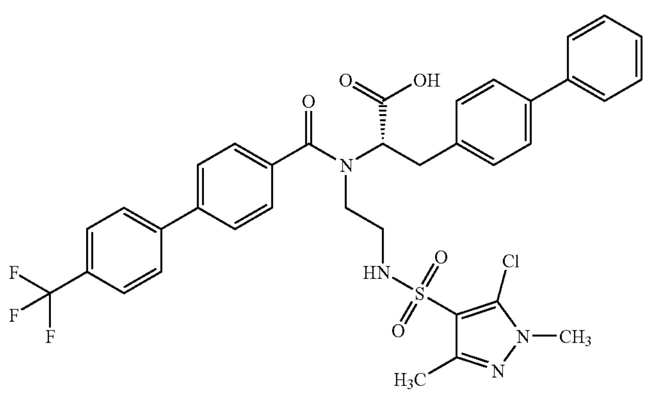 | 3-Biphenyl-4-yl-(2S)-[[2-(5-chloro-1,3-dimethyl-1H-pyrazole-4-sulfonylamino)-ethyl]-(4'-trifluoromethyl-biphenyl-4-carbonyl)-amino]-propionic acid |
| 627 | 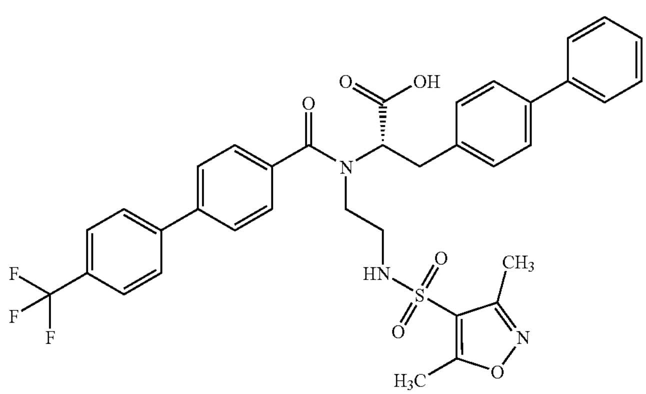 | 3-Biphenyl-4-yl-(2S)-[[2-(3,5-dimethyl-isoxazole-4-sulfonylamino)-ethyl]-(4'-trifluoromethyl-biphenyl-4-carbonyl)-amino]-propionic acid |

TABLE 1-continued

| Example | Structure | Name |
|---|---|---|
| 628 | 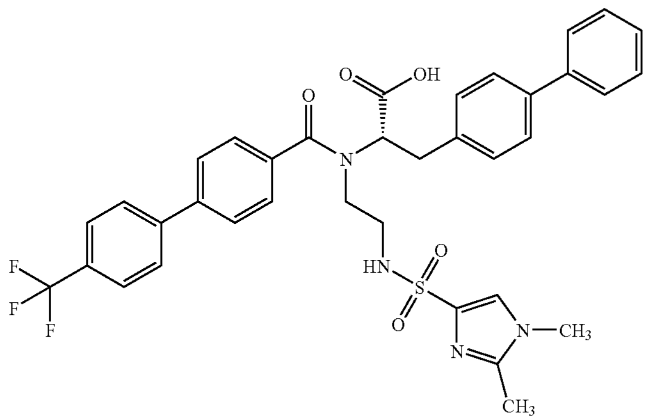 | 3-Biphenyl-4-yl-(2S)-[[2-(1,2-dimethyl-1H-imidazole-4-sulfonylamino)-ethyl]-(4'-trifluoromethyl-biphenyl-4-carbonyl)-amino]-propionic acid |
| 629 | 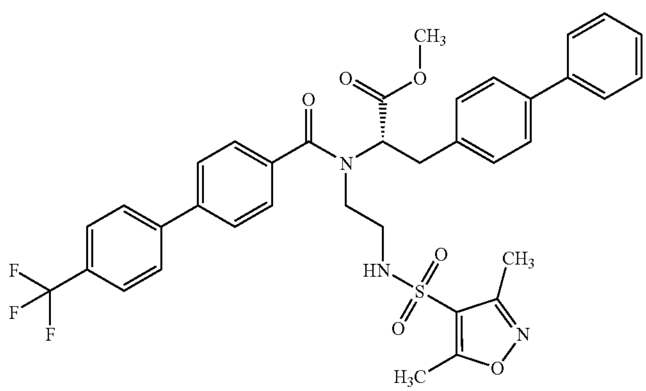 | 3-Biphenyl-4-yl-(2S)-[[2-(3,5-dimethyl-isoxazole-4-sulfonylamino)-ethyl]-(4'-trifluoromethyl-biphenyl-4-carbonyl)-amino]-propionic acid methyl ester |
| 630 | 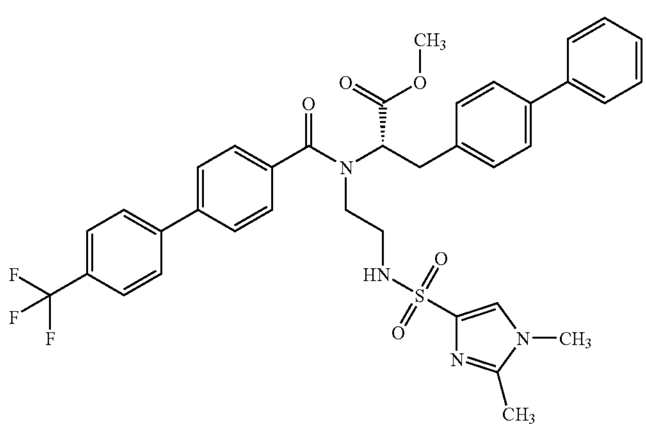 | 3-Biphenyl-4-yl-(2S)-[[2-(1,2-dimethyl-1H-imidazole-4-sulfonylamino)-ethyl]-(4'-trifluoromethyl-biphenyl-4-carbonyl)-amino]- propionic acid methyl ester |

TABLE 1-continued

| Example | Structure | Name |
|---|---|---|
| 631 | 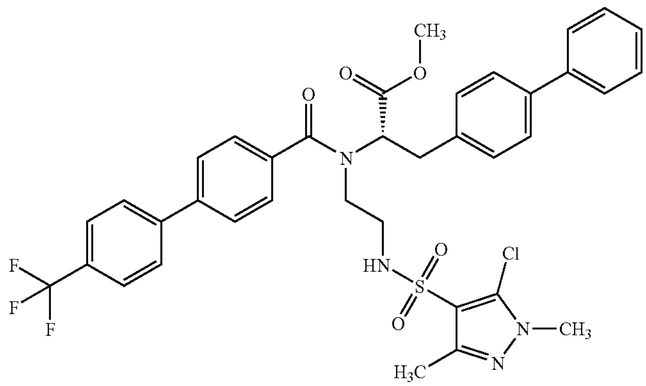 | 3-Biphenyl-4-yl-(2S)-[[2-(5-chloro-1,3-dimethyl-1H-pyrazole-4-sulfonylamino)-ethyl]-(4'-trifluoromethyl-biphenyl-4-carbonyl)-amino]-propionic acid methyl ester |
| 632 | 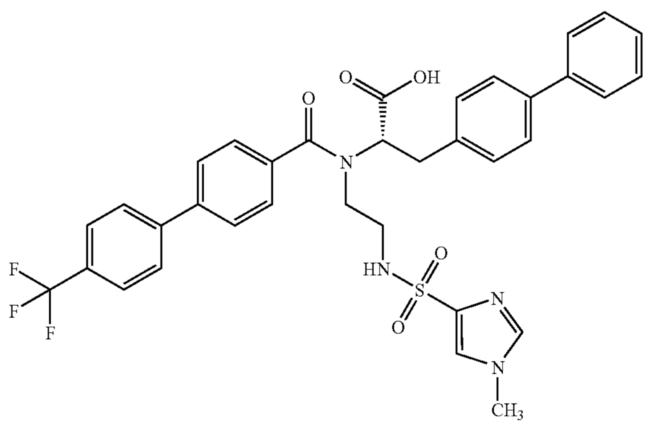 | 3-Biphenyl-4-yl-(2S)-[[2-(1-methyl-1H-imidazole-4-sulfonylamino)-ethyl]-(4'-trifluoromethyl-biphenyl-4-carbonyl)-amino]-propionic acid |
| 633 | 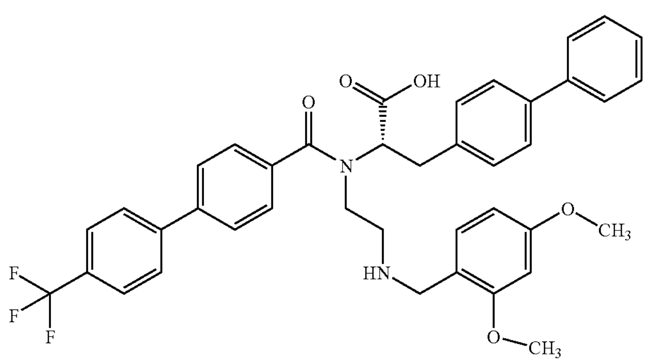 | 3-Biphenyl-4-yl-(2S)-[[2-(2,4-dimethoxy-benzylamino)-ethyl]-(4'-trifluoromethyl-biphenyl-4-carbonyl)-amino]-propionic acid |
| 634 | 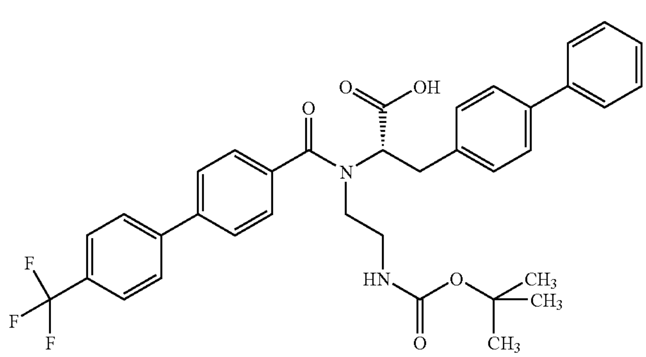 | 3-Biphenyl-4-yl-(2S)-[(2-tert-butoxycarbonylamino-ethyl)-(4'-trifluoromethyl-biphenyl-4-carbonyl)-amino]-propionic acid |

TABLE 1-continued

| Example | Structure | Name |
|---|---|---|
| 635 | 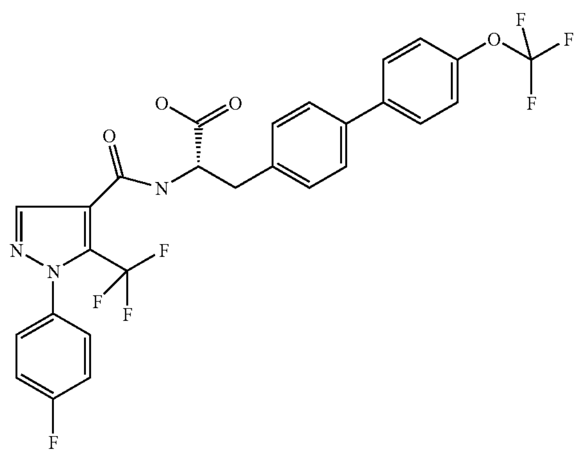 | 2-{[1-(4-Fluoro-phenyl)-5-trifluoromethyl-1H-pyrazole-4-carbonyl]-amino}-3-(4'-trifluoromethoxy-biphenyl-4-yl)-propionic acid |
| 636 | 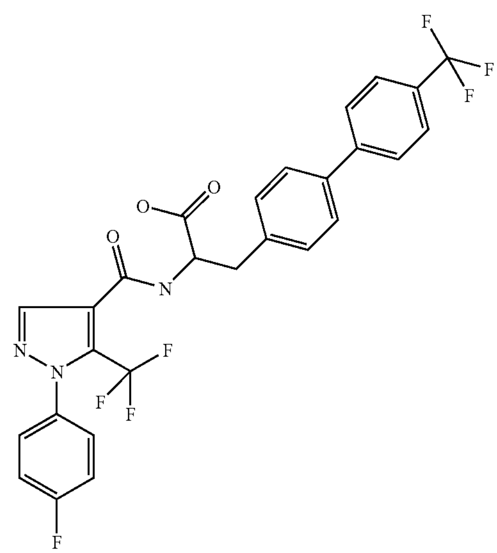 | 2-{[1-(4-Fluoro-phenyl)-5-trifluoromethyl-1H-pyrazole-4-carbonyl]-amino}-3-(4'-trifluoromethyl-biphenyl-4-yl)-propionic acid |
| 637 | 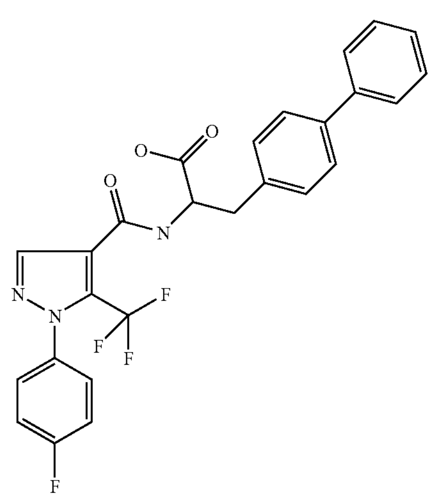 | 3-Biphenyl-4-yl-2-{[1-(4-fluoro-phenyl)-5-trifluoromethyl-1H-pyrazole-4-carbonyl]-amino}-propionic acid |

TABLE 1-continued

| Example | Structure | Name |
|---|---|---|
| 638 | 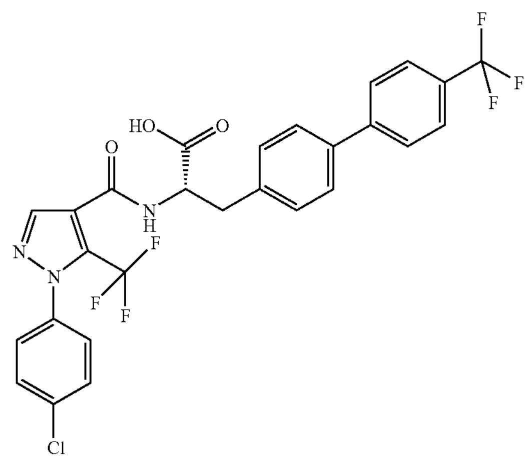 | (2S)-{[1-(4-Chloro-phenyl)-5-trifluoromethyl-1H-pyrazole-4-carbonyl]-amino}-3-(4'-trifluoromethyl-biphenyl-4-yl)-propionic acid |
| 639 | 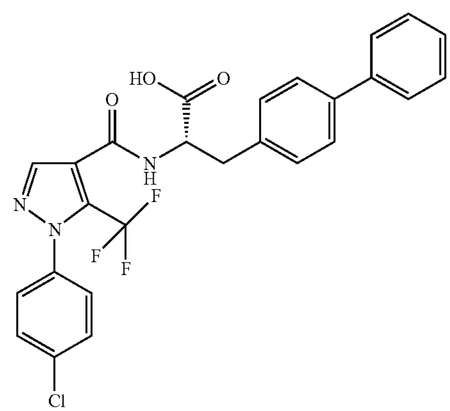 | 3-Biphenyl-4-yl-(2S)-{[1-(4-chloro-phenyl)-5-trifluoromethyl-1H-pyrazole-4-carbonyl]-amino}-propionic acid |
| 640 | 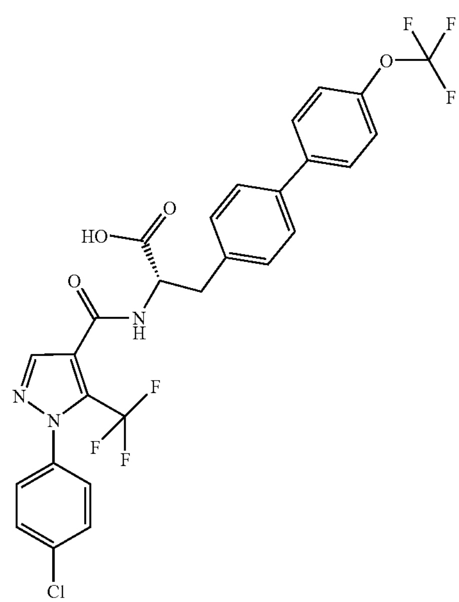 | (2S)-{[1-(4-Chloro-phenyl)-5-trifluoromethyl-1H-pyrazole-4-carbonyl]-amino}-3-(4'-trifluoromethoxy-biphenyl-4-yl)-propionic acid |

TABLE 1-continued

| Example | Structure | Name |
|---|---|---|
| 641 | 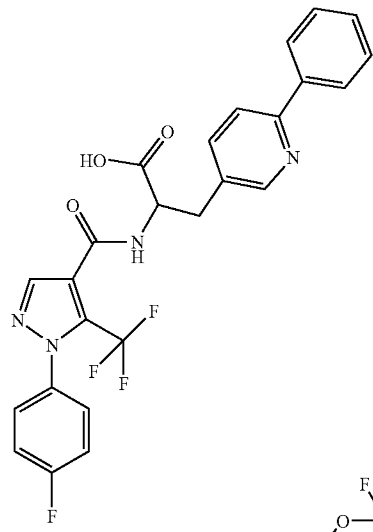 | 2-{[1-(4-Fluoro-phenyl)-5-trifluoromethyl-1H-pyrazole-4-carbonyl]-amino}-3-(6-phenyl-pyridin-3-yl)-propionic acid |
| 642 | 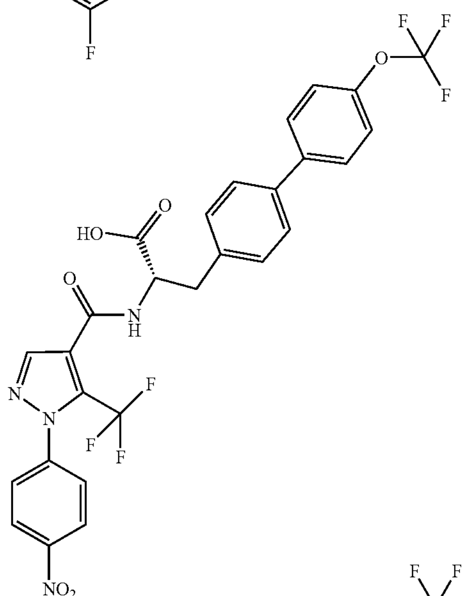 | (2S)-{[1-(4-Nitro-phenyl)-5-trifluoromethyl-1H-pyrazole-4-carbonyl]-amino}-3-(4'-trifluoromethoxy-biphenyl-4-yl)-propionic acid |
| 643 | 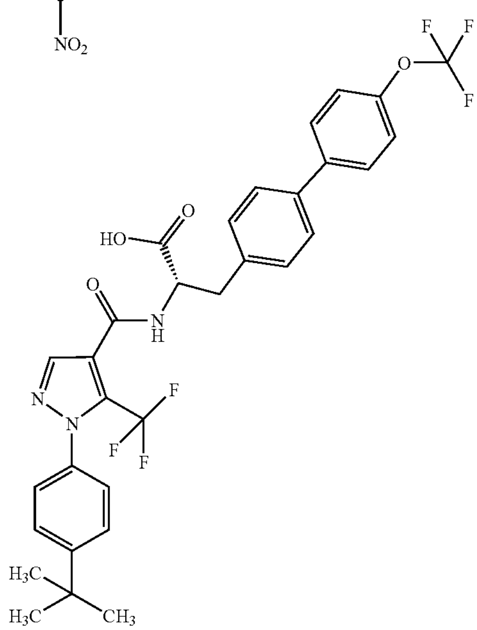 | (2S)-{[1-(4-tert-Butyl-phenyl)-5-trifluoromethyl-1H-pyrazole-4-carbonyl]-amino}-3-(4'-trifluoromethoxy-biphenyl-4-yl)-propionic acid |

TABLE 1-continued

| Example | Structure | Name |
|---|---|---|
| 644 | 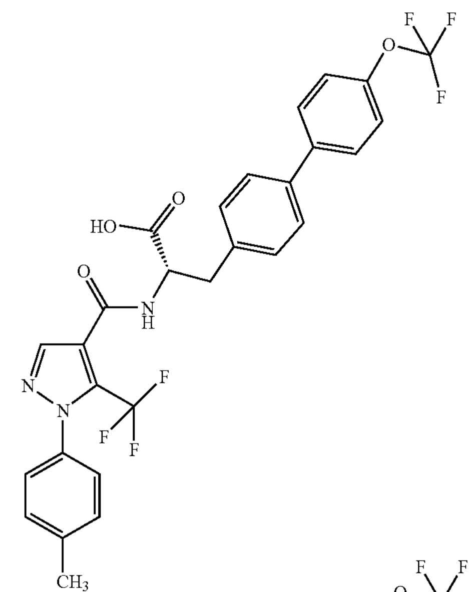 | (2S)-[(1-p-Tolyl-5-trifluoromethyl-1H-pyrazole-4-carbonyl)-amino]-3-(4'-trifluoromethoxy-biphenyl-4-yl)-propionic acid |
| 645 | 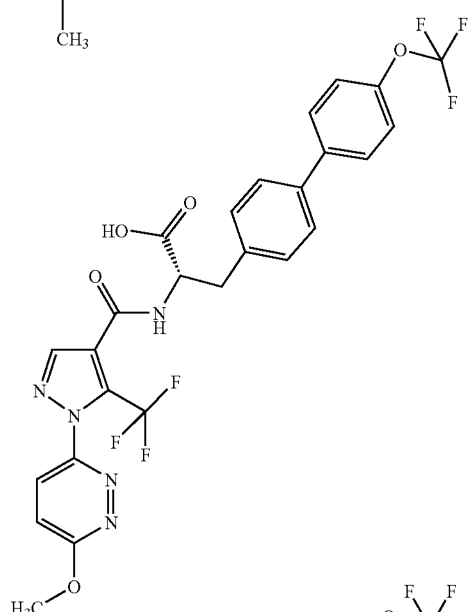 | (2S)-{[1-(6-Methoxy-pyridazin-3-yl)-5-trifluoromethyl-1H-pyrazole-4-carbonyl]-amino}-3-(4'-trifluoromethoxy-biphenyl-4-yl)-propionic acid |
| 646 | 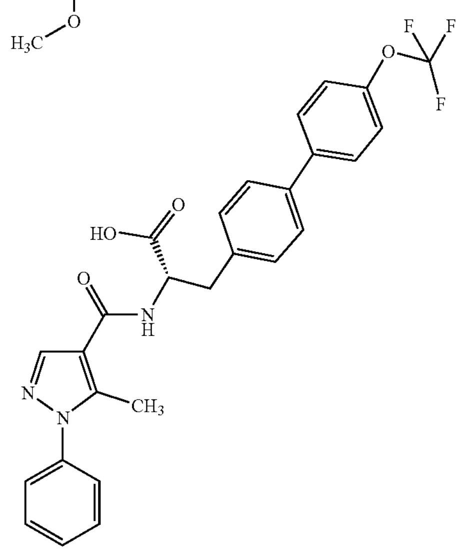 | (2S)-[(5-Methyl-1-phenyl-1H-pyrazole-4-carbonyl)-amino]-3-(4'-trifluoromethoxy-biphenyl-4-yl)-propionic acid |

TABLE 1-continued

| Example | Structure | Name |
|---|---|---|
| 647 | 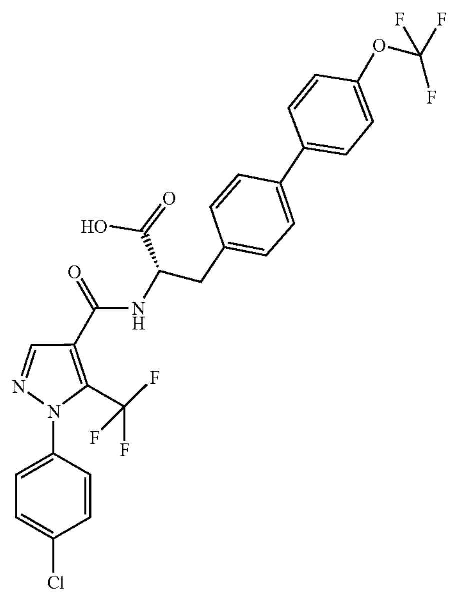 | (2S)-{[1-(4-Chloro-phenyl)-5-trifluoromethyl-1H-pyrazole-4-carbonyl]-amino}-3-(4'-trifluoromethoxy-biphenyl-4-yl)-propionic acid |
| 648 | 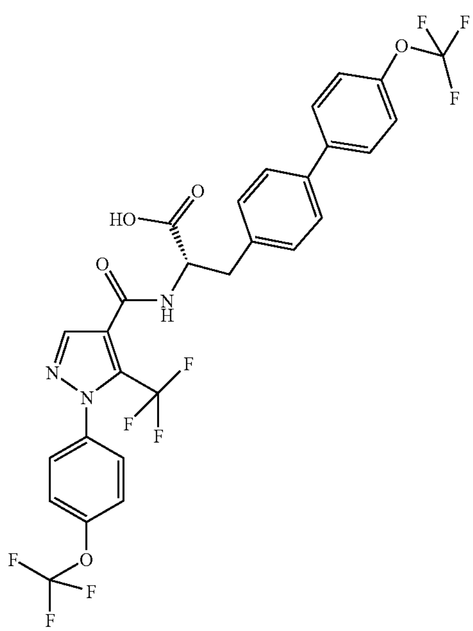 | 3-(4'-Trifluoromethoxy-biphenyl-4-yl)-(2S)-{[1-(4-trifluoromethoxy-phenyl)-5-trifluoromethyl-1H-pyrazole-4-carbonyl]-amino}-propionic acid |

TABLE 1-continued

| Example | Structure | Name |
|---|---|---|
| 649 | 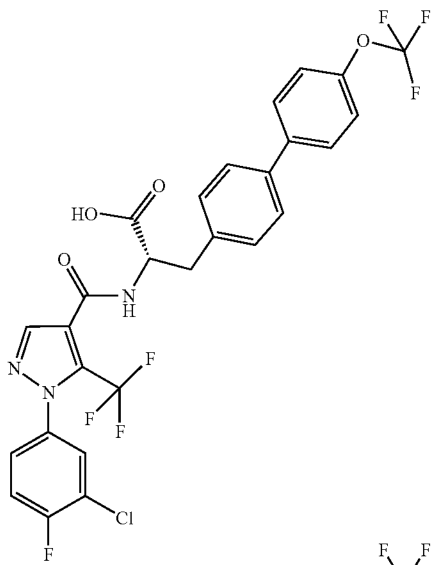 | (2S)-{[1-(3-Chloro-4-fluoro-phenyl)-5-trifluoromethyl-1H-pyrazole-4-carbonyl]-amino}-3-(4'-trifluoromethoxy-biphenyl-4-yl)-propionic acid |
| 650 | 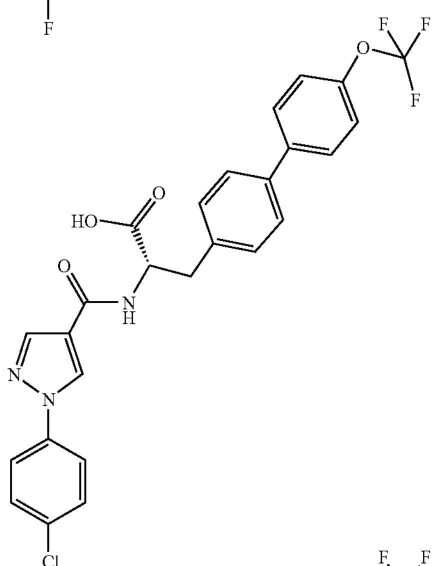 | (2S)-{[1-(4-Chloro-phenyl)-1H-pyrazole-4-carbonyl]-amino}-3-(4'-trifluoromethoxy-biphenyl-4-yl)-propionic acid |
| 651 | 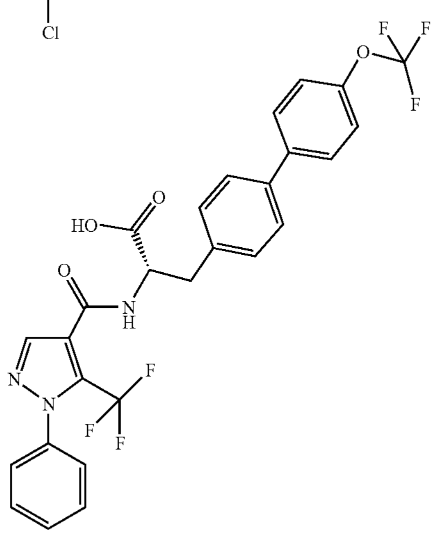 | (2S)-[(1-Phenyl-5-trifluoromethyl-1H-pyrazole-4-carbonyl)-amino]-3-(4'-trifluoromethoxy-biphenyl-4-yl)-propionic acid |

TABLE 1-continued

| Example | Structure | Name |
|---|---|---|
| 652 | 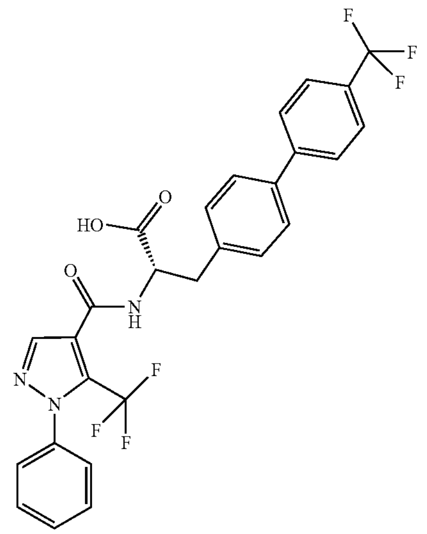 | (2S)-[(1-Phenyl-5-trifluoromethyl-1H-pyrazole-4-carbonyl)-amino]-3-(4'-trifluoromethyl-biphenyl-4-yl)-propionic acid |
| 653 | 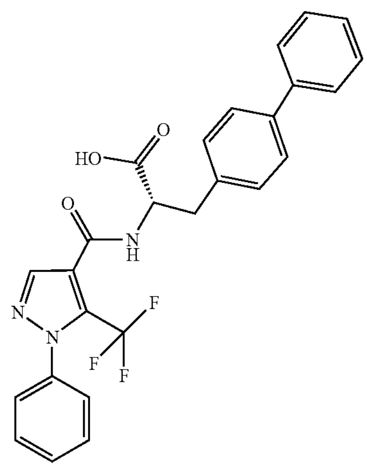 | 3-Biphenyl-4-yl-(2S)-[(1-phenyl-5-trifluoromethyl-1H-pyrazole-4-carbonyl)-amino]-propionic acid |
| 654 | 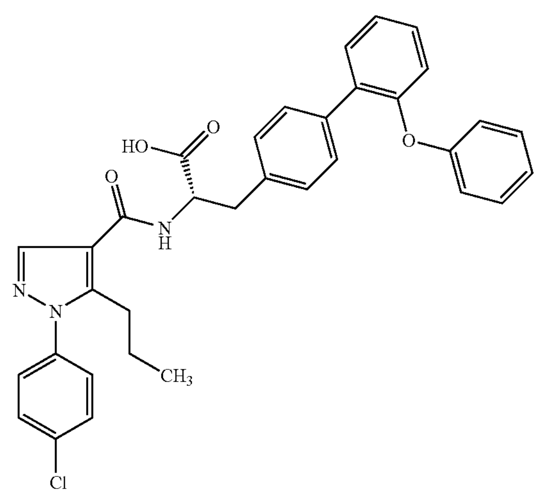 | (2S)-{[1-(4-Chloro-phenyl)-5-propyl-1H-pyrazole-4-carbonyl]-amino}-3-(2'-phenoxy-biphenyl-4-yl)-propionic acid |

TABLE 1-continued

| Example | Structure | Name |
|---|---|---|
| 655 | 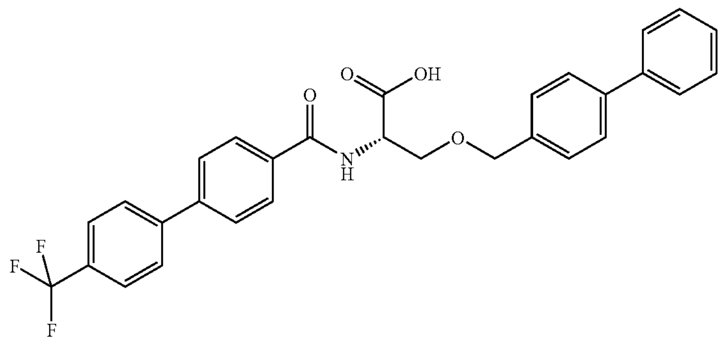 | 3-(Biphenyl-4-ylmethoxy)-(2S)-[(4'-trifluoromethyl-biphenyl-4-carbonyl)-amino]-propionic acid |
| 656 | 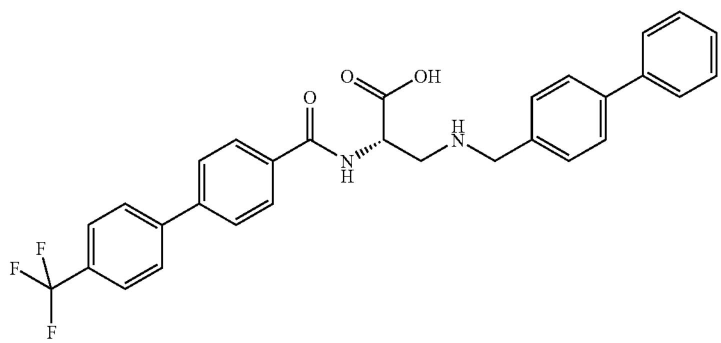 | 3-[(Biphenyl-4-ylmethyl)-amino]-(2S)-[(4'-trifluoromethyl-biphenyl-4-carbonyl)-amino]-propionic acid. |
| 657 | 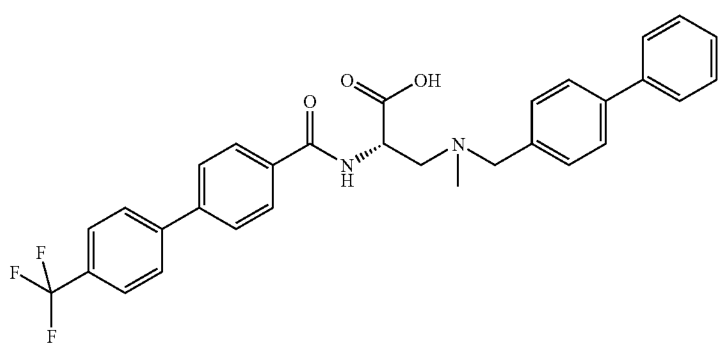 | 3-(Biphenyl-4-ylmethyl-methyl-amino)-(2S)-[(4'-trifluoromethyl-biphenyl-4-carbonyl)-amino]-propionic acid: |
| 658 | 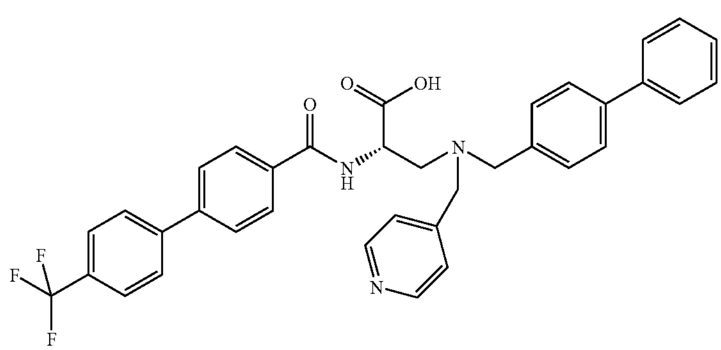 | 3-(Biphenyl-4-ylmethyl-pyridin-4-ylmethyl-amino)-(2S)-[(4'-trifluoromethyl-biphenyl-4-carbonyl)-amino]-propionic acid: |

TABLE 1-continued

| Example | Structure | Name |
|---|---|---|
| 659 | 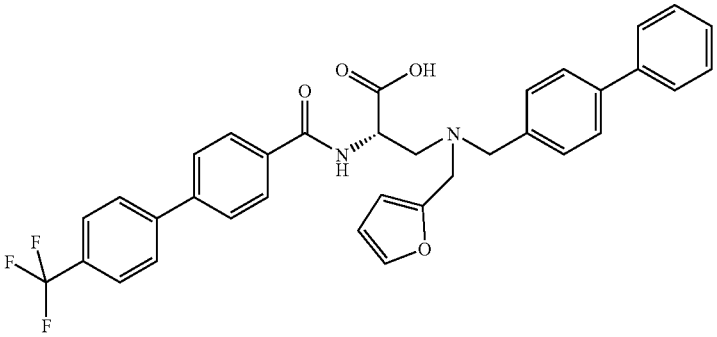 | 3-(Biphenyl-4-ylmethyl-furan-2-ylmethyl-amino)-(2S)-[(4'-trifluoromethyl-biphenyl-4-carbonyl)-amino]-propionic acid: |
| 660 | 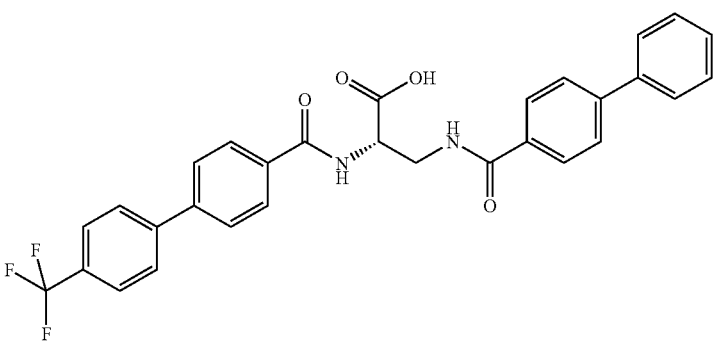 | 3-(Biphenyl-4-carbonyl)-amino]-(2S)-[(4'-trifluoromethyl-biphenyl-4-carbonyl)-amino]-propionic acid: |
| 661 | 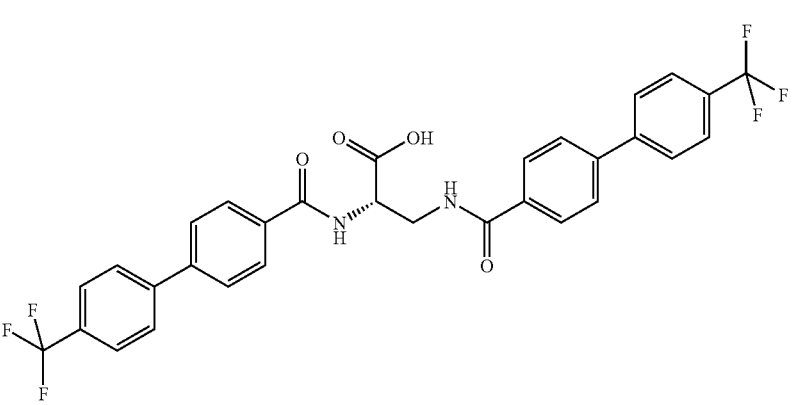 | (2S), 3-Bis-[(4'-trifluoromethyl-biphenyl-4-carbonyl)-amino]- propionic acid: |
| 662 | 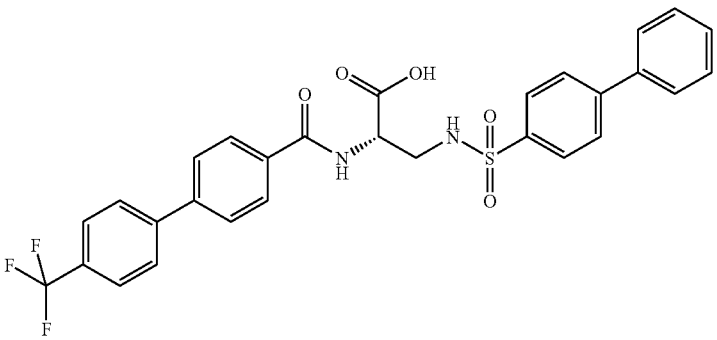 | 3-(Biphenyl-4-sulfonylamino)-(2S)-[(4'-trifluoromethyl-biphenyl-4-carbonyl)-amino]-propionic acid: |

In another aspect, the present invention comprises a pharmaceutical composition comprising the compound of Formula (I) and one or more pharmaceutically acceptable carriers, excipients, or diluents.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or $S(O)_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or $S(O)_2$ atoms. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or $S(O)_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or $S(O)_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or $S(O)_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or $S(O)_2$ atoms. Examples of "alkynylene" as used herein include, but are not limited to, ethyne-1,2-diyl, propyne-1,3-diyl, and the like.

As used herein, "cycloalkyl" refers to a alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" refers to a three to twelve-membered heterocyclic ring optionally possessing one or more degrees of unsaturation, containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-dyil, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, di(lower alkyl) aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, di(lower alkyl) aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

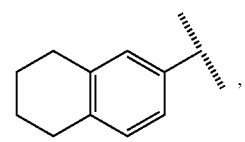

and the like.

As used herein, the term "fused cycloalkylarylene" refers to a fused cycloalkylaryl, wherein the aryl group is divalent. Examples include

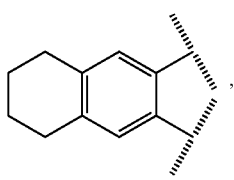

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

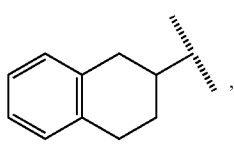

and the like.

As used herein, the term "fused arylcycloalkylene" refers to a fused arylcycloalkyl, wherein the cycloalkyl group is divalent. Examples include

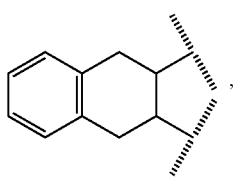

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

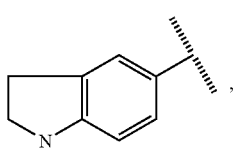

and the like

As used herein, the term "fused heterocyclylarylene" refers to a fused heterocyclylaryl, wherein the aryl group is divalent. Examples include

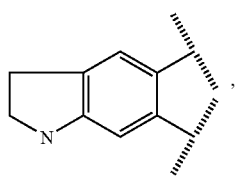

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

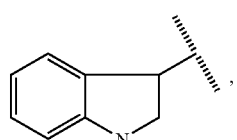

and the like.

As used herein, the term "fused arylheterocyclylene" refers to a fused arylheterocyclyl, wherein the heterocyclyl group is divalent. Examples include

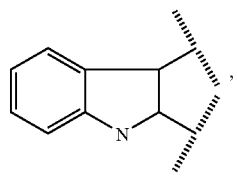

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

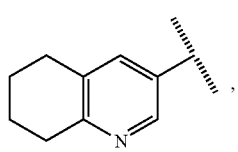

and the like.

As used herein, the term "fused cycloalkylheteroarylene" refers to a fused cycloalkylheteroaryl, wherein the heteroaryl group is divalent. Examples include

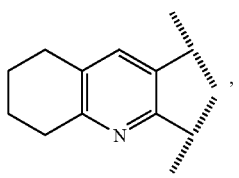

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

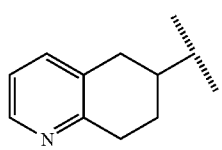

and the like.

As used herein, the term "fused heteroarylcycloalkylene" refers to a fused heteroarylcycloalkyl, wherein the cycloalkyl group is divalent. Examples include

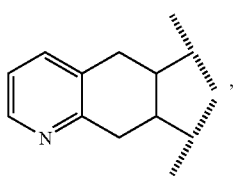

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

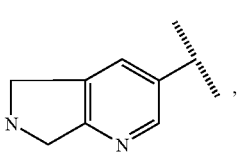

and the like.

As used herein, the term "fused heterocyclylheteroarylene" refers to a fused heterocyclylheteroaryl, wherein the heteroaryl group is divalent. Examples include

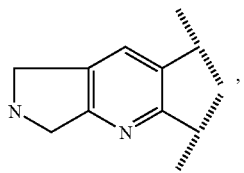

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroarylheterocyclyl" used herein include -5-aza-2,3-dihydrobenzofuran-2-yl,

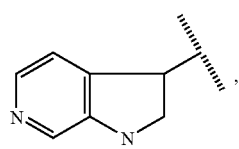

and the like.

As used herein, the term "fused heteroarylheterocyclylene" refers to a fused heteroarylheterocyclyl, wherein the heterocyclyl group is divalent. Examples include

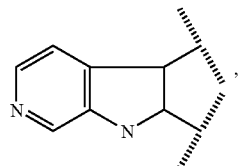

and the like.

As used herein, the term "acid isostere" refers to a substituent group which will ionize at physiological pH to bear a net negative charge. Examples of such "acid isosteres" include but are not limited to heteroaryl groups such as but not limited to isoxazol-3-ol-5-yl, 1H-tetrazole-5-yl, or 2H-tetrazole-5-yl. Such acid isosteres include but are not limited to heterocyclyl groups such as but not limited to imidazolidine-2,4-dione-5-yl, imidazolidine-2,4-dione-1-yl, 1,3-thiazolidine-2,4-dione-5-yl, or 5-hydroxy-4H-pyran-4-on-2-yl.

As used herein, the term "direct bond", where part of a structural variable specification, refers to the direct joining of the substituents flanking (preceding and succeeding) the variable taken as a "direct bond".

As used herein, the term "alkoxy" refers to the group $R_aO$—, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS-$, where $R_a$ is alkynyl.

As used herein, the term "alkylsulfenyl" refers to the group $R_aS(O)-$, where $R_a$ is alkyl.

As used herein, the term "alkenylsulfenyl" refers to the group $R_aS(O)-$, where $R_a$ is alkenyl.

As used herein, the term "alkynylsulfenyl" refers to the group $R_aS(O)-$, where $R_a$ is alkynyl.

As used herein, the term "alkylsulfonyl" refers to the group $R_aSO_2-$, where $R_a$ is alkyl.

As used herein, the term "alkenylsulfonyl" refers to the group $R_aSO_2-$, where $R_a$ is alkenyl.

As used herein, the term "alkynylsulfonyl" refers to the group $R_aSO_2-$, where $R_a$ is alkynyl.

As used herein, the term "acyl" refers to the group $R_aC(O)-$, where $R_a$ is alkyl, alkenyl, alkynyl, cycloalkyl, cycloalkenyl, or heterocyclyl.

As used herein, the term "aroyl" refers to the group $R_aC(O)-$, where $R_a$ is aryl.

As used herein, the term "heteroaroyl" refers to the group $R_aC(O)-$, where $R_a$ is heteroaryl.

As used herein, the term "alkoxycarbonyl" refers to the group $R_aOC(O)-$, where $R_a$ is alkyl.

As used herein, the term "acyloxy" refers to the group $R_aC(O)O-$, where $R_a$ is alkyl, alkenyl, alkynyl, cycloalkyl, cycloalkenyl, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, $-CH_2-O-CH_2-$, $-CH_2-SO_2-CH_2-$, $-CH_2-NH-CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent $=O$.

As used herein, the term "halogen" or "halo" shall include iodine, bromine, chlorine and fluorine.

As used herein, the term "mercapto" shall refer to the substituent $-SH$.

As used herein, the term "carboxy" shall refer to the substituent $-COOH$.

As used herein, the term "cyano" shall refer to the substituent $-CN$.

As used herein, the term "aminosulfonyl" shall refer to the substituent $-SO_2NH_2$.

As used herein, the term "carbamoyl" shall refer to the substituent $-C(O)NH_2$.

As used herein, the term "sulfanyl" shall refer to the substituent $-S-$.

As used herein, the term "sulfenyl" shall refer to the substituent $-S(O)-$.

As used herein, the term "sulfonyl" shall refer to the substituent $-S(O)_2-$.

The compounds can be prepared readily according to the following reaction Schemes (in which variables are as defined before or are defined) using readily available starting materials, reagents and conventional synthesis procedures. In these reactions, it is also possible to make use of variants which are themselves known to those of ordinary skill in this art, but are not mentioned in greater detail.

The present invention also provides a method for the synthesis of compounds useful as intermediates in the preparation of compounds of Formula (I) along with methods for the preparation of compounds of Formula (I).

Scheme I describes the synthesis of an intermediate of structure (4).

$Ar_3$ and $Ar_4$ are, independently, groups such as, but not limited to, a heteroaryl, heteroarylene, arylene, or aryl ring system.

As shown in Scheme I, in one embodiment, bromo- or iodo-substituted aryl alanine methyl ester (or amino acid esterified in linkage to Wang resin) (1) is treated with a carboxylic acid in the presence of a coupling reagent, such as, but not limited to, diisopropyl carbodiimide (DIC) to form the amide (2). The resulting amide is then subjected to coupling with an arylboronic acid in the presence of a catalyst such as but not limited to tetrakis(triphenylphosphine)palladium (0), in the presence of base such as, but not limited to, sodium carbonate to form compound (3). The methyl ester (3) is hydrolyzed using a base such as, but not limited to, LiOH to provide the free carboxylic acid (4), where $Ar_1$ and $Ar_2$ are as defined for Formula (I).

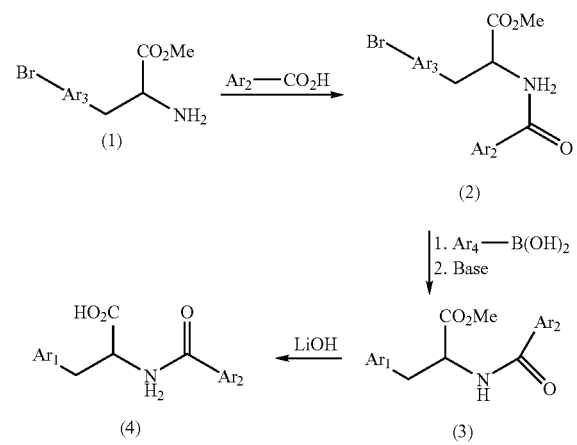

Scheme I

Scheme II describes the preparation of a compound of structure (4).

$Ar_3$ and $Ar_4$ are, independently, groups such as but not limited to a heteroaryl, heteroarylene, arylene, or aryl ring system.

As shown in Scheme II, in another embodiment, an aryl hydroxy amino acid methyl ester (or amino acid esterified in linkage to Wang resin) (5) is treated with a carboxylic acid $Ar_2$—$CO_2H$ in the presence of a coupling reagent such as, but not limited to, diisopropyl carbodiimide (DIC) to form the amide (6). The resulting amide is then subjected to: 1) nucleophilic substitutions with an optionally substituted electron-deficient fluoroaromatic or fluoroheteroaromatic in the presence of base such as, but not limited to, potassium carbonate; or 2) coupling with an aryl bromide, or heteroaryl bromide, and copper iodide in the presence of a base including, but not limited to, cesium carbonate to form compound (7). The methyl ester in (7) is hydrolyzed using a base such as LiOH to provide the free carboxylic acid (4), where $Ar_1$ and $Ar_2$ are as defined for Formula (I)

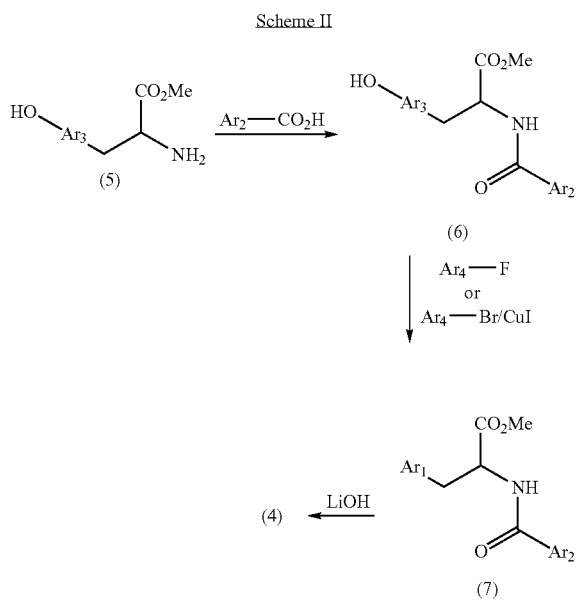

Scheme III describes the preparation of a compound of formula (4).

$Ar_5$ and $Ar_6$ are, independently, groups such as but not limited to a heteroaryl, heteroarylene, arylene, or aryl ring system.

As shown in Scheme III, in another embodiment, an amino acid methyl ester (or, alternately, an amino acid esterified in linkage to Wang resin) (8) is treated with a bromo-substituted aryl carboxylic acid in the presence of a coupling reagent such as, but not limited to, diisopropyl carbodiimide (DIC) to form the amide (9). The resulting amide then is subjected to coupling with an arylboronic acid or heteroarylboronic acid in the presence of a catalyst such as but not limited to tetrakis(triphenylphosphine)palladium (0), in the presence of base such as, but not limited to, sodium carbonate to form compound (10). The methyl ester (10) is hydrolyzed using a base such as, but not limited to, LiOH to provide the free carboxylic acid (4), where $Ar_1$ and $Ar_2$ are as defined for Formula (I)

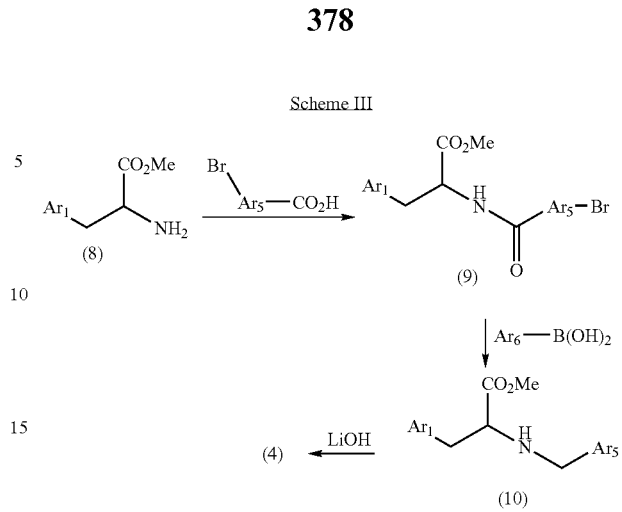

Scheme IV describes the synthesis of a compound of formula (4).

$Ar_3$, $Ar_7$, $Ar_5$ and $Ar_6$ are, independently, groups such as but not limited to a heteroaryl, heteroarylene, arylene, or aryl ring system.

As shown in Scheme IV, in another embodiment, a bromo or iodo aryl alanine methyl ester (or amino acid esterified in linkage to Wang resin) (11) is subjected to coupling with an arylboronic acid in the presence of a catalyst such as but not limited to tetrakis(triphenylphosphine)palladium(0), in the presence of base such as but not limited to sodium carbonate to form compound (12). The resulting compound is treated with a bromo- or iodo-substituted aryl carboxylic acid in the presence of a coupling reagent such as, but not limited to, diisopropyl carbodiimide (DIC) to form the amide (13). The resulting amide is then subjected to coupling with a arylboronic acid or heteroarylboronic acid in the presence of a catalyst such as but not limited to tetrakis(triphenylphosphine)plladium(0), in the presence of base such as, but not limited to, sodium carbonate, and the product methyl ester is hydrolyzed using a base such as LiOH to provide the free carboxylic acid (4), where $Ar_1$ and $Ar_2$ are as defined for Formula (I).

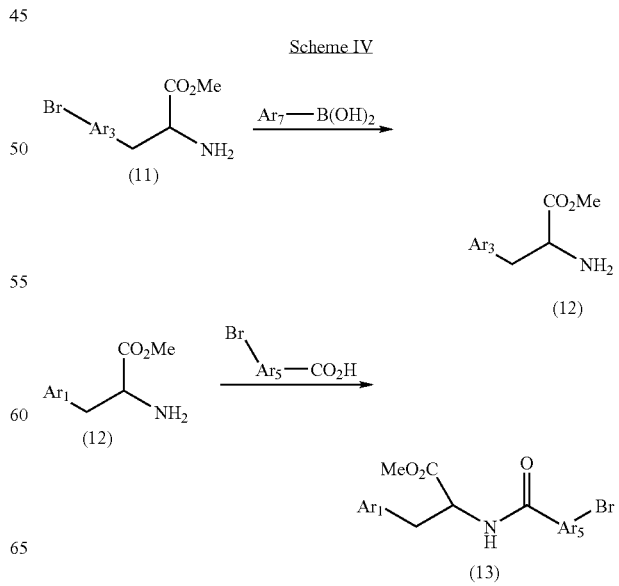

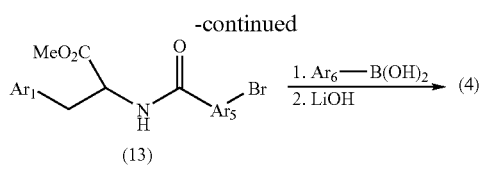

(13)

Scheme V describes the preparation of a compound of formula (16).

Ar$_3$ and Ar$_7$ are, independently, groups such as but not limited to a heteroaryl, heteroarylene, arylene, or aryl ring system.

Pol is a functionalized polymeric support, such as but not limited to Wang Resin.

As shown in Scheme V, in another embodiment, a hydroxy aryl ester loaded onto the Wang Bromo resin or Merrifield resin using base such as, but not limited to, sodium methoxide in DMA, and hydrolyzed to give (14), is coupled with a bromo- or iodo-substituted aryl amino acid methyl ester (11) in the presence of a coupling reagent such as, but not limited to, diisopropyl carbodiimide (DIC) to give the amide (15). The resulting amide (15) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate followed by cleavage from the resin with TMSBr/TFA/DCM (1:1:1) or a similar suitable cleavage cocktail to yield the desired product (16), where Ar$_1$ and Ar$_2$ are as defined for Formula (I)

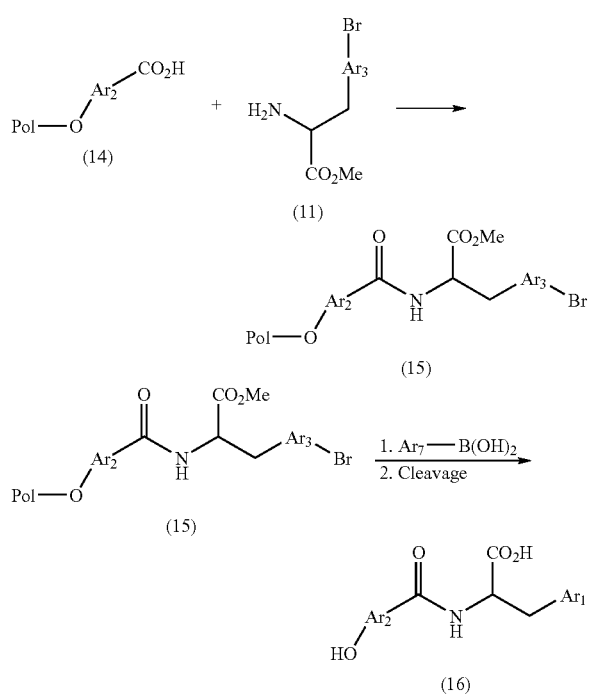

Scheme VI describes the preparation of a compound of formula (19).

Ar$_6$ and Ar$_8$ are, independently, groups such as but not limited to a heteroaryl, heteroarylene, arylene, or aryl ring system.

Pol is a functionalized polymeric support, such as but not limited to Wang Resin.

As shown in Scheme VI, in another embodiment, a hydroxy aryl ester loaded onto the Wang Bromo resin, Merrifiend resin, or other suitable support using base such as, but not limited to, sodium methoxide in DMA, is hydrolyzed to give (17), and is coupled with an amino acid methyl ester (8) in the presence of a coupling reagent such as, but not limited to, diisopropyl carbodiimide (DIC) to give the amide (18). The resulting amide (18) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate, and is then cleaved from the resin with TMSBr/TFA/DCM (1:1:1) or a similar suitable cleavage cocktail to yield the desired product (19), where Ar$_1$ and Ar$_2$ are as defined for Formula (I).

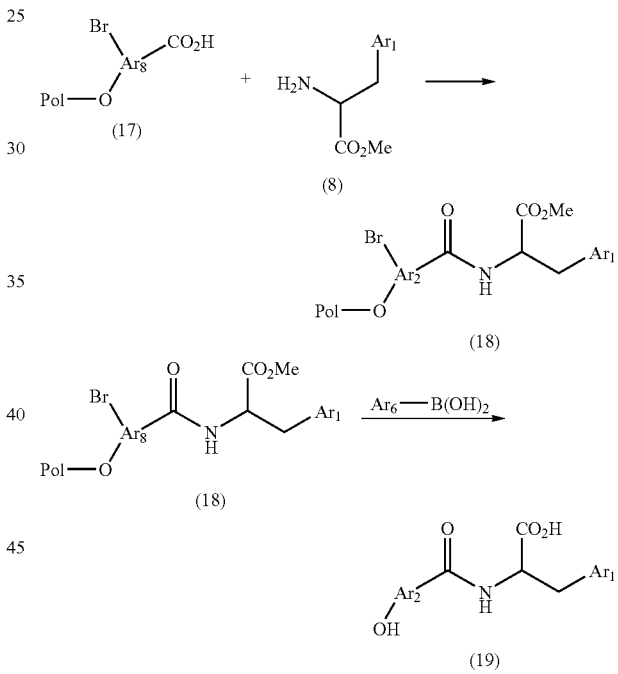

Scheme VII describes the synthesis of a compound of formula (23).

Ar$_3$, Ar$_7$, and Ar$_6$ are, independently, groups such as but not limited to a heteroaryl, heteroarylene, arylene, or aryl ring system.

Pol is a functionalized polymeric support, such as but not limited to Wang Resin.

As shown in Scheme VII, in another embodiment, a bromo hydroxy aryl ester (20) loaded onto Wang Bromo resin, Merrifield resin, or other suitable support using base such as, but not limited to, sodium methoxide in DMF, is then subjected to a coupling with an arylboronic acid or heteroarylboronic acid in the presence of a catalyst such as but not limited to tetrakis(triphenylphosphine)plladium(0), in the presence of base such as, but not limited to, sodium carbonate, followed by hydrolysis of the product ester to yield the acid (21). The resulting carboxylic acid (21) is then subjected to coupling with a bromo- or iodo-substituted aryl amino acid methyl ester (11) in the presence of a coupling reagent such as, but not limited to, diisopropyl carbodiimide (DIC) to give the amide (22). The resulting amide (22) is then subjected to a coupling with an arylboronic acid or heteroaryl boronic acid in the presence of a catalyst such as but not limited to tetrakis(triphenylphosphine)plladium(0), in the presence of base such as, but not limited to, sodium carbonate followed by cleavage from the resin with TMSBr/TFA/DCM (1:1:1) or a similar cleavage cocktail to yield the desired product (23), where $Ar_1$ and $Ar_2$ are as defined for Formula (I).

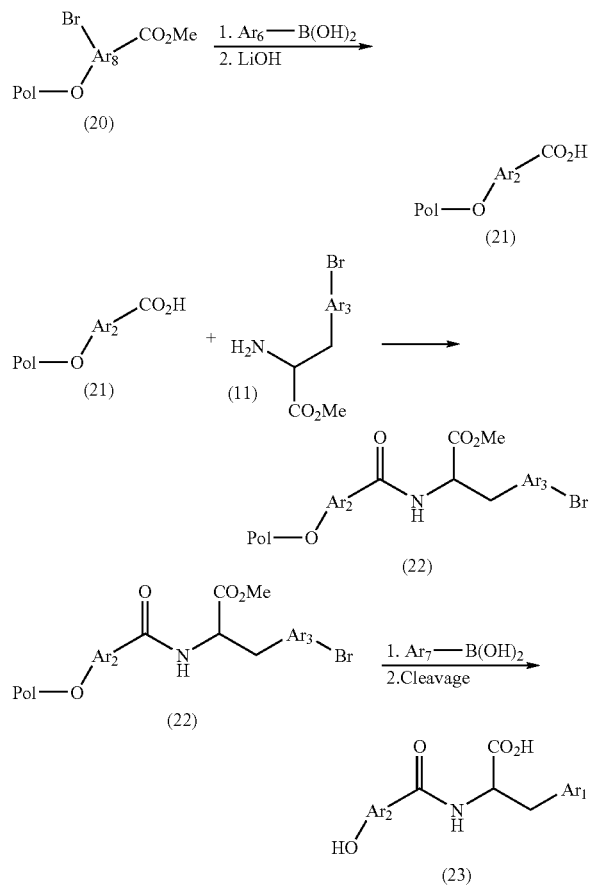

Scheme VIII describes the preparation of a compound of formula (29).

$Ar_7$, $Ar_9$, $Ar_{10}$, and $Ar_{11}$ are, independently, groups such as but not limited to a heteroaryl, heteroarylene, arylene, or aryl ring system.

As shown in Scheme VIII, in another embodiment, a fluoro nitro phenol (24) loaded onto a polymer such as Wang Bromo resin using base such as, but not limited to, sodium methoxide in DMA, is then treated with a hydroxy aryl compound (25) in the presence of base, followed by reduction of the nitro group to give the free amine (26). The resulting amine (26) is then subjected to coupling with a bromo- or iodo-substituted aryl acid (27) in the presence of a coupling reagent such as, but not limited to, diisopropyl carbodiimide (DIC) to give the amide (28). The resulting amide (28) is then subjected to a coupling with an arylboronic acid or heteroarylboronic acid in the presence of a catalyst such as but not limited to tetrakis(triphenylphosphine)palladium(0), in the presence of base such as, but not limited to, sodium carbonate followed by cleavage from the resin with TMSBr/TFA/DCM (1:1:1) or a similar suitable cleavage cocktail to yield the desired product (29), where $Ar_1$ and $Ar_2$ are as defined for Formula (I).

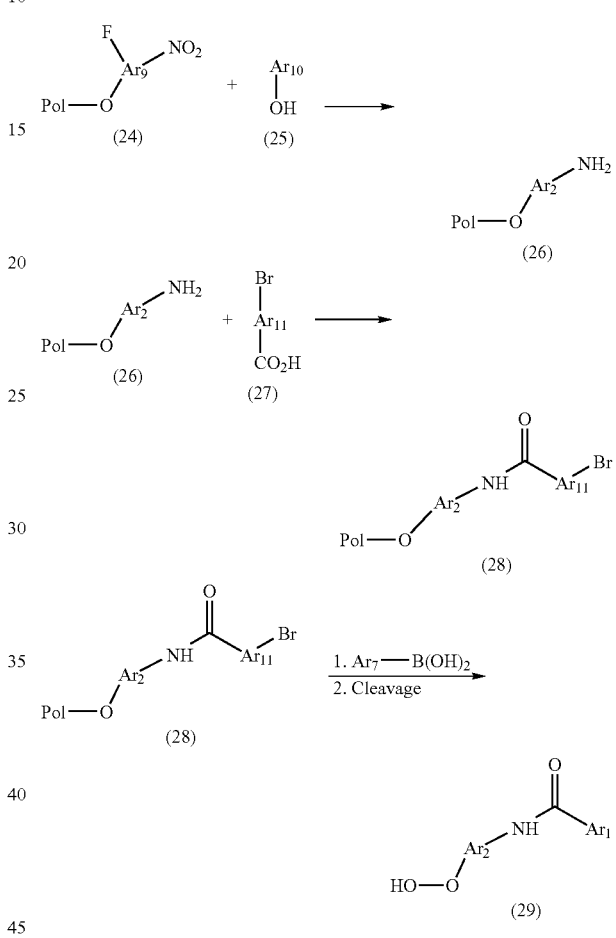

Scheme IX describes the preparation of a compound of formula (32).

$Ar_6$, $Ar_{12}$, and $Ar_{13}$ are, independently, groups such as but not limited to a heteroaryl, heteroarylene, arylene, or aryl ring system.

$PG_1$ is an amino protecting group such as allyloxycarbonyl or tert-butoxycarbonyl.

As shown in Scheme IX, In another embodiment, an aryl amino acid methyl ester (8) is reacted with an iodo-substituted aryl amino carboxylic acid (the amino group of which may be protected with an amino protecting group $PG_1$) in the presence of a coupling reagent such as, but not limited to, diisopropyl carbodiimide (DIC) giving the amide (30). The amino group of the amide (30) may be then deprotected, if desired, by treatment with, in the case of $PG_1$ as tert-butoxycarbonyl, TFA, and is then treated with an aroyl chloride in the presence of a base such as pyridine or TEA to give the iodo amide (31). The amide (31) is subjected to coupling with an arylboronic acid or heteroaryl boronic acid in the presence of a catalyst such as but not limited to tetrakis(triphenylphosphine)palladium(0), in the presence of base such as, but not limited to, sodium carbonate. Hydrolysis of the product methyl ester with an alkaline reagent such as LiOH provides compound (32), where $Ar_1$ and $Ar_2$ are as defined for Formula (I).

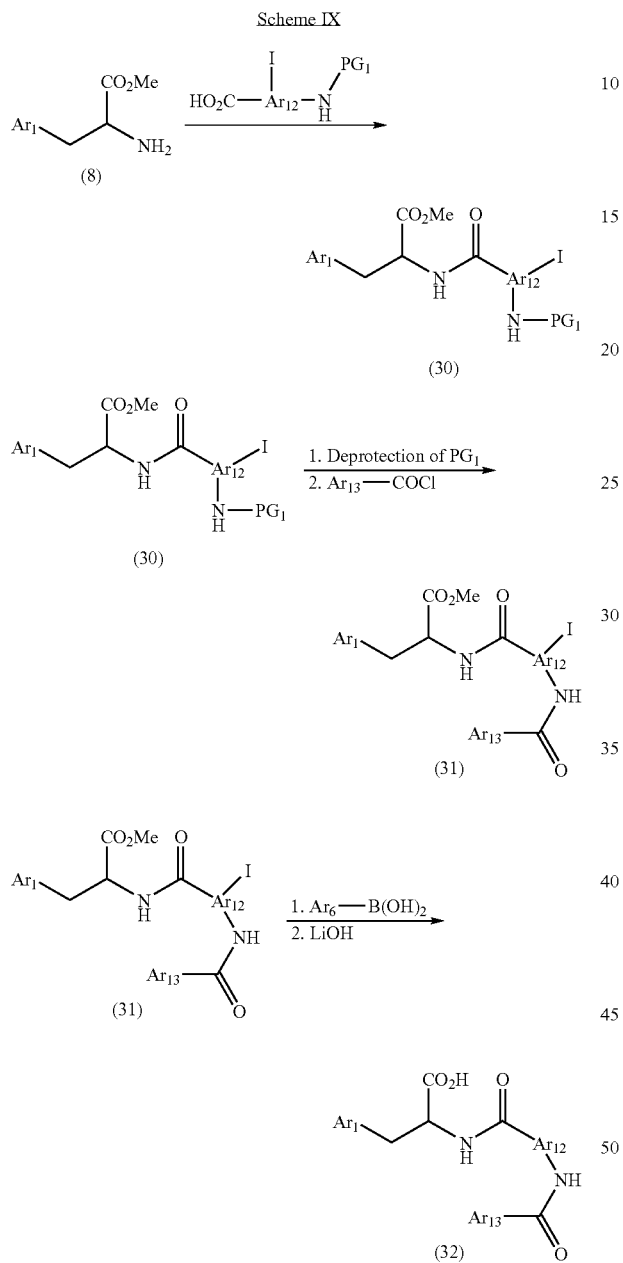

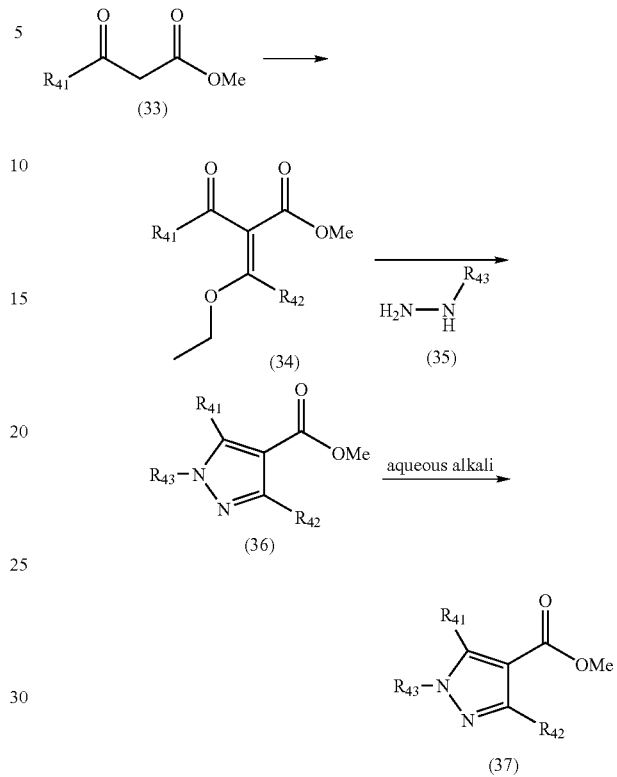

In Scheme X, in another embodiment, a beta ketoester (33) may be treated with a reagent such as triethyl orthoformate of triethyl orthoacetate in the presence of acetic anhydride and heat to afford the ethoxy olefin derivative (34). $R_{41}$ is a group such as but not limited to aryl, heteroaryl, or alkyl. The derivative (34) may be treated with a hydrazine derivative (35) to afford the pyrazole (36). Hydrolysis of the ester of (36) with aqueous alkali and mild acidification with a weak acid such as aqueous citric acid affords (37).

In Scheme XI, in another embodiment, is described the derivitization of aniline and amine nitrogen atoms. $L_1$ is either a direct bond or a group such as an alkylene group. An amide derivative (38) may be prepared substantially in like manner as (30) and may be deprotected to afford (39). For example, where $PG_1$ is a tert-butoxycarbonyl group, treatment of (38) with TFA followed by neutralization affords (39). (39) may be treated with $R_{44}$—C(O)OH in the presence of a coupling agent such as HBTU or DCC to afford (40), or $R_{44}$—COCl in the presence of a weak base such as triethylamine, to afford (40). (39) may be treated with an aldehyde or ketone and a reducing agent such as sodium cyanoborohydroide or sodium triacetoxyborohydride to afford (42). (39) may be treated with a sulfonyl chloride $R_{44}SO_2Cl$ in the presence of a weak base such as triethylamine or pyridine to afford (43). (39) may also be treated with an activated aromatic halide such as 4-fluorobenzonitrile in the presence of a weak base such as DIEA, in a solvent such as DMF, at a temperature of from 25° C. to 120° C., to afford the product of ipso halide displacement (41). Other activated or electron-deficient heteroaryl or aryl groups may be employed in this reaction. Alternately, where $L_1$ is a direct bond, the aniline may be arylated by treatment of (39) with cuprous acetate and $Ar_{14}$—$B(OH)_2$, and a weak base such as triethylamine, in a solvent such as DCM or 1,2-dichloroethane, to afford (41).

The derivative (42) may be reductively aminated a second time in the manner described above. (42) may also be acylated or sulfenylated as described above to afford (45) and (46), respectively.

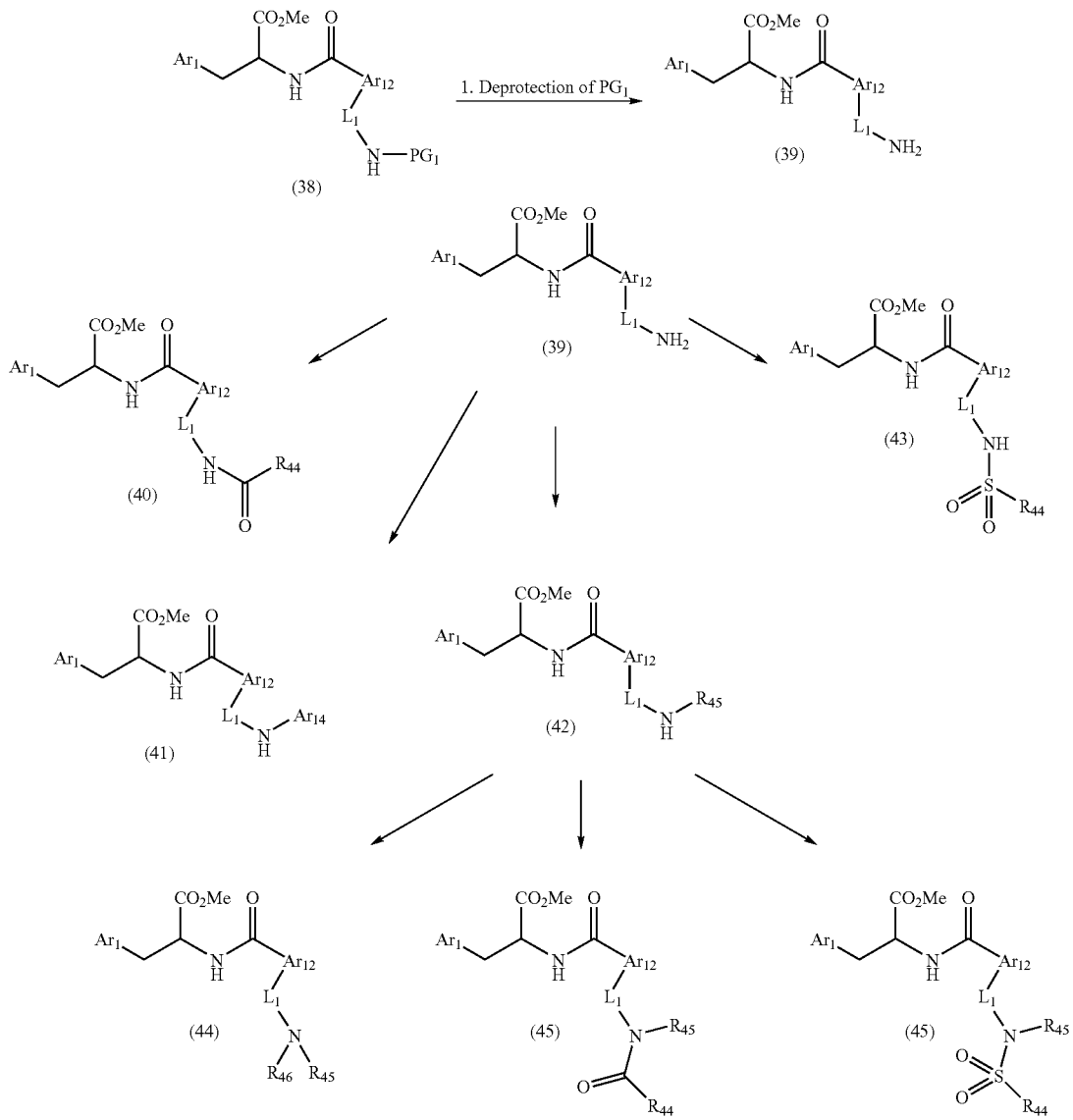

Scheme XII describes an additional embodiment. In Scheme XII, an amino ester and a protected phenolic aryl carboxylic acid or similar species are coupled as in Scheme 1. The protecting group $PG_2$ is removed, where $PG_2$ is a hydroxyl or alcohol protecting group. For example, where $PG_2$ is a tert-butyldimethylsilyl group, treatment of (49) with tetrabutylammonium fluoride in THF affords (50). (50) may be treated with a reagent such as but not limited to potassium carbonate and an alkyl halide $R_{47}$—X, where $R_{47}$ is a group such as alkyl or substituted alkyl and X is a group such as bromo or iodo, to afford (51). Alternately, where $R_{47}$ is an activated or unactivated aromatic or heteroaromatic ring system and X is fluoro, treatment of (50) with $R_{47}$—X in the presence of a base such as but not limited to potassium carbonate in a solvent such as DMF, at a temperature of 25° C. to 120° C., affords (51). Hydrolysis of the ester as described previously affords (52).

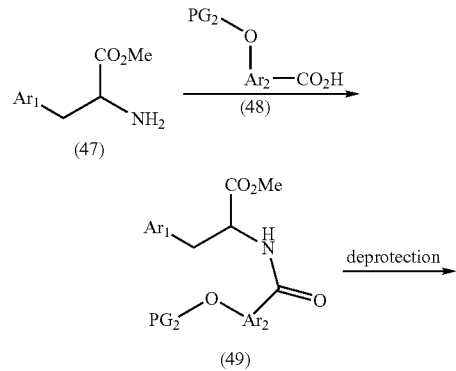

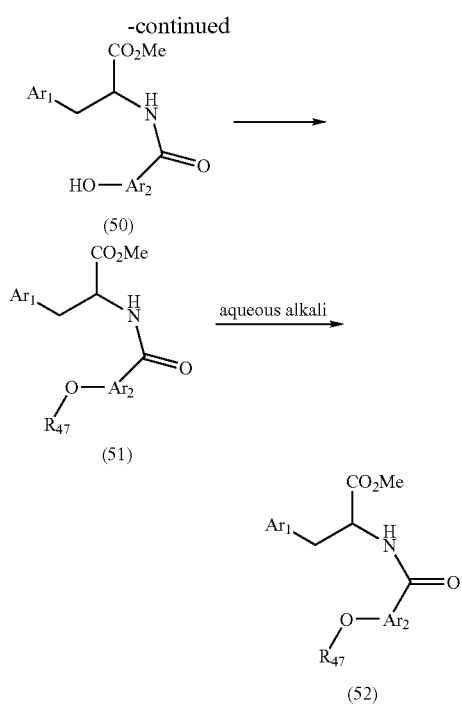

Scheme XIII describes another embodiment. $L_3$ is a group such as -alkylene-. The amino ester (53) may be coupled with a carboxylic acid as described in Scheme I to afford 54.

The protecting group $PG_3$ may be removed. Where J is NH and $PG_3$ is, for example, a tert-butoxycarbonylamino group, treatment of (54) with TFA or HCl in dioxane solvent affords the amine salt (55). Where J is O and $PG_3$ is, for example, a benzyl group, treatment of (54) with a reagent such as but not limited to palladium on carbon in a solvent such as methanol or ethanol under a hydrogen atmosphere affords (55). Where J is S and $PG_3$ is, for example, a trityl group, treatment of (54) with catalytic HCl or other acid in a solvent such as methanol under a nitrogen atmosphere affords (55). (55) where J is O or S may be alkylated with a reagent $R_{48}$—X, where $R_{48}$ is (un)substituted alkyl and X is bromo or iodo or chloro, by reacting (55) with a base such as sodium hydride in a solvent such as THF or DMF and treating the reaction mixture with $R_{48}$—X. The resulting compounds (56) and (57) may be processed on to compounds of formula (I). Additionally, (56) may be oxidized to the sulfoxide or sulfone, respectively, by treatment with one or two equivalents of an oxidizing agent such as m-chloroperbenzoic acid in a solvent such as DCM or 1,2-dichloroethane. (55) may be treated with a carboxylic acid $R_{49}$—COOH and a coupling agent such as DCC under conditions described previoulsy to afford (59), where $L_4$ is —C(O)—. Alternately, (55) may be treated with a sulfonyl chloride $R_{49}$—$SO_2Cl$ in the presence of a base such as TEA or pyridine to afford (59), where $L_4$ is —$SO_2$—. The amine (55) may be reductively aminated employing a ketone or aldehyde under conditions described previously to afford (58), and (58) may be reductively aminated with a ketone or aldehyde to afford (60). Alternately, the amine (58) may be sulfenylated or acylated as described above to afford (61), where $L_4$ is —$SO_2$— or —C(O)—.

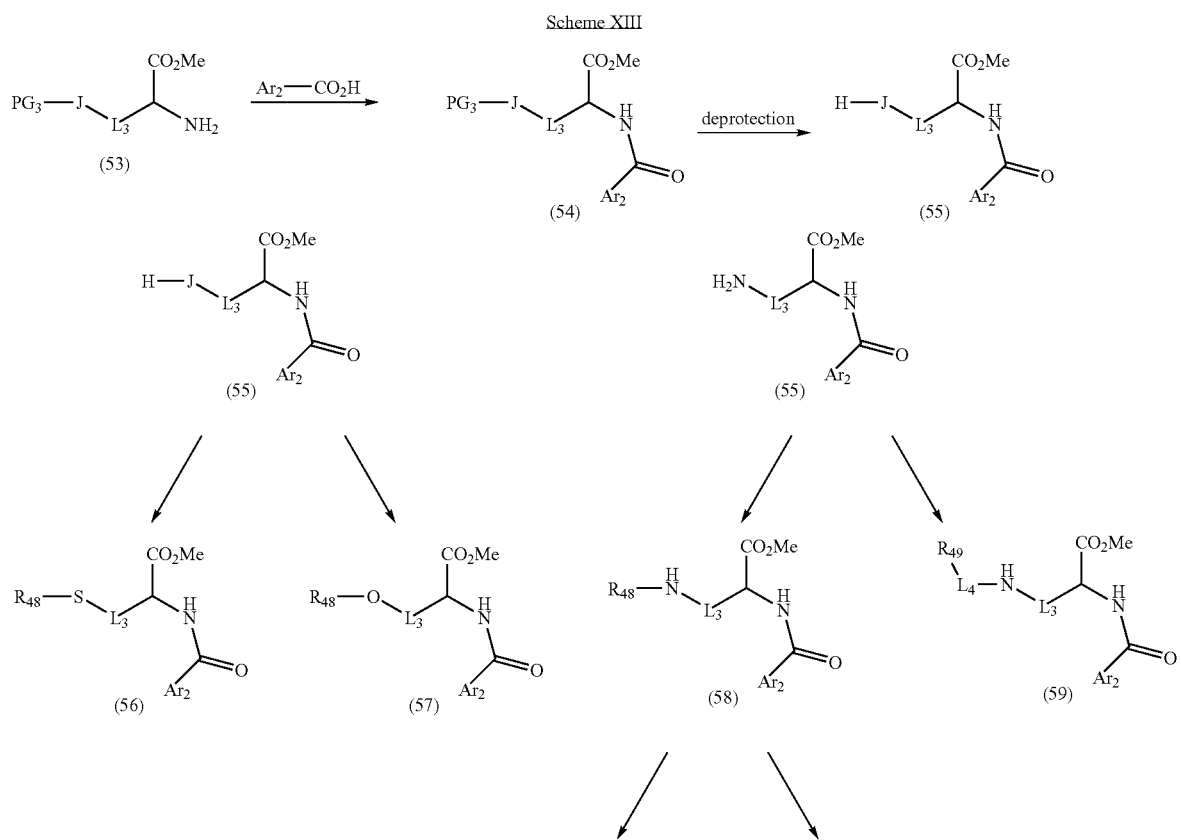

-continued

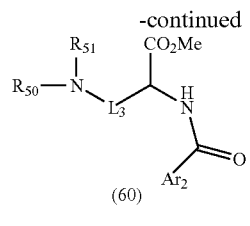

(60)

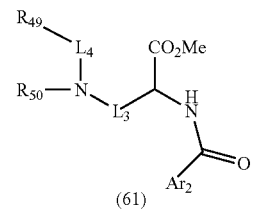

(61)

The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenyl-benzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected amino" or "protected amino group" defines an amino group substituted with an amino-protecting group discussed above.

The term "hydroxyl protecting group" as used herein refers to substituents of the alcohol group commonly employed to block or protect the alcohol functionality while reacting other functional groups on the compound. Examples of such alcohol-protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of of alcohol-protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected hydroxyl" or "protected alcohol" defines a hydroxyl group substituted with a hydroxyl-protecting group as discussed above.

The term "carboxyl protecting group" as used herein refers to substituents of the carboxyl group commonly employed to block or protect the —OH functionality while reacting other functional groups on the compound. Examples of such alcohol-protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected carboxyl" defines a carboxyl group substituted with a carboxyl-protecting group as discussed above.

The general procedures used in the methods of the present invention are described below.

General Experimental:

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The mass spectrometer used was a Micromass ZMD instrument. All data was obtained in the positive mode unless otherwise noted. $^1$H NMR data was obtained on a Varian 400 MHz spectrometer.

Common names and definitions for resin reagents used in the disclosure are;

| | |
|---|---|
| Merrifield | p-Chloromethyl polystyrene |
| Hydroxy-Merrifield | p-Hydroxymethyl polystyrene |
| Wang | (4-Hydroxymethyl)phenoxymethyl polystyrene |
| Wang carbonate | 4-(p-nitrophenyl carbonate) phenoxymethyl polystyrene |
| Rink Resin | 4-(2',4'-Dimethoxyphenyl-Fmco-aminomethyl)-phenoxy polystyrene resin |
| Wang Bromo Resin | (4-Bromomethyl)phenoxymethyl polystyrene |
| THP Resin | 3,4-Dihydro-2H-pyran-2-ylmethoxymethyl polystyrene |

Aldehyde resin can refer to the following:
    4-Benzyloxybenzaldehyde polystyrene
    3-Benzyloxybenzaldehyde polystyrene
    4-(4-Formyl-3-methoxyphenoxy)butyryl-aminomethyl polystyrene
    2-(4-Formyl-3-methoxyphenoxy)ethyl polystyrene
    2-(3,5-dimethoxy-4-formylphenoxy)ethoxy-methyl polystyrene
    2-(3,5-dimethoxy-4-formylphenoxy)ethoxy polystyrene
    (3-Formylindolyl)acetamidomethyl polystyrene
    (4-Formyl-3-methoxyphenoxy) grafted (polyethyleneglycol)-polystyrene; or
    (4-Formyl-3-methoxyphenoxy)methylpolystyrene.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide
DCE=1,2-dichloroethane
DCM=dichloromethane
DIC=diisopropylcarbodiimide
DIEA=diisopropylethylamine
DMA=N,N-dimethylacetamide
DMAP=dimethylaminopyridine
DME=1,2 dimethoxyethane
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral
PBS=phosphate buffered saline solution
PMA=phorbol myristate acetate
ppm=parts per million
psi=pounds per square inch
$R_f$=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
TMSBr=bromotrimethylsilane, trimethylsilylbromide
$T_r$=retention time Thus, in an embodiment, the following compounds were synthesized according to the Schemes described herein.

General Procedure A:

To a solution of a carboxylic acid (1.0–1.5 mmol) in DMF (6 mL) was added an amino acid methyl ester (1.0–1.5 mmol), HBTU (1.0–1.5 mmol), and DIEA (2.0–3.0 mmol) and the mixture was stirred overnight. After completion of the reaction, sufficient amount of water was added and the mixture was extracted with ethyl acetate (3×15 ml). The combined organic layer was washed with water and brine, and then dried over sodium sulfate. The solvent was removed in vacuum to afford the amide, which was used for further transformation without further purification or purified by flash chromatography.

General Procedure B:

To a mixture of phenol and the aryl fluoride (2 eq) in DMF was added solid potassium carbonate (10 eq), and the mixture was heated at 80° C. for 12 h. After completion of the reaction, sufficient amount of water was added, and the mixture was extracted with ethyl acetate. The combined organic layer was washed with water and brine, dried over sodium sulfate. The solvent was removed in vacuum and the crude material obtained was purified by flash chromatography to afford the desired aryl ethers.

General Procedure C:

To a solution of ester in THF, CH$_3$OH (4:1), 2N-lithium hydroxide solution (5 eq) was added, and the resulting reaction mixture was stirred at 0° C. for 30 minutes and then warmed to room temperature. After completion of the reaction, 2N HCl was used to neutralize the base, extracted with ethyl acetate, the organic layer was washed with brine, dried over sodium sulfate, and the solvent was removed in vacuum to afford the product.

General Procedure D:

To a solution of phenyl bromide in DME or Toluene were added corresponding boronic acid (5 eq), Pd(PPh$_3$)$_4$ (0.5% eq), 2N Na$_2$CO$_3$ solution (5 eq). The mixture was heated at 75° C. for 12 h. After completion of the reaction, solvent was evaporated in vacuo. During the reaction, most of the ester was hydrolyzed to the corresponding acid. Therefore, crude product so obtained was re-esterfied by dissolving it in CH$_3$OH containing 1% of HCl. The mixture was refluxed for 6 h and after the completion of the reaction, the reaction mixture was concentrated under reduced pressure. The residue was purified by column chromatography (silica, CH$_2$Cl$_2$) to provide the desired ester. The resulting ester was hydrolyzed as described in procedure C yielding the acid.

General Procedure E:

To a solution of an aniline (1.0 mmol) in DCE (10 mL) was added an aldehyde (2.0–2.2 mmol), acetic acid (3.0 mmol) and sodium triacetoxyborohydride (2.5 mmol) or sodium cyanoborohydride and the mixture was stirred overnight. After completion of the reaction, 50 mL of DCM was added and the organic layer was washed with saturated sodium bicarbonate solution and brine, and then dried over sodium sulfate. The solvent was removed in vacuum to afford the amine, which was purified by flash chromatography.

General Procedure F:

To a solution of an aniline (1.0 mmol) in DCM (10 mL) was added a sulfonyl chloride (1.0 mmol), and pyridine (10.0 mmol) and the mixture was stirred overnight. After completion of the reaction, 50 mL of DCM was added and the organic layer was washed with 1N HCl, saturated sodium bicarbonate solution and brine, and then dried over sodium sulfate. The solvent was removed in vacuum to afford the sulfonamide, which was purified by flash chromatography.

General Procedure G:

A flask is charged with phenol or aniline (1.0 equiv), Cu(OAc)$_2$ (1.0 equiv), arylboronic acid (1.0–3.0), and powdered 4 Å molecular sieves. The reaction mixture is diluted with CH$_2$Cl$_2$ to yield a solution approximately 0.1M in phenol or aniline, and the Et$_3$N (5.0 equiv) is added. After stirring the colored heterogeneous reaction mixture for 24 h at 25° C. under ambient atmosphere, the resulting slurry is filtered and the diaryl ether or diaryl amine is isolated from the organic filtrate by flash chromatography.

General Procedure H:

To a solution of a phenol (1.0 mmol) in DMF (5 mL) was added an alkyl halide (1.2 mmol) (a catalytic amount of NaI is added for alkyl chlorides), and potassium carbonate (2.5 mmol) and the mixture heated at 70° C. overnight. After completion of the reaction, 5 mL of ethyl acetate and 5 mL of water was added. The organic layer was washed with water, and then dried over sodium sulfate. The solvent was removed in vacuum to afford the ether, which was purified by flash chromatography.

General Procedure I:

To a solution of ester in THF was added lithium hydroxide (3–4 eq), water, and methanol. The ratio of THF/water/methanol is 4:1:1. The reaction mixture was stirred at RT for 1–1.5 h. A 10% solution of citric acid was added to adjust the pH between 6–7. Ethyl acetate was added and the organic layer is separated. The aqueous layer was extracted with ethyl acetate twice. The combined organic layer was washed with brine, dried (Na$_2$SO$_4$), and concentrated under reduced pressure to give the product.

General Procedure J:

To a stirring solution of an aniline (2 mmol) dissolved in DCM containing pyridine (4 mmol) was added acid chloride (2.5 mmol) at 0° C. The reaction mixture was stirred at rt for 3 h, extracted with DCM, washed with 1M HCl and brine evaporation followed by column chromatography purification gave amide.

The above general methods are for illustration only; Alternative conditions that may optionally be used include: Use of alternative solvents, alternative stoichiometries of reagents, alternative reaction temperatures and alternative methods of purification.

Synthesis of
4'-Trifluoromethyl-biphenyl-4-carboxylic acid

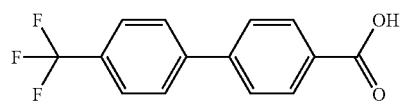

The title compound was made as described in general procedure D using 4-bromo benzoic acid (10 g, 49.4 mmol), 4-trifluoromethyl phenylboronic acid (14.17 g, 74.61 mmol), palladium tetrakis-triphenylphosphine (5.7 g, 4.974 mmol) and 2N Na$_2$CO$_3$ aq. solution (150 mL, 149.2 mmol) in 500 ml of Toluene. After the reaction is complete, the reaction mixture was neutralized with 2N HCl then filtered. The resulting solid was dissolved in ethyl acetate then passed through a short column of silica gel giving 9.7 g (75%) of the compound as a white solid.

Synthesis of Amino Acids:

(2S)-Amino-3-(2'-phenoxy-biphenyl-4-yl)-propionic acid methyl ester

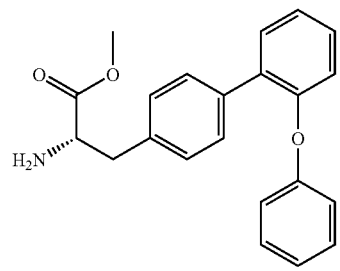

The title compound was prepared following the procedure D using (L)-4-bromophenylalanine (8.55 g, 35.0 mmol), 2-phenoxyphenyl boronic acid (10.00 g, 46.73 mmol), and palladium tetrakis-triphenylphosphine (4.0 g, 10% mmol)) and 2N Na$_2$CO$_3$ aq. solution (70 mL, 140 mmol) in 140 ml of DME. After removal of solvents, the solid was washed with ether to afford the title compound as the HCl salt (10.0 g, 26.20 mmol, 75% yield).

(2S)-Amino-3-(4'-trifluoromethoxy-biphenyl-4-yl)-propionic acid methyl ester

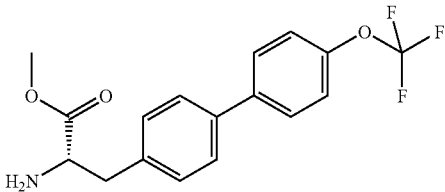

The title compound was prepared following the procedure D using (L)-4-bromophenylalanine (8.0 g, 32.7 mmol), 4-trifluoromethoxybenzene boronic acid (10.1 g, 49.1 mmol), palladium tetrakis-triphenylphosphine (3.7 g, 3.2 mmol), and $Na_2CO_3$ (2.0 N, 80.0 mL, 160 mmol) in DME (300 mL). After removal of solvent, the solid was washed with ether to afford the title compound as the HCl salt (10.8 g, 28.7 mmol, 88% yield).

(2S)-Amino-3-(4'-trifluoro-biphenyl-4-yl)-propionic acid methyl ester

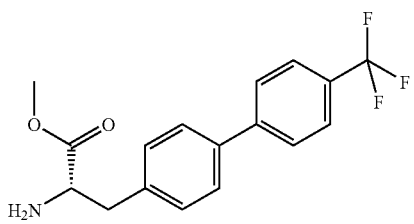

The title compound was prepared exactly following the procedure D using (L)-4-bromophenylalanine (9.0 g, 36.8 mmol), 4-trifluoromethylbenzene boronic acid (10.48 g, 55.2 mmol), palladium tetrakis-triphenylphosphine (4.25 g, 3.6 mmol), and aqueous $Na_2CO_3$ (2.0 N, 90.0 mL, 185 mmol) in DME (300 mL). After removal of solvent, the solid was washed with ether to afford the title compound as the HCl salt (10.5 g, 29.2 mmol, 79% yield).

EXAMPLE 1

3-Biphenyl-4-yl-(2S)-[(isoquinoline-3-carbonyl)-amino]-propionic acid

2-L-amino-3-biphenyl-4-yl-propionic acid methyl ester (100 mg, 0.1 mmol) was reacted with isoquinoline-3-carboxylic acid (78 mg, 0.5 mmol) as described in general procedure A. The resulting compound was hydrolyzed according to general procedure C to afford the title product (132 mg, 81%) as a white solid.

$^1$H-NMR (400 MHz, $CD_3COCD_3$): 3.38(dd, 1H), 3.47 (dd, 1H), 5.09 (m, 1H), 7.32 (m, 1H), 7.42 (m, 4H), 7.60 (m, 4H), 7.82 (m, 1H), 7.89 (m, 1H), 8.17 (m, 1H), 8.23 (m, 1H), 8.58 (s, 1H), 8.76 (m, 1H), 9.30 (d, 1H); LC/MS (m/z): 397$(M+1)^+$.

EXAMPLE 2

(2S)-[(Isoquinoline-3-carbonyl)-amino]-3-(4'-trifluoromethyl-biphenyl-4-yl)-propionic acid 3-(4-Bromo-phenyl)-(2S)-[(isoquinoline-3-carbonyl)-amino]-propionic acid methyl ester (720 mg, 90%) was prepared starting from 2-L-amino-3-(4-bromo-phenyl)-propionic acid methyl ester (500 mg, 1.9 mmol) and isoquinoline-3-carboxylic acid (400 mg, 2.3 mmol) according to general procedure A.

The resulting amide (100 mg, 0.24 mmol) was reacted with 4-trifluoromethylphenyl boronic acid (95 mg, 0.5 mmol) as described in general procedure D yielding the title compound (80 mg, 80%) as a white solid.

$^1$H-NMR(400 MHz, $CDCl_3$): 3.33(m, 2H), 5.08 (m, 1H), 7.11 (d, 1H), 7.36 (t, 2H), 7.49 (m, 1H), 7.61 (s, 2H), 7.77 (m, 3H), 8.00 (m, 3H), 8.60 (d, 1H), 8.75 (m, 1H), 9.16 (s, 1H); LC/MS (m/z): 465$(M+1)^+$.

EXAMPLE 3

(2S)-[(Isoquinoline-3-carbonyl)-amino]-3-(3;5'-bis-trifluoromethyl-biphenyl-4-yl)-propionic acid 3-(4-Bromo-phenyl-(2S)-[(isoquinoline-3-carbonyl)-amino]-propionic acid methyl ester (100 mg, 0.24 mmol) prepared as in example 2 was reacted with 3,5-bis(trifluoromethyl)phenyl boronic acid (129 mg, 0.5 mmol) as described in general procedure D to afford the title compound (100 mg, 79%) as a white solid.

$^1$H-NMR(400 MHz, $CDCl_3$): 3.36(dd, 1H), 3.48 (dd, 1H), 5.18 (m, 1H), 7.40 (d, 2H), 7.51 (d, 2H), 7.74 (m, 2H), 7.79 (m, 1H), 7.94 (m, 2H), 8.00 (m, 2H), 8.59 (s, 1H), 8.74 (d, 1H), 9.14 (s, 1H); LC/MS (m/z): 533$(M^++1)^+$.

EXAMPLE 4

(2S)-[(Isoquinoline-3-carbonyl)-amino]-3-(4'-methoxy-biphenyl-4-yl)-propionic acid 3-(4-Bromo-phenyl-(2S)-[(isoquinoline-3-carbonyl)-amino]-propionic acid methyl ester (100 mg, 0.24 mmol) prepared as in example 2 was reacted with 4-methoxyphenyl boronic acid (76 mg, 0.5 mmol) as described in general procedure D yielding the title compound (84 mg, 82%) as a white solid.

$^1$H-NMR(400 MHz, $CDCl_3$): 3.32(m, 2H), 3.81 (s, 3H), 5.12 (m, 1H), 6.91 (m, 1H), 7.11 (d, 1H), 7.26 (m, 2H), 7.32 (m, 2H), 7.46 (m, 2H), 7.74 (m, 3H), 7.98 (m, 2H), 8.59 (d, 1H), 8.74 (m, 1H), 9.14 (s, 1H); LC/MS (m/z): 427$(M+1)^+$.

EXAMPLE 5

3-[4-(4'-Cyano-phenoxy)-phenyl]-(2S)-[(isoquinoline-3-carbonyl)-amino]-propionic acid 3-(4-Hydroxyphenyl)-(2S)-[(isoquinoline-3-carbonyl)-amino]-propionic acid methyl ester (807 mg, 90%) was prepared from (2S)-amino-3-(4-hydroxy-phenyl)-propionic acid methyl ester (500 mg, 3.0 mmol) and isoquinoline-3-carboxylic acid (530 mg, 2.3 mmol) according to general procedure A.

The resulting amide (100 mg, 0.28 mmol) was reacted with 4-cyano fluorobenzene (36 mg, 0.30 mmol) as described in general procedure B. The resulting aryl ether was hydrolyzed as described in general procedure C yielding the title compound (47 mg, 72%) as a white solid.

$^1$H-NMR(400 MHz, CDCl$_3$): 3.30(dd, 1H), 3.44 (dd, 1H), 5.10 (m, 1H), 6.96 (m, 3H), 7.27 (m, 1H), 7.31 (d, 2H), 7.53 (d, 2H), 7.77 (m, 2H), 7.99 (d, 1H), 8.05 (d, 1H), 8.59 (s, 1H), 8.70 (d, 1H), 9.15 (s, 1H); LC/MS (m/z): 438(M+1)$^+$.

EXAMPLE 6

3-[4-(4'-Nitro-phenoxy)-phenyl]-(2S)-[(isoquinoline-3-carbonyl)-amino]-propionic acid 3-(4-Hydroxy-phenyl)-(2S)-[(isoquinoline-3-carbonyl)-amino]-propionic acid methyl ester (50 mg, 0.15 mmol) prepared as in example 5 was reacted with 4-nitro-fluorobenzene (42 mg, 0.30 mmol) as described in general procedure B and hydrolyzed as described in general procedure C yielding the title compound (49 mg, 71%) as a light yellow solid. LC/MS (m/z): 456 (M+1)$^+$ By analogous methods to those described above the following Examples were synthesized.

| EX-AMPLE | NAME | LC/MS(m/z) |
|---|---|---|
| 7 | 3-(3'-Chloro-4'-fluoro-biphenyl-4-yl)-(2S)-[(isoquinoline-3-carbonyl)-amino]-propionic acid | 449 |
| 8 | 3-(4'-Cyano-biphenyl-4-yl)-(2S)-[(isoquinoline-3-carbonyl)-amino]-propionic acid | 422 |
| 9 | (2S)-[(Isoquinoline-3-carbonyl)-amino]-3-(3'-trifluoromethyl-biphenyl-4-yl)-propionic acid | 465 |
| 10 | (2S)-[(Isoquinoline-3-carbonyl)-amino]-3-(3'-nitro-biphenyl-4-yl)-propionic acid | 442 |

EXAMPLE 11

3-Biphenyl-4-yl-(2S)-[(7-bromo-isoquinoline-3-carbonyl)-amino]-propionic acid To a solution of 4-bromophthalic acid (3.0 g, 12.24 mmol) in 30 mL of THF was added a solution of borane-THF complex (1.0M) dropwise at 0° C. The solution was warmed to rt and stirred for 3 h. The reaction mixture was quenched by addition of HCl (2N) at 0° C. The product was extracted with ethyl acetate and washed with sat. NaCl, dried over Na$_2$SO$_4$, and concentrated under reduced pressure to afford 2.8 g (100%) of 4-bromo-2-hydroxymethylbenzyl alcohol as a colorless oil. $^1$H NMR (CDCl$_3$) 7.28 (m, 2H), 7.26 (m, 1H), 4.69 (s, 4H), 2.80 (bs, 2H).

To a solution of oxalyl chloride (2.37 mL, 4.607 mmol) in DCM (20 mL) was added dropwise DMSO (1.95 mL) at −78° C. The mixture was stirred at −78° C. for 30 min and a solution of the diol (1.00 g, 4.607 mmol) was added dropwise. The reaction mixture was stirred for 2 hr and TEA (11.5 mL) was added. The reaction mixture was warmed to rt and water was added. The organic layer was separated and washed with sat. NaCl, dried over Na$_2$SO$_4$, and concentrated under reduced pressure to give 4-bromo-benzene-1,2-dicarbaldehyde as a yellow oil (0.450 g, 46%).

A mixture of 4-bromo-benzene-1,2-dicarbaldehyde (0.450 g, 2.137 mmol), diethylamino malonate (0.452 g, 2.137 mmol), and sodium ethoxide (0.218 g, 3.20 mmol) in anhydrous ethanol (15 mL) was refluxed for 4 hr. The solution was cooled to rt and concentrated under reduced pressure. The crude residue was purified by flash column chromatography (silica gel, 0.5% MeOH in CHCl$_3$) to obtain 0.460 g (78%) of the 7-bromo-isoquinoline-3-carboxylic acid ethyl ester which was hydrolyzed according to general procedure C yielding the 0.350 g (85%) of 7-bromo-isoquinoline-3-carboxylic acid as a white solid. LC/MS (m/z): 253 (M+1)$^+$.

(2S)-amino-3-biphenyl-4yl-propionic acid methyl ester (340 mg, 13.9 mmol) was reacted with 7-bromo-isoquinoline-3-carboxylic acid (350 mg, 13.9 mmol) as described in general procedure A. The resulting compound was hydrolyzed by following general procedure C yielding the title compound (132 mg, 81%) as a white solid.

EXAMPLE 12

3-Biphenyl-4-yl-(2S)-{[7-(4-trifluoromethyl-phenyl)-isoquinoline-3-carbonyl]-amino}-propionic acid Example 11 (50 mg, 0.1 mmol) was reacted with 4-trifluoromethylphenyl boronic acid (42.5 mg, 0.3 mmol) as described in general procedure D yielding the title compound (45 mg, 80%) as a white solid.

$^1$H-NMR (400 MHz, CDCl$_3$): 8.94 (s, 1H), 8.75 (3s, 1H), 8.67 (m, 1H), 8.47 (m, 1H), 7.82 (m, 2H), 7.51 (m, 12H), 5.07 (m, 1H), 3.28 (m, 2H); LC/MS (m/z): 541 (M+1)$^+$.

EXAMPLE 13

3-Biphenyl-4-yl-(2S)-{[7-(3-chloro-4-fluoro-phenyl)-isoquinoline-3-carbonyl]-amino}-propionic acid Example 11 (50 mg, 0.1 mmol) was reacted with 3-chloro-4-fluoro-phenyl boronic acid (109 mg, 0.3 mmol) as described in general procedure D yielding the title compound (45 mg, 80%) as a white solid.

$^1$H-NMR (400 MHz, CDCl$_3$): 9.11 (s, 1H), 8.74 (s, 1H), 8.58 (m, 1H), 8.01 (m, 1H), 7.82–7.26 (m, 13H), 5.13 (m, 1H), 3.44 (m, 2H); LC/MS (m/z): 541 (M+1)$^+$.

EXAMPLE 14

2-Biphenyl-4-yl-N-(1-bromo-isoquinolin-3-yl)-acetamide

To a solution of 4-biphenylacetic acid (1.0 g, 4.7 mmol) in 10 ml of anhydrous DMF was added HBTU (2.1 g, 5.7 mmol) and 1.0 ml of DIEA. The mixture was stirred at room temperature for 10 min, and then 1-bromo-3-isoquinolinamine (0.68 g, 4.7 mmol) was added. After stirring overnight, the mixture was poured into water, acidified with 10% citric acid, and extracted with ethyl acetate. The organic extracts were washed with water and brine, dried over Na$_2$SO$_4$. After the condensation of the solvent, the residue was purified by flash column chromatography (SiO$_2$, 1:1 hexane:ethyl aceate) to provide the title compound (1.7 g, 86%) as a light yellow solid.

$^1$H-NMR (400 MHz, CDCl$_3$): 3.83 (s, 3H), 7.33–7.37 (m, 1H), 7.42–7.48 (m, 4H), 7.52–7.58 (m, 1H), 7.60–7.64 (m, 4H), 7.65–7.70 (m, 1H), 7.80 (d, 1H,), 7.61 (s, 1H), 8.18 (d, 1H), 8.56 (s, 1H); LC/MS (m/z): 418 (M+1)$^+$.

EXAMPLE 15

2-Biphenyl-4-yl-N-[1(4-trifluoromethyl-phenyl)-isoquinolin-3-yl]-acetamide

A mixture of Example 14 (0.1 g, 0.24 mmol), 3-trifluoromethylphenylboronic acid (0.14 g, 0.72 mmol), Pd(PPh$_3$)$_4$ (0.028 g, 0.024 mmol) and 2N Na$_2$CO$_3$ solution (0.1 ml) in DME was heated at 75° C. for 12 h under nitrogen. The reaction mixture was cooled, and the solvent was evaporated. The resulting residue was purified by flash column chromatography (SiO$_2$, 10% ethyl acetate in hexane) to provide the title compound (0.1 g, 87%) as a light yellow solid.
$^1$H-NMR(400 MHz, CDCl$_3$): 3.85(s, 3H), 7.34–7.39 (m, 1H), 7.42–7.46 (m, 5H), 7.56–7.67 (m, 6H), 7.77 (d, 1H), 7.8 (d, 1H), 7.85–7.91 (m, 3H), 8.15 (s, 1H), 8.65 (s, 1H); LC/MS (m/z): 483 (M+1)$^+$.

EXAMPLE 16

N-[1(4-aminomethyl-phenyl)-isoquinolin-3-yl]-2-biphenyl-4-yl-acetamide

The title compound was prepared (0.1 g, 85%) from Example 14 (0.1 g, 0.24 mmol) employing 4-amino methyl phenylboronic acid (0.1 g, 0.72 mmol) as described in Example 15. LC/MS (m/z): 444 (M+1)$^+$.

EXAMPLE 17

3-Biphenyl-4-yl-(2S)-{[4-(2-biphenyl-4-yl-ethylamino)-quinazoline-2-carbonyl]-amino}-propionic acid 2.18 g (10 mmol) of 2-ethoxycarbonylquinazolin-4-one was suspended in 20 ml of phosphorus oxychloride. The mixture was refluxed for one hour, and the solvent was removed by rotary evaporation. The resulting residue was dissolved in ethyl acetate, and the obtained solution was washed with saturated sodium bicarbonate solution three times, dried over anhydrous sodium sulfate, filtered, and evaporated to give 2.13 g (90% mmol) of 2-ethoxycarbonyl-4-chloroquinazoline as a pale-yellow solid. LC/MS (m/z) 237 (M+1)$^+$.

236 mg (1.0 mmol) of 2-ethoxycarbonyl-4-chloroquinazoline obtained above, 210 mg (1.05 mmol) of biphenylethylamine and 1.0 ml (5.74 mmol) of diisopropylethylamine were mixed with 10 ml of isopropyl alcohol. The mixture was refluxed for 12 hours. The residue obtained after removing the solvent was purified by chromatography (5% ethyl acetate in DCM) to give 360 mg (0.9 mmol) of 2-ethoxycarbonyl-4-biphenylethylaminoquinazoline as a white solid. The ethyl ester was hydrolyzed according to general procedure C yielding the 295 mg (90%) of 4-biphenylethylaminoquinazoline-2-carboxylic acid as a white solid. LC/MS (m/z): 398 (M+1)$^+$.

To 200 mg (~0.2 mmol) of Wang resin (1.1 mmol/g) loaded with L-4-biphenylalanine were added 220 mg of (0.6 mmol) 4-biphenylethylaminoquinazoline-2-carboxylic acid, 0.6 mL (0.6 mmol) of 1.0 M DIC in DMF, 0.6 mL (0.6 mmol) of 1.0 M HOBt in DMF, and a catalytic amount of DMAP. The resulting mixture was left on shaker overnight. The resin was washed with DMF, MeOH, DCM three times of each and cleaved with 20% TFA in DCM. The residue obtained after removing the solvent was purified by chromatography (10% methanol in DCM) to give 72 mg (60%) of the title compound.

$^1$H NMR (400 MHz, CD$_3$OD): 2.91 (t, 2H), 3.30–3.36 (m, 2H), 3.90–4.00 (m, 2H), 4.98 (t, 1H), 7.06 (d, 2H), 7.12–7.21 (m, 4H), 7.22–7.31 (m, 9H), 7.33–7.38 (m, 3H), 7.72 (td, 1H), 7.90–7.96 (m, 2H), 8.22 (d, 1H); LC/MS (m/z): 593 (M+1)$^+$.

EXAMPLE 18

3-Biphenyl-4-yl-(2S)-{[4-tert-butyl-benzylamino)-quinazoline-2-carbonyl]-amino}-propionic acid 4-tert-butyl benzyl aminoquinazoline-2-carboxylic acid (290 mg, 90%) was synthesized from 236 mg (1.0 mmol) of 2-ethoxycarbonyl-4-chloroquinazoline, 210 mg (1.05 mmol) of 4-tert-butyl benzylamine and 1.0 ml (5.74 mmol) of diisopropylethylamine as described in Example 17.

4-tert-butyl benzyl aminoquinazoline-2-carboxylic acid (290 mg, 0.6 mmol) so obtained was reacted with 200 mg (~0.2 mmol) of Wang resin (1.1 mmol/g) loaded with L-4-biphenylalanine as described in Example 17 yielding the title compound (70 mg, 60%). LC/MS (m/z) 559 (M+1)$^+$.

EXAMPLE 19

3-Biphenyl-4-yl-(2S)-{[6-(3-chloro-4-fluoro-phenyl)-pyridine-2-carbonyl]-amino}-propionic acid 3-Biphenyl-4-yl-(2S)-[(6-bromo-pyridine-2-carbonyl)-amino]-propionic acid methyl ester (1.5 g, 90%) was prepared by following general procedure A from commercially available 5-bromo picolinic acid (0.95 g, 4.7 mmol) and (2S)-amino-3-biphenyl-4-yl-propionic acid methyl ester (1.0 g, 3.9 mmol).

The above compound (80 mg, 0.20 mmol) was reacted with 3-chloro-4-fluoro phenylboronic acid (87 mg, 0.5 mmol) as described in general procedure D yielding 3-Biphenyl-4-yl-2-{[6-(3-chloro-4-fluoro-phenyl)-pyridine-2-carbonyl]-amino}-propionic acid (75 mg, 79%) as a light yellow solid. LC/MS (m/z): 475 (M+1)$^+$.

EXAMPLE 20

3-Biphenyl-4-yl-(2S)-{[6-(3-chloro-4-fluorophenyl)-pyridine-2-carbonyl]-amino}-propionic acid 3-Biphenyl-4-yl-(2S)-[(6-bromo-pyridine-2-carbonyl)-amino]-propionic acid methyl ester (80 mg, 0.20 mmol) was reacted with 4-trifluoro methyl phenylboronic acid (87 mg, 0.5 mmol) as described in general procedure D to afford the title compound (75 mg, 79%) as a light yellow solid. LC/MS (m/z): 475 (M+1)$^+$.

By analogous methods to those described above the following compounds were synthesized.

| EXAMPLE | NAME | LC/MS(m/z) |
|---|---|---|
| 21 | 3-Biphenyl-4-yl-(2S)-{[6-(4-trifluoromethoxy-phenyl)-pyridine-2-carbonyl]-amino}-propionic acid | 507 |
| 22 | 3-Biphenyl-4-yl-(2S)-{[6-(4-fluoro-3-methyl-phenyl)-pyridine-2-carbonyl]-amino}-propionic acid | 455 |
| 23 | (2S){[6-(4-Amino-phenyl)-pyridine-2-carbonyl]-amino}-3-biphenyl-4-yl-propionic acid | 438 |

-continued

| EX-AMPLE | NAME | LC/MS(m/z) |
|---|---|---|
| 24 | 3-Biphenyl-4-yl-(2S)-{[6-(3-cyano-phenyl)-pyridine-2-carbonyl]-amino}-propionic acid | 448 |
| 25 | 3-Biphenyl-4-yl-(2S)-{[6-(4-methanesulfonyl-phenyl)-pyridine-2-carbonyl]-amino}-propionic acid | 501 |
| 26 | 3-Biphenyl-4-yl-(2S)-{[6-(4-methoxy-phenyl)-pyridine-2-carbonyl]-amino}-propionic acid | 453 |
| 27 | 3-Biphenyl-4-yl-(2S)-{[6-(3-carbamimidoyl-phenyl)-pyridine-2-carbonyl]-amino}-propionic acid | 465 |
| 28 | 3-Biphenyl-4-yl-(2S)-{[6-(4-phenoxy-phenyl)-pyridine-2-carbonyl]-amino}-propionic acid | 515 |
| 29 | 3-Biphenyl-4-yl-(2S)-{[6-(4-tert-butyl-phenyl)-pyridine-2-carbonyl]-amino}-propionic acid | 479 |

EXAMPLE 30

3-Biphenyl-4-yl-(2S)-{[5-(3-chloro-4-fluoro-phenyl)-pyridine-2-carbonyl]-amino}-propionic acid 3-Biphenyl-4-yl-(2S)-[(5-bromo-pyridine-2-carbonyl)-amino]-propionic acid methyl ester (1.5 g, 90%) was prepared by following general procedure A from commercially available 5-bromo picolinic acid (0.9 g, 4.7 mmol) and (2S)-amino-3-biphenyl-4-yl-propionic acid methyl ester (1.0 g, 3.9 mmol).

The above compound (80 mg, 0.20 mmol) was reacted with 3-chloro-4-fluoro phenylboronic acid (87 mg, 0.5 mmol) as described in general procedure D yielding the title compound (75 mg, 79%) as a light yellow solid. LC/MS (m/z): 475(M+1)$^+$.

By analogous methods to those described above the following compounds were synthesized.

| EX-AMPLE | NAME | LC/MS(m/z) |
|---|---|---|
| 31 | 3-Biphenyl-4-yl-(2S)-{[5-(4-trifluoromethyl-phenyl)-pyridine-2-carbonyl]-amino}-propionic acid | 491 |
| 32 | 3-Biphenyl-4-yl-(2S)-{[5-(4-methoxy-phenyl)-pyridine-2-carbonyl]-amino}-propionic acid | 453 |

EXAMPLE 33

3-Biphenyl-4-yl-(2S)-{[4-(3-chloro-4-fluoro-phenyl)-pyridine-2-carbonyl]-amino}-propionic acid 3-Biphenyl-4-yl-(2S)-[(4-chloro-pyridine-2-carbonyl)-amino]-propionic acid methyl ester (1.26 g, 85%) was prepared by following general procedure A from commercially available 4-chloro picolinic acid (0.7 g, 4.4 mmol) and (2S)-amino-3-biphenyl-4-yl-propionic acid methyl ester (1.0 g, 3.9 mmol).

The above compound (80 mg, 20 mmol) was reacted with 3-chloro 4-fluoro phenylboronic acid (70 mg, 0.40 mmol) as described in general procedure D yielding the title compound (48 mg, 51%) as a white solid. LC/MS (m/z): 475 (M+1)$^+$.

EXAMPLE 34

3-Biphenyl-4-yl-(2S)-{[4-(4-methoxy-phenyl)-pyridine-2-carbonyl]-amino}-propionic acid 3-Biphenyl-4-yl-(2S)-[(4-chloro-pyridine-2-carbonyl)-amino]-propionic acid methyl ester (80 mg, 0.20 mmol) was reacted with 4-methoxy phenylboronic acid (61 mg, 0.40 mmol) as described in general procedure D to afford the title compound (42 mg, 46%) as a light yellow solid. LC/MS (m/z): 453 (M+1)$^+$.

By analogous methods to those described above the following compounds were synthesized

| EXAMPLE | NAME | LC/MS (m/z) |
|---|---|---|
| 35 | 3-Biphenyl-4-yl-(2S)-{[4-(4-trifluoromethyl-phenyl)-pyridine-2-carbonyl]-amino}-propionic acid | 491 |
| 36 | 3-Biphenyl-4-yl-(2S)-{[4-(3-trifluoromethyl-phenyl)-pyridine-2-carbonyl]-amino}-propionic acid | 491 |

EXAMPLE 37

3-Hydroxy-naphthalene-2-carboxylic acid (2-biphenyl-4yl-ethyl)-amide

To 40.40 g (200 mmol) of Methyl 3-hydroxy-2-naphthoate, 11.0 g (220 mmol) of sodium methoxide in 500 mL of anhydrous DMA was added 13.30 g (71 mmol) of Merrifield resin. The mixture was heated at 110° C. overnight. The resin was washed with H$_2$O, DMF, MeOH, DCM three times each, and dried. The resulting resin-bound methyl naphthoate was hydrolyzed with LiOH/H$_2$O/THF/ethanol at rt for 3 days.

To 1.0 g (2.5 mmol) of above resulting resin-bound naphthoic acid was added mixture of 1.5 g (7.5 mmol) of 4-bromophenethylamine, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give the resin-bound N-2-(4-bromophenyl)ethyl-3-hydroxyl-2-naphthamide.

To 0.05 g (0.1 mmol) of above resin-bound N-2-(4-Bromophenyl)ethyl-3 hydroxyl-2-naphthamide in 2.0 mL of DME were added 36.6 mg (0.3 mmol) of phenylboronic acid, 30 mg (0.03 mmol) of Pd(PPh$_3$)$_4$, and 0.3 mL (0.6 mmol) of 2N Na$_2$CO$_3$ solution. The mixture was heated to 80° C. for 12 h. The resin was washed with H$_2$O, DMF, MeOH, DCM three times of each and cleaved with TMSBr/TFA/DCM (1:1:5) at rt for 4 h. The residue obtained after removing the solvent was purified by chromatography (100% methylene chloride) to give 22 mg (60%) of the title compound.

$^1$H NMR (400 MHz, CDCl$_3$): 3.04 (t, 2H), 3.82 (dd, 2H), 6.60 (m, 1H), 7.28–7.38 (m, 5H), 7.43–7.49 (m, 3H), 7.59–7.61 (m, 4H), 7.67–7.70 (m, 2H), 7.81 (s, 1H), 11.75 (s, 1H); LC/MS (m/z): 368 (M+1)$^+$.

EXAMPLE 38

3-[(3'-Chloro-4'-fluoro)-biphenyl-4-yl]-(2S)-[(3-hydroxy-naphthalene-2-carbonyl)-amino]-propionic acid To 1.0 g (2.5 mmol) of resin-bound naphthoic acid obtained in Example 37 was added 1.95 g (7.5 mmol) of L-4-bromophenylalanine methyl ester, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give resin-bound 3-(4-bromophenyl)ethyl-2-[3-(hydroxy-napthalene-2-carbonyl)amino]-propionic acid methyl ester.

To 0.05 g (0.1 mmol) of the above resin-bound 3-(4-bromophenyl)ethyl-(2S)-[3-(hydroxy-napthalene-2-carbonyl)-amino]-propionic acid methyl ester in 2.0 mL of DME were added 52.0 mg (0.3 mmol) of 3-chloro-4-fluorophenylboronic acid, 30 mg (0.03 mmol) of $Pd(PPh_3)_4$, and 0.3 mL (0.6 mmol) of 2N $Na_2CO_3$ solution. The mixture was heated to 80° C. for 12 h. The resin was washed with $H_2O$, DMF, MeOH, DCM three times of each and cleaved with TMSBr/TFA/DCM (1:1:5) at rt for 4 h. The residue obtained after removing the solvent was purified by chromatography (DCM) to give 30 mg (60%) of 3-[(3'-Chloro-4'-fluoro)-biphenyl-4-yl]-(2S)-[(3-hydroxy-napthalene-2-carbonyl)-amino]-propionic acid methyl ester which was hydrolyzed as described in general procedure C yielding the title compound (28.5 mg, 100%). LC/MS (m/z) 464 $(M+1)^+$.

EXAMPLE 39

3-(Biphenyl-4-yl)-(2S)-[(3-hydroxy-napthalene-2-carbonyl)-amino]-propionic acid The title compound (26 mg, 65%) was prepared from 0.05 g (0.1 mmol) of resin-bound 3-(4-bromophenyl)ethyl-(2S)-[3-(hydroxy-napthalene-2-carbonyl)-amino]-propionic acid methyl ester and 36.0 mg (0.3 mmol) of phenyl boronic acid as described in Example 38. LC/MS (m/z): 412 $(M+1)^+$.

EXAMPLE 40

(2S)-[(3-Hydroxy-napthalene-2-carbonyl)-amino]-3-[(3'-nitro)-biphenyl-4-yl]-propionic acid The title compound (27 mg, 60%) was prepared from 0.05 g (0.1 mmol) of resin-bound 3-(4-bromophenyl)ethyl-(2S)-[3-(hydroxy-napthalene-2-carbonyl)-amino]-propionic acid methyl ester and 50.0 mg (0.3 mmol) of 3-nitro-phenyl boronic acid as described in Example 38. LC/MS (m/z): 457 $(M+1)^+$.

EXAMPLE 41

3-(Biphenyl-4-yl)-(2S)-[(3'-chloro-4'-fluoro-4-hydroxy-biphenyl-3-carbonyl)-amino]-propionic acid methyl ester To 1.0 g (2.5 mmol) of resin-bound 5-bromo-2-hydroxybenzoic acid obtained by a similar procedure as in Example 37 were added 1.92 g (7.5 mmol) of (2S)-amino-3-biphenyl-4yl-propionic acid methyl ester, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give resin-bound 3-(biphenyl-4-yl)-(2S)-(5-bromo-4-hydroxy-benzoylamino)-propionic acid methyl ester.

To 0.05 g (0.1 mmol) of above resin-bound 3-(biphenyl-4-yl)-(2S)-(5-bromo-4-hydroxy-benzoylamino)-propionic acid methyl ester in 2.0 mL of DME were added 52.0 mg (0.3 mmol) of 3-chloro-4-fluorophenylboronic acid, 30 mg (0.03 mmol) of $Pd(PPh_3)_4$, and 0.3 mL (0.6 mmol) of 2N $Na_2CO_3$ solution. The mixture was heated to 80° C. for 12 h. The resin was washed with $H_2O$, DMF, MeOH, DCM three times of each and cleaved with TMSBr/TFA/DCM (1:1:5) at rt for 4 h. The residue obtained after removing the solvent was purified by chromatography (DCM) to give 35 mg (70%) of title compound LC/MS (m/z): 490 $(M+1)^+$.

EXAMPLE 42

3-(Biphenyl-4-yl)-(2S)-[(4'-trifluoromethyl-4-hydroxy-biphenyl-3-carbonyl)-amino]-propionic acid methyl ester The resin-bound 3-(biphenyl-4-yl)-(2S)-(5-bromo-4-hydroxy-benzoyl-amino)-propionic acid methyl ester (50 mg, 0.1 mmol) obtained as in Example 37 was reacted with 4-trifluoromethyl phenyl boronic acid (56.7 mg, 0.3 mmol) as generally described in Example 41 to provide the title compound (36 mg, 70%) as a white solid. LC/MS (m/z): 520 $(M+1)^+$.

EXAMPLE 43

(2S)-[(3'-Chloro-4'-fluoro-4-hydroxy-biphenyl-3-carbonyl)-amino]-3-(3'-trifluoromethyl-biphenyl-4-yl)-propionic acid methyl ester To 2.50 g (5.0 mmol) of resin-bound methyl 5-bromo-2-hydroxy-benzoate obtained by a similar procedure as in Example 37 in 30 mL of DME were added 2.60 g (15 mmol) of 3-chloro-4-fluorophenylboronic acid, 1.12 g (1.0 mmol) of $Pd(PPh_3)_4$, and 15 mL (30.0 mmol) of 2N $Na_2CO_3$ solution. The mixture was heated to 80° C. for 12 h. The resin was washed with $H_2O$, DMF, MeOH, DCM three times of each, and was hydrolyzed by $LiOH/H_2O$/THF/ethanol at rt for 3 days to give the resin-bound 3'-chloro-4'-fluoro-4-hydroxy-biphenyl-3-carboxylic acid.

To 1.5 g (2.5 mmol) of above resin-bound 3'-chloro-4'-fluoro-4-hydroxy-biphenyl-3-carboxylic acid were added 1.95 g (7.5 mmol) of L-4-bromophenylalanine methyl ester, 7.5 mL (7.5 mmol) of 1.0 M DIC in DMF, 7.5 mL (7.5 mmol) of 1.0 M HOBt in DMF, and catalytic amount of DMAP. The resulting mixture was left on a shaker overnight. The resin was washed with DMF, MeOH, DCM three times of each to give resin-bound 3-(4-bromo-phenyl)-2-[(3'-Chloro-4'-fluoro-4-hydroxy-biphenyl-3-carbonyl)-amino]-propionic acid methyl ester.

To 0.05 g (0.1 mmol) of above resin-bound 3-(4-bromo-phenyl)-(2S)-[(3'-Chloro-4'-fluoro-4-hydroxy-biphenyl-3-carbonyl)-amino]-propionic acid methyl ester in 2.0 mL of DME were added 58.0 mg (0.3 mmol) of 3-(trifluoromethyl) phenylboronic acid, 30 mg (0.03 mmol) of $Pd(PPh_3)_4$, and 0.3 mL (0.6 mmol) of 2N $Na_2CO_3$ solution. The mixture was heated at 80° C. for 12 h. The resin was washed with $H_2O$, DMF, MeOH, DCM three times of each and cleaved with TMSBr/TFA/DCM (1:1:5) at rt for 4 h. The residue obtained after removing the solvent was purified by chromatography (100% DCM) to give 29 mg (50%) of the title compound. LC/MS (m/z): 572 $(M+1)^+$.

EXAMPLE 44

3-(4'-Nitro-biphenyl-4-yl)-(2S)-[(4'-trifluoromethyl-4-hydroxy-biphenyl-3-carbonyl)-amino]-propionic acid methyl ester The resin-bound 3-(4-bromo-phenyl)-(2S)-[(4'-trifluoromethyl-4-hydroxy-biphenyl-3-carbonyl)-amino]-propionic acid methyl ester (50 mg, 0.1 mmol) prepared as generally described in Example 37 was reacted with 4-nitro-phenyl boronic acid (50.1 mg, 0.3 mmol) by adapting the procedure as described in Example 43 to give title compound (28.2 mg, 50%). LC/MS (m/z): 565 (M+1)+.

EXAMPLE 45

3-(3'-Trifluoromethyl-biphenyl-4-yl)-(2S)-[(4'-trifluoromethyl-4-hydroxy-biphenyl-3-carbonyl)-amino]-propionic acid methyl ester The resin-bound 3-(4-bromo-phenyl)-(2S)-[(4'-trifluoromethyl-4-hydroxy-biphenyl-3-carbonyl)-amino]-propionic acid methyl ester (50 mg, 0.1 mmol) prepared as described in above Example 44 was reacted with 3-trifluoromethyl-phenyl boronic acid (57.2 mg, 0.3 mmol) by following as generally described in Example 44 to give title compound (29.2 mg, 50%). LC/MS (m/z): 588 (M+1)+.

EXAMPLE 46

3-(4'-Trifluoromethyl-biphenyl-4-yl)-(2S)-[(4'-trifluoromethyl-4-hydroxy-biphenyl-3-carbonyl)-amino]-propionic acid methyl ester The resin-bound 3-(4-bromo-phenyl)-(2S)-[(4'-trifluoromethyl-4-hydroxy-biphenyl-3-carbonyl)-amino]-propionic acid methyl ester (50 mg, 0.1 mmol) prepared as generally described in Example 37 was reacted with 4-trifluoromethyl-phenyl boronic acid (57.2 mg, 0.3 mmol) by adapting the procedure in Example 45 to give the title compound (29.2 mg, 50%).

$^1$H NMR (400 MHz, CDCl$_3$): 3.30–3.42 (m, 2H), 3.84 (s, 3H), 5.11 (dd, 1H), 6.82 (d, 1H), 7.10 (d, 1H), 7.43–7.45 (m, 2H), 7.53–7.57 (m, 4H), 7.60–7.70 (m, 6H); LC/MS (m/z): 588 (M+1)+.

By analogous methods to those described above the following Examples were synthesized;

| EXAMPLE | NAME | LC/MS (m/z) |
|---|---|---|
| 47 | 3-Biphenyl-4-yl-(2S)-[(2',4'-difluoro-4-hydroxy-biphenyl-3-carbonyl)-amino]-propionic acid | 488 |
| 48 | 3-Biphenyl-4-yl-(2S)-[(4'-chloro-3'-fluoro-4-hydroxy-biphenyl-3-carbonyl)-amino]-propionic acid methyl ester | 504 |
| 49 | 3-Biphenyl-4-yl-(2S)-[(3'-chloro-4'-fluoro-4-hydroxy-biphenyl-3-carbonyl)-amino]-propionic acid | 490 |
| 50 | 3-Biphenyl-4-yl-(2S)-[(4-hydroxy-3'-nitro-biphenyl-3-carbonyl)-amino]-propionic acid methyl ester | 499 |
| 51 | 3-Biphenyl-4-yl-(2S)-[(4-hydroxy-4'-trifluoromethoxy-biphenyl-3-carbonyl)-amino]-propionic acid methyl ester | 536 |
| 52 | (2S)-[(4-Hydroxy-4'-trifluoromethyl-biphenyl-3-carbonyl)-amino]-3-(3'-nitro-biphenyl-4-yl)-propionic acid | 553 |
| 53 | (2S)-[(4-Hydroxy-4'-trifluoromethyl-biphenyl-3-carbonyl)-amino]-3-(3'-nitro-biphenyl-4-yl)-propionic acid methyl ester | 566 |
| 54 | (2S)-[(3'-Chloro-4'-fluoro-4-hydroxy-biphenyl-3-carbonyl)-amino]-3-(3'-nitro-biphenyl-4-yl)-propionic acid methyl ester | 551 |
| 55 | 3-Biphenyl-4-yl-(2S)-[(4'-fluoro-4-hydroxy-biphenyl-3-carbonyl)-amino]-propionic acid methyl ester | 470 |
| 56 | 3-Biphenyl-4-yl-(2S)-[(4-hydroxy-4'-methoxy-biphenyl-3-carbonyl)-amino]-propionic acid methyl ester | 482 |
| 57 | 3-Biphenyl-4-yl-(2S)-[(4'-tert-butyl-4-hydroxy-biphenyl-3-carbonyl)-amino]-propionic acid methyl ester | 508 |
| 58 | (2S)-[(4-Hydroxy-3'-nitro-biphenyl-3-carbonyl)-amino]-3-(3'-rifluoromethyl-biphenyl-4-yl)-propionic acid methyl ester | 567 |
| 59 | 3-(3'-Chloro-4'-fluoro-biphenyl-4-yl)-(2S)-[(4-hydroxy-3'-nitro-biphenyl-3-carbonyl)-amino]-propionic acid methyl ester | 551 |
| 60 | (2S)-[(4'-Amino-4-hydroxy-biphenyl-3-carbonyl)-amino]-3-biphenyl-4-yl-propionic acid methyl ester | 467 |
| 61 | (2S)-[(3'-Amino-4-hydroxy-biphenyl-3-carbonyl)-amino]-3-biphenyl-4-yl-propionic acid methyl ester | 467 |
| 62 | 3-Biphenyl-4-yl-(2S)-[(5'-fluoro-4-hydroxy-2'-methoxy-biphenyl-3-carbonyl)-amino]-propionic acid methyl ester | 500 |
| 63 | 3-Biphenyl-4-yl-(2S)-[(3'-fluoro-4-hydroxy-biphenyl-3-carbonyl)-amino]-propionic acid methyl ester | 470 |
| 64 | 3-Biphenyl-4-yl-(2S)-[(4-hydroxy-3'-trifluoromethyl-biphenyl-3-carbonyl)-amino]-propionic acid methyl ester | 520 |
| 65 | 3-Biphenyl-4-yl-(2S)-[(4-hydroxy-3',5'-bis-trifluoromethyl-biphenyl-3-carbonyl)-amino]-propionic acid methyl ester | 588 |
| 66 | 3-Biphenyl-4-yl-(2S)-[(3'-chloro-4-hydroxy-biphenyl-3-carbonyl)-amino]-propionic acid methyl ester | 486 |
| 67 | 3-Biphenyl-4-yl-(2S)-[(4'-chloro-4-hydroxy-biphenyl-3-carbonyl)-amino]-propionic acid methyl ester | 486 |
| 68 | 3-Biphenyl-4-yl-(2S)-[(3',5'-difluoro-4-hydroxy-biphenyl-3-carbonyl)-amino]-propionic acid methyl ester | 488 |
| 69 | 3-Biphenyl-4-yl-(2S)-[(4'-fluoro-4-hydroxy-3'-methyl-biphenyl-3-carbonyl)-amino]-propionic acid methyl ester | 483 |
| 70 | (2S)-[(3'-Chloro-4'-fluoro-4-hydroxy-biphenyl-3-carbonyl)-amino]-3-(4'-trifluoromethyl-biphenyl-4-yl)-propionic acid methyl ester | 572 |
| 71 | (2S)-[(3'-Chloro-4'-fluoro-4-hydroxy-biphenyl-3-carbonyl)-amino]-3-(4'-methoxy-biphenyl-4-yl)-propionic acidmethyl ester | 534 |
| 72 | 3-Biphenyl-4-yl-(2S)-[(4-hydroxy-4'-trifluoromethoxy-biphenyl-3-carbonyl)-amino]-propionic acid | 522 |
| 73 | 3-Biphenyl-4-yl-(2S)-[(4'-tert-butyl-4-hydroxy-biphenyl-3-carbonyl)-amino]-propionic acid | 494 |
| 74 | 3-Biphenyl-4-yl-(2S)-[(4-hydroxy-3',4'-dimethoxy-biphenyl-3-carbonyl)-amino]-propionic acid methyl ester | 512 |
| 75 | (2S)-(5-Benzo[1, 3]dioxol-5-yl-2-hydroxy-benzoylamino)-3-biphenyl-4-yl-propionic acid methyl ester | 496 |
| 76 | 3-(3'-Chloro-4'-fluoro-biphenyl-4-yl)-(2S)-[(4-hydroxy-4'-trifluoromethyl-biphenyl-3-carbonyl)-amino]-propionic acid methyl ester | 572 |

-continued

| EX-AMPLE | NAME | LC/MS (m/z) |
|---|---|---|
| 77 | 3-Biphenyl-4-yl-(2S)-[(4-hydroxy-4'-methanesulfonyl-biphenyl-3-carbonyl)-amino]-propionic acid methyl ester | 530 |
| 78 | (2S)-[(3'-Amino-4-hydroxy-biphenyl-3-carbonyl)-amino]-3-(3'-trifluoromethyl-biphenyl-4-yl)-propionic acid methyl ester | 535 |
| 79 | 3-(3',5'-Bis-trifluoromethyl-biphenyl-4-yl)-(2S)-[(3'-chloro-4'-fluoro-4-hydroxy-biphenyl-3-carbonyl)-amino]-propionic acid methyl ester | 640 |
| 80 | 3-(3',5'-Bis-trifluoromethyl-biphenyl-4-yl)-(2S)-[(4'-fluoro-4-hydroxy-biphenyl-3-carbonyl)-amino]-propionic acid methyl ester | 606 |
| 81 | 3-(3',5'-Bis-trifluoromethyl-biphenyl-4-yl)-(2S)-[(4-hydroxy-4'-trifluoromethyl-biphenyl-3-carbonyl)-amino]-propionic acid methyl ester | 656 |
| 82 | (2S)-[(3'-Chloro-4'-fluoro-4-hydroxy-biphenyl-3-carbonyl)-amino]-3-(3'-trifluoromethyl-biphenyl-4-yl)-propionic acid | 558 |
| 83 | (2S)-[(4-Hydroxy-4'-trifluoromethyl-biphenyl-3-carbonyl)-amino]-3-(3'-trifluoromethoxy-biphenyl-4-yl)-propionic acid methyl ester | 604 |
| 84 | (2S)-[(4-Hydroxy-3'-trifluoromethyl-biphenyl-3-carbonyl)-amino]-3-(3'-trifluoromethyl-biphenyl-4-yl)-propionic acid methyl ester | 588 |
| 85 | 4'-{(2S)-[(4-Hydroxy-4'-trifluoromethyl-biphenyl-3-carbonyl)-amino]-2-methoxycarbonyl-ethyl}-5-nitro-biphenyl-3-carboxylic acid methyl ester | 623 |
| 86 | (2S)-[(4-Hydroxy-4'-trifluoromethyl-biphenyl-3-carbonyl)-amino]-3-(3',4',5'-trimethoxy-biphenyl-4-yl)-propionic acid methyl ester | 610 |
| 87 | (2S)-[(3'-Chloro-4'-fluoro-4-hydroxy-biphenyl-3-carbonyl)-amino]-3-(3'-trifluoromethoxy-biphenyl-4-yl)-propionic acid methyl ester | 588 |
| 88 | 3-Biphenyl-4-yl-(2S)-[(4-hydroxy-4'-trifluoromethyl-biphenyl-3-carbonyl)-amino]-propionic acid | 506 |
| 89 | (2S)-[(4-Hydroxy-2'-trifluoromethyl-biphenyl-3-carbonyl)-amino]-3-(2'-trifluoromethyl-biphenyl-4-yl)-propionic acid methyl ester | 588 |
| 90 | 3-(3'-Chloro-4'-fluoro-biphenyl-4-yl)-(2S)-[(3'-chloro-4'-fluoro-4-hydroxy-biphenyl-3-carbonyl)-amino]-propionic acid methyl ester | 556 |
| 91 | (2S)-[(4-Hydroxy-3'-nitro-biphenyl-3-carbonyl)-amino]-3-(3'-nitro-biphenyl-4-yl)-propionic acid methyl ester | 542 |
| 92 | (2S)-[(4-Hydroxy-3'-trifluoromethyl-biphenyl-3-carbonyl)-amino]-3-(3'-nitro-biphenyl-4-yl)-propionic acid methyl ester | 565 |
| 93 | (2S)-[(4-Hydroxy-3'-trifluoromethyl-biphenyl-3-carbonyl)-amino]-3-(4'-trifluoromethyl-biphenyl-4-yl)-propionic acid methyl ester | 588 |
| 94 | 3-(3'-Chloro-4'-fluoro-biphenyl-4-yl)-(2S)-[(4-hydroxy-3'-trifluoromethyl-biphenyl-3-carbonyl)-amino]-propionic acid methyl ester | 572 |
| 95 | 3-Biphenyl-4-yl-(2S)-[(4-hydroxy-2'-trifluoromethyl-biphenyl-3-carbonyl)-amino]-propionic acid methyl ester | 520 |
| 96 | 3-(3',5'-Bis-trifluoromethyl-biphenyl-4-yl)-(2S)-[(4-hydroxy-3'-trifluoromethyl-biphenyl-3-carbonyl)-amino]-propionic acid methyl ester | 656 |
| 97 | (2S)-[(4-Hydroxy-3'-trifluoromethyl-biphenyl-3-carbonyl)-amino]-3-(2'-trifluoromethyl-biphenyl-4-yl)-propionic acid methyl ester | 588 |

EXAMPLE 98

(2S)-[2-(4-Benzyloxy-benzyloxy)-5-bromo-benzoylamino]-3-biphenyl-4-yl-propionic acid 3-Biphenyl-4-yl-(2S)-(5-bromo-2-hydroxy-benzoylamino)-propionic acid methyl ester (2.75 g, 35%) was prepared from (2S)-amino-3-biphenyl-4-yl-propionic acid methyl ester-hydrochloride (5.0 g, 17.2 mmol), 5-bromo-2-hydroxy-benzoic acid (3.7 g, 17.2 mmol) as described in general procedure A except for an adapted work-up. After reaction completion, the reaction mixture was poured onto 150 mL of 1N HCl and 150 mL of EtOAc. The organic layer was washed with 1N HCl, saturated sodium bicarbonate, dried over sodium sulfate and evaporated. The crude material was purified over silica gel (7:3, DCM-hexanes).

(2S)-[2-(4-Benzyloxy-benzyloxy)-5-bromo-benzoylamino]-3-biphenyl-4-yl-propionic acid methyl ester (302 mg, 50%) was prepared from (2S)-3-Biphenyl-4-yl-2-(5-bromo-2-hydroxy-benzoylamino)-propionic acid methyl ester (400 mg, 0.92 mmol) and 4-benzyloxybenzyl chloride (256 mg, 0.39) as described in general procedure H and purified over silica gel (8:2, DCM-hexanes).

(2S)-[2-(4-Benzyloxy-benzyloxy)-5-bromo-benzoylamino]-3-biphenyl-4-yl-propionic acid methyl ester (60 mg, 0.092 mmol) was dissolved in 5 mL of THF-MeOH (4-1), cooled to 0° C. and 1.1 equiv of 2 N LiOH added. After 30 minutes, 2.2 additional equiv of 2N LiOH was added and the reaction stirred for 30 minutes. The reaction was worked up according to general procedure C to give (2S)-[2-(4-Benzyloxy-benzyloxy)-5-bromo-benzoylamino]-3-biphenyl-4-yl-propionic acid (35 mg, 60%).
$^1$H-NMR(400 MHz, DMSO-d$_6$): 2.90 (m, 1H), 3.17 (m, 1H), 4.69 (m, 1H), 4.98 (s, 2H), 5.18 (s, 2H), 6.92 (m, 2H), 7.21 (m, 3H), 7.33 (m, 10H), 7.53 (d, 2H), 7.61 (m, 3H), 7.84 (d, 1H), 8.51 (d, 1H); LC/MS (m/z): 638.1 (M+2)$^+$.

EXAMPLE 99

3-Biphenyl-4-yl-(2S)-{[4-(4-tert-butyl-benzyloxy)-3'-chloro-4'-fluoro-biphenyl-3-carbonyl]-amino}-propionic acid 5-Bromo-2-(4-t-butyl-benzyloxy)-benzoic acid methyl ester (338 mg, 90%) was made from 5-bromosalicilic acid methyl ester (230 mg, 1.0 mmol) and t-butyl-benzyl bromide (226 mg, 1.0 mmol) following general procedure H, then hydrolyzed as in general procedure C to give the corresponding acid (310 mg, 95%). The above acid (40 mg, 0.11 mmol) was reacted with biphenyl alanine methyl ester (44 mg, 0.15 mmol) as described in general procedure A to give 3-biphenyl-4-yl-(2S)-[2-(4-t-butyl-benzyloxy)-5-bromo-benzoylamino]-propionic acid methyl ester. The methyl ester (60 mg, 0.1 mmol) so obtained was reacted with 3-chloro-4-fluorophenyl boronic acid (35 mg, 0.2 mmol) as described in general procedure D to provide the (2S)-[(3'-chloro-4'-fluoro-4-tert-butyl-benzyloxy-biphenyl-3-carbonyl)-amino]-3-biphenyl-4-yl-propionic acid methyl ester (52 mg, 80%). The ester was hydrolyzed following general procedure C to give the title compound (48 mg, 95%).
$^1$H NMR (400 MHz, CDCl$_3$): 1.27 (s, 9H), 2.89 (m, 1H), 3.30 (m, 1H), 4.93 (m, 1H), 5.11 (m, 2H), 7.00 (m, 2H), 7.26–7.60 (m, 17H), 8.41 (d, 1H), 8.58 (d, 1H); LC/MS (m/z): 636 (M+1)$^+$.

EXAMPLE 100

(2S)-[5-Bromo-2-(4-trifluoromethylbenzyloxy)-benzoylamine]-3-(2'-phenoxybiphenyl-4-yl)-propionic acid 5-Bromo-salicylic acid (2.16 g, 10 mmol) was first transformed into 2-acetyl-5-bromo-salicylic acid (252 g, 98%) with acetyl chloride (2.34 g, 30 mmol) and pyridine (3.95 g, 50 mmol) in DCM. The above acid (1.29 g, 5.0 mmol) was converted into acid chloride by using oxyl chloride (1.97 g, 15 mmol) and catalytic amount of DMF in DCM, then 2-phenoxy-biphenyl alanine (1.45 g, 5.0 mmol) and DIEA (0.77 g, 6.0 mmol) were added to the acid chloride to form (2S)-[5-Bromo-2-hydroxybenzoylamine]-3-(2'-phenoxybiphenyl-4-yl)-propionic acid methyl ester (1.92 g, 85%). The above methyl ester (50 mg, 0.092 mmol) was reacted with 4-trifluoromethyl benzyl bromide (44 mg, 0.18 mmol) as described in general procedure H to provide (2S)-[5-Bromo-2-(4-trifluoromethylbenzyloxy)-benzoylamine]-3-(2'-phenoxybiphenyl-4-yl)-propionic acid methyl ester (55 mg, 85%). The ester was hydrolyzed following general procedure C to give the title compound (52 mg, 96%).

$^1$H NMR (400 MHz, CDCl$_3$): 3.03, 3.22 (ABX, 2H), 4.92 (m, 3H), 6.64 (d, 1H), 6.76 (m, 2H), 6.85(dd, 1H), 6.93 (m, 2H), 7.00 (d, 2H), 7.07–7.24 (m, 7H), 7.39 (m, 4H), 8.22 (d, 1H), 8.26 (d, 1H); LC/MS (m/z): 690 (M+1)$^+$.

EXAMPLE 101

(2S)-(5-Bromo-2-heptyloxy-benzoylamino)-3-[2'-(4-trifluoromethyl-phenoxy)-biphenyl-4-yl]-propionic acid 5-Bromo-2-heptyloxy-benzoic acid was prepared by reacting 5-bromo-2-hydroxy-benzoic acid methyl ester (1.0 g, 4.32 mmol) with iodoheptane (1.46 g, 6.49 mmol) as per general procedure H with potassium carbonate (1.5 g, 10.8 mmol) added. The ester thus obtained was subjected to hydrolysis as per general procedure C to yield the 5-Bromo-2-heptyloxy-benzoic acid (0.950 gm, 70%).

(2S)-Amino-3-(2'-hydroxy-biphenyl-4-yl)-propionic acid was prepared from 4-bromophenylalanine (5.0 g, 20.48 mmol), 2-hydroxyphenylboronic acid (4.23 g, 30.72 mmol) and Pd(PPh$_3$)$_4$ (2.36 g, 2.038 mmol) as per procedure D to yield the corresponding amino acid which was further esterified with methanolic solution of anhydrous HCl to yield the corresponding HCl salt of the (2S)-Amino-3-(2'-hydroxy-biphenyl-4-yl)-propionic acid methyl ester (5.0 g, 90% crude yield).

5-Bromo-2-heptyloxy-benzoic acid (0.231 g, 0.738 mmol) and the (2S)-amino-3-(2'-hydroxy-biphenyl-4-yl)-propionic acid methyl ester (0.200 g, 0.738 mmol) were then combined as per general procedure A with HBTU (0.335 g, 0.885 mmol) and diisopropylethylamine (0.285 g, 2.21 mmol) to yield the (2S)-(5-bromo-2-heptyloxy-benzoylamino)-3-(2'-hydroxy-biphenyl-4-yl)-propionic acid methyl ester (0.200 g, 50%).

The title compound was the prepared from (2S)-(5-bromo-2-heptyloxy-benzoylamino)-3-(2'-hydroxy-biphenyl-4-yl)-propionic acid methyl ester (0.080 g, 0.140 mmol) and 4-trifluoromethylphenylboronic acid (0.050 g, 0.281 mmol) as per general procedure G to give (2S)-(5-bromo-2-heptyloxy-benzoylamino)-3-[2'-(4-trifluoromethyl-phenoxy)-biphenyl-4-yl]-propionic acid methyl ester which was further hydrolyzed as per general procedure C to give the title compound (0.020 g, 30% yield).

$^1$H-NMR(400 MHz, CDCl$_3$): 1.14(t, 3H), 1.53 (m, 8H), 1.92(m, 2H), 3.6(m, 2H), 4.21(m, 2H), 5.21(m, 1H), 7.12(d, 1H), 7.22(m, 2H), 7.36(d, 1H), 7.5(d, 2H), 7.58(m, 2H), 7.66(m, 1H), 7.78 (m, 6H), 8.62 (S, 1H), 8.9 (bs, 1H). LC/MS (m/z): 700.2(M+2).

EXAMPLE 102

2S-(5-Chloro-2-heptyloxy-benzoylamino)-3-(4'-trifluoromethoxy-biphenyl-4-yl)-propionic acid 5-Chloro-2-hydroxy-benzoic acid (2.5 g, 28.97 mmol) was coupled with 2-amino-3-(4-bromo-phenyl)-propionic acid methyl ester hydrochloride (4.26 g, 28.96 mmol) with HBTU (6.59 g, 34.76 mmol) and diisopropylethylamine (8 ml, 86.91 mmol) as per general procedure A to yield the corresponding 3-(4-Bromo-phenyl)-(2S)-(5-chloro-2-hydroxy-benzoylamino)-propionic acid methyl ester in 50% yield.

The above hydroxy compound (0.500 g, 1.21 mmol) was then alkylated with heptyliodide (0.410 g, 1.815 mmol) and potassium carbonate (0.050 g, 3.025 mmol) as per general procedure H to yield the 3-(4-bromo-phenyl)-(2S)-(5-chloro-2-heptyloxy-benzoylamino)-propionic acid methyl ester (0.500 g, 80%)

The title compound was then prepared from 3-(4-bromo-phenyl)-(2S)-(5-chloro-2-heptyloxy-benzoylamino)-propionic acid methyl ester (0.090 g, 0.176 mmol) and trifluoromethyl boronic acid (0.067 g, 0.352 mmol) with Pd(PPh$_3$) (0.020 g, 0.0176 mmol) and 2 N Na$_2$CO$_3$ (0.528 ml, 0.528 mmol) as per general procedure D to yield the (2S)-(5-chloro-2-heptyloxy-benzoylamino)-3-(4'-trifluoromethoxy-biphenyl-4-yl)-propionic acid methyl ester which was further hydrolyzed as per general procedure C to give the title compound (0.050 g, 50%)%). $^1$H-NMR(400 MHz, CDCl$_3$): 1.11(t, 3H), 1.44(m, 8H), 1.87(m, 2H), 3.65(dddd, 2H), 4.27(m, 2H), 5.50(m, 1H), 7.18(m, 2H), 7.4(d, 1H), 7.57(m, 4H), 7.68–7.85(m, 4H), 8.52 (S, 1H), 8.98 (bs, 1H). LC/MS (m/z): 578.2(M+2).

By analogous methods to those described above the following compounds were synthesized.

| EX-AMPLE | NAME | LC/MS (m/z) |
|---|---|---|
| 103 | 3-Biphenyl-4-yl-(2S)-[2-(3,4-bis-benzyloxy-benzyloxy)-5-bromo-benzoylamino]-propionic acid methyl ester | 757 |
| 104 | 3-Biphenyl-4-yl-(2S)-[2-(3,4-bis-benzyloxy benzyloxy)-5-bromo-benzoylamino]-propionic acid | 743 |
| 105 | (2S)-[2-(4-Benzyloxybenzyloxy)-5-bromo benzoylamino]-3-biphenyl-4-yl-propionic acid methyl ester | 651 |
| 106 | 3-Biphenyl-4-yl-(2S)-[5-bromo-2-(4-bromo-benzyloxy)-benzoylamino]-propionic acid methyl ester | 624 |
| 107 | 3-Biphenyl-4-yl-(2S)-[5-bromo-2-(4-bromo-benzyloxy)-benzoylamino]-propionic acid | 610 |
| 108 | 3-Biphenyl-4-yl-(2S)-[5-bromo-2-(4-tert-butyl-benzyloxy)-benzoylamino]-propionic acid methyl ester | 601 |
| 109 | 3-Biphenyl-4-yl-(2S)-[5-bromo-2-(4-tert-butyl-benzyloxy)-benzoylamino]-propionic acid | 587 |
| 110 | 3-Biphenyl-4-yl-(2S)-[2-(biphenyl-4-ylmethoxy)-5-bromo-benzoylamino]-propionic acid | 607 |
| 111 | 3-Biphenyl-4-yl-(2S)-(5-chloro-2-methoxy-benzoyl amino)-propionic acid | 410 |
| 112 | 3-Biphenyl-4-yl-(2S)-[2-(4-tert-butyl-benzyloxy)-5-chloro-benzoylamino]-propionic acid | 542 |
| 113 | 3-Biphenyl-4-yl-(2S)-[2-(4-tert-butyl-benzyloxy)-5-(4-trifluoromethylphenyl)-benzoylamino]-propionic acid | 636 |
| 114 | (2S)-[5-Bromo-2-(3-methyl-benzyloxy)-benzoylamino]-3-(2'-phenoxy-biphenyl-4-yl)-propionic acid methyl ester | 652 |

-continued

| EX-AMPLE | NAME | LC/MS (m/z) |
|---|---|---|
| 115 | (2S)-[5-Bromo-2-(4-methyl-benzyloxy)-benzoylamino]-3-(2'-phenoxy-biphenyl-4-yl)-propionic acid | 637 |
| 116 | (2S)-[5-Bromo-2-(3-methyl-benzyloxy)-benzoylamino]-3-(2'-phenoxy-biphenyl-4-yl)-propionic acid | 637 |
| 117 | (2S)-[5-Bromo-2-(4-carboxy-benzyloxy)-benzoylamino]-3-(2'-phenoxy-biphenyl-4-yl)-propionic acid | 667 |
| 118 | (2S)-[5-Bromo-2-(4-trifluoromethyl-phenoxy)-benzoylamino]-3-(2'-phenoxy-biphenyl-4-yl)-propionic acid | 677 |
| 119 | (2S)-(5-Bromo-2-heptyloxy-benzoylamin-3-(2'-phenoxy-biphenyl-4-yl)-propionic acid methyl ester | 645 |
| 120 | 3-Biphenyl-4-yl-(2S)-(5-bromo-2-heptyloxy-benzoylamino)-propionic acid methyl ester | 553 |
| 121 | 3-Biphenyl-4-yl-(2S)-(5-bromo-2-heptyloxy-benzoylamino)-propionic acid | 539 |
| 122 | (2S)-(5-Bromo-2-heptyloxy-benzoylamino)-3-(2'-phenoxy-biphenyl-4-yl)-propionic acid | 631 |
| 123 | 3-Biphenyl-4-yl-(2S)-[5-chloro-2-(4-pyrazol-1-yl-benzyloxy)-benzoylamino]-propionic acid | 552 |
| 124 | (2S)-[5-Bromo-2-(4-tert-butyl-benzyloxy)-benzoylamino]-3-(2'-phenoxy-biphenyl-4-yl)-propionic acid | 679 |
| 125 | (2S)-(2-Benzyloxy-5-bromo-benzoylamino)-3-(2'-phenoxy-biphenyl-4-yl)-propionic acid methyl ester | 637 |
| 126 | (2S)-(2-Benzyloxy-5-bromo-benzoylamino)-3-(2'-phenoxy-biphenyl-4-yl)-propionic acid | 623 |
| 127 | (2S)-[5-Bromo-2-(4-bromo-benzyloxy)-benzoylamino]-3-(2'-phenoxy-biphenyl-4-yl)-propionic acid | 702 |
| 128 | (2S)-(5-Bromo-2-propoxy-benzoylamino)-3-(2'-phenoxy-biphenyl-4-yl)-propionic acid | 575 |
| 129 | (2S)-[(5-Bromo-2,3-dihydro-benzofuran-7-carbonyl)-amino]-3-(2'-phenoxy-biphenyl-4-yl)-propionic acid | 559 |
| 130 | (2S)-[5-Bromo-2-(3-phenyl-allyloxy)-benzoylamino]-3-(2'-phenoxy-biphenyl-4-yl)-propionic acid methyl ester | 663 |
| 131 | (2S)-[5-Bromo-2-(3-phenyl-allyloxy)-benzoylamino]-3-(2'-phenoxy-biphenyl-4-yl)-propionic acid | 649 |
| 132 | (2S)-[5-Bromo-2-(4-methanesulfonyl-benzyloxy)-benzoylamino]-3-(2'-phenoxy-biphenyl-4-yl)-propionic acid methyl ester | 715 |
| 133 | (2S)-[5-Bromo-2-(4-methanesulfonyl-benzyloxy)-benzoylamino]-3-(2'-phenoxy-biphenyl-4-yl)-propionic acid | 701 |
| 134 | (2S)-[5-Bromo-2-(3-methyl-butoxy)-benzoylamino]-3-(2'-phenoxy-biphenyl-4-yl)-propionic acid methyl ester | 617 |
| 135 | (2S)-[5-Bromo-2-(3-methyl-butoxy)-benzoylamino]-3-(2'-phenoxy-biphenyl-4-yl)-propionic acid | 603 |
| 136 | (2S)-[2-(Biphenyl-4-ylmethoxy)-5-bromo-benzoylamino]-3-(2'-phenoxy-biphenyl-4-yl)-propionic acid methyl ester | 713 |
| 137 | (2S)-[2-(Biphenyl-4-ylmethoxy)-5-bromo-benzoylamino]-3-(2'-phenoxy-biphenyl-4-yl)-propionic acid | 699 |
| 138 | (2S)-[5-Bromo-2-(4-methoxy-phenoxy)-benzoylamino]-3-(2'-phenoxy-biphenyl-4-yl)-propionic acid | 639 |
| 139 | (2S)-[5-Bromo-2-(4-phenoxy-benzyloxy)-benzoylamino]-3-(2'-phenoxy-biphenyl-4-yl)-propionic acid | 715 |
| 140 | (2S)-[5-Bromo-2-(1-methyl-butoxy)-benzoylamino]-3-(2'-phenoxy-biphenyl-4-yl)-propionic acid methyl ester | 617 |
| 141 | (2S)-[5-Bromo-2-(1-methyl-butoxy)-benzoylamino]-3-(2'-phenoxy-biphenyl-4-yl)-propionic acid | 603 |
| 142 | (2S)-(5-Bromo-2-isopropoxy-benzoylamino)-3-(2'-phenoxy-biphenyl-4-yl)-propionic acid | 575 |

-continued

| EX-AMPLE | NAME | LC/MS (m/z) |
|---|---|---|
| 143 | (2S)-[5-Bromo-2-(3-trifluoromethyl-phenoxy)-benzoylamino]-3-(2'-phenoxy-biphenyl-4-yl)-propionic acid | 677 |
| 144 | (2S)-(5-Bromo-2-heptyloxy-benzoylamino)-3-[2'-(4-methoxy-phenoxy)-biphenyl-4-yl]-propionic acid | 661 |
| 145 | (2S)-[5-Bromo-2-(2-morpholin-4-yl-ethoxy)-benzoylamino]-3-(2'-phenoxy-biphenyl-4-yl)-propionic acid methyl ester | 660 |
| 146 | (2S)-{5-Bromo-2-[2-(2-methoxy-ethoxy)-ethoxy]-benzoylamino}-3-(2'-phenoxy-biphenyl-4-yl)-propionic acid methyl ester | 649 |
| 147 | (2S)-(5-Bromo-2-{2-[-(2-methoxy-ethoxy)-ethoxy]-ethoxy}-benzoylamino)-3-(2'-phenoxy-biphenyl-4-yl)-propionic acid methyl ester | 693 |
| 148 | (2S)-(5-Bromo-2-{2-[2-(2-methoxy-ethoxy)-ethoxy]-ethoxy}-benzoylamino)-3-(2'-phenoxy-biphenyl-4-yl)-propionic acid methyl ester | 658 |
| 149 | (2S)-{5-Bromo-2-[2-(2-oxo-pyrrolidin-1-yl)-ethoxy]-benzoylamino}-3-(2'-phenoxy-biphenyl-4-yl)-propionic acid methyl ester | 658 |
| 150 | (2S)-[5-Bromo-2-(2-phenyl-cyclopropylmethoxy)-benzoylamino]-3-(2'-phenoxy-biphenyl-4-yl)-propionic acid | 663 |
| 151 | (2S)-(5-Bromo-2-sec-butoxy-benzoylamino)-3-(2'-phenoxy-biphenyl-4-yl)-propionic acid | 589 |
| 152 | (2S)-(5-Chloro-2-heptyloxy-benzoylamino)-3-(2'-phenoxy-biphenyl-4-yl)-propionic acid methyl ester | 600 |
| 153 | (2S)-(5-Chloro-2-heptyloxy-benzoylamino)-3-(2'-phenoxy-biphenyl-4-yl)-propionic acid | 586 |
| 154 | (2S)-(5-Bromo-2-isobutoxy-benzoylamino)-3-(2'-phenoxy-biphenyl-4-yl)-propionic acid methyl ester | 603 |
| 155 | (2S)-(5-Bromo-2-isobutoxy-benzoylamino)-3-(2'-phenoxy-biphenyl-4-yl)-propionic acid | 588 |
| 156 | (2S)-(5-Bromo-2-ethoxycarbonyloxy-benzoylamino)-3-(2'-phenoxy-biphenyl-4-yl)-propionic acid methyl ester | 619 |
| 157 | (2S)-(5-Bromo-2-dimethylcarbamoyloxy-benzoylamino)-3-(2'-phenoxy-biphenyl-4-yl)-propionic acid methyl ester | 618 |
| 158 | (2S)-{5-Bromo-2-[2-(2-methoxy-ethoxy)-ethoxy]-benzoylamino}-3-(2'-phenoxy-biphenyl-4-yl)-propionic acid | 635 |
| 159 | (2S)[5-Bromo-2-(4-phenyl-butoxy)-benzoylamino]-3-(2'-phenoxy-biphenyl-4-yl)-propionic acid | 665 |
| 160 | (2S)-[5-Bromo-2-(5-phenyl-pentyloxy)-benzoylamino]-3-(2'-phenoxy-biphenyl-4-yl)-propionic acid | 679 |
| 161 | (2S)-[5-Bromo-2-(6-phenyl-hexyloxy)-benzoylamino]-3-(2'-phenoxy-biphenyl-4-yl)-propionic acid | 693 |
| 162 | (2S)-(5-Bromo-2-heptyloxy-benzoylamino)-3-[2'-(4-trifluoromethoxy-phenoxy)-biphenyl-4-yl]-propionic acid | 715 |
| 163 | (2S)-(5-Bromo-2-{2-[2-(2-methoxy-ethoxy)-ethoxy]-ethoxy}-benzoylamino)-3-(2'-phenoxy-biphenyl-4-yl)-propionic acid | 679 |
| 164 | (2S)-[5-Bromo-2-(2-piperidin-1-yl-ethoxy)-benzoylamino]-3-(2'-phenoxy-biphenyl-4-yl)-propionic acid | 644 |
| 165 | (2S)-(5-Bromo-2-heptyloxy-benzoylamino)-3-[2'-(4-tert-butyl-phenoxy)-biphenyl-4-yl]-propionic acid | 687 |
| 166 | (2S)-(5-Chloro-2-heptyloxy-benzoylamino)-3-(4'-trifluoromethyl-biphenyl-4-yl)-propionic acid | 562 |
| 167 | 3-(3'-Chloro-4'-fluoro-biphenyl-4-yl)-(2S)-(5-chloro-2-heptyloxy-benzoylamino)-propionic acid | 546 |
| 168 | (2S)-[5-Bromo-2-(3-phenyl-propoxy)-benzoylamino]-3-(2'-phenoxy-biphenyl-4-yl)-propionic acid | 651 |
| 169 | (2S)-{5-Bromo-2-[3-(3,4-dimethoxy-phenyl)-propoxy]-benzoylamino}-3-(2'-phenoxy-biphenyl-4-yl)-propionic acid | 711 |

-continued

| EX- AMPLE | NAME | LC/MS (m/z) |
|---|---|---|
| 170 | (2S)-[5-Bromo-2-(3-pyridin-3-yl-propoxy)-benzoylamino]-3-(2'-phenoxy-biphenyl-4-yl)-propionic acid | 652 |
| 171 | (2S)-[5-Bromo-2-(3-pyridin-4-yl-propoxy)-benzoylamino]-3-(2'-phenoxy-biphenyl-4-yl)-propionic acid | 652 |
| 172 | (2S)-(5-Bromo-2-dimethylcarbamoyloxy-benzoylamino)-3-(2'-phenoxy-biphenyl-4-yl)-propionic acid | 604 |
| 173 | (2S)-[5-Bromo-2-(3-morpholin-4-yl-propoxy)-benzoylamino]-3-(2'-phenoxy-biphenyl-4-yl)-propionic acid | 660 |
| 174 | (2S)-[5-Bromo-2-(4,4,4-trifluoro-butoxy)-benzoylamino]-3-(2'-phenoxy-biphenyl-4-yl)-propionic acid | 643 |
| 175 | (2S)-(5-Chloro-2-heptyloxy-benzoylamino)-3-(4'-cyclohexyl-biphenyl-4-yl)-propionic acid | 576 |
| 176 | (2S)-(5-Chloro-2-heptyloxy-benzoylamino)-3-(3',4'-dichloro-biphenyl-4-yl)-propionic acid | 562 |
| 177 | (2S)-(5-Bromo-2-butoxy-benzoylamino)-3-(2'-phenoxy-biphenyl-4-yl)-propionic acid | 589 |
| 178 | (2S)-[5-Bromo-2-(2-methyl-butoxy)-benzoylamino]-3-(2'-phenoxy-biphenyl-4-yl)-propionic acid | 603 |
| 179 | (2S)-(5-Bromo-2-cyclopropylmethoxy-benzoylamino)-3-(2'-phenoxy-biphenyl-4-yl)-propionic acid methyl ester | 601 |
| 180 | (2S)-(5-Bromo-2-cyclopropylmethoxy-benzoylamino)-3-(2'-phenoxy-biphenyl-4-yl)-propionic acid | 587 |
| 181 | (2S)-[5-Bromo-2-(4-[1,2,4]triazol-1-yl-benzyloxy)-benzoylamino]-3-(2'-phenoxy-biphenyl-4-yl)-propionic acid | 690 |
| 182 | (2S)-[5-Bromo-2-(isoquinolin-1-ylmethoxy)-benzoylamino]-3-(2'-phenoxy-biphenyl-4-yl)-propionic acid | 674 |
| 183 | (2S)-[2-(3-Benzyloxy-benzyloxy)-5-bromo-benzoylamino]-3-(4'-phenoxy-biphenyl-4-yl)-propionic acid methyl ester | 743 |
| 184 | (2S)-[2-(3-Benzyloxy-benzyloxy)-5-bromo-benzoylamino]-3-(4'-phenoxy-biphenyl-4-yl)-propionic acid | 728 |
| 185 | (2S)-[5-Bromo-2-(4-trifluoromethoxy-benzyloxy)-benzoylamino]-3-(2'-phenoxy-biphenyl-4-yl)-propionic acid methyl ester | 721 |
| 186 | (2S)-[5-Bromo-2-(4-trifluoromethoxy-benzyloxy)-benzoylamino]-3-(2'-phenoxy-biphenyl-4-yl)-propionic acid | 707 |
| 187 | (2S)-[5-Bromo-2-(4-phenyl-butoxy)-benzoylamino]-3-(4'-phenoxy-biphenyl-4-yl)-propionic acid methyl ester | 679 |
| 188 | (2S)-[5-Bromo-2-(6-phenyl-hexyloxy)-enzoylamino]-3-(4'-phenoxy-biphenyl-4-yl)-propionic acid methyl ester | 707 |
| 189 | (2S)-(5-Chloro-2-heptyloxy-benzoylamino)-3-(4'-dimethylamino-biphenyl-4-yl)-propionic acid | 537 |
| 190 | (2S)-[5-Bromo-2-(4-phenyl-butoxy)-benzoylamino]-3-(4'-phenoxy-biphenyl-4-yl)-propionic acid | 665 |
| 191 | (2S)-[5-Bromo-2-(6-phenyl-hexyloxy)-benzoylamino]-3-(4'-phenoxy-biphenyl-4-yl)-propionic acid | 693 |
| 192 | (2S)-[5-Bromo-2-(2-cyclohexyl-ethoxy)-benzoylamino]-3-(2'-phenoxy-biphenyl-4-yl)-propionic acid methyl ester | 657 |
| 193 | (2S)-[5-Bromo-2-(2-cyclohexyl-ethoxy)-benzoylamino]-3-(2'-phenoxy-biphenyl-4-yl)-propionic acid | 643 |
| 194 | (2S)-(5-Bromo-2-cyclohexylmethoxy-benzoylamino)-3-(2'-phenoxy-biphenyl-4-yl)-propionic acid | 629 |
| 195 | (2S)-(5-Bromo-2-cyclohexyloxy-benzoylamino)-3-(2'-phenoxy-biphenyl-4-yl)-propionic acid methyl ester | 629 |
| 196 | (2S)-(5-Bromo-2-cyclohexyloxy-benzoylamino)-3-(2'-phenoxy-biphenyl-4-yl)-propionic acid | 615 |

EXAMPLE 197

N-[2-Hydroxy-4-(4-trifluoromethyl-phenoxy)-phenyl]-2-(3'-methoxy-biphenyl-4-yl)-acetamide To 4.0 g (4.0 mmol) of resin-bound 5-fluoro-2-nitrophenol obtained by a similar procedure as in Example 37 in 8.0 mL of DMF were added 1.31 g (8.0 mmol) of 4-hydroxybenzotrifluoride, and 1.20 g (8.0 mmol) of $K_2CO_3$. The mixture was heated to 110° C. for 12 h. The resin was washed with $H_2O$, DMF, MeOH, DCM three times of each, and was reduced by $SnCl_2$ hydrate in NMP at rt for 4 h to give the resin-bound 2-amino-5-(4-trifluoromethyl-phenoxy)-phenol.

To 3.0 g (2.5 mmol) of above resin-bound 2-amino-5-(4-trifluoromethyl-phenoxy)-phenol were added 1.62 g (7.5 mmol) of 4-bromophenylacetic acid, 7.5 mL (7.5 mmol) of 1.0 M DIC in DMF, 7.5 mL (7.5 mmol) of 1.0 M HOBt in DMF, and a catalytic amount of DMAP. The resulting mixture was left on a shaker overnight. The resin was washed with DMF, MeOH, DCM three times of each to give resin-bound 2-(4-bromo-phenyl)-N-[2-Hydroxy-4-(4-trifluoromethyl-phenoxy)-phenyl]-acetamide.

To 120 mg (0.1 mmol) of above resin-bound 2-(4-bromo-phenyl)-N-[2-Hydroxy-4-(4-trifluoromethyl-phenoxy)-phenyl]-acetamide in 2.0 mL of DME were added 46.0 mg (0.3 mmol) of 3-methoxyphenylboronic acid, 30 mg (0.03 mmol) of $Pd(PPh_3)_4$, and 0.3 mL (0.6 mmol) of 2N $Na_2CO_3$ solution. The mixture was heated to 80° C. for 12 h. The resin was washed with $H_2O$, DMF, MeOH, DCM three times of each and cleaved with TMSBr/TFA/DCM (1:1:5) at rt for 4 h. The residue obtained after removing the solvent was purified by chromatography (100% methylene chloride) to give 25 mg (50%) of the title compound. LC/MS (m/z) 494 $(M+1)^+$.

EXAMPLE 198

N-[2-Hydroxy-4-(3,4-dichloro-phenoxy)-phenyl]-2-(4'-trifluoromethyl-biphenyl-4-yl)-acetamide The resin-bound 2-(4-bromo-phenyl)-N-[2-Hydroxy-4-(3,4-dichloro-phenoxy)-phenyl]-acetamide (120 mg, 0.1 mmol) prepared as described in Example 197 was reacted with 4-trifluoromethyl-phenyl boronic acid (56.7 mg, 0.3 mmol) as generally described in Example 197 to afford (26.9 mg, 50%) the title compound.

$^1$H NMR (400 MHz, $CDCl_3$): 3.88 (s, 2H), 6.48 (dd, 1H), 6.66 (d, 1H), 6.79–6.85 (m, 2H), 7.05 (d, 1H), 7.36 (d, 2H), 7.46–7.48 (m, 2H), 7.66–7.68 (m, 2H), 7.71 (m, 4H), 8.92 (s, 1H); LC/MS (m/z): 532 $(M+1)^+$.

EXAMPLE 199

N-[2-Hydroxy-4-(2,4-dichloro-6-methyl-phenoxy)-phenyl]-2-(4'-trifluoromethyl-biphenyl-4-yl)-acetamide The resin-bound 2-(4-bromo-phenyl)-N-[2-Hydroxy-4-(3,4-dichloro-6-methyl-phenoxy)-phenyl]-acetamide (120 mg, 0.1 mmol) prepared as described in Example 197 was reacted with 4-trifluormethyl-phenyl boronic acid (56.7 mg, 0.3 mmol) as generally described in Example 197 to afford (27.5 mg, 50%) of title compound.

$^1$H NMR (400 MHz, $CDCl_3$): 2.13 (s, 3H), 3.86 (s, 2H), 6.33 (dd, 1H), 6.36 (d, 1H), 6.69 (d, 1H, 7.15 (d, 1H, 7.29 (d, 1H), 7.45 (d, 2H), 7.64–7.71 (m, 6H), 8.92 (s, 1H); LC/MS (m/z): 546 $(M+1)^+$.

EXAMPLE 200

N-[2-Hydroxy-4-(2,4-dichloro-6-methyl-phenoxy)-phenyl]-2-(3'-trifluoromethyl-biphenyl-4-yl)-acetamide The resin-bound 2-(4-bromo-phenyl)-N-[2-Hydroxy-4-(3,4-dichloro-6-methyl-phenoxy)-phenyl]-acetamide (120 mg, 0.1 mmol) prepared as described in Example 197 was reacted with 3-trifluormethyl-phenyl boronic acid (56.7 mg, 0.3 mmol) as generally described in Example 197 to afford (27.5 mg, 50%) of title compound.

$^1$H NMR (400 MHz, CDCl$_3$): 2.13 (s, 1H), 3.86 (s, 2H), 6.33 (dd, 1H), 6.37 (d, 1H), 6.69 (d, 1H), 7.15 (m, 1H), 7.30 (d, 1H), 7.45 (dd, 2H), 7.59–7.65 (m, 4H), 7.78 (m, 1H), 7.84 (s, 1H), 8.84 (s, 1H); LC/MS (m/z): 546 (M+1)$^+$.

By analogous methods to those described above the following compounds were synthesized

| EXAMPLE | NAME | LC/MS (m/z) |
|---|---|---|
| 201 | 3-(3'-Chloro-4'-fluoro-biphenyl-4-yl)-N-[4-(2,4-dichloro-6-methyl-phenoxy)-2-hydroxy-phenyl]-propionamide | 544 |
| 202 | N-[4-(2-Fluoro-6-methoxy-phenoxy)-2-hydroxy-phenyl]-3-(3'-methoxy-biphenyl-4-yl)-propionamide | 488 |
| 203 | N-[4-(2,4-Dichloro-6-methyl-phenoxy)-2-hydroxy-phenyl]-2-(4'-methoxy-biphenyl-4-yl)-acetamide | 508 |
| 204 | 2-(3'-Chloro-4'-fluoro-biphenyl-4-yl)-N-[4-(2,4-dichloro-6-methyl-phenoxy)-2-hydroxy-phenyl]-acetamide | 530 |
| 205 | 2-Biphenyl-4-yl-N-[2-hydroxy-4-(4'-methoxy-biphenyl-4-yloxy)-phenyl]-acetamide | 502 |
| 206 | 2-Biphenyl-4-yl-N-[2-hydroxy-4-(4'-trifluoromethyl-biphenyl-4-yloxy)-phenyl]-acetamide | 540 |
| 207 | N-[4-(3,4-Dichloro-phenoxy)-2-hydroxy-phenyl]-2-(3'-nitro-biphenyl-4-yl)-acetamide | 508 |

EXAMPLE 208

N-[5-(3-Chloro-phenyl)-pyridin-2-yl]-2-[4-(3-hydroxy-4-nitro-phenoxy)-phenyl]-acetamide To 4.0 g (4.0 mmol) of resin-bound 5-fluoro-2-nitrophenol prepared as generally described in Example 37 in 8.0 mL of DMF were added 1.34 g (8.0 mmol) of methyl 4-hydroxyphenylacetate, and 1.20 g (8.0 mmol) of K$_2$CO$_3$. The mixture was heated to 110° C. for 12 h. The resin was washed with H$_2$O, DMF, MeOH, DCM three times of each, and was hydrolyzed by LiOH/H$_2$O/THF/ethanol at rt for 12 h to give the resin-bound [4-(3-hydroxy-4-nitro-phenoxy)-phenyl]-acetic acid.

To 3.0 g (2.5 mmol) of above resin-bound [4-(3-hydroxy-4-nitro-phenoxy)-phenyl]-acetic acid were added 1.30 g (7.5 mmol) of 2-amino-5-bromopyridine, 7.5 mL (7.5 mmol) of 1.0 M DIC in DMF, 7.5 mL (7.5 mmol) of 1.0 M HOBt in DMF, and catalytic amount of DMAP. The resulting mixture was left on a shaker overnight. The resin was washed with DMF, MeOH, DCM three times of each to give resin-bound N-(5-bromo-pyridin-2-yl)-2-[4-(3-hydroxy-4-nitro-phenoxy)-phenyl]-acetamide.

To 120 mg (0.1 mmol) of above resin-bound bound N-(5-bromo-pyridin-2-yl)-2-[4-(3-hydroxy-4-nitro-phenoxy)-phenyl]-acetamide in 2.0 mL of DME were added 48.0 mg (0.3 mmol) of 3-chlorophenylboronic acid, 30 mg (0.03 mmol) of Pd(PPh$_3$)$_4$, and 0.3 mL (0.6 mmol) of 2N Na$_2$CO$_3$ solution. The mixture was heated to 80° C. for 12 h. The resin was washed with H$_2$O, DMF, MeOH, DCM three times of each and cleaved with TMSBr/TFA/DCM (1:1:5) at rt for 4 h. The residue obtained after removing the solvent was purified by chromatography (silica gel, DCM) to give 20 mg (40%) of the title compound.

$^1$H NMR (400 MHz, CDCl$_3$): 3.81 (s, 2H), 6.51–6.55 (m, 1H), 6.60–6.63 (m, 1H), 7.11–7.13 (m, 2H), 7.26–7.45 (m, 5H), 7.52 (m, 1H), 7.91 (dd, 1H), 8.08 (m, 1H), 8.34 (d, 1H), 8.43 (m, 1H), 10.89 (s, 1H); LC/MS (m/z): 476 (M+1)$^+$.

EXAMPLE 209

N-[5-(3,4-Dichloro-phenyl)-pyridin-2-yl]-2-[4-(3-hydroxy-4-nitro-phenoxy)-phenyl]-acetamide The resin-bound N-(5-bromo-pyridin-2-yl)-2-[4-(3-hydroxy-4-nitro-phenoxy)-phenyl]-acetamide (120 mg, 0.1 mmol) was reacted with 3,4-dichloro-phenyl boronic acid (57 mg, 0.3 mmol) as described in example 208 to afford 25 mg (45%) of the title compound. LC/MS (m/z): 510 (M+1)$^+$.

EXAMPLE 210

N-[5-(3-Trifluromethyl-phenyl)-pyridin-2-yl]-2-[4-(3-hydroxy-4-nitro-phenoxy)-phenyl]-acetamide The resin-bound N-(5-bromo-pyridin-2-yl)-2-[4-(3-hydroxy-4-nitro-phenoxy)-phenyl]-acetamide (120 mg, 0.1 mmol) was reacted with 3-trifluoromethyl-phenyl boronic acid (57 mg, 0.3 mmol) as described in example 208 to afford 22.9 mg (45%) of the title compound.

$^1$H NMR (400 MHz, CDCl$_3$): 3.72 (s, 2H), 3.89 (s, 3H), 6.52 (m, 1H), 6.58–6.63 (m, 1H), 7.07–7.11 (m, 2H), 7.48–7.50 (m, 2H), 7.66–7.78 (m, 4H), 8.06–8.09 (m, 1H), 8.25 (dd, 1H), 8.43 (dd, 1H), 8.72 (d, 1H), 10.90 (s, 1H); LC/MS (m/z): 510 (M+1)$^+$.

EXAMPLE 211

N-[5-(4-Methoxy-phenyl)-pyridin-2-yl]-2-[4-(3-hydroxy-4-nitro-phenoxy)-phenyl]-acetamide The resin-bound N-(5-bromo-pyridin-2-yl)-2-[4-(3-hydroxy-4-nitro-phenoxy)-phenyl]-acetamide (120 mg, 0.1 mmol) was reacted with 4-methoxy-phenyl boronic acid (45 mg, 0.3 mmol) as described in example 208 to afford 21.2 mg (45%) of the title compound.

$^1$H NMR (400 MHz, CDCl$_3$): 3.87 (s, 3H), 3.88 (s, 2H), 6.52 (d, 1H), 6.61 (dd, 1H), 7.01–7.03 (m, 2H), 7.08–7.10 (m, 2H), 7.46–7.50 (m, 4H), 8.08 (d, 1H), 8.16 (dd, 1H), 8.36 (dd, 1H), 8.62 (d, 1H), 10.89 (s, 1H); LC/MS (m/z): 472 (M+1)$^+$.

EXAMPLE 212

3-Biphenyl-4-yl-(2S)-[(4'-trifluoromethyl-biphenyl-4-carbonyl)-amino]-propionic acid (2S)-Amino-3-biphenyl-4-yl-propionic acid methyl ester (1.00 g mg, 4.1 mmol) was reacted with 4-bromo-benzoic acid (1.07 g mg, 5.3 mmol) as described in general procedure A yielding 3-biphenyl-4-yl-(2S)-[(5-bromo-benzoyl-amino)-propionic acid (1.48 g, 85%).

3-Biphenyl-4-yl-(2S)-[(5-bromo-benzoylamino)-propionic acid (100 mg, 0.23 mmol) was reacted with 4-trifluoromethyl phenyl boronic acid (0.133 mg, 0.69 mmol) by following general procedure D yielding the title compound (98 mg, 85%) as a white solid.

$^1$H-NMR(400 MHz, DMSO-d$_6$): 3.07–3.25(m, 2H), 4.63–4.69 (m, 1H), 7.26–7.32 (m, 1H), 7.39–7.42 (m, 4H), 7.56–7.62 (m, 4H), 7.1–7.84 (m, 4H), 7.81–7.84 (m, 4H), 7.92–7.95 (m, 4H), 8.86 (d, 1H); LC/MS (m/z): 490 (M+1)$^+$.

EXAMPLE 213

3-Biphenyl-4-yl-(2S)-[(3'-chloro-4'-fluoro-biphenyl-4-carbonyl)-amino]-propionic acid 3-Biphenyl-4-yl-(2S)-[(5-bromo-benzoyl-amino)-propionic acid (100 mg, 0.23 mmol) was reacted with 3-chloro-4-fluoro-phenyl boronic acid (0.123 mg, 0.69 mmol) by following general procedure D to afford title compound (89 mg, 80%) as a white solid. $^1$H NMR (400 MHz, CD$_3$COCD$_3$): 4.05 (dd, 2H), 5.00 (m, 1H), 7.32 (m, 1H), 7.44 (m, 4H), 7.62 (m, 4H), 7.71 (m, 1H), 7.74 (m, 2H), 7.84 (m, 1H), 7.96 (m, 3H). LC/MS (m/z): 474 (M+1)$^+$.

EXAMPLE 214

3-Biphenyl-4-yl-(2S)-[(4'-trifluoromethoxy-biphenyl-4-carbonyl)-amino]-propionic acid 3-Biphenyl-4-yl-(2S)-[(5-bromo-benzoyl-amino)-propionic acid (100 mg, 0.23 mmol) was reacted with 4-trifluoromethoxyphenylboronic acid (0.145 mg, 0.69 mmol) by following general procedure D yielding the title compound (101 mg, 85%) as a white solid:

$^1$H-NMR(400 MHz, DMSO-d$_6$): 3.08–3.15 (m, 1H), 3.20–3.25 (m, 1H), 4.62–4.68 (m, 1H), 7.28–7.32 (m, 1H), 7.39–7.46 (m, 6H), 7.55–7.61 (m, 4H), 7.77 (d, 2H), 7.82 (d, 2H), 7.92 (d, 2H), 8.84 (d, 1H); LC/MS (m/z): 524 (M+1)$^+$.

EXAMPLE 215

3-Biphenyl-4-yl-(2S)-[(4'-ethyl-biphenyl-4-carbonyl)-amino]-propionic acid

3-Biphenyl-4-yl-(2S)-[(5-bromo-benzoyl-amino)-propionic acid (100 mg, 0.23 mmol) was reacted with 4-ethyl phenyl boronic acid (0.145 mg, 0.69 mmol) by following general procedure D yielding the title compound (101 mg, 85%) as a white solid. LC/MS (m/z): 450 (M+1)$^+$.

EXAMPLE 216

3-Biphenyl-4-yl-(2S)-[(3'-ethyl-biphenyl-3-carbonyl)-amino]-propionic acid (2S)-amino-3-biphenyl-4yl-propionic acid methyl ester (1.0 g mg, 4.1 mmol) was reacted with 3-bromo-benzoic acid (1.07 g mg, 5.3 mmol) as described in general procedure A yielding 3-biphenyl-4-yl-(2S)-(3-bromo-benzoylamino)-propionic acid (1.48 g, 85%).

3-Biphenyl-4-yl-(2S)-[(3-bromo-benzoyl-amino)-propionic acid (100 mg, 0.23 mmol) was reacted with 4-ethyl phenyl boronic acid (0.145 mg, 0.69 mmol) by following general procedure D yielding the title compound (101 mg, 85%) as a white solid.

$^1$H-NMR(400 MHz, DMSO-d$_6$): 1.22 (t, 3H), 2.61 (q, 2H), 3.25–3.30 (m, 1H), 3.37–3.39 (m, 1H), 5.06–5.08 (m, 1H), 6.75 (d, 1H, J=6.4 Hz), 7.15 (d, 2H), 7.24–7.26 (m, 2H), 7.30–7.33 (m, 1H), 7.36–7.43 (m, 5H), 7.49 (t, 4H), 7.60 (d, 1H), 7.64 (d, 1H), 7.85 (s, 1H); LC/MS (m/z): 450 (M+1)$^+$.

EXAMPLE 217

3-Biphenyl-4-yl-(2S)-[(4'-tert-butyl-biphenyl-3-carbonyl)-amino]-propionic acid

3-Biphenyl-4-yl-(2S)-[(3-bromo-benzoyl-amino)-propionic acid (100 mg, 0.23 mmol) was reacted with 4-tert-butyl phenyl boronic acid (0.125 mg, 0.69 mmol) by following general procedure D yielding the title compound (95 mg, 85%) as a white solid.

$^1$H-NMR(400 MHz, DMSO-d$_6$): 1.31 (s, 9H), 3.34–3.42 (m, 1H), 3.42–3.46 (m, 1H), 5.10–5.14 (m, 1H), 6.62 (bs, 1H), 7.25 (s, 1H), 7.28 (d, 1H), 7.31–7.35 (m, 1H), 7.37–7.43 (m, 4H), 7.44–7.49 (m, 3H), 7.52–7.56 (m, 4H), 7.64 (d, 1H), 7.70–7.72 (m, 1H,), 7.4 (s, 1H); LC/MS (m/z): 478 (M+1)$^+$.

EXAMPLE 218

3-Biphenyl-4-yl-(2S)-[(4'-methoxy-biphenyl-3-carbonyl)-amino]-propionic acid

3-Biphenyl-4-yl-(2S)-[(3-bromo-benzoyl-amino)-propionic acid (100 mg, 0.23 mmol) was reacted with 4-methoxy-phenyl boronic acid (0.106 mg, 0.69 mmol) by following general procedure D yielding the title compound (85 mg, 80%) as a white solid.

$^1$H-NMR(400 MHz, DMSO-d$_6$): 3.26–3.31 (m, 1H), 3.39–3.40 (m, 1H), 3.77 (s, 3H), 5.02–5.04 (m, 1H), 6.73 (bs, 1H), 6.85 (d, 1H), 7.79 (m, 17H); LC/MS (m/z): 452 (M+1)$^+$.

EXAMPLE 219

3-Biphenyl-4-yl-(2S)-[(4'-methane-sulfonyl-biphenyl-3-carbonyl)-amino]-propionic acid 3-Biphenyl-4-yl-(2S)-[(3-bromo-benzoyl-amino)-propionic acid (100 mg, 0.23 mmol) was reacted with 4-methanesulfonyl-phenyl boronic acid (0.141 mg, 0.69 mmol) by following general procedure D yielding the title compound (102 mg, 87%) as a light yellow solid.

$^1$H-NMR(400 MHz, CDCl$_3$): 3.11–3.17 (m, 1H), 3.26–3.30 (m, 1H,), 4.69–4.74 (m, 1H), 7.30–7.34 (m, 1H), 7.58–7.63 (m, 5H), 7.87–7.93 (m, 2H), 7.98–8.05 (m, 4H), 8.14 (s, 1H), 8.97 (d, 1H); LC/MS (m/z): 500 (M+1)$^+$.

EXAMPLE 220

3-Biphenyl-4-yl-(2S)-[(4'-tert-butyl-4-chloro-biphenyl-3-carbonyl)-amino]-propionic acid (2S)-Amino-3-biphenyl-4yl-propionic acid methyl ester (1.0 g mg, 4.1 mmol) was reacted with 5-bromo-2-chloro-benzoic acid (1.07 g mg, 5.3 mmol) as described in general procedure A yielding 3-biphenyl-4-yl-(2S)-(5-bromo-2-chloro-benzoyl-amino)-propionic acid (1.5 g, 85%) as white solid.

3-Biphenyl-4-yl-(2S)-[(2-chloro-5-bromo-benzoyl-amino)-propionic acid (100 mg, 0.23 mmol) was reacted with 4-trifluoromethyl-phenyl boronic acid (0.141 mg, 0.69 mmol) by following general procedure D yielding the title compound (114 mg, 75%) as a white solid.

¹H-NMR(400 MHz, DMSO-d$_6$): 2.98–3.02 (m, 1H), 3.24–3.28 (m, 1H), 4.71–4.73 (m, 1H), 7.25 (d, 1H), 7.31–7.34 (m, 1H), 7.38–7.41 (m, 4H), 7.56–7.60 (m, 5H), 7.70 (d, 2H), 7.74–7.77 (m, 3H), 8.9 (d, 1H); LC/MS (m/z): 524 (M+1)$^+$.

EXAMPLE 221

(2S)-[(4-Chloro-4'-trifluoromethyl-biphenyl-3-carbonyl)-amino]-3-(4'-trifluoromethyl-biphenyl-4-yl)-propionic acid (2S)-Amino-3-(4-bromo-phenyl)-propionic acid methyl ester (1.0 g mg, 3.8 mmol) was reacted with 5-bromo-2-chloro-benzoic acid (1.09 g mg, 4.5 mmol) as described in general procedure A yielding (2S)-(5-bromo-2-chloro-benzoyl-amino)-3-(4-bromophenyl)-propionic acid (1.35 g, 75%).

(2S)-(5-Bromo-2-chloro-benzoyl-amino)-3-(4-bromo-phenyl)-propionic acid (100 mg, 0.21 mmol) was reacted with 4-trifluoromethyl-phenyl-boronic acid (243 mg, 1.2 mmol) by following general procedure D yielding the title compound (114 mg, 75%) as a light yellow solid.

¹H-NMR(400 MHz, DMSO-d$_6$): 3.01–3.04 (m, 1H), 3.27–3.29 (m, 1H), 4.74–4.76 (m, 1H), 7.17 (d, 1H), 7.46 (d, 2H), 7.57 (d, 1H), 7.64 (d, 2H, J=8 Hz), 7.67–7.82 (m, 9H), 8.91 (d, 1H, J=8.4 Hz); LC/MS (m/z): 592 (M+1)$^+$.

EXAMPLE 222

(2S)-[(-4'-Methoxy-biphenyl-3-carbonyl)-amino]-3-(4'-methoxyl-biphenyl-4-yl)-propionic acid (2S)-Amino-3-(4-bromo-phenyl)-propionic acid methyl ester (1.0 g, 3.8 mmol) was reacted with 3-bromo-benzoic acid (0.91 g, 4.5 mmol) as described in general procedure A yielding (2S)-(3-bromo-benzoyl-amino)-3-(4-bromo-phenyl)-propionic acid methyl ester (1.38 g, 81%).

(2S)-(3-Bromo-benzoyl-amino)-3-(4-bromo-phenyl)-propionic acid methyl ester (100 mg, 0.22 mmol) was reacted with 4-methoxy-phenyl-boronic acid (204 mg, 1.4 mmol) according to general procedure D yielding the title compound (90 mg, 83%) as a white solid.

¹H-NMR (400 MHz, DMSO-d$_6$): 3.08 (m, 1H), 3.22 (m, 1H), 3.74 (s, 3H), 3.76 (s, 3H), 4.38 (m, 1H), 6.96–7.01 (m, 3H), 7.25 (d, 2H), 7.43–7.48 (m, 3H), 7.52 (d, 2H), 7.62–7.07 (m, 3H), 7.70 (d, 1H), 7.87 (s, 1H), 8.10 (d, 1H); LC/MS (m/z): 482 (M+1)$^+$.

EXAMPLE 223

3-Biphenyl-4-yl-(2S)-[3-nitro-4-(3-trifluoromethyl-phenoxy)-benzoylamino]-propionic acid

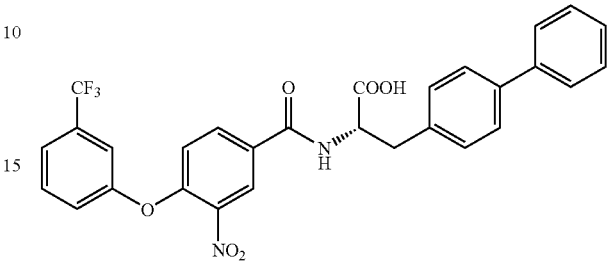

3-Nitro-4-(3-trifluoromethyl-phenoxy)-benzoic acid (530 mg, 81%) was prepared from 4-fluoro-3-nitro-benzoic acid (370 mg, 2.0 mmol) and 3-trifluoromethyl phenol (324 mg, 2.0 mmol) as in general procedure B. To Wang resin (60 mg, 0.06 mmol, 1.1 mmol/g) loaded with 4-L-biphenylalanine were added 82 mg of (0.25 mmol) 3-nitro-4-(3-trifluoromethyl-phenoxy)-benzoic acid (82 mg, 0.25 mmol), 1.0 M DIC (1.5 mL, 1.5 mmol) in DMF, 1.0 M HOBt (1.5 mL, 1.5 mmol) in DMF, and a catalytic amount of DMAP. The resulting mixture was left on shaker overnight. The resin was washed with DMF, MeOH, DCM three times of each and cleaved with 20% TFA in DCM. The residue obtained after removing the solvent was purified by chromatography to give the title compound (26 mg, 79%).

¹H NMR (400 MHz, CDCl$_3$): 3.35, 3.40 (ABX, 2H), 5.18 (dd, 1H), 6.64 (d, 1H), 7.03 (dd, 2H), 7.28 (m, 1H), 7.34 (m, 2H), 7.42 (m, 2H), 7.55 (m, 5H), 7.91 (dd, 1H), 8.21 (dd, 1H), 8.36 (d, 1H), 8.69 (d, 1H); LC/MS (m/z): 551 (M+1)$^+$.

EXAMPLE 224

3-(4'-Trifluoromethyl-biphenyl-4-yl)-(2S)-[4-(4-trifluoromethyl-phenoxy)-benzoylamino]-propionic acid

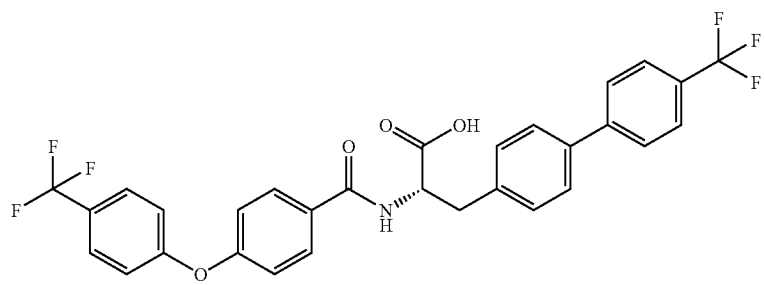

4-(4-Trifluoromethyl-phenoxy)benzoic acid (474 mg, 80%) was prepared from 1-fluoro-4-trifluoromethyl benzene (328 mg, 2.0 mmol) and 4-hydroxy benzoic acid methyl ester (304 mg, 2.0 mmol) following general procedure B, then hydrolyzed following general procedure C to give the corresponding acid (450 mg, 80%). 3-(4'-Trifluoromethyl-biphenyl-4-yl)-(2S)-[4-(4-trifluoromethyl-phenoxy)-benzoylamino]-propionic acid methyl ester (121 mg, 82%) was prepared starting from the above acid (70 mg, 0.25 mmol) and 2-amino-3-(4'-trifluoromethyl-biphenyl-4-yl)-(2S)-propionic acid methyl ester (108 mg, 0.30 mmol) according to general procedure A. The ester was hydrolyzed following general procedure C to give the title compound (105 mg, 89%)
$^1$H NMR (400 MHz, CDCl$_3$): 3.40 (m, 2H), 5.10 (m, 1H), 6.58 (m, 1H), 7.08 (m, 4H), 7.33 (m, 2H), 7.64 (m, 10H); LC/MS (m/z): 574 (M+1)$^+$.

EXAMPLE 225

3-Biphenyl-4-yl-(2S)-[4-(5-trifluoromethyl-pyridin-2-yloxy)-benzoylamino]-propionic acid 5-(Trifluoromethyl)-2-pyridinol (1.63 g, 10 mmol) was reacted with 4-fluorobenzaldehyde (1.24 g, 10 mmol) as described in general procedure B. The resulting compound was oxidized by AgNO$_3$ (20 mmol) in 2N NaOH aq. solution (20 mL, 40 mmol) to afford 4-(5-(trifluoromethyl-pyridin-2-yloxy)-benzoic acid (5.10 g, 80%) as a white solid.
2-L-amino-3-biphenyl-4-yl-propionic acid methyl ester (128 mg, 0.5 mmol) was reacted with above 4-(5-(trifluoromethyl-pyridin-2-yloxy)-benzoic acid (142 mg, 0.5 mmol) as described in general procedure A. The resulting compound was hydrolyzed according to general procedure C to afford the title product (225 mg, 80%) as a white solid.
$^1$H-NMR(400 MHz, CDCl$_3$): 3.21 (dd, 1H), 3.36 (dd, 1H), 5.02 (dd, 1H), 6.74 (d, 1H), 7.39–7.27 (m, 8H), 7.56–7.48 (m, 5H), 7.67 (s, 1H), 7.79 (d, 2H); LC/MS (m/z): 507(M+1)$^+$

EXAMPLE 226

3-[4-(4-Trifluoromethyl-phenoxy)-phenyl]-(2S)-[(4'-trifluoromethyl-biphenyl-4-carbonyl)-amino]-propionic acid 3-(4-Hydroxy-phenyl)-(2S)-[(4'-trifluoromethyl-biphenyl-4-carbonyl)-amino]-propionic acid methyl ester (664 mg, 75%) was prepared starting from 4'-trifluoromethyl-biphenyl-4-carboxylic acid (532 mg, 2.0 mmol) and tyrosine methyl ester (462 mg, 2.0 mmol) according to general procedure A. The above compound (443 mg, 1.0 mmol) was treated with 1-fluoro-4-trifluorobenzene (246 mg, 1.5 mmol) following general procedure B to give 3-[4-(4-trifluoromethyl-phenoxy)-phenyl]-(2S)-[(4'-trifluoromethyl-biphenyl-4-carbonyl)-amino]-propionic acid methyl ester (305 mg, 52%). The ester was hydrolyzed following general procedure C to give the title compound (296 mg, 99%). $^1$H NMR (400 MHz, CDCl$_3$): 3.22, 3.36 (ABX, 2H), 5.04 (dd, 1H), 6.56 (d, 1H), 6.94 (m, 4H), 7.17 (m, 2H), 7.49 (d, 2H), 7.63 (m, 6H), 7.76 (d, 2H); LC/MS (m/z): 574 (M+1)$^+$.

EXAMPLE 227

3-[4-(4-Cyano-phenoxy)-phenyl]-(2S)-[(4'-trifluoromethyl-biphenyl-4-carbonyl)-amino]-propionic acid 3-(4-Hydroxy-phenyl)-(2S)-[(4'-trifluoromethyl-biphenyl-4-carbonyl)-amino]-propionic acid methyl ester (664 mg, 75%) was prepared starting from 4'-trifluoromethyl-biphenyl-4-carboxylic acid (532 mg, 2.0 mmol) and tyrosine methyl ester (462 mg, 2.0 mmol) according to general procedure A. The above compound (443 mg, 1.0 mmol) was treated with 1-fluoro-4-cyanobenzene (181 mg, 1.5 mmol) following general procedure B to give 3-[4-(4-cyano-phenoxy)-phenyl]-(2S)-[(4'-trifluoromethyl-biphenyl-4-carbonyl)-amino]-propionic acid methyl ester (360 mg, 66%). The ester was hydrolyzed following general procedure C to give the title compound (345 mg, 99%)
$^1$H NMR (400 MHz, CDCl$_3$): 3.28, 3.44 (ABX, 2H), 5.12 (dd, 1H), 6.65 (d, 1H), 6.99 (m, 4H), 7.28 (m, 2H), 7.58 (d, 2H), 7.69 (m, 6H), 7.84 (d, 2H); LC/MS (m/z): 530 (M+1)$^+$.

EXAMPLE 228

(2S)-(4-Benzyloxy-benzoylamino)-3-biphenyl-4-yl-propionic acid

2-L-amino-3-biphenyl-4-yl-propionic acid methyl ester (255 mg, 1.0 mmol) was reacted with 4-(benzyloxy)-benzoic acid (228 mg, 1.0 mmol) as described in general procedure A. The resulting compound was hydrolyzed according to general procedure C to afford the title product (370 mg, 82%) as a white solid. $^1$H-NMR(400 MHz, CDCl$_3$): 3.31 (dd, 1H), 3.40 (dd, 1H), 5.09–5.05 (m, 3H), 6.56 (d, 1H), 6.96 (d, 2H), 7.27 (d, 2H), 7.36–7.32 (m, 2H), 7.43–7.38 (m, 6H), 7.57–7.52 (m, 4H), 7.67 (d, 2H); LC/MS (m/z): 452 (M+1)$^+$.

By analogous methods to those described above the following compounds were synthesized

| EXAMPLE | NAME | LC/MS (m/z) |
|---|---|---|
| 229 | 3-Biphenyl-4-yl-(2S)-[(4'-trifluoromethyl-biphenyl-3-carbonyl)-amino]-propionic acid | 490 |
| 230 | 3-Biphenyl-4-yl-(2S)-[(3-chloro-4'-trifluoromethyl-biphenyl-4-carbonyl)-amino]-propionic acid | 524 |
| 231 | 3-Biphenyl-4-yl-(2S)-[4-(4-nitro-phenoxy)-benzoylamino]-propionic acid | 483 |
| 232 | 3-Biphenyl-4-yl-(2S)-[4-(3,4-dimethyl-phenoxy)-3-nitro-benzoylamino]-propionic acid | 511 |
| 233 | 3-Biphenyl-4-yl-(2S)-[(3'-trifluoromethyl-biphenyl-4-carbonyl)-amino]-propionic acid | 490 |
| 234 | 3-Biphenyl-4-yl-(2S)-[(3',5'-bis-trifluoromethyl-biphenyl-4-carbonyl)-amino]-propionic acid | 558 |
| 235 | 3-Biphenyl-4-yl-(2S)-[(4'-tert-butyl-biphenyl-4-carbonyl)-amino]-propionic acid | 478 |
| 236 | 3-Biphenyl-4-yl-(2S)-[(4'-dimethylamino-biphenyl-4-carbonyl)-amino]-propionic acid | 465 |
| 237 | 3-Biphenyl-4-yl-(2S)-[(4'-methoxy-biphenyl-4-carbonyl)-amino]-propionic acid | 452 |
| 238 | 3-Biphenyl-4-yl-2-[(3',4'-dichloro-biphenyl-4-carbonyl)-amino]-propionic acid | 490 |
| 239 | 3-Biphenyl-4-yl-(2S)-[(5'-chloro-2'-methoxy-biphenyl-4-carbonyl)-amino]-propionic acid | 486 |
| 240 | (2S)-[(3'-Amino-biphenyl-4-carbonyl)-amino]-3-biphenyl-4-yl-propionic acid | 437 |
| 241 | (2S)-[(4'-Trifluoromethoxy-biphenyl-4-carbonyl)-amino]-3-(4'-trifluoromethyl-biphenyl-4-yl)-propionic acid | 574 |
| 242 | 3-(4'-Trifluoromethoxy-biphenyl-4-yl)-(2S)-[(4'-trifluoromethyl-biphenyl-4-carbonyl)-amino]-propionic acid | 574 |
| 243 | 3-(4-Pyridin-4-yl-phenyl)-(2S)-[(4'-trifluoromethyl-biphenyl-4-carbonyl)-amino]-propionic acid | 491 |
| 244 | 3-Biphenyl-4-yl-(2S)-[4-(5-trifluoromethyl-pyridin-2-yl)-benzoylamino]-propionic acid | 491 |

-continued

| EXAMPLE | NAME | LC/MS (m/z) |
|---|---|---|
| 245 | 3-(4-Pyridin-4-yl-phenyl)-(2S)-[4-(5-trifluoromethyl-pyridin-2-yl)-benzoylamino]-propionic acid | 492 |
| 246 | 3-(4'-Methanesulfonylamino-biphenyl-4-yl)-(2S)-[(4'-trifluoromethyl-biphenyl-4-carbonyl)-amino]-propionic acid | 583 |
| 247 | 3-(3'-Chloro-4'-fluoro-biphenyl-4-yl)-(2S)-[(4'-trifluoromethyl-biphenyl-4-carbonyl)-amino]-propionic acid | 542 |
| 248 | 3-(4'-Cyano-biphenyl-4-yl)-(2S)-[(4'-trifluoromethyl-biphenyl-4-carbonyl)-amino]-propionic acid | 515 |
| 249 | 3-(5-Phenyl-pyridin-2-yl)-2-[(4'-trifluoromethoxy-biphenyl-4-carbonyl)-amino]-propionic acid | 507 |
| 250 | 3-(4'-Amino-biphenyl-4-yl)-(2S)-[(4'-trifluoromethyl-biphenyl-4-carbonyl)-amino]-propionic acid | 505 |
| 251 | 3-(4'-Dimethylamino-biphenyl-4-yl)-(2S)-[(4'-trifluoromethyl-biphenyl-4-carbonyl)-amino]-propionic acid | 533 |
| 252 | 3-(4'-Trifluoromethoxy-biphenyl-4-yl)-(2S)-[4-(5-trifluoromethyl-pyridin-2-yl)-benzoylamino]-propionic acid | 575 |
| 253 | 3-(4'-Trifluoromethyl-biphenyl-4-yl)-(2S)-[4-(5-trifluoromethyl-pyridin-2-yl)-benzoylamino]-propionic acid | 559 |
| 254 | 3-(4'-Trifluoromethoxy-biphenyl-4-yl)-(2S)-[4-(4-trifluoromethyl-phenoxy)-benzoylamino]-propionic acid | 590 |
| 255 | 3-Biphenyl-4-yl-(2S)-[4-(4-trifluoromethyl-phenoxy)-benzoylamino]-propionic acid | 506 |
| 256 | 3-Biphenyl-4-yl-(2S)-[4-(4-formyl-phenoxy)-benzoylamino]-propionic acid | 466 |
| 257 | 3-(5'-Chloro-2'-methoxy-biphenyl-4-yl)-(2S)-[(4'-trifluoromethyl-biphenyl-4-carbonyl)-amino]-propionic acid | 554 |
| 258 | 3-(4'-Chloro-biphenyl-4-yl)-(2S)-[(4'-trifluoromethyl-biphenyl-4-carbonyl)-amino]-propionic acid | 524 |
| 259 | 3-Biphenyl-4-yl-(2R)-[(4'-trifluoromethyl-biphenyl-4-carbonyl)-amino]-propionic acid | 490 |
| 260 | 3-(5-Phenyl-pyridin-2-yl)-2-[(4'-trifluoromethyl-biphenyl-4-carbonyl)-amino]-propionic acid | 491 |
| 261 | 3-(3'-Acetylamino-biphenyl-4-yl)-(2S)-[(4'-trifluoromethyl-biphenyl-4-carbonyl)-amino]-propionic acid | 547 |
| 262 | 3-(3',4'-Dichloro-biphenyl-4-yl)-(2S)-[(4'-trifluoromethyl-biphenyl-4-carbonyl)-amino]-propionic acid | 558 |
| 263 | 3-(5'-Fluoro-2'-methoxy-biphenyl-4-yl)-(2S)-[(4'-trifluoromethyl-biphenyl-4-carbonyl)-amino]-propionic acid | 538 |
| 264 | 3-[4'-(Acetylamino-methyl)-biphenyl-4-yl]-(2S)-[(4'-trifluoromethyl-biphenyl-4-carbonyl)-amino]-propionic acid | 561 |
| 265 | 3-(4'-Trifluoromethoxy-biphenyl-4-yl)-(2S)-[4-(5-trifluoromethyl-pyridin-2-yloxy)-benzoylamino]-propionic acid | 591 |
| 266 | 3-Biphenyl-4-yl-(2S)-[4-(5-trifluoromethyl-pyridin-2-yloxy)-benzoylamino]-propionic acid | 507 |
| 267 | 3-[4-(4-Nitro-phenoxy)-phenyl]-(2S)-[(4'-trifluoromethyl-biphenyl-4-carbonyl)-amino]-propionic acid | 553 |
| 268 | 3-[4-(4-Formyl-phenoxy)-phenyl]-(2S)-[(4'-trifluoromethyl-biphenyl-4-carbonyl)-amino]-propionic acid | 534 |
| 269 | 3-(4-Thiophen-3-yl-phenyl)-(2S)-[(4'-trifluoromethyl-biphenyl-4-carbonyl)-amino]-propionic acid | 496 |
| 270 | 3-(4-Thiophen-3-yl-phenyl)-(2S)-[(4'-trifluoromethoxy-biphenyl-4-carbonyl)-amino]-propionic acid | 512 |
| 271 | (2S)-(4-Benzyloxy-benzoylamino)-3-(4'-trifluoromethoxy-biphenyl-4-yl)-propionic acid | 536 |
| 272 | 3-(2'-Phenoxy-biphenyl-4-yl)-(2S)-[(4'-trifluoromethyl-biphenyl-4-carbonyl)-amino]-propionic acid | 537 |
| 273 | 3-(4'-Phenoxy-biphenyl-4-yl)-(2S)-[(4'-trifluoromethyl-biphenyl-4-carbonyl)-amino]-propionic acid | 582 |

EXAMPLE 274

3-Biphenyl-4-yl-(2S)-[2-(4-tert-butyl-benzoylamino)-5-iodo-benzoyl-amino]-propionic acid (2S)-(2-Amino-5-iodo-benzoyl-amino)-3-biphenyl-4-yl-propionic acid methyl ester (1.53 g, 80%) was prepared from (2S)-amino-3-biphenyl-4-yl-propionic acid methyl ester (1.0 g, 4.1 mmol), 5-iodo-2-amino-benzoic acid (1.23 g, 4.9 mmol) as described in general procedure A.

3-Biphenyl-4-yl-(2S)-[2-(4-tert-butyl-benzoylamino)-5-iodo-benzoyl-amino]-propionic acid methyl ester was prepared as a white solid from (2S)-(2-amino-5-iodo-benzoyl-amino)-3-biphenyl-4-yl-propionic acid methyl ester (1.0 g, 2 mmol) prepared above, pyridine (1.58 g, 4 mmol), t-butyl-benzoyl chloride (1.20 g, 2.5 mmol) as described in general procedure K. The title compound (1.23 g, 100%) as a white solid ((1.23 g, 100%) was obtained after hydrolysis according to general procedure C $^1$H-NMR(400 MHz, DMSO-$d_6$): 1.26 (s, 9H), 3.09–3.19 (m, 1H), 3.21–3.29 (m, 1H), 4.74–4.76 (m, 1H), 7.27–7.29 (m, 1H ), 7.42–7.39 (m, 4H), 7.44–7.57 (m, 7H), 7.67–7.77 (m, 3H), 7.99 (s, 1H), 8.54 (d, 1H), 9.32 (d, 1H), 11.98 (s, 1H); LC/MS (m/z): 647 (M+1)$^+$.

EXAMPLE 275

3-Biphenyl-4-yl-(2S)-{[4-(4-tert-butyl-benzoylamino)-3'-trifluoromethyl-biphenyl-3-carbonyl]-amino}-propionic acid Example 274 (100 mg, 0.15 mmol) was reacted with 3-trifluoromethyl phenyl boronic acid (87.5 mg, 4.5 mmol) as described in general procedure D yielding the title compound (92 mg, 90%) as white solid. LC/MS (m/z): 665 (M+1)$^+$.

EXAMPLE 276

3-Biphenyl-4-yl-(2S)-{[4-(4-tert-butyl-benzoylamino)-4'-nitro-biphenyl-3-carbonyl]-amino}-propionic acid Example 274 (100 mg, 0.15 mmol) was reacted with 4-nitro-phenyl boronic acid (77 mg, 4.5 mmol) as described in general procedure D yielding the title compound (92 mg, 90%) as white solid. LC/MS (m/z): 642 (M+1)$^+$.

EXAMPLE 277

3-Biphenyl-4-yl-(2S)-{[4-(4-tert-butyl-benzoylamino)-3'-chloro-4'-fluoro-biphenyl-3-carbonyl]-amino}-propionic acid Example 274 (100 mg, 0.15 mmol) was reacted with 3-chloro-4-fluoro-phenyl boronic acid (80 mg, 4.5 mmol) as described in general procedure D yielding the title compound (95 mg, 95%) as a white solid.

$^1$H-NMR(400 MHz, DMSO-d$_6$): 1.28 (s, 9H), 3.09–3.19 (m, 1H), 3.21–3.29 (m, 1H), 4.74–4.76 (m, 1H), 7.27–7.29 (m, 1H), 7.32–7.44 (m, 6H), 7.44–7.57 (m, 7H), 7.50–7.59 (m, 2H), 7.71–7.77 (m, 2H), 7.80–7.86 (m, 2H), 7.88–7.90 (m, 3H), 8.3 (s, 2H), 8.7 (d, 1H), 9.38 (d, 1H), 12.00 (s, 1H); LC/MS (m/z): 647 (M+1)$^+$.

EXAMPLE 278

3-Biphenyl-4-yl-(2S)-[4-(4-tert-butyl-benzoylamino)-5-(4-chloro-3-trifluromethyl-phenoxy)-benzoylamino]-propionic acid Example 274 (100 mg, 0.15 mmol), 4-chloro-3-trifluoromethyl phenol (60.4 mg, 0.3 mmol), cesium carbonate (0.3 mmol), CuI (0.15 mmol) were added to 10 mL of toluene containing 4 Å molecular sieves. The mixture was degassed and filled with nitrogen three times. This mixture was then heated to reflux under nitrogen and followed by HPLC until completion of the reaction. The reaction with diluted with toluene and filtered. The toluene was evaporated, and the residue was dissolved in ethyl acetate washed with 2M HCl and then saturated NaCl. The title compound (70 mg, 65%) was isolated by flash chromatography (silica, 1% MeOH in DCM) as a white solid. $^1$H-NMR (400 MHz, CDCl$_3$): 1.35 (s, 9H), 3.22–3.27 (m, 1H), 3.32–3.37 (m, 1H, 5.03–5.13 (m, 1H), 6.69 (d, 1H), 6.98–7.01 (m, 1H), 7.13–7.18 (m, 4H), 7.28–7.53 (m, 10H), 7.93 (d, 1H), 8.85 (d, 1H), 11.72 (s, 1H); LC/MS (m/z): 715 (M+1)$^+$.

EXAMPLE 279

3-Biphenyl-4-yl-(2S)-[2-(3,5-bis-trifluoromethyl-benzoylamino)-5-bromo-benzoylamino]-propionic acid To a solution of fmoc-L-biphenylalanine (40.0 mmol) in DMF (40 mL) was added Wang resin (16.0 mmol), HOBt (40.0 mmol) in DMF (40 mL), DIC (40.0 mmol) in DMF (40 mL) and DMAP (0.40 mmol) and the mixture was shaken overnight. The reaction mixture was drained and the resin washed with DMF, methanol and DCM (3×150 mL each solvent).

The resulting resin-bound fmoc-L-biphenylalanine was deprotected with 20% piperidine in DMF (150 mL) for 2 hours. The reaction mixture was drained and washed with DMF, methanol and DCM (3×150 mL each solvent).

To the resin-bound L-biphenylalanine (12 mmol), a solution of 2-amino-5-bromobenzoic acid (30 mmol) in DMF (30 mL), HOBt (30 mmol) in DMF (30 mL) and DIC (30 mmol) in DMF (30 mL) were added and the mixture was shaken overnight. The reaction mixture was drained and washed with DMF, methanol and DCM (3×150 mL each solvent).

To the resin-bound (S)-2-(2-amino-5-bromo-benzoylamino)-3-biphenyl-4-yl-propionic acid (0.12 mmol) was added a solution of 3,5-bis-(trifluoromethyl)benzoyl chloride (0.3 mmol) and pyridine (0.3 mmol) and the mixture agitated for 72 hours. The reaction mixture was drained and washed with DMF, methanol and DCM (3×5 mL each solvent).

Resin bound (S)-3-biphenyl-4-yl-2-[2-(3,5-bistrifluoromethyl-benzoylamino)-5-bromo-benzoylamino]propionic acid was treated with 20% TFA in DCM (2 mL) for 1 hour. The filtrate was collected and evaporated to give (S)-3-biphenyl-4-yl-2-[2-(3,5-bis(trifluoromethyl)-benzoylamino)-5-bromo-benzoylamino]propionic acid (0.0412 g, 50%). The product was purified via chromatography (silica, DCM/ethyl acetate). LC/MS (m/z): 680 (M+1)$^+$.

EXAMPLE 280

(2S)-[5-Bromo-(2S)-(2-cyclopentyl-acetylamino)-benzoylamino]-3-(2'-phenoxy-biphenyl-4-yl)-propionic acid (S)-(2-Amino-5-bromo-benzoylamino)-3-(2'-phenoxy-biphenyl-4-yl)-propionic acid methyl ester (1.53 g, 80%) was prepared from (2S)-Amino-3-(2'-phenoxy-biphenyl-4-yl)-propionic acid methyl ester HCl salt (1.0 g, 2.6 mmol, 5-bromo-2-amino-benzoic acid (0.5 g, 2.9 mmol) as described in general procedure A.

(S)-(2-Amino-5-bromo-benzoylamino)-3-(2'-phenoxy-biphenyl-4-yl)-propionic acid methyl ester (0.2 g, 0.04 mmol) in 5 ml of DCM was reacted with cyclopentyl acetyl chloride (82.6 mg, 0.06 mmol) and pyridine (60 mg, 0.08 mmol) as described in general procedure K. The resulting ester was hydrolyzed according to the general procedure C to afford the title compound (0.2 g, 83.3%) as a white solid. LCMS: 642 (M+1)$^+$. $^1$H NMR (CDCl$_3$): 1.1–1.26 [m, 3H], 1.5–1.75 [m, 3H], 1.8–1.90 [m, 2H], 2.2–2.41 [m, 2H], 2.48 [d, 1H], 3.1–3.4 [m, 2H], 5.0–5.1 [m, 1H], 6.6 [d, 1H], 6.89–6.97 [m, 4H], 7.18–7.26 [m, 6H], 7.43–7.52 [m, 5H], 8.48 (d, 1), 10.73 (s, 1H).

EXAMPLE 281

(2S)-[5-Bromo-2-(3,3,5-trimethyl-hexanoylamino)-benzoylamino]-3-(2'-phenoxy-biphenyl-4-yl)-propionic acid A solution of (2S)-(2-amino-5-bromo-benzoylamino)-3-(2'-phenoxy-biphenyl-4-yl)-propionic acid methyl ester (54.5 mg, 0.10 mmol) from example 294 in 1 mL dry CH$_2$Cl$_2$ was treated with 3,5,5-trimethylhexanoyl chloride (1.2 eq., 23 microL, 0.12 mmol) and pyridine (1.5 eq., 12 microL, 0.15 mmol) in succession and stirred under an atmosphere of dry N$_2$ for one hour, then concentrated in vacuo. The crude residue was purified by flash column chromatography (hexanes, EtOAc) to afford the desired amide, (2S)-[5-Bromo-2-(3,3,5-trimethyl-hexanoylamino)-benzoylamino]-3-(2'-phenoxy-biphenyl-4-yl)-propionic acid methyl ester, in quantitative yield (68 mg, 100%). The methyl ester (20 mg, 29 micromol) was dissolved in 2.0 mL THF and 0.5 mL MeOH and saponified with 2N aqueous LiOH solution (0.25 mL), as described in general procedure C, to afford the title compound, (2S)-[5-Bromo-2-(3,3,5-trimethyl-hexanoylamino)-benzoylamino]-3-(2'-phenoxy-biphenyl-4-yl)-propionic acid (20 mg, 100%), as a white solid. LCMS 673 (M+1)$^+$. $^1$H NMR (400 MHz, CDCl$_3$) 10.74 [s, 1H], 8.51 [d, 1H], 7.51 [m, 3H], 7.43 [m, 2H], 7.27–7.30 [m, 2H], 7.16–7.26 [m, 5H], 6.98 [d, 2H], 6.88 [d, 2H], 6.59 [d, 1H], 5.03 [dd, 1H], 3.28 [dq, 2H], 2.36 [m, 1H], 2.14 [m, 1H], 1.11–1.25 [m, 3H], 1.00 [s, 3H], 0.92 [s, 3H], 0.91 [d, 6H].

EXAMPLE 282

(2S)-[5-Chloro-2-(4-phenoxy-benzoylamino)-benzoylamino]-3-(2'-isopropoxy-biphenyl-4-yl)-propionic acid 2-Amino-5-chloro-benzoic acid (0.702 g, 4.09 mmol) was coupled with 2-Amino-3-(4-bromo-phenyl)-propionic acid methyl ester hydrochloride (1 g, 4.09 mmol) using HBTU (1.86 g, 4.908 mmol) and diisopropylethylamine (1.32 ml, 10.22 mmol) as per general procedure A to yield the 2-(2-amino-5-chloro-benzoylamino)-3-(4-bromo-phenyl)-propionic acid methyl ester in 60% yield.

The above compound (0.500 g, 1.21 mmol) was reacted with 4-phenoxy-benzoyl chloride (0.337 g, 1.45 mmol) in dry dichloromethane at 0° C. as described in general procedure J to get 3-(4-Bromo-phenyl)-2-[5-chloro-2-(4-phenoxy-benzoylamino)-benzoylamino]-propionic acid methyl ester (0.590 g, 80%).

The above compound (0.100 g, 0.164 mmol) was then subjected to Suzuki coupling with 2-isopropoxyphenylboronic acid (0.059 g, 0.328 mmol) and with Pd(PPh$_3$) (0.018 g, 0.016 mmol) and 2N Na$_2$CO$_3$ (0.410 ml, 0.410 mmol) as per general procedure D to yield (2S)-[5-chloro-2-(4-phenoxy-benzoylamino)-benzoylamino]-3-(2'-isopropoxy-biphenyl-4-yl)-propionic acid methyl ester which was further hydrolyzed as per general procedure C to give the title compound (0.050 g, 50%)%). $^1$H-NMR(400 MHz, CDCl$_3$): 1.56(d, 6H), 3.65(dddd, 2H), 4.76(m, 1H), 5.42(m, 1H), 7.30–7.38(m, 6H), 7.39–7.58(m, 8H), 7.59–7.83(m, 6H), 8.27 (m, 2H), 9.01(d, 1H). LC/MS (m/z): 649(M+1).

By analogous methods to those described above the following compounds were synthesized.

| EXAMPLE | NAME | LC/MS (m/z) |
|---|---|---|
| 283 | 3-Biphenyl-4-yl-(2S)-[2-(4-tert-butyl-benzoylamino)-benzoylamino]-propionic acid | 521 |
| 284 | 3-Biphenyl-4-yl-(2S)-[5-chloro-2-(2,4-dichloro-benzoylamino)-benzoylamino]-propionic acid | 567 |
| 285 | (2S)-({4-[(Biphenyl-4-carbonyl)-amino]-3'-chloro-4'-fluoro-biphenyl-3-carbonyl}-amino)-3-biphenyl-4-yl-propionic acid | 669 |
| 286 | (2S)-{2-[(Biphenyl-4-carbonyl)-amino]-benzoylamino}-3-(3'-chloro-4'-fluoro-biphenyl-4-yl)-propionic acid | 593 |
| 287 | (2S)-[2-(4-tert-Butyl-benzoylamino)-benzoylamino]-3-(3'-chloro-4'-fluoro-biphenyl-4-yl)-propionic acid | 573 |
| 288 | 3-Biphenyl-4-yl-(2S)-[5-bromo-2-(4-tert-butyl-benzoylamino)-benzoylamino]-propionic acid | 600 |
| 289 | 3-Biphenyl-4-yl-(2S)-{[4-(4-tert-butyl-benzoylamino)-4'-cyano-biphenyl-3-carbonyl]-amino}-propionic acid | 622 |
| 290 | (2S)-{[4'-Amino-4-(4-tert-butyl-benzoylamino)-biphenyl-3-carbonyl]-amino}-3-biphenyl-4-yl-propionic acid | 612 |
| 291 | 3-Biphenyl-4-yl-(2S)-{[4-(4-tert-butyl-benzoylamino)-3'-cyano-biphenyl-3-carbonyl]-amino}-propionic acid | 622 |
| 292 | (2S)-({3-[(Biphenyl-4-carbonyl)-amino]-naphthalene-2-carbonyl}-amino)-3-(3'-chloro-4'-fluoro-biphenyl-4-yl)-propionic acid | 643 |
| 293 | (2S)-{[3-(4-tert-Butyl-benzoylamino)-naphthalene-2-carbonyl]-amino}-3-(3'-chloro-4'-fluoro-biphenyl-4-yl)-propionic acid | 623 |
| 294 | (2S)-{[3'-Aminomethyl-4-(4-tert-butyl-benzoylamino)-biphenyl-3-carbonyl]-amino}-3-biphenyl-4-yl-propionic acid | 626 |
| 295 | 3-Biphenyl-4-yl-(2S)-{[4-(4-tert-butyl-benzoylamino)-4'-carbamimidoyl-biphenyl-3-carbonyl]-amino}-propionicacid | 639 |
| 296 | 3-Biphenyl-4-yl-(2S)-[2-(4-tert-butyl-benzoylamino)-5-(4-nitro-phenoxy)-benzoylamino]-propionic acid | 658 |
| 297 | (2S)-{[4-(4-tert-Butyl-benzoylamino)-3'-trifluoromethyl-biphenyl-3-carbonyl]-amino}-3-(3'-trifluoromethyl-biphenyl-4-yl)-propionic acid | 733 |
| 298 | (2S)-{[4-(4-tert-Butyl-benzoylamino)-3'-chloro-4-fluoro-biphenyl-3-carbonyl]-amino}-3-(3'-chloro-4'-fluoro-biphenyl-4-yl)-propionic acid | 701 |
| 299 | (2S)-{[4-(4-tert-Butyl-benzoylamino)-4'-trifluoromethyl-biphenyl-3-carbonyl]-amino}-3-(4'-trifluoromethyl-biphenyl-4-yl)-propionic acid | 733 |
| 300 | 3-Biphenyl-4-yl-(2S)-[5-bromo-2-(3-phenyl-acryloylamino)-benzoylamino]-propionic acid | 570 |
| 301 | 3-Biphenyl-4-yl-(2S)-{5-bromo-2-[(naphthalene-2-carbonyl)-amino]-benzoylamino}-propionic acid | 594 |
| 302 | 3-Biphenyl-4-yl-(2S)-[5-bromo-2-(2-cyclopentyl-acetylamino)-benzoylamino]-propionic acid | 550 |
| 303 | 3-Biphenyl-4-yl-(2S)-[5-bromo-2-(4-trifluoromethoxy-benzoylamino)-benzoylamino]-propionic acid | 628 |
| 304 | 3-Biphenyl-4-yl-(2S)-[5-bromo-2-(4-phenoxy-butyrylamino)-benzoylamino]-propionic acid | 602 |
| 305 | 3-Biphenyl-4-yl-(2S)-{5-bromo-2-[2-(4-tert-butyl-phenoxy)-acetylamino]-benzoylamino}-propionic acid | 630 |
| 306 | (2S)-[2-(4-tert-Butyl-benzoylamino)-5-chloro-benzoylamino]-3-(4'-phenoxy-biphenyl-4-yl)-propionic acid | 647 |
| 307 | 2-[5-Bromo-(2S)-(4-tert-butyl-benzoylamino)-benzoylamino]-3-(4'-phenoxy-biphenyl-4-yl)-propionic acid | 692 |
| 308 | 3-Biphenyl-4-yl-(2S)-[4-chloro-2-(4-trifluoromethyl-benzoylamino)-benzoylamino]-propionic acid | 567 |
| 309 | 3-Biphenyl-4-yl-(2S)-[2-(4-tert-butyl-benzoylamino)-5-(4-trifluoromethyl-phenoxy)-benzoylamino]-propionic acid | 681 |
| 310 | 3-Biphenyl-4-yl-(2S)-[2-(4-trifluoromethyl-benzoylamino)-5-(4-trifluoromethyl-phenoxy)-benzoylamino]-propionic acid | 693 |
| 311 | 3-Biphenyl-4-yl-(2S)-[2-(4-tert-butyl-benzoylamino)-4-(4-trifluoromethyl-phenoxy)-benzoylamino]-propionic acid | 681 |
| 312 | (2S)-[2-(4-tert-Butyl-benzoylamino)-5-chloro-benzoylamino]-3-(2'-phenoxy-biphenyl-4-yl)-propionic acid | 647 |
| 313 | (2S)-[5-Chloro-2-(4-phenoxy-benzoylamino)-benzoylamino]-3-(2'-phenoxy-biphenyl-4-yl)-propionic acid | 683 |
| 314 | (2S)-[2-(4-Benzyloxy-benzoylamino)-5-chloro-benzoylamino]-3-(2'-phenoxy-biphenyl-4-yl)-propionic acid | 697 |
| 315 | (2S)-(5-Bromo-2-phenylacetylamino-benzoylamino)-3-(2'-phenoxy-biphenyl-4-yl)-propionic acid | 650 |
| 316 | (2S)-[5-Bromo-2-(4-bromo-benzoylamino)-benzoylamino]-3-(2'-phenoxy-biphenyl-4-yl)-propionic acid | 715 |
| 317 | (2S)-{5-Bromo-2-[2-(4-fluoro-phenyl)-acetylamino]-benzoylamino}-3-(2'-phenoxy-biphenyl-4-yl)-propionic acid | 668 |
| 318 | 2-{5-Bromo-(2S)-[(naphthalene-2-carbonyl)-amino]-benzoylamino}-3-(2'-phenoxy-biphenyl-4-yl)-propionic acid | 686 |
| 319 | (2S)-{5-Bromo-2-[(naphthalene-1-carbonyl)-amino]-benzoylamino}-3-(2'-phenoxy-biphenyl-4-yl)-propionic acid | 686 |
| 320 | (2S)-[5-Chloro-2-(3-phenoxy-benzoylamino)-benzoylamino]-3-(2'-phenoxy-biphenyl-4-yl)-propionic acid | 683 |

| EXAMPLE | NAME | LC/MS (m/z) |
|---|---|---|
| 321 | -S-[2-(3-Benzyloxy-benzoylamino)-5-chloro-benzoylamino]-3-(2'-phenoxy-biphenyl-4-yl)-propionic acid | 697 |
| 322 | (2S)-[5-Bromo-2-(4-phenoxy-benzoylamino)-benzoylamino]-3-(2'-phenoxy-biphenyl-4-yl)-propionic acid | 728 |
| 323 | (2S)-[5-Bromo-2-(4-hexyl-benzoylamino)-benzoylamino]-3-(2'-henoxy-biphenyl-4-yl)-propionic acid | 720 |
| 324 | (2S)-[5-Bromo-2-(4-fluoro-benzoylamino)-benzoylamino]-3-(2'-phenoxy-biphenyl-4-yl)-propionic acid | 654 |
| 325 | (2S)-{5-Bromo-2-[(thiophene-2-carbonyl)-amino]-benzoylamino}-3-(2'-phenoxy-biphenyl-4-yl)-propionic acid | 642 |
| 326 | (2S)-[5-Bromo-2-(2-thiophen-2-yl-acetylamino)-benzoylamino]-3-(2'-phenoxy-biphenyl-4-yl)-propionic acid | 656 |
| 327 | (2S)-[5-Bromo-2-(cyclopropanecarbonyl-amino)-benzoylamino]-3-(2'-phenoxy-biphenyl-4-yl)-propionic acid | 600 |
| 328 | (2S)-[5-Bromo-2-(cyclobutanecarbonyl-amino)-benzoylamino]-3-(2'-phenoxy-biphenyl-4-yl)-propionic acid | 614 |
| 329 | (2S)-[5-Bromo-2-(cyclopentanecarbonyl-amino)-benzoylamino]-3-(2'-phenoxy-biphenyl-4-yl)-propionic acid | 628 |
| 330 | (2S)-[5-Bromo-2-(2-propyl-pentanoylamino)-benzoylamino]-3-(2'-phenoxy-biphenyl-4-yl)-propionic acid | 658 |
| 345 | (2S)-[5-Bromo-2-(2-phenoxy-propionylamino)-benzoylamino]-3-(2'-phenoxy-biphenyl-4-yl)-propionic acid | 680 |
| 332 | (2S)-[2-(3,5-Bis-rifluoromethyl-benzoylamino)-5-chloro-benzoylamino]-3-(3'-phenoxy-biphenyl-4-yl)-propionic acid | 727 |
| 333 | (2S)-[5-Bromo-2-(3,4,5-trimethoxy-benzoylamino)-benzoylamino]-3-(2'-phenoxy-biphenyl-4-yl)-propionic acid | 726 |
| 334 | (2S)-{2-[(Adamantane-1-carbonyl)-amino]-5-bromo-benzoylamino}-3-(2'-phenoxy-biphenyl-4-yl)-propionic acid | 694 |
| 335 | (2S)-(5-Bromo-2-{[1-(4-chloro-phenyl)-cyclopropanecarbonyl]-amino}-benzoylamino)-3-(2'-phenoxy-biphenyl-4-yl)-propionic acid | 710 |
| 336 | (2S)-(5-Bromo-2-{[1-(2,4-dichloro-phenyl)-cyclopropanecarbonyl]-amino}-benzoylamino)-3-(2'-phenoxy-biphenyl-4-yl)-propionic acid | 744 |
| 337 | (2S)-{5-Bromo-2-[(2,2-dichloro-1-methyl-cyclopropanecarbonyl)-amino]-benzoylamino}-3-(2'-phenoxy-biphenyl-4-yl)-propionic acid | 682 |
| 338 | (2S)-{5-Chloro-2-[(6-chloro-pyridine-3-carbonyl)-amino]-benzoylamino}-3-(2'-phenoxy-biphenyl-4-yl)-propionic acid | 626 |
| 339 | (2S)-(5-Chloro-2-{[1-(4-trifluoromethyl-pyrimidin-2-yl)-piperidine-4-carbonyl]-amino}-enzoylamino)-3-(2'-phenoxy-biphenyl-4-yl)-propionic acid | 744 |
| 340 | (2S)-{5-Bromo-2-[(1-phenyl-cyclopropanecarbonyl)-amino]-benzoylamino}-3-(2'-phenoxy-biphenyl-4-yl)-propionic acid | 676 |
| 341 | (2S)-{5-Bromo-2-[(2-phenyl-cyclopropanecarbonyl)-amino]-benzoylamino}-3-(2'-phenoxy-biphenyl-4-yl)-propionic acid | 676 |
| 342 | (2S)-[5-Chloro-2-(2-phenoxy-benzoylamino)-benzoylamino]-3-(2'-phenoxy-biphenyl-4-yl)-propionic acid | 683 |
| 343 | 3-(2'-Benzyloxy-biphenyl-4-yl)-(2S)-[2-(3,5-bis-trifluoromethyl-benzoylamino)-5-chloro-benzoylamino]-propionic acid | 741 |
| 344 | (2S)-{5-Chloro-2-[(6-phenoxy-pyridine-3-carbonyl)-amino]-benzoylamino}-3-(2'-phenoxy-biphenyl-4-yl)-propionic acid | 684 |
| 345 | (2S)-[5-Chloro-2-(4-phenoxy-benzoylamino)-benzoylamino]-3-(2'-cyclopentyloxy-biphenyl-4-yl)-propionic acid | 675 |
| 346 | (2S)-[5-Chloro-2-(4-phenoxy-benzoylamino)-benzoylamino]-3-[2'-(4-trifluoromethyl-benzyloxy)-biphenyl-4-yl]-propionic acid | 765 |
| 347 | 3-[2'-(4-tert-Butyl-benzyloxy)-biphenyl-4-yl]-(2S)-[5-chloro-2-(4-phenoxy-benzoylamino)-benzoylamino]-propionic acid | 753 |
| 348 | (2S)-[5-Chloro-2-(4-[1,2,3]thiadiazol-4-yl-benzoylamino)benzoylamino]-3-(2'-phenoxy-biphenyl-4-yl)-propionic acid | 675 |
| 349 | (2S)-{5-Chloro-2-[4-(pyridin-4-ylmethoxy)-benzoylamino]-benzoylamino}-3-(2'-phenoxy-biphenyl-4-yl)-propionic acid | 698 |
| 350 | (2S)-(5-Chloro-2-{[1-(4-chloro-phenyl)-5-trifluoromethyl-1H-pyrazole-4-carbonyl]-amino}-benzoylamino)-3-(2'-phenoxy-biphenyl-4-yl)-propionic acid | 759 |
| 351 | (2S)-(5-Chloro-2-{[1-(4-chloro-phenyl)-5-propyl-1H-pyrazole-4-carbonyl]-amino}-benzoylamino)-3-(2'-phenoxy-biphenyl-4-yl)-propionic acid | 733 |
| 352 | (2S)-[5-Bromo-2-(3-phenyl-propionylamino)-benzoylamino]-3-(2'-phenoxy-biphenyl-4-yl)-propionic acid | 664 |
| 353 | (2S)-[2-(3,5-Bis-trifluoromethyl-benzo ylamino)-5-chloro-benzoylamino]-3-[2'-(4-pentyl-phenoxy)-biphenyl-4-yl]-propionic acid | 796 |
| 354 | (2S)-{2-[(Benzofuran-2-carbonyl)-amino]-5-bromo-benzoylamino}-3-(2'-phenoxy-biphenyl-4-yl)-propionic acid | 676 |
| 355 | (2S)-{2-[(Benzo[b]thiophene-2-carbonyl)-amino]-5-bromo-benzoylamino}-3-(2'-phenoxy-biphenyl-4-yl)-propionic acid | 692 |
| 356 | (2S)-{5-Bromo-2-[(3-chloro-benzo[b]thiophene-2-carbonyl)-amino]-benzoylamino}-3-(2'-phenoxy-biphenyl-4-yl)-propionic acid | 726 |

EXAMPLE 357

(2S)-{2-[(3,5-Bis-trifluoromethyl-benzoyl)-pentyl-amino]-5-chloro-benzoylamino}-3-(2'-phenoxy-biphenyl-4-yl)-propionic acid (2S)-amino-3-(2'-phenoxy-biphenyl-4-yl-propionic acid methyl ester (192 mg, 0.5 mmol), which was prepared in the general section of syntheses of amino acids, was reacted with 5-bromoanthranilic acid (90 mg, 0.5 mmol) as described in general procedure A. The resulting crude compound was alkylated by valeraldehyde (86 mg, 1.0 mmol) as described in general reductive amination procedure E. The purified compound was reacted with 3,5-bis(trifluoromethyl)benzoyl chloride (210 mg, 0.75 mmol) as described in general procedure F. The resulting compound was hydrolyzed according to general procedure C to afford the title product (200 mg, 50%) as a white solid. $^1$H-NMR(400 MHz, CDCl$_3$): 0.86 (t, 3H), 3.71–2.91 (m, 8H), 4.29–4.23 (m, 1H), 4.85 (broad, 1H), 5.09–4.99 (m, 1H), 6.91–6.87 (m, 2H), 7.03–6.96 (m, 2H), 7.30–7.15 (m, 8H), 7.59–7.35 (m, 4H), 8.11–7.91 (m, 2H), 8.52 (s, 1H)

LC/MS (m/z): 797(M+1)$^+$.

EXAMPLE 358

(2S)-{2-[(Biphenyl-4-carbonyl)-(4-methyl-benzyl)-amino]-5-chloro-benzoylamino}-3-biphenyl-4-yl-propionic acid To the resin-bound L-biphenylalanine (1.2 mmol) which was made in example 279, a solution of 2-amino-5-chloro benzoic acid (3.0 mmol), HOBt (30 mmol), DIC (30 mmol) and DMAP (0.03 mmol) in DMF (30 mL) were added and the mixture was shaken overnight. The reaction mixture was drained and washed with DMF, methanol and DCM (3×150 mL each solvent).

To the resin-bound (2S)-(2-amino-5-chloro-benzoylamino)-3-biphenyl-4-yl-propionic acid (0.12 mmol) synthesized above was suspended in DCE (5 mL) was added 4-methyl benzaldehyde (0.6 mmol), acetic acid (0.6 mmol) and sodium cyanoborohydride (1.2 mmol) and the mixture was shaken overnight. Upon completion of the reaction, the reaction mixture was drained and washed with DMF, methanol and DCM (3×5 mL each solvent).

To the resin-bound 3-Biphenyl-4-yl-(2S)-[5-chloro-2-(4-methyl-benzylamino)-benzoylamino]-propionic acid (0.12 mmol) was added a solution of Biphenyl-4-carbonyl chloride (0.3 mmol) and pyridine (0.3 mmol) and the mixture agitated for 24 hours. The reaction mixture was drained and washed with DMF, methanol and DCM (3×5 mL each solvent).

Resin bound 2S-{2-[(Biphenyl-4-carbonyl)-(4-methyl-benzyl)-amino]-5-chloro-benzoylamino}-3-biphenyl-4-yl-propionic acid was treated with 20% TFA in DCM (2 mL) for 1 hour. The filtrate was collected and evaporated to give 10 mg of the title compound with 95% purity. LC/MS (m/z): 679 (m+1)$^+$ By analogous methods to those described above the following Examples were synthesized.

| EXAMPLE | NAME | LC/MS (m/z) |
|---|---|---|
| 359 | 3-Biphenyl-4-yl-(2S){5-chloro-2-[(3,5-dichloro-benzoyl)-(4-methyl-benzyl)-amino]-benzoylamino}-propionic acid | 671 |
| 360 | (2S)-{2-[(Biphenyl-4-carbonyl)-(3-phenyl-propyl)-amino]-5-chloro-benzoylamino}-3-biphenyl-4-yl-propionic acid | 693 |
| 361 | 3-Biphenyl-4-yl-(2S)-{5-chloro-2-[(2,4-dichloro-benzoyl)-(3-phenyl-propyl)-amino]-benzoylamino}-propionic acid | 685 |
| 362 | (2S)-{2-[(Biphenyl-4-carbonyl)-biphenyl-4-ylmethyl-amino]-5-chloro-benzoylamino}-3-biphenyl-4-yl-propionic acid | 741 |
| 363 | 3-Biphenyl-4-yl-(2S)-{2-[biphenyl-4-ylmethyl-(2,4-dichloro-benzoyl)-amino]-5-chloro-benzoylamino}-propionic acid | 733 |
| 364 | (2S)-{2-[(Biphenyl-4-carbonyl)-(4-isopropyl-benzyl)-amino]-5-chloro-benzoylamino}-3-biphenyl-4-yl-propionicacid | 707 |
| 365 | (2S)-{2-[(Biphenyl-4-carbonyl)-(4-isoproxy-benzyl)-amino]-5-chloro-benzoylamino}-3-biphenyl-4-yl-propionic acid | 723 |
| 366 | (2S)-{5-Bromo-2-[(2-methyl-butyl)-(4-phenoxy-benzoyl)-amino]-benzoylamino}-3-(2'-phenoxy-biphenyl-4-yl)-propionic acid | 798 |

EXAMPLE 367

(2S)-[5-Chloro-2-(5-dibutylamino-naphthalene-1-sulfonylamino)-benzoylamino]-3-(2'-phenoxy-biphenyl-4-yl)-propionic acid methyl ester A solution of 2-(2-amino-5-chloro-benzoylamino)-3-(2'-phenoxy-biphenyl-4-yl)-propionic acid (0.05 g, 0.1 mmol) [prepared by reacting (2S)-amino-3-(2'-phenoxy-biphenyl-4-yl)propionic acid methyl ester hydrochloride salt and 2-amino-5-chlorobenzoic acid by general procedure A] in $CH_2Cl_2$ was treated with (0.035 g, 0.1 mmol) of bansyl chloride according to the general procedure F. Product was purified by flash column chromatography on silicagel using ethyl acetate hexanes to give product as pale yellow solid (0.06 g, 74.0% yield).
$^1$HNMR (400 MHz, $CDCl_3$): 0.8 (t, 6H), 1.14–1.28 (m, 4H), 1.34–1.44 (m, 4H), 2.98–3.11 (m, 5H), 3.16 (dd, 1H), 3.73 (s, 3H), 4.91 (dd, 1H), 6.42 (d, 1H), 6.88 (d, 2H), 6.93–7.20 (m, 4H), 7.16–7.32 (m, 7H), 7.40–7.47 (m, 4H), 7.54–7.61 (m, 2H), 8.24–8.29 (m, 1H), 8.35 (d, 1H), 8.56 (d, 1H), 11.11 (s, 1H).
LC/MS (m/z): 818.3 (M+1)$^+$.

EXAMPLE 368

(2S)-[5-Bromo-2-(4-tert-butyl-benzenesulfonylamino)-benzoylamino]-3-(2'-phenoxy-biphenyl-4-yl)-propionic acid A solution of 2-(2-amino-5-bromo-benzoylamino)-3-(2'-phenoxy-biphenyl-4-yl)-propionic acid (0.06 g, 0.11 mmol) [prepared by reacting (2S)-amino-3-(2'-phenoxy-biphenyl-4-yl)propionic acid methyl ester hydrochloride salt and 2-amino-5-bromobenzoic acid by general procedure A]] in $CH_2Cl_2$ was treated with of 4-tert-butylbenzenesulfonyl chloride (0.025 g, 0.11 mmol) according to the general procedure F. Product was purified by flash column chromatography on silicagel using ethyl acetate hexanes to give product as white solid (0.065 g, 79.6% yield).
2-[5-Bromo-2-(4-t-butyl-benzenesulfonylamino)-benzoylamino]-3-(2'-phenoxy-biphenyl-4-yl)propionic acid methyl ester (0.04 g, 0.054 mmol) was treated with LiOH (2 eq, 1N aqueous solution) according to the general procedure C to give 0.034 g (87.0%) of 2-[5-Bromo-2-(4-t-butyl-benzenesulfonylamino)-benzoylamino]-3-(2'-phenoxy-biphenyl-4-yl)propionic acid.
$^1$HNMR (400 MHz, DMSO-$d_6$): 1.2 (s, 9H) 3.04 (dd, 1H), 3.21 (dd, 1H), 4.58–4.70 (m, 1H), 6.83–6.87 (m, 2H), 6.94–6.99 (m, 2H), 7.20–7.39 (m, 6H), 7.42–7.49 (m, 4H), 7.51–7.56 (m, 2H), 7.64–7.72 (m, 3H), 7.86 (d, 1H), 9.29 (d, 1H), 11.38 (s, 1H), 13.06 (s, 1H)
LC/MS (m/z): 727.1 (M+1)$^+$.

EXAMPLE 369

(2S)-[5-Bromo-2-(4-tert-butyl-benzenesulfonylamino)-benzoylamino]-3-(4'-phenoxy-biphenyl-4-yl)-propionic acid To a mixture of (L)-4-bromophenylalanine (8.55, 35.0 mmol), 2-phenoxyphenyl boronic acid (10.00 g, 46.73 mmol), and palladium tetrakis-triphenylphosphine (4.0 g, 10% mmol) were added DME (140 mL) and 2N $Na_2CO_3$ aq. solution (70 mL, 140 mmol). The resulting mixture was heated at 90° C. under $N_2$ for 20 h. While the reaction solution was hot, the aqueous layer was removed and the top organic layer was concentrated. The residue was neutralized with HCl and washed with diethyl ether, and then was dissolved in methanol and the insoluble solid was removed by filtration. The methanol filtrate was refluxed with HCl/Ether for 6 h. After removal of solvents, the solid was washed with ether to afford (2S)-amino-3-(4'-phenoxy-biphenyl-4-yl-propionic acid methyl ester in HCl salt form (11.0 g, 28.65 mmol, 82% yield).

(2S)-amino-3-(4'-phenoxy-biphenyl-4-yl-propionic acid methyl ester (192 mg, 0.5 mmol) was reacted with 5-bromoanthranilic acid (110 mg, 0.5 mmol) as described in general procedure A. The resulting crude compound was sulfonylated by 4-tert-butylbenzenesulfonyl chloride (175 mg, 0.75 mmol) as described in general procedure F. The resulting compound was hydrolyzed according to general procedure C to afford the title product (219 mg, 60%) as a white solid. $^1$H-NMR(400 MHz, CDCl$_3$): 1.25 (s, 9H), 3.25 (dd, 1H), 3.35 (dd, 1H), 5.01 (dd, 1H), 6.62 (d, 1H), 7.05–7.03 (m, 4H), 7.12 (t, 1H), 7.21 (d, 2H), 7.45–7.33 (m, 6H), 7.54–7.49 (m, 5H), 7.60 (d, 2H), 10.61 (s, 1H)
LC/MS (m/z): 727 (M+1)$^+$.

EXAMPLE 370

3-Biphenyl-4-yl-(2S)-[2-(3,4-dichloro-benzenesulfonylamino)-5-iodo-benzoylamino]-propionic acid To the resin-bound L-biphenylalanine (1.2 mmol) which was made in example 279, a solution of 2-amino-5-iodo benzoic acid (3.0 mmol), HOBt (30 mmol), DIC (30 mmol) and DMAP (0.03 mmol) in DMF (30 mL) were added and the mixture was shaken overnight. The reaction mixture was drained and washed with DMF, methanol and DCM (3×150 mL each solvent).

To the resin-bound (2S)-(2-amino-5-iodo-benzoylamino)-3-biphenyl-4-yl-propionic acid (0.12 mmol) was added a solution of 3,4-dichloro benzenesulfonyl chloride (0.3 mmol) and pyridine (0.3 mmol) in 5 ml of DCM and the mixture agitated for 24 hours. The reaction mixture was drained and washed with DMF, methanol and DCM (3×5 mL each solvent).

Resin bound 3-Biphenyl-4-yl-(2S)-[2-(3,4-dichloro-benzenesulfonylamino)-5-iodobenzoylamino]-propionic acid was treated with 20% TFA in DCM (2 mL) for 1 hour. The filtrate was collected and evaporated to give 10 mg of the title compound with 95% purity. LC/MS (m/z): 695 (m+1)$^+$

EXAMPLE 371

(2S)-(2-[(Biphenyl-4-sulfonyl)-(4-methyl-benzyl)-amino]-5-chloro-benzoylamino)-3-biphenyl-4-yl-propionic acid To the resin-bound 3-Biphenyl-4-yl-(2S)-[5-chloro-2-(4-methyl-benzylamino)-benzoylamino]-propionic acid (0.12 mmol) prepared in example 358 was added a solution of biphenyl-4-sulfonyl chloride (0.3 mmol) and pyridine (0.3 mmol) and the mixture agitated for 72 hours. The reaction mixture was drained and washed with DMF, methanol and DCM (3×5 mL each solvent).

Resin bound (2S)-{2-[(biphenyl-4-sulfonyl)-(4-methyl-benzyl)-amino]-5-chloro-benzoylamino}-3-biphenyl-4-yl-propionic acid was treated with 20% TFA in DCM (2 mL) for 1 hour. The filtrate was collected and evaporated to give 10 mg of the title compound with 95% purity. LC/MS (m/z): 715 (m+1)$^+$ By analogous methods to those described above the following compounds were synthesized.

| EXAMPLE | NAME | LC/MS (m/z) |
|---|---|---|
| 372 | (2S)-[2-(Biphenyl-4-sulfonylamino)-5-chloro-benzoylamino]-3-biphenyl-4-yl-propionic acid | 611 |
| 373 | 3-Biphenyl-4-yl-(2S)[2-(4-tert-butyl-benzenesulfonylamino)-5-iodo-benzoylamino]-propionic acid | 683 |
| 374 | 3-Biphenyl-4-yl-(2S){[4-(4-tert-butyl-benzenesulfonylamino)-3'-chloro-4'-fluoro-biphenyl-3-carbonyl]-amino}-propionic acid | 685 |
| 375 | 3-Biphenyl-4-yl-(2S)[5-iodo-2-(2,4,5-trichloro-benzenesulfonylamino)-benzoylamino]-propionic acid | 729 |
| 376 | 3-Biphenyl-4-yl-(2S)-[2-(2,5-dichloro-benzenesulfonylamino)-5-iodo-benzoylamino]-propionic acid | 695 |
| 377 | 3-Biphenyl-4-yl-(2S)-[2-(2,4-difluoro-benzenesulfonylamino)-5-iodo-benzoylamino]-propionic acid | 663 |
| 378 | 3-Biphenyl-4-yl-(2S)-[5-iodo-2-(4-propyl-benzenesulfonylamino)-benzoylamino]-propionic acid | |
| 379 | 3-Biphenyl-4-yl-(2S)-(5-iodo-2-pentamethylbenzenesulfonylamino-benzoylamino)-propionic acid | 697 |
| 380 | 3-Biphenyl-4-yl-(2S)-[5-iodo-2-(toluene-4-sulfonylamino)-benzoylamino]-propionic acid | |
| 381 | 3-Biphenyl-4-yl-(2S)-[2-(4-bromo-benzenesulfonylamino)-5-iodo-benzoylamino]-propionic acid | 706 |
| 382 | 3-Biphenyl-4-yl-(2S)-[5-iodo-2-(naphthalene-2-sulfonylamino)-benzoylamino]-propionic acid | 677 |
| 383 | 3-Biphenyl-4-yl-(2S)-[5-bromo-2-(4-tert-butyl-benzenesulfonylamino)-benzoylamino]-propionic acid | 636 |
| 384 | 2-[5-Acetylamino-(2S)-(4-tert-butyl-benzenesulfonylamino)-benzoylamino]-3-biphenyl-4-yl-propionic acid | 614 |
| 385 | 3-Biphenyl-4-yl-(2R)-[5-bromo-2-(4-tert-butyl-benzenesulfonylamino)-benzoylamino]-propionic acid methyl ester | 650 |
| 386 | 3-Biphenyl-4-yl-(2S)-[5-bromo-2-(6-morpholin-4-yl-pyridine-3-sulfonylamino)-benzoylamino]-propionic acid | 665 |
| 387 | 3-Biphenyl-4-yl-(2S)-[5-bromo-2-(4-vinyl-benzenesulfonylamino)-benzoylamino]-propionic acid | 606 |
| 388 | 3-Biphenyl-4-yl-(2S)-[5-bromo-2-(3,4-dichloro-benzenesulfonylamino)-benzoylamino]-propionic acid | 648 |
| 389 | 3-Biphenyl-4-yl-(2S)-[5-bromo-2-(4-nitro-benzenesulfonylamino)-benzoylamino]-propionic acid | 625 |
| 390 | 3-Biphenyl-4-yl-(2S)-[5-bromo-2-(2-phenyl-ethenesulfonylamino)-benzoylamino]-propionic acid | 608 |
| 391 | 3-Biphenyl-4-yl-(2S)-{5-bromo-2-[5-(5-trifluoromethyl-isoxazol-3-yl)-thiophene-2-sulfonylamino]-benzoylamino}-propionic acid | 721 |
| 392 | 3-Biphenyl-4-yl-(2S)-[5-bromo-2-(4-bromo-benzenesulfonylamino)-benzoylamino]-propionic acid | 659 |
| 393 | 3-Biphenyl-4-yl-(2S)-[5-bromo-2-(3,4-dimethoxy-benzenesulfonylamino)-benzoylamino]-propionic acid | 640 |
| 394 | (2S)-[2-(4-Acetylamino-benzenesulfonylamino)-5-bromo-benzoylamino]-3-biphenyl-4-yl-propionic acid | 637 |

| EXAMPLE | NAME | LC/MS (m/z) |
|---|---|---|
| 395 | 3-Biphenyl-4-yl-(2S)-[5-bromo-2-(4-isopropyl-benzenesulfonylamino)-benzoylamino]-propionic acid | 622 |
| 396 | 3-Biphenyl-4-yl-(2S)-[5-bromo-2-(2,5-dichloro-benzenesulfonylamino)-benzoylamino]-propionic acid | 648 |
| 397 | 3-Biphenyl-4-yl-(2S)-[5-bromo-2-(2-rifluoromethoxy-benzenesulfonylamino)-benzoylamino]-propionic acid | 664 |
| 398 | (2S)-[5-Bromo-2-(5-dibutylamino-naphthalene-1-sulfonylamino)-benzoylamino]-3-(4'-phenoxy-biphenyl-4-yl)-propionic acid | 849 |
| 399 | (2S)-[5-Chloro-2-(5-dibutylamino-naphthalene-1-sulfonylamino)-benzoylamino]-3-(2'-phenoxy-biphenyl-4-yl)-propionic acid | 804 |
| 400 | (2S)-[5-Chloro-2-(5-dimethylamino-naphthalene-1-sulfonylamino)-benzoylamino]-3-(2'-phenoxy-biphenyl-4-yl)-propionic acid methyl ester | 734 |
| 401 | (2S)-[5-Bromo-2-(5-dimethylamino-naphthalene-1-sulfonylamino)-benzoylamino]-3-(2'-phenoxy-biphenyl-4-yl)-propionic acid methyl ester | 780 |
| 402 | (2S)-[5-Chloro-2-(5-dimethylamino-naphthalene-1-sulfonylamino)-benzoylamino]-3-(2'-phenoxy-biphenyl-4-yl)-propionic acid | 720 |
| 403 | (2S)-[5-Bromo-2-(5-dimethylamino-naphthalene-1-sulfonylamino)-benzoylamino]-3-(2'-phenoxy-biphenyl-4-yl)-propionic acid | 765 |
| 404 | (2S)-[5-Bromo-2-(5-dibutylamino-naphthalene-1-sulfonylamino)benzoylamino]-3-(2'-phenoxy-biphenyl-4-yl)-propionic acid | 849 |
| 405 | (2S)-(2-Benzenesulfonylamino-5-chloro-benzoylamino)-3-(2'-phenoxy-biphenyl-4-yl)-propionic acid methyl ester | 641 |
| 406 | (2S)-(2-Benzenesulfonylamino-5-chloro-benzoylamino)-3-(2'-phenoxy-biphenyl-4-yl)-propionic acid | 627 |
| 407 | (2S)-[5-Chloro-2-(naphthalene-1-sulfonylamino)-benzoylamino]-3-(2'-phenoxy-biphenyl-4-yl)-propionic acid methyl ester | 691 |
| 408 | (2S)-[5-Chloro-2-(naphthalene-1-sulfonylamino)-benzoylamino]-3-(2'-phenoxy-biphenyl-4-yl)-propionic acid | 677 |
| 409 | (2S)-[5-Chloro-2-(naphthalene-2-sulfonylamino)-benzoylamino]-3-(2'-phenoxy-biphenyl-4-yl)-propionic acid methyl ester | 691 |
| 410 | (2S)-[5-Chloro-2-(naphthalene-2-sulfonylamino)-benzoylamino]-3-(2'-phenoxy-biphenyl-4-yl)-propionic acid | 677 |
| 411 | (2S)-[2-(4-tert-Butyl-benzenesulfonylamino)-5-chloro-benzoylamino]-3-(2'-phenoxy-biphenyl-4-yl)-propionic acid methyl ester | 697 |
| 412 | (2S)-[2-(4-tert-Butyl-benzenesulfonylamino)-5-chloro-benzoylamino]-3-(2'-phenoxy-biphenyl-4-yl)-propionic acid | 683 |
| 413 | (2S)-[2-(Biphenyl-4-sulfonylamino)-5-chloro-benzoylamino]-3-(2'-phenoxy-biphenyl-4-yl)-propionic acid methyl ester | 717 |
| 414 | (2S)-[2-(Biphenyl-4-sulfonylamino)-5-chloro-benzoylamino]-3-(2'-phenoxy-biphenyl-4-yl)-propionic acid | 703 |
| 415 | (2S)-[5-Chloro-2-(quinoline-8-sulfonylamino)-benzoylamino]-3-(2'-phenoxy-biphenyl-4-yl)-propionic acid methyl ester | 692 |
| 416 | (2S)-[5-Chloro-2-(quinoline-8-sulfonylamino)-benzoylamino]-3-(2'-phenoxy-biphenyl-4-yl)-propionic acid | 678 |
| 417 | (2S)-[5-Chloro-2-(5-chloro-1,3-dimethyl-1H-pyrazole-4-sulfonylamino)-benzoylamino]-3-(2'-phenoxy-biphenyl-4-yl)-propionic acid | 679 |
| 418 | (2S)-[5-Chloro-2-(1-methyl-1H-imidazole-4-sulfonylamino)-benzoylamino]-3-(2'-phenoxy-biphenyl-4-yl)-propionic acid | 631 |
| 419 | (2S)-[5-Chloro-2-(6-phenoxy-pyridine-3-sulfonylamino)-benzoylamino]-3-(2'-phenoxy-biphenyl-4-yl)-propionic acid | 720 |
| 420 | (2S)-[5-Chloro-2-(4-pyrazol-1-yl-benzenesulfonylamino)-benzoylamino]-3-(2'-phenoxy-biphenyl-4-yl)-propionic acid | 693 |
| 421 | (2S)-[5-Chloro-2-(5-chloro-1,3-dimethyl-1H pyrazole-4-sulfonylamino)-benzoylamino]-3-(2'-phenoxy-biphenyl-4-yl)-propionic acid methyl ester | 693 |
| 422 | (2S)-{5-Chloro-2-[3-(5-methyl-[1,3,4]oxadiazol-2-yl)-benzenesulfonylamino]-benzoylamino}-3-(2'-phenoxy-biphenyl-4-yl)-propionic acid methyl ester | 723 |
| 423 | (2S)-[5-Chloro-2-(6-phenoxy-pyridine-3-sulfonylamino)-benzoylamino]-3-(2'-phenoxy-biphenyl-4-yl)-propionic acid methyl ester | 734 |
| 424 | (2S)-[5-Chloro-2-(4-pyrazol-1-yl-benzenesulfonylamino)-benzoylamino]-3-(2'-phenoxy-biphenyl-4-yl)-propionic acid methyl ester | 707 |
| 425 | (2S)-[5-Chloro-2-(1-methyl-1H-imidazole-4-sulfonylamino)-benzoylamino]-3-(2'-phenoxy-biphenyl-4-yl)-propionic acid methyl ester | 645 |
| 426 | (2S)-[5-Chloro-2-(3,5-dimethyl-isoxazole-4-ulfonylamino)-benzoylamino]-3-(2'-phenoxy-biphenyl-4-yl)-propionic acid ethyl ester | 660 |
| 427 | (2S)-[5-Chloro-2-(6-morpholin-4-yl-pyridine-3-sulfonylamino)-benzoylamino]-3-(2'-phenoxy-biphenyl-4-yl)-propionic acid methyl ester | 727 |
| 428 | (2S)-[5-Chloro-2-(6-morpholin-4-yl-pyridine 3-sulfonylamino)-benzoylamino]-3-(2'-phenoxy-biphenyl-4-yl)-propionic acid | 713 |
| 429 | (2S)-{5-Chloro-2-[5-(2-methylsulfanyl-pyrimidin-4-yl)-thiophene-2-sulfonylamino]-benzoylamino}-3-(2'-phenoxy-biphenyl-4-yl)-propionic acid methyl ester | 771 |
| 430 | (2S)-{5-Chloro-2-[5-(2-methylsulfanyl-pyrimidin-4-yl)-thiophene-2-sulfonylamino]-benzoylamino}-3-(2'-phenoxy-biphenyl-4-yl)-propionic acid | 757 |
| 431 | (2S)-{5-Chloro-2-[4-(5-methyl-[1,3,4]oxadiazol-2-yl)-benzenesulfonylamino]-benzoylamino}-3-(2'-phenoxy-biphenyl-4-yl)-propionic acid | 709 |
| 432 | 3-Biphenyl-4-yl-(2S)-[2-(2,5-dichloro-benzenesulfonylamino)-5-iodo-benzoylamino]-propionic acid methyl ester | 709 |
| 433 | 3-Biphenyl-4-yl-(2S)-[2-(4-bromo-benzenesulfonylamino)-5-iodo-benzoylamino]-propionic acid methyl ester | 720 |
| 434 | 3-Biphenyl-4-yl-(2S)-[2-(3,5-bis-trifluoromethyl-benzenesulfonylamino)-5-chloro-benzoylamino]-propionic acid | 671 |
| 435 | (2S)-[5-Chloro-2-(4-oxazol-5-yl-benzenesulfonylamino)-benzoylamino]-3-(2'-phenoxy-biphenyl-4-yl)-propionic acid methyl ester | 708 |

| EXAMPLE | NAME | LC/MS (m/z) |
|---|---|---|
| 436 | (2S)-[5-Chloro-2-(4-oxazol-5-yl-benzenesulfonylamino)-benzoylamino]-3-(2'-phenoxy-biphenyl-4-yl)-propionic acid | 694 |
| 437 | (2S)-[5-Chloro-2-(4-phenoxy-benzenesulfonylamino)-benzoylamino]-3-(2'-phenoxy-biphenyl-4-yl)-propionic acid methyl ester | 733 |
| 438 | (2S)-[5-Chloro-2-(4-phenoxy-benzenesulfonylamino)-benzoylamino]-3-(2'-phenoxy-biphenyl-4-yl)-propionic acid | 719 |
| 439 | (2S)-[5-Chloro-2-(3-nitro-benzenesulfonylamino)-benzoylamino]-3-(2'-phenoxy-biphenyl-4-yl)-propionic acid | 672 |
| 440 | (2S)-[2-(3,5-Bis-trifluoromethyl-benzenesulfonylamino)-5-chloro-benzoylamino]-3-(2'-phenoxy-biphenyl-4-yl)-propionic acid methyl ester | 777 |
| 441 | (2S)-[2-(3,5-Bis-trifluoromethyl-benzenesulfonylamino)-5-chloro-benzoylamino]-3-(2'-phenoxy-biphenyl-4-yl)-propionic acid | 763 |
| 442 | (2S)-[2-(3-Amino-benzenesulfonylamino)-5-chloro-benzoylamino]-3-(2'-phenoxy-biphenyl-4-yl)-propionic acid methyl ester | 656 |
| 443 | (2S)-{5-Chloro-2-[5-(2-methyl-5-trifluoromethyl-2H-pyrazol-3-yl)-thiophene-2-sulfonylamino]-benzoylamino}-3-(2'-phenoxy-biphenyl-4-yl)-propionic acid methyl ester | 795 |
| 444 | (2S)-{5-Chloro-2-[5-(2-methyl-5-trifluoromethyl-2H-pyrazol-3-yl)-thiophene-2-sulfonylamino]-benzoylamino}-3-(2'-phenoxy-biphenyl-4-yl)-propionic acid | 781 |
| 445 | 3-Biphenyl-4-yl-(2S)-[5-chloro-2-(5-dibutylamino-naphthalene-1-sulfonylamino)-enzoylamino]-propionic acid methyl ester | 726 |
| 446 | 3-Biphenyl-4-yl-(2S)-[5-chloro-2-(5-dibutylamino-naphthalene-1-sulfonylamino)-benzoylamino]-propionic acid | 712 |
| 447 | (2S)-[5-Bromo-2-(4-tert-butyl-benzenesulfonylamino)-benzoylamino]-3-(2'-phenoxy-biphenyl-4-yl)-propionic acid methyl ester | 742 |
| 448 | (2S)-[5-Bromo-2-(4-tert-butyl-benzenesulfonylamino)-benzoylamino]-3-(4'-phenoxy-biphenyl-4-yl)-propionic acid methyl ester | 742 |
| 449 | 3-Biphenyl-4-yl-(2S)-{5-chloro-2-[naphthalen-1-ylmethyl-(4-nitro-benzenesulfonyl)-amino]-benzoylamino}-propionic acid | 720 |
| 450 | (2S)-{2-[(Biphenyl-4-sulfonyl)-(3-methyl-thiophen-2-ylmethyl)-amino]-5-chloro-benzoylamino}-3-biphenyl-4-yl-propionic acid | 721 |
| 451 | (2S)-{2-[(Biphenyl-4-sulfonyl)-(3-phenyl-propyl)-amino]-5-chloro-benzoylamino}-3-biphenyl-4-yl-propionic acid | 729 |
| 452 | (2S)-{2-[(Biphenyl-4-sulfonyl)-biphenyl-4-ylmethyl-amino]-5-chloro-benzoylamino}-3-biphenyl-4-yl-propionic acid | 777 |
| 453 | (2S)-{2-[(Biphenyl-4-sulfonyl)-naphthalen-1-ylmethyl-amino]-5-chloro-benzoylamino}-3-biphenyl-4-yl-propionic acid | 751 |
| 454 | (2S)-{2-[(Biphenyl-4-sulfonyl)-(4-isopropyl-benzyl)-amino]-5-chloro-benzoylamino}-3-biphenyl-4-yl-propionic acid | 753 |
| 455 | 3-Biphenyl-4-yl-(2S)-{2-[biphenyl-4-ylmethyl-(2,4-dichloro-benzenesulfonyl)-amino]-5-chloro-benzoylamino}-propionic acid | 769 |
| 456 | (2S)-{2-[(Biphenyl-4-sulfonyl)-ethyl-amino]-5-chloro-benzoylamino}-3-biphenyl-4-yl-propionic acid | 639 |
| 457 | (2S)-{2-[(Biphenyl-4-sulfonyl)-ethyl-amino]-5-iodo-benzoylamino}-3-biphenyl-4-yl-propionic acid | 731 |

EXAMPLE 458

2-{5-Chloro-2-[(naphthalen-1-ylmethyl)-amino]-benzoylamino}-3-(4'-trifluoromethyl-biphenyl-4-yl)-propionic acid A solution of 2-amino-5-chlorobenzoic acid (0.58 g, 3.37 mmol) in DMF (7.0 mL) was reacted with (L)-4-bromophenylalanine methyl ester hydrochloride (1.00 g, 3.37 mmol), HBTU (1.20 g, 3.37 mmol), and DIEA (1.80 mL, 10.13 mmol) by the general procedure A. The crude product was purified by flash column chromatography on silica gel using DCM (+50% hexane) followed by DCM to give 0.890 g (64%) of 2-(2-amino-5-chloro-benzoylamino)-3-(4-bromo-phenyl)-propionic acid methyl ester as a white solid. A solution of 2-(2-amino-5-chloro-benzoylamino)-3-(4-bromo-phenyl)-propionic acid methyl ester (0.600 g, 1.45 mmol) in DME (10.0 mL) was reacted with 4-trifluoromethylbenzene boronic acid (0.55 g, 2.91 mmol), Pd(PPh$_3$)$_4$ (0.70 g, 0.14 mmol), and Na$_2$CO$_3$ (2.0 N, 3.50 mL, 3.64 mmol) by the general procedure D to form 0.850 g of 2-(2-amino-5-chloro-benzoylamino)-3-(4'-trifluoromethyl-biphenyl-4-yl)-propionic acid methyl ester as a brown oil.

A solution of 2-(2-amino-5-chloro-benzoylamino)-3-(4-bromo-phenyl)-propionic acid methyl ester (0.830 g, 1.74 mol) in DCE (15 mL) was reacted with 1-naphthaldehyde (0.244 g, 3.50 mmol), sodium triacetoxyborohydride (0.553 g, 2.61 mmol), and acetic acid/DCM (1.0 M, 2.0 mL) by the general procedure E. The crude product was purified by flash column chromatography on silica gel using DCM (+35% hexane) to give 0.580 g (54%) of 2-{5-Chloro-2-[(naphthalen-1-ylmethyl)-amino]-benzoylamino}-3-(4'-trifluoromethyl-biphenyl-4-yl)-propionic acid methyl ester as a colorless oil. This ester was treated with LiOH (0.123 g, 2.92 mmol) by the general procedure J to give 0.405 g (92%) of the title compound. 2-{5-chloro-2-[(naphthalen-1-ylmethyl)-amino]-benzoylamino}-3-(4'-trifluoromethyl-biphenyl-4-yl)-propionic acid as a white solid. LCMS 603 (M+1)$^+$. $^1$H NMR (DMSO-d$_6$) 8.62 [d, 1H], 8.10 [m, 1H], 8.03 [m, 1H], 7.92 [m, 1H], 7.81 [m, 2H], 7.72 [m, 2H], 7.59 [m, 3H], 7.50 [m, 2H], 7.38 [m, 3H], 7.23 [dd, 1H], 6.67 [d, 1H], 4.47 [m, 1H], 3.25 [dd, 1H], 3.16 [s, 2H], 3.07 [m, 1H].

EXAMPLE 459

(2S)-{2-[3-(4-tert-Butyl-phenoxy)-benzylamino]-5-chloro-benzoylamino}-3-(4'-cyclohexyl-biphenyl-4-yl)-propionic acid (2S)-(2-Amino-5-chloro-benzoylamino)-3-biphenyl-4-yl-propionic acid methyl ester was prepared following General Procedure A using 2-amino-5-chloro-benzoic acid (1.751 g, 98%, 10 mmol), (S)-2-amino-3-(4-bromo-phenyl)-propionic acid methyl ester hydrochloride salt (2.95 g, 10 mmol), HBTU (4.55 g, 12 mmol) and DIEA (6.33 mL, 99%, 36 mmol) in DMF (60 mL). Purification by flash chromatography (ethyl acetate/hexanes 1:3, 1:2, 1:1.5) gave solid (3.48 g, 8.45 mmol, 85% yield).

(2S)-(2-Amino-5-chloro-benzoylamino)-3-(4'-cyclohexyl-biphenyl-4-yl)propionic acid methyl ester compound was prepared following General Procedure D using (S)-2-(2-amino-5-chloro-benzoylamino)-3-(4-bromo-phenyl)-propionic acid methyl ester (1.803 g, 4.38 mmol), 4-cyclohexyl-benzene boronic acid (1.61 g, 98%, 7.88 mmol), palladium tetrakis-triphenylphosphine (0.462 g, 0.4 mmol), and aqueous $Na_2CO_3$ (2.0 N, 16 mL, 32 mmol) in DME (32 mL). The mixture was heated at 80° C. for 14 h. Purification by flash chromatography (ethyl acetate/hexanes 1:3, 1:2) gave product as a red solid (2.01 g, 4.09 mmol, 93% yield).

Reductive amination was carried out using (2S)-(2-amino-5-chloro-benzoylamino)-3-(4'-cyclohexyl-biphenyl-4-yl)propionic acid methyl ester (123 mg, 0.25 mmol), 3-(4-tert-butyl-phenoxy)-benzaldehyde (130 mg, 98%, 0.5 mmol), acetic acid (0.7 mmol), sodium triacetoxyborohydride (131 mg, 97%, 0.6 mmol) and DCE (2.5 mL). The mixture was stirred for 7 h. Purification by flash chromatography (ethyl acetate/hexanes 1:9) gave the title compound as colorless oil (139 mg, 0.19 mmol, 76% yield).

The title compound was prepared following General Procedure C using (S)-2-{2-[3-(4-tert-Butyl-phenoxy)-benzylamino]-5-chloro-benzoylamino}-3-(4'-cyclohexyl-biphenyl-4-yl)-propionic acid methyl ester (135 mg, 0.19 mmol), LiOH(aq) (2.0 N, 0.22 mL, 0.44 mmol), THF (4 mL) and MeOH (1 mL). The mixture was stirred at 0° C. for 12 h. The product was obtained as off-white solid (115 mg, 0.16 mmol, 84% yield).

$^1$H-NMR (400 MHz, DMSO-$d_6$): 12.82 (s, 1H), 8.77(d, 1H), 8.06(t, 1H), 7.62(d, 1H), 6.75–7.54(m, 17H), 6.54(d, 1H), 4.59(ddd, 1H), 4.33(d, 2H), 3.08–3.31(m, 3H), 1.33–1.79(m, 10H), 1.24(s, 9H); LC-MS m/z: 715 (M+1)$^+$.

EXAMPLE 460

(2S)-{5-Chloro-2-[(naphthalen-1-ylmethyl)-amino]-benzoylamino}-3-(2'-phenoxy-biphenyl-4-yl)-propionic acid 2-Amino-5-chlorobenzoic acid methyl ester (1.85 g, 10.0 mmol) was treated with 1-napthaldehyde (1.56 g, 10.0 mmol) and sodium triacetoxyborohydride (4.23 g, 20.0 mmol) in 1,2-dichloroethane as described in general procedure E to give 5-chloro-2-[(napthalen-1yl-methyl)-amino]-benzoic acid methyl ester (2.54 g, 78%). This methyl ester (2.0 g, 6.13 mmol) was treated with LiOH (2 eq, 1N aqueous solution) according to the general procedure C gave 5-chloro-2-[(napthalen-1yl-methyl)-amino]-benzoic acid (1.64 g, 86.0%).

5-Chloro-2-[(napthalen-1-yl-methyl)-amino]-benzoic acid (0.1 g, 0.32 mmol) was treated with (2S)-amino-3-(2'-phenoxy-biphenyl-4-yl)propionic acid methyl ester hydrochloride salt (0.123 g, 0.32 mmol) according to the general procedure A to give 2-{5-Chloro-2-[(naphthalene-1-yl-methyl)-amino]-3-(2'phenoxy-biphenyl-4-yl)-propionic acid methyl ester (0.155 g, 75.6%). This methyl ester (0.15 g, 0.23 mmol) was treated with LiOH (2 eq, 1N aqueous solution) according to the general procedure C to give 2-{5-chloro-2-[(naphthalene-1-yl-methyl)-amino]-3-(2'phenoxy-biphenyl-4-yl)-propionic acid (0.13 g, 90.0%) as white solid. $^1$HNMR (400 MHz, DMSO-$d_6$): 3.36 (dd, 1H), 3.46 (dd, 1H), 4.79–4.88 (m, 1H), 5.10 (d, 2H), 7.01 (d, 1H), 7.18 (d, 2H), 7.26 (d, 1H), 7.33 (t, 1H), 7.50–7.90 (m, 14H), 7.96 (d, 1H), 8.10–8.20 (m, 1H), 8.22–8.30 (m, 1H), 8.32–8.48 (m, 2H), 9.07 (d, 1H), 13.10 (s, 1H). LC/MS (m/z): 627.2 (M+1)$^+$.

EXAMPLE 461

(2S)-{5-Chloro-2-[(naphthalen-2-ylmethyl)-amino]-benzoylamino}-3-(2'-piperidin-1-ylmethyl-biphenyl-4-yl)-propionic acid The (2S)-(2-Amino-5-chloro-benzoylamino)-3-(4-bromo-phenyl)-propionic acid methyl ester (0.400 g, 0.972 mmol) was made according to the procedure for Example 282 and this was subjected to reductive amination with naphthalene-2-carbaldehyde (0.227 g, 1.45 mmol) and sodium triacetoxyborohydride (0.515 g, 2.43 mmol) as per general procedure E to yield the 3-(4-Bromo-phenyl)-2-{5-chloro-2-[(naphthalen-2-ylmethyl)-amino]-benzoylamino}-propionic acid methyl ester (0.428 g, 80%).

The above compound (0.360 g, 0.653 mmol) was then subjected to Suzuki coupling with 2-(formylphenyl)boronic acid (0.195 g, 1.306 mmol) and Pd(PPh$_3$) (0.075 g, 0.0653 mmol) and 2N Na$_2$CO$_3$ (2.0 ml, 1.956 mmol) as per general procedure D to yield (2S)-{5-Chloro-2-[(naphthalen-2-ylmethyl)-amino]-benzoylamino}-3-(2'-formyl-biphenyl-4-yl)-propionic acid methyl ester (0.244 g, 65%).

The title compound was hen prepared by reductive amination on (2S)-{5-chloro-2-[(naphthalen-2-ylmethyl)-amino]-benzoylamino}-3-(2'-formyl-biphenyl-4-yl)-propionic acid methyl ester (0.100 g, 0.173 mmol) with piperidine (0.0345 g, 0.347 mmol) as per general procedure E to give the (2S)-{5-chloro-2-[(naphthalen-2-ylmethyl)-amino]-benzoylamino}-3-(2'-piperidin-4-ylmethyl-biphenyl-4-yl)-propionic acid methyl ester which was further hydrolyzed as per general procedure C to give the title compound (0.56 g, 50%). LC/MS (m/z): 632(M+1).

By analogous methods to those described above the following compounds were synthesized.

| EXAMPLE | NAME | LC/MS (m/z) |
|---|---|---|
| 462 | 2S-[5-Chloro-2-(2-methyl-butylamino)-benzoylamino]-3-(2'-phenoxy-biphenyl-4-yl)-propionic acid | 557 |
| 463 | 3-Biphenyl-4-yl-2S-{5-chloro-2-[(naphthalen-1-ylmethyl)-amino]-benzoylamino}-propionic acid | 535 |
| 464 | 3-(4'-tert-Butyl-biphenyl-4-yl)-(2S)-{5-chloro-2-[(naphthalen-1-ylmethyl)-amino]-benzoylamino}-propionic acid | 591 |
| 465 | (2S)-{5-Chloro-2-[(naphthalen-1-ylmethyl)-amino]-benzoylamino}-3-(4'-methanesulfonyl-biphenyl-4-yl)-propionic acid | 613 |
| 466 | (2S)-(5-Chloro-2-hexylamino-benzoylamino)-3-(4'-trifluoromethyl-biphenyl-4-yl)-propionic acid | 547 |
| 467 | (2S)-(5-Chloro-2-hexylamino-benzoylamino)-3-(4'-dimethylamino-biphenyl-4-yl)-propionic acid | 522 |
| 468 | (2S)-[2-(4-tert-Butyl-benzylamino)-5-chloro-benzoylamino]-3-(4'-dimethylamino-biphenyl-4-yl)-propionic acid | 584 |
| 469 | (2S)-{2-[3-(4-tert-Butyl-phenoxy)-benzylamino]-5-chloro-benzoylamino}-3-(4'-dimethylamino-biphenyl-4-yl)-propionic acid | 676 |
| 470 | (2S)-{5-Chloro-2-[(naphthalen-1-ylmethyl)-amino]-benzoylamino}-3-(4'-phenoxy-biphenyl-4-yl)-propionic acid | 627 |
| 471 | (2S)-[2-(4-tert-Butyl-benzylamino)-5-chloro-benzoylamino]-3-(4'-cyclohexyl-biphenyl-4-yl)-propionic acid | 623 |

-continued

| EXAMPLE | NAME | LC/MS (m/z) |
|---|---|---|
| 472 | (2S)-(5-Chloro-2-heptylamino-benzoylamino)-3-(4'-phenoxy-biphenyl-4-yl)-propionic acid | 585 |
| 473 | (2S)-(5-Chloro-2-heptylamino-benzoylamino)-3-(4'-cyclohexyl-biphenyl-4-yl)-propionic acid | 575 |
| 474 | (2S)-{5-Chloro-2-[(naphthalen-1-ylmethyl)-amino]-benzoylamino}-3-(4'-cyclohexyl-biphenyl-4-yl)-propionic acid | 617 |
| 475 | (2S)-{5-Chloro-2-[(naphthalen-1-ylmethyl)-amino]-benzoylamino}-3-(4'-pentyl-biphenyl-4-yl)-propionic acid | 605 |
| 476 | (2S)-[2-(4-tert-Butyl-benzylamino)-5-iodo-benzoylamino]-3-(4'-phenoxy-biphenyl-4-yl)-propionic acid | 725 |
| 477 | 3-(4'-Amino-biphenyl-4-yl)-2S)-{5-chloro-2-[(naphthalen-1-ylmethyl)-amino]-benzoylamino}-propionic acid | 550 |
| 478 | 3-Biphenyl-4-yl-2S-[2-(4-tert-butyl-benzylamino)-5-(3,4-dichloro-phenoxy)-benzoylamino]-propionic acid | 667 |
| 479 | 3-Biphenyl-4-yl-2S-[2-(4-tert-butyl-benzylamino)-5-(3-chloro-4-fluoro-phenoxy)-benzoylamino]-propionic acid | 651 |
| 480 | 3-Biphenyl-4-yl-(2S)-[2-(4-tert-butyl-benzylamino)-5-(3-trifluoromethyl-phenoxy)-benzoylamino]-propionic acid | 667 |
| 481 | 3-Biphenyl-4-yl-(2S)-[2-(4-tert-butyl-benzylamino)-5-(2,3,4-trichloro-phenoxy)-benzoylamino]-propionic acid | 701 |
| 482 | 3-Biphenyl-4-yl-(2S)-[2-(4-tert-butyl-benzylamino)-4-chloro-benzoylamino]-propionic acid | 541 |
| 483 | 3-Biphenyl-4-yl-(2S)-[2-(4-tert-butyl-benzylamino)-5-(4-chloro-phenoxy)-benzoylamino]-propionic acid | 633 |
| 484 | 3-Biphenyl-4-yl-2S-[2-(4-tert-butyl-benzylamino)-5-(4-chloro-3-fluoro-phenoxy)-benzoylamino]-propionic acid | 651 |
| 485 | 3-Biphenyl-4-yl-(2S)-[2-(4-tert-butyl-benzylamino)-5-(3,4-dimethoxy-phenoxy)-benzoylamino]-propionic acid | 659 |
| 486 | 3-(2'-Benzyloxy-biphenyl-4-yl)-(2S)-{5-chloro-2-[(naphthalen-1-ylmethyl)-amino]-benzoylamino}-propionic acid | 641 |
| 487 | 3-(3'-Benzyloxy-biphenyl-4-yl)-(2S)-{5-chloro-2-[(naphthalen-1-ylmethyl)-amino]-benzoylamino}-propionic acid | 641 |
| 488 | (2S)-{5-Chloro-2-[(naphthalen-1-ylmethyl)-amino]-benzoylamino}-3-(2'-trifluoromethyl-biphenyl-4-yl)-propionic acid | 603 |
| 489 | (2S)-{2-[3-(4-tert-Butyl-phenoxy)-benzylamino]-5-chloro-benzoylamino}-3-(2'-phenoxy-biphenyl-4-yl)-propionic acid | 725 |
| 490 | (2S)-[2-(4-tert-Butyl-benzylamino)-5-chloro-benzoylamino]-3-(2'-phenoxy-biphenyl-4-yl)-propionic acid | 633 |
| 491 | (2S)-[5-Bromo-2-(4-tert-butyl-benzylamino)-benzoylamino]-3-(2'-phenoxy-biphenyl-4-yl)-propionic acid | 678 |
| 492 | (2S)-[5-Bromo-2-(2-methyl-pentylamino)-benzoylamino]-3-(2'-phenoxy-biphenyl-4-yl)-propionic acid | 616 |
| 493 | 3-Biphenyl-4-yl-(2S)-{5-chloro-2-[(piperidin-4-ylmethyl)-amino]-benzoylamino}-propionic acid | 492 |
| 494 | 3-(2'-Benzyloxy-biphenyl-4-yl)-(2S)-{2-[3-(4-tert-butyl-phenoxy)-benzylamino]-5-chloro-benzoylamino}-propionic acid | 739 |
| 495 | 3-(2'-Benzyloxy-biphenyl-4-yl)-(2S)-[2-(4-tert-butyl-benzylamino)-5-chloro-benzoylamino]-propionic acid | 647 |
| 496 | (2S)-[5-Chloro-2-(3-phenoxy-benzylamino)-benzoylamino]-3-(2'-phenoxy-biphenyl-4-yl)-propionic acid | 669 |
| 497 | (2S)-[2-(3,5-Bis-trifluoromethyl-benzylamino)-5-chloro-benzoylamino]-3-(2'-phenoxy-biphenyl-4-yl)-propionic acid | 713 |
| 498 | (2S)-[5-Chloro-2-(4-phenoxy-benzylamino)-benzoylamino]-3-(2'-phenoxy-biphenyl-4-yl)-propionic acid | 669 |
| 499 | (2S)-[2-(4-Benzyloxy-benzylamino)-5-chloro-benzoylamino]-3-(2'-phenoxy-biphenyl-4-yl)-propionic acid | 683 |
| 500 | 3-Biphenyl-4-yl-(2S)-[5-(2-chloro-4-trifluoromethyl-phenoxy)-2-(2-methyl-butylamino)-benzoylamino]-propionic acid | 625 |
| 501 | (2S)-[3,5-Dichloro-2-(2-methyl-butylamino)-benzoylamino]-3-(2'-phenoxy-biphenyl-4-yl)-propionic acid | 591 |
| 502 | (2S)-[5-Bromo-2-(cyclohexylmethyl-amino)-benzoylamino]-3-(2'-phenoxy-biphenyl-4-yl)-propionic acid | 628 |
| 503 | (2S)-(5-Chloro-2-pentylamino-benzoylamino)-3-(2'-phenoxy-biphenyl-4-yl)-propionic acid | 557 |
| 504 | (2S)-{2-[3-(4-tert-Butyl-phenoxy)-benzylamino]-5-chloro-benzoylamino}-3-(2'-hydroxy-biphenyl-4-yl)-propionic acid | 649 |
| 505 | (2S)-(5-Chloro-2-hexa-2,4-dienylamino-benzoylamino)-3-(2'-phenoxy-biphenyl-4-yl)-propionic acid | 567 |
| 506 | (2S)-[5-Chloro-2-(3-phenyl-propylamino)-benzoylamino]-3-(2'-phenoxy-biphenyl-4-yl)-propionic acid | 605 |
| 507 | (2S)-(5-Chloro-2-octylamino-benzoylamino)-3-(2'-phenoxy-biphenyl-4-yl)-propionic acid | 599 |
| 508 | (2S)-(5-Chloro-2-hexylamino-benzoylamino)-3-(2'-phenoxy-biphenyl-4-yl)-propionic acid | 571 |
| 509 | (2S)-[5-Chloro-2-(2,2-dimethyl-propylamino)-benzoylamino]-3-(2'-phenoxy-biphenyl-4-yl)-propionic acid | 557 |
| 510 | (2S)-[5-Chloro-2-(2-methyl-pent-2-enylamino)-benzoylamino]-3-(2'-phenoxy-biphenyl-4-yl)-propionic acid | 569 |
| 511 | (2S)-(5-Chloro-2-ethylamino-benzoylamino)-3-(2'-phenoxy-biphenyl-4-yl)-propionic acid | 515 |

EXAMPLE 512

(2S)-(5-Chloro-2-diethylamino-benzoylamino)-3-(2'-phenoxy-biphenyl-4-yl)-propionic acid (2S)-(2-Amino-5-chloro-benzoylamino)-3-(2'-phenoxy-biphenyl-4-yl)-propionic acid methyl ester was prepared (0.6 g, 80%) from (2S)-Amino-3-(2'-phenoxy-biphenyl-4-yl)-propionic acid methyl ester (0.5 g, 1.5 mmol), 5-chloro-2-amino-benzoic acid (0.28 g, 1.65 mmol) as desribed in general procedure A.

(2S)-(2-Amino-5-chloro-benzoylamino)-3-(2'-phenoxy-biphenyl-4-yl)-propionic acid methyl ester (0.5 g, 1.0 mmol), was reacted with acetaldehyde (0.175 g, 3.0 mmol), sodium cyanoboro hydride (10 ml 1.0M solution in THF, 10 mmol), in DCM (50 ml) as described in the general procedure E. The crude product was purified by flash column chromatography on silica gel using DCM as an eluent to give ester wich was hydrolyzed by following the general procedure I to give 0.4 g (69% of over all) of the title compound. LCMS: 543 (M+1)$^+$. $^1$H NMR (CDCl$_3$) [t, 6H], 2.88 [q, 4H], 3.45 [m, 1H], 3.58 [m, 1H], 5.12 [m, 1H], 7.17–7.7 [m, 16H], 8.48 [d, 1H], 11.57 [s, 1H].

EXAMPLE 513

2-(5-Chloro-2-diethylamino-benzoylamino)-3-[3'-(4-trifluoromethyl-phenoxy)-biphenyl-4-yl]-propionic acid A solution of (L)-4-bromophenylalanine (7.0 g, 28.6 mmol) in DME (100 mL) was reacted with 3-hydroxyphenyl boronic acid (5.14 g, 37.2 mmol), palladium tetrakis-triphenylphosphine (3.3 g, 2.8 mmol), and $Na_2CO_3$ (2.0 N, 43.0 mL, 86 mmol) by the general procedure D. After removal of solvent, the solid was washed with ether and DCM to afford 2-amino-3-(3'-hydroxy-biphenyl-4-yl)propionic acid methyl ester in HCl salt form (8.20 g, 31.9 mmol, 93% yield).

A solution of 2-amino-5-chloro-benzoic acid (1.95 g, 11.38 mmol) in DMF (10.0 mL) was reacted with 2-amino-3-(3'-hydroxy-biphenyl-4-yl)propionic acid methyl ester (3.50 g, 11.38 mmol), HBTU (3.98 g, 10.50 mmol), and DIEA (6.08 mL, 34.15 mmol) by the general procedure A. The crude product was purified by flash column chromatography on silical gel using DCM (+15% hexane) and increasing the gradient to DCM and finally DCM (+0.25% methanol) to give 1.75 g, (36%) of 2-(2-amino-5-chloro-benzoylamino)-3-(3'-hydroxy-biphenyl-4-yl)-propionic acid methyl ester as a white solid. LCMS: 425 (M+1)$^+$.

A solution 2-(2-amino-5-chloro-benzoylamino)-3-(3'-hydroxy-biphenyl-4-yl)-propionic acid methyl ester (0.850 g, 2.00 mmol) was reacted with acetaldehyde (0.350 g, 6.01 mmol), sodium triacetoxyborohydride (0.850 g, 4.00 mmol), and acetic acid/DCM (1.0 M, 3.00 mL) by the general procedure E. The crude product was purified by flash column chromatography on silica gel using DCM (+15% hexane) and increasing the gradient to DCM and finally DCM (+0.25% methanol) to give 0.540 g, (56%) of the phenolic etser.

A solution of this phenolic ester (0.240 g, 0.49 mmol) in DCM (5.0 mL) was reacted with copper acetate (0.100 g, 0.54 mmol), and 4-trifluoromethylbenzene boronic acid (0.236 g, 1.24 mmol), and triethyl amine (0.350 mL) by the general procedure G. The crude product was purified by the flash column chromatography on silica gel using DCM (+5% hexane) to give 0.133 g, (43%) of 2-(5-Chloro-2-diethylamino-benzoylamino)-3-[3'-(4-trifluoromethyl-phenoxy)-biphenyl-4-yl]-propionic acid methyl ester. This ester (0.110 g, 0.17 mmol) was reacted with LiOH (0.030 g, 0.70 mmol) by the general procedure J to give 0.095 g (89%) of 2-(5-Chloro-2-diethylamino-benzoylamino)-3-[3'-(4-trifluoromethyl-phenoxy)-biphenyl-4-yl]-propionic acid as a white solid. LCMS: 612 (M+1)$^+$. $^1$H NMR (CDCl$_3$) 11.56 [s, 1H], 8.28 [d, 1H], 7.59 [d, 2H], 7.42 [dd, 1H], 7.35 [dd, 1H], 7.28 [m, 4H], 7.19 [t, 1H], 7.15 [d, 1H], 7.09 [d, 1H], 7.02 [dd, 1H], 7.00 [dd, 1H], 5.05 [m, 1H], 3.32 [m, 2H], 2.79 [q, 4H], 0.69 [t, 6H].

EXAMPLE 514

To a solution of 5-chloro-2-fluoro-benzonitrile (0.700 g, 4.499 mmol) in anhydrous DMF (8.0 mL) was added 3,5-dimethylpiperdine (0.713 g, 6.299 mmol) and cesium carbonate (4.30 g, 13.497 mmol). The reaction mixture was heated at 80 C for 2 h. Upon cooling to rt, water and ethylacetate was added. The organic layer was separated and the aqueous layer was extracted twice with ethyl acetate. To the combined organic layer was added ether and the organic layer was washed with water and brine, dried (Na2SO4) and concentrated under reduced pressure to give 1.15 g (96%) of 5-chloro-2-(3,5-dimethyl-piperidin-1-yl)-benzonitrile as solid. LCMS 249(M+1)$^+$. The compound was >98% purity and was hence used directly for the next step To a solution of 5-chloro-2-(3,5-dimethyl-piperidin-1-yl)-benzonitrile (1.05 g, 4.220 mmol) in Diethylene glycol monomethyl ether (2.50 mL) was added KOH (0.947 g, 16.883 mmol) and water (0.750 ml). The reaction was heated at 130–135° C. overnight. Upon cooling to rt, water and ethyl acetate was added the organic layer was discarded and the aqueous layer is acidified to pH~6–7. The aqueous layer was then extracted with ethyl acetate three times. The combined organic layer was washed with water, brine, dried (Na2SO4), and concentrated to give required 5-chloro-2-(3,5-dimethyl-piperidin-1-yl)-benzoic acid (0.850 g, 75%) as an off white solid. LCMS 268(M+1)$^+$.

A solution of 5-chloro-2-(3,5-dimethyl-piperidin-1-yl)-benzoic acid (0.250 g, 0.933 mmol) in DMF (4.0 mL) was reacted with (2S)-amino-3-(2'-phenoxy-biphenyl-4-yl)-propionic acid methyl ester hydrochloride (0.360 g, 0.933 mmol), HBTU (0.355 g, 0.933 mmol), and DIEA (0.500 mL, 2.800 mmol) by the general procedure A. The crude product was purified by flash column chromatography on silica gel using DCM (+20% hexane) to give 0.435 g (62%) of 2-[5-Chloro-2-(3,5-dimethyl-piperidin-1-yl)-benzoylamino]-3-(2'-phenoxy-biphenyl-4-yl)-propionic acid methyl ester. A solution of this ester (0.200 g, 0.334 mmol) in THF (4.0 mL) was reacted with LiOH (0.050 g, 1.172 mmol) by the general procedure I to give 0.182 g (93%) of 2-[5-Chloro-2-(3,5-dimethyl-piperidin-1-yl)-benzoylamino]-3-(2'-phenoxy-biphenyl-4-yl)-propionic acid as a white solid. LCMS: 584 (M+1)$^+$. $^1$H NMR (CDCl$_3$) 11.20 [d, 1H], 8.21 [d, 1H], 7.45 [m, 2H], 7.39 [m, 2H], 7.23 [m, 8H], 7.02 [m, 2H], 6.86 [m, 2H], 4.90 [m, 1H], 3.38 [dd, 5.60 Hz, 1H], 3.26 [dd, 1H], 2.80 [m, 2H], 2.16 [t, 1H], 2.04 [t, 1H], 1.70 [m, 2H], 1.43 [m, 1H], 0.76 [m, 6H], 0.58 [m, 1H].

By analogous methods to those described above the following compounds were synthesized.

| EXAMPLE | NAME | LC/MS (m/z) |
| --- | --- | --- |
| 515 | 3-Biphenyl-4-yl-(2S)-{2-[bis-(4-benzyloxy-benzyl)-amino]-5-chloro-benzoylamino}-propionic acid | 787 |
| 516 | 3-Biphenyl-4-yl-(2S)-[2-(bis-naphthalen-1-ylmethyl-amino)-5-chloro-benzoylamino]-propionic acid | 675 |
| 517 | 3-Biphenyl-4-yl-(2S)-[2-(bis-biphenyl-4-ylmethyl-amino)-5-chloro-benzoylamino]-propionic acid | 727 |
| 518 | (2S)-(5-Bromo-2-dibutylamino-benzoylamino)-3-(2'-phenoxy-biphenyl-4-yl)-propionic acid | 644 |
| 519 | (2S)-(5-Bromo-2-dihexylamino-benzoylamino)-3-(2'-phenoxy-biphenyl-4-yl)-propionic acid | 700 |
| 520 | (2S)-(5-Chloro-2-dipentylamino-benzoylamino)-3-(2'-phenoxy-biphenyl-4-yl)-propionic acid | 627 |
| 521 | (2S)-(5-Chloro-2-piperidin-1-yl-benzoylamino)-3-(2'-phenoxy-biphenyl-4-yl)-propionic acid | 555 |
| 522 | (2S)-(5-Bromo-2-diethylamino-benzoylamino)-3-(2'-phenoxy-biphenyl-4-yl)-propionic acid | 588 |
| 523 | (2S)-(5-Chloro-2-diethylamino-benzoylamino)-3-[3'-(3-chloro-4-fluoro-phenoxy)-biphenyl-4-yl]-propionic acid | 595 |

-continued

| EXAMPLE | NAME | LC/MS (m/z) |
|---|---|---|
| 524 | (2S)-(5-Bromo-2-piperidin-1-yl-benzoylamino)-3-(2'-phenoxy-biphenyl-4-yl)-propionic acid | 600 |
| 525 | (2S)-(5-Chloro-2-diethylamino-benzoylamino)-3-[3'-(4-methoxy-phenoxy)-biphenyl-4-yl]-propionic acid | 573 |
| 526 | (2S)-(5-Chloro-2-diethylamino-benzoylamino)-3-[3'-(4-trifluoromethoxy-phenoxy)-biphenyl-4-yl]-propionic acid | 627 |
| 527 | 3-[3'-(4-tert-Butyl-phenoxy)-biphenyl-4-yl]-(2S)-(5-chloro-2-diethylamino-benzoylamino)-propionic acid | 599 |
| 528 | (2S)-(5-Bromo-2-diethylamino-benzoylamino)-3-[3'-(4-trifluoromethyl-phenoxy)-biphenyl-4-yl]-propionic acid | 656 |
| 529 | (2S)-(5-Bromo-2-diethylamino-benzoylamino)-3-[3'-(3-fluoro-phenoxy)-biphenyl-4-yl]-propionic acid | 606 |
| 530 | (2S)-(5-Bromo-2-pyrrolidin-1-yl-benzoylamino)-3-(2'-phenoxy-biphenyl-4-yl)-propionic acid | 586 |
| 531 | (2S)-[5-Chloro-2-(4-methyl-piperazin-1-yl)-benzoylamino]-3-(2'-phenoxy-biphenyl-4-yl)-propionic acid | 570 |
| 532 | (2S)-[5-Chloro-2-(4-phenyl-piperazin-1-yl)-enzoylamino]-3-(2'-phenoxy-biphenyl-4-yl)-propionic acid | 632 |
| 533 | (2S)-[5-Chloro-2-(3,4-dihydro-1H-isoquinolin-2-yl)-benzoylamino]-3-(2'-phenoxy-biphenyl-4-yl)-propionic acid | 603 |
| 534 | (2S)-(5-Chloro-2-morpholin-4-yl-benzoylamino)-3-(2'-phenoxy-biphenyl-4-yl)-propionic acid | 557 |
| 535 | (2S)-(2-Azepan-1-yl-5-chloro-benzoylamino)-3-(2'-phenoxy-biphenyl-4-yl)-propionic acid | 569 |
| 536 | (2S)-[5-Chloro-2-(4-trifluoromethyl-piperidin-1-yl)-benzoylamino]-3-(2'-phenoxy-biphenyl-4-yl)-propionic acid | 623 |

EXAMPLE 537

(2S)-[5-Chloro-2-(4-methylsulfanyl-phenylamino)-benzoylamino]-3-(2'-phenoxy-biphenyl-4-yl)-propionic acid A solution of (2S)-(2-amino-5-chloro-benzoylamino)-3-(2'-phenoxy-biphenyl-4-yl)-propionic acid (0.154 g, 0.307 mmol), prepared by reacting (2S)-amino-3-(2'-phenoxy-biphenyl-4-yl)-propionic acid methyl ester and 2-amino-5-chlorobenzoic acid by the general procedure A) was reacted with 4-(methylthio)phenylboronic acid (0.130 g, 0.768 mmol), copper acetate (0.084 g, 0.460 mmol), and triethyl amine (0.215 mL, 1.535 mmol) by the general procedure G. The crude product was purified by flash column chromatography on silica gel using DCM (+25% hexane) to give 0.075 g (39%) of 2-[5-chloro-2-(4-methylsulfanyl-phenylamino)-benzoylamino]-3-(2'-phenoxy-biphenyl-4-yl)-propionic acid methyl ester as a colorless oil. This ester was treated with LiOH (0.019 g, 0.441 mmol) by the general procedure I to give 0.049 g (92%) of 2-[5-chloro-2-(4-methylsulfanyl-phenylamino)-benzoylamino]-3-(2'-phenoxy-biphenyl-4-yl)-propionic acid. LCMS: 610 (M+1)$^+$. $^1$H NMR (CDCl$_3$) 8.94 [bs, 1H], 7.49 [d, 2H], 7.47 [d, 1H], 7.22 [m, 10H], 7.06 [d, 2H], 6.99 [d, 2H], 6.88 [d, 2H], 6.50 [d, 1H], 4.99 [m, 1H], 3.30 [m, 2H], 2.45 [s, 3H].

EXAMPLE 538

2S-[5-Chloro-2-(3-chloro-4-fluoro-phenylamino)-benzoylamino]-3-(2'-phenoxy-biphenyl-4-yl)-propionic acid (2S)-(2-amino-5-chloro-benzoylamino)-3-(2'-phenoxy-biphenyl-4-yl)-propionic acid (0.154 g, 0.307 mmol) prepared above was reacted with 3-Cl, 4-F-phenyl boronic acid (0.13 g, 0.77 mmol), copper acetate (0.084 g, 0.460 mmol), and triethyl amine (0.215 mL, 1.535 mmol) as described in the general procedure G. The crude product was purified by column chromatography using DCM as an eluent then hydrolyzed as described in the general proceudure I to get the title compound (20 mg, 10%) as a light yellow solid. LCMS: 615 (M+1)$^+$. $^1$H NMR (CDCl$_3$) 3.12 [m, 1H], 3.39 [m, 1H], 4.84 [m, 1H], 6.61 [m, 1H], 6.79–7.58 [m, 19H], 8.88 [s, 1H].

By analogous methods to those described above the following compounds were synthesized.

| EXAMPLE | NAME | LC/MS (m/z) |
|---|---|---|
| 539 | (2S)-[5-Bromo-2-(4-trifluoromethyl-phenylamino)-benzoylamino]-3-(2'-phenoxy-biphenyl-4-yl)-propionic acid | 676 |
| 540 | (2S)-(5-Bromo-2-phenylamino-benzoylamino)-3-(2'-phenoxy-biphenyl-4-yl)-propionic acid | 608 |
| 541 | (2S)-(5-Chloro-2-phenylamino-benzoylamino)-3-(2'-phenoxy-biphenyl-4-yl)-propionic acid | 563 |
| 542 | (2S)-[5-Chloro-2-(4-trifluoromethyl-phenylamino)-benzoylamino]-3-(2'-phenoxy-biphenyl-4-yl)-propionic acid | 631 |
| 543 | (2S)-[5-Chloro-2-(3,5-dimethyl-phenylamino)-benzoylamino]-3-(2'-phenoxy-biphenyl-4-yl)-propionic acid | 591 |
| 544 | (2S)-[5-Chloro-2-(3-trifluoromethyl-phenylamino)-benzoylamino]-3-(2'-phenoxy-biphenyl-4-yl)-propionic acid | 631 |
| 545 | (2S)-[5-Chloro-2-(4-methoxy-phenylamino)-benzoylamino]-3-(2'-phenoxy-biphenyl-4-yl)-propionic acid | 593 |
| 546 | (2S)-[2-(4-tert-Butyl-phenylamino)-5-chloro-benzoylamino]-3-(2'-phenoxy-biphenyl-4-yl)-propionic acid | 619 |
| 547 | (2S)-[5-Chloro-2-(3,4-difluoro-phenylamino)-benzoylamino]-3-(2'-phenoxy-biphenyl-4-yl)-propionic acid | 599 |
| 548 | (2S)-[5-Chloro-2-(4-fluoro-3-methyl-phenylamino)-benzoylamino]-3-(2'-phenoxy-biphenyl-4-yl)-propionic acid | 595 |
| 549 | (2S)-[5-Chloro-2-(3,4-dichloro-phenylamino)-benzoylamino]-3-(2'-phenoxy-biphenyl-4-yl)-propionic acid | 631 |
| 550 | (2S)-[5-Chloro-2-(4-trifluoromethoxy-phenylamino)-benzoylamino]-3-(2'-phenoxy-biphenyl-4-yl)-propionic acid | 647 |
| 551 | (2S)-[5-Chloro-2-(4-methanesulfonyl-phenylamino)-benzoylamino]-3-(2'-phenoxy-biphenyl-4-yl)-propionic acid | 641 |
| 552 | (2S)-[2-(4-Benzyloxy-phenylamino)-5-chloro-benzoylamino]-3-(2'-phenoxy-biphenyl-4-yl)-propionic acid | 669 |
| 553 | (2S)-[5-Chloro-2-(naphthalen-1-ylamino)-benzoylamino]-3-(2'-phenoxy-biphenyl-4-yl)-propionic acid | 613 |
| 554 | (2S)-[5-Chloro-2-(naphthalen-2-ylamino)-benzoylamino]-3-(2'-phenoxy-biphenyl-4-yl)-propionic acid | 613 |
| 555 | (2S)-[2-(3,5-Bis-trifluoromethyl-phenylamino)-5-chloro-benzoylamino]-3-(2'-phenoxy-biphenyl-4-yl)-propionic acid | 699 |

-continued

| EXAMPLE | NAME | LC/MS (m/z) |
|---|---|---|
| 556 | (2S)-[5-Chloro-2-(4-cyclohexyl-phenylamino)-benzoylamino]-3-(2'-phenoxy-biphenyl-4-yl)-propionic acid | 645 |
| 557 | (2S)-[2-(Biphenyl-4-ylamino)-5-chloro-benzoylamino]-3-(2'-phenoxy-biphenyl-4-yl)-propionic acid | 639 |
| 558 | (2S)-[2-(3-Butoxy-phenylamino)-5-chloro-benzoylamino]-3-(2'-phenoxy-biphenyl-4-yl)-propionic acid | 635 |
| 559 | (2S)-[5-Chloro-2-(4-ethoxy-phenylamino)-benzoylamino]-3-(2'-phenoxy-biphenyl-4-yl)-propionic acid | 607 |
| 560 | (2S)-[5-Chloro-2-(4-fluoro-3-methoxy-phenylamino)-benzoylamino]-3-(2'-phenoxy-biphenyl-4-yl)-propionic acid | 611 |
| 561 | (2S)-[5-Chloro-2-(4-chloro-phenylamino)-benzoylamino]-3-(2'-phenoxy-biphenyl-4-yl)-propionic acid | 597 |
| 562 | (2S)-[5-Chloro-2-(3-chloro-phenylamino)-benzoylamino]-3-(2'-phenoxy-biphenyl-4-yl)-propionic acid | 597 |
| 563 | (2S)-[5-Chloro-2-(2,4-dichloro-phenylamino)-benzoylamino]-3-(2'-phenoxy-biphenyl-4-yl)-propionic acid | 631 |
| 564 | (2S)-[2-(Benzo[1,3]dioxol-5-ylamino)-5-chloro-benzoylamino]-3-(2'-phenoxy-biphenyl-4-yl)-propionic acid | 607 |
| 565 | (2S)-[5-Chloro-2-(4-cyano-phenylamino)-benzoylamino]-3-(2'-phenoxy-biphenyl-4-yl)-propionic acid | 588 |
| 566 | (2S)-[5-Chloro-2-(4-methoxy-3-methyl-phenylamino)-benzoylamino]-3-(2'-phenoxy-biphenyl-4-yl)-propionic acid | 607 |
| 567 | (2S)-[5-Chloro-2-(3-isopropyl-phenylamino)-benzoylamino]-3-(2'-phenoxy-biphenyl-4-yl)-propionic acid | 605 |
| 568 | (2S)-[5-Chloro-2-(4-nitro-phenylamino)-benzoylamino]-3-(2'-phenoxy-biphenyl-4-yl)-propionic acid | 608 |
| 569 | (2S)-[5-Chloro-2-(4-methyl-3-nitro-phenylamino)-benzoylamino]-3-(2'-phenoxy-biphenyl-4-yl)-propionic acid | 622 |

EXAMPLE 570

(2S)-{[(2-Biphenyl-4-yl-methoxycarbonyl-ethyl)-(4'-trifluoromethyl-biphenyl-carbonyl)-amino]-methyl}-(2S)-pyrrolidine-1-carboxylic acid tert-butyl ester To a solution of 2-biphenyl-4-yl-(1S)-(methoxycarbonyl) ethylammonium chloride (1.337 g, 4.58 mmol) and (2S)-formyl-pyrrolidine-1-carboxylic acid tert-butyl ester (1.0 eq., 913 mg, 4.58 mmol) in a mixture of 25 mL methanol and 25 mL THF was added glacial acetic acid (1.5 eq., 0.40 mL, 6.87 mmol) and the mixture was stirred at ambient temperature for ten minutes. To this was added a 1.0 N solution of NaCNBH$_3$ in THF (1.5 eq., 6.87 mL, 6.87 mmol) in small portions and the reaction mixture was stirred at r.t. overnight. The solvent was removed and the residue was dissolved in water and DCM and partitioned. The organic portion was dried over Na$_2$SO$_4$, filtered and concentrated. The crude product was purified by flash column chromatography (2:1 EtOAc:Hexanes, EtOAc) to provide (2S)-[(2-biphenyl-4-yl-(1S)-1-methoxycarbonyl-ethylamino)-methyl]-pyrrolidine-1-carboxylic acid tert-butyl ester (1.440 g, 72%) as a clear colorless oil.

A portion of the product (584 mg, 1.33 mmol), dissolved in 13 mL dry CH$_2$Cl$_2$, was subsequently condensed with 4'-trifluoromethyl-biphenyl-4-carbonyl chloride (1.2 eq., 455 mg, 1.60 mmol) (synthesized from 4'-trifluoromethyl-biphenyl-4-carboxylic acid by heating at reflux in a neat solution of thionyl chloride, followed by removal of excess reagent and volatiles in vacuo) in dry CH$_2$Cl$_2$ (13 mL), in the presence of triethylamine (3.0 eq., 3.99 mmol, 0.56 mL) at 0° C. The reaction was stirred at that temperature and gradually allowed to warm to ambient temperature until the reaction was shown to be complete by TLC. The solvent was removed and the crude residue was purified by flash column chromatography (1:1 EtOAc:hexanes) to afford the title compound, (2S)-{[(2-biphenyl-4-yl-(1S)-methoxycarbonyl-ethyl)-(4'-trifluoromethyl-biphenyl-4-carbonyl)-amino]-methyl}-(2S)-pyrrolidine-1-carboxylic acid tert-butyl ester (600 mg, 76%), as a white solid. LCMS 687 (M+1)$^+$.

EXAMPLE 571

(2S)-(2-{[(2-Biphenyl-4-yl-1-methoxycarbonyl-ethyl)-(4'-trifluoromethyl-biphenyl-4-carbonyl)-amino]-methyl}-(2S)-pyrrolidine-1-sulfonyl)-benzoic acid methyl ester Into a dry flask was placed 2-(2S)-{[(2-biphenyl-4-yl-(1S)-methoxycarbonyl-ethyl)-(4'-trifluoromethyl-biphenyl-4-carbonyl)-amino]-methyl}-pyrrolidine-1-carboxylic acid tert-butyl ester (333 mg, 0.485 mmol) (for preparation, see Example 570), and the flask was capped and purged with dry N$_2$. The flask was then charged with 5 mL of 4N HCl/dioxane and stirred at rt for about one hour. The solvent was removed and the crude product was rinsed with ether and dried in vacuo to afford 302 mg (100%) of the desired product, (2S)-{[(2-biphenyl-4-yl-(1S)-methoxycarbonyl-ethyl)-(4'-trifluoromethyl-biphenyl-4-carbonyl)-amino]-methyl}-pyrrolidinium; chloride, which was used without further purification.

The amine hydrochloride (40 mg, 64 micromol) was dissolved in anhydrous acetonitrile (2 mL) and to this was added 2-chlorosulfonyl-benzoic acid methyl ester (3.0 eq., 50 mg, 0.193 mmol), pyridine (0.2 mL) and DMAP (0.1 eq., 0.8 mg, 6.4 micromol) and the reaction carried out as described in general procedure F. The crude product was purified by flash column chromatography to afford 40 mg (79%) of the title compound, 2-(2S)-{[(2-Biphenyl-4-yl-(1S)-methoxycarbonyl-ethyl)-(4'-trifluoromethyl-biphenyl-4-carbonyl)-amino]-methyl}-pyrrolidine-1-sulfonyl)-benzoic acid methyl ester. LC/MS 785 (M+1)$^+$.

EXAMPLE 572

3-Biphenyl-4-yl-(2S)-[[(2R)-1-(2-thiophen-2-yl-acetyl)-pyrrolidine-2-methyl]-(4'-trifluoromethyl-biphenyl-4-carbonyl)-amino]-propionic acid The synthesis of the title compound proceeds through the intermediacy of (2S)-{[(2-biphenyl-4-yl-(1S)methoxycarbonyl-ethyl)-(4'-trifluoromethyl-biphenyl-4-carbonyl)-amino]-methyl}-(2R)-pyrrolidinium chloride, similar in all respects to the intermediate in the synthesis of Example 570, (2S)-{[(2-biphenyl-4-yl-(1S)-methoxycarbonyl-ethyl)-(4' trifluoromethyl-biphenyl-4-carbonyl)-amino]-methyl}-(2S)-pyrrolidinium chloride, in all respects except for the stereochemical orientation at the 2-position of the pyrrolidine ring. Thus, the synthesis of this intermediate proceeds as described in Examples 570 and 571 with the exception that (2S)-formyl-pyrrolidine-1-carboxylic acid tert-butyl ester is replaced with (2R)-formyl-pyrrolidine-1-carboxylic acid tert-butyl ester in the first step of the sequence.

To a solution of (2S)-{[(2-biphenyl-4-yl-(1S)methoxycarbonyl-ethyl)-(4'trifluoromethyl-biphenyl-4-carbonyl)-amino]-methyl}-(2R)-pyrrolidinium chloride (15 mg, 24 micromol) in dry CH$_2$Cl$_2$ under dry N$_2$ at 0° C. was added 2-thiophene acetyl chloride (3.0 eq., 72 µmol, 8.9 µL) followed by triethylamine (5.0 eq., 0.12 mmol, 17 µL) and the mixture was stirred at 0° C. for one hour, then the solvent was removed. The residue was purified by flash column chromatography (4:1 EtOAc:hexanes) to yield the purified amide, 3-biphenyl-4-yl-(2S)-[[1-(2-thiophen-2-yl-acetyl)-pyrrolidin-(2R)-ylmethyl]-(4'trifluoromethyl-biphenyl-4-carbonyl)-amino]-propionic acid methyl ester (17 mg, 100%). The ester was saponified according to general procedure C. Thus, 3-biphenyl-4-yl-(2S)-[[1-(2-thiophen-2-yl-acetyl)-pyrrolidin-(2R)-ylmethyl]-(4'trifluoromethyl-biphenyl-4-carbonyl)-amino]-propionic acid methyl ester (16 mg, 23 µmol) was dissolved in 1 mL of a 4:1 mixture of THF and methanol and cooled to 0° C. for the addition of 0.1 mL of 2N aq. LiOH. The reaction furnished the title compound, 3-Biphenyl-4-yl-(2S)-[[1-(2-thiophen-2-yl-acetyl)-pyrrolidin-(2R)-ylmethyl]-(4'-trifluoromethyl-biphenyl-4-carbonyl)-amino]-propionic acid (14 mg, 100%) LCMS: 697 (M+1)$^+$.

EXAMPLE 573

(2S)-[[2-(2-Acetylamino-4-methyl-thiazole-5-sulfonylamino)-ethyl]-(4'-trifluoromethyl-biphenyl-4-carbonyl)-amino]-3-biphenyl-4-yl-propionic acid methyl ester To a solution of 2-biphenyl-4-yl-(1S)-methoxycarbonylethyl-ammonium chloride (1.833 g, 6.28 mmol) and (2-oxoethyl)-carbamic acid tert-butyl ester (1.0 eq., 1.00 g, 6.28 mmol), dissolved in a mixture of 25 mL each of THF and methanol, was added glacial acetic acid (2.0 eq., 0.72 mL, 12.56 mmol), and after stirring for 10 minutes, NaCNBH$_3$ in small portions. The reaction mixture was stirred overnight at rt then the volatiles were removed in vacuo. The crude residue was purified by flash column chromatography (3:2 EtOAc:hexanes) to afford the desired secondary amine, 3-Biphenyl-4-yl-(2S)-(2-tert-butoxycarbonylamino-ethylamino)-propionic acid methyl ester (775 mg, 31%).

This secondary amine (803 mg, 2.02 mmol) was reacted with 4'-rifluoromethyl-biphenyl-4-carbonyl chloride (1.24 eq., 713 mg, 2.50 mmol) (see Example 591 for preparation) in 40 mL anhydrous CH$_2$Cl$_2$ in the presence of triethylamine (3.0 eq., 0.84 mL, 6.06 mmol) at 0° C. for one hour, then the mixture was allowed to warm to ambient temperature and stirred overnight. The volatiles were removed in vacuo and the residue was purified by flash column chromatography (1:1 EtOAc:hexanes) to afford 3-biphenyl-4-yl-(2S)-[(2-tert-butoxycarbonylamino-ethyl)-(4'-trifluoromethyl-biphenyl-4-carbonyl)-amino]-propionic acid methyl ester (996 mg, 76%). A portion of this compound (395 mg, 0.61 mmol) was placed in a dry flask, capped with a septum and purged with dry N$_2$. The flask was charged with 10 mL of 4N HCl/dioxane solution and stirred at r.t. for 1 hour, at which point the reaction was shown to be complete by TLC. The volatiles were removed and the residue was dissolved in ether and triturated with hexanes. The crude product, 2-[(2-biphenyl-4-yl-(1S)-methoxycarbonyl-ethyl)-(4'-trifluoromethyl-biphenyl-4-carbonyl)-amino]-ethyl-ammonium chloride (356 mg, 100%) was used without further purification.

To a mixture of 2-[(2-biphenyl-4-yl-(1S)-methoxycarbonyl-ethyl)-(4'-trifluoro-methyl-biphenyl-4-carbonyl)-amino]-ethyl-ammonium chloride (40 mg, 69 mmol) and 2-acetyl-amino-4-methyl-thiazole-5-sulfonyl chloride (3.0 eq., 52.4 mg, 0.21 mmol), in 2 mL anhydrous CH$_2$Cl$_2$ at 0° C., was added pyridine (5.0 eq., 28 µL, 0.34 mmol) and DMAP (0.1 eq., 0.8 mg, 6.9 µmol) and the mixture was allowed to gradually warm to ambient temperature and stirred overnight. The solvent was removed and the residue was purified by flash column chromatography (EtOAc) to afford the title compound, (2S)-[[2-(2-Acetylamino-4-methyl-thiazole-5-sulfonylamino)-ethyl]-(4'-trifluoromethyl-biphenyl-4-carbonyl)-amino]-3-biphenyl-4-yl-propionic acid methyl ester (42 mg, 80%). LCMS 765 (M+1)$^+$.

By analogous methods to those described above the following compounds were synthesized.

| EXAMPLE | NAME | LC/MS (m/z) |
|---|---|---|
| 574 | (2S)-[(Biphenyl-4-carbonyl)-(2-hydroxy-benzyl)-amino]-3-biphenyl-4-yl-propionic acid | 528 |
| 575 | (2S)-[(Biphenyl-4-carbonyl)-(4-isopropyl-benzyl)-amino]-3-biphenyl-4-yl-propionic acid | 554 |
| 576 | 3-Biphenyl-4-yl-(2S)-[(4-isopropyl-benzyl)-(naphthalene-2-carbonyl)-amino]-propionic acid | 528 |
| 577 | 3-Biphenyl-4-yl-(2S)-[(4-tert-butyl-benzoyl)-(4-isopropyl-benzyl)amino]-propionic acid | 534 |
| 578 | 3-Biphenyl-4-yl-(2S)-[(3,4-dichloro-benzoyl)-(4-isopropyl-benzyl)-amino]-propionic acid | 546 |
| 579 | (2S)-[(Biphenyl-4-carbonyl)-naphthalen-1-ylmethyl-amino]-3-biphenyl-4-yl-propionic acid | 562 |
| 580 | 3-Biphenyl-4-yl-(2S)-[(naphthalene-2-carbonyl)-naphthalen-1-ylmethyl-amino]-propionic acid | 536 |
| 581 | 3-Biphenyl-4-yl-(2S)-[(4-tert-butyl-benzoyl)-naphthalen-1-ylmethyl-amino]-propionic acid | 542 |
| 582 | 3-Biphenyl-4-yl-(2S)-[(3,5-dichloro-benzoyl)-naphthalen-1-ylmethyl-amino]-propionic acid | 554 |
| 583 | 3-Biphenyl-4-yl-(2S)-[(naphthalene-1-carbonyl)-naphthalen-1-ylmethyl-amino]-propionic acid | 536 |
| 584 | 3-Biphenyl-4-yl-(2S)-[(3,4-dichloro-benzoyl)-naphthalen-1-ylmethyl-amino]-propionic acid | 554 |
| 585 | 3-Biphenyl-4-yl-(2S)-[(4-methyl-benzoyl)-naphthalen-1-ylmethyl-amino]-propionic acid | 500 |
| 586 | 3-Biphenyl-4-yl-(2S)-[(2,4-dichloro-benzoyl)-naphthalen-1-ylmethyl-amino]-propionic acid | 554 |
| 587 | 3-Biphenyl-4-yl-(2S)-[naphthalen-1-yl-methyl-(4-nitro-benzoyl)-amino]-propionic acid | 531 |
| 588 | 3-Biphenyl-4-yl-(2S)-[(4-chloro-benzoyl)-naphthalen-1-ylmethyl-amino]-propionic acid | 520 |
| 589 | (2S)-[(Biphenyl-4-carbonyl)-(4-chloro-benzyl)-amino]-3-biphenyl-4-yl-propionic acid | 546 |
| 590 | 3-Biphenyl-4-yl-(2S)-[(4-chloro-benzyl)-(3,5-dichloro-benzoyl)-amino]-propionic acid | 538 |
| 591 | (2S)-[(Biphenyl-4-carbonyl)-(5-tert-butyl-2-hydroxy-benzyl)-amino]-3-biphenyl-4-yl-propionic acid | 584 |
| 592 | Biphenyl-4-carboxylic acid (2S)-{[(biphenyl-4-carbonyl)-(2-biphenyl-4-yl-1-carboxy-ethyl)-amino]-methyl}-4-tert-butyl-phenyl ester | 764 |

| EXAMPLE | NAME | LC/MS (m/z) |
|---|---|---|
| 593 | 3-Biphenyl-4-yl-(2S)-[(4-bromo-benzoyl)-(2-tert-butoxycarbonylamino-ethyl)-amino]-propionic acid | 568 |
| 594 | 3-Biphenyl-4-yl-(2S)-[(2-tert-butoxycarbonylamino-ethyl)-(4'-trifluoromethoxy-biphenyl-4-carbonyl)-amino]-propionic acid | 649 |
| 595 | (2S)-[(2-Amino-ethyl)-(4-bromo-benzoyl)-amino]-3-biphenyl-4-yl-propionic acid methyl ester | 482 |
| 596 | (2S)-[(2-Amino-ethyl)-(4-bromo-benzoyl)-amino]-3-biphenyl-4-yl-propionic acid | 468 |
| 597 | 3-Biphenyl-4-yl-(2S)-[(4-chloro-benzyl)-(4'-trifluoromethyl-biphenyl-4-carbonyl)-amino]-propionic acid | 614 |
| 598 | (2S)-{2-[(2-Biphenyl-4-yl-1-carboxy-ethyl)-(4'-trifluoromethyl-biphenyl-4-carbonyl)-amino]-ethylsulfamoyl}-benzoic acid | 717 |
| 599 | 3-Biphenyl-4-yl-(2S)-[[2-(2-methanesulfonyl-benzenesulfonylamino)-ethyl]-(4'-trifluoromethyl-biphenyl-4-carbonyl)-amino]-propionic acid | 751 |
| 600 | (2S)-{[(2-Biphenyl-4-yl-1-methoxycarbonyl-ethyl)-(4'-trifluoromethyl-biphenyl-4-carbonyl)-amino]-methyl}-pyrrolidine-1-carboxylic acid tert-butyl ester | 687 |
| 601 | (2S)-{2-[(2-Biphenyl-4-yl-1-methoxycarbonyl-ethyl)-(4'-trifluoromethyl-biphenyl-4-carbonyl)-amino]-ethylsulfamoyl}-benzoic acid methyl ester | 745 |
| 602 | 3-Biphenyl-4-yl-(2S)-[[2-(2-methanesulfonyl-benzenesulfonylamino)-ethyl]-(4'-trifluoromethyl-biphenyl-4-carbonyl)-amino]-propionic acid methyl ester | 765 |
| 603 | 3-Biphenyl-4-yl-(2S)-[[2-(4-methanesulfonyl-benzenesulfonylamino)-ethyl]-(4'-trifluoromethyl-biphenyl-4-carbonyl)-amino]-propionic acid methyl ester | 765 |
| 604 | 3-Biphenyl-4-yl-(2S)-[[1-(2-methanesulfonyl-benzenesulfonyl)-pyrrolidin-2-ylmethyl]-(4'-trifluoromethyl-biphenyl-4-carbonyl)-amino]-propionic acid methyl ester | 805 |
| 605 | 3-Biphenyl-4-yl-(2S)-[[1-(4-methanesulfonyl-benzenesulfonyl)-pyrrolidin-2-ylmethyl]-(4'-trifluoromethyl-biphenyl-4-carbonyl)-amino]-propionic acid methyl ester | 805 |
| 606 | (2S)-{[(2-Biphenyl-4-yl-1-carboxy-ethyl)-(4'-trifluoromethyl-biphenyl-4-carbonyl)-amino]-methyl}-pyrrolidine-1-carboxylic acid tert-butyl ester | 673 |
| 607 | (2S)-{[(2-Biphenyl-4-yl-1-carboxy-ethyl)-(4'-trifluoromethyl-biphenyl-4-carbonyl)-amino]-methyl}-pyrrolidine-1-carboxylic acid tert-butyl ester | 673 |
| 608 | (2S)-(2-{[(2-Biphenyl-4-yl-1-carboxy-ethyl)-(4'-trifluoromethyl-biphenyl-4-carbonyl)-amino]-methyl}-pyrrolidine-1-sulfonyl)-benzoic acid methylester | 771 |
| 609 | 3-Biphenyl-4-yl-(2S)-[[1-(2-methanesulfonyl-benzenesulfonyl)-pyrrolidin-2-ylmethyl]-(4'-trifluoromethyl-biphenyl-4-carbonyl)-amino]-propionic acid | 791 |
| 610 | 3-Biphenyl-4-yl-(2S)-[[1-(4-methanesulfonyl-benzenesulfonyl)-pyrrolidin-2-ylmethyl]-(4'-trifluoromethyl-biphenyl-4-carbonyl)-amino]-propionic acid | 791 |
| 611 | (2S)-(2-{[(2-Biphenyl-4-yl-1-methoxycarbonyl-ethyl)-(4'-trifluoromethyl-biphenyl-4-carbonyl)-amino]-methyl}-pyrrolidine-1-sulfonyl)-benzoic acid methyl ester | 785 |
| 612 | 3-Biphenyl-4-yl-(2S)-[[1-(2-methanesulfonyl-benzenesulfonyl)-pyrrolidin-2-ylmethyl]-(4'-trifluoromethyl-biphenyl-4-carbonyl)-amino]-propionic acid methyl ester | 805 |
| 613 | 3-Biphenyl-4-yl-(2S)-[[1-(4-methanesulfonyl-benzenesulfonyl)-pyrrolidin-2-ylmethyl]-(4'-trifluoromethyl-biphenyl-4-carbonyl)-amino]-propionic acid methyl ester | 805 |
| 614 | 3-Biphenyl-4-yl-(2S)-[[1-(2-thiophen-2-yl-acetyl)-pyrrolidin-2-ylmethyl]-(4'-trifluoromethyl-biphenyl-4-carbonyl)-amino]-propionic acid methyl ester | 711 |
| 615 | (2S)-(2-{[(2-Biphenyl-4-yl-1-carboxy-ethyl)-(4'-trifluoromethyl-biphenyl-4-carbonyl)-amino]-methyl}-pyrrolidine-1-sulfonyl)-benzoic acid methyl ester | 771 |
| 616 | 3-Biphenyl-4-yl-(2S)-[[1-(2-methanesulfonyl-benzenesulfonyl)-pyrrolidin-2-ylmethyl]-(4'-trifluoromethyl-biphenyl-4-carbonyl)-amino]-propionic acid | 791 |
| 617 | 3-Biphenyl-4-yl-(2S)-[(1-cyclopentanecarbonyl-pyrrolidin-2-ylmethyl)-(4'-trifluoromethyl-biphenyl-4-carbonyl)-amino]-propionic acid methyl ester | 683 |
| 618 | 3-Biphenyl-4-yl-(2S)-[(1-cyclopropanecarbonyl-pyrrolidin-2-ylmethyl)-(4'-trifluoromethyl-biphenyl-4-carbonyl)-amino]-propionic acid methyl ester | 655 |
| 619 | 3-Biphenyl-4-yl-(2S)-[[1-(4-methanesulfonyl-benzenesulfonyl)-pyrrolidin-2-ylmethyl]-(4'-trifluoromethyl-biphenyl-4-carbonyl)-amino]-propionic acid | 791 |
| 620 | (2S)-[(1-Acetyl-pyrrolidin-2-ylmethyl)-(4'-trifluoromethyl-biphenyl-4-carbonyl)-amino]-3-biphenyl-4-yl-propionic acid | 615 |
| 621 | 3-Biphenyl-4-yl-(2S)-[[1-(2,2-dimethyl-propionyl)-pyrrolidin-2-ylmethyl]-(4'-trifluoromethyl-biphenyl-4-carbonyl)-amino]-propionic acid | 657 |
| 622 | 3-Biphenyl-4-yl-(2S)-[(1-cyclopentanecarbonyl-pyrrolidin-2-ylmethyl)-(4'-trifluoromethyl-biphenyl-4-carbonyl)-amino]-propionic acid | 669 |
| 623 | (2S)-[(1-Acetyl-pyrrolidin-2-ylmethyl)-(4'-trifluoromethyl-biphenyl-4-carbonyl)-amino]-3-biphenyl-4-yl-propionic acid | 615 |
| 624 | 3-Biphenyl-4-yl-(2S)-[(1-cyclopropanecarbonyl-pyrrolidin-2-ylmethyl)-(4'-trifluoromethyl-biphenyl-4-carbonyl)-amino]-propionic acid | 641 |
| 625 | (2S)-[[2-(2-Acetylamino-4-methyl-thiazole-5-sulfonylamino)-ethyl]-(4'-trifluoromethyl-biphenyl-4-carbonyl)-amino]-3-biphenyl-4-yl-propionic acid | 751 |
| 626 | 3-Biphenyl-4-yl-(2S)-[[2-(5-chloro-1,3-dimethyl-1H-pyrazole-4-sulfonylamino)-ethyl]-(4'-trifluoromethyl-biphenyl-4-carbonyl)-amino]-propionic acid | 725 |
| 627 | 3-Biphenyl-4-yl-(2S)-[[2-(3,5-dimethyl-isoxazole-4-sulfonylamino)-ethyl]-(4'-trifluoromethyl-biphenyl-4-carbonyl)-amino]-propionic acid | 692 |

-continued

| EXAMPLE | NAME | LC/MS (m/z) |
|---|---|---|
| 628 | 3-Biphenyl-4-yl-(2S)-[[2-(1,2-dimethyl-1H-imidazole-4-sulfonylamino)-ethyl]-(4'-trifluoromethyl-biphenyl-4-carbonyl)-amino]-propionic acid | 691 |
| 629 | 3-Biphenyl-4-yl-(2S)-[[2-(3,5-dimethyl-isoxazole-4-sulfonylamino)-ethyl]-(4'-trifluoromethyl-biphenyl-4-carbonyl)-amino]-propionic acid methyl ester | 706 |
| 630 | 3-Biphenyl-4-yl-(2S)-[[2-(1,2-dimethyl-1H-imidazole-4-sulfonylamino)-ethyl]-(4'-trifluoromethyl-biphenyl-4-carbonyl)-amino]-propionic acid methyl ester | 705 |
| 631 | 3-Biphenyl-4-yl-(2S)-[[2-(5-chloro-1,3-dimethyl-1H-pyrazole-4-sulfonylamino)-ethyl]-(4'-trifluoromethyl-biphenyl-4-carbonyl)-amino]-propionic acid methyl ester | 739 |
| 632 | 3-Biphenyl-4-yl-(2S)-[[2-(1-methyl-1H-imidazole-4-sulfonylamino)-ethyl]-(4'-trifluoromethyl-biphenyl-4-carbonyl)-amino]-propionic acid | 677 |
| 633 | 3-Biphenyl-4-yl-(2S)-[[2-(2,4-dimethoxy-benzylamino)-ethyl]-(4'-trifluoromethyl-biphenyl-4-carbonyl)-amino]-propionic acid | 683 |
| 634 | 3-Biphenyl-4-yl-(2S)-[(2-tert-utoxycarbonylamino-ethyl)-(4'-rifluoromethyl—biphenyl-4-carbonyl)-amino]-propionic acid | 633 |

EXAMPLE 635

2-{[1-(4-Fluoro-phenyl)-5-trifluoromethyl-1H-pyrazole-4-carbonyl]-amino}-3-(4'-trifluoromethoxy-biphenyl-4-yl)-propionic acid A solution of hydrazine (1.00 mmol), ethyl 2-(ethoxymethylene)-4,4,4-trifluoroacetoacetate (1.00 mmol), and DIEA (1.00 mmol) in anhydrous acetonitrile was stirred at rt for 2 h. The reaction mixture was concentrated under reduced pressure and purified by flash column chromatography to give the desired ester as a white solid. This ester was then hydrolyzed by general procedure J to give the desired 1-(4-Fluoro-phenyl)-5-trifluoromethyl-1H-pyrazole-4-carboxylic acid as a white solid.

A solution of above acid in DMF (3.0 mL) was reacted with (2S)-amino-3-(4'-trifluoromethoxy-biphenyl-4-yl)-propionic acid methyl ester Hydrochloride (0.300 g, 0.797 mmol), HBTU (0.300 g, 0.797 mmol), and DIEA (0.425 mL, 2.40 mmol) as described in general procedure A. The crude compound was purified by flash column chromatography on silica gel using CHCl$_3$ as the mobile phase to give 0.290 g (61%) of 2-{[1-(4-fluoro-phenyl)-5-trifluoromethyl-1H-pyrazole-4-carbonyl]-amino}-3-(4'-trifluoromethoxy-biphenyl-4-yl)-propionic acid methyl ester. A solution of this ester (0.140 g, 0.235 mmol) in THF (4.0 mL) was treated with LiOH (0.035 g) by general procedure I to afford (0.125 g, 92%) of the title compound 2-{[1-(4-Fluoro-phenyl)-5-trifluoromethyl-1H-pyrazole-4-carbonyl]-amino}-3-(4'-trifluoromethyl-biphenyl-4-yl)-propionic acid as a white solid. LCMS: 582 (M+1)$^+$. $^1$H NMR (DMSO-d$_6$) 8.94 [d, 1H], 8.07 [s, 1H], 7.76 [m, 2H], 7.57 [m, 4H], 7.42 [m, 6H], 4.64 [m, 1H], 3.22 [m, 1H], 3.05 [m, 1H].

EXAMPLE 636

2-{[1-(4-Fluoro-phenyl)-5-trifluoromethyl-1H-pyrazole-4-carbonyl]-amino}-3-(4'-trifluoromethyl-biphenyl-4-yl)-propionic acid A solution of 1-(4-Fluoro-phenyl)-5-trifluoromethyl-1H-pyrazole-4-carboxylic acid (0.300 g, 1.097 mmol, prepared in example 635) in DMF (4.0 mL) was reacted with (2S)-amino-3-(4'-trifluoromethyl-biphenyl-4-yl)propionic acid methyl ester Hydrochloride (0.394 g, 1.097 mmol), HBTU (0.416 g, 1.097 mmol), and DIEA (0.585 mL, 3.29 mmol) as described in general procedure A. The crude compound was purified by washing with ethyl ether to give 0.300 g (47%) of 2-{[1-(4-Fluoro-phenyl)-5-trifluoromethyl-1H-pyrazole-4-carbonyl]-amino}-3-(4'-trifluoromethyl-biphenyl-4-yl)-propionic acid methyl ester. A solution of this ester (0.125 g, 0.215 mmol) in THF (4.0 mL) was treated with LiOH (0.031 g) by general procedure I to afford (0.105 g, 87%) the title compound 2-{[1-(4-Fluoro-phenyl)-5-trifluoromethyl-1H-pyrazole-4-carbonyl]-amino}-3-(4'-trifluoromethyl-biphenyl-4-yl)-propionic acid as a white solid. LCMS: 565 (M+1)$^+$. $^1$H NMR (DMSO-d$_6$) 8.92 [d, 1H], 8.39 [s, 1H], 8.18 [d, 2H], 8.09 [d, 2H], 7.96 [d, 2H], 7.87 [m, 2H], 7.71 [m, 4H], 4.83 [m, 1H], 3.58 [m, 1H], 3.36 [m, 1H].

EXAMPLE 637

(2S)-{[1-(4-Fluoro-phenyl)-5-trifluoromethyl-1H-pyrazole-4-carbonyl]-amino}-3-(4'-trifluoromethyl-biphenyl-4-yl)-propionic acid A solution of 1-(4-fluoro-phenyl)-5-trifluoromethyl-1H-pyrazole-4-carboxylic acid (0.200 g, 0.731 mmol, prepared in example 635) in DMF (4.0 mL) was reacted with 2-L-amino-3-biphenyl-4-yl-propionic acid methyl ester hydrochloride (0.213 g, 0.731 mmol), HBTU (0.277 g, 0.731 mmol), and DIEA (0.450 mL, 2.566 mmol) as described in general procedure A. The crude compound was purified by flash column chromatography on silica gel using CHCl$_3$ (+10% hexane) to give 0.150 g (41%) of 3-biphenyl-4-yl-2-{[1-(4-fluoro-phenyl)-5-trifluoromethyl-1H-pyrazole-4-carbonyl]-amino}-propionic acid methyl ester. A solution of this ester (0.085 g, 0.166 mmol) in THF (3.0 mL) was treated with LiOH (0.025 g) by general procedure I to afford (0.070 g, 85%) of the title compound 3-Biphenyl-4-yl-2-{[1-(4-fluoro-phenyl)-5-trifluoromethyl-1H-pyrazole-4-carbonyl]-amino}-propionic acid as a white solid. LCMS: 498 (M+1)$^+$. $^1$H NMR (DMSO-d$_6$) 8.94 [d, 1H], 8.08 [s, 1H], 7.58 [m, 6H], 7.42 [m, 7H], 4.63 [m, 1H], 3.22 [m, 1H], 3.04 [m, 1H].

3-Biphenyl-4-yl-(2S)-{[1-(4-fluoro-phenyl)-5-trifluoromethyl-1H-pyrazole-4-carbonyl]-amino}-propionic acid By analogous methods to those described above the following compounds were synthesized.

| EXAMPLE | NAME | LC/MS (m/z) |
|---|---|---|
| 638 | (2S)-{[1-(4-Chloro-phenyl)-5-trifluoromethyl-1H-pyrazole-4-carbonyl]-amino}-3-(4'-trifluoromethyl-biphenyl-4-yl)-propionic acid | 582 |

-continued

| EXAMPLE | NAME | LC/MS (m/z) |
|---|---|---|
| 639 | 3-Biphenyl-4-yl-(2S)-{[1-(4-chloro-phenyl)-5-trifluoromethyl-1H-pyrazole-4-carbonyl]-amino}-propionic acid | 514 |
| 640 | (2S)-{[1-(4-Chloro-phenyl)-5-trifluoromethyl-1H-pyrazole-4-carbonyl]-amino}-3-(4'-trifluoromethoxy-biphenyl-4-yl)-propionic acid | 598 |
| 641 | 2-{[1-(4-Fluoro-phenyl)-5-trifluoromethyl-1H-pyrazole-4-carbonyl]-amino}-3-(6-phenyl-pyridin-3-yl)-propionic acid | 499 |
| 642 | (2S)-{[1-(4-Nitro-phenyl)-5-rifluoromethyl-1H-pyrazole-4-carbonyl]-amino}-3-(4'-trifluoromethoxy-biphenyl-4-yl)-propionic acid | 609 |
| 643 | (2S)-{[1-(4-tert-Butyl-phenyl)-5-trifluoromethyl-1H-pyrazole-4-carbonyl]-amino}-3-(4'-trifluoromethoxy-biphenyl-4-yl)-propionic acid | 620 |
| 644 | (2S)-[(1-p-Tolyl-5-trifluoromethyl-1H-pyrazole-4-carbonyl)-amino]-3-(4'-trifluoromethoxy-biphenyl-4-yl)-propionic acid | 578 |
| 645 | (2S)-{[1-(6-Methoxy-pyridazin-3-yl)-5-trifluoromethyl-1H-pyrazole-4-carbonyl]-amino}-3-(4'-trifluoromethoxy-biphenyl-4-yl)-propionic acid | 596 |
| 646 | (2S)-[(5-Methyl-1-phenyl-1H-pyrazole-4-carbonyl)-amino]-3-(4'-trifluoromethoxy-biphenyl-4-yl)-propionic acid | 510 |
| 647 | (2S)-{[1-(4-Chloro-phenyl)-5-trifluoromethyl-1H-pyrazole-4-carbonyl]-amino}-3-(4'-trifluoromethoxy-biphenyl-4-yl)-propionic acid | 598 |
| 648 | 3-(4'-Trifluoromethoxy-biphenyl-4-yl)-(2S)-{[1-(4-trifluoromethoxy-phenyl)-5-trifluoromethyl-1H-pyrazole-4-carbonyl]-amino}-propionic acid | 648 |
| 649 | (2S)-{[1-(3-Chloro-4-fluoro-phenyl)-5-trifluoromethyl-1H-pyrazole-4-carbonyl]-amino}-3-(4'-trifluoromethoxy-biphenyl-4-yl)-propionic acid | 616 |
| 650 | (2S)-{[1-(4-Chloro-phenyl)-1H-pyrazole-4-carbonyl]-amino}-3-(4'-trifluoromethoxy-biphenyl-4-yl)-propionic acid | 530 |
| 651 | (2S)-[(1-Phenyl-5-trifluoromethyl-1H-pyrazole-4-carbonyl)-amino]-3-(4'-trifluoromethoxy-biphenyl-4-yl)-propionic acid | 564 |
| 652 | (2S)-[(1-Phenyl-5-trifluoromethyl-1H-pyrazole-4-carbonyl)-amino]-3-(4'-trifluoromethyl-biphenyl-4-yl)-propionic acid | 548 |
| 653 | 3-Biphenyl-4-yl-(2S)-[(1-phenyl-5-trifluoromethyl-1H-pyrazole-4-carbonyl)-amino]-propionic acid | 480 |
| 654 | (2S)-{[1-(4-Chloro-phenyl)-5-propyl-1H-pyrazole-4-carbonyl]-amino}-3-(2'-phenoxy-biphenyl-4-yl)-propionic acid | 580 |

EXAMPLE 655

3-(Biphenyl-4-ylmethoxy)-(2S)-[(4'-trifluoromethyl-biphenyl-4-carbonyl)-amino]-propionic acid To a solution of 2-tert-Butoxycarbonylamino-3-hydroxy-propionic acid methyl ester (0.400 g, 1.82 mmol) in dimethylformamide (15 ml) was added sodium hydride (65%) (0.145 g, 3.64 mmol) at 0° C. after the evolution of hydrogen gas ceased, the freshly distilled benzyl bromide (0.449 g, 1.82 mmol) was added to the solution. The reaction mixture was stirred at 25–30° C. for 5 hr to give a clear solution The solvent was then removed under reduced pressure below 40° C. The residue was dissolved in water (30 ml) and the solution extracted with ethyl acetate (two 20 ml portions). The combined organic layers were further washed with brine and dried over anhydrous sodium sulfate. The ethyl acetate was then removed under reduced pressure to give the 3-(biphenyl-4-ylmethoxy)-(2S)-tert-butoxycarbonylamino-propionic acid methyl ester as colorless oil (0.421 g, 60%). LC/MS (m/z): 386(M+1).

To 3-(Biphenyl-4-ylmethoxy)-(2S)-tert-butoxycarbonylamino-propionic acid methyl ester (0.421 gms, 1.1 mmol) was added 2 ml of 4M HCl in dioxane (8.8 mmol) and stirred for 30 min. The HCl was then removed under reduced pressure and the residue was then triturated with dichloromethane and hexane for 2–3 times and the solvents were removed under reduced pressure to yield the HCl salt of the compound (2S)-amino-3-(biphenyl-4-ylmethoxy)-propionic acid methyl ester hydrochloride as a white solid (0.300 g, 90%). LC/MS (m/z): 286 (M+1).

(2S)-Amino-3-(biphenyl-4-ylmethoxy)-propionic acid methyl ester hydrochloride (0.150 g, 0.483 mmol) was reacted with 4'-trifluoromethyl-biphenyl-4-carboxylic acid (0.136 g, 0.483 mmol) as described in general procedure A yielding the 3-(biphenyl-4-ylmethoxy)-(2S)-[(4'-trifluoromethyl-biphenyl-4-carbonyl)-amino]-propionic acid methyl ester. The resulting compound was then hydrolyzed by following the general procedure C to yield the title compound (0.200 g, 80%).
$^1$H-NMR(400 MHz, CDCl$_3$): 4.2 (m, 2H), 4.9 (S, 2H), 5.1 (m, 1H), 7.72 (m, 1H), 7.74 (m, 4H), 7.94 (m, 4H), 8.17 (m, 4H), 8.28 (d, 2H), 8.34 (d, 2H), 8.62 (S, 1H), 9.3 (d, 1H); LC/MS (m/z): 520.2 (M+1)$^+$.

EXAMPLE 656

3-[(Biphenyl-4-ylmethyl)-amino]-(2S)-[(4'-trifluoromethyl-biphenyl-4-carbonyl)-amino]-propionic acid (2S)-amino-3-tert-butoxycarbonylamino-propionic acid methyl ester hydrochloride (0.200 g, 0.785 mmol) was reacted with 4'-trifluoromethyl-biphenyl-4-carboxylic acid (0.208 g, 0.785 mmol) as described in general procedure A yielding 3-tert-butoxycarbonylamino-(2S)-[(4'-trifluoromethyl-biphenyl-4-carbonyl)-amino]-propionic acid methyl ester (0.313 g, 85%). LC/MS (m/z): 367 (M+1).

To 3-tert-butoxycarbonylamino-(2S)-[(4'-trifluoromethyl-biphenyl-4-carbonyl)amino]-propionic acid methyl ester (0.313 g, 0.671 mmol) was added 2 ml of 4M HCl in dioxane (3.3 mmol) and stirred for 30 min. The HCl was then removed under reduced pressure and the residue was then triturated with dichloromethane and hexane for 2–3 times and the solvents were removed under reduced pressure to yield the HCl salt of the compound 3-amino-(2S)-[(4'-trifluoromethyl-biphenyl-4-carbonyl)-amino]-propionic acid methyl ester hydrochloride as a white solid (0.300 g, 90%). LC/MS (m/z): 267 (M+1).

3-Amino-(2S)-[(4'-trifluoromethyl-biphenyl-4-carbonyl)-amino]-propionic acid methyl ester hydrochloride (0.200 g, 0.493 mmol) was subjected to reductive amination as per general procedure E with biphenyl-4-carbaldehyde (0.080 g, 0.444 mmol) and sodium triacetoxyborohydride (0.208 g, 0.986 mmol) to yield the 3-[(biphenyl-4-ylmethyl)-amino]-(2S)-[(4'-trifluoromethyl-biphenyl-4-carbonyl)-amino]-propionic acid methyl ester which was further hydrolyzed as per general procedure C to yield 3-[(biphenyl-4-ylmethyl)-amino]-(2S)-[(4'-trifluoromethyl-biphenyl-4-carbonyl)-amino]-propionic acid (0.190 g, 70%).

$^1$H-NMR(400 MHz, DMSOd$_6$): 3.9 (m, 2H) 4.6 (m, 2H), 5.2 (m, 1H), 7.72 (m, 1H), 7.78 (m, 2H), 7.98 (m, 4H), 8.05 (bd, 2H), 8.19 (m, 4H), 8.27 (d, 2H), 8.40 (d, 2H), 8.7 (S, 1H), 9.5 (d, 1H); LC/MS (m/z): 519.3 (M+1).

EXAMPLE 657

3-(Biphenyl-4-ylmethyl-methyl-amino)-(2S)-[(4'-trifluoromethyl-biphenyl-4-carbonyl)-amino]-propionic acid 3-[(Biphenyl-4-ylmethyl)-amino]-(2S)-[(4'-trifluoromethyl-biphenyl-4-carbonyl)amino]-propionic acid methyl ester (0.050 g, 0.093 mmol) prepared as per the above listed example 656 was subjected to reductive amination as per procedure E with formaldehyde (0.010 ml, 0.093 mmol) and sodium triacetoxyborohydride (0.039 gms, 0.186 mmol) to yield the corresponding 3-(Biphenyl-4-ylmethyl-methyl-amino)-(2S)-[(4'-trifluoromethyl-biphenyl-4-carbonyl)-amino]-propionic acid methyl ester which was then hydrolyzed as per general procedure C to yield the title compound (0.040 g, 80%). $^1$H-NMR (400 MHz, DMSOd$_6$): 3.17 (s, 3H), 3.9 (m, 2H), 4.76 (m, 2H), 5.31 (s, 1H), 7.69 (m, 1H), 7.77 (m, 2H), 7.97 (m, 4H), 8.05 (bd, 2H), 8.19 (m, 4H), 8.27 (d, 2H), 8.40 (d, 2H), 9.5 (s, 1H); LC/MS (m/z): 533.3 (M+1).

EXAMPLE 658

3-(Biphenyl-4-ylmethyl-pyridin-4-ylmethyl-amino)-(2S)-[(4'-trifluoromethyl-biphenyl-4-carbonyl)-amino]-propionic acid 3-[(Biphenyl-4-ylmethyl)-amino]-(2S)-[(4'-trifluoromethyl-biphenyl-4-carbonyl)-amino]-propionic acid methyl ester (0.050 g, 0.093 mmol) prepared as per the above listed example 656 was subjected to reductive amination as per procedure E with 4-pyridine carbaldehyde (0.010 ml, 0.093 mmol) and sodium triacetoxyborohydride (0.039 gms, 0.186 mmol) to yield the corresponding 3-(Biphenyl-4-ylmethyl-pyridin-4-ylmethyl-amino)-(2S)-[(4'-trifluoromethyl-biphenyl-4-carbonyl)-amino]-propionic acid methyl ester which was then hydrolyzed as per general procedure C to yield the title compound (0.040 g, 80%). $^1$H-NMR(400 MHz, DMSOd$_6$): 3.3 (m, 2H), 4.001 (s, 4H), 5.18 (m, 1H), 7.62–7.75 (m, 8H), 7.8–7.93 (m, 4H), 8.17 (m, 4H), 8.27 (m, 4H), 8.77 (d, 2H), 9.1 (d, 1H), 8.7 (S, 1H); LC/MS (m/z): 610.4 (M+1).

EXAMPLE 659

3-(Biphenyl-4-ylmethyl-furan-2-ylmethyl-amino)-(2S)-[(4'-trifluoromethyl-biphenyl-4-carbonyl)-amino]-propionic acid 3-[(Biphenyl-4-ylmethyl)-amino]-(2S)-[(4'-trifluoromethyl-biphenyl-4-carbonyl)-amino]-propionic acid methyl ester (0.050 g, 0.093 mmol) prepared as per the above listed example 657 and was subjected to reductive amination as per procedure E with furan-2-carbaldehyde (0.009 g, 0.093 mmol) and sodium triacetoxyborohydride (0.039 gms, 0.186 mmol) to yield the corresponding 3-(biphenyl-4-ylmethyl-furan-2-ylmethyl-amino)-(2S)-[(4'-trifluoromethyl-biphenyl-4-carbonyl)-amino]-propionic acid methyl ester which was then hydrolyzed as per general procedure C to yield the title compound (0.030 g, 60%). $^1$H-NMR(400 MHz, DMSOd$_6$): 3.21 (m, 2H), 4.0 (m, 3H), 6.7 (d, 1H), 7.6 (m, 2H), 7.8 (m, 8H), 8.24 (m, 8H); LC/MS (m/z): 599.3 (M+1).

EXAMPLE 660

3-[(Biphenyl-4-carbonyl)-amino]-(2S)-[(4'-trifluoromethyl-biphenyl-4-carbonyl)-amino]-propionic acid The 3-amino-(2S)-[(4'-trifluoromethyl-biphenyl-4-carbonyl)-amino]-propionic acid methyl ester hydrochloride (0.100 g, 0.273 mmol) prepared as per the above listed Example 656 was reacted with biphenylcarboxylic acid as per general procedure A to yield the corresponding 3-[(biphenyl-4-carbonyl)-amino]-(2S)-[(4'-trifluoromethyl-biphenyl-4-carbonyl)-amino]-propionic acid methyl ester which was then hydrolyzed as per general procedure C to yield the title compound (0.095 g, 65%). $^1$H-NMR(400 MHz, DMSOd$_6$): 4.16 (m, 2H), 4.98 (m, 1H), 7.71 (m, 2H), 7.79 (m, 2H), 8.08 (dd, 4H), 8.2–8.4 (m, 9H), 9.16 (m, 1H), 9.2 (d, 1H); LC/MS (m/z): 533.2 (M+1).

EXAMPLE 661

(2S)-2,3-Bis-[(4'-trifluoromethyl-biphenyl-4-carbonyl)-amino]-propionic acid (2S)-2,3-Diamino-propionic acid methyl ester (0.080 g, 0.421 mmol) was reacted with 4'-trifluoromethyl-biphenyl-4-carboxylic acid (0.224 g, 0.841 mmol) as described in general procedure A yielding the corresponding (2S)-3-bis-[(4'-trifluoromethyl-biphenyl-4-carbonyl)-amino]-propionic acid methyl ester which was then hydrolyzed as per general procedure C to yield the title compound (0.150 g, 60%). $^1$H-NMR(400 MHz, DMSOd$_6$): 4.16 (m, 2H), 5.0 (m, 1H), 8.17 (m, 8H), 8.28 (m, 8H), 9.18 (m, 1H), 9.21 (d, 1H); LC/MS (m/z): 601.2 (M+1).

EXAMPLE 662

3-(Biphenyl-4-sulfonylamino)-(2S)-[(4'-trifluoromethyl-biphenyl-4-carbonyl)-amino]-propionic acid To 3-amino-(2S)-[(4'-trifluoromethyl-biphenyl-4-carbonyl)-amino]-propionic acid methyl ester hydrochloride (0.100 g, 0.273 mmol) prepared as per the above listed example 656 was added dry dichloromethane (10 ml) followed by diisopropylethylamine (0.095 g, 0.738 mmol) and stirred for 10 min. To this mixture at 0° C. was added Biphenyl-4-sulfonyl chloride (0.062 g, 0273 mmol) and the reaction was stirred at ambient temperature. After 2 hrs the reaction mixture was diluted with dichloromethane and washed with water (20 ml) followed by brine (20 ml). The organic layers were collected and dried over sodium sulfate and concentrated under reduced pressure to yield the 3-(Biphenyl-4-sulfonylamino)-2-[(4'-trifluoromethyl-biphenyl-4-carbonyl)-amino]-propionic acid methyl ester which was then hydrolyzed as per procedure C to yield the title compound (0.045 g, 50%). $^1$H-NMR(400 MHz, DMSOd$_6$): 3.65 (m, 2H), 4.85 (m, 1H), 7.78 (m, 4H), 8.02 (d, 2H), 8.17 (m, 7H), 8.27 (m, 4H), 8.62 (S, 1H), 8.9 (bs, 1H). LC/MS (m/z): 569.1 (M+1).

Biological Assay

The following assay methods are utilized to identify compounds of Formula (I) that are effective in antagonizing the function of factor IX. Compounds of Formula (I) are effective in antagonizing the function of factor IX and are useful as inhibitors of the intrinsic clotting pathway.

General Assay Procedure

Factor IXa Florescence Based Molecular Assay:

Method where a Fluorescent product is generated based on factor IXa cleaving the substrate $CH_3SO_2$-(D)-CHG-Gly-Arg-AMC AcOH (methyl sulfonyl-D-cyclohexylglycylglycyl-arginine-7-amino-4-methylcoumarid monoacetate) available from Centerchem, Inc.

12 μL of 4× compound dilutions (final 1% DMSO) is incubated for 10 min at room temp with 24 μL FIXa (HCIXA-0050 Haemotologic Technologies Inc. Essex Junction, Vt.) 3.9 units/mL in Buffer containing 80% Ethylene glycol, 10 mM $CaCl_2$, 200 mM NaCl, and 100 mM Tris (pH 7.4). The reaction is started by the addition of 12 μL of 0.5 mM FIXa substrate (Pefa-10148 from Pentapharm Basel, Switzerland). After incubating the reaction for 10 min at room temp, the plate is read in a Spectromax Gemini fluorescence plate reader with and exitation wavelenth of 340 nm and an emmision wavelength of 440 nm. From the varying concentrations of test compound, $IC_{50}$'s are then calculated. The Examples in Table 1 inhibit Factor IX in this assay with $IC_{50}$ of less than 30 micromolar.

Factor IXa In Vitro Clotting Assay:

Method where inhibition of clotting using citrated human plasma with exogenous human factor IXa is measured by turbidity.

Potential inhibitors of factor IX are added to a mixture of citrated human plasma, Cephalin, and human factor IX to give a final concentration of 0.8 U/ml. The mixture is allowed to incubate at 37° C. for 10 minutes. Clotting is initiated by the addition of 10 mM $CaCl_2$. The optical density is measured at 405 nm for 5 minutes. Relative $IC_{50}$'s as well as maximum efficacy are calculated.

A first control assay is performed using a mixture of citrated human plasma, Cephalin, and human factor IX. A second control assay is performed using a mixture of citrated human plasma and Cephalin. Clotting for the two control assays is initiated by the addition of $CaCl_2$, and the optical density is measured at 405 nm for 5 minutes.

Analysis of graphs of optical density versus time for the two control assays and various concentrations of compounds of Formula (I) demonstrates that factor IX decreases the time for $Ca^{+2}$ induced clotting of human serum. Analysis also demonstrates that compounds of Formula (I) prolong the $Ca^{+2}$ induced clotting time in the presence of factor IX.

Factor Xa in vitro clotting assays were performed using compounds of Formula (I) under the same or similar conditions as the factor IXa in vitro clotting assay. These data demonstrate that compounds of Formula (I) are partial inhibitors or partial antagonists of factor IX. For example, where a range of concentrations of a compound of Formula (I) in the presence of factor IX prolong the $Ca^{+2}$ induced clotting time from 700 seconds to 1500 seconds, the same range of concentrations of a compound of Formula (I) in the presence of factor Xa did not alter the $Ca^{+2}$ induced clotting time from 200 seconds.

The invention further provides pharmaceutical compositions comprising the factor IX modulating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The term "factor IX" is used herein to refer to blood coagulation factor IX, including both activated and non-activated forms thereof.

The term "therapeutically effective amount" is used herein to denote that amount of a drug or pharmaceutical agent that will elicit the therapeutic response of an animal or human that is being sought.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles. The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines. Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Methanesulfonate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1–19.

Other salts which are not pharmaceutically acceptable may be useful in the preparation of compounds of the invention and these form a further aspect of the invention.

In addition, some of the compounds of Formula (I) may form solvates with water or common organic solvents. Such solvates are also encompassed within the scope of the invention.

Thus, in another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents. In an embodiment of the pharmaceutical composition, the compound of Formula (I) is an antagonist of factor IX activity. In another embodiment of the pharmaceutical composition, the compound of Formula (I) is a partial antagonist of factor IX activity, wherein a partial antagonist comprises a compound that inhibits less than complete activity at a physiologically tolerable dose. In another embodiment of the pharmaceutical composition, the compound of Formula (I) is a partial antagonist of factor IX activity, wherein the compound of Formula (I) inhibits up to 95% of factor IX activity. In another embodiment of the pharmaceutical composition, the compound of Formula (I) is a partial antagonist of factor IX activity, wherein the compound of Formula (I) inhibits up to 80% of factor IX activity. In another embodiment of the pharmaceutical composition, the compound of Formula (I) is a partial antagonist of factor IX activity, wherein the compound of Formula (I) inhibits up to 50% of factor IX activity. In another embodiment of the pharmaceutical composition, the compound of Formula (I) antagonizes blood clotting mediated by factor IX.

In another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents, wherein said therapeutically effective amount of Formula (I) preferentially inhibits the intrinsic clotting cascade as compared to the extrinsic clotting cascade. In an embodiment of the pharmaceutical composition, said therapeutically effective amount of Formula (I) inhibits the intrinsic clotting cascade by greater than 80% and inhibits the extrinsic clotting cascade by less than 50%. In another embodiment of the pharmaceutical composition, said therapeutically effective amount of Formula (I) comprises an amount sufficient to achieve and maintain a sustained blood level that at least partially antagonizes factor IX biological activity. Preferably, said sustained blood level comprises a concentration ranging from about 0.01 µM to 2 mM, more preferably from about 1 µM to 300 µM, and even more preferably from about 20 µM to about 100 µM.

In another aspect of the present invention, there is provided a pharmaceutical composition comprising a therapeutically effective amount of a compound of Formula (I), or a pharmaceutically acceptable salt, solvate, or prodrug therof, and one or more pharmaceutically acceptable carriers, excipients, or diluents, wherein said therapeutically effective amount comprises a sufficient amount of the compound of Formula (I) to at least partially inhibit the biological activity of factor IX in a subject, a sufficient amount of the compound of Formula (I) for at least partial amelioration of at least one factor IX-mediated disease, or a sufficient amount of the compound of Formula (I) to at least partially inhibit the intrinsic clotting cascade in a subject. In an embodiment of the pharmaceutial composition, said factor IX-mediated disease comprises stroke. In another embodiment of the pharmaceutial composition, said factor IX-mediated disease comprises deep vein thrombosis. In another embodiment of the pharmaceutial composition, said factor IX-mediated disease comprises deep vein thrombosis, wherein said thrombosis is associated with surgical procedures, long periods of confinement, acquired or inherited pro-coagulant states including anti-phospholipid antibody syndrome, protein C deficiency and protein S deficiency, or acute and chronic inflammation including recurrent miscarriage or Systemic Lupus Erythmatosis (SLE). In another embodiment, said factor IX-mediated disease comprises excessive clotting associated with the treatment of kidney diseases by hemodialysis and/or venous hemofiltration. In another embodiment, said factor IX-mediated disease comprises cardiovascular disease. In another embodiment, said factor IX-mediated disease comprises cardiovascular disease, wherein said cardiovascular disease comprises myocardial infarction, arrhythmia, or aneurysm.

In another aspect, the present invention provides a pharmaceutical composition comprising a therapeutically effective amount of the compound of Formula (I), and one or more pharmaceutically acceptable carriers, excipients, or diluents, wherein said pharmaceutical composition is used to replace or supplement compounds that reduce clotting.

In another aspect, the present invention provides a pharmaceutical composition comprising a therapeutically effective amount of the compound of Formula (I), and one or more pharmaceutically acceptable carriers, excipients, or diluents, further comprising one or more therapeutic agents.

In another aspect, the present invention provides a method for the inhibition of the normal biological function of factor IX comprising administering to a subject in need thereof a compound of Formula (I). In embodiment of the method, said compound of Formula (I) is an antagonist of factor IX activity. In another embodiment of the method, said compound of Formula (I) antagonizes blood clotting mediated by factor IX. In another embodiment of the method, said compound of Formula (I) is administered in an amount sufficient to partially antagonize the biological activity of factor IX in said subject. In another embodiment of the method, said compound of Formula (I) is an antagonist of factor IX activity. In another embodiment of the method, said compound of Formula (I) antagonizes blood clotting mediated by factor IX. In another embodiment of the method, said compound of Formula (I) is administered in an amount sufficient to partially antagonize the biological activity of factor IX in said subject. In another embodiment of the method, said pharmaceutical composition is administered in the form of an oral dosage or parenteral dosage unit. In another embodiment of the method, said compound of Formula (I) is administered as a dose in a range from about 0.01 to 1,000 mg/kg of body weight per day. In another embodiment of the method, said compound of Formula (I) is administered as a dose in a range from about 0.1 to 100 mg/kg of body weight per day. In another embodiment of the method, said compound of Formula (I) is administered as a dose in a range from about 0.5 to 10 mg/kg of body weight per day. In another embodiment, said compound of Formula (I) is used to replace or supplement compounds that reduce clotting.

In another aspect, the present invention provides a method for the inhibition of the normal biological function of factor IX comprising administering to a subject in need thereof a compound of Formula (I), wherein said compound of Formula (I) is administered to said subject as a pharmaceutical composition comprising a therapeutically effective amount of said compound of Formula (I) and one or more pharmaceutically acceptable carriers, excipients, or diluents. In an embodiment of the method, said therapeutically effective amount of the compound of Formula (I) comprises a sufficient amount of the compound of Formula (I) to at least partially inhibit the intrinsic clotting cascade in said subject. In another embodiment of the method, said therapeutically effective amount of Formula (I) preferentially inhibits the intrinsic clotting cascade as compared to the extrinsic clotting cascade. In another embodiment of the method, said therapeutically effective amount of Formula (I) inhibits the intrinsic clotting cascade by greater than 80% and inhibits the extrinsic clotting cascade by less than 50%. In another embodiment of the method, said therapeutically effective amount of the compound of Formula I comprises an amount sufficient to achieve and maintain a sustained blood level that at least partially antagonizes factor IX biological activity. Preferably, said sustained blood level comprises a concentration ranging from about 0.01 µM to 2 mM, more preferably from about 1 µM to 300 µM, and even more preferably from about 20 µM to about 100 µM. In another embodiment of the method, said pharmaceutical composition further comprises one or more therapeutic agents.

In another aspect, the present invention provides a method for the inhibition of the normal biological function of factor IX comprising administering to a subject in need thereof a compound of Formula (I), wherein said compound of Formula (I) is a partial antagonist of factor IX, wherein a partial antagonist comprises a compound that inhibits less than complete activity at a physiologically tolerable dose. In an embodiment of the method, said compound of Formula (I) inhibits up to 95% of factor IX activity. In another embodiment of the method, said compound of Formula (I) inhibits up to 80% of factor IX activity. In another embodiment of the method, said compound of Formula (I) inhibits up to 50% of factor IX activity.

In another aspect, the present invention provides a method for the inhibition of the normal biological function of factor IX comprising administering to a subject in need thereof a compound of Formula (I), wherein said compound of Formula (I) is administered to said subject as a pharmaceutical composition comprising a therapeutically effective amount of said compound of Formula (I) and one or more pharmaceutically acceptable carriers, excipients, or diluents, wherein said therapeutically effective amount of the compound of Formula (I) comprises a sufficient amount of the compound of Formula (I) for treatment or prevention of factor IX-mediated diseases. In an embodiment of the method, said factor IX-mediated disease comprises stroke. In another embodiment of the method, said factor IX-mediated disease comprises deep vein thrombosis. The thrombosis may be associated with surgical procedures, long periods of confinement, acquired or inherited pro-coagulant states including anti-phospholipid antibody syndrome, protein C deficiency and protein S deficiency, or acute and chronic inflammation including recurrent miscarriage or Systemic Lupus Erythmatosis (SLE). In another embodiment of the method, said factor IX-mediated disease comprises clotting associated with the treatment of kidney disease by hemodialysis and/or venous hemofiltration. In another embodiment of the method, said factor IX-mediated disease comprises cardiovascular disease. The cardiovascular disease may be associated myocardial infarction, arrhythmia, or aneurysm.

In a further aspect of the present invention, the factor IXa modulators of the invention are utilized in adjuvant therapeutic or combination therapeutic treatments with other known therapeutic agents.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

The following is a non-exhaustive listing of adjuvants and additional therapeutic agents which may be utilized in combination with the factor IXa antagonists of the present invention:
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids In a further preferred embodiment, the present invention provides a method of treating or preventing a factor IXa mediated diseases, the method comprising administering to a subject in need thereof, a therapeutically effective amount of a compound of Formula (I) alone or in combination with therapeutic agents selected from the group consisting of antibiotics, hormones, biologic response modifiers, analgesics, NSAIDs, DMARDs, glucocorticoids, thrombolytic agents, antidepressants, and anticonvulsants.

Generally speaking, the compound of the present invention, preferably Formula (I), is administered at a dosage level of from about 0.01 to 1000 mg/kg of the body weight of the subject being treated, with a preferred dosage range between 0.01 and 100 mg/kg, most preferably 0.5 to 10 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage has to be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

While the invention has been described and illustrated with reference to certain preferred embodiments therof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for factor IXa-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

What is claimed is:
1. The compound of Formula (I):

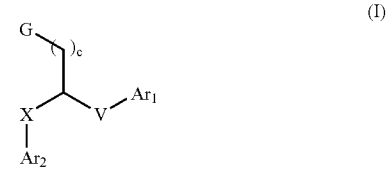

wherein
  c is 0,
  G is: —CO$_2$R$_1$, wherein R$_1$ is selected from the group consisting of: -hydrogen, -alkyl, -aryl, -arylene-alkyl, -alkylene-aryl, and -alkylene-arylene-alkyl,
  V is: —(CH$_2$)$_a$—, in which a is equal to 1;
  wherein
    the alkylene groups of V is optionally substituted 1 to 4 times with a substituent selected from the group consisting of: -alkyl, -aryl, -alkylene-aryl, -arylene-alkyl, -alkylene-arylene-alkyl, —O-alkyl, —O-aryl, and -hydroxyl,
  X is: —N(R$_8$)CO—;
  wherein
    R$_8$ is: -hydrogen, -alkyl, -aryl, -arylene-alkyl, -alkylene-aryl, -alkylene-arylene-alkyl, -alkylene-cycloalkylene-C(O)-alkylene-aryl, -alkylene-heterocyclylene-C(O)-alkylene-aryl, -alkylene-C(H)(R$_{10}$)(R$_{11}$), or -alkylene-N—(R$_{10}$)(R$_{11}$), wherein $R_{10}$ is H, -alkyl, -alkylene-aryl, -alkylene-heteroaryl, -aryl or -heteroaryl, and $R_{11}$ is H, -alkyl, -alkylene-aryl, -alkylene-heteroaryl, -aryl, -heteroaryl, —C(O)—O-alkyl, —C(O)—O-alkylene-aryl, —C(O)—O-alkylene-heteroaryl, —C(O)-alkyl, —C(O)-alkylene-aryl, —C(O)-alkylene-heteroaryl, —S(O)$_2$-alkyl, —S(O)$_2$-aryl, —S(O)$_2$-heteroaryl, —S(O)$_2$-alkylene-aryl, —S(O)$_2$-alkylene-heteroaryl, —S(O)$_2$—NH-alkyl, —S(O)$_2$—NH-alkylene-aryl, —S(O)$_2$—NH-alkylene-heteroaryl, —S(O)$_2$—NH-aryl, or —S(O)$_2$—NH-heteroaryl; or $R_{10}$ and $R_{11}$ may be taken together to form a ring having the formula —(CH$_2$)$_m$-Z-(CH$_2$)$_n$— bonded to the nitrogen or carbon atom to which $R_{10}$ and $R_{11}$ are attached, wherein m and n are, independently, 1, 2, 3, or 4; Z is —OH$_2$—, —C(O)—, —O—, —N(H)—, —S—, —S(O)—, —S(O$_2$)—, —CON(H)—, —NHC(O)—, —NHC(O)N(H)—, —NH(SO$_2$)—, —S(O$_2$)N(H)—, —(O)CO—, —NHS(O$_2$)NH—, —OC(O)—, —N(R$_{12}$)—, —N(C(O)R$_{12}$)—, —N(C(O)NHR$_{12}$)—, —N(S(O$_2$)NHR$_{12}$)—, —N(SO$_2$R$_{12}$)—, or —N(C(O)OR$_{12}$)—; wherein $R_{12}$ is -hydrogen, -aryl, -alkyl, or -alkylene-aryl; or $R_{10}$ and $R_{11}$ may be taken together, with the nitrogen or carbon atom to which they are attached, to form a heterocyclyl or heteroaryl ring, $Ar_1$ is a biphenyl group optionally substituted 1 to 7 times, wherein the substituent(s) are independently selected from the group consisting of:
a) -alkyl;
b) -cycloalkyl;
c) -phenylene-alkyl;
d) -D$_1$-alkyl;
e) -D$_1$-cycloalkyl;
f) -D$_1$-heterocyclyl; and
g) -D$_1$-R$_{13}$;
wherein $D_1$ is —CH$_2$—, -alkylene-, -alkenylene-, -alkylene-S—, —S-alkylene-, -alkylene-O—, —O-alkylene-, -alkylene-S(O)$_2$—, —S(O)$_2$-alkylene, —O—, —N(R$_{15}$)—, —C(O)—, —CON(R$_{15}$)—, —N(R$_{15}$)C(O)—, —N(R$_{15}$)CON(R$_{16}$)—, —N(R$_{15}$)C(O)O—, —OC(O)N(R$_{15}$)—, —N(R$_{15}$)SO$_2$—, —SO$_2$N(R$_{15}$)—, —C(O)—O—, —O—C(O)—, —S—, —S(O)—, —S(O$_2$)—, —N(R$_{15}$)SO$_2$N(R$_{16}$)—,

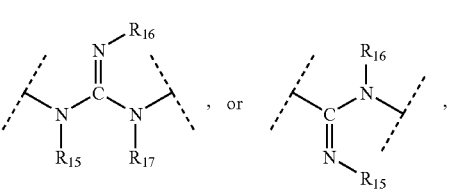

and wherein $R_{13}$, $R_{15}$, $R_{16}$, and $R_{17}$ independently selected from the group consisting of: -hydrogen, -alkyl, -aryl, -heteroaryl, -arylene-alkyl, -heteroarylene-alkyl, -alkylene-aryl, -alkylene-heteroaryl, -alkylene-arylene-alkyl, and -alkylene-heteroarylene-alkyl;

$Ar_2$ is 4'-trifluoromethyl-biphenyl-4-yl or 4'-trifluoromethoxy-biphenyl-4-yl, and wherein the alkyl, aryl, heteroaryl, alkylene, and arylene groups in $Ar_1$, $R_1$, $R_{10}$, $R_{11}$, $R_{12}$, $R_{13}$, $R_{15}$, $R_{16}$, and $R_{17}$, may be optionally substituted 1 to 4 times with a substituent independently selected from the group consisting of:
a) -hydrogen;
b) -fluoro;
c) -chloro;
d) -bromo;
e) -iodo;
f) -cyano;
g) -nitro;
h) -perfluoroalkyl;
i) -Q-perfluoroalkyl;
j) -Q-R$_{24}$;
k) -Q-alkyl;
l) -Q-aryl;
m) -Q-alkylene-aryl;
n) -Q-alkylene-NR$_{25}$R$_{26}$; and
o) -Q-alkyl-W—R$_{27}$;
wherein Q and W are independently selected from the group consisting of: —CH$_2$—, —O—, —N(R$_{28}$)—, —C(O)—, —CON(R$_{28}$)—, —N(R$_{28}$)C(O)—, —N(R$_{28}$)CON(R$_{29}$)—, —N(R$_{28}$)C(O)O—, —OC(O)N(R$_{28}$)—, —N(R$_{28}$)SO$_2$—, —SO$_2$N(R$_{28}$)—, —C(O)—O—, —O—C(O)—, and —N(R$_{28}$)SO$_2$N(R$_{29}$)—, wherein $R_{24}$, $R_{25}$, $R_{26}$, $R_{27}$, $R_{28}$, and $R_{29}$ are independently selected from the group consisting of: -hydrogen, -alkyl, -aryl, -arylene-alkyl, -alkylene-aryl, and -alkylene-arylene-alkyl, or a pharmaceutically acceptable salt thereof.

2. The compound of Formula (I) in claim 1, wherein
c is equal to 0;
G is —CO$_2$H;
V is —CH$_2$—;
X is —N(R$_8$)CO—;
wherein R$_8$ is: -hydrogen;
$Ar_1$ is a biphenyl group optionally substituted with a substituent selected from the group consisting of: -alkyl and -D$_1$-alkyl,
wherein
$D_1$ is —O—, or —N(R$_{15}$)—,
wherein
$R_{15}$ is: -hydrogen, -alkyl, or -phenyl; and
wherein the alkyl, phenyl, alkylene, and phenylene groups in $Ar_1$, may be optionally substituted 1 to 4 times with a substituent independently selected from the group consisting of: -hydrogen, -fluoro, -chloro, -bromo, iodo, -cyano, -nitro, and -perfluoroalkyl.

3. The compound of Formula (I) in claim 1, wherein G is —CO$_2$R$_1$; wherein R$_1$ is: -hydrogen, -alkyl, or -phenyl.

4. The compound of Formula (I) in claim 1, wherein G is —CO$_2$H.

5. The compound of Formula (I) in claim 1, wherein X is —N(R$_8$)CO—,
wherein
R$_8$ is: -hydrogen, -alkyl, -phenyl, -phenylene-alkyl, -alkylene-phenyl, or -alkylene-phenylene-alkyl.

6. The compound of Formula (I) in claim 1, wherein $Ar_1$ is a biphenyl group optionally having 1 to 5 substituents, wherein the substituents are independently selected from the group consisting of:
a) -alkyl;
b) -cycloalkyl;
c) -phenylene-alkyl;
d) -$D_1$-alkyl;
e) -$D_1$-cycloalkyl;
f) -$D_1$-heterocyclyl; and
g) -$D_1$-$R_{13}$;
wherein
$D_1$ is —$CH_2$—, -alkylene-, -alkenylene-, -alkylene-S—, —S-alkylene-, -alkylene-O—, —O-alkylene-, -alkylene-S(O)$_2$—, —S(O)$_2$-alkylene, —O—, —N($R_{15}$)—, —C(O)—, —CON($R_{15}$)—, —N($R_{15}$)C(O)—, —N($R_{15}$)CON($R_{16}$)—, —N($R_{15}$)C(O)O—, —OC(O)N($R_{15}$)—, —N($R_{15}$)SO$_2$—, —SO$_2$N($R_{15}$)—, —C(O)—O—, —O—C(O)—, —S—, —S(O)—, —S(O$_2$)—, —N($R_{15}$)SO$_2$N($R_{16}$)—,

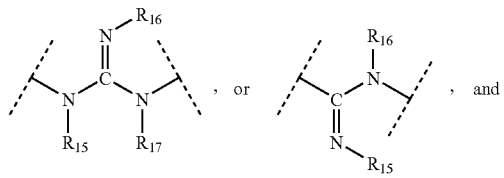

and
wherein $R_{13}$, $R_{15}$, $R_{16}$, and $R_{17}$ are independently selected from the group consisting of: -hydrogen, -alkyl, -phenyl, -heteroaryl, -phenylene-alkyl, -heteroarylene-alkyl, -alkylene-phenyl, -alkylene-heteroaryl, -alkylene-phenylene-alkyl or -alkylene-heteroarylene-alkyl;
wherein the alkyl, phenyl, alkylene, and phenylene groups in $Ar_1$ may be optionally substituted 1 to 4 times with a substituent independently selected from the group consisting of: -hydrogen, -fluoro, -chloro, -bromo, iodo, -cyano, -nitro, and -perfluoroalkyl.

7. The compound of Formula (I) in claim 1, wherein $Ar_1$ is a biphenyl group optionally substituted with a substituent selected from the group consisting of: -alkyl and -$D_1$-alkyl; wherein
$D_1$ is —O—, —N($R_{11}$)—, —CON($R_{11}$)—, or —N($R_{11}$)C(O)—, and wherein $R_{11}$ is: -hydrogen; -alkyl; or -phenyl;
wherein the alkyl, phenyl, alkylene, and phenylene groups in $Ar_1$ may be optionally substituted 1 to 4 times with a substituent independently selected from the group consisting of: -hydrogen, -fluoro, -chloro, -bromo, iodo, -cyano, -nitro, and -perfluoroalkyl.

8. The compound of Formula (I) in claim 1, wherein $Ar_1$ is selected from the group consisting of:
2'-phenoxy-biphenyl-4-yl,
2'-(4-methoxy-phenoxy)-biphenyl-4-yl,
2'-(4-pentyl-phenoxy)-biphenyl-4-yl,
2'-(4-tert-butyl-phenoxy)-biphenyl-4-yl,
2'-(4-trifluoromethoxy-phenoxy)-biphenyl-4-yl,
2'-Benzyloxy-biphenyl-4-yl,
2'-cyclopentyloxy-biphenyl-4-yl,
2'-hydroxy-biphenyl-4-yl,
2'-isopropoxy-biphenyl-4-yl,
2'-piperidin-1-ylmethyl-biphenyl-4-yl,
2'-trifluoromethyl-biphenyl-4-yl,
3',4',5'-trimethoxy-biphenyl-4-yl,
3',4'-dichloro-biphenyl-4-yl,
3',5'-Bis-trifluoromethyl-biphenyl-4-yl,
3'-Chloro-4'-fluoro-biphenyl-4-yl,
3'-methoxy-biphenyl-4-yl,
3'-trifluoromethyl-biphenyl-4-yl,
3'-Acetylamino-biphenyl-4-yl,
3'-Benzyloxy-biphenyl-4-yl,
Biphenyl-4-yl,
3-(3-chloro-4-fluorophenoxy)-biphenyl-4-yl,
3-(3-fluoro-phenoxy)-biphenyl-4-yl,
3'-nitro-biphenyl-4-yl,
3'-phenoxy-biphenyl-4-yl,
4'-(Acetylamino-methyl)-biphenyl-4-yl,
4'-methoxy-biphenyl-4-yl,
4'-Nitro-biphenyl-4-yl,
4'-trifluoromethyl-biphenyl-4-yl,
4'-Amino-biphenyl-4-yl,
4'-Chloro-biphenyl-4-yl,
4'-cyclohexyl-biphenyl-4-yl,
4'-Dimethylamino-biphenyl-4-yl,
4'-Methanesulfonylamino-biphenyl-4-yl,
(4-methoxy-phenoxy)-biphenyl-4-yl,
4'-pentyl-biphenyl-4-yl,
4'-phenoxy-biphenyl-4-yl,
(4-tert-Butyl-benzyloxy)-biphenyl-4-yl,
4'-tert-Butyl-biphenyl-4-yl,
(4-tert-Butyl-phenoxy)-biphenyl-4-yl,
4'-trifluoromethoxy-biphenyl-4-yl,
(4-trifluoromethyl-phenoxy)-biphenyl-4-yl,
5'-Chloro-2'-methoxy-biphenyl-4-yl,
5'-Fluoro-2'-methoxy-biphenyl-4-yl, and
4'-cyano-biphenyl-4-yl.

9. The compound of Formula (I) in claim 1, wherein X is —N($R_8$)CO— wherein $R_8$ is
hydrogen,
(1-Acetyl-(2R)-pyrrolidin-2-yl)-methyl,
2-(1-methyl-1H-imidazole-4-sulfonylamino)-ethyl,
(1-(2,2-dimethyl-propionyl)-(2S)-pyrrolidin-2-yl)-methyl,
2-(1,2-dimethyl-1H-imidazole-4-sulfonylamino)-ethyl,
(1-Acetyl-(2S)-pyrrolidin-2-yl)-methyl,
2-(2-Acetylamino-4-methyl-thiazole-5-sulfonylamino)-ethyl,
2-(5-chloro-1,3-dimethyl-1H-pyrazole-4-sulfonylamino)-ethyl,
2-(2,4-dimethoxy-benzylamino)-ethyl,
2-Amino-ethyl,
2-hydroxy-benzyl,
2-tert-butoxycarbonylamino-ethyl,
4-chloro-benzyl,
4-isopropyl-benzyl,
5-tert-butyl-2-hydroxy-benzyl, or
naphthalen-1-yl-methyl.

10. The compound of Formula (I) in claim 1 wherein the compound of Formula (I) is 3-Biphenyl-4-yl-(2S)-[(4'-trifluoromethyl-biphenyl-4-carbonyl)-amino]-propionic acid or a pharmaceutically acceptable salt thereof.

11. The compound of Formula (I) in claim 1 wherein the compound of Formula (I) is 3-Biphenyl-4-yl-(2S)-[(4'-trifluoromethoxy-biphenyl-4-carbonyl)-amino]-propionic acid or a pharmaceutically acceptable salt thereof.

12. The compound of Formula (I) in claim 1 wherein the compound of Formula (I) is (2S)-[(4'-Trifluoromethoxybiphenyl-4-carbonyl)-amino]-3-(4'-trifluoromethyl-biphenyl-4-yl)-propionic acid or a pharmaceutically acceptable salt thereof.

13. The compound of Formula (I) in claim 1 wherein the compound of Formula (I) is 3-(4'-Trifluoromethoxy-biphenyl-4-yl)-(2S)-[(4'-trifluoromethyl-biphenyl-4-carbonyl)-amino]-propionic acid or a pharmaceutically acceptable salt thereof.

14. A pharmaceutical composition comprising a therapeutically effective amount of the compound of Formula (I) as claimed in claim 1 or a pharmaceutically acceptable salt thereof, and one or more pharmaceutically acceptable carriers, excipients, or diluents.

15. The pharmaceutical composition of claim 14, in the form of an oral dosage or parenteral dosage unit.

16. The pharmaceutical composition of claim 14, further comprising one or more therapeutic agents.

17. A pharmaceutical composition comprising a therapeutically effective amount of the compound in claim 2 or a pharmaceutically acceptable salt thereof, and a pharmaceutically acceptable carrier, excipient, diluent, or mixture thereof.

18. A pharmaceutical composition comprising a therapeutically effective amount of the compound in claim 3 or a pharmaceutically acceptable salt thereof, and a pharmaceutically acceptable carrier, excipient, diluent, or mixture thereof.

19. A pharmaceutical composition comprising a therapeutically effective amount of the compound in claim 4 or a pharmaceutically acceptable salt thereof, and a pharmaceutically acceptable carrier, excipient, diluent, or mixture thereof.

20. A pharmaceutical composition comprising a therapeutically effective amount of the compound in claim 5 or a pharmaceutically acceptable salt thereof, and a pharmaceutically acceptable carrier, excipient, diluent, or mixture thereof.

21. A pharmaceutical composition comprising a therapeutically effective amount of the compound in claim 6 or a pharmaceutically acceptable salt thereof, and a pharmaceutically acceptable carrier, excipient, diluent, or mixture thereof.

22. A pharmaceutical composition comprising a therapeutically effective amount of the compound in claim 7 or a pharmaceutically acceptable salt thereof, and a pharmaceutically acceptable carrier, excipient, diluent, or mixture thereof.

23. A pharmaceutical composition comprising a therapeutically effective amount of the compound in claim 8 or a pharmaceutically acceptable salt thereof, and a pharmaceutically acceptable carrier, excipient, diluent, or mixture thereof.

24. A pharmaceutical composition comprising a therapeutically effective amount of the compound in claim 9 or a pharmaceutically acceptable salt thereof, and a pharmaceutically acceptable carrier, excipient, diluent, or mixture thereof.

25. A pharmaceutical composition comprising a therapeutically effective amount of the compound in claim 10 or a pharmaceutically acceptable salt thereof, and a pharmaceutically acceptable carrier, excipient, diluent, or mixture thereof.

26. A pharmaceutical composition comprising a therapeutically effective amount of the compound in claim 11 or a pharmaceutically acceptable salt thereof, and a pharmaceutically acceptable carrier, excipient, diluent, or mixture thereof.

27. A pharmaceutical composition comprising a therapeutically effective amount of the compound in claim 12 or a pharmaceutically acceptable salt thereof, and a pharmaceutically acceptable carrier, excipient, diluent, or mixture thereof.

28. A pharmaceutical composition comprising a therapeutically effective amount of the compound in claim 13 or a pharmaceutically acceptable salt thereof, and a pharmaceutically acceptable carrier, excipient, diluent, or mixture thereof.

29. A compound having the formula:

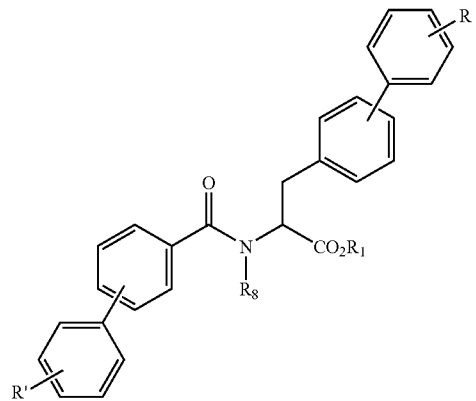

wherein
$R_1$ is -hydrogen or -alkyl
$R_8$ is: -hydrogen, -alkyl, -phenyl, -phenylene-alkyl, -alkylene-phenyl, -alkylene-phenylene-alkyl, -alkylene-cycloalkylene-C(O)-alkylene-phenyl, -alkylene-heterocyclylene-C(O)-alkylene-phenyl, -alkylene-C(H)($R_{10}$)($R_{11}$), or -alkylene-N-($R_{10}$)($R_{11}$),
wherein
$R_{10}$ is H, -alkyl, -alkylene-phenyl, -alkylene-heteroaryl, -phenyl, or -heteroaryl, and
$R_{11}$ is H, -alkyl, -alkylene-phenyl, -alkylene-heteroaryl, -phenyl, -heteroaryl, —C(O)—O-alkyl, —C(O)—O-alkylene-phenyl, —C(O)-O-alkylene-heteroaryl, —C(O)-alkyl, —C(O)-alkylene-phenyl, —C(O)-alkylene-heteroaryl, —S(O)$_2$-alkyl, —S(O)$_2$-phenyl, —S(O)$_2$-heteroaryl, —S(O)$_2$-alkylene-phenyl, —S(O)$_2$-alkylene-heteroaryl, —S(O)$_2$—NH-alkyl, —S(O)$_2$—NH-alkylene-phenyl, —S(O)$_2$—NH-alkylene-heteroaryl, —S(O)$_2$—NH-phenyl, or —S(O)$_2$—NH-heteroaryl; or
$R_{10}$ and $R_{11}$ may be taken together to form a ring having the formula —(CH$_2$)$_m$-Z-(CH$_2$)$_n$— bonded to the nitrogen or carbon atom to which $R_{10}$ and $R_{11}$ are attached, wherein m and n are, independently, 1, 2, 3, or 4; Z is —OH$_2$—, —C(O)—, —O—, —N(H)—, —S—, —S(O)—, —S(O$_2$)—, —CON(H)—, —NHC(O)—, —NHC(O)N(H)—, —NH(SO$_2$)—, —S(O$_2$)N(H)—, —(O)CO—, —NHS(O$_2$)NH—, —OC(O)—, —N(R$_{12}$)—, —N(C(O)R$_{12}$)—, —N(C(O)NHR$_{12}$)—, —N(S(O$_2$)NHR$_{12}$)—, —N(SO$_2$R$_{12}$)—, or —N(C(O)OR$_{12}$)—; wherein $R_{12}$ is -hydrogen, -phenyl, -alkyl, or -alkylene-phenyl; or
$R_{10}$ and $R_{11}$ may be taken together, with the nitrogen or carbon atom to which they are attached, to form a heterocyclyl or heteroaryl ring;

R is selected from the group consisting of:
- -hydrogen,
- —CN,
- —NO$_2$,
- —NH$_2$,
- —Cl,
- —OH,
- -alkyl,
- -cycloalkyl,
- —CF$_3$,
- -phenyl,
- —O-alkyl,
- —O-CF$_3$,
- —O-phenyl,
- —O-phenylene-CF$_3$,
- —O-phenylene-O—CH$_3$,
- —O-phenylene-O—CF$_3$,
- —O—CH$_2$-phenyl,
- —O—CH$_2$-phenylene-CF$_3$,
- —O-cycloalkyl,
- —O—CH$_2$-phenylene-alkyl,
- —N(CH$_3$)$_2$,
- —NHSO$_2$CH$_3$,
- —NHC(O)CH$_3$,
- —CH$_2$NHC(O)CH$_3$, and
- —S(O)$_2$CH$_3$, and R' is selected from the group consisting of:
- —CF$_3$, and
- —OCF$_3$, or a pharmaceutically acceptable salt thereof.

30. The compound of claim 29, wherein $R_1$ is -hydrogen and $R_8$ is -hydrogen.

31. A compound having the formula:

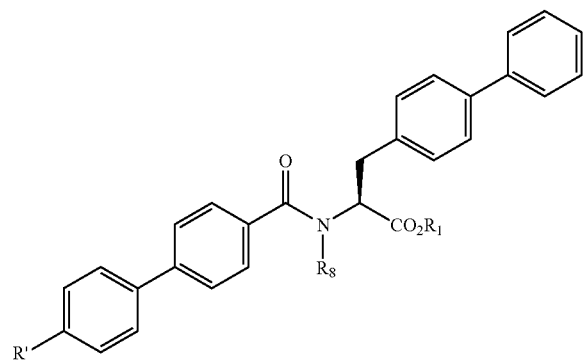

wherein $R_1$ is -hydrogen or -alkyl, and $R_8$ is: -hydrogen, -alkyl, -phenyl, -phenylene-alkyl, -alkylene-phenyl, -alkylene-phenylene-alkyl, -alkylene-cycloalkylene-C(O)-alkylene-phenyl, -alkylene-heterocyclylene-C(O)-alkylene-phenyl, -alkylene-C(H)($R_{10}$)($R_{11}$), or -alkylene-N—($R_{10}$)($R_{11}$), wherein $R_{10}$ is H, -alkyl, -alkylene-phenyl, -alkylene-heteroaryl, -phenyl, or -heteroaryl, and $R_{11}$ is H, -alkyl, -alkylene-phenyl, -alkylene-heteroaryl, -phenyl, -heteroaryl, —C(O)—O-alkyl, —C(O)—O-alkylene-phenyl, —C(O)—O-alkylene-heteroaryl, —C(O)-alkyl, —C(O)-alkylene-phenyl, —C(O)-alkylene-heteroaryl, —S(O)$_2$-alkyl, —S(O)$_2$-phenyl, —S(O)$_2$-heteroaryl, —S(O)$_2$-alkylene-phenyl, —S(O)$_2$-alkylene-heteroaryl, —S(O)$_2$—NH-alkyl, —S(O)$_2$—NH-alkylene-phenyl, —S(O)$_2$—NH-alkylene-heteroaryl, —S(O)$_2$—NH-phenyl, or —S(O)$_2$—NH-heteroaryl; or $R_{10}$ and $R_{11}$ may be taken together to form a ring having the formula —(CH$_2$)$_m$-Z-(CH$_2$)$_n$— bonded to the nitrogen or carbon atom to which $R_{10}$ and $R_{11}$ are attached, wherein m and n are, independently, 1, 2, 3, or 4; Z is —CH$_2$—, —C(O)—, —O—, —N(H)—, —S—, —S(O)—, —S(O$_2$)—, —CON(H)—, —NHC(O)—, —NHC(O)N(H)—, —NH(SO$_2$)—, —S(O$_2$)N(H)—, —(O)CO—, —NHS(O$_2$)NH—, —OC(O)—, —N(R$_{12}$)—, —N(C(O)R$_{12}$)—, —N(C(O)NHR$_{12}$)—, —N(S(O$_2$)NHR$_{12}$)—, —N(SO$_2$R$_{12}$)—, or —N(C(O)OR$_{12}$)—; wherein $R_{12}$ is -hydrogen, -phenyl, -alkyl, or -alkylene-phenyl; or $R_{10}$ and $R_{11}$ may be taken together, with the nitrogen or carbon atom to which they are attached, to form a heterocyclyl or heteroaryl ring; and R' is selected from the group consisting of: —CF$_3$ and —O—CF$_3$, or a pharmaceutically acceptable salt thereof.

32. The compound of claim 31, wherein $R_1$ is -hydrogen and $R_8$ is -hydrogen.

33. A pharmaceutical composition comprising a therapeutically effective amount of the compound in claim 29 or a pharmaceutically acceptable salt thereof, and a pharmaceutically acceptable carrier, excipient, diluent, or mixture thereof.

34. A pharmaceutical composition comprising a therapeutically effective amount of the compound in claim 30 or a pharmaceutically acceptable salt thereof, and a pharmaceutically acceptable carrier, excipient, diluent, or mixture thereof.

35. A pharmaceutical composition comprising a therapeutically effective amount of the compound in claim 31 or a pharmaceutically acceptable salt thereof, and a pharmaceutically acceptable carrier, excipient, diluent, or mixture thereof.

36. A pharmaceutical composition comprising a therapeutically effective amount of the compound in claim 32 or a pharmaceutically acceptable salt thereof, and a pharmaceutically acceptable carrier, excipient, diluent, or mixture thereof.

* * * * *